United States Patent
Jung et al.

(10) Patent No.: US 9,960,367 B2
(45) Date of Patent: May 1, 2018

(54) CONDENSED CYCLIC COMPOUND AND ORGANIC LIGHT-EMITTING DEVICE INCLUDING THE SAME

(71) Applicants: Samsung Electronics Co., Ltd., Suwon-si, Gyeonggi-do (KR); Samsung SDI Co., Ltd., Yongin-si, Gyeonggi-do (KR)

(72) Inventors: Yongsik Jung, Yongin-si (KR); Miyoung Chae, Yongin-si (KR); Eunsuk Kwon, Suwon-si (KR); Sangmo Kim, Hwaseong-si (KR); Hyunjung Kim, Suwon-si (KR); Jhunmo Son, Yongin-si (KR); Saeyoun Lee, Suwon-si (KR); Soonok Jeon, Seoul (KR); Yeonsook Chung, Seoul (KR); Dalho Huh, Suwon-si (KR); Joonghyuk Kim, Seoul (KR); Myungsun Sim, Suwon-si (KR)

(73) Assignees: SAMSUNG ELECTRONICS CO., LTD., Gyeonggi-Do (KR); SAMSUNG SDI CO., LTD., Gyeonggi-Do (KR)

(*) Notice: Subject to any disclaimer, the term of this patent is extended or adjusted under 35 U.S.C. 154(b) by 0 days. days.

(21) Appl. No.: 15/170,226

(22) Filed: Jun. 1, 2016

(65) Prior Publication Data

US 2017/0186974 A1 Jun. 29, 2017

(30) Foreign Application Priority Data

Dec. 24, 2015 (KR) .................. 10-2015-0186775

(51) Int. Cl.
*H01L 51/00* (2006.01)
*C09K 11/00* (2006.01)
(Continued)

(52) U.S. Cl.
CPC ...... *H01L 51/0072* (2013.01); *C07D 491/048* (2013.01); *C09K 11/025* (2013.01);
(Continued)

(58) Field of Classification Search
CPC . H01L 51/0072; H01L 51/009; H01L 51/008; H01L 51/0085; H01L 51/0071;
(Continued)

(56) References Cited

U.S. PATENT DOCUMENTS

| 8,889,271 | B2* | 11/2014 | Park | C07D 209/82 257/40 |
| 2012/0181520 | A1* | 7/2012 | Kim | C07B 59/001 257/40 |
| 2013/0009137 | A1* | 1/2013 | Brown | C08L 65/00 257/40 |
| 2014/0225046 | A1* | 8/2014 | Jatsch | C07D 405/14 252/519.3 |

(Continued)

FOREIGN PATENT DOCUMENTS

| JP | 2011-054696 A | 3/2011 |
| JP | 2011-091355 A | 5/2011 |

(Continued)

*Primary Examiner* — Michael M Bernshteyn
(74) *Attorney, Agent, or Firm* — Cantor Colburn LLP

(57) ABSTRACT

A condensed cyclic compound represented by Formula 1:

$$Ar_1-L_1-L_2-Ar_2 \quad \text{Formula 1}$$

wherein in Formula 1, $Ar_1$, $Ar_2$, $L_1$, and $L_2$ are the same as described in the specification.

20 Claims, 1 Drawing Sheet

(51) Int. Cl.
  *C07D 491/04* (2006.01)
  *C09K 11/02* (2006.01)
  *C09K 11/06* (2006.01)
  *C07D 491/048* (2006.01)
  *H01L 51/50* (2006.01)

(52) U.S. Cl.
  CPC .......... C09K 11/06 (2013.01); H01L 51/008 (2013.01); H01L 51/009 (2013.01); H01L 51/0071 (2013.01); H01L 51/0085 (2013.01); *C09K 2211/1007* (2013.01); *C09K 2211/1022* (2013.01); *C09K 2211/1044* (2013.01); *C09K 2211/185* (2013.01); *H01L 51/5012* (2013.01); *H01L 51/5096* (2013.01)

(58) Field of Classification Search
  CPC .......... H01L 51/5012; H01L 51/5096; C09K 11/025; C09K 11/06; C09K 2211/1007; C09K 2211/1022; C09K 2211/1044; C09K 2211/185; C07D 491/048
  USPC .......................................... 428/690
  See application file for complete search history.

(56) References Cited

U.S. PATENT DOCUMENTS

| | | |
|---|---|---|
| 2017/0062752 A1 | 3/2017 | Ihn et al. |
| 2017/0069853 A1 | 3/2017 | Kim et al. |
| 2017/0077421 A1 | 3/2017 | Ihn et al. |
| 2017/0194570 A1 | 7/2017 | Kang et al. |

FOREIGN PATENT DOCUMENTS

| | | |
|---|---|---|
| JP | 2011-176258 A | 9/2011 |
| KR | 2011-0066766 A | 6/2011 |
| KR | 2012-0020816 A | 3/2012 |
| KR | 1144358 B1 | 5/2012 |
| KR | 10-2013-0011405 A | 1/2013 |
| KR | 10-2013-0117534 A | 10/2013 |
| KR | 10-2014-0142021 A | 12/2014 |
| KR | 1478990 B1 | 12/2014 |
| KR | 10-2015-0024735 A | 3/2015 |
| WO | WO 2012045710 A1 * | 4/2012 |
| WO | 2013-041176 A1 | 3/2013 |
| WO | WO 2013055132 A2 * | 4/2013 |

* cited by examiner

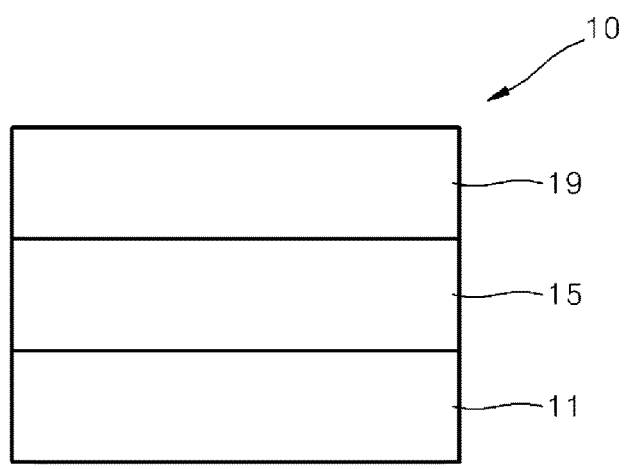

CONDENSED CYCLIC COMPOUND AND ORGANIC LIGHT-EMITTING DEVICE INCLUDING THE SAME

CROSS-REFERENCE TO RELATED APPLICATION

This application claims priority to Korean Patent Application No. 10-2015-0186775, filed on Dec. 24, 2015, in the Korean Intellectual Property Office, and all the benefits accruing therefrom under 35 U.S.C. § 119, the content of which is incorporated herein in its entirety by reference.

BACKGROUND

1. Field

The present disclosure relates to a condensed cyclic compound and an organic light-emitting device including the same.

2. Description of the Related Art

Organic light-emitting devices (OLEDs) are self-emitting devices that have wide viewing angles, high contrast ratios, and short response times. In addition, the OLEDs display excellent brightness, driving voltage, and response speed characteristics, and can produce full-color images.

In an example, an organic light-emitting device may include an anode, a cathode, and an organic layer disposed between the anode and the cathode. The organic layer may include an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. Carriers, such as holes and electrons, recombine in the emission layer to produce excitons. These excitons transit from an excited state to a ground state, thereby generating light.

Various types of organic light emitting devices are known. However, there still remains a need in OLEDs having low driving voltage, high efficiency, high brightness, and long lifespan.

SUMMARY

Provided are a novel condensed cyclic compound and an organic light-emitting device including the same.

Additional aspects will be set forth in part in the description which follows and, in part, will be apparent from the description, or may be learned by practice of the presented embodiments.

According to an aspect of an embodiment, provided is a condensed cyclic compound represented by Formula 1:

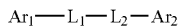

Formula 1

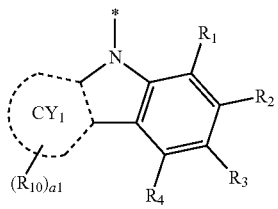

Formula 2

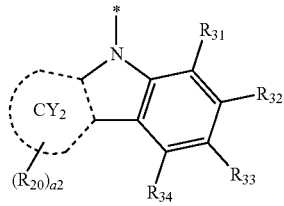

Formula 3

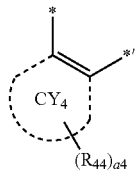

Formula 4

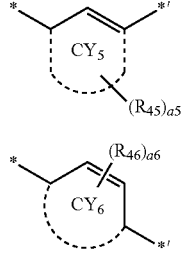

Formula 5

Formula 6 wherein, in Formulae 1 to 6, $Ar_1$ may be a group represented by Formula 2, $Ar_2$ may be a group represented by Formula 3, $CY_1$ may be selected from a fluorene group, a carbazole group, a dibenzofuran group, and a dibenzothiophene group, $CY_2$ may be selected from a benzene group, a fluorene group, a carbazole group, a dibenzofuran group, and a dibenzothiophene group, $L_1$ and $L_2$ may each independently be selected from a group represented by Formula 4, a group represented by Formula 5, or a group represented by Formula 6, $CY_4$ to $CY_6$ may each independently a $C_5$-$C_{30}$ carbocyclic group, $R_1$ to $R_4$, $R_{10}$, $R_{20}$, $R_{31}$ to $R_{34}$, and $R_{44}$ to $R_{46}$ may each independently be selected from hydrogen, deuterium, —F, —Cl, —Br, —I, a hydroxy group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), and —B($Q_8$)($Q_7$), provided that a group represented by *-$L_1$-$L_2$-*' in Formula 1 includes at least one cyano group, wherein the number of the cyano groups included in the group represented by *-$L_1$-$L_2$-*' in Formula 1 is 1, 2, 3, or 4, a1, a2, and a4 to a6 may each independently be an integer selected from 0 to 10,

*and *' may each indicate a binding site to a neighboring atom, at least one substituent of the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —$CD_3$, —$CD_2H$, —$CDH_2$, —F, —Cl, —Br, —I, a hydroxy group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —$CD_3$, —$CD_2H$, —$CDH_2$, —F, —Cl, —Br, —I, a hydroxy group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{14})(Q_{15})$, and —$B(Q_{16})(Q_{17})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —$CD_3$, —$CD_2H$, —$CDH_2$, —F, —Cl, —Br, —I, a hydroxy group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{21})(Q_{22})(Q_{23})$, —$N(Q_{24})(Q_{25})$, and —$B(Q_{26})(Q_{27})$; and —$Si(Q_{31})(Q_{32})(Q_{33})$, —$N(Q_{34})(Q_{35})$, and —$B(Q_{36})(Q_{37})$, wherein $Q_1$ to $Q_7$, $Q_{11}$ to $Q_{17}$, $Q_{21}$ to $Q_{27}$, and $Q_{31}$ to $Q_{37}$ may each independently be selected from hydrogen, deuterium, —F, —Cl, —Br, —I, a hydroxy group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

According to an aspect of another embodiment, provided is an organic light-emitting device including:

a first electrode;

a second electrode; and an organic layer disposed between the first electrode and the second electrode, wherein the organic layer includes an emission layer, and wherein the organic layer includes at least one of the condensed cyclic compounds represented by Formula 1.

BRIEF DESCRIPTION OF THE DRAWING

These and/or other aspects will become apparent and more readily appreciated from the following description of the embodiments, taken in conjunction with FIG. 1 which is a schematic cross-sectional view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present disclosure. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

An aspect of the present disclosure includes a condensed cyclic compound represented by Formula 1:

$$Ar_1-L_1-L_2-Ar_2. \qquad \text{Formula 1}$$

In Formula 1,
$Ar_1$ may be a group represented by Formula 2,
$Ar_2$ may be a group represented by Formula 3, and
$L_1$ and $L_2$ may each independently be a group represented by Formula 4, a group represented by Formula 5, or a group represented by Formula 6:

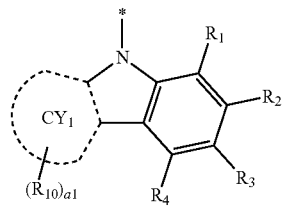

Formula 2

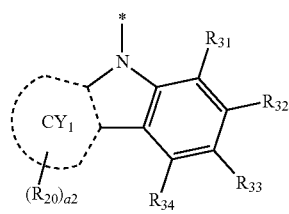

Formula 3

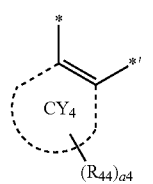

Formula 4

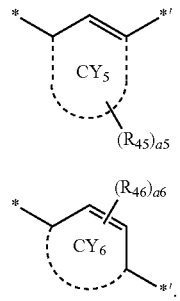

Formula 5

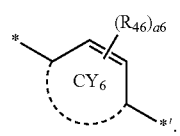

Formula 6

In Formula 2, $CY_1$ may be selected from a fluorene group, a carbazole group, a dibenzofuran group, and a dibenzothiophene group.

In Formula 3, $CY_2$ may be selected from a benzene group, a fluorene group, a carbazole group, a dibenzofuran group, and a dibenzothiophene group.

In Formulae 4 to 6, $CY_4$ to $CY_6$ may each independently be a $C_5$-$C_{30}$ carbocyclic group.

In an embodiment, $CY_4$ to $CY_6$ in Formulae 4 to 6 may each independently be selected from a benzene group, a naphthalene group, a fluorene group, a carbazole group, a dibenzofuran group, and a dibenzothiophene group.

In various embodiments, $CY_4$ to $CY_6$ in Formulae 4 to 6 may each independently be a benzene group, but are not limited thereto.

In the formulae above, $R_1$ to $R_4$, $R_{10}$, $R_{20}$, $R_{31}$ to $R_{34}$, and $R_{44}$ to $R_{46}$ may each independently be selected from hydrogen, deuterium, —F, —Cl, —Br, —I, a hydroxy group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), and —B($Q_6$)($Q_7$), wherein $Q_1$ to $Q_7$ may each independently be selected from hydrogen, deuterium, —F, —Cl, —Br, —I, a hydroxy group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In an embodiment, $R_1$ to $R_4$, $R_{10}$, $R_{20}$, $R_{31}$ to $R_{34}$, and $R_{44}$ to $R_{46}$ in the formulae above may each independently be selected from:

hydrogen, deuterium, —F, —Cl, —Br, —I, a hydroxy group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxy group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a biphenyl group, a terphenyl group, and a naphthyl group;

a cyclopentyl group, a cyclohexyl group, a cyclopentenyl group, a cyclohexenyl group, a cycloheptenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, an imidazopyridinyl group, a pyridoindolyl group, a benzofuropyridinyl group, a benzothienopyridinyl group, a pyrimidoindolyl group, a benzopyrimidinyl group, a benzothienopyrimidinyl group, a phenoxazinyl group, a pyridobenzoxazinyl group, and a pyridobenzothiazinyl group;

a cyclopentyl group, a cyclohexyl group, a cyclopentenyl group, a cyclohexenyl group, a cycloheptenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, an imidazopyridinyl group, a pyridoindolyl group, a benzofuropyridinyl group, a benzothienopyridinyl group, a pyrimidoindolyl group, a benzopyrimidinyl group, a benzothienopyrimidinyl group, a phenoxazinyl group, a pyridobenzoxazinyl group, and a pyridobenzothiazinyl group, each substituted with at least one selected from deuterium, —F, —Cl, —Br, —I, a hydroxy group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a biphenyl group, a terphenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, a quinazolinyl group, —Si($Q_{31}$)($Q_{32}$)($Q_{33}$), —N($Q_{34}$)($Q_{35}$), and —B($Q_{36}$)($Q_{37}$); and —Si($Q_1$)($Q_2$)($Q_3$), —N($Q_4$)($Q_5$), and —B($Q_6$)($Q_7$), wherein $Q_1$ to $Q_7$ and $Q_{31}$ to $Q_{37}$ may each independently be selected from hydrogen, a $C_1$-$C_{20}$ alkyl group, a $C_1$-$C_{20}$ alkoxy group, a phenyl group, a biphenyl group, a terphenyl group, a naphthyl group, a fluorenyl group, a carbazolyl group, a dibenzofuranyl group, and a dibenzothiophenyl group, but embodiments are not limited thereto.

In various embodiments, $R_1$ to $R_4$, $R_{10}$, $R_{20}$, $R_{31}$ to $R_{34}$, and $R_{44}$ to $R_{46}$ in the formulae above may each independently be selected from:

hydrogen, deuterium, a cyano group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, a cyano group, a phenyl group, a biphenyl group, a terphenyl group, and a naphthyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, and a dibenzothiophenyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, and a dibenzothiophenyl group, each substituted with at least one selected from deuterium, a cyano group, $C_1$-$C_{20}$ alkyl group, a $C_1$-$C_{20}$ alkoxy group, a phenyl group, a biphenyl group, a terphenyl group, a naphthyl group, and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ may each independently be selected from hydrogen, a $C_1$-$C_{20}$ alkyl group, a $C_1$-$C_{20}$ alkoxy group, a phenyl group, a biphenyl group, a terphenyl group, and a naphthyl group, but they are not limited thereto.

In Formula 2, a1 indicates the number of groups $R_{10}$, and may be an integer selected from 0 to 10, wherein when a1 is 2 or more, two or more groups $R_{10}$ may be identical to or different from each other. Descriptions of a2 and a4 to a6 may each be understood by referring to the description provided herein in connection with a1 and the structures of Formulae 2 to 6.

For example, a1, a2, and a4 to a6 in the formulae above may each independently be 0, 1, or 2, but are not limited thereto.

For example, $Ar_1$ in Formula 1 may be selected from groups represented by Formulae 2-1 to 2-6, and $Ar_2$ in Formula 1 may be selected from groups represented by Formulae 3-1 to 3-7:

Formula 2-1

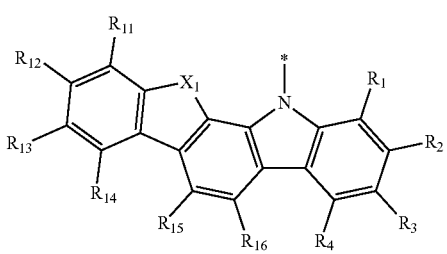

Formula 2-2

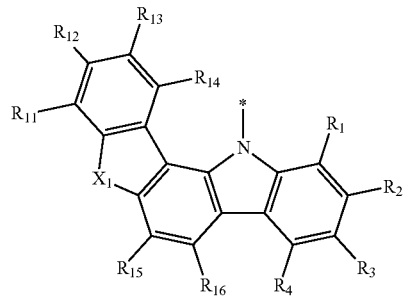

Formula 2-3

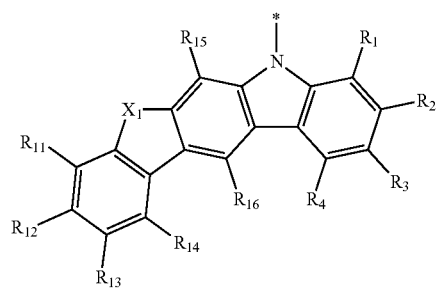

Formula 2-4

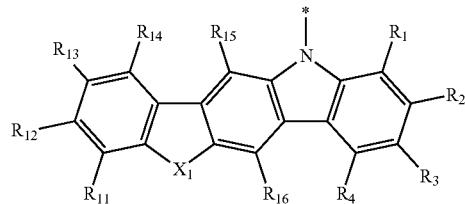

Formula 2-5

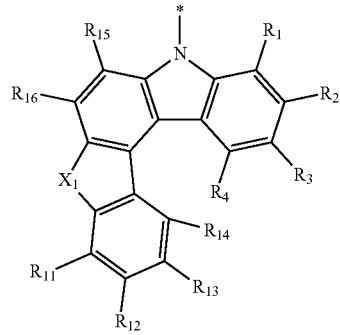

Formula 2-6

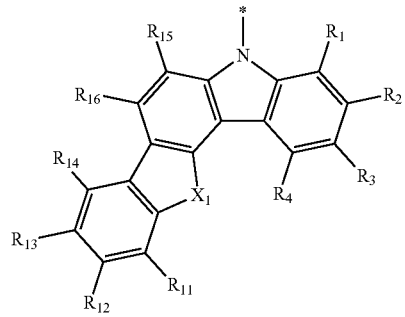

Formula 3-1
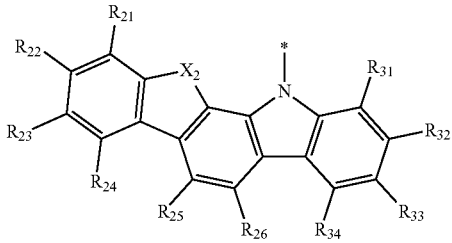

Formula 3-2
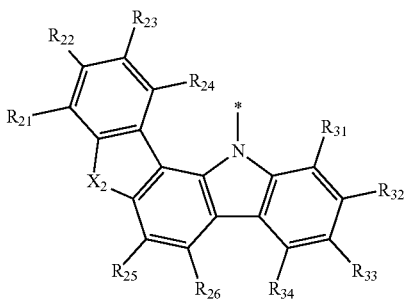

Formula 3-3
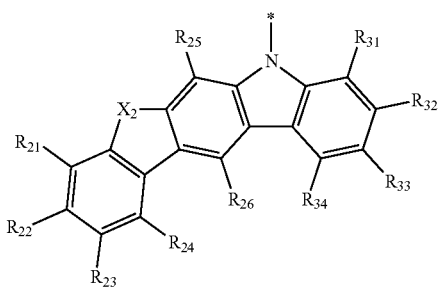

Formula 3-4
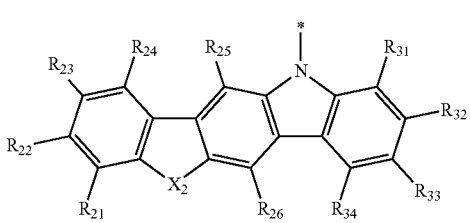

Formula 3-5
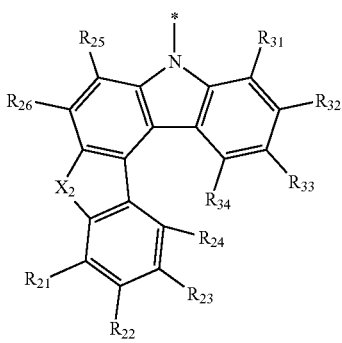

Formula 3-6
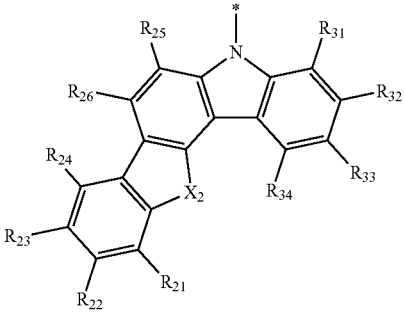

Formula 3-7
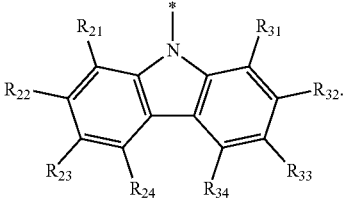

In Formulae 2-1 to 2-6 and 3-1 to 3-7,
$X_1$ may be $C(R_{17})(R_{18})$, $N(R_{19})$, O, or S,
$X_2$ may be $C(R_{27})(R_{28})$, $N(R_{29})$, O, or S,
descriptions of $R_1$ to $R_4$ may each be understood by the descriptions provided in the present specification,
descriptions of $R_{11}$ to $R_{19}$ may each be understood by the description provided herein in connection with $R_{10}$,
descriptions of $R_{21}$ to $R_{29}$ may each be understood by the description provided herein in connection with $R_{20}$, and
descriptions of $R_{31}$ to $R_{34}$ may each be understood by the descriptions provided in the present specification.

For example, in Formulae 2-1 to 2-6 and 3-1 to 3-7, $R_1$ to $R_4$, $R_{11}$ to $R_{19}$, $R_{21}$ to $R_{29}$, and $R_{31}$ to $R_{34}$ may each independently be selected from:

hydrogen, deuterium, a cyano group, a $C_1$-$C_{20}$ alkyl group, and a $C_1$-$C_{20}$ alkoxy group;

a phenyl group, a biphenyl group, a terphenyl group, a fluorenyl group, a carbazolyl group, a dibenzofuranyl group, and a dibenzothiophenyl group; and a phenyl group, a biphenyl group, a terphenyl group, a fluorenyl group, a carbazolyl group, a dibenzofuranyl group, and a dibenzothiophenyl group, each substituted with at least one selected from deuterium, a cyano group, a $C_1$-$C_{20}$ alkyl group, a $C_1$-$C_{20}$ alkoxy group, a phenyl group, a biphenyl group, and a terphenyl group, but embodiments are not limited thereto.

In an embodiment, $Ar_1$ in Formula 1 may be selected from groups represented by Formulae 2-1 to 2-6, and $Ar_2$ in Formula 1 may be selected from groups represented by Formulae 3-1 to 3-7, wherein at least one selected from $R_3$, $R_{13}$, $R_{23}$, and $R_{33}$ in Formula 1 may be a cyano group.

In an embodiment, at least one selected from $L_1$ and $L_2$ in Formula 1 may be the group represented by Formula 4 or the group represented by Formula 5.

In various embodiments, $L_1$ and $L_2$ in Formula 1 may each independently be the group represented by Formula 4 or the group represented by Formula 5, but $L_1$ and $L_2$ are not limited thereto.

In various embodiments, at least one selected from $L_1$, and $L_2$ in Formula 1 may be the group represented by Formula 4, but is not limited thereto. In this regard, the condensed cyclic compound represented by Formula 1 may cause steric hindrance, and may accordingly have high triplet energy values and exhibit excellent charge delivering characteristics.

In Formula 1, a group represented by *-$L_1$-$L_2$-*' may include at least one cyano group, wherein the number of the cyano groups included in the group represented by *-$L_1$-L-*' in Formula 1 may be 1, 2, 3, or 4.

In an embodiment, 1, 2, 3, or 4 substituents of the group represented by *-$L_1$-$L_2$-*' in Formula 1 may each independently be selected from:
a cyano group; and
a $C_1$-$C_{10}$ alkyl group, a $C_1$-$C_{10}$ alkoxy group, a phenyl group, a biphenyl group, and a terphenyl group, each substituted with at least one cyano group, but embodiments are not limited thereto.

In various embodiments, 1, 2, 3, or 4 substituents of the group represented by *-$L_1$-$L_2$-*' in Formula 1 may each independently be a cyano group.

In an embodiment, the condensed cyclic compound represented by Formula 1 may be represented by one of Formulae 1-1 to 1-9:

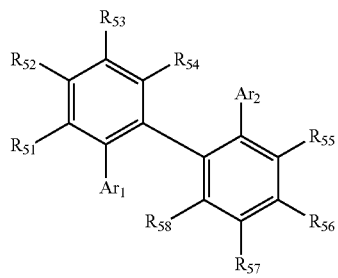

Formula 1-1

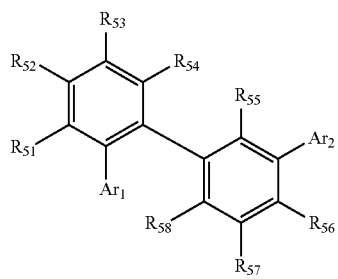

Formula 1-2

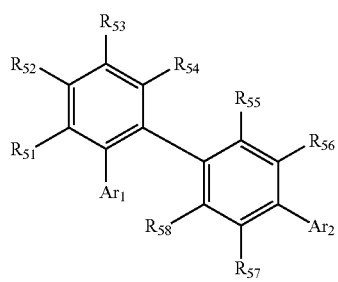

Formula 1-3

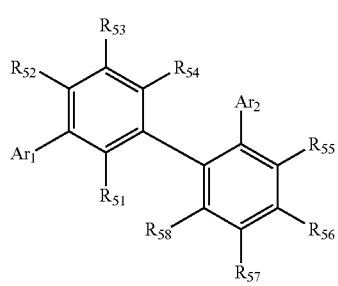

Formula 1-4

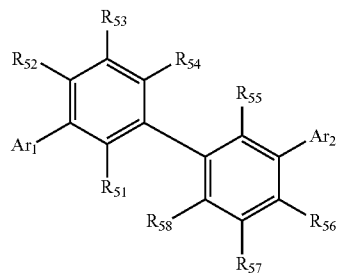

Formula 1-5

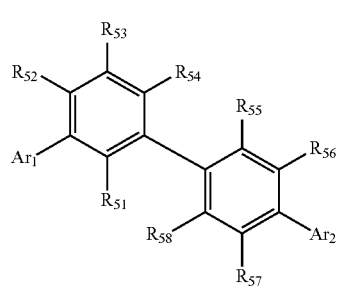

Formula 1-6

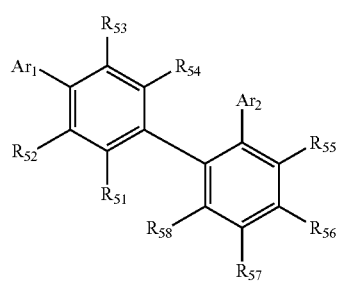

Formula 1-7

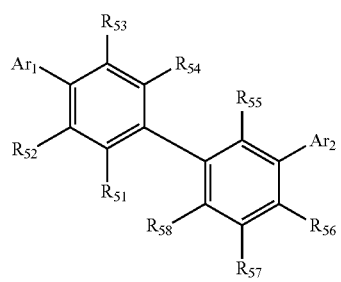

Formula 1-8

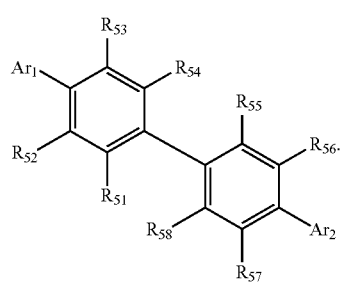

Formula 1-9

In Formulae 1-1 to 1-9, descriptions of $Ar_1$ and $Ar_2$ may each be understood by referring to the descriptions descriptions of $R_{51}$ to $R_{58}$ may each be understood by referring to the descriptions provided herein in connection with $R_{44}$, and the total number of cyano groups included in $R_{51}$ to $R_{58}$ may be 1, 2, 3, or 4.

For example, in Formulae 1-1 to 1-9, $R_{51}$ to $R_{58}$ may each independently be selected from:

hydrogen, deuterium, a cyano group, a $C_1$-$C_{20}$ alkyl group, and a $C_1$-$C_{20}$ alkoxy group;

a phenyl group, a biphenyl group, a terphenyl group, a fluorenyl group, a carbazolyl group, a dibenzofuranyl group, and a dibenzothiophenyl group; and a phenyl group, a biphenyl group, a terphenyl group, a fluorenyl group, a carbazolyl group, a dibenzofuranyl group, and a dibenzothiophenyl group, each substituted with at least one selected from deuterium, a cyano group, a $C_1$-$C_{20}$ alkyl group, a $C_1$-$C_{20}$ alkoxy group, a phenyl group, a biphenyl group, and a terphenyl group, but embodiments are not limited thereto.

In Formulae 1-1 to 1-9, one, two, three or four of $R_{51}$ to $R_{58}$ may each independently be selected from:

a cyano group; and a $C_1$-$C_{10}$ alkyl group, a $C_1$-$C_{10}$ alkoxy group, a phenyl group, a biphenyl group, and a terphenyl group, each substituted with at least one cyano group.

In an embodiment, in Formulae 1-1 to 1-9, one, two, three or four of $R_{51}$ to $R_{58}$ may each independently be a cyano group; or one or two of $R_{51}$ to $R_{58}$ may each independently be a cyano group.

In various embodiments, the condensed cyclic compound represented by Formula 1 may be represented by Formula 1-1, 1-2, 1-4, or 1-5.

In various embodiments, the condensed cyclic compound represented by Formula 1 may be represented by Formula 1 1-1, 1-2, 1-3, 1-4, or 1-7.

The condensed cyclic compound represented by Formula 1 may be selected from Compounds 1 to 852, but is not limited thereto:

1

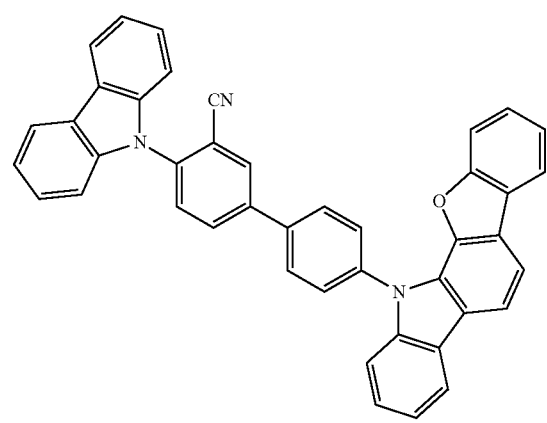

2

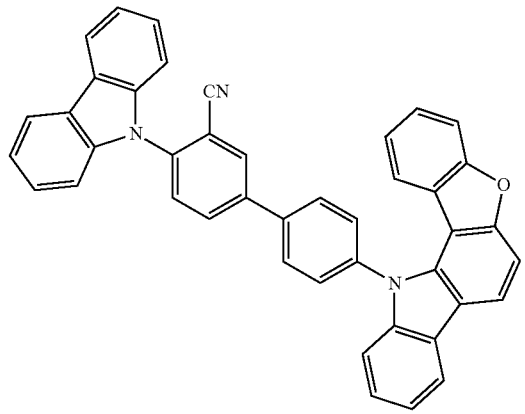

3

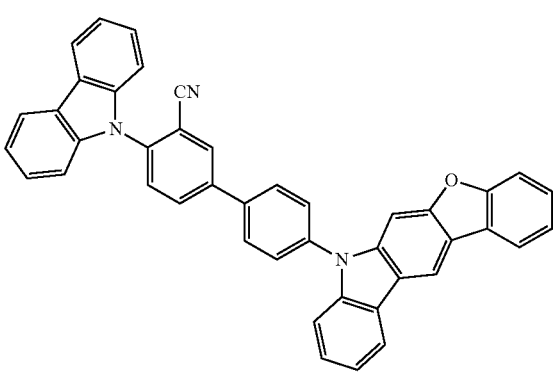

4

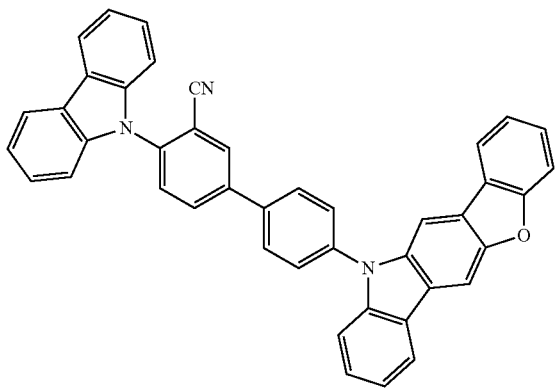

5

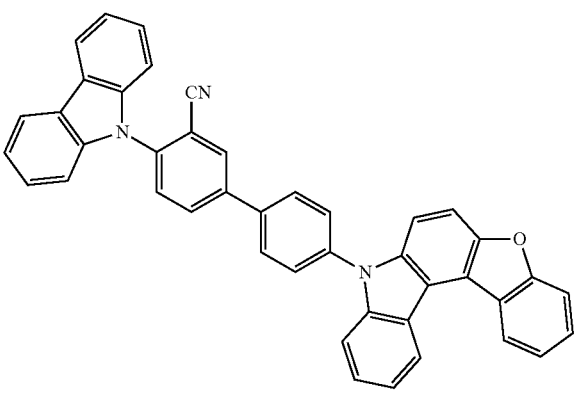

6
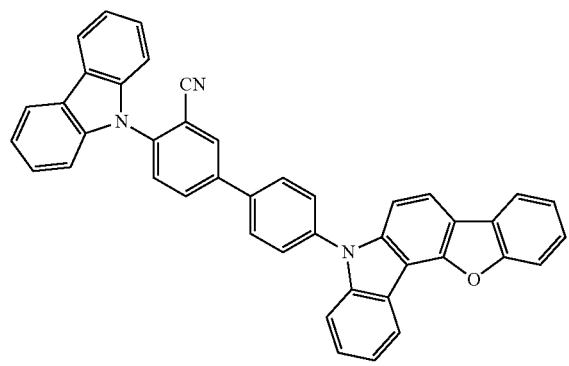
7
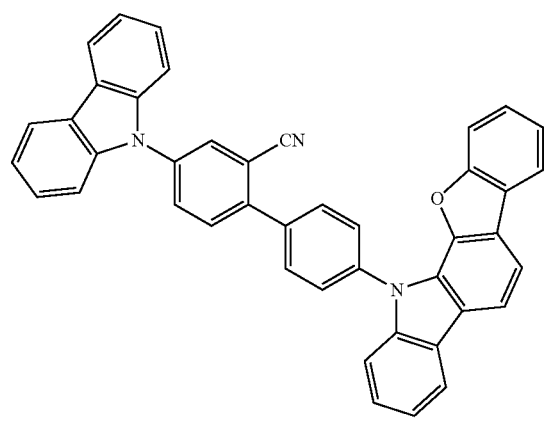
8
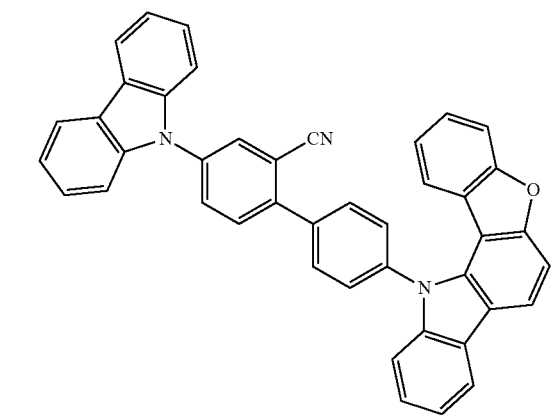
9
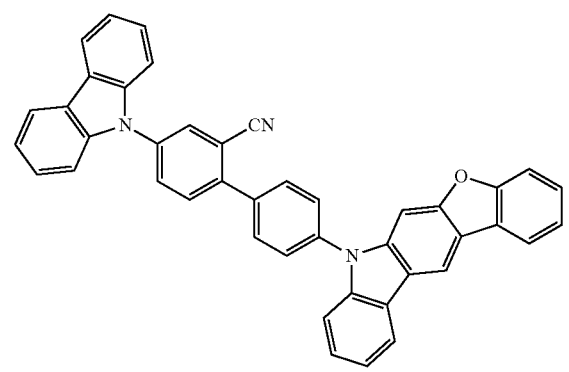
10
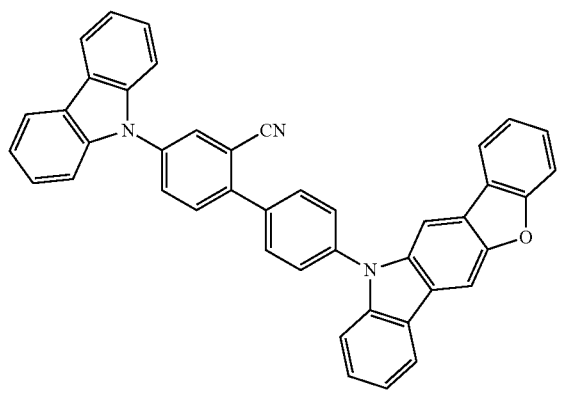
11
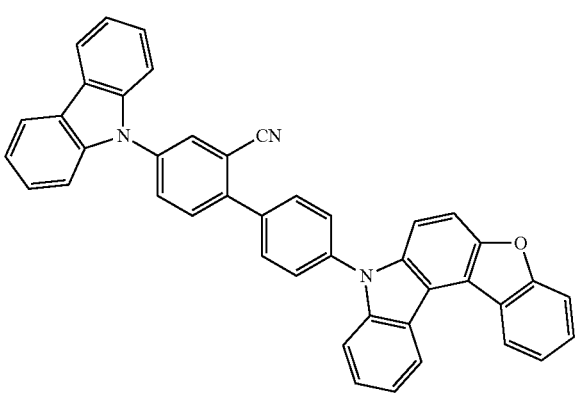
12
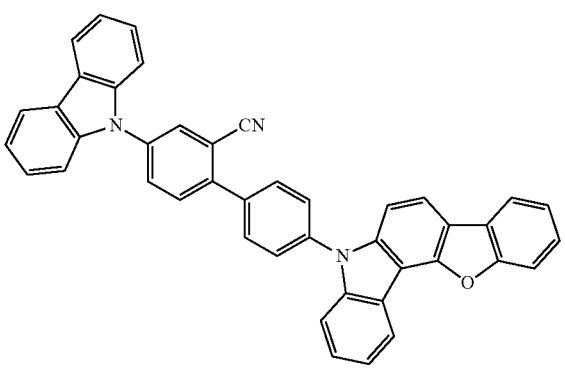
13
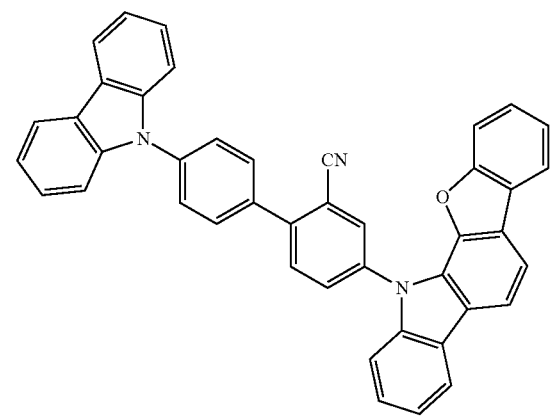

14
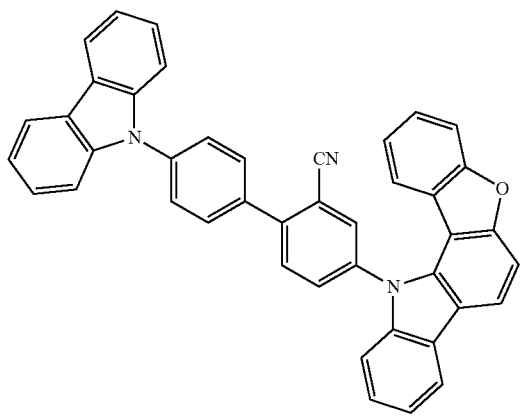
15
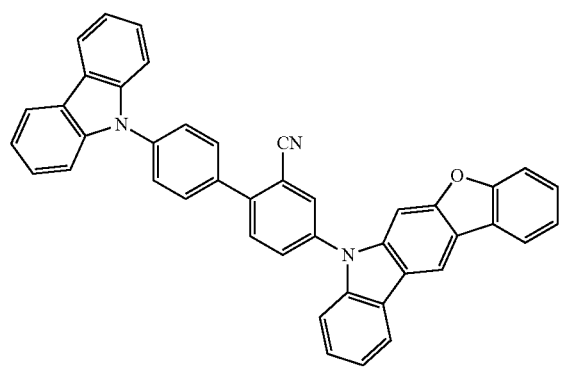
16
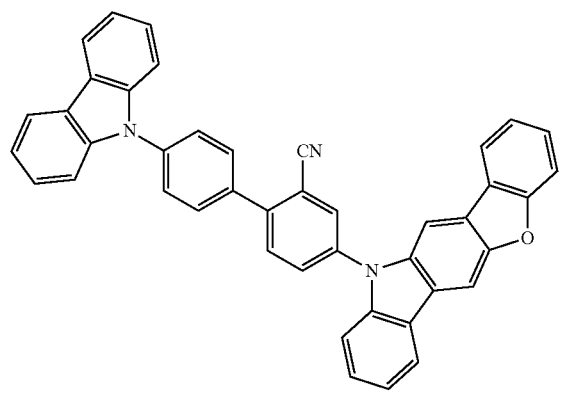
17
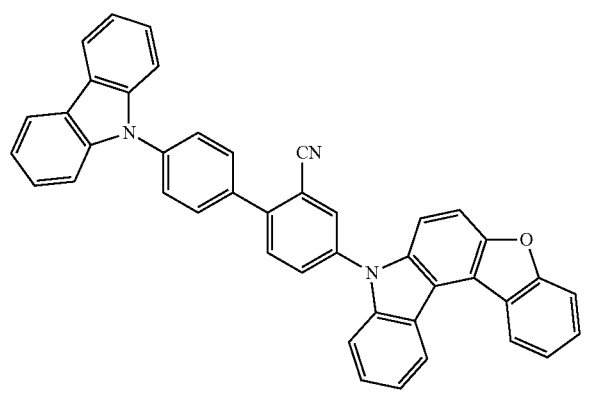
18
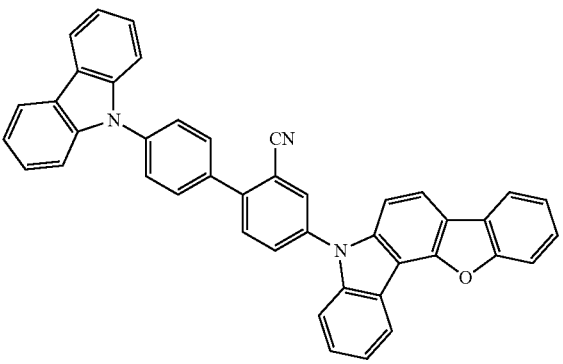
19
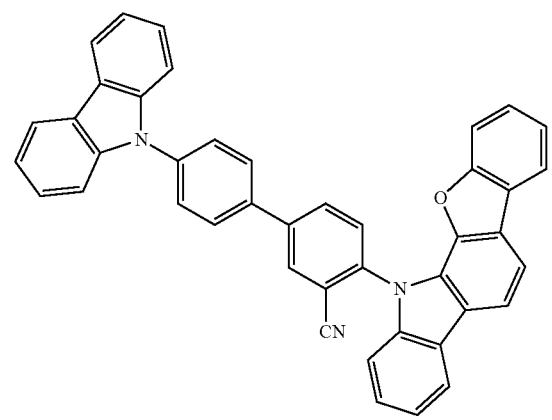
20
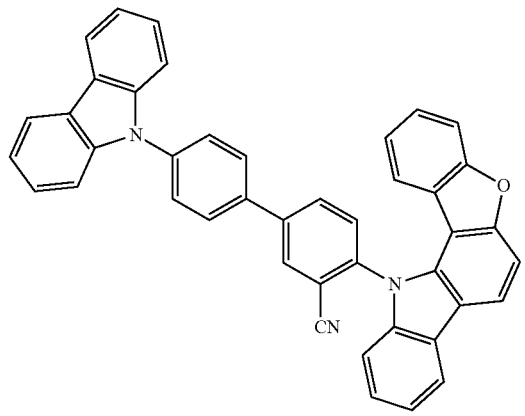
21
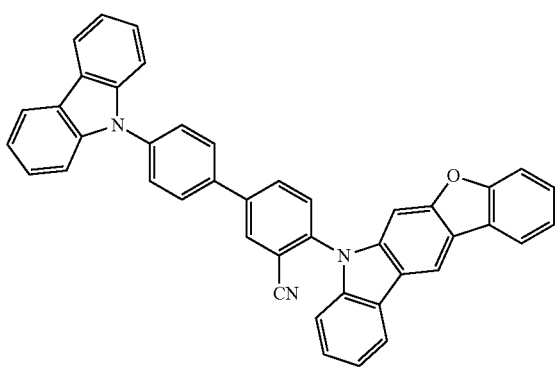

22
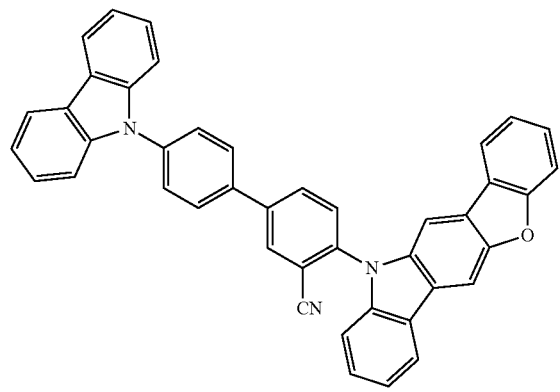
23
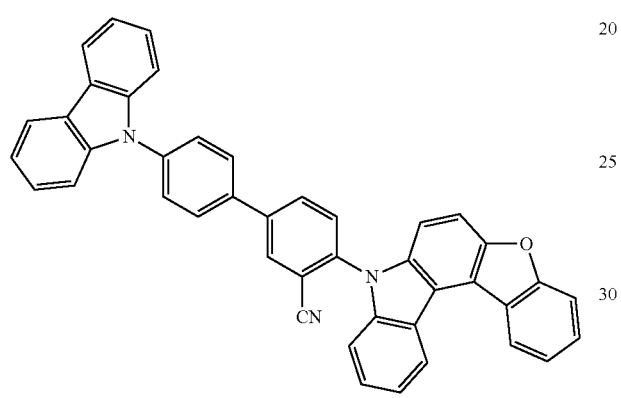
24
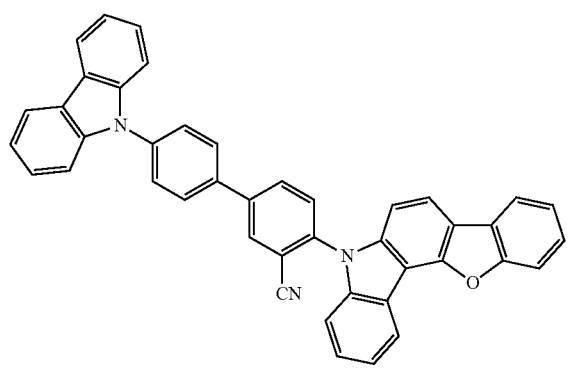
25
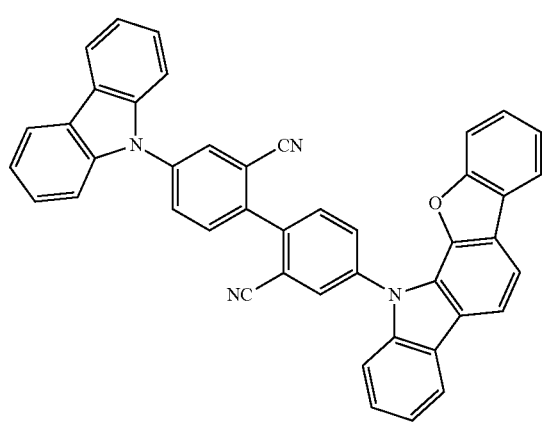
26
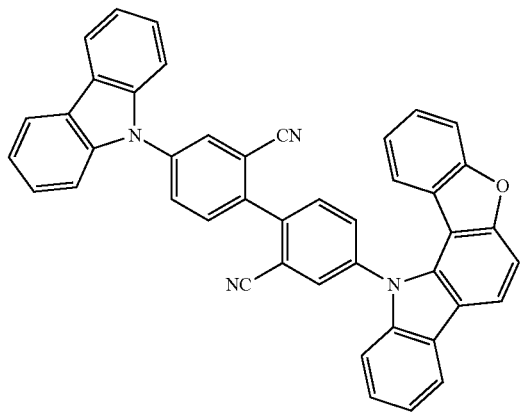
27
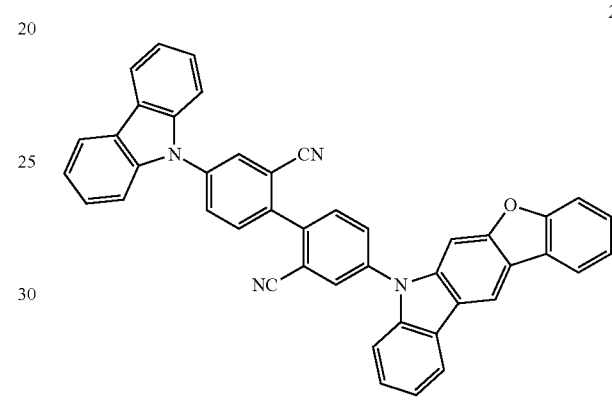
28
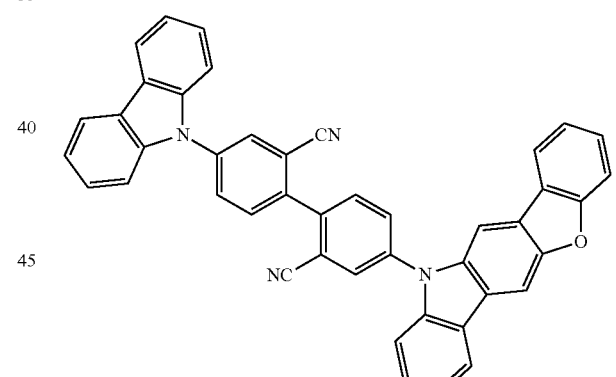
29
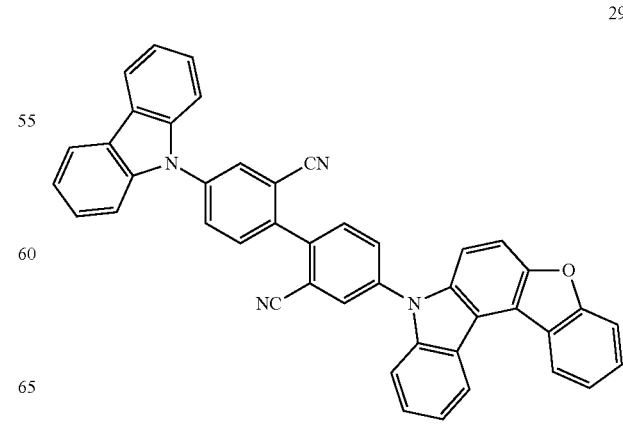

30
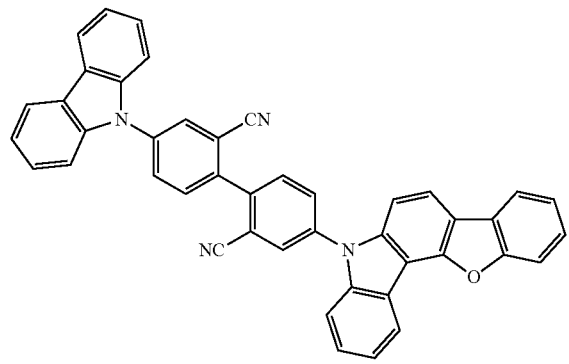
31
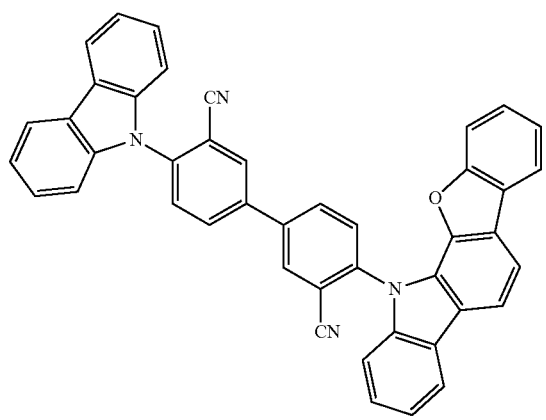
32
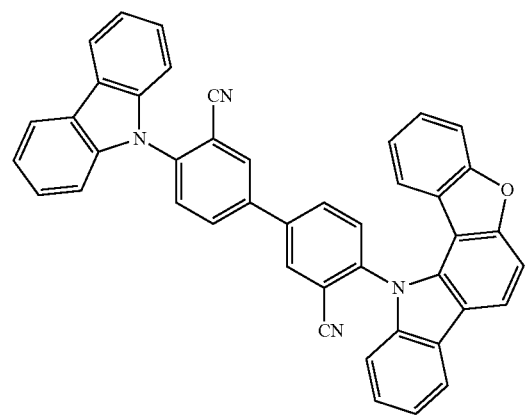
33
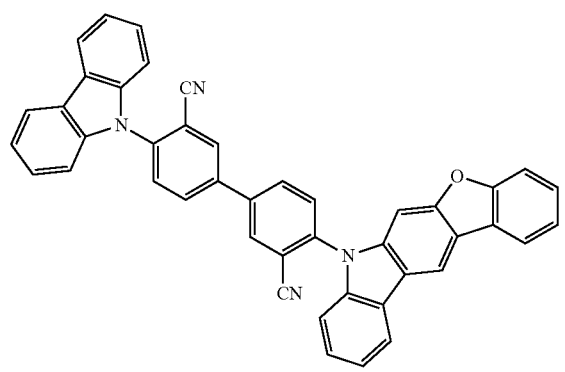
34
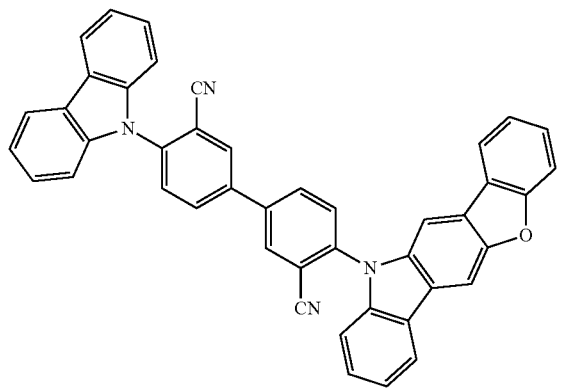
35
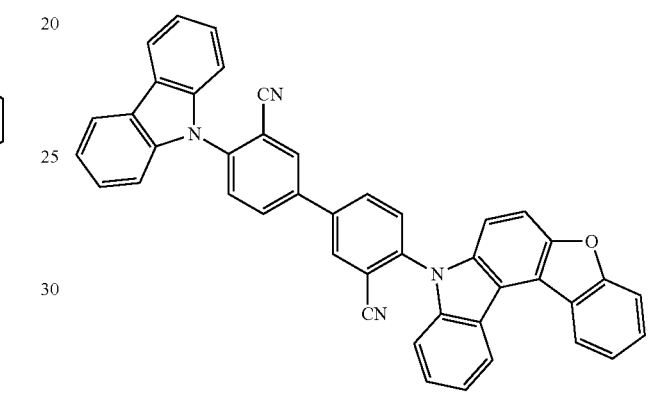
36
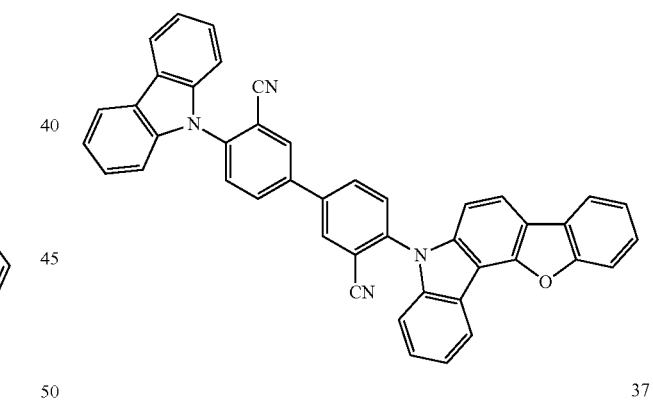
37
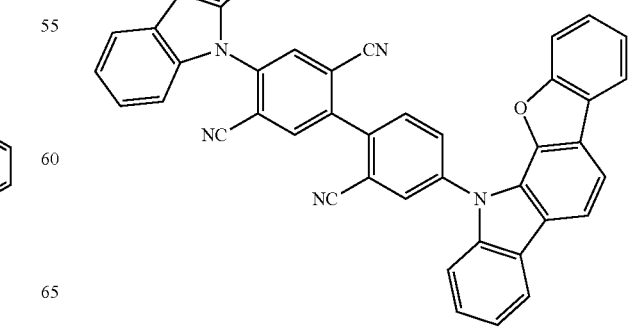

-continued
38
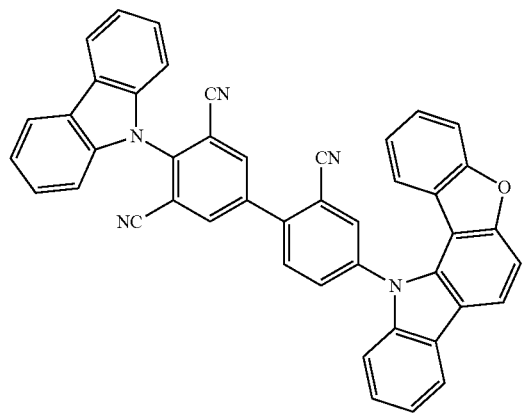
39
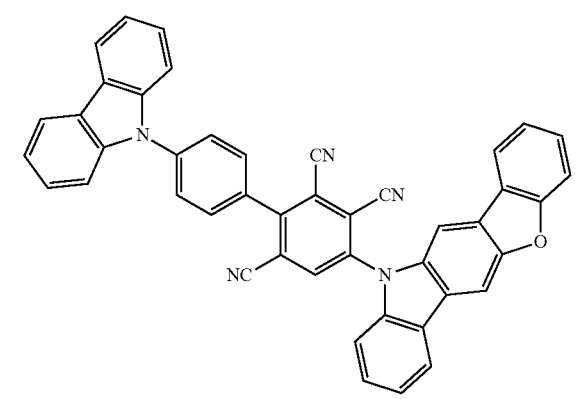
40
41
42
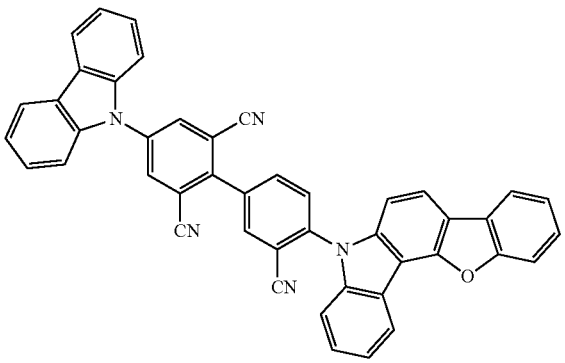
43
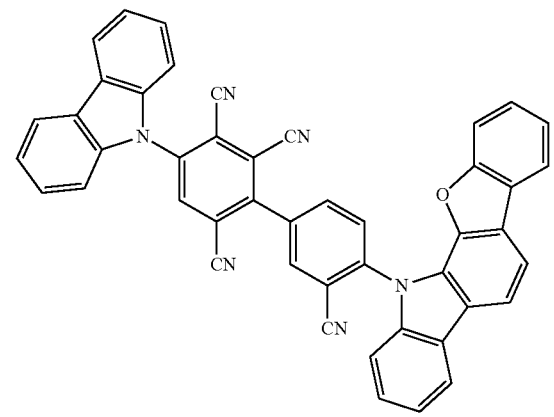
44
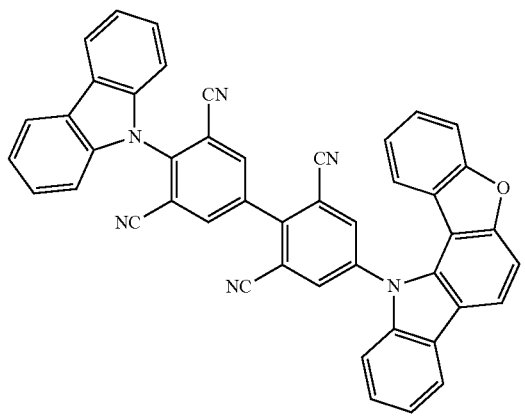
45
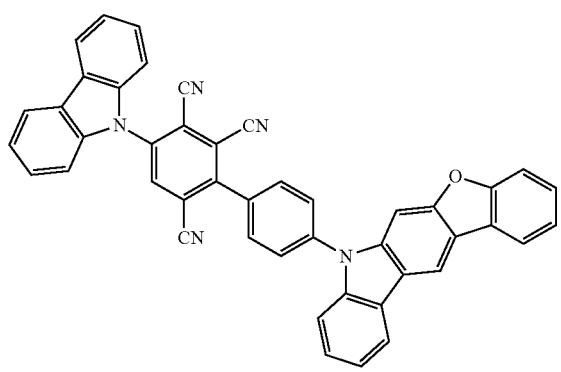

46
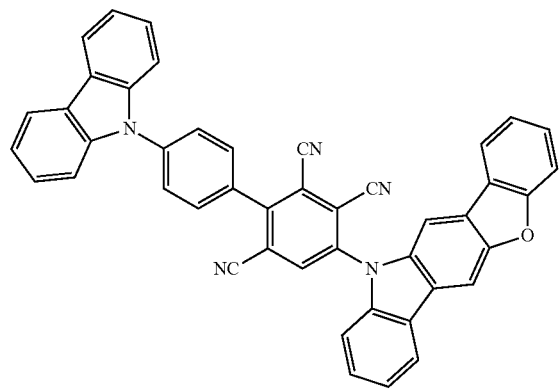
47
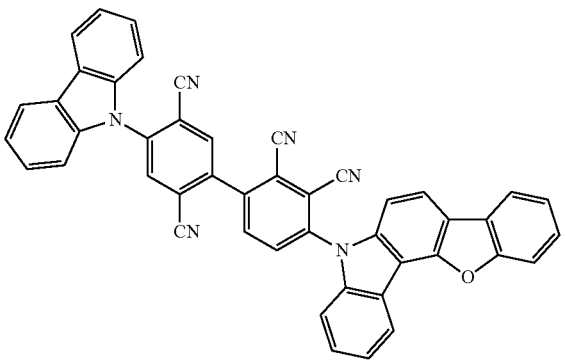
48
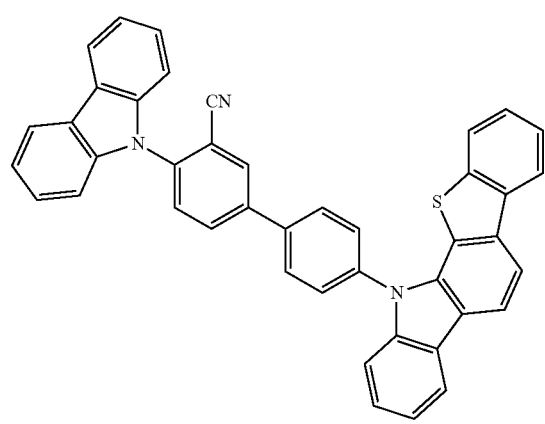
49
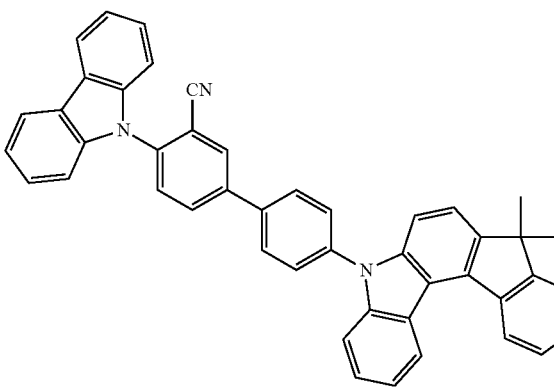
50
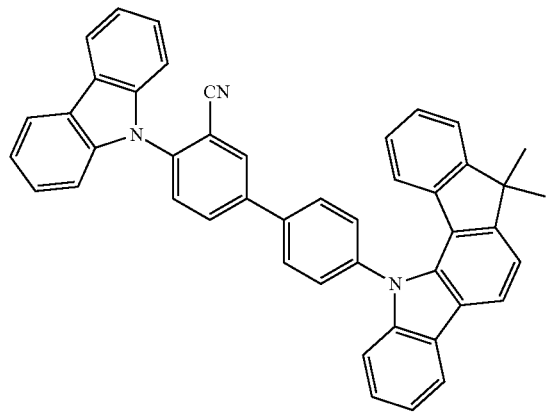
51
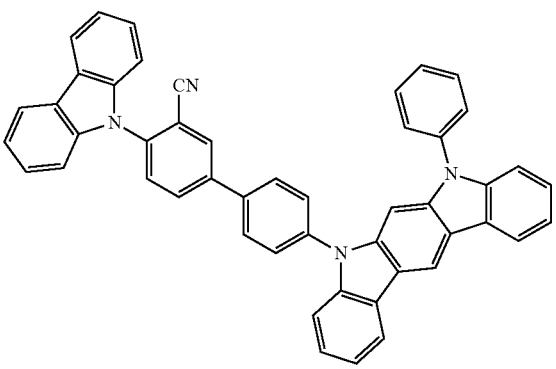
52
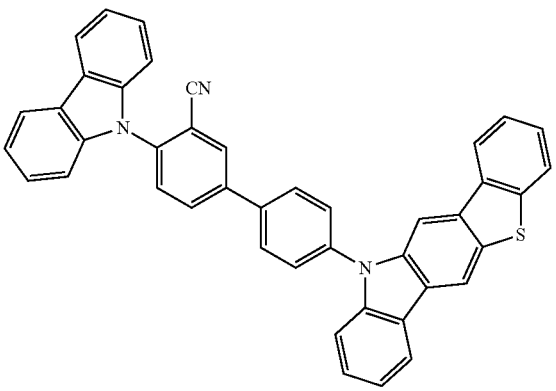
53

54
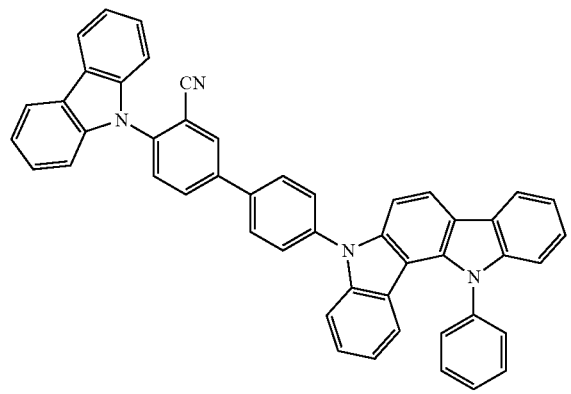
55
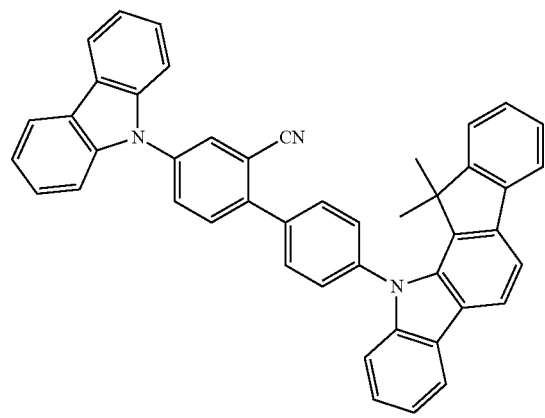
56
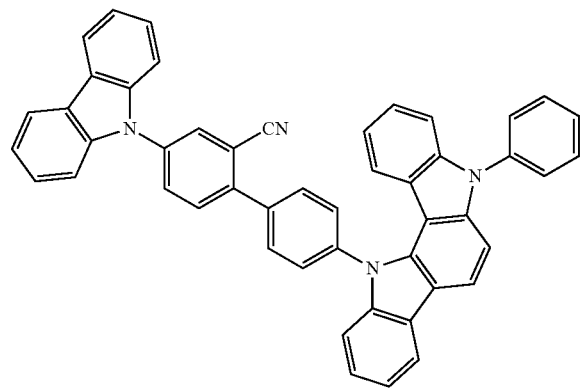
57
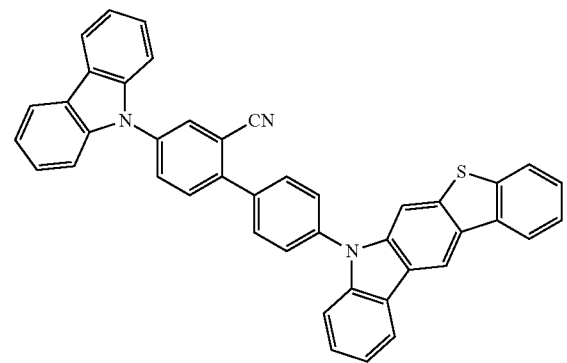
58
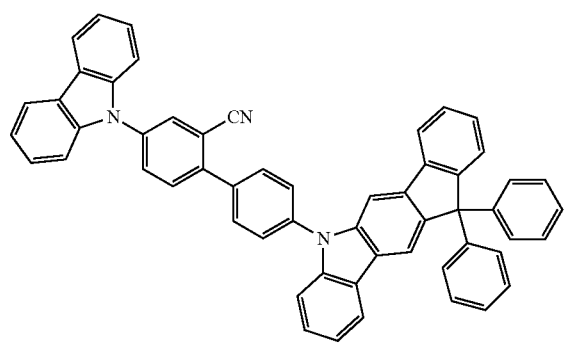
59
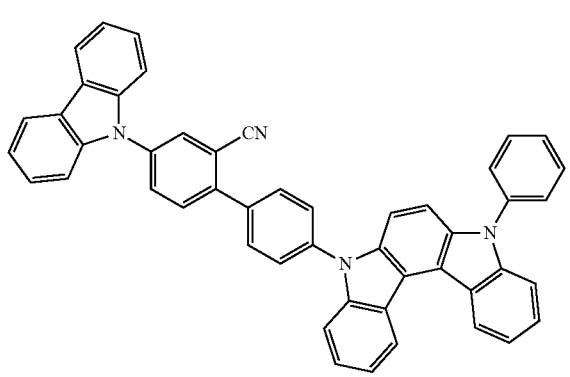
60
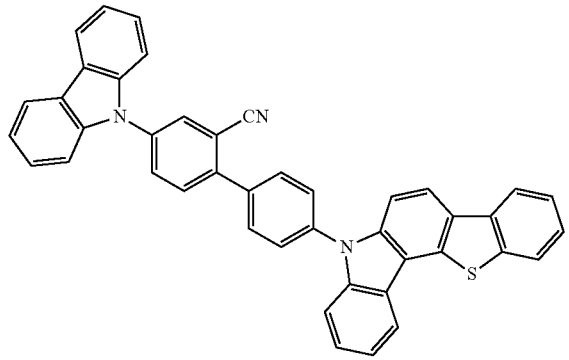
61
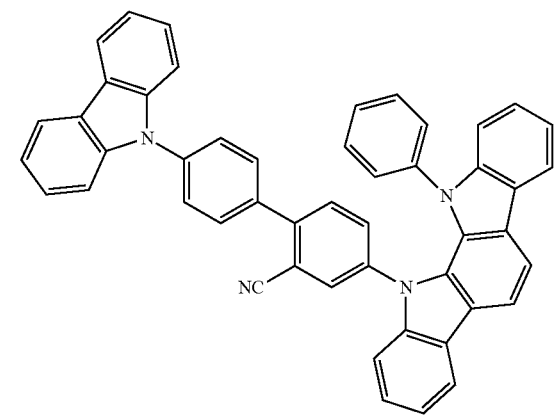

62
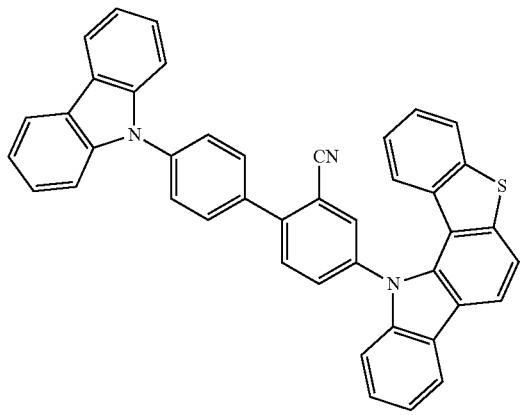
63
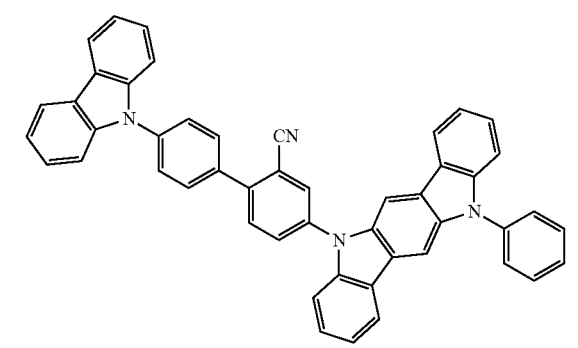
64
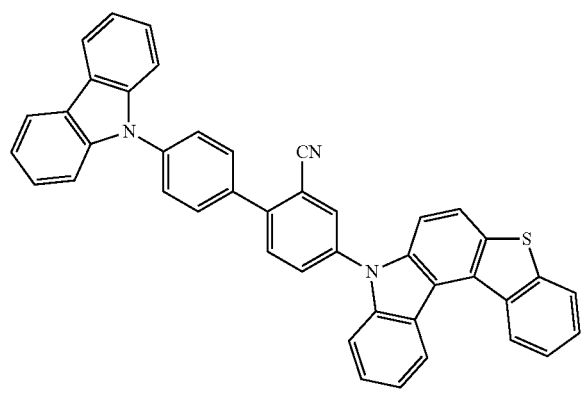
65
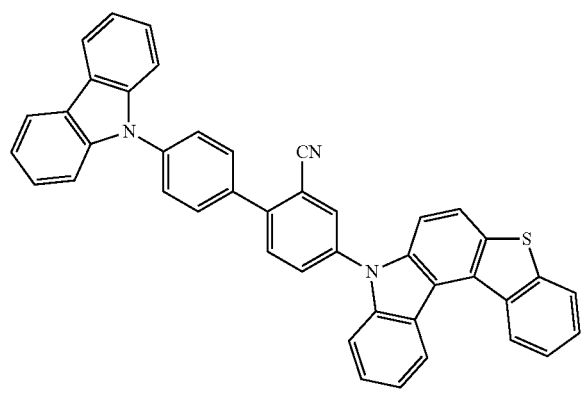
66
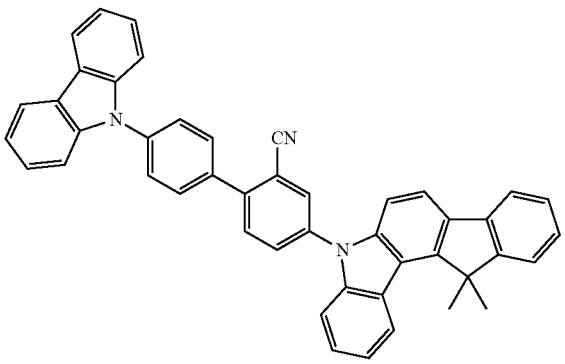
67
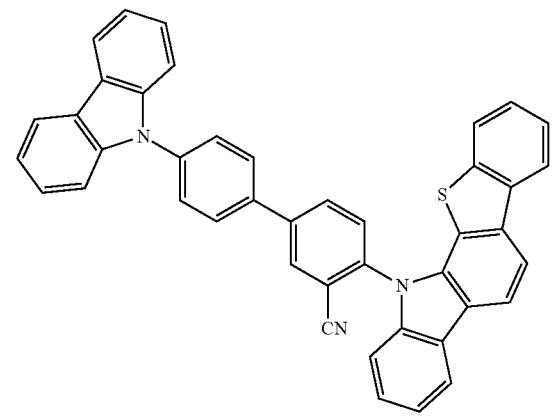
68
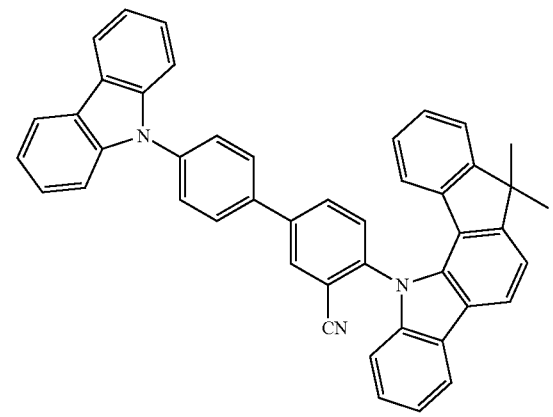
69
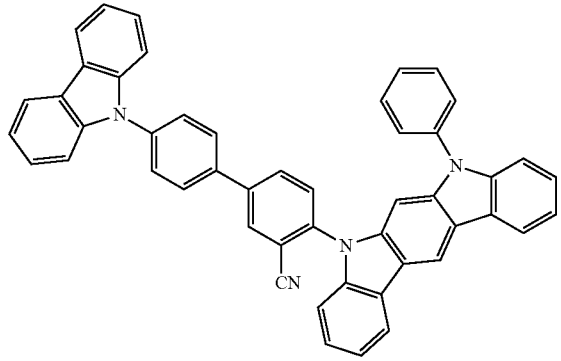

70
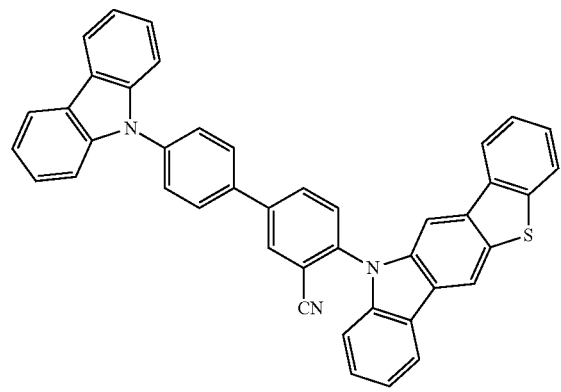
71
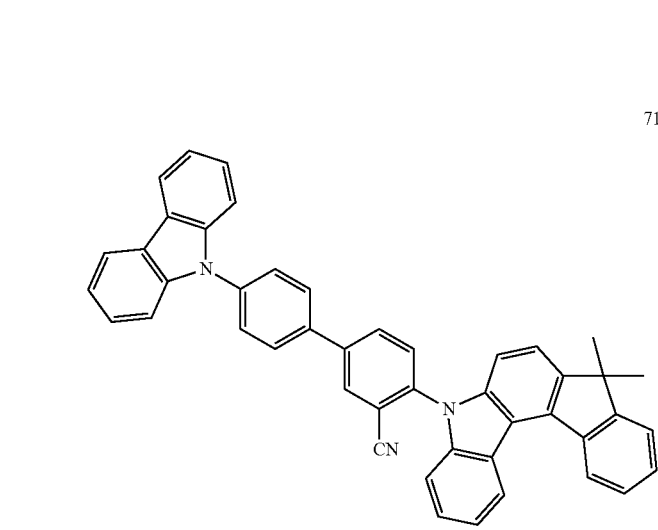
72
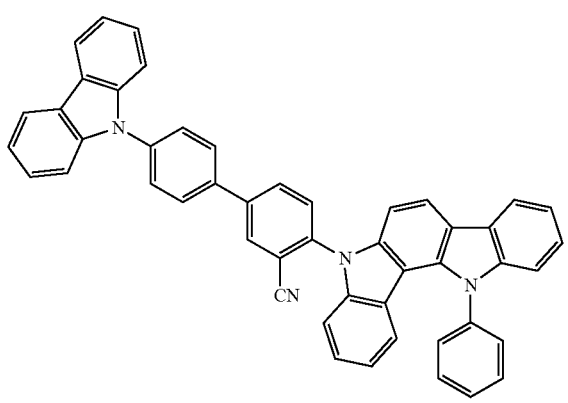
73
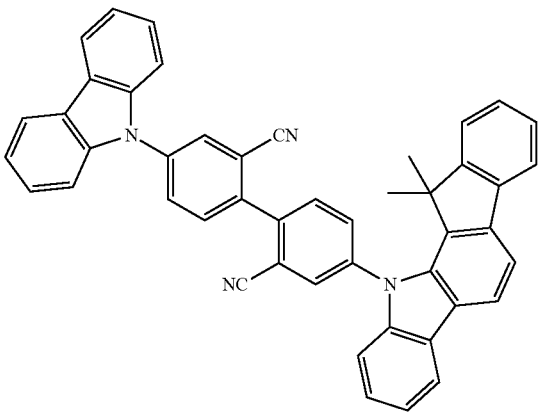
74
75
76
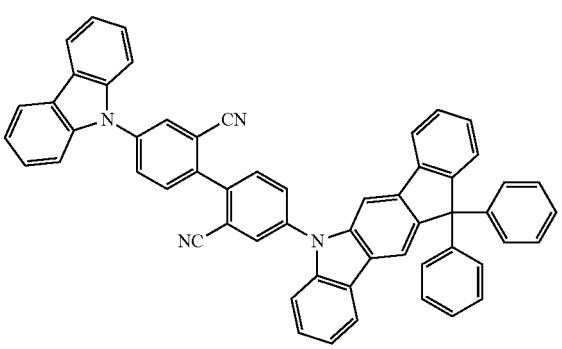

77
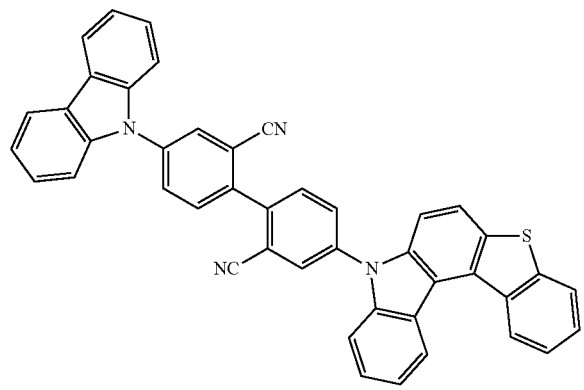
78
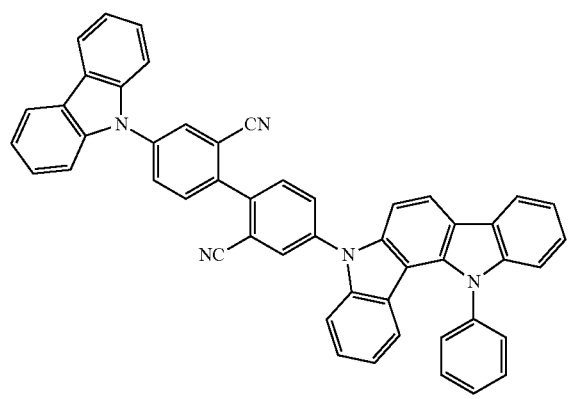
79
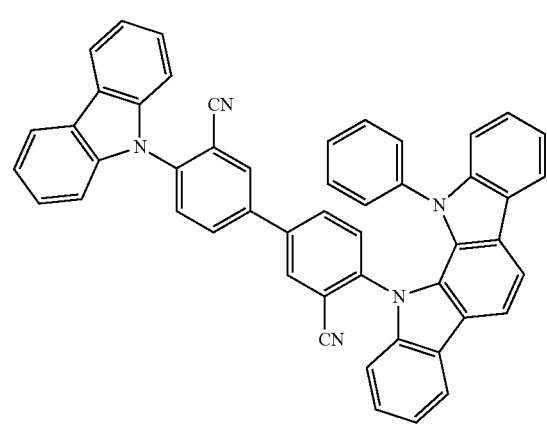
80
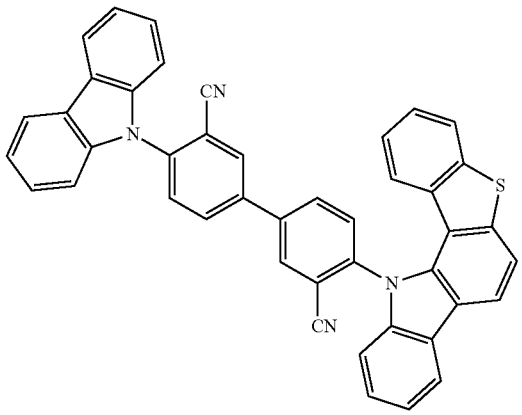
81
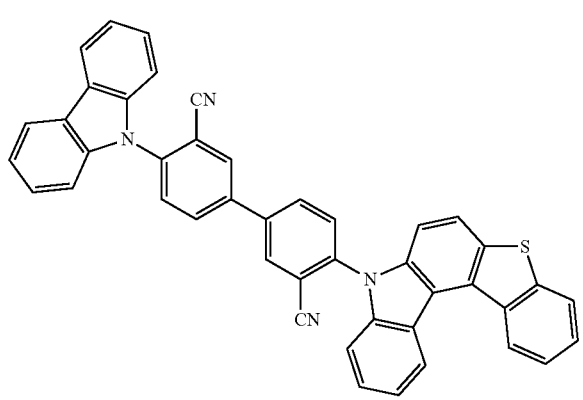
82
83

84
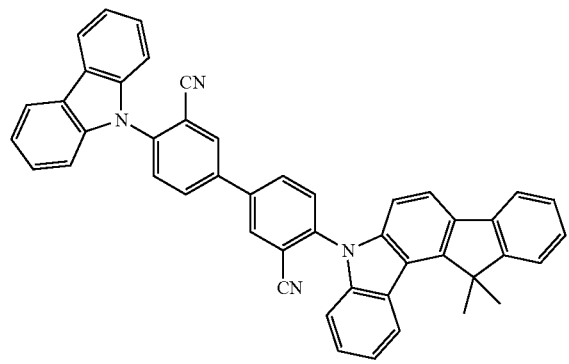
85
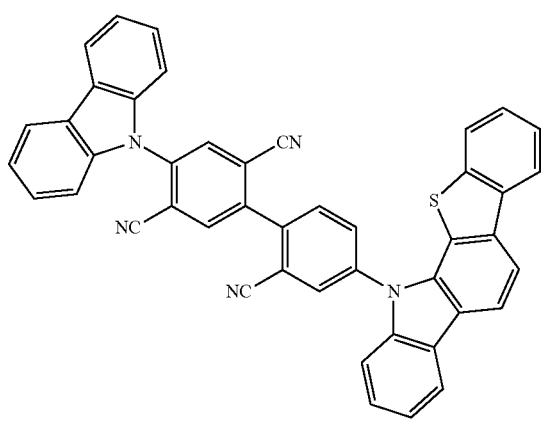
86
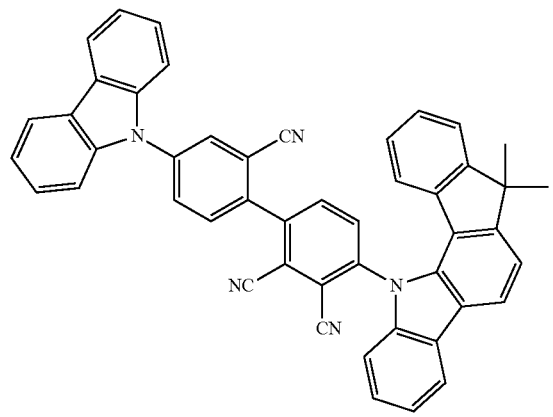
87
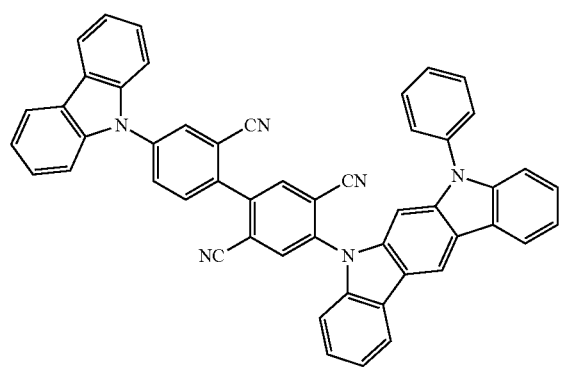
88
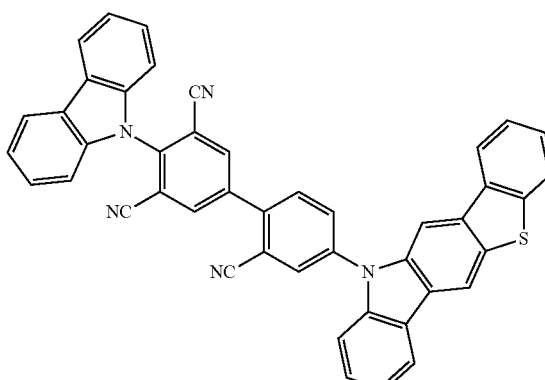
89
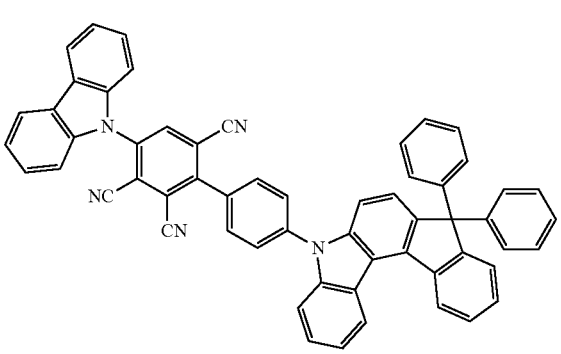
90
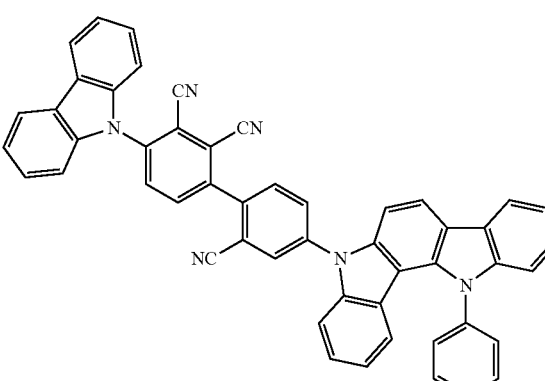
91
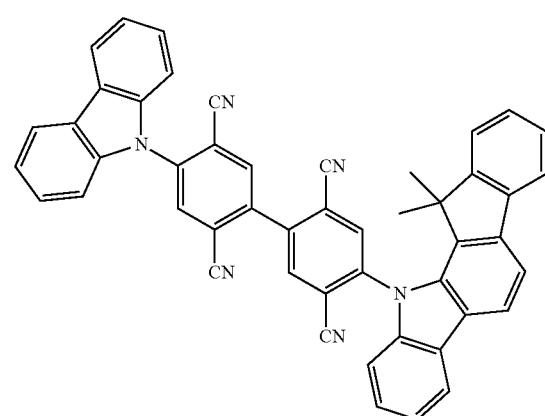

-continued
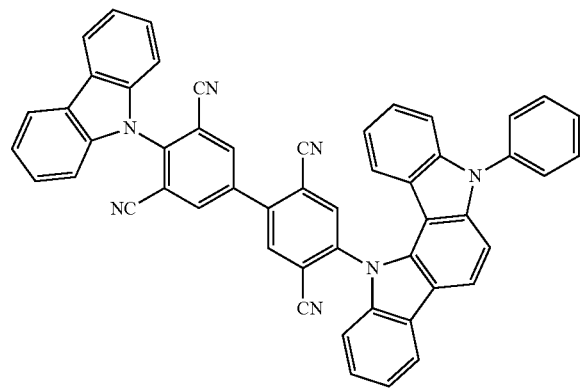
92
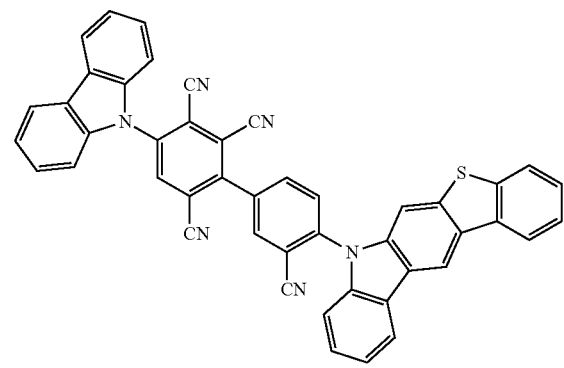
93
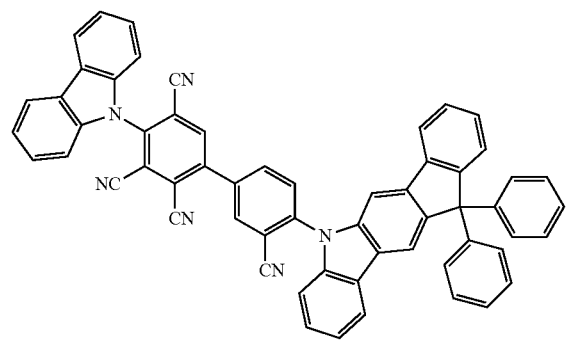
94
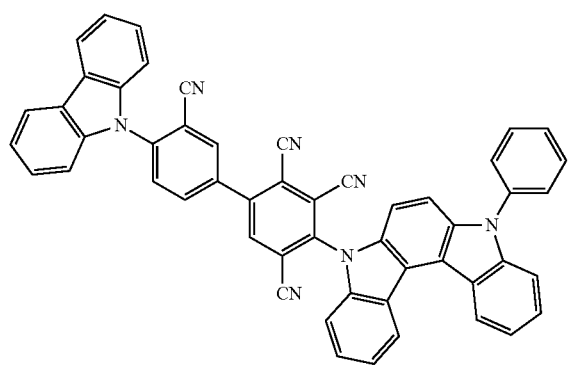
95
-continued
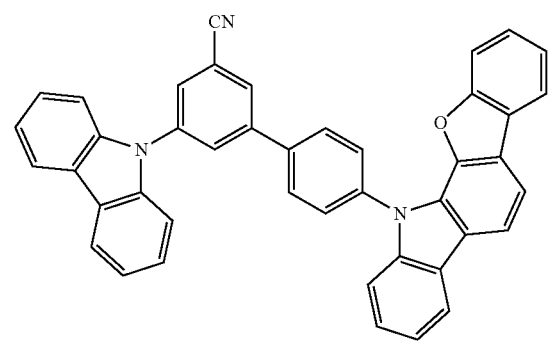
96
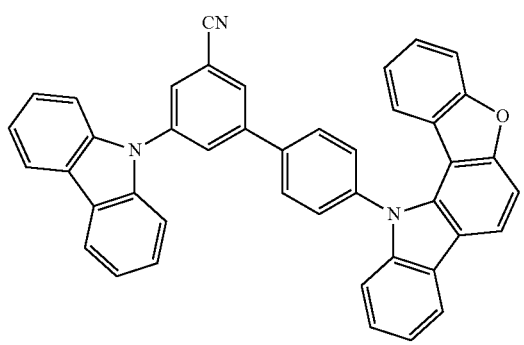
97
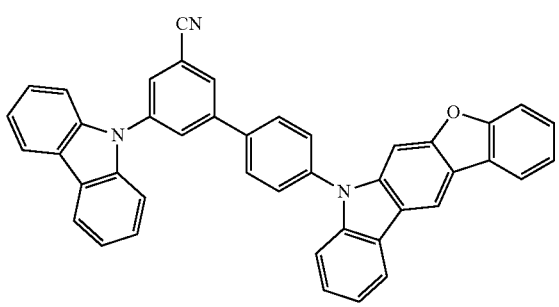
98
99

-continued
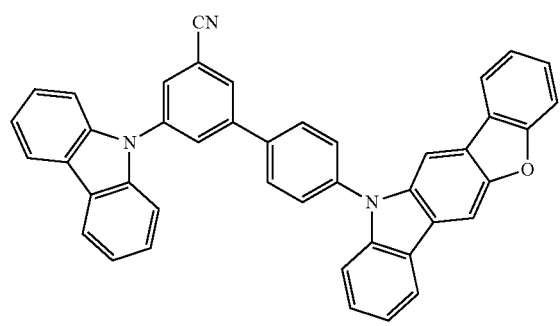
100
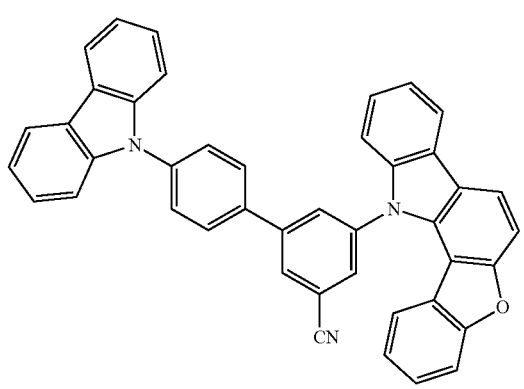
104
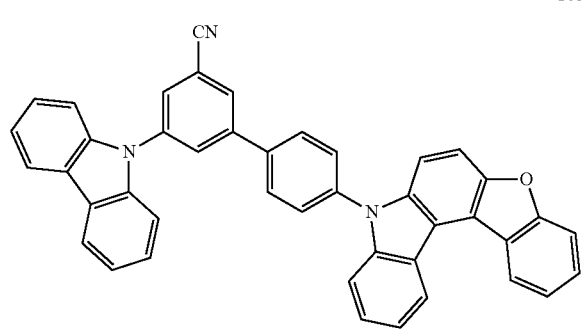
101
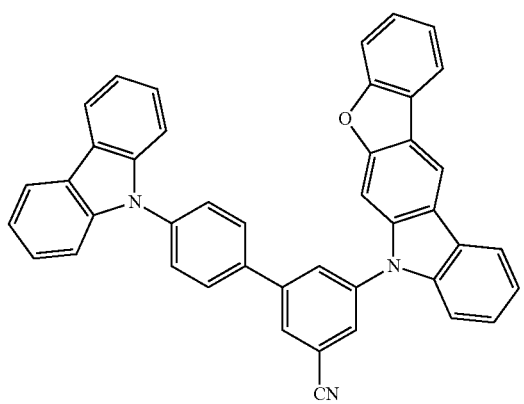
105
102
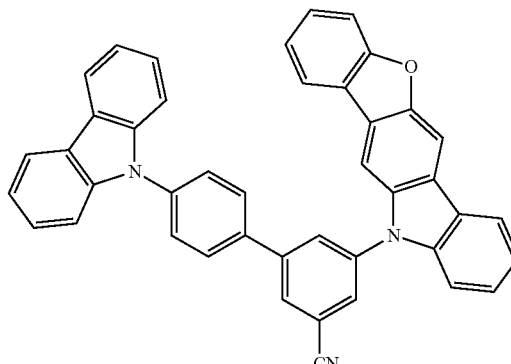
106
103
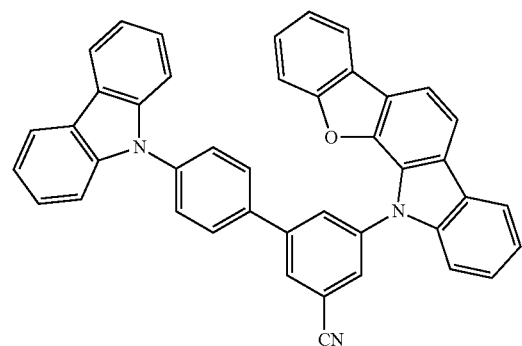
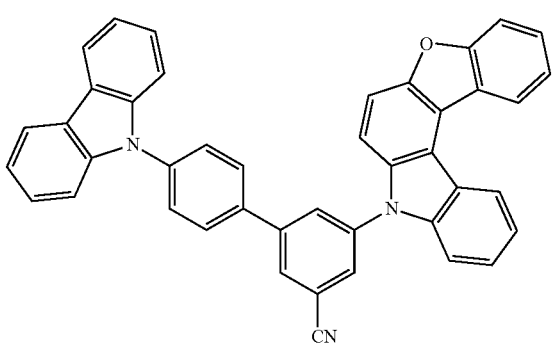
107

-continued
108
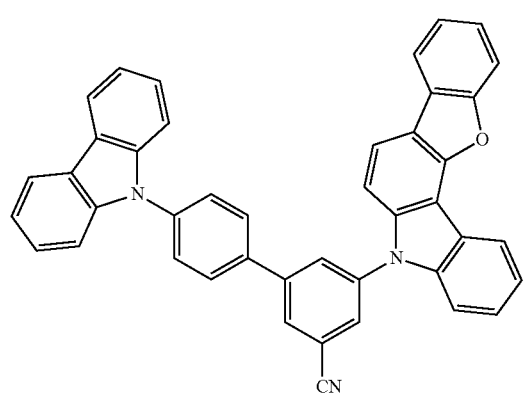
109
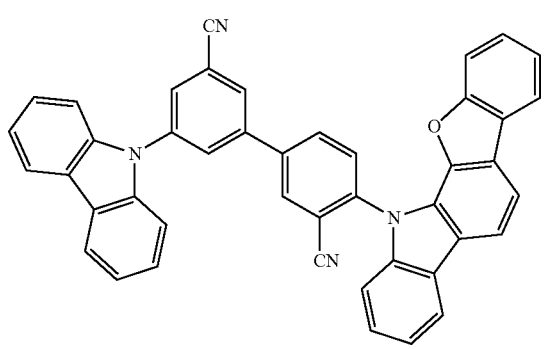
110
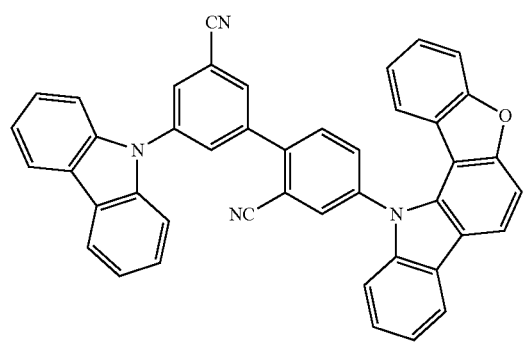
111
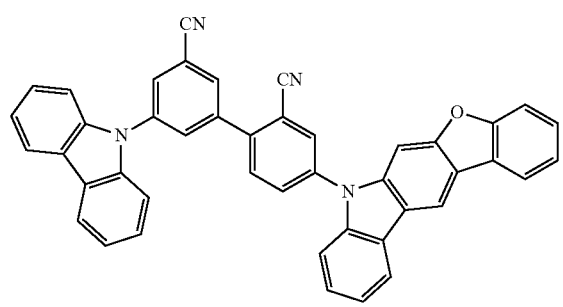
-continued
112
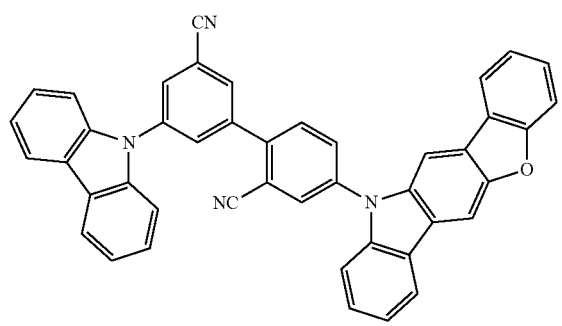
113
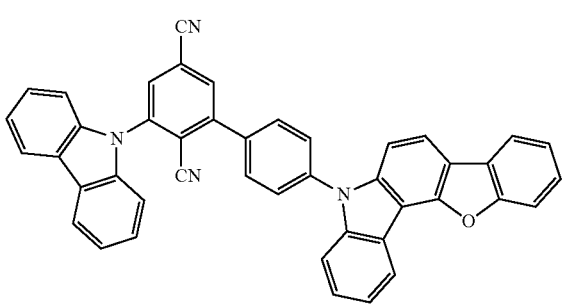
114
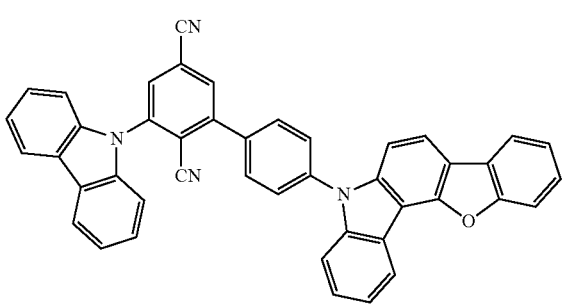
115
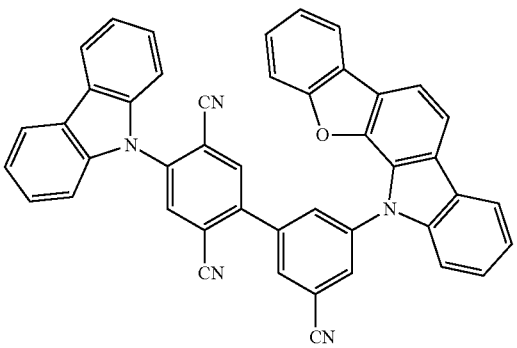

116
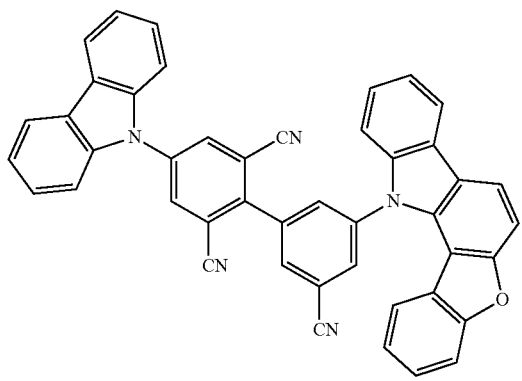
120
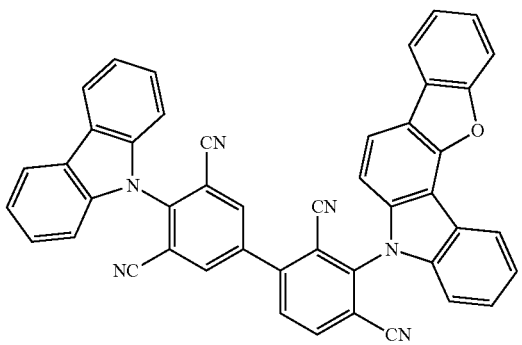
117
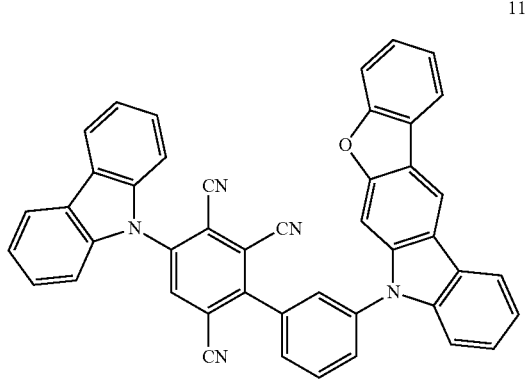
121
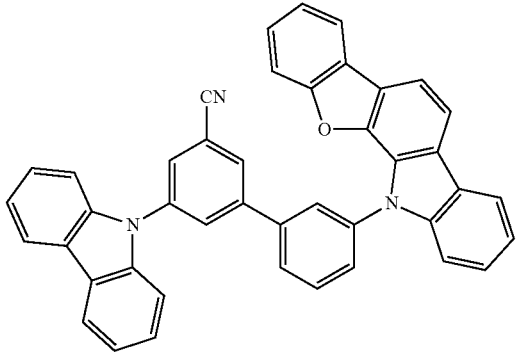
118
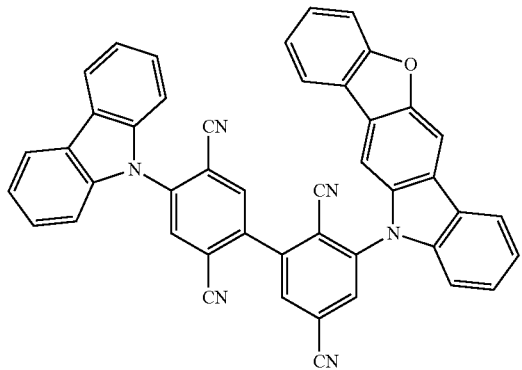
122
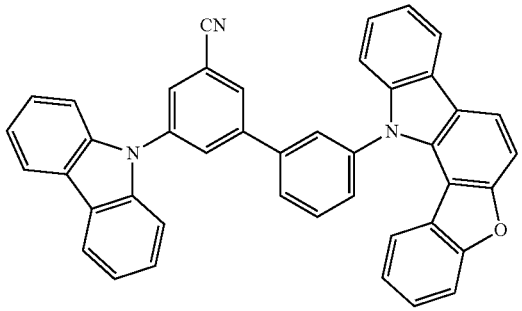
119
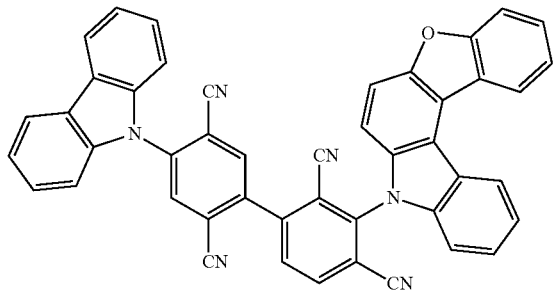
123
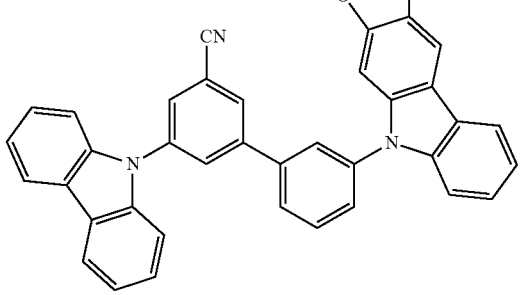

-continued
124
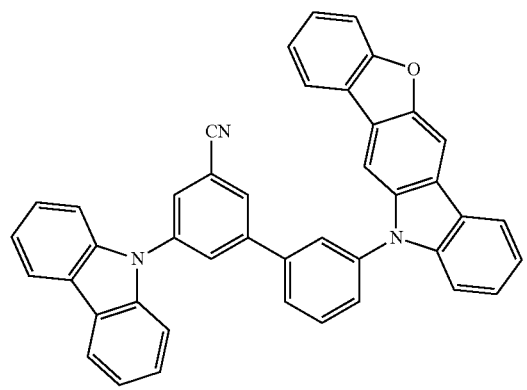
125
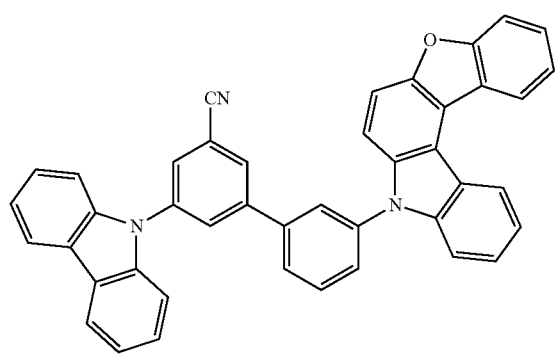
126
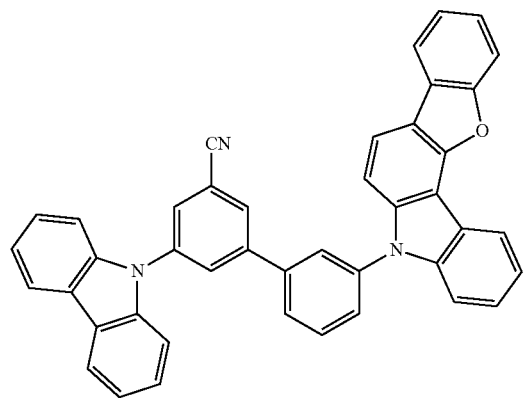
127
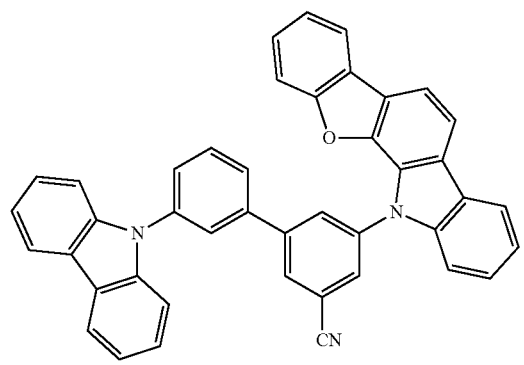
-continued
128
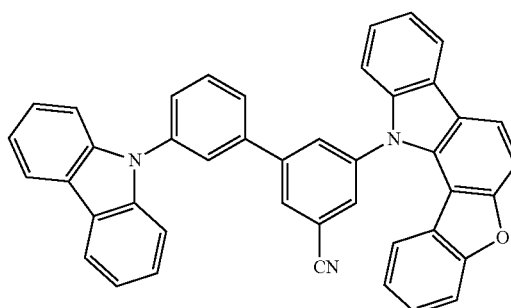
129
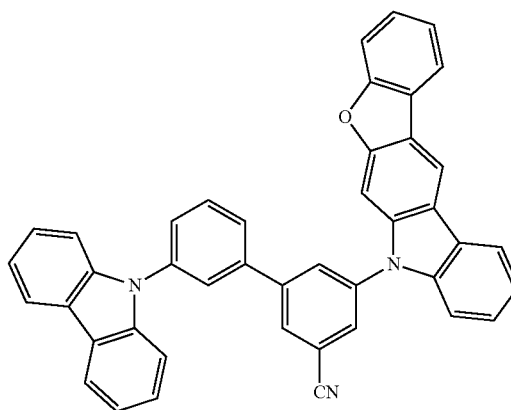
130
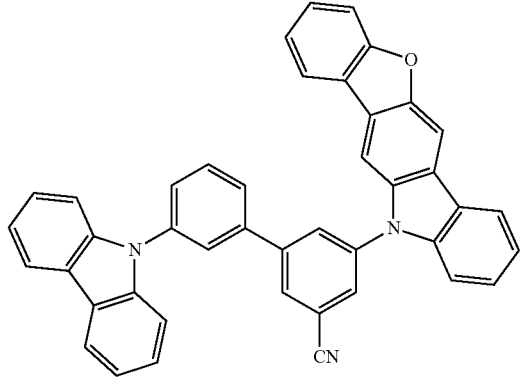
131
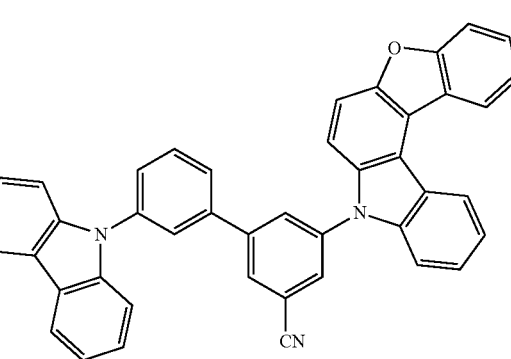

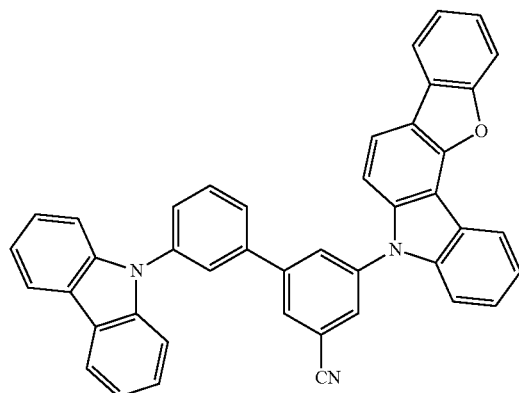
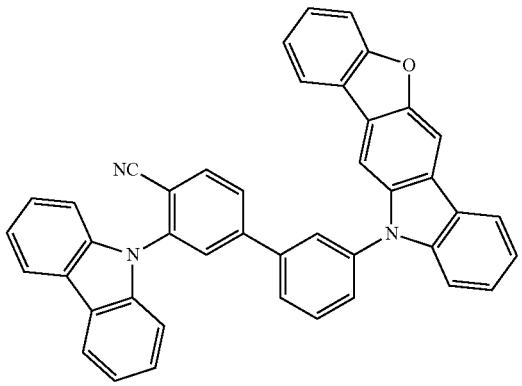
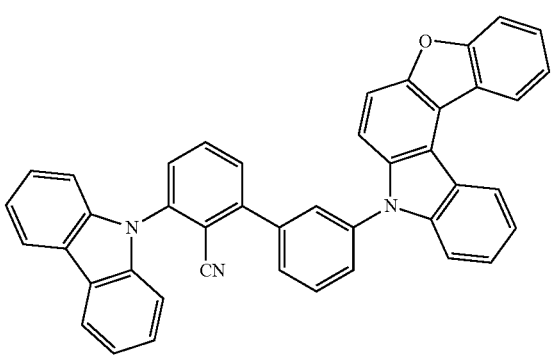
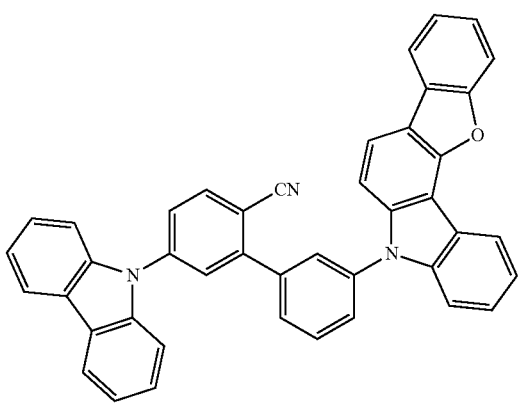
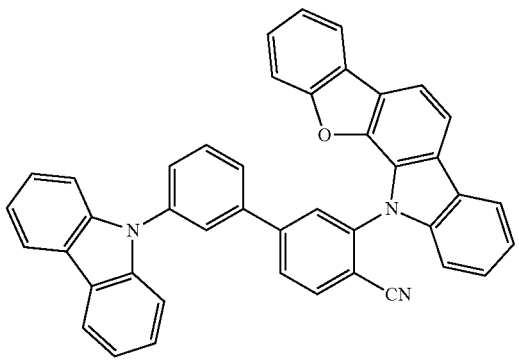

140
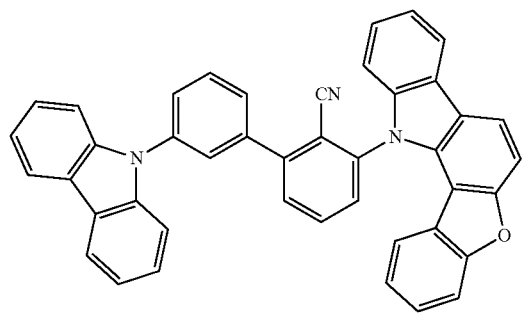
141
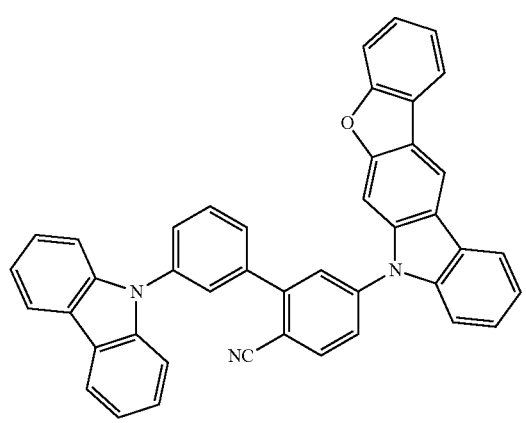
142
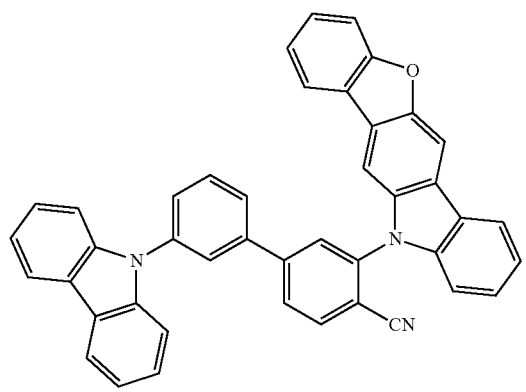
143
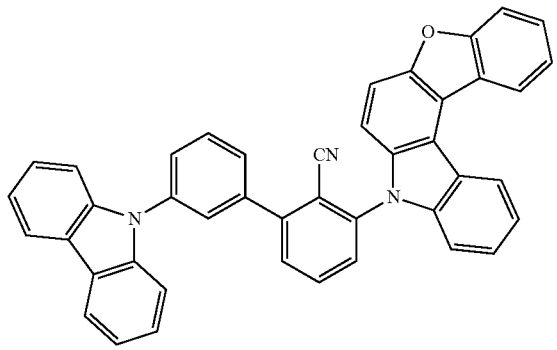
144
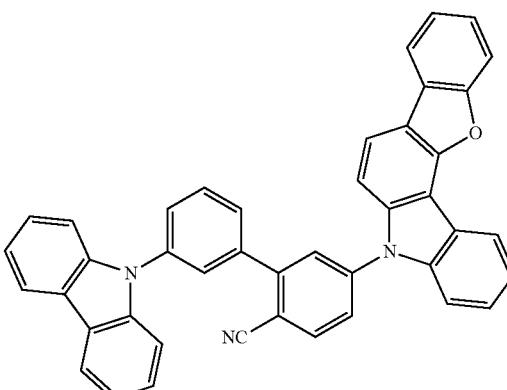
145
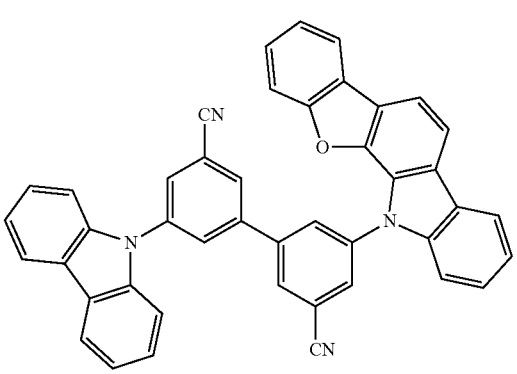
146
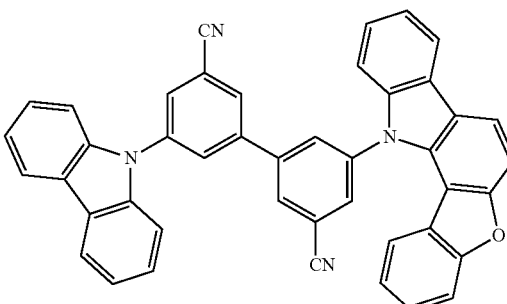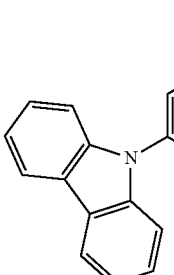
147
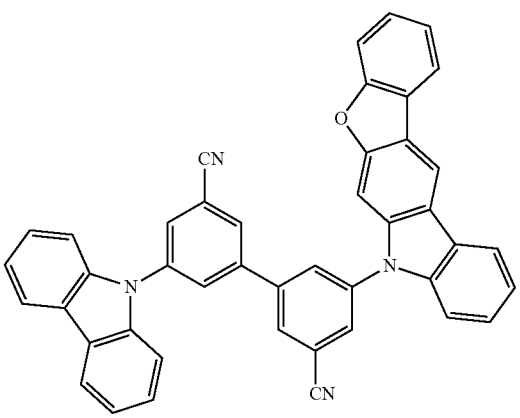

148
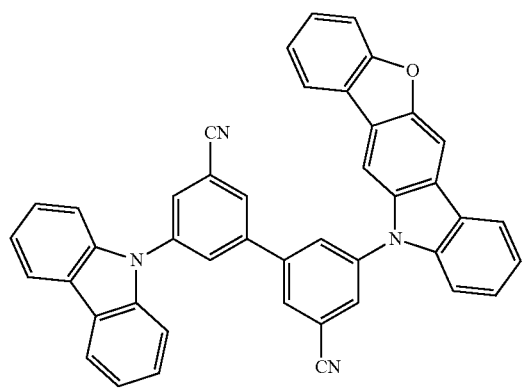
149
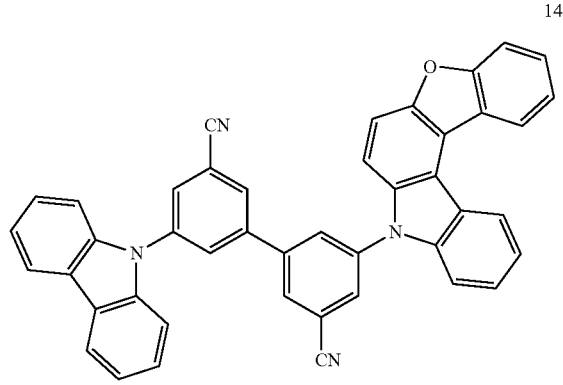
150
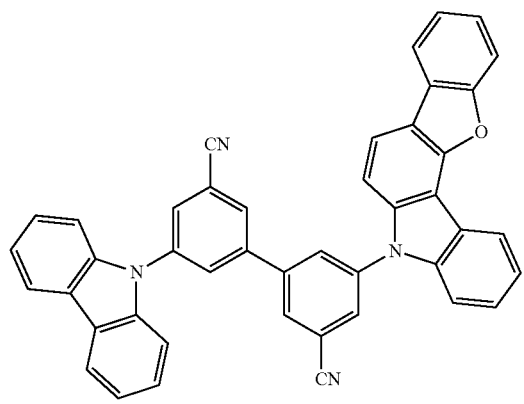
151
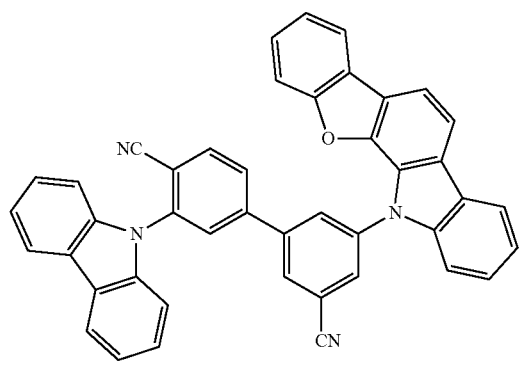
152
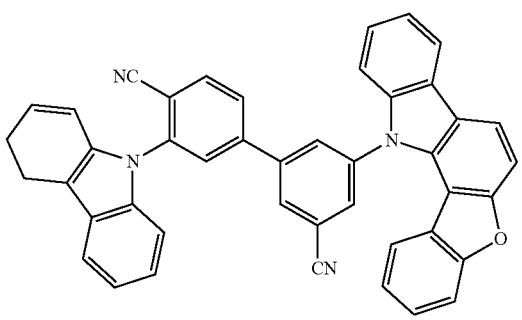
153
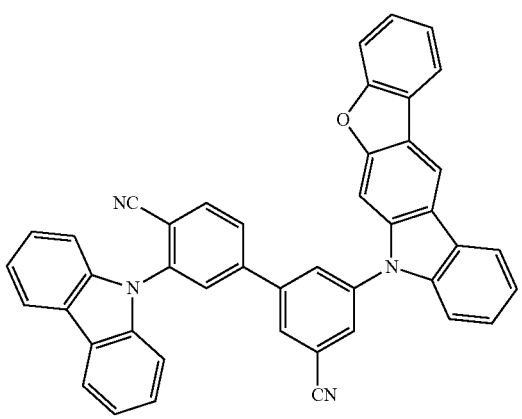
154
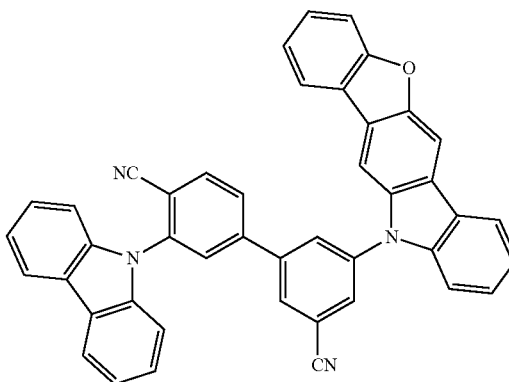
155
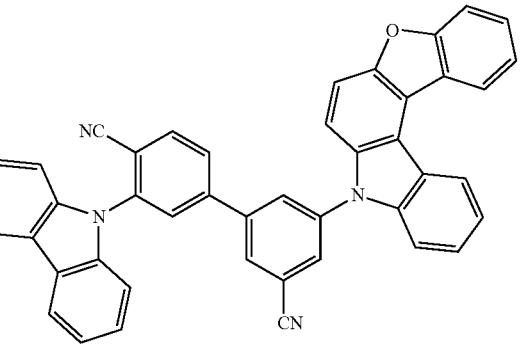

-continued
156
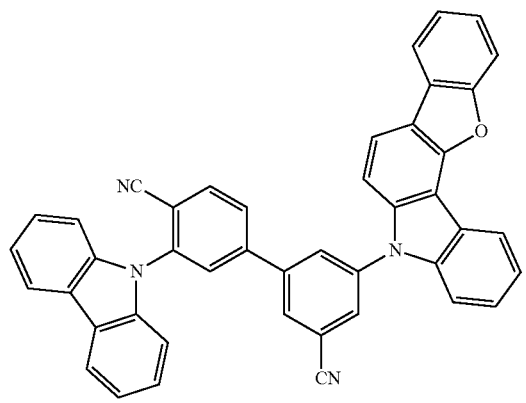
157
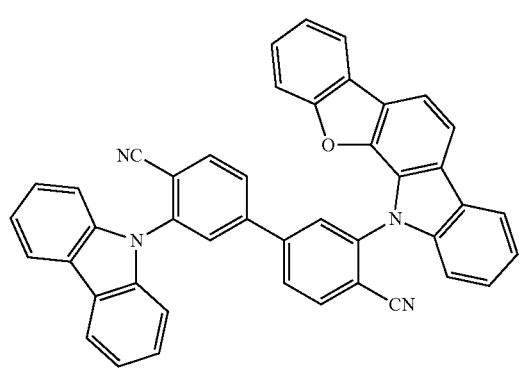
158
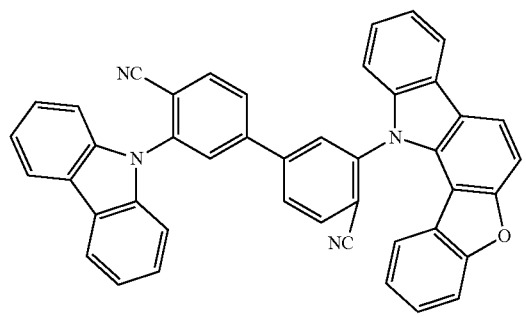
159
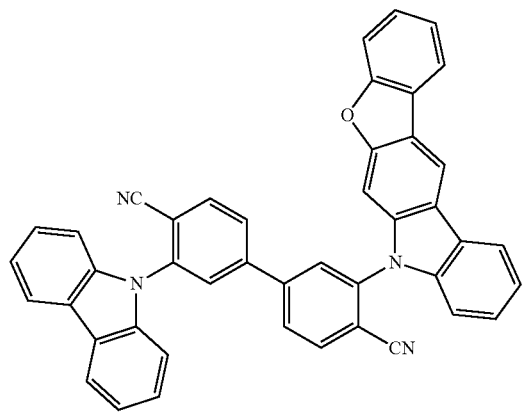
-continued
160
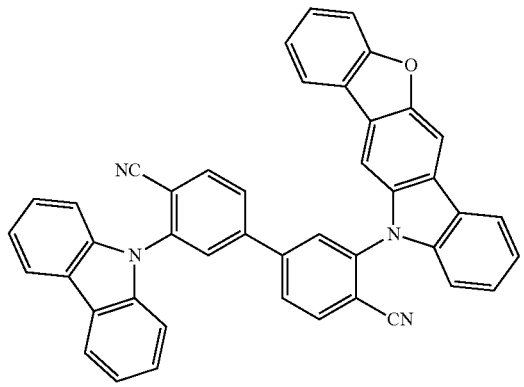
161
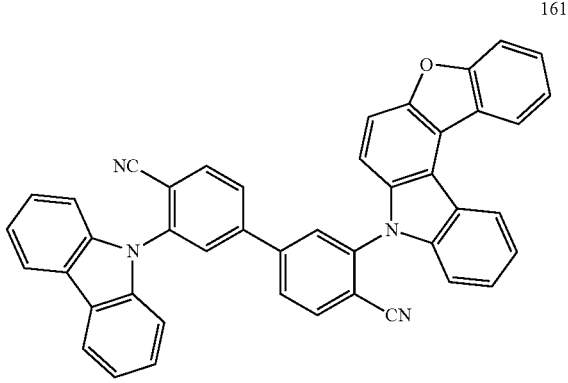
162
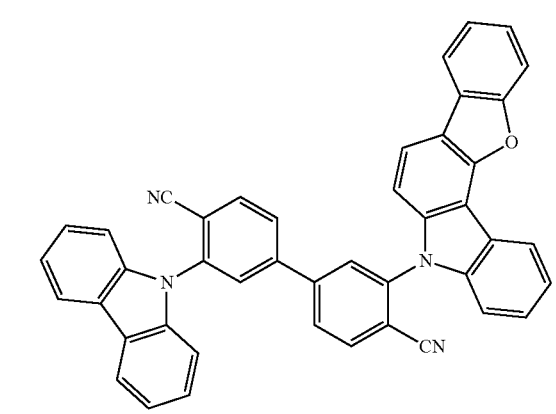
163
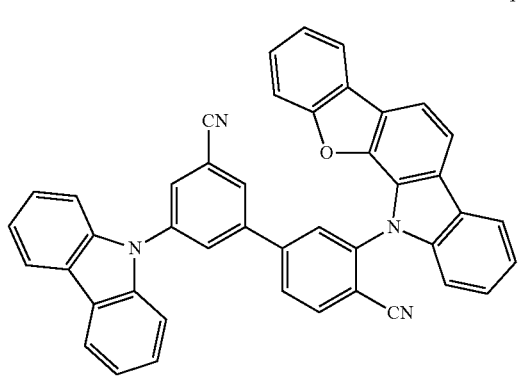

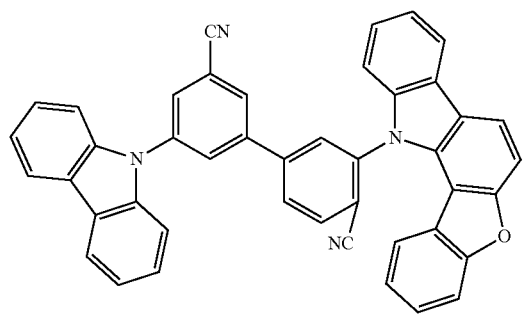
164
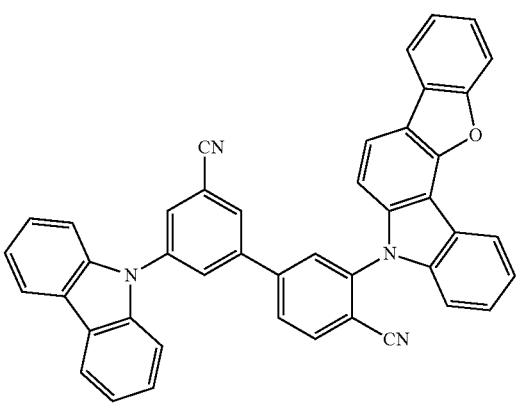
168
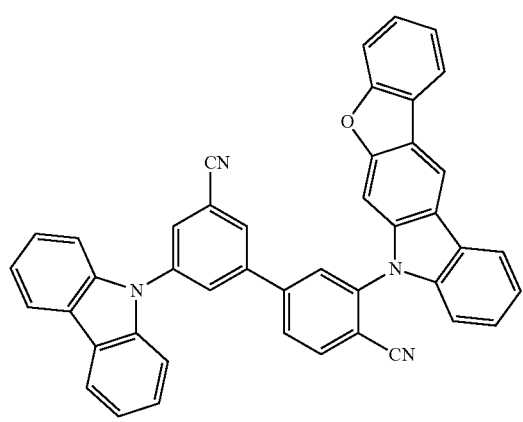
165
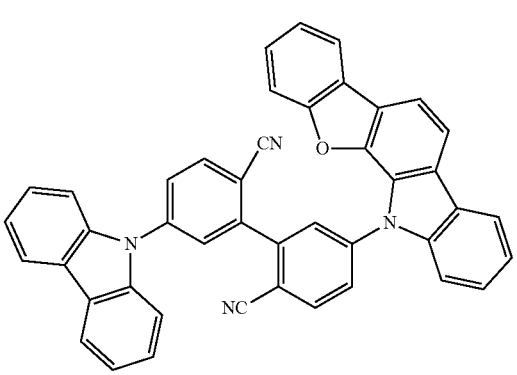
169
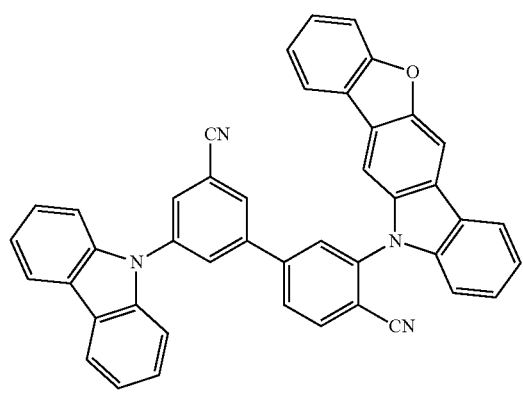
166
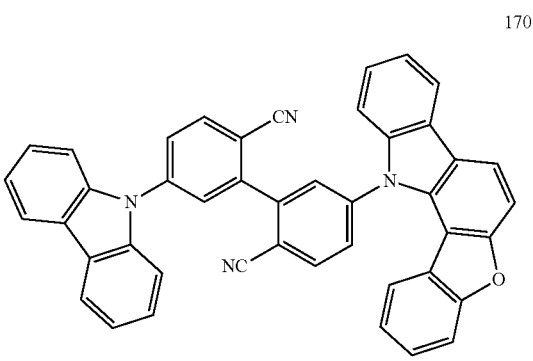
170
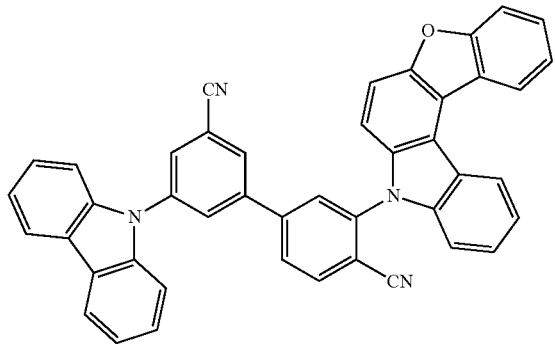
167
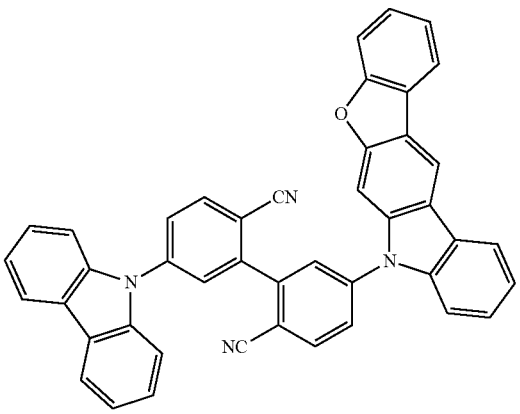
171

-continued
172
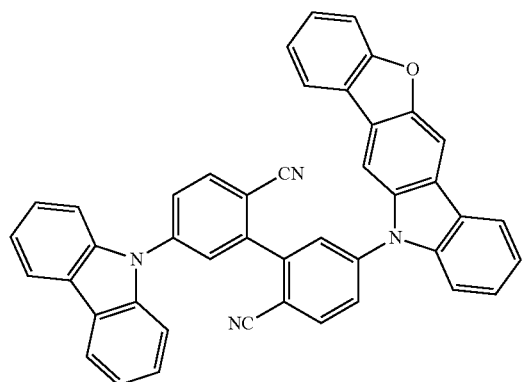
173
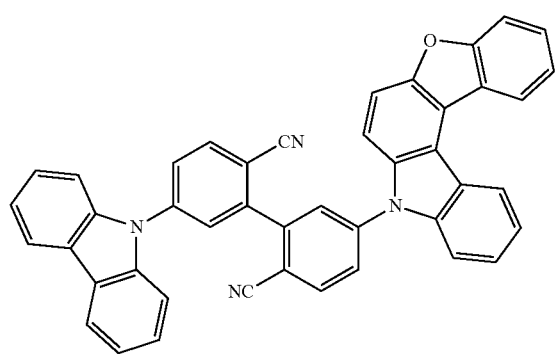
174
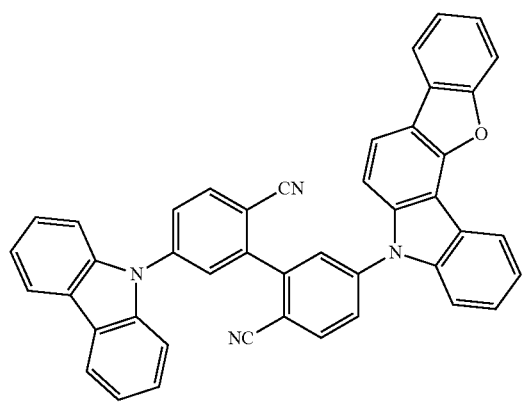
175
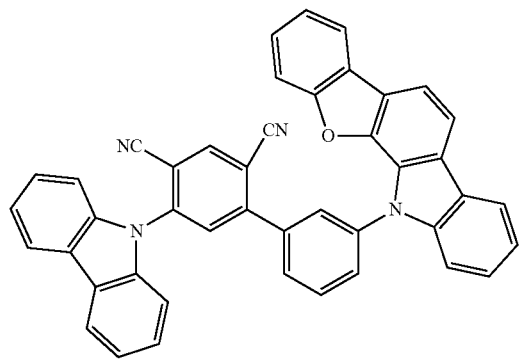
-continued
176
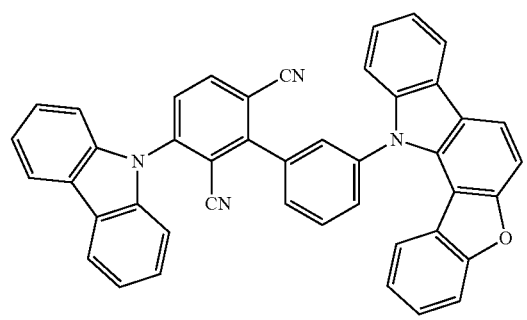
177
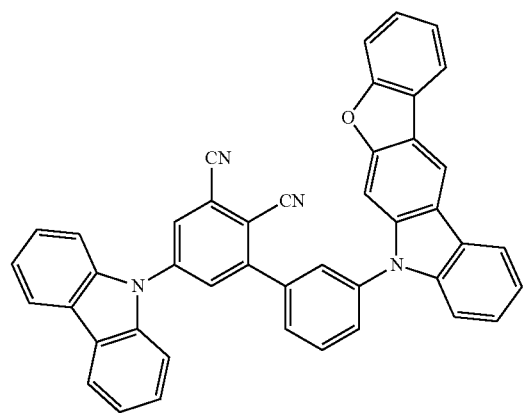
178
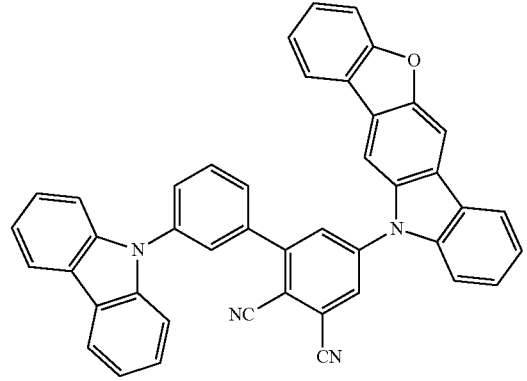
179
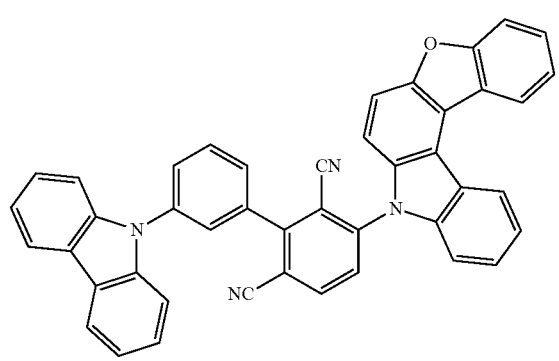

180
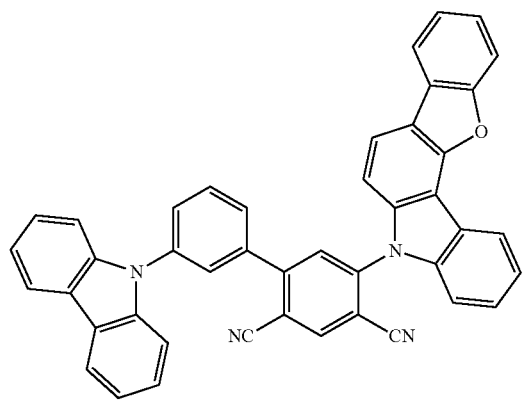
181
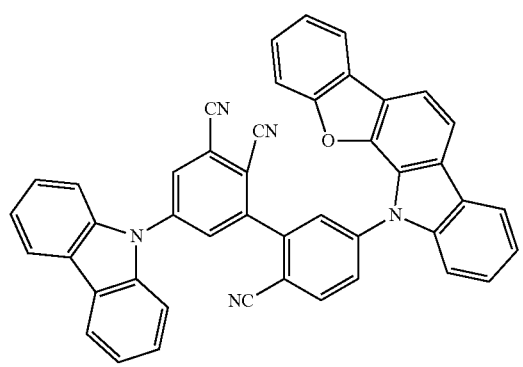
182
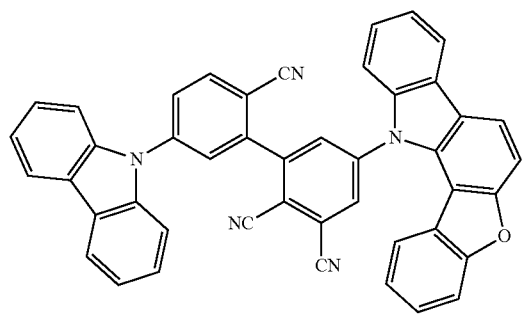
183
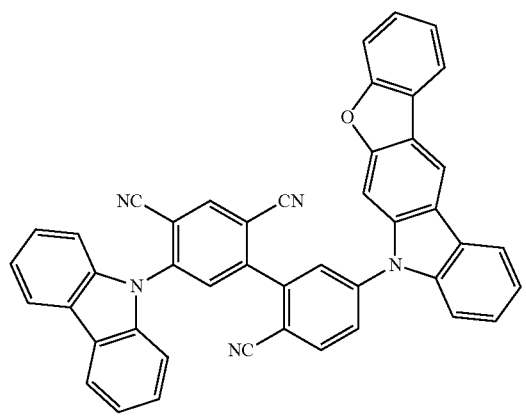
184
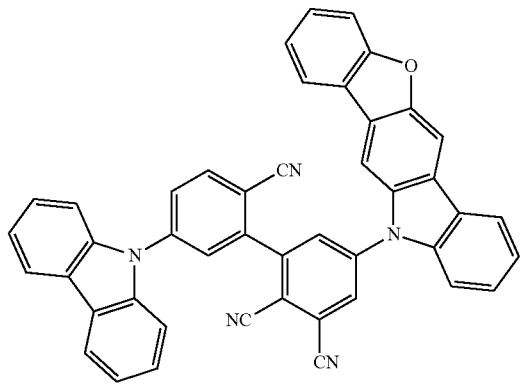
185
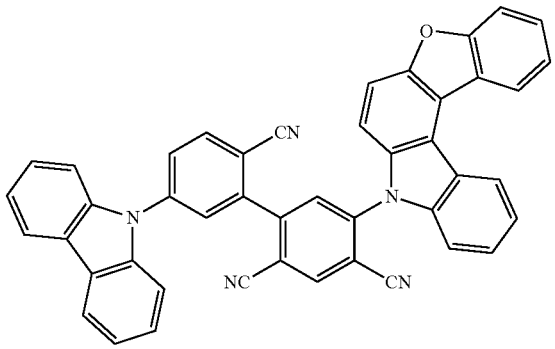
186
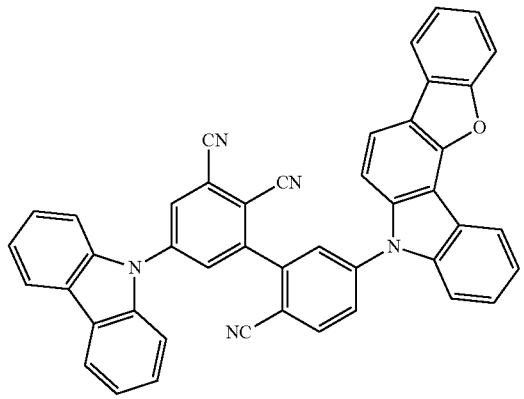
187
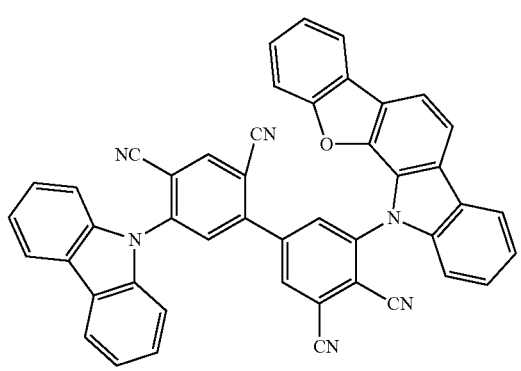

188
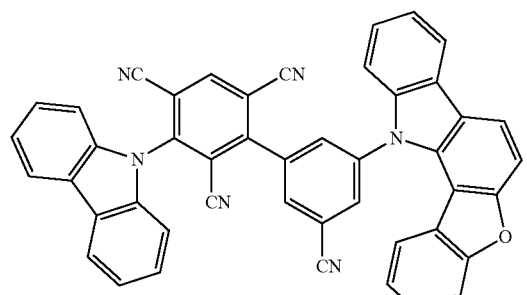
189
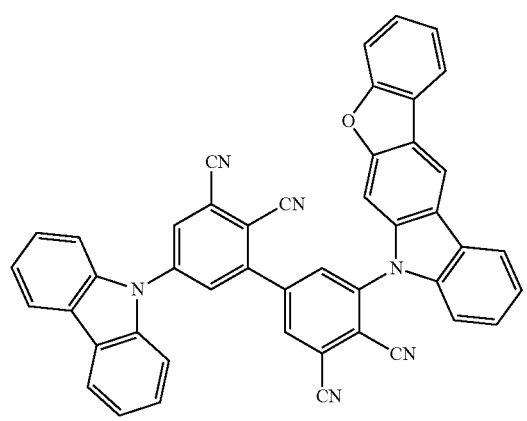
190
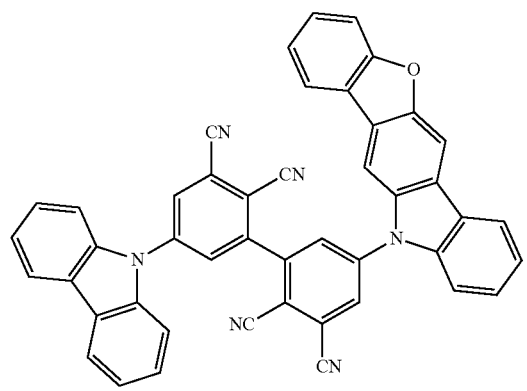
191
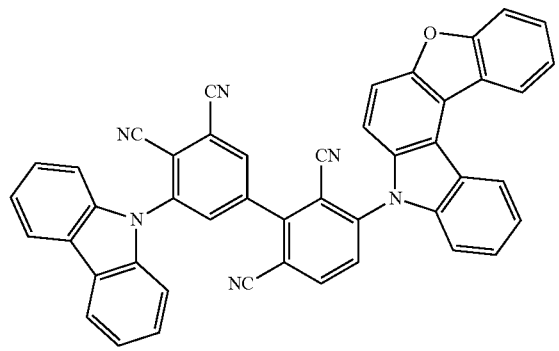
192
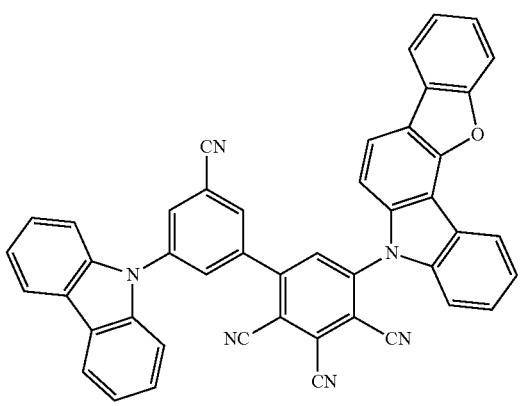
193
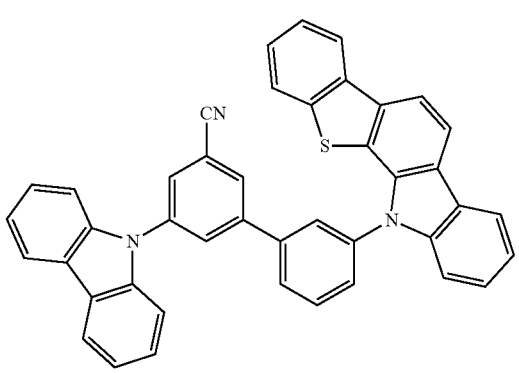
194
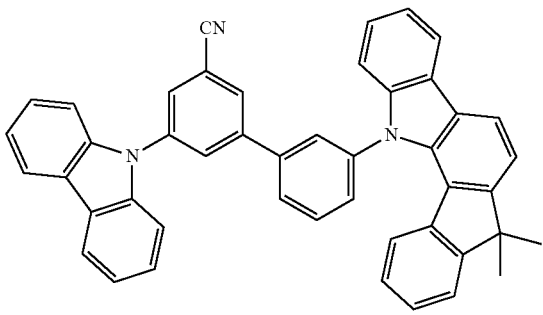
195
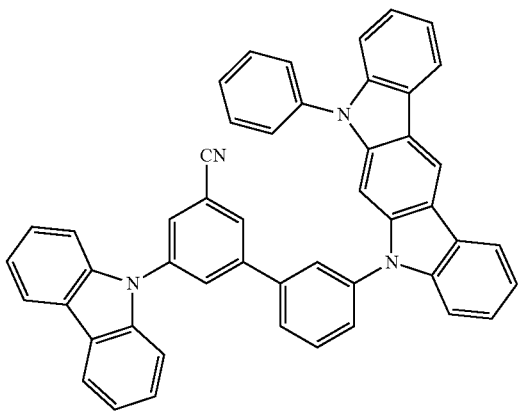

-continued
196
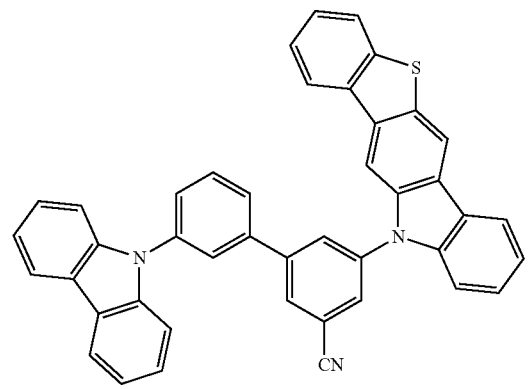
197
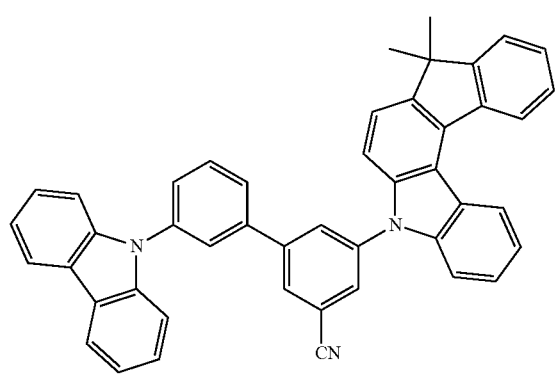
198
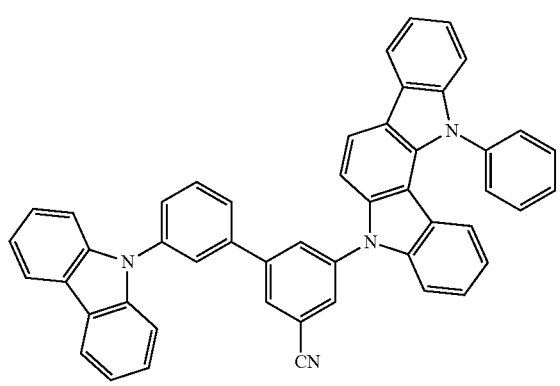
199
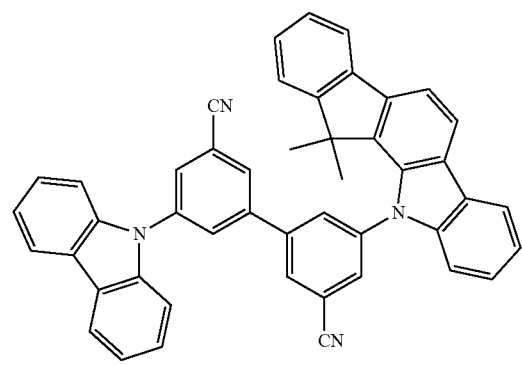
-continued
200
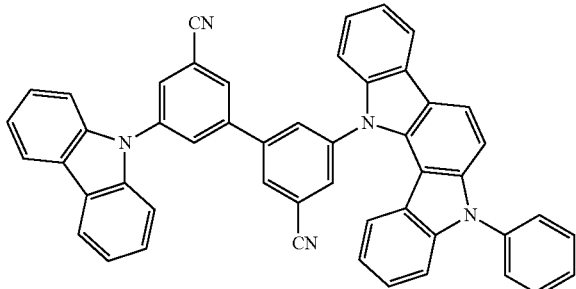
201
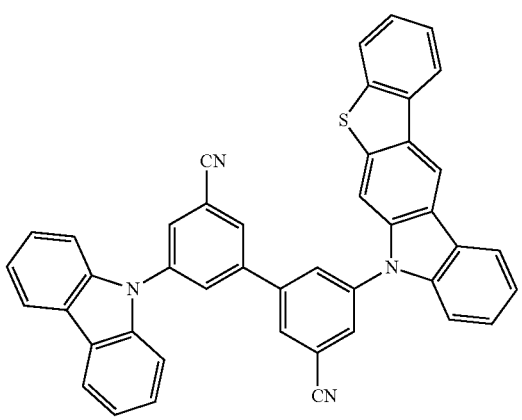
202
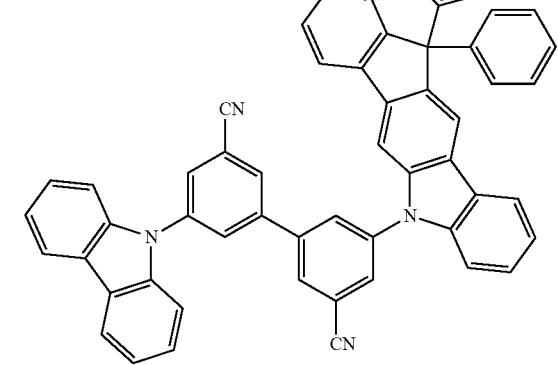

203
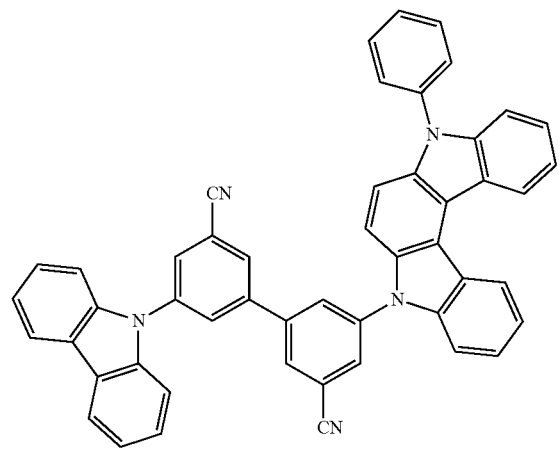
204
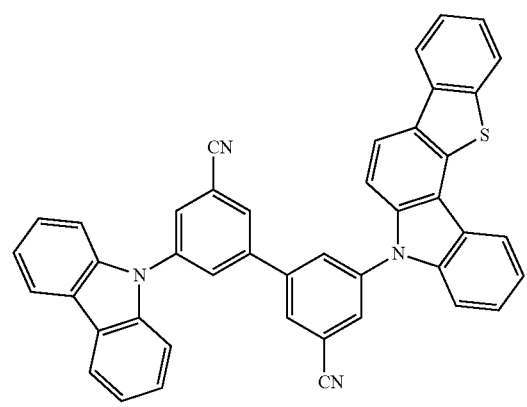
205
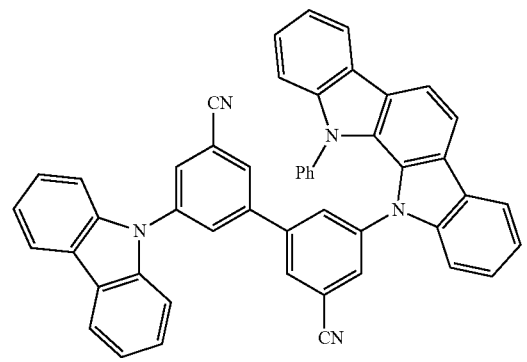
206
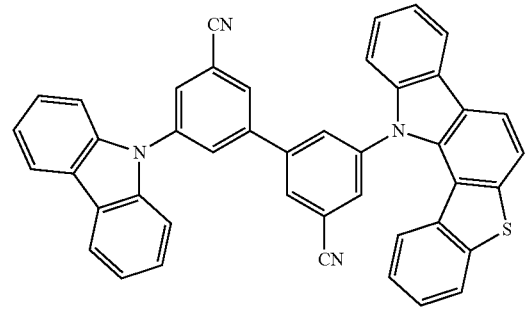
207
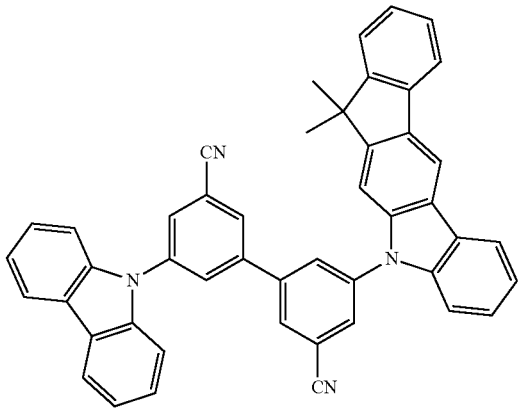
208
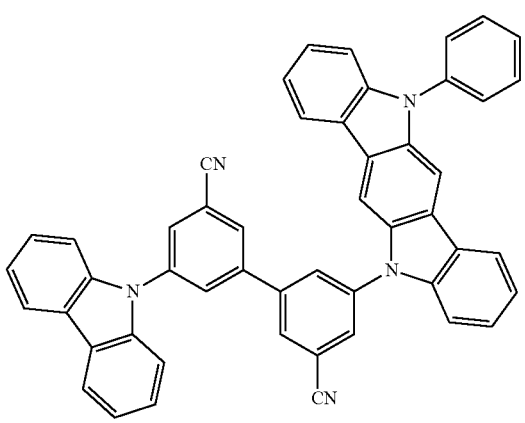
209
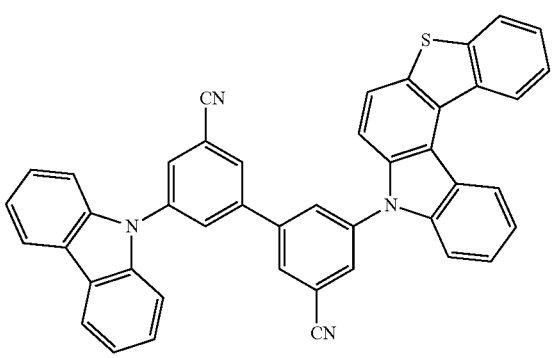
210
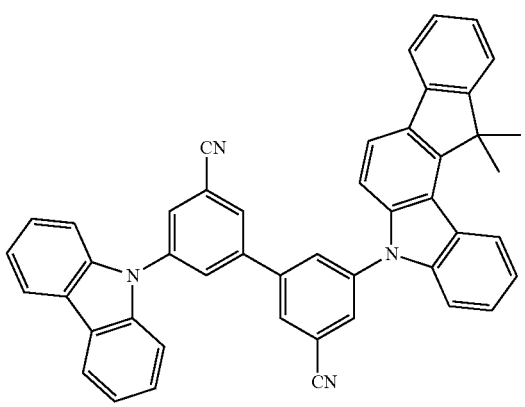

-continued
211
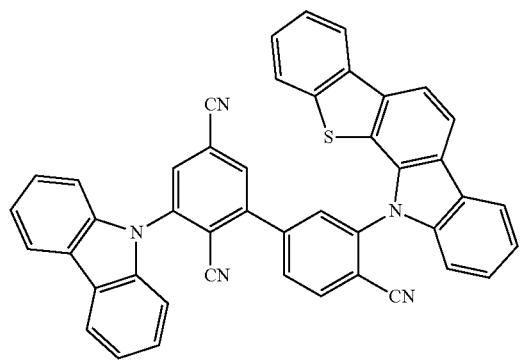
212
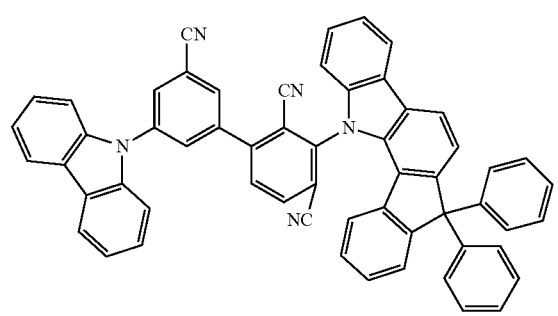
213
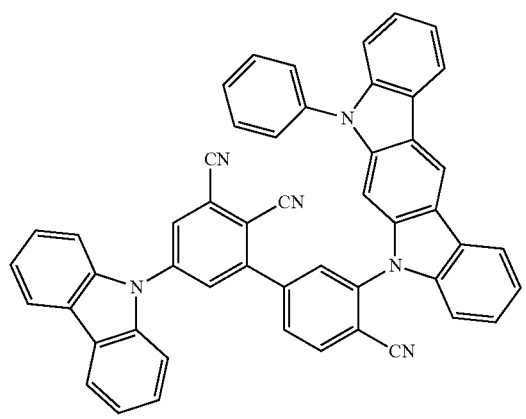
214
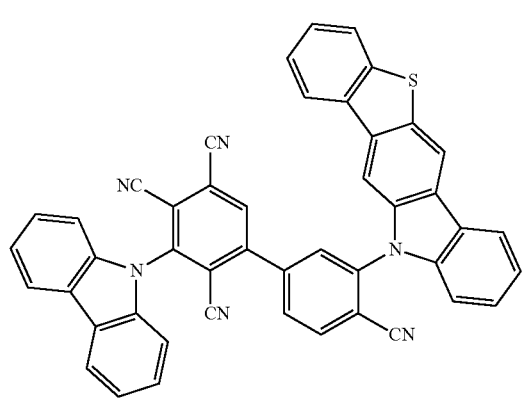
-continued
215
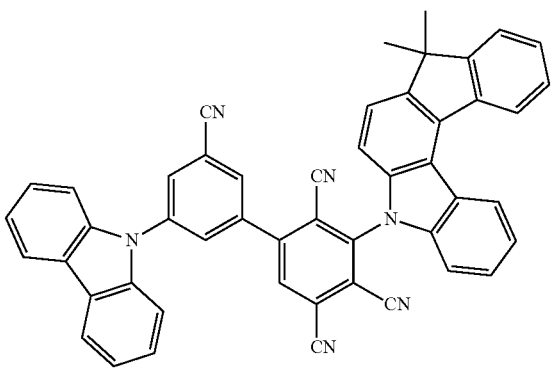
216
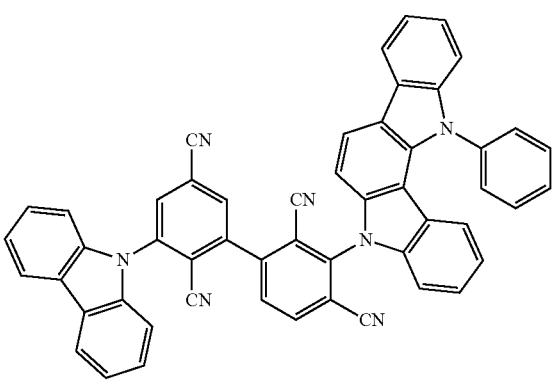
217
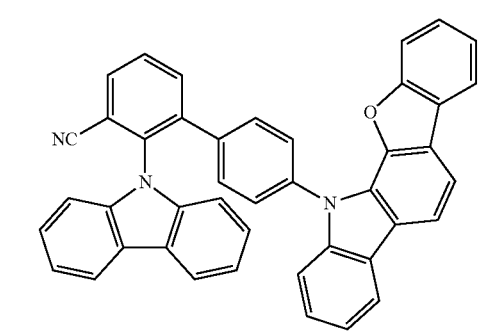
218
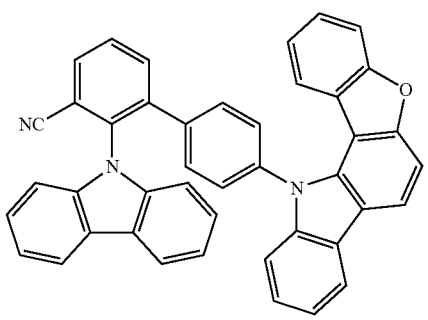

71
-continued
219
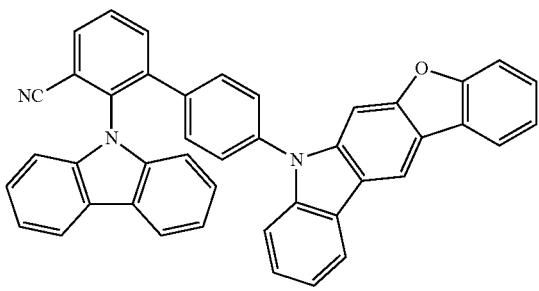
220
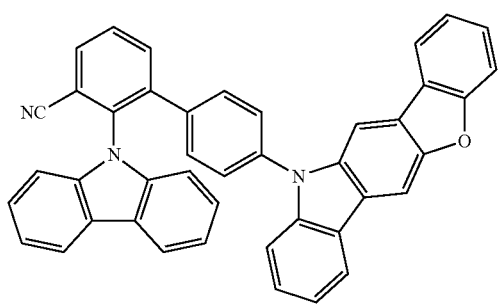
221
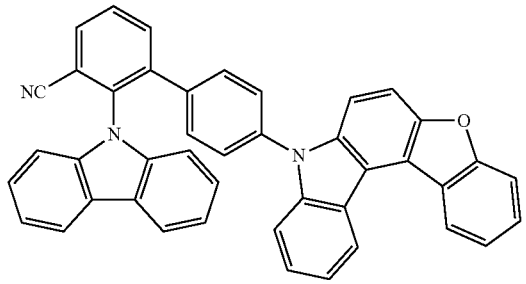
222
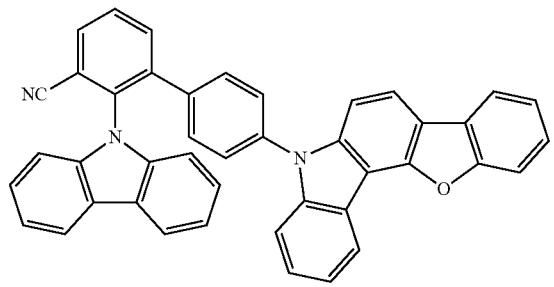
223
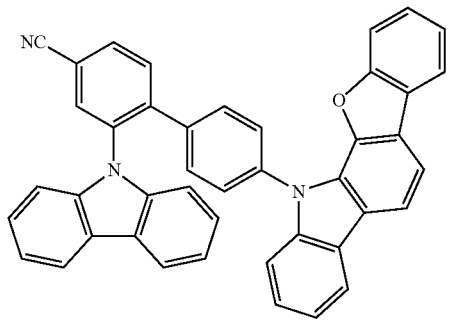
72
-continued
224
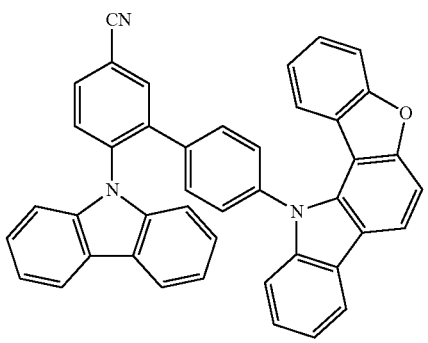
225
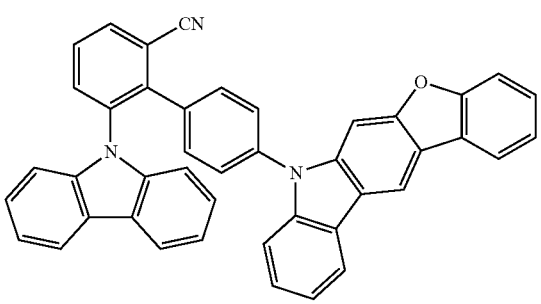
226
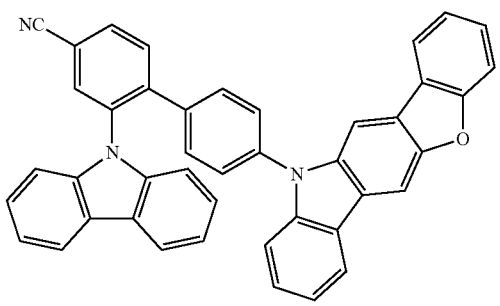
227
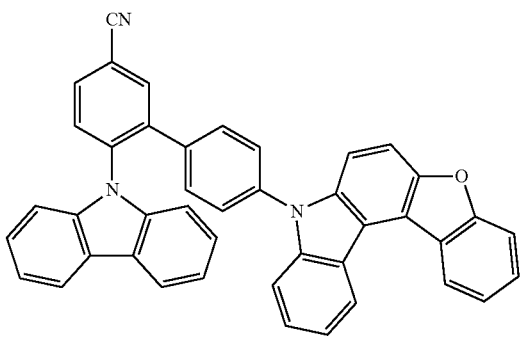
228
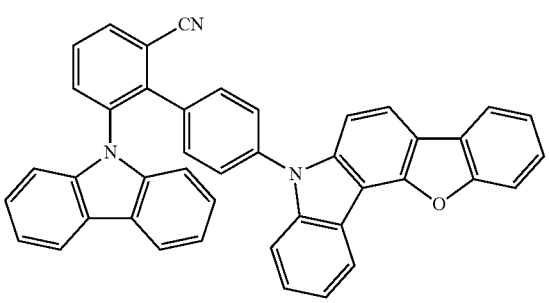

229
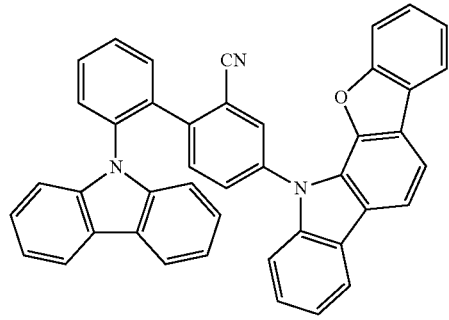
230
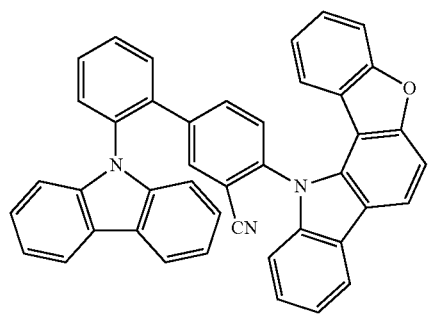
231
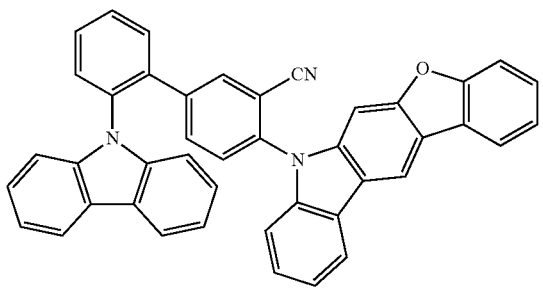
232
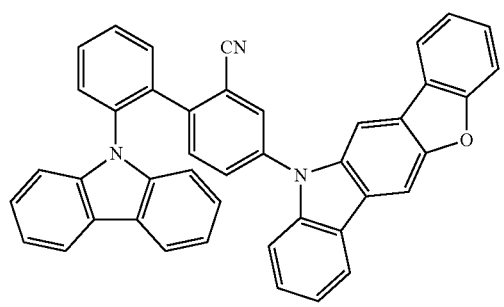
233
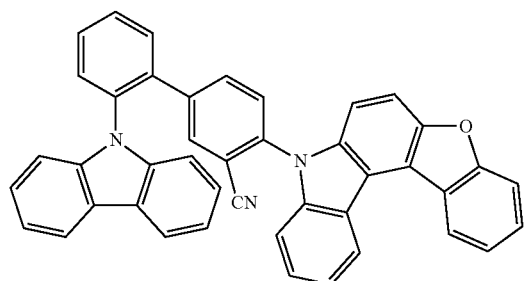
234
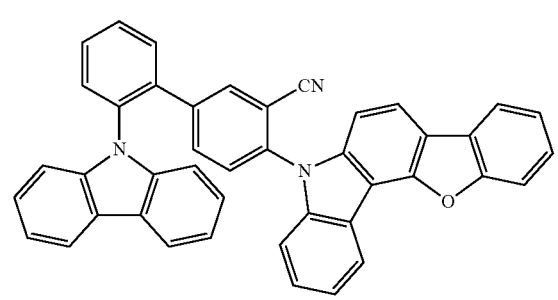
235
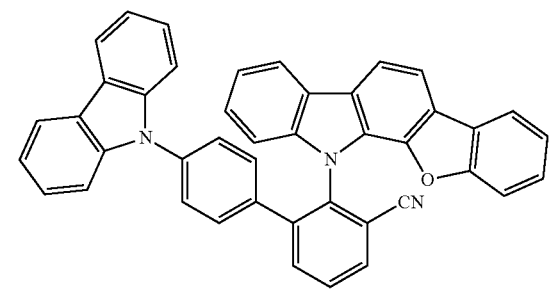
236
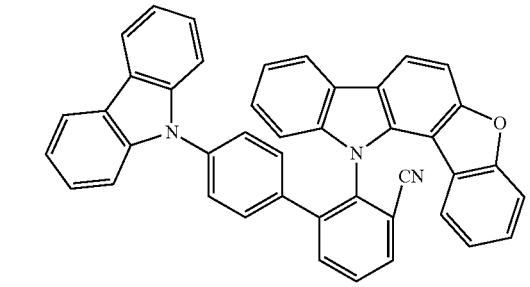
237
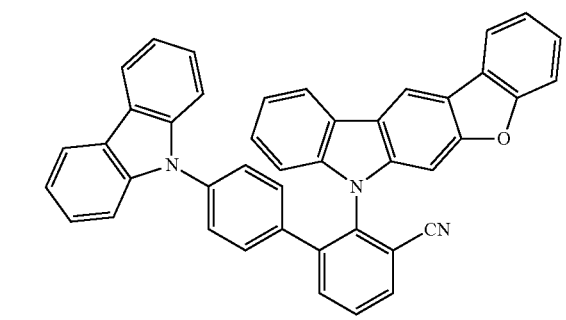
238
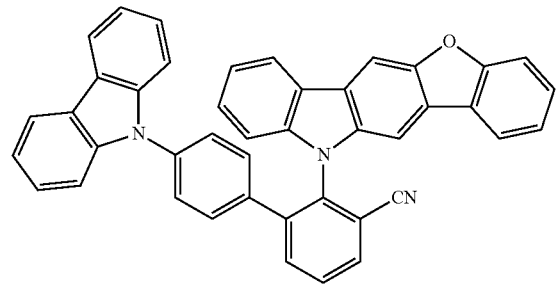

239 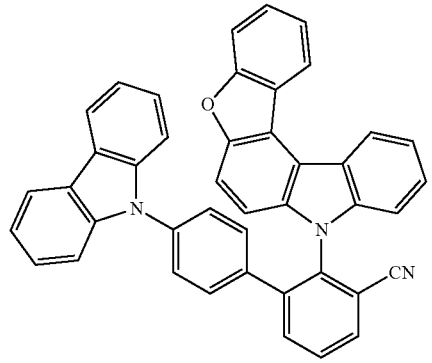
240 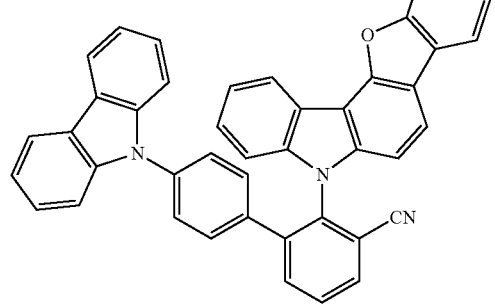
241 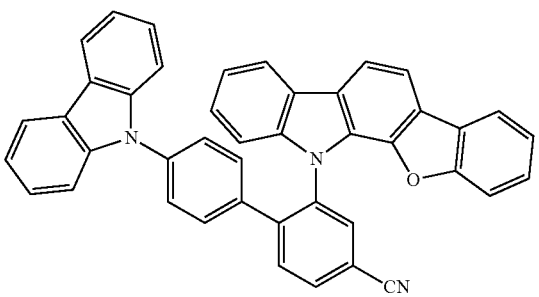
242 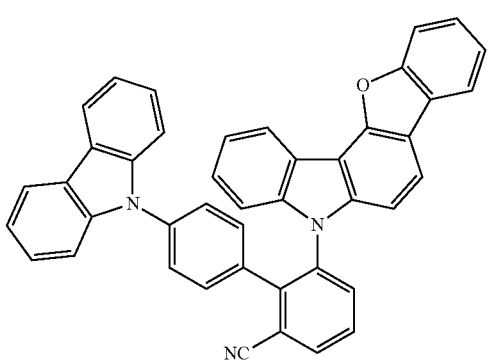
243 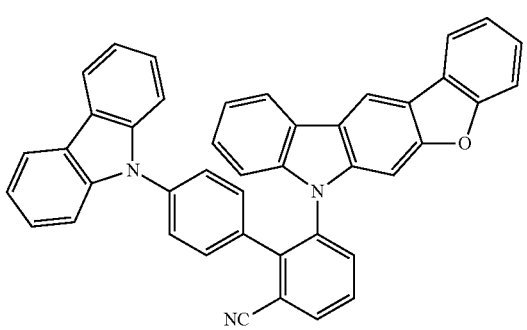
244 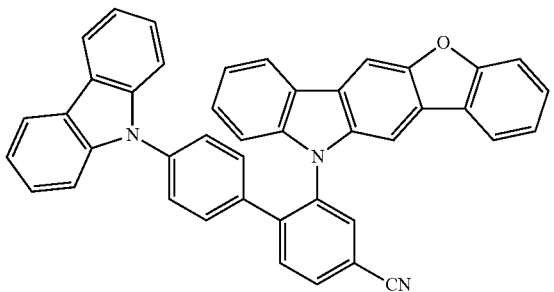
245 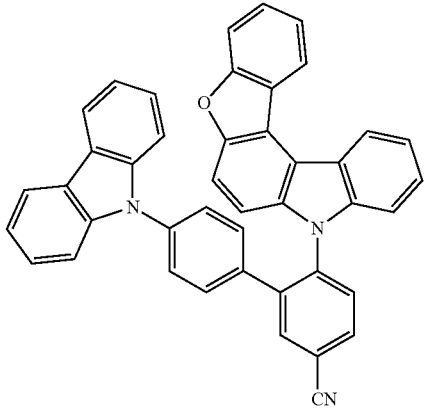
246

247
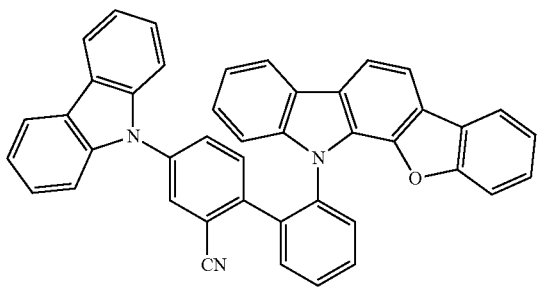
248
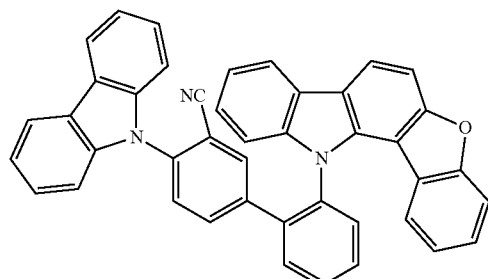
249
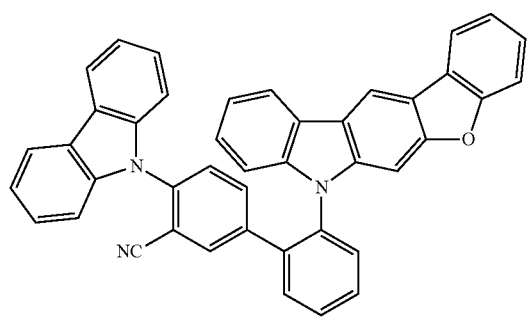
250
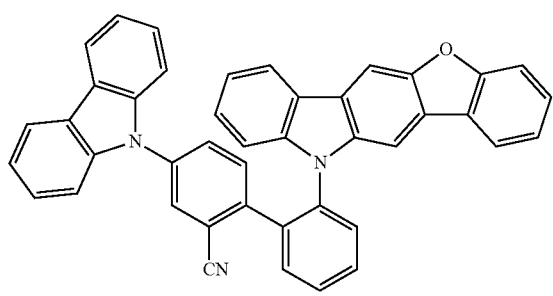
251
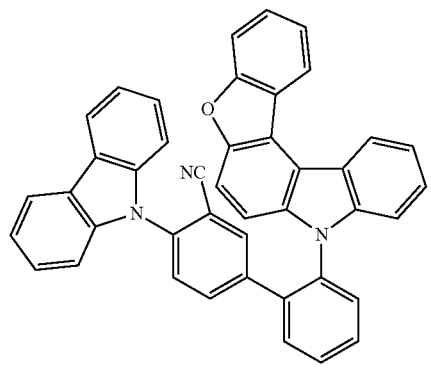
252
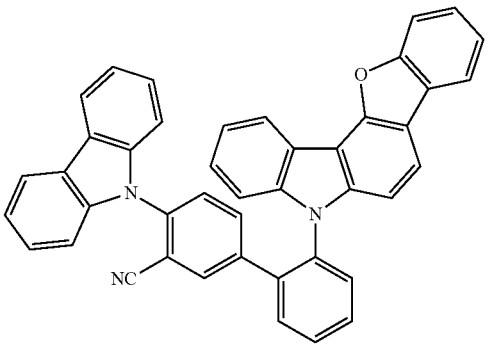
253
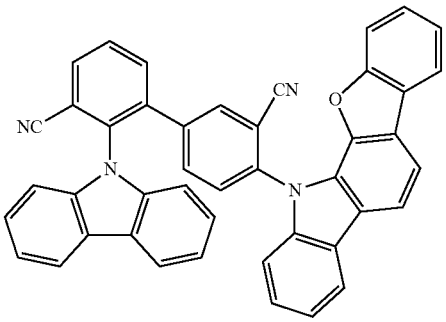
254
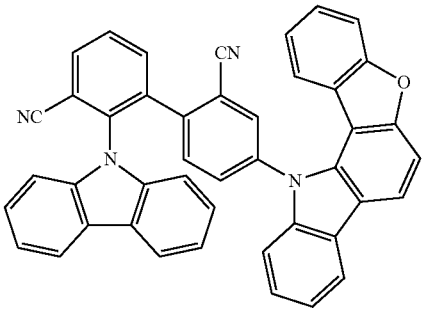
255
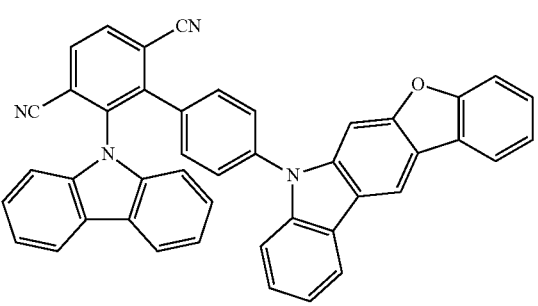
256
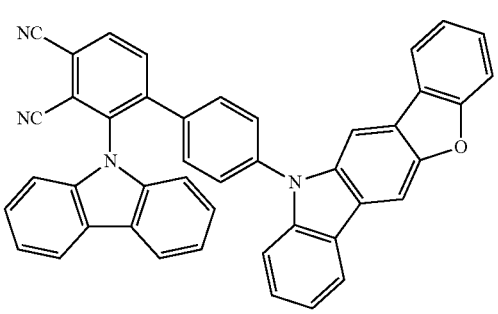

257
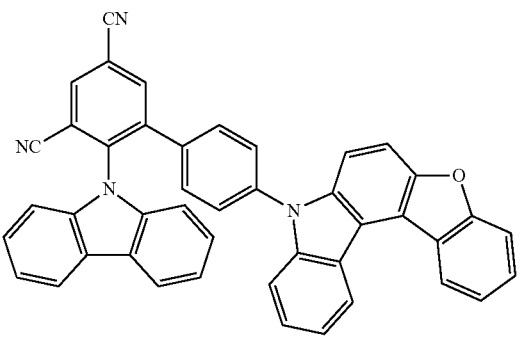
258
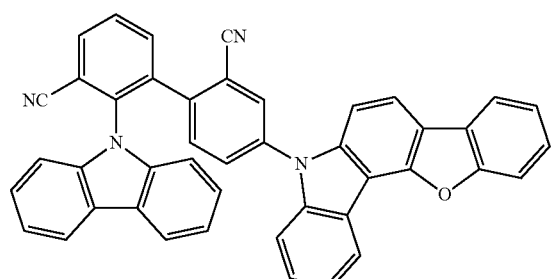
259
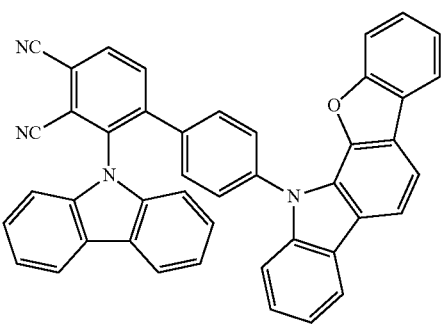
260
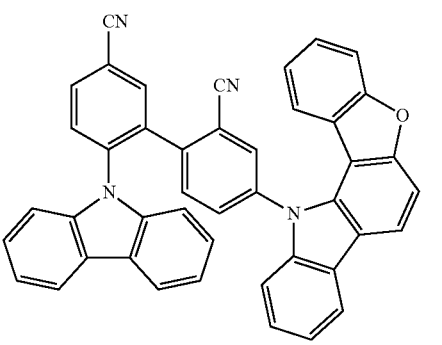
261
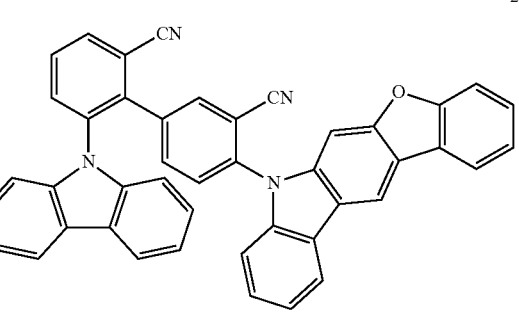
262
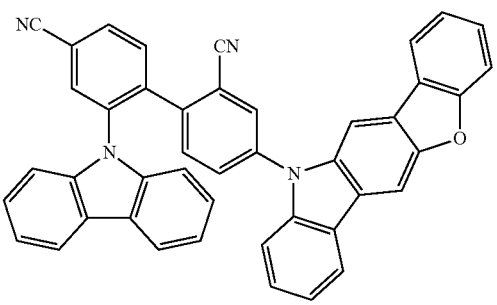
263
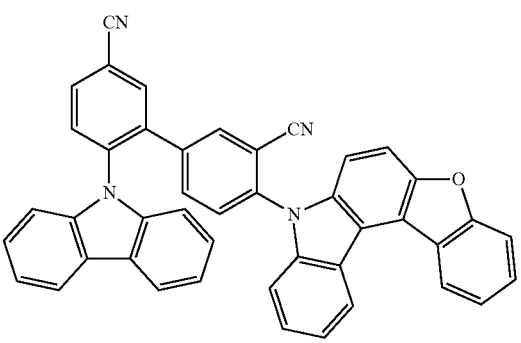
264
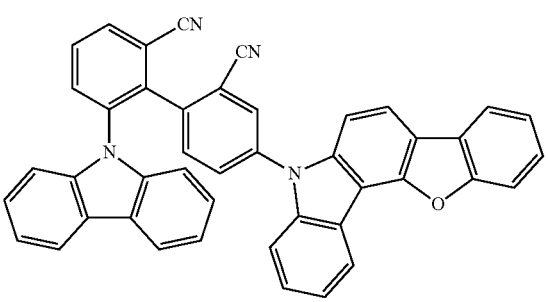
265
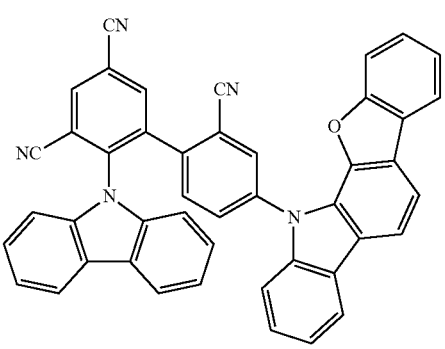
266
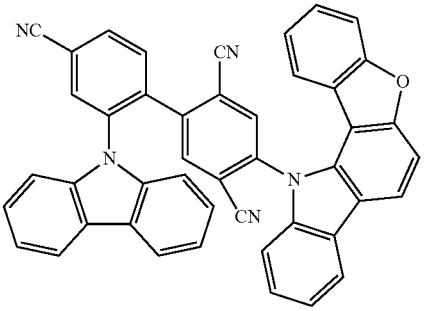

267
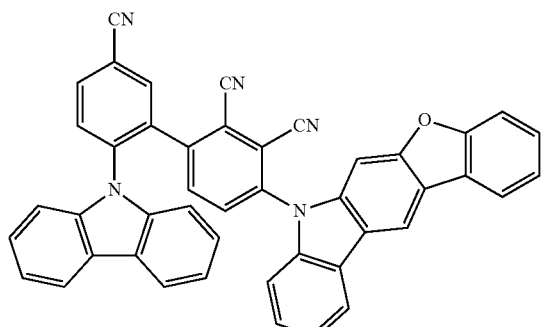
268
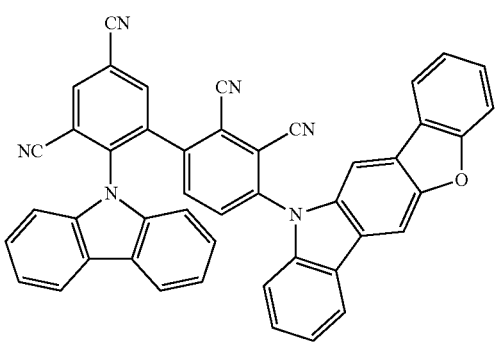
269
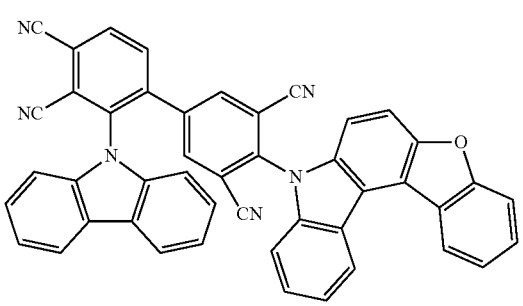
270
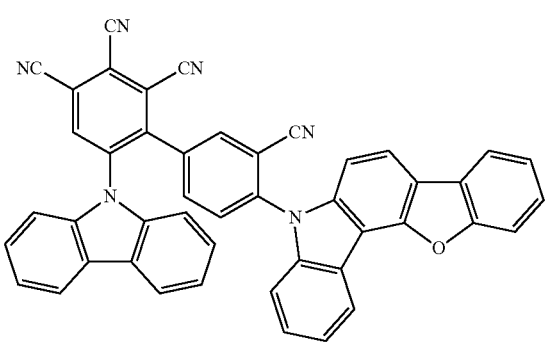
271
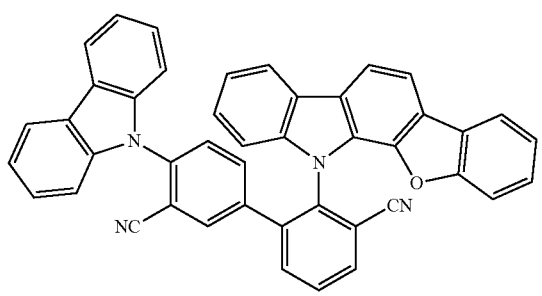
272
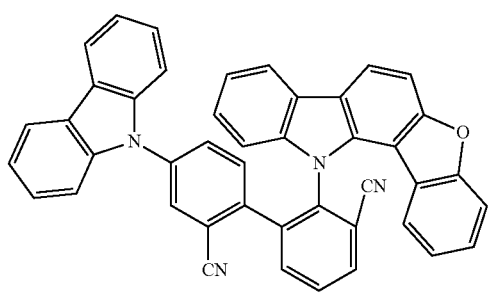
273
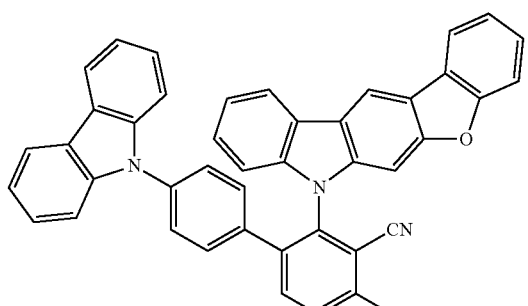
274
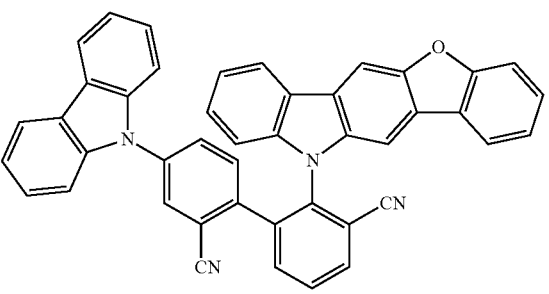
275
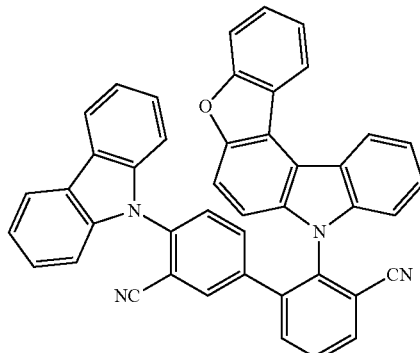

-continued
276
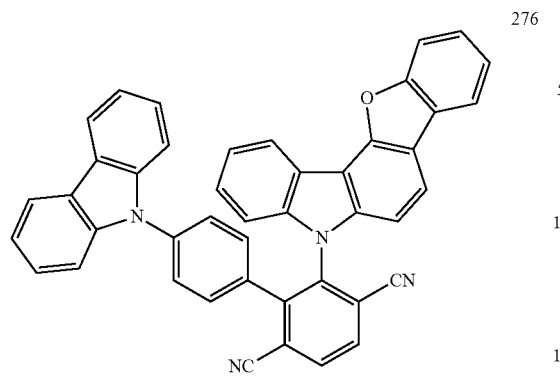
277
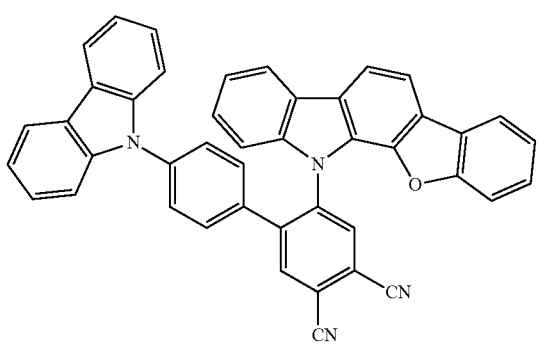
278
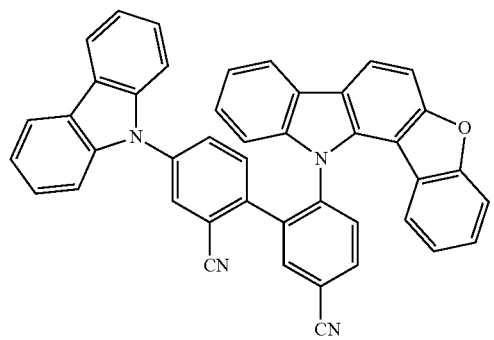
279
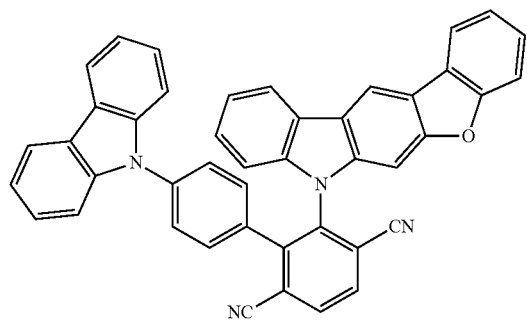
-continued
280
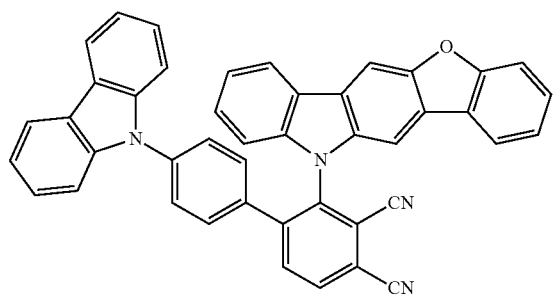
281
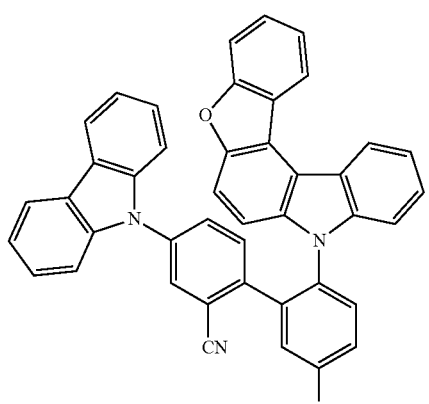
282
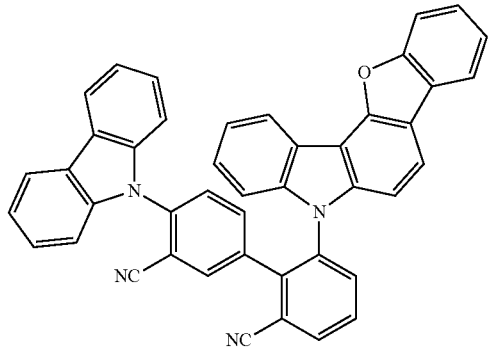
283
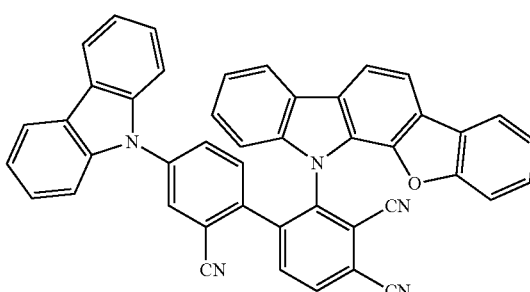

-continued
284
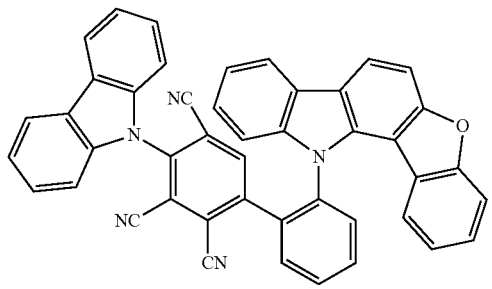
285
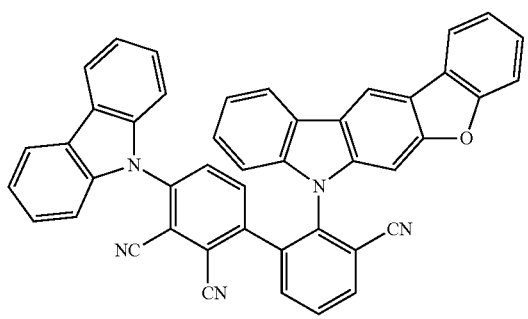
286
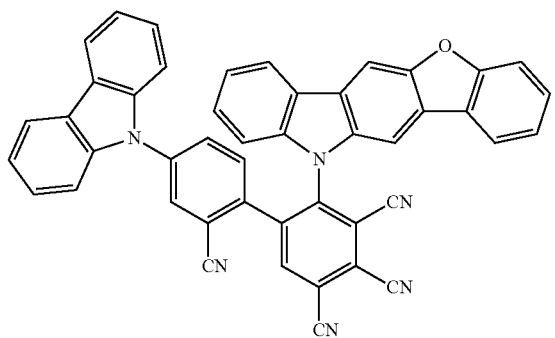
287
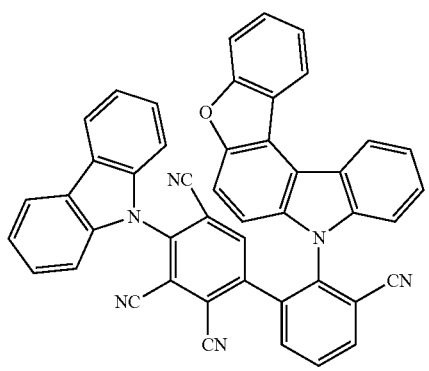
-continued
288
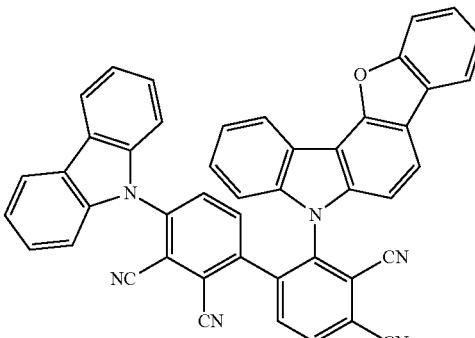
289
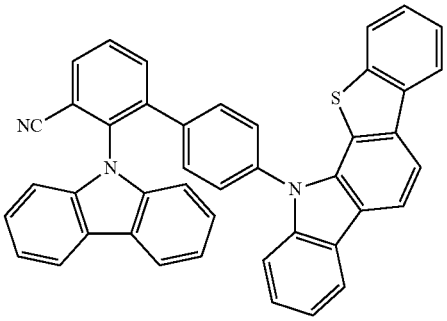
290
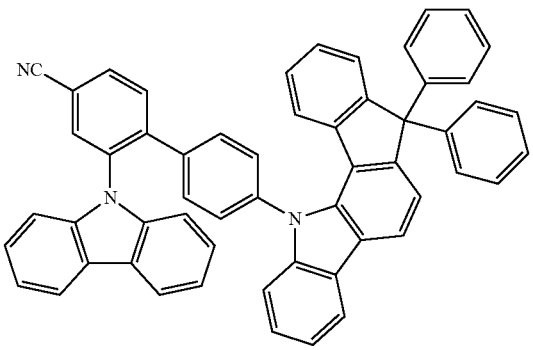
291
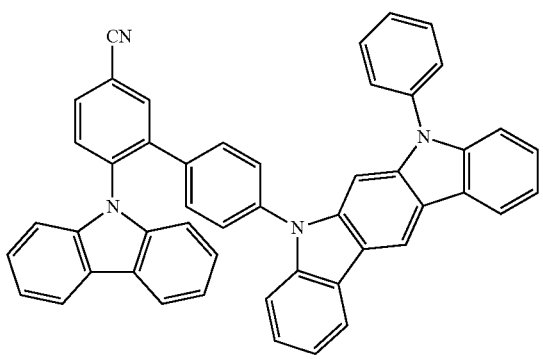

292
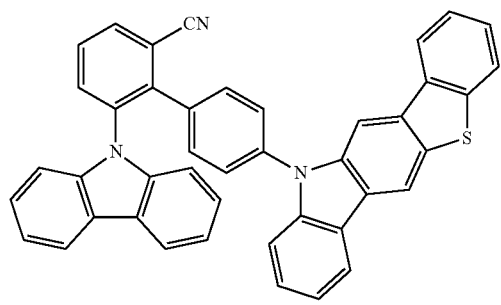
296
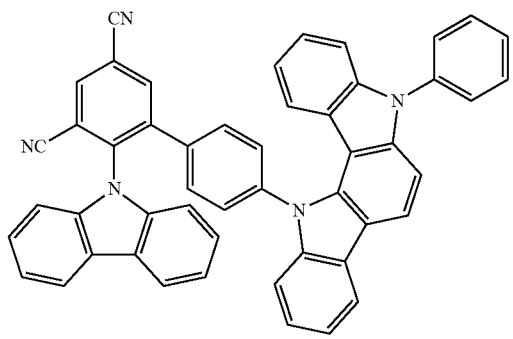
293
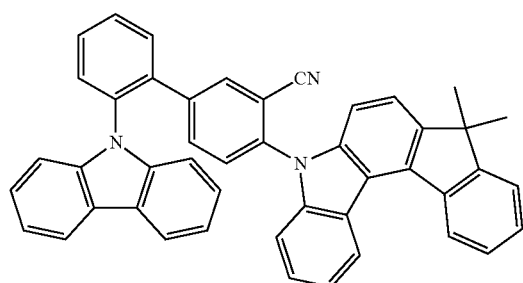
297
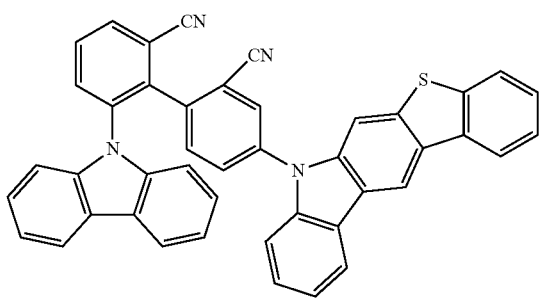
294
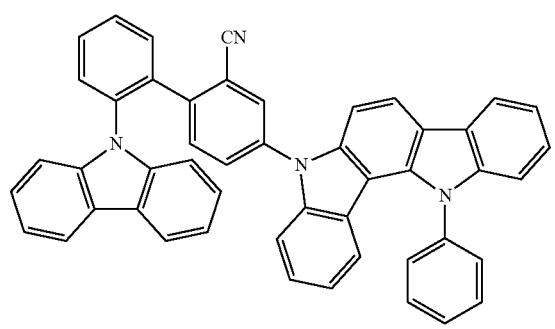
298
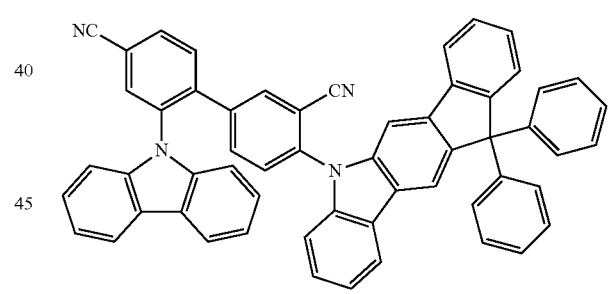
295
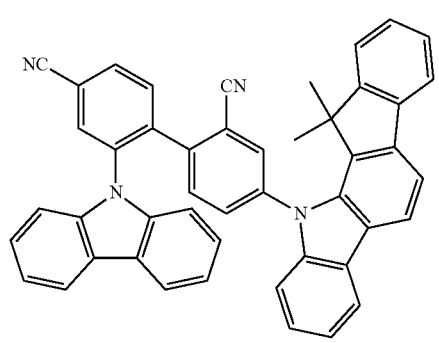
299
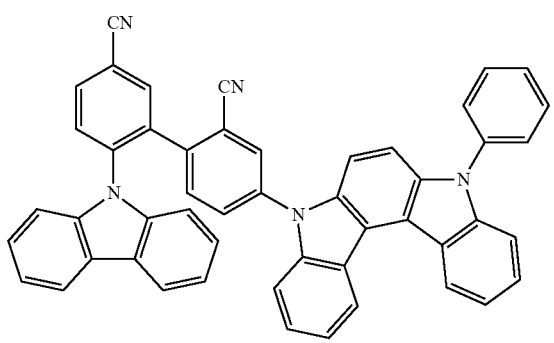

300
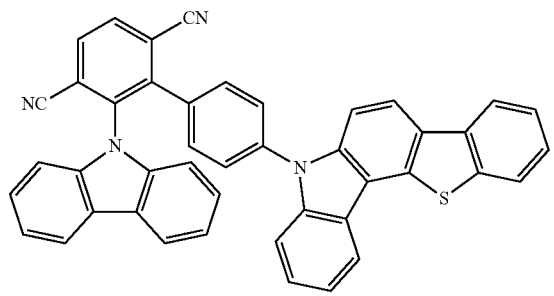
301
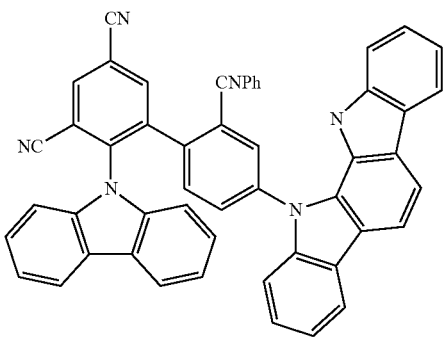
302
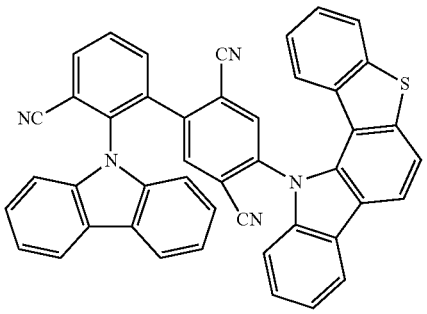
303
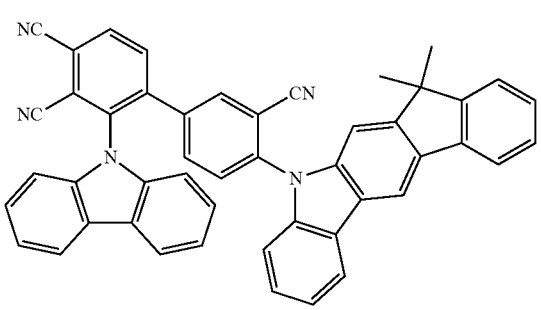
304
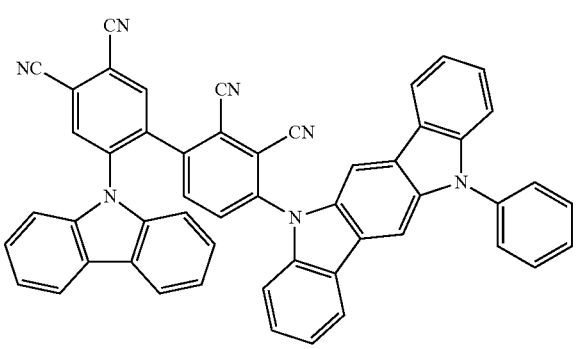
305
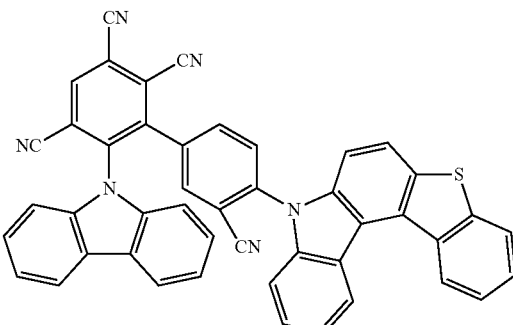
306
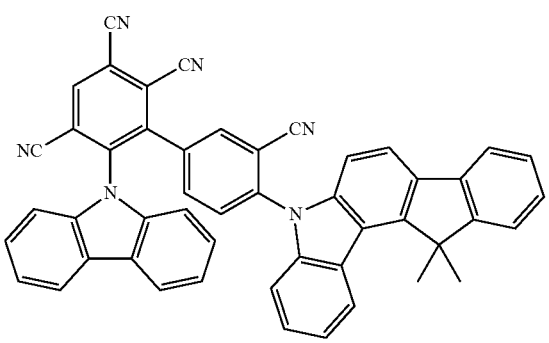
307
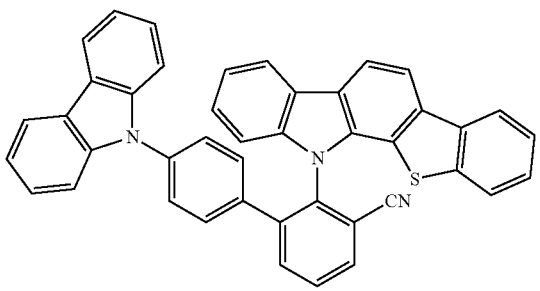
308
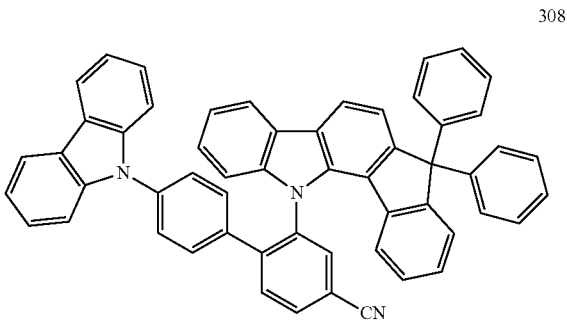

-continued
309
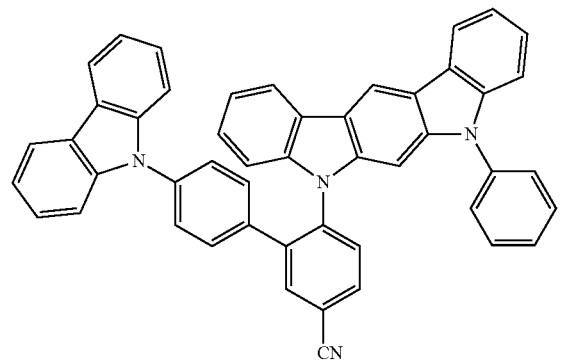
310
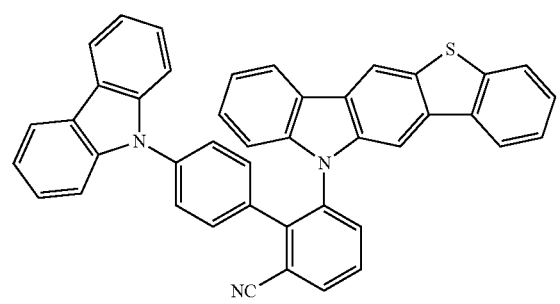
311
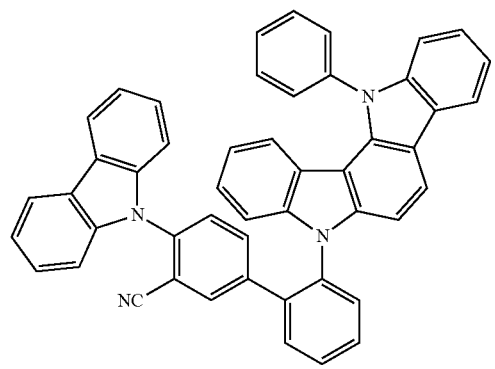
312
313
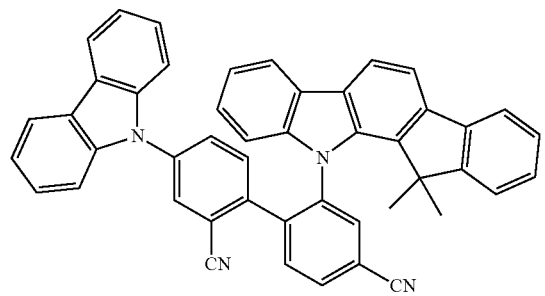
314
315
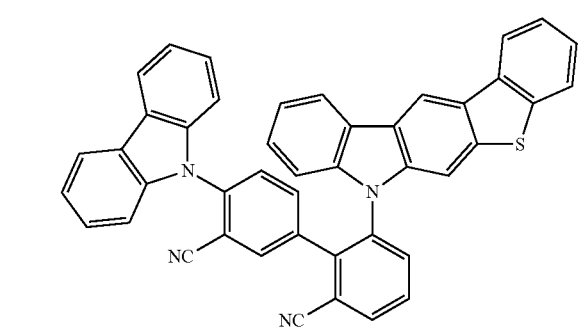
316
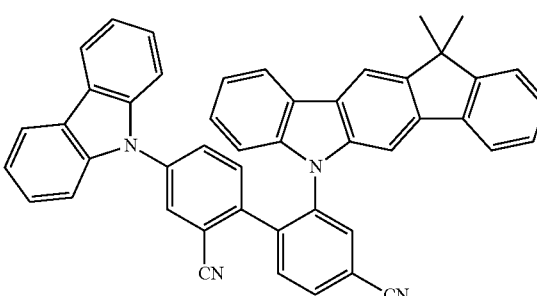

-continued
317
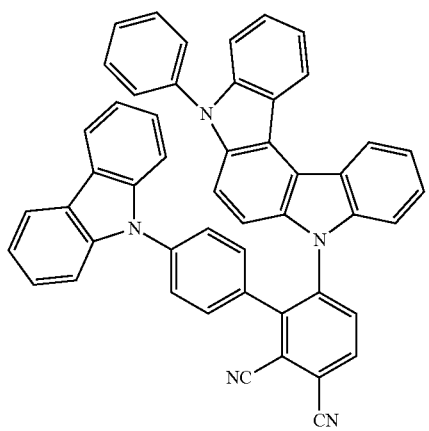
318
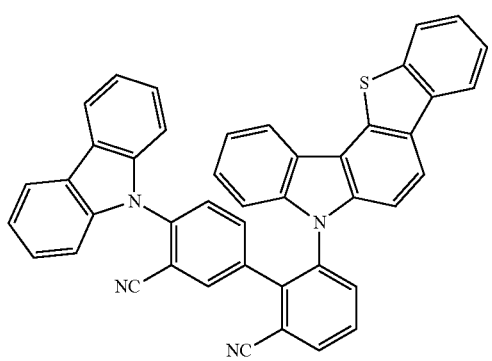
319
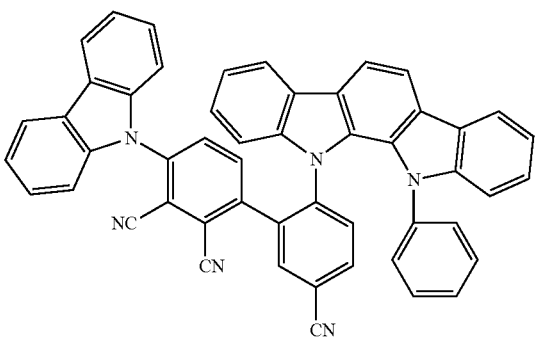
320
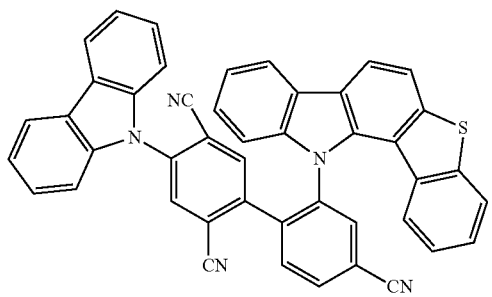
-continued
321
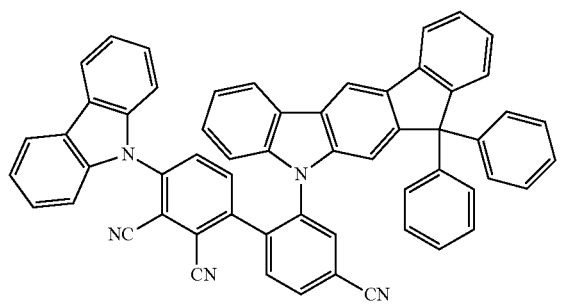
322
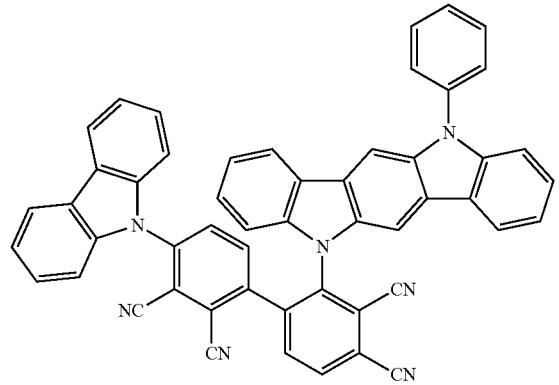
323
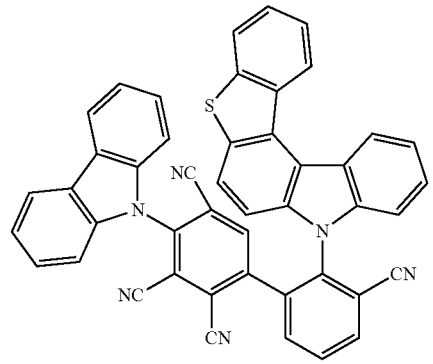
324
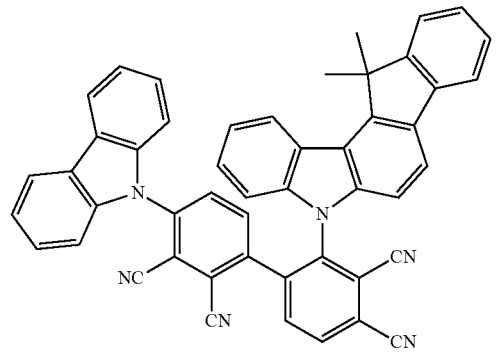

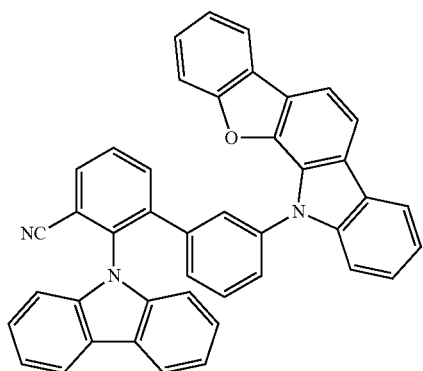
325
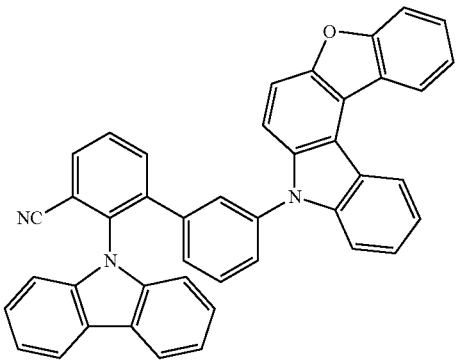
329
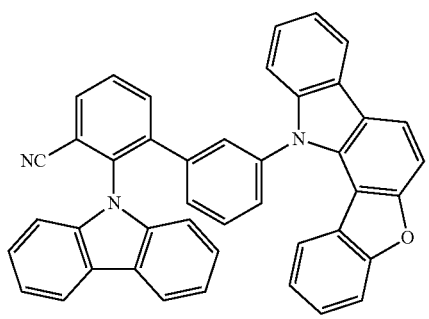
326
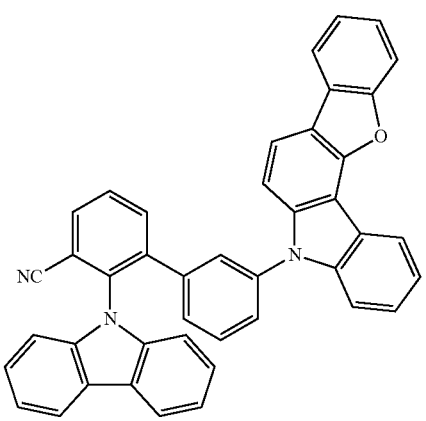
330
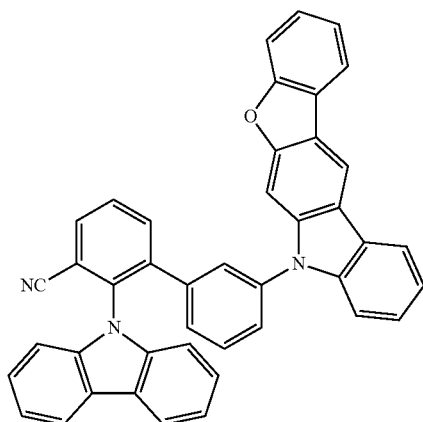
327
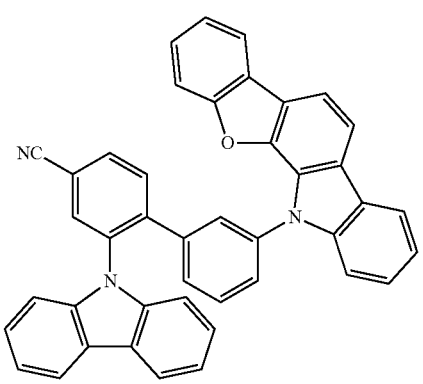
331
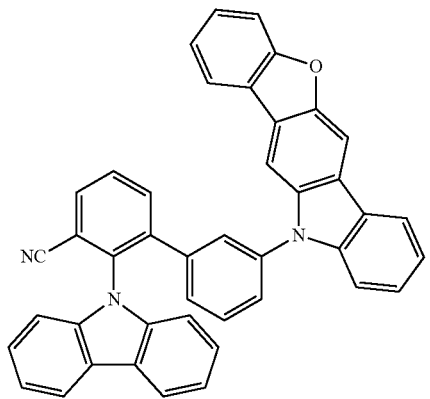
328
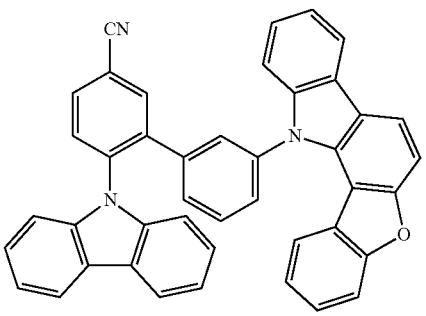
332

-continued
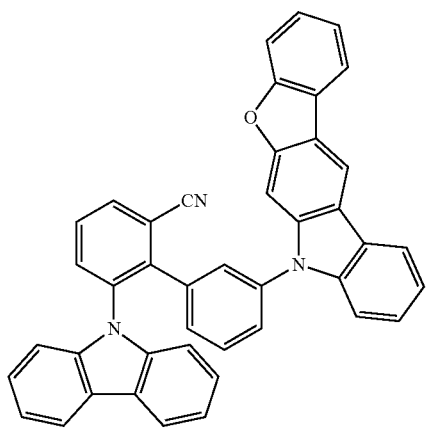
333
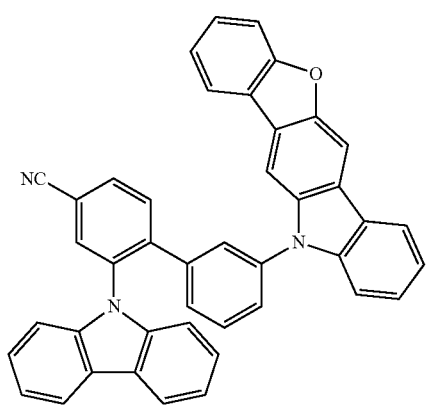
334
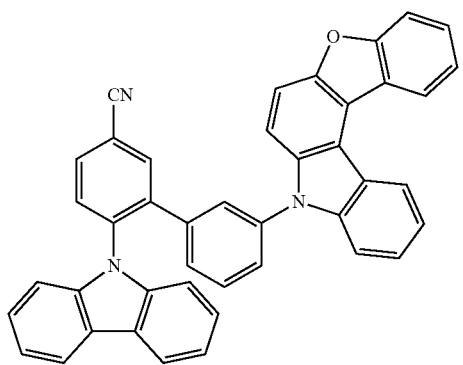
335
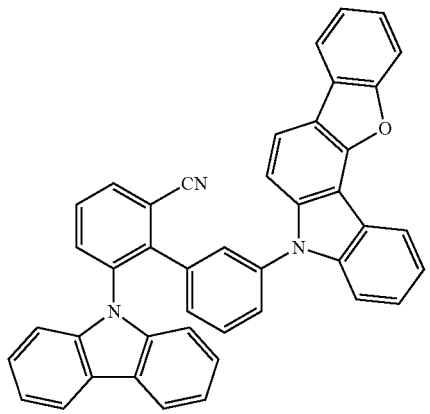
336

341
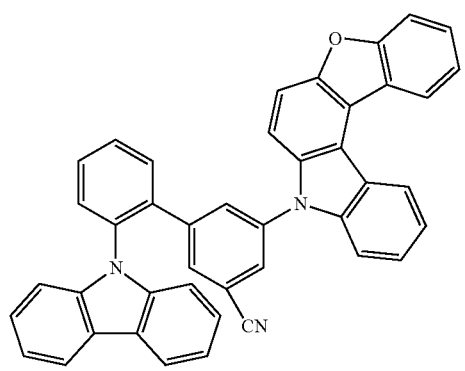
342
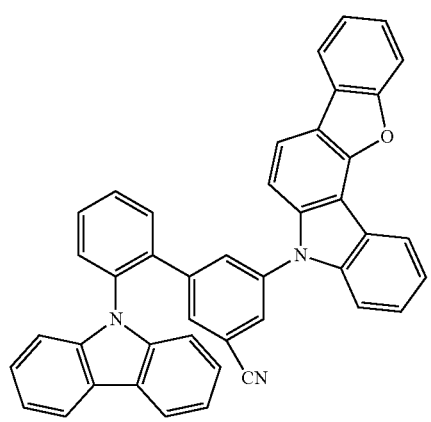
343
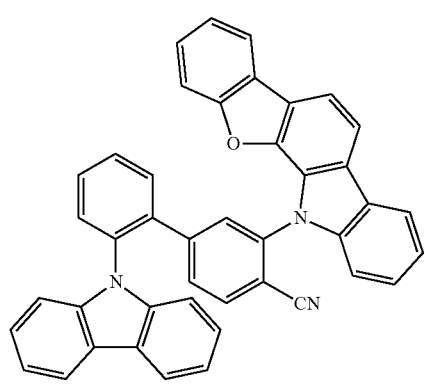
344
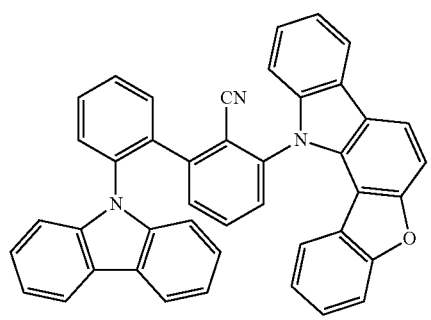
345
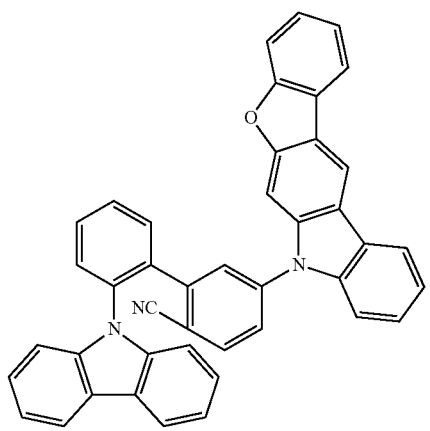
346
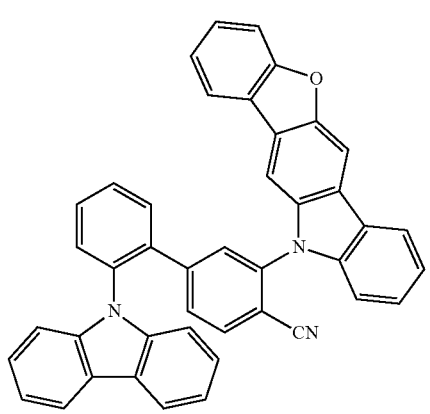
347
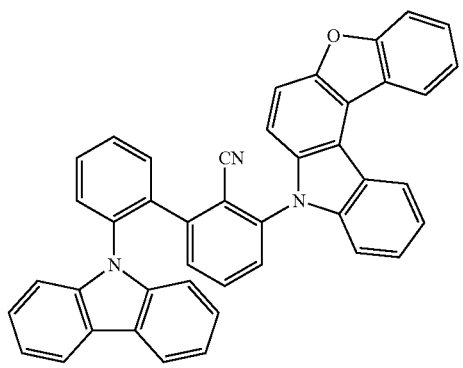
348
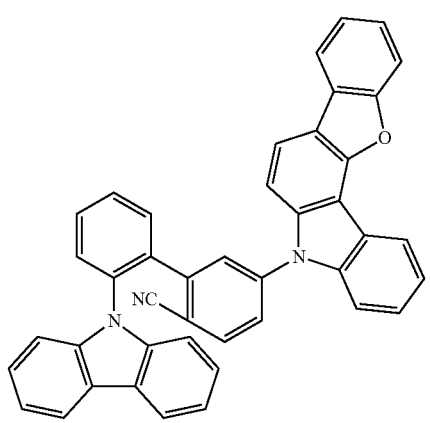

101
-continued
349
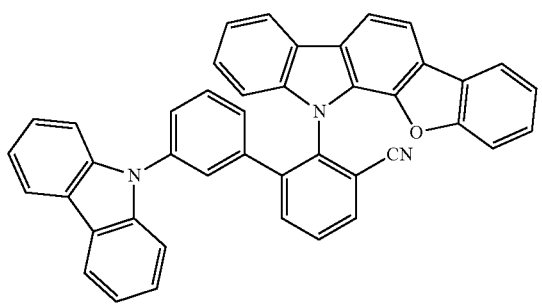
350
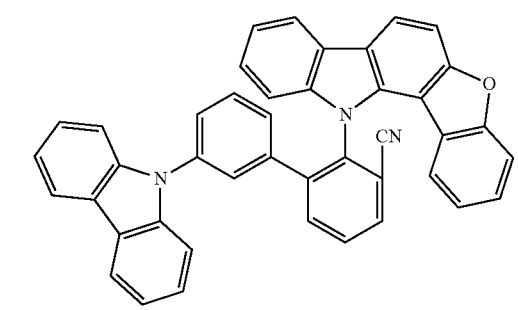
351
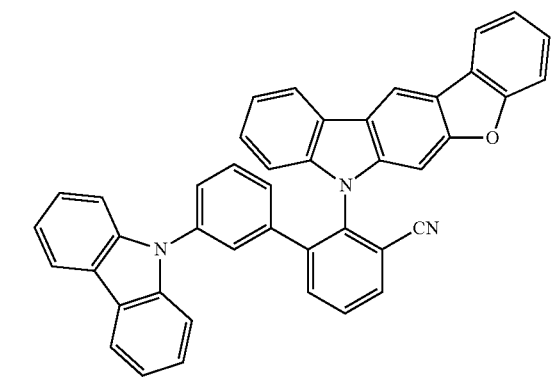
352
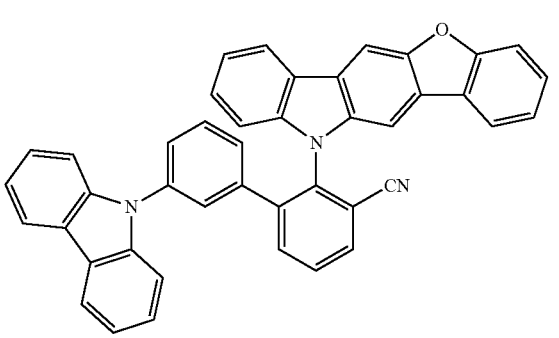
102
-continued
353
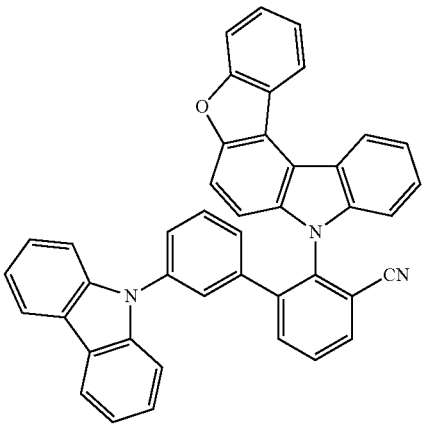
354
355
356

103
-continued
357
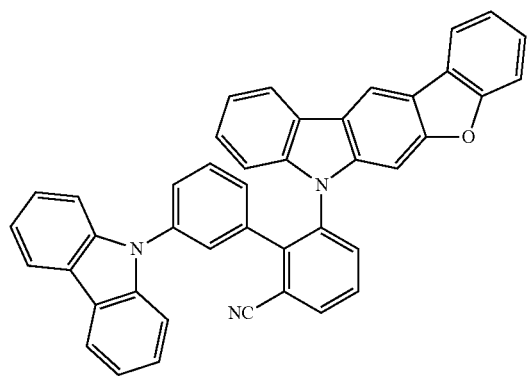
358
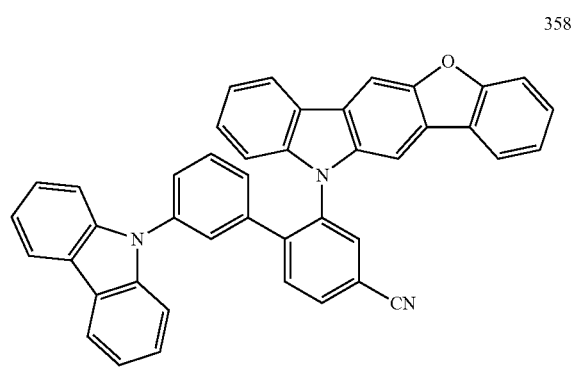
359
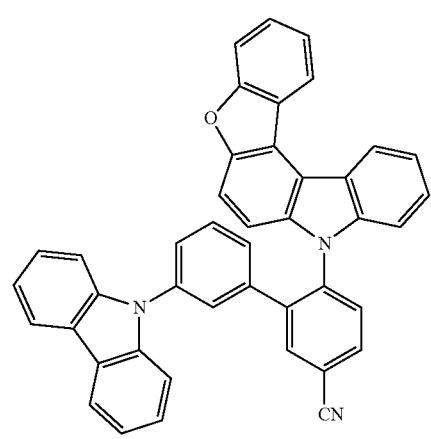
360
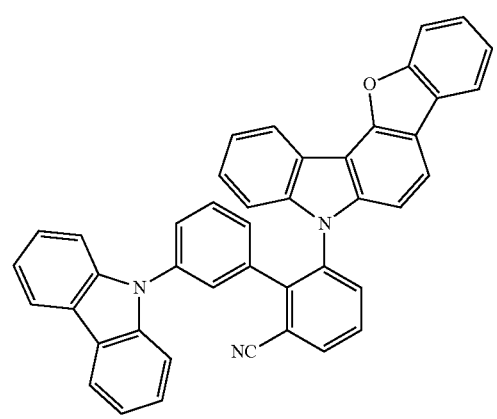
104
-continued
361
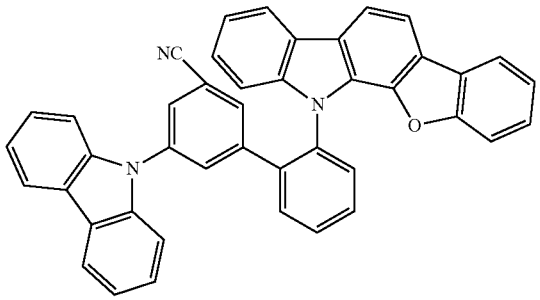
362
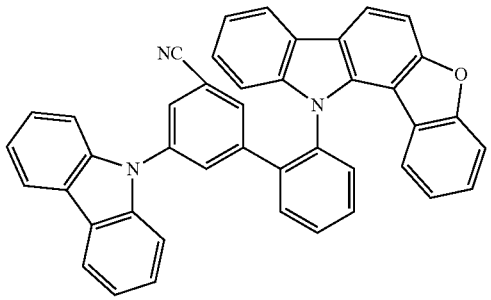
363
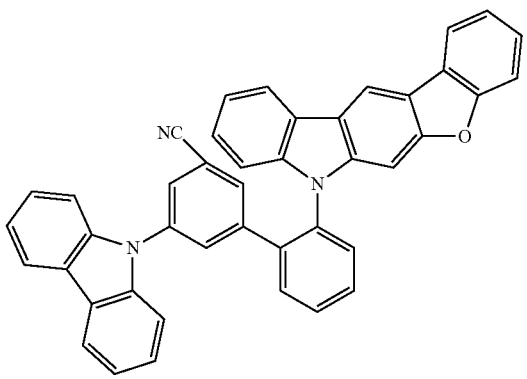
364
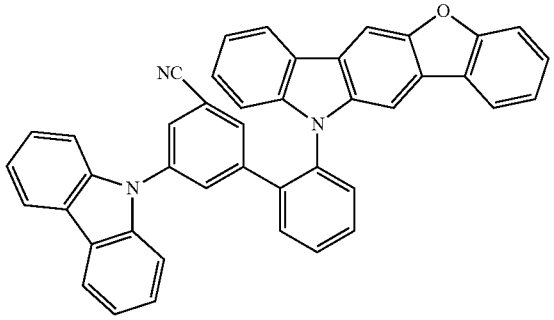

365
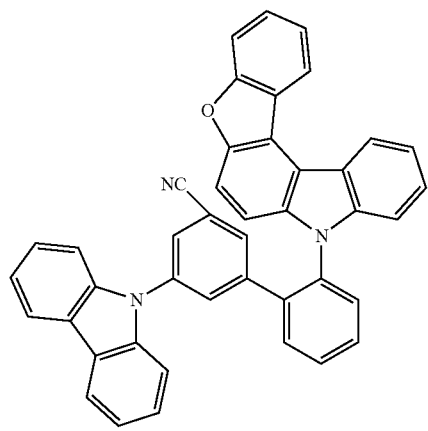
366
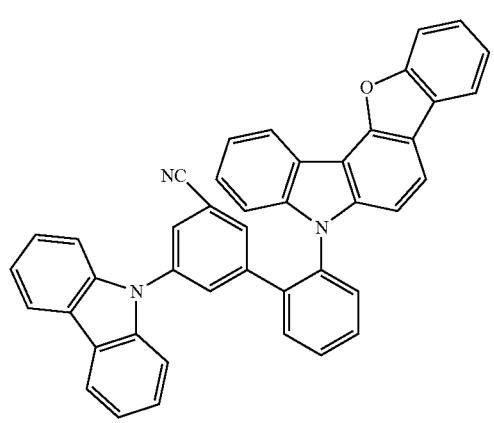
367
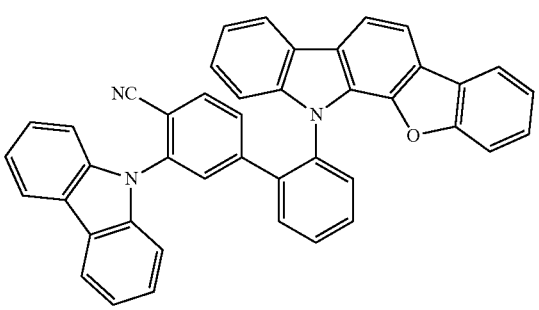
368
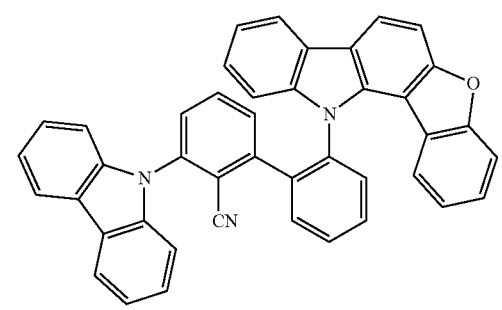
369
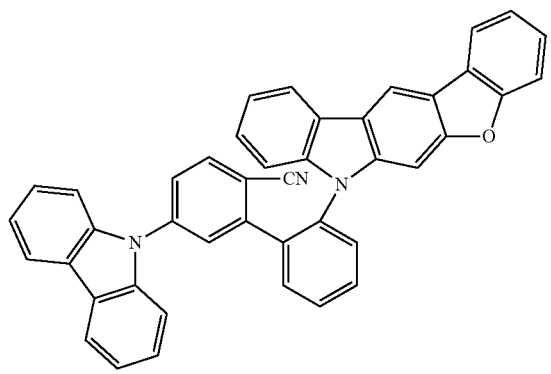
370
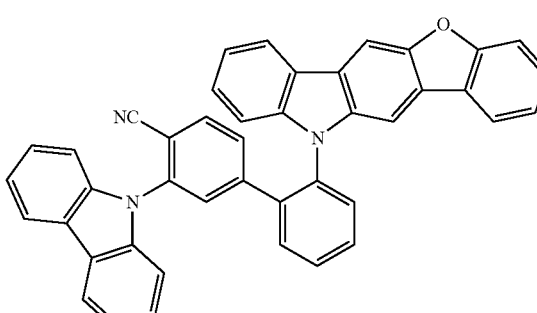
371
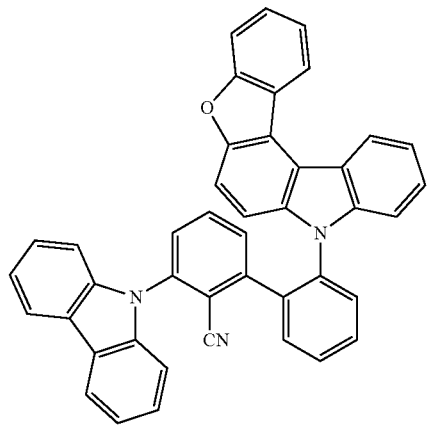
372
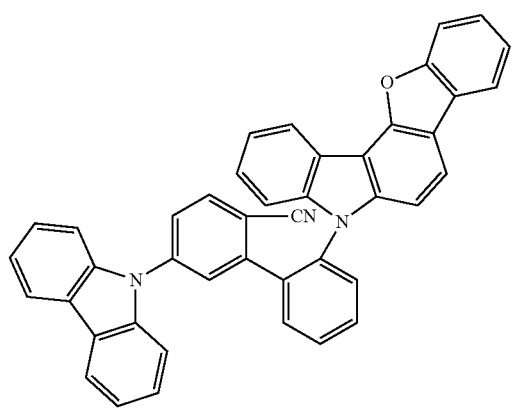

373
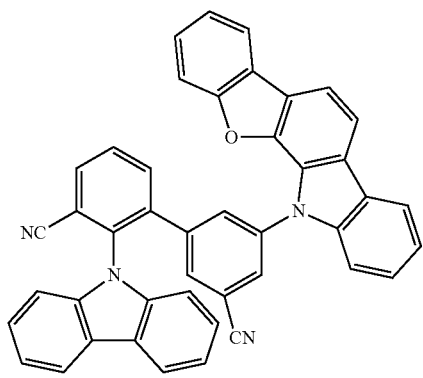
374
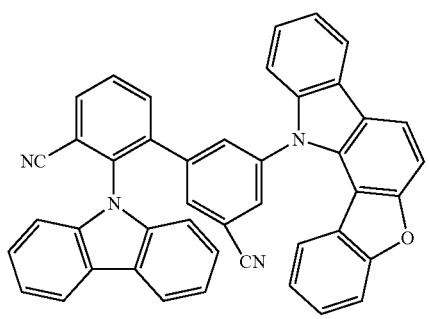
375
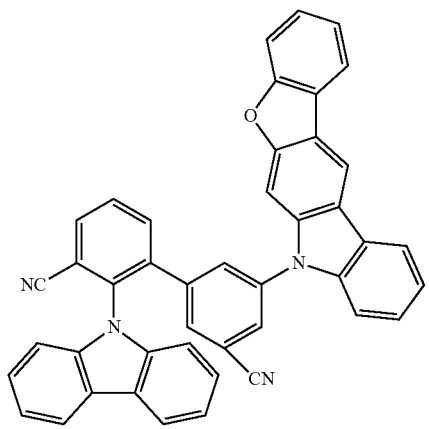
376
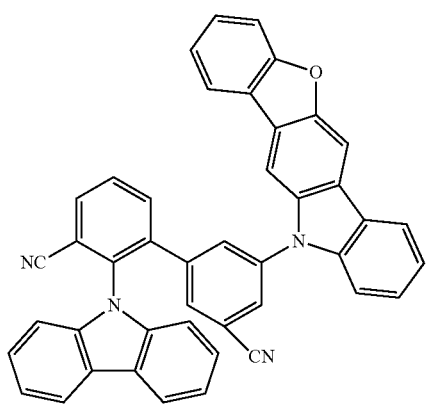
377
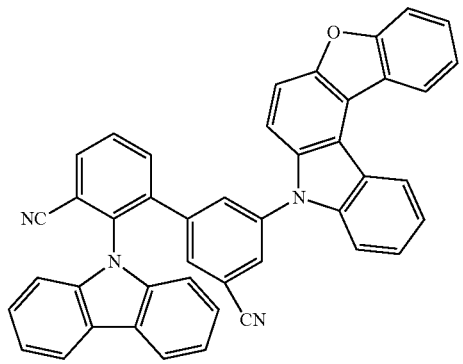
378
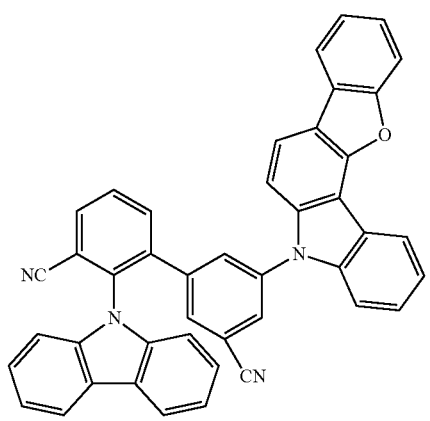
379
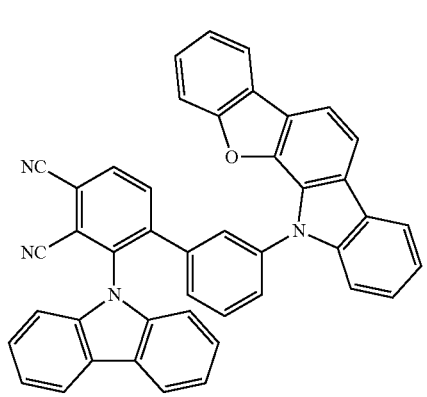
380
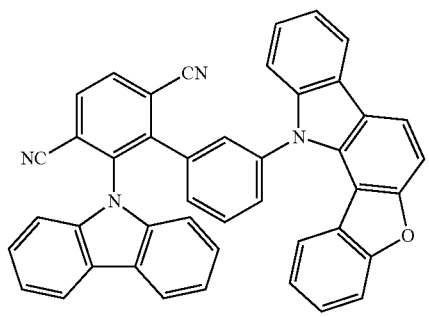

381 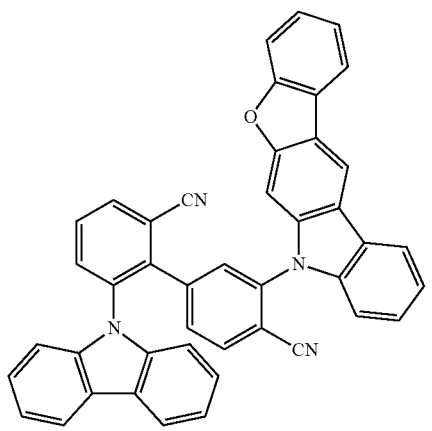
382 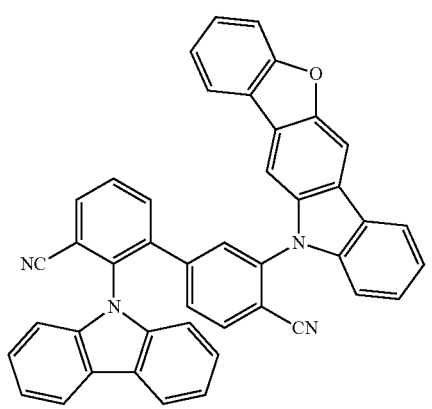
383 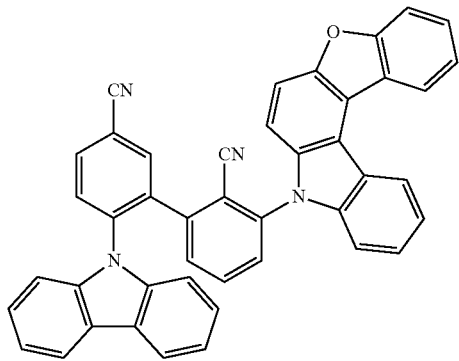
384 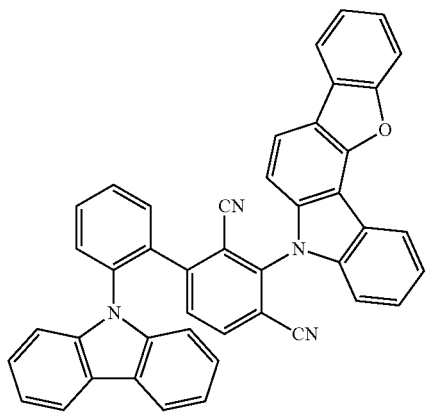
385 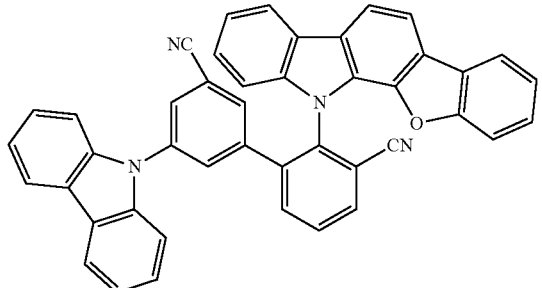
386 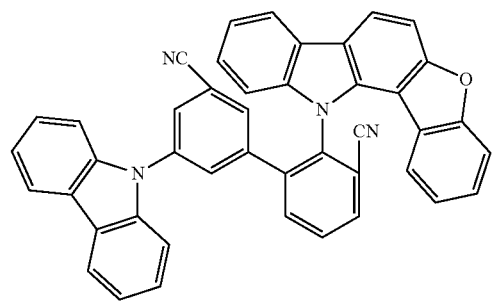
387 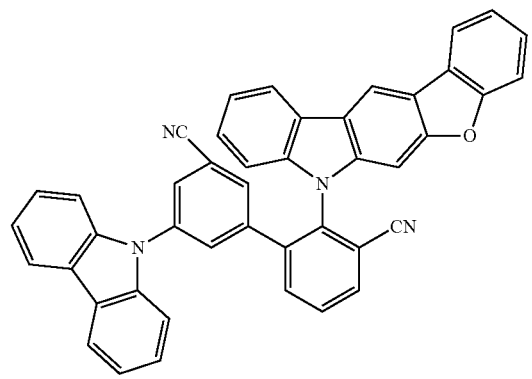
388 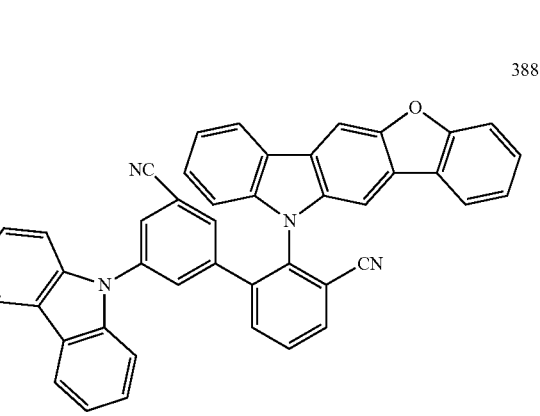

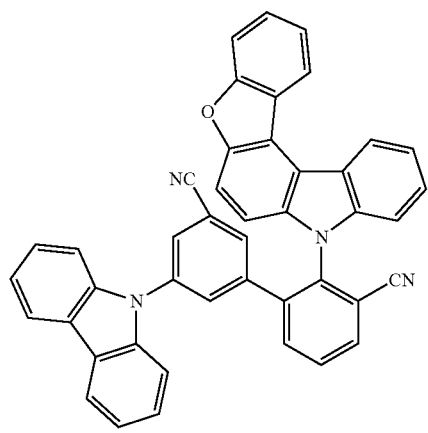
389

393
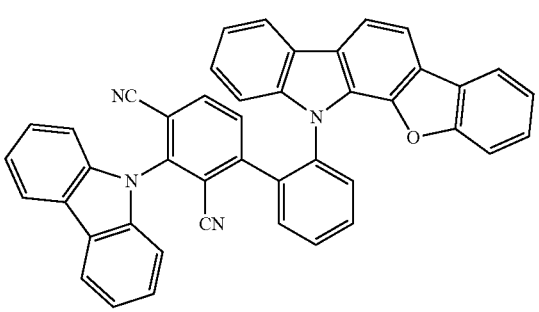
390
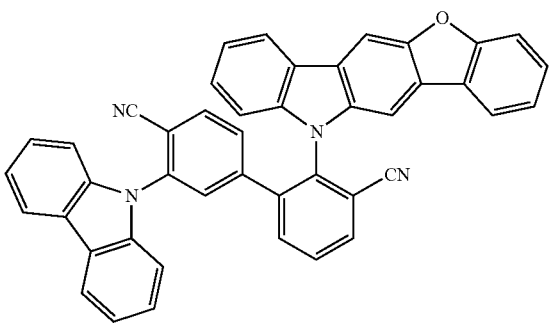
394
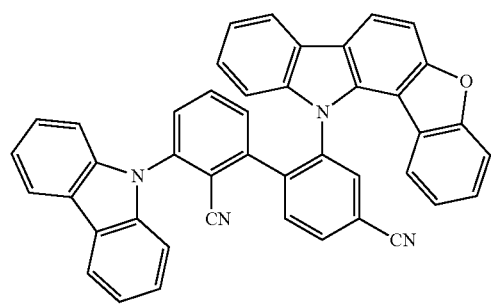
391
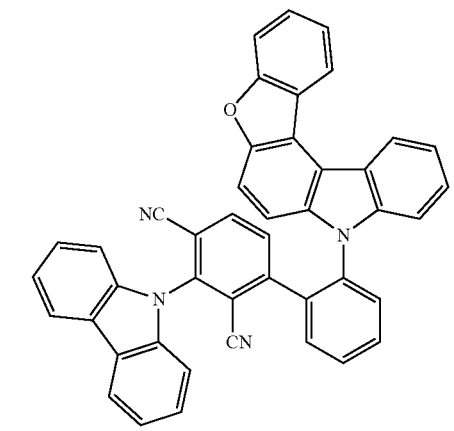
395
392
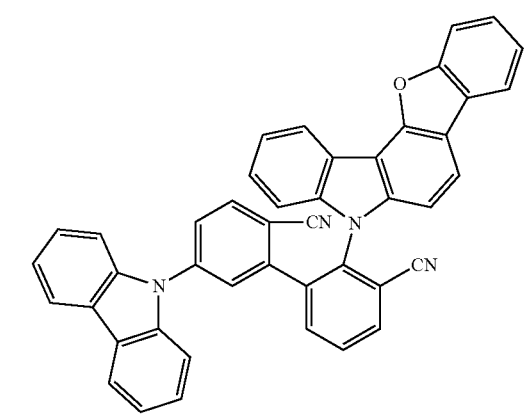
396

113
-continued

397

398

399

400

114
-continued

401

402

403

404

-continued
405
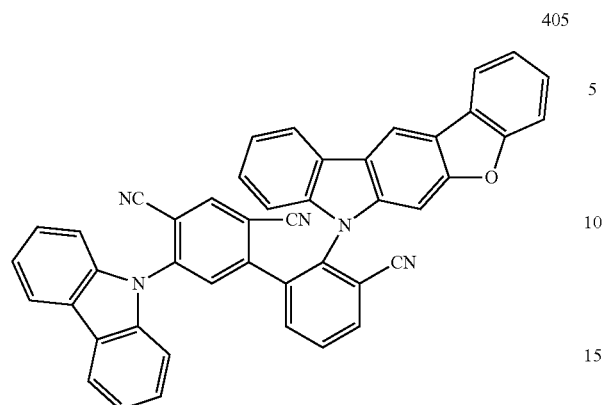
406
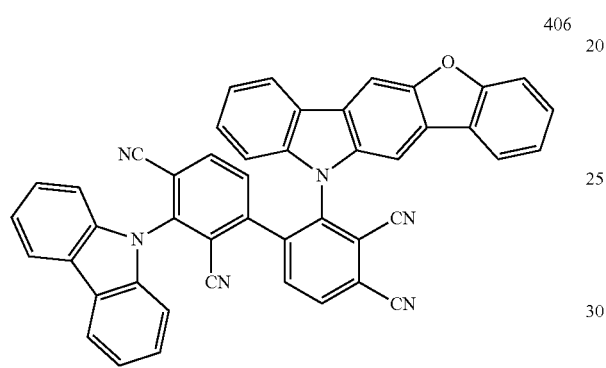
407
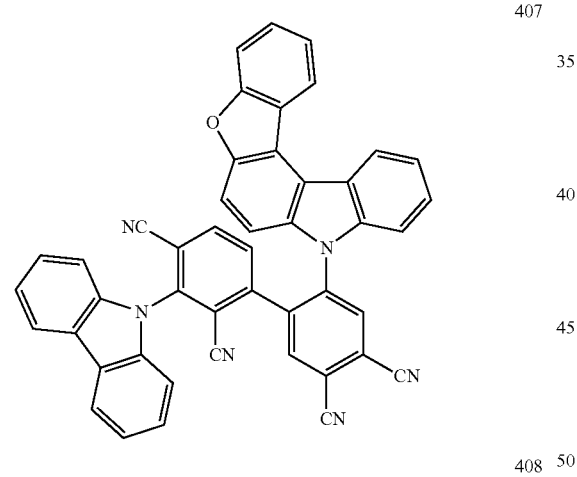
408
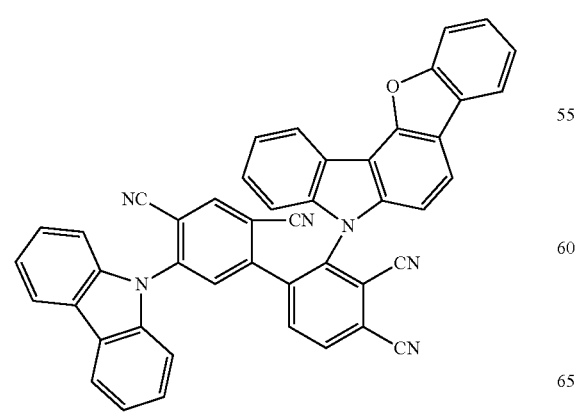
-continued
409
410
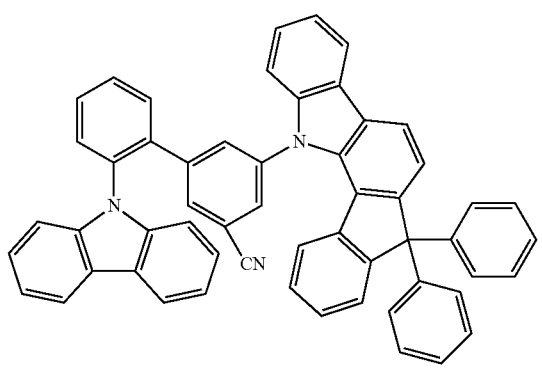
411
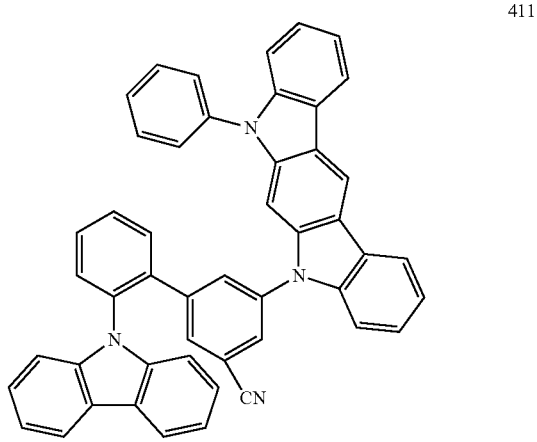
412
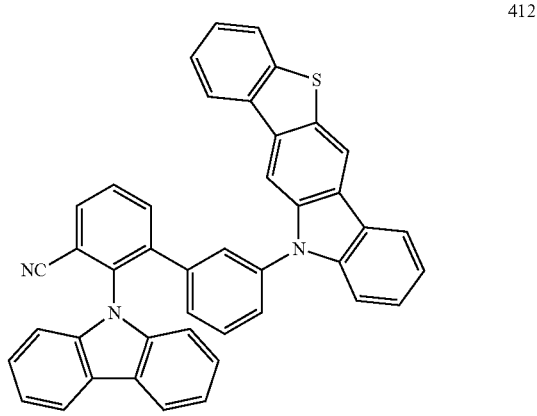

413
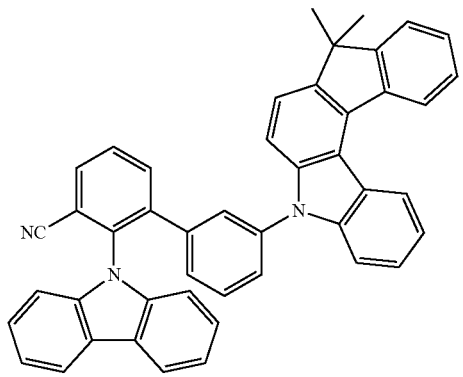
414
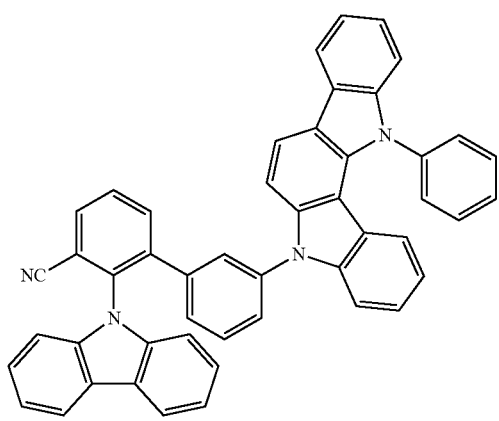
415
416
417
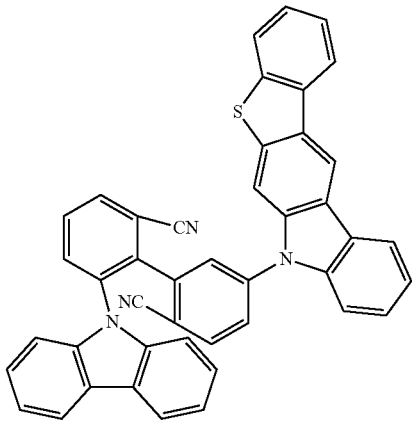
418
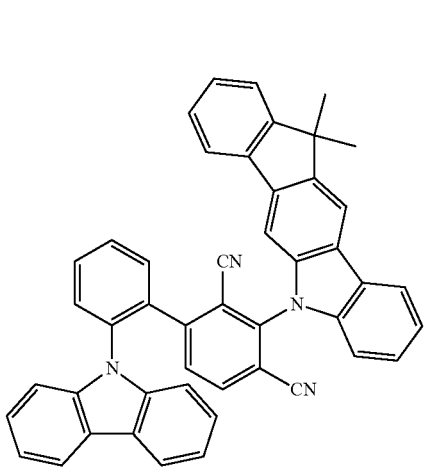
419
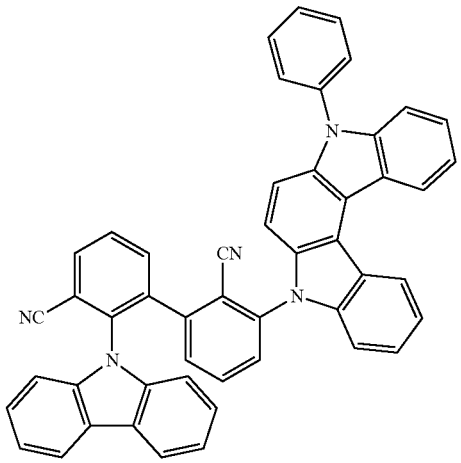

-continued
420
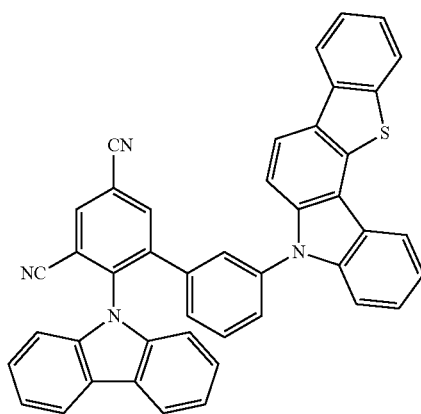
421
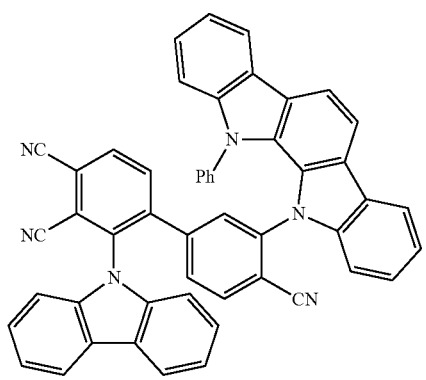
422
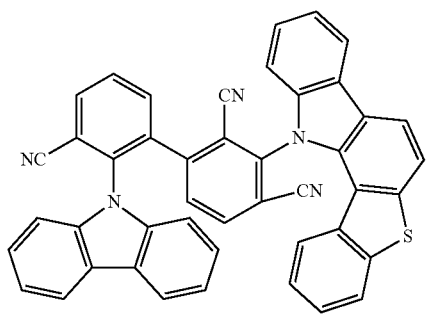
423
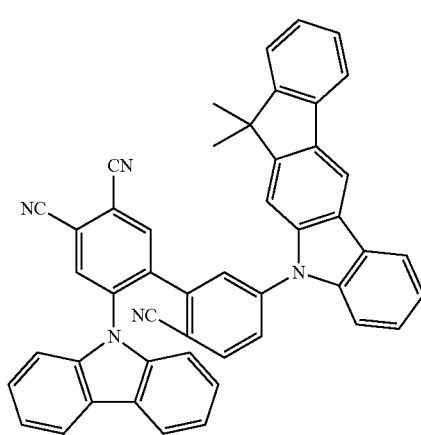
-continued
424
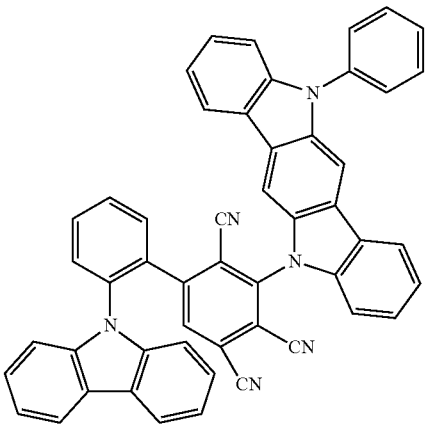
425
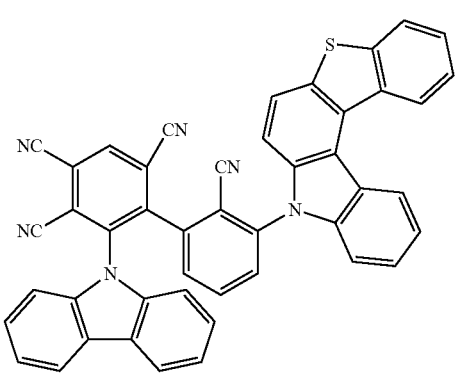
426
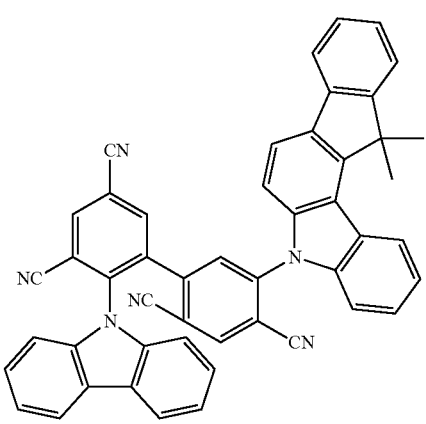
427
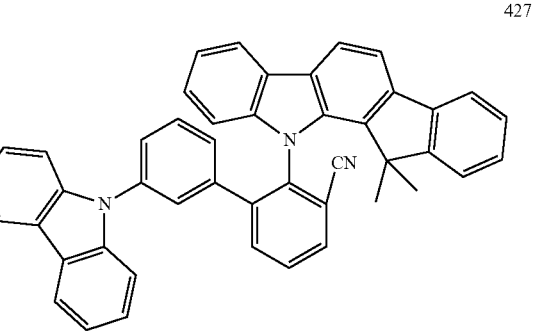

-continued
428
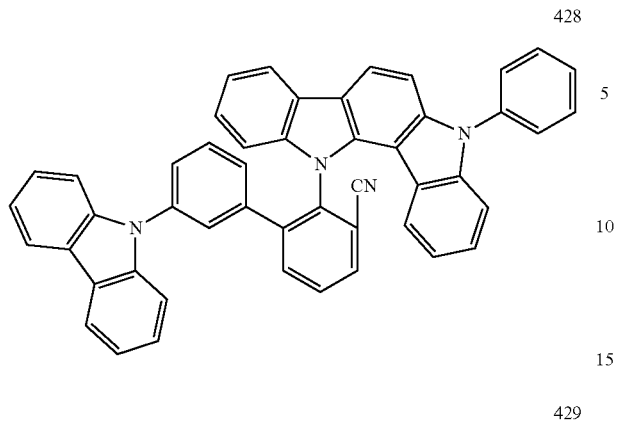
429
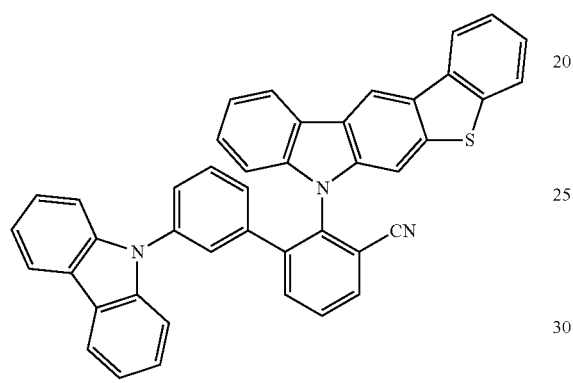
430
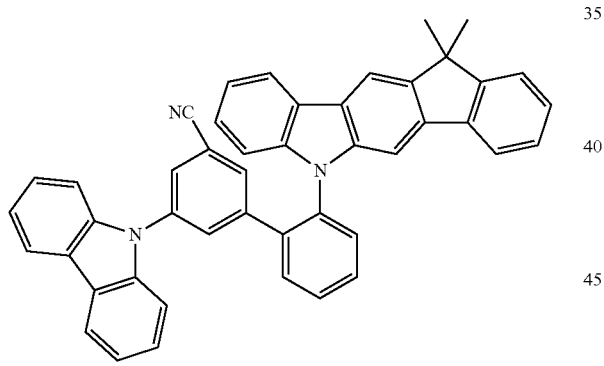
431
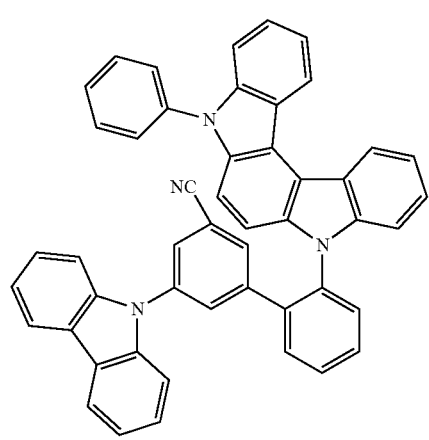
-continued
432
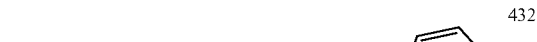
433
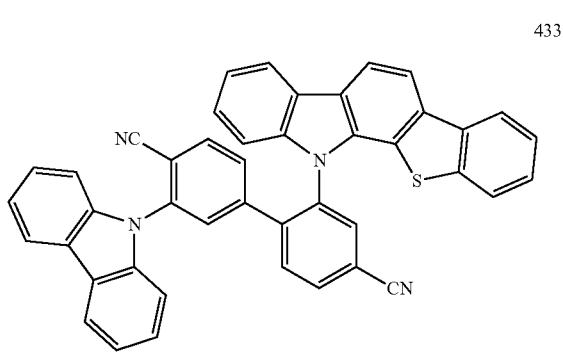
434
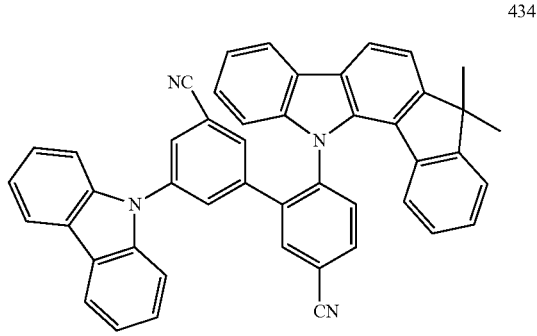
435
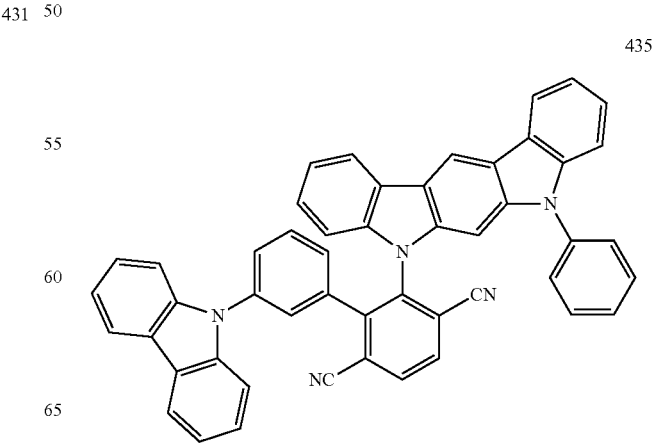

-continued
436
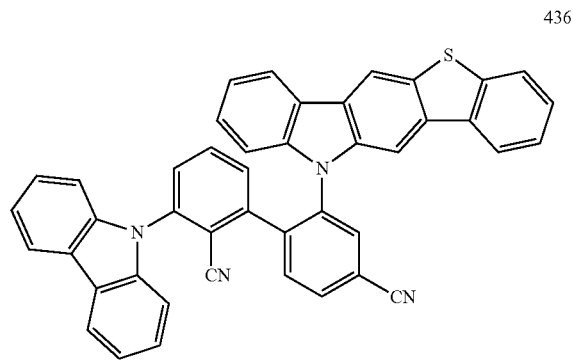
437
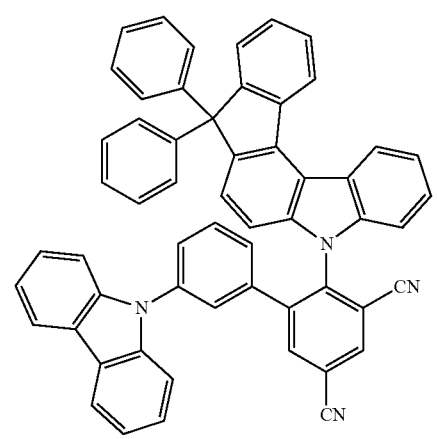
438
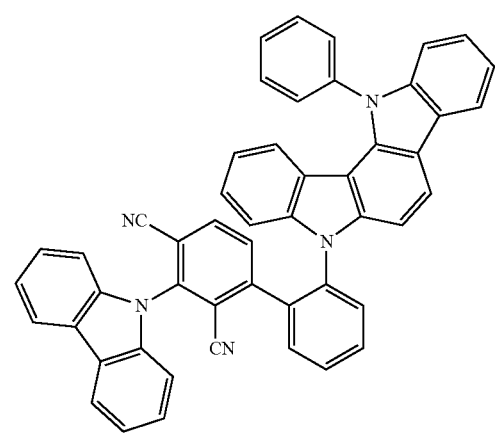
439
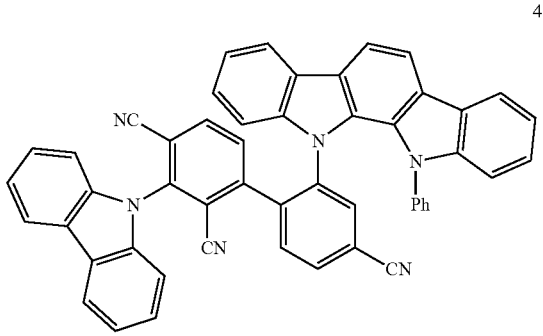
-continued
440
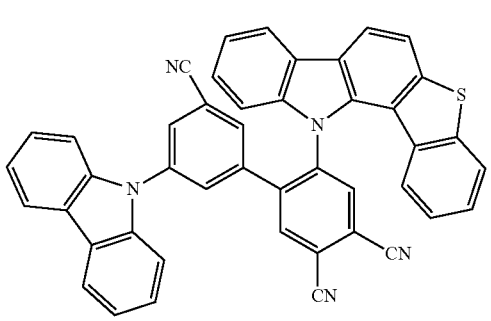
441
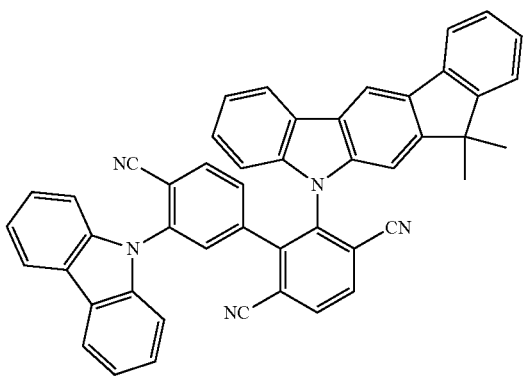
442
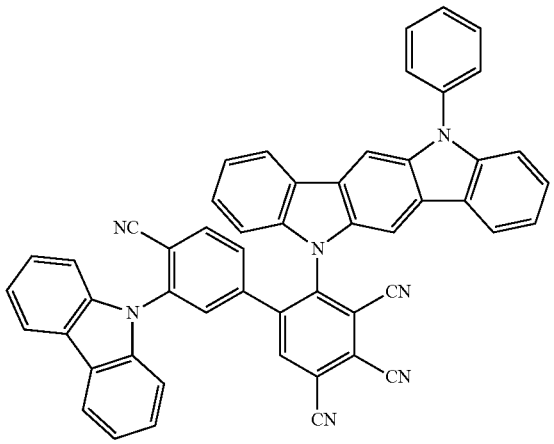
443
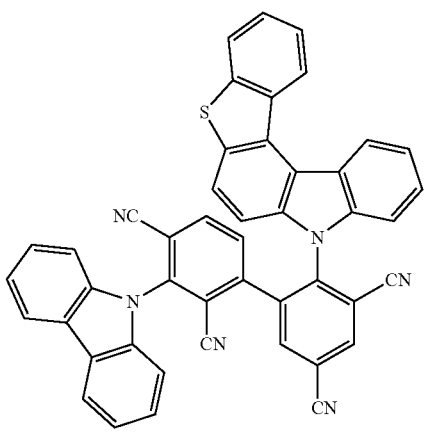

444
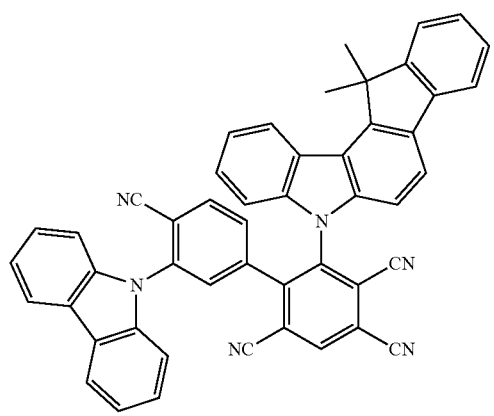
445
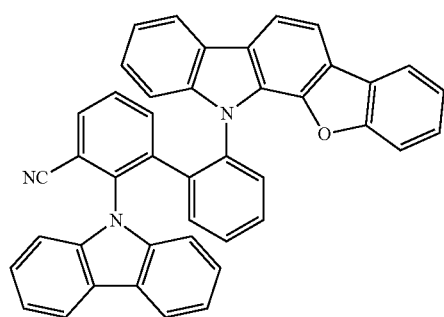
446
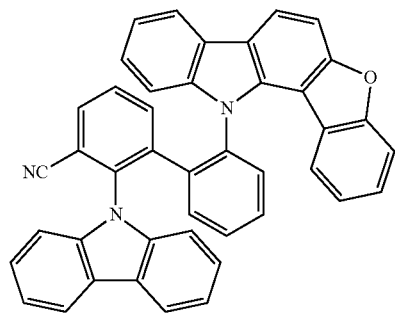
447
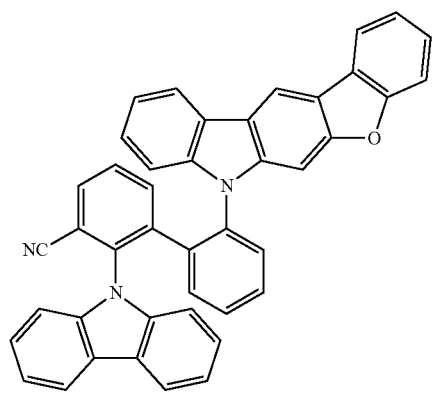
448
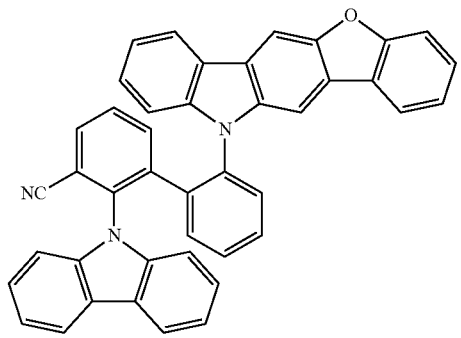
449
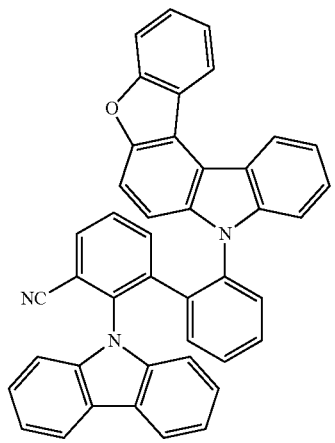
450
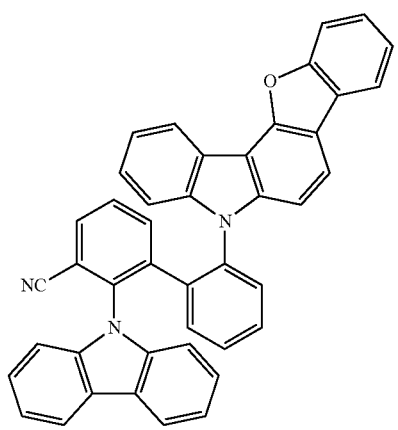
451
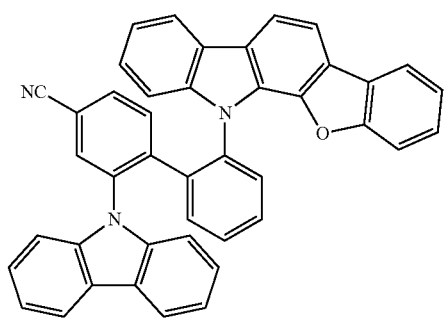

127
-continued
452
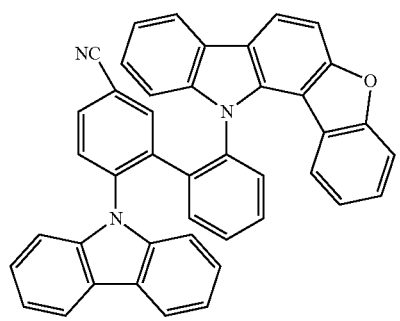
453
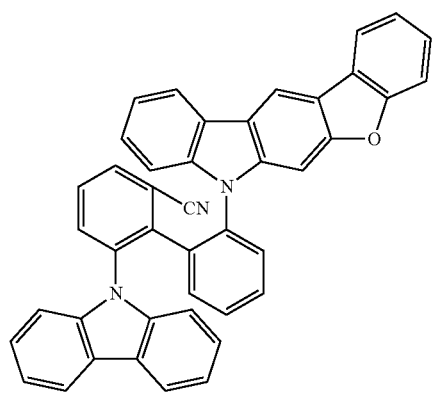
454
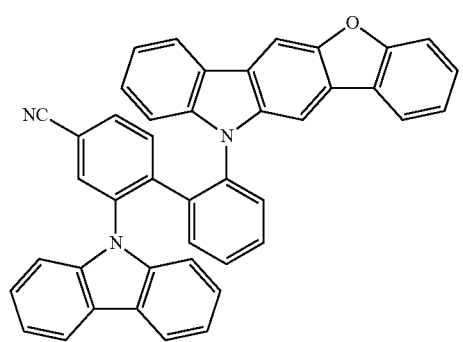
455
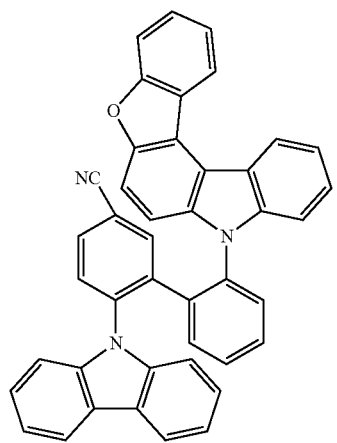
128
-continued
456
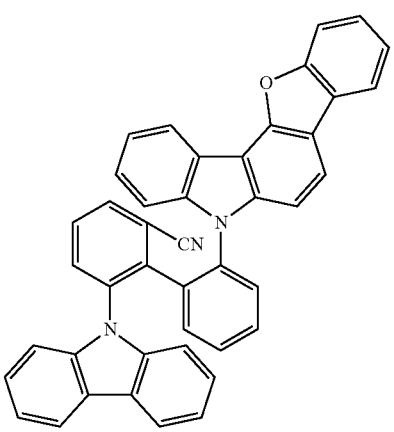
457
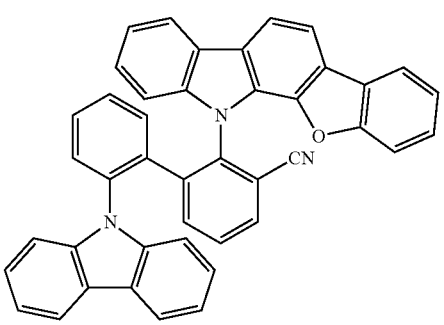
458
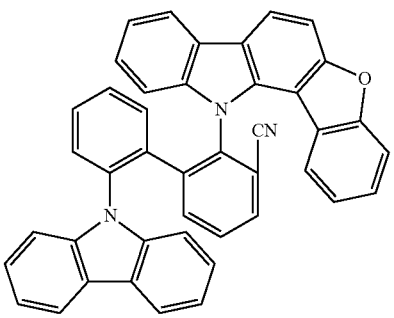
459
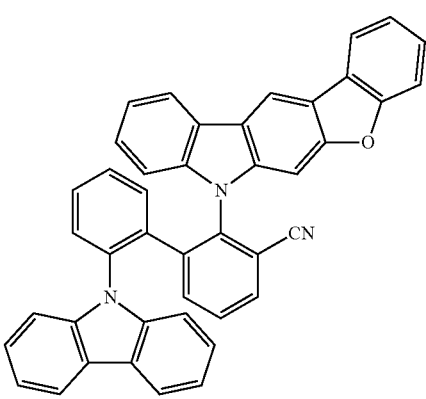

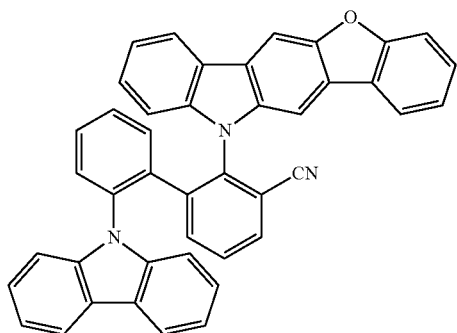
460
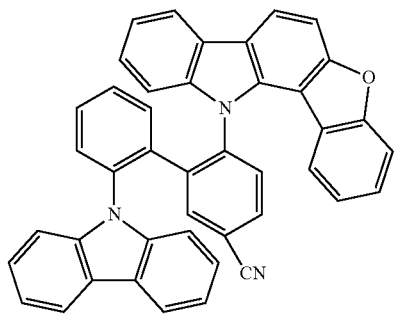
464
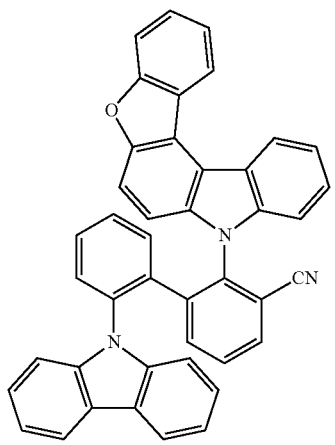
461
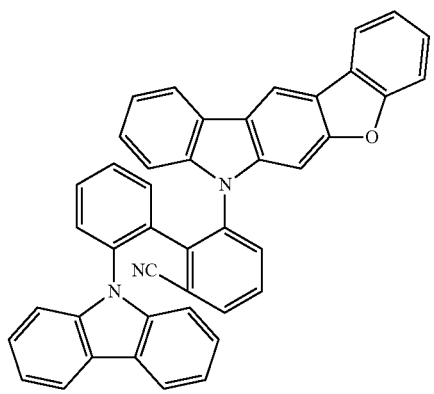
465
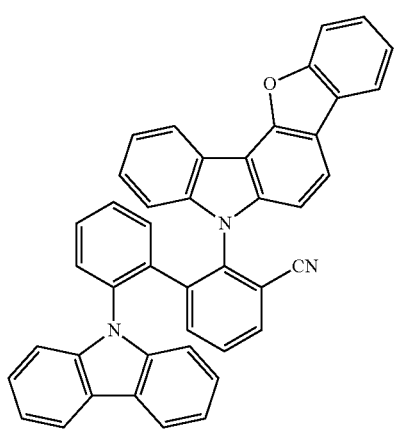
462
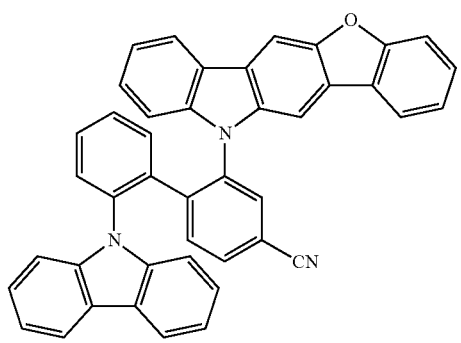
466
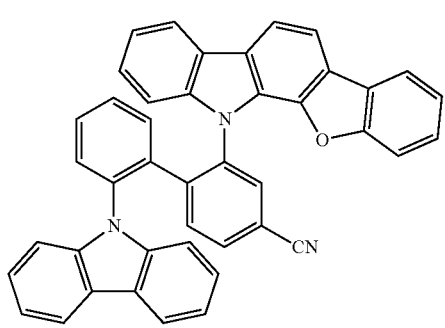
463
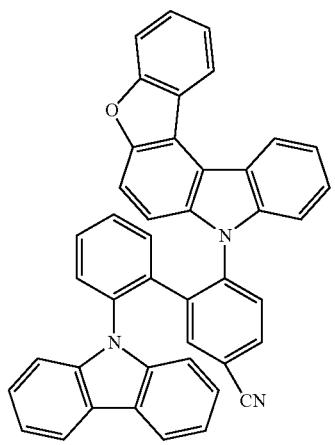
467

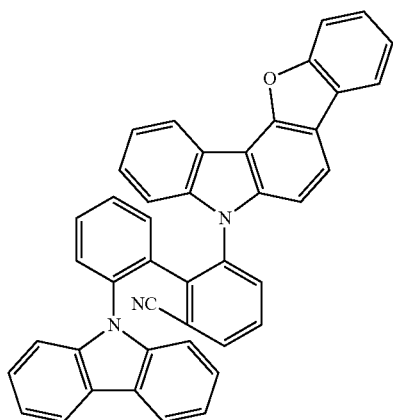
468
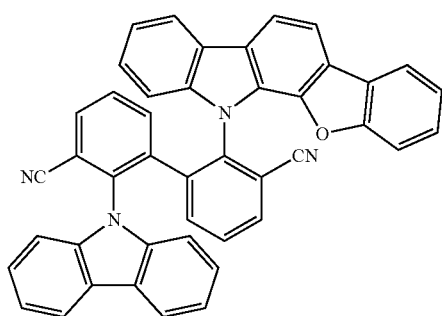
469
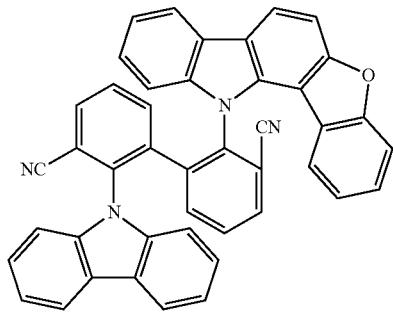
470
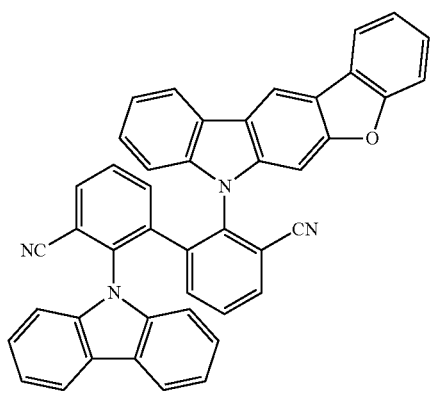
471
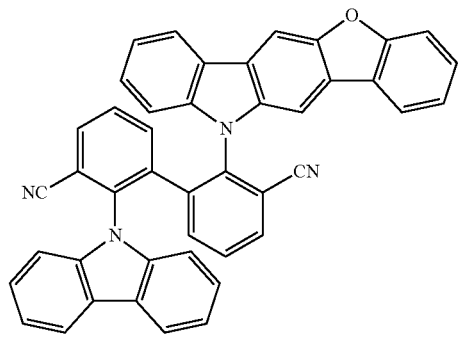
472
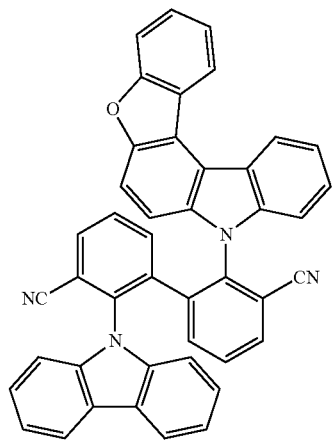
473
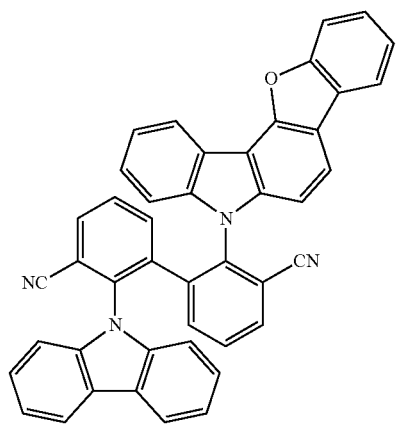
474
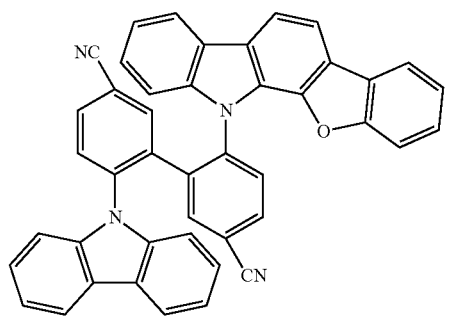
475

476 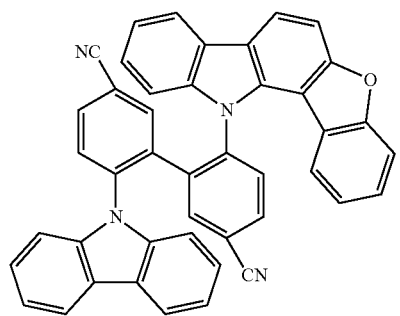
477 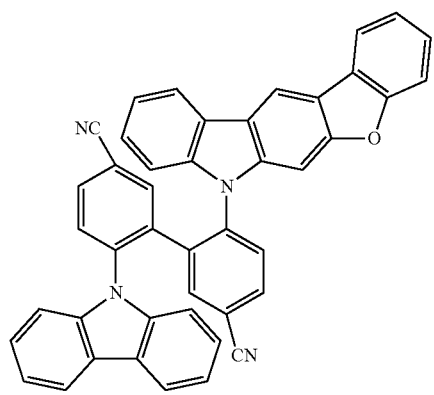
478 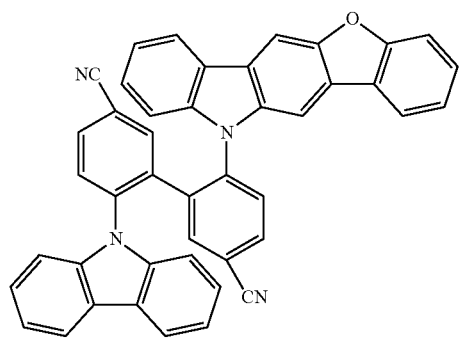
479 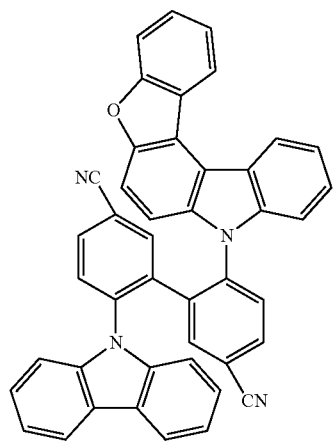
480 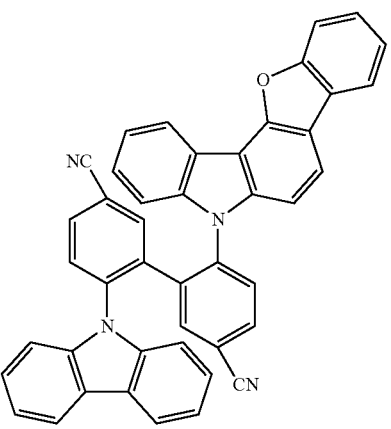
481 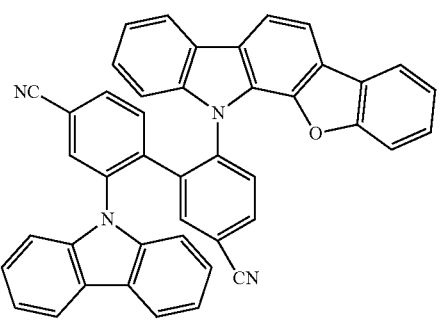
482 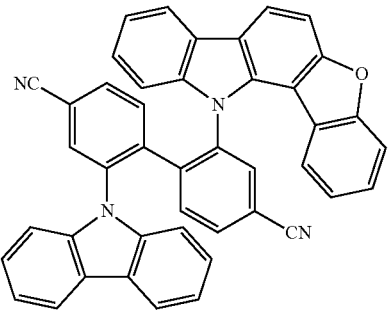
483 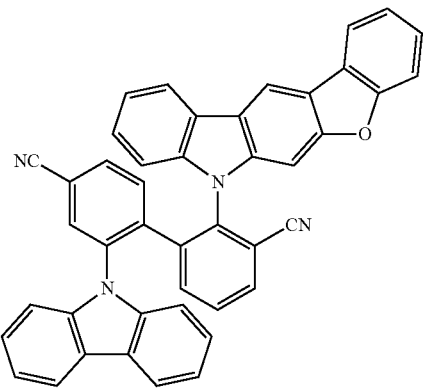

484
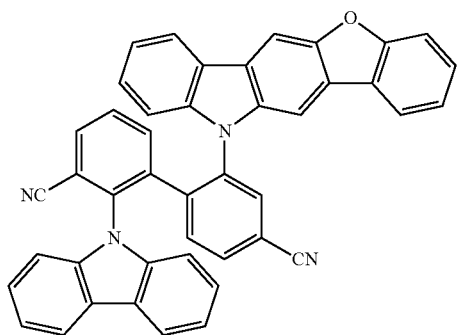
485
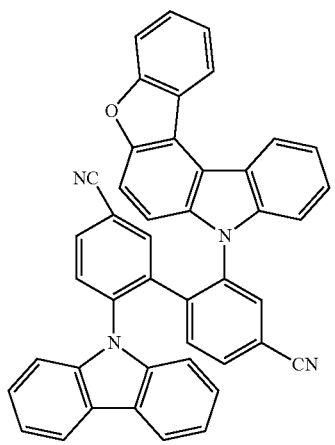
486
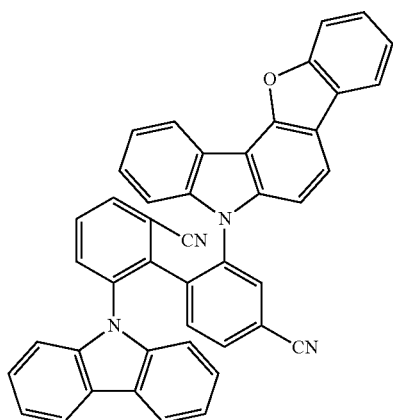
487
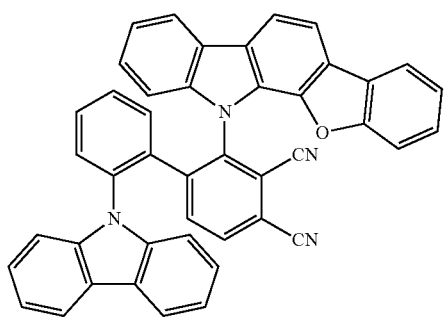
488
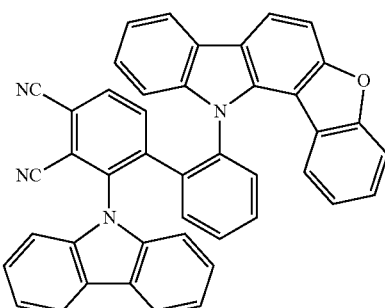
489
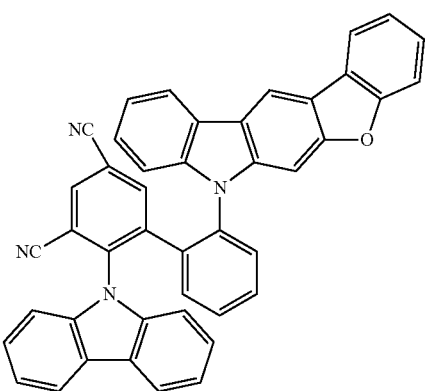
490
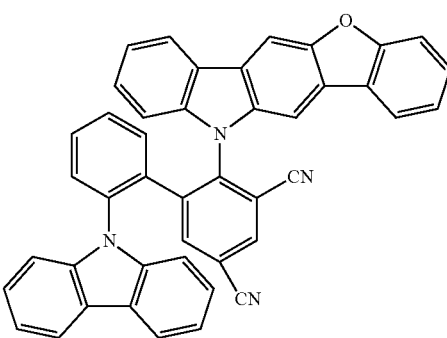
491
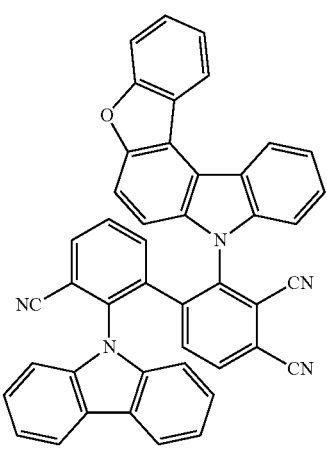

137
-continued
492
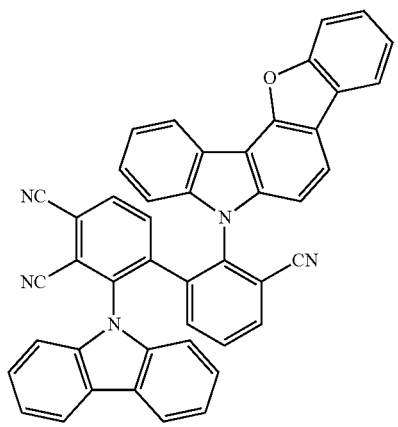
493
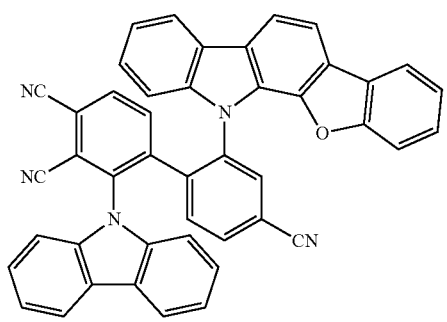
494
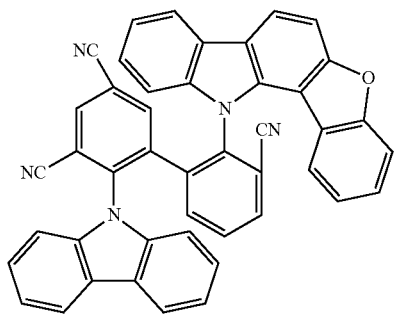
495
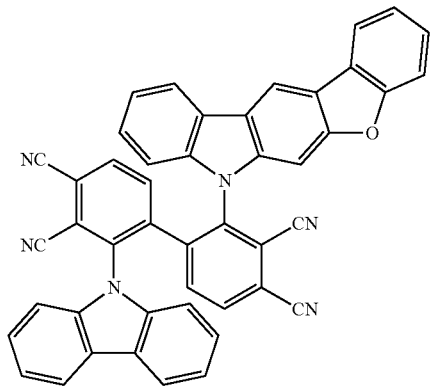
138
-continued
496
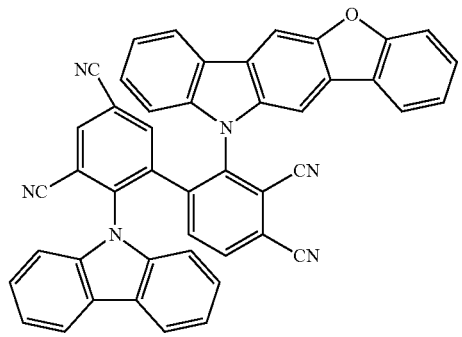
497
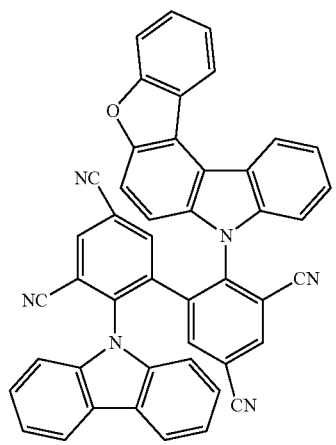
498
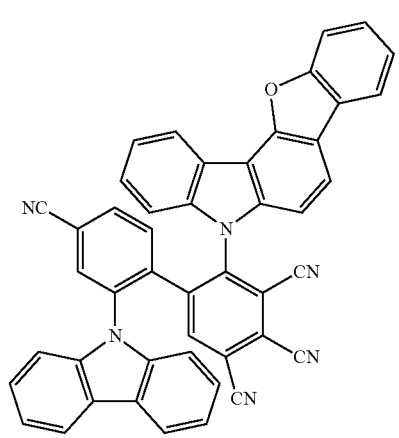
499
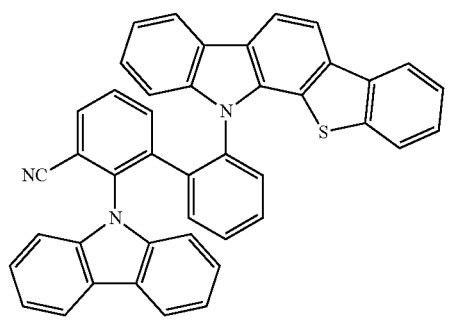

-continued
500
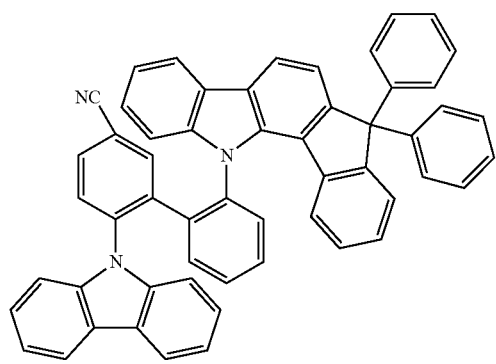
501
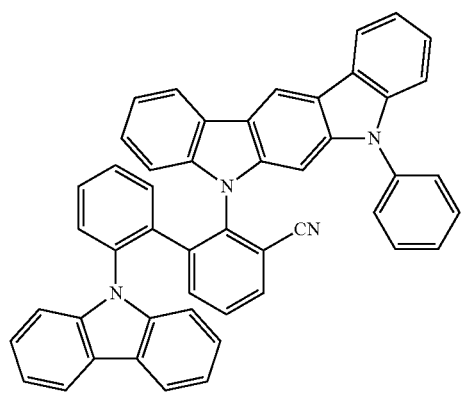
502
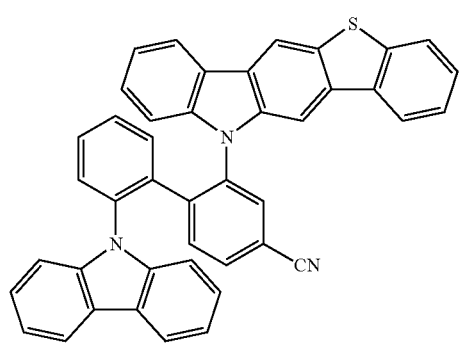
503
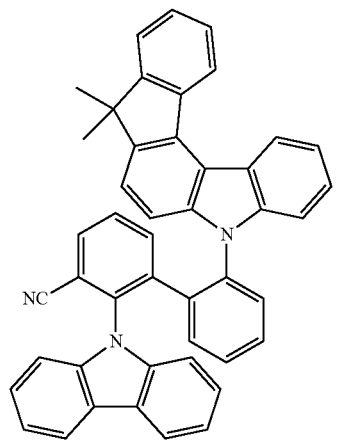
-continued
504
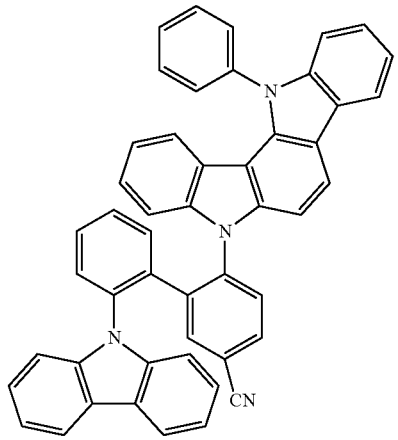
505
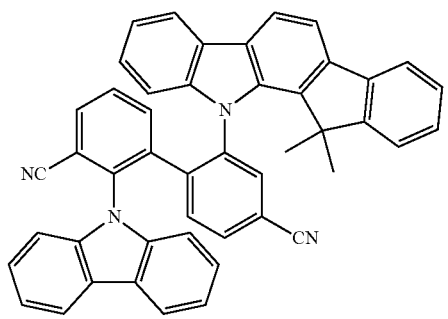
506
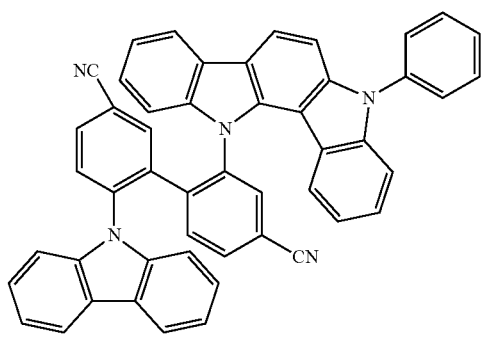
507
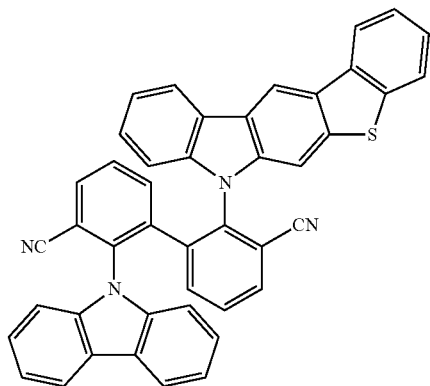

508
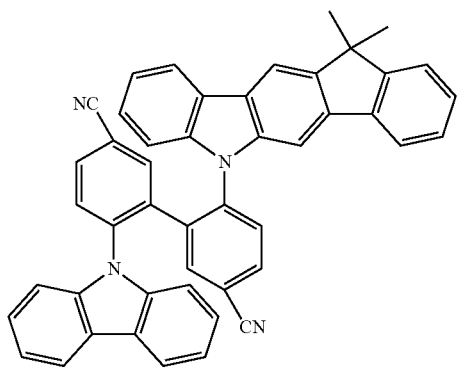
509
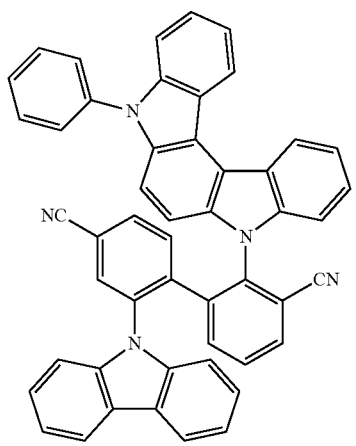
510
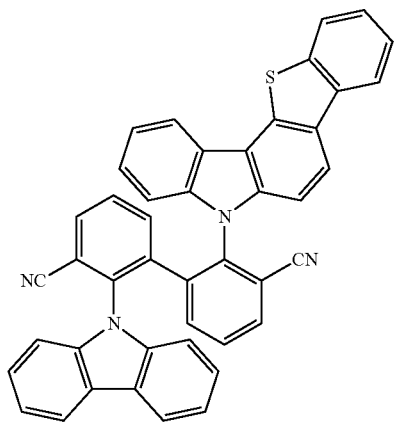
511
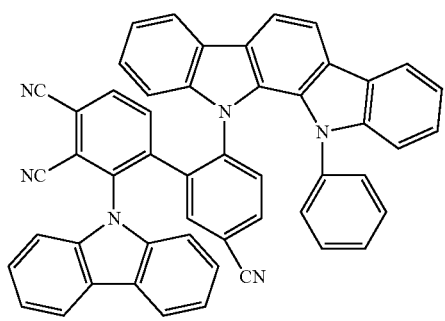
512
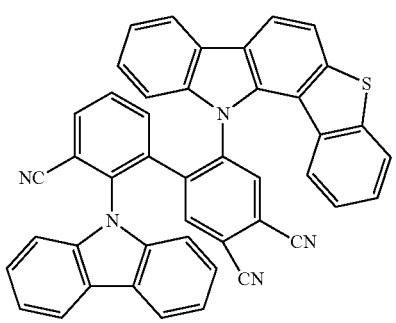
513
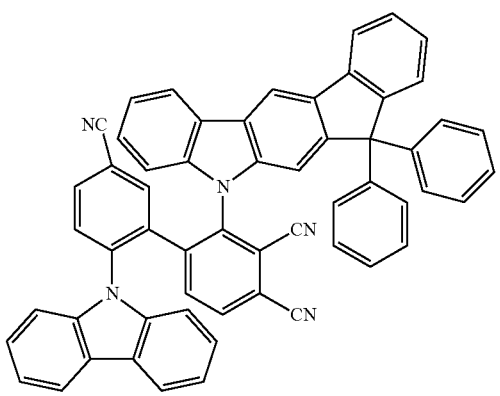
514
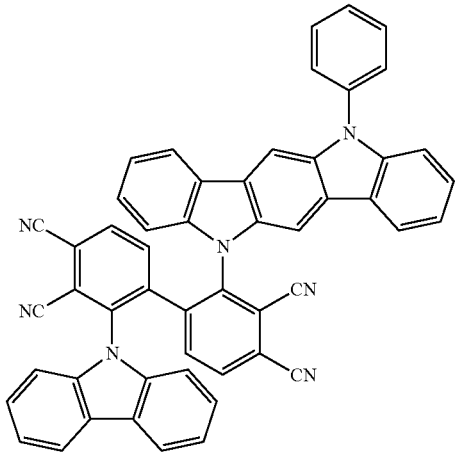
515
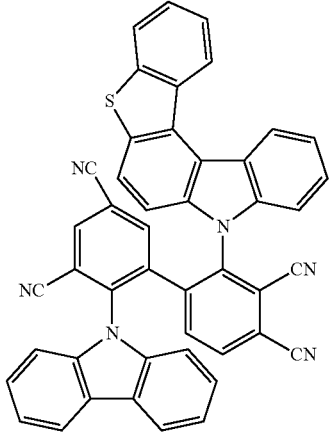

516 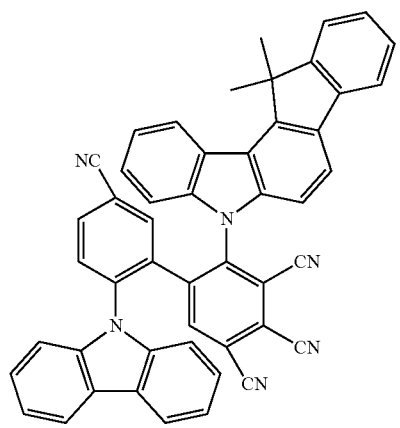
517 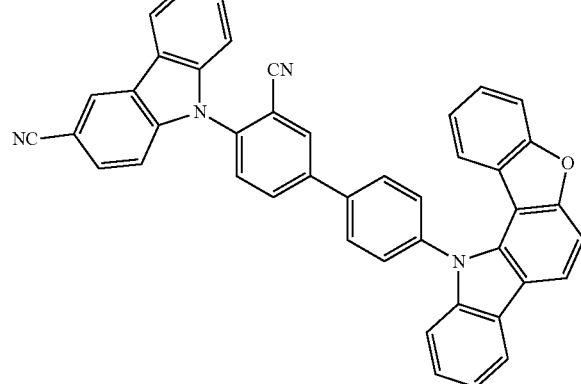
518 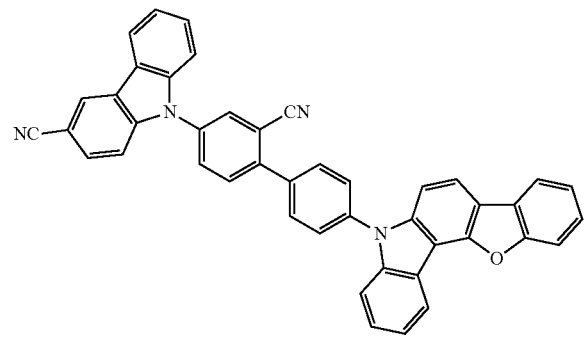
519 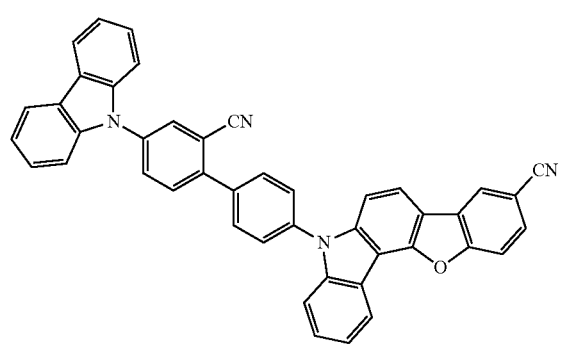
520 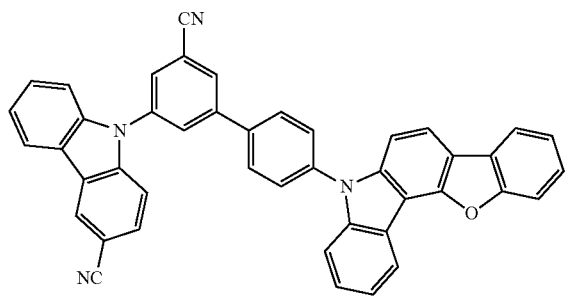
521 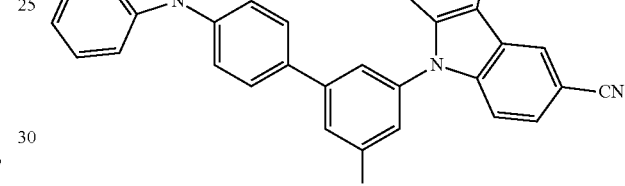
522 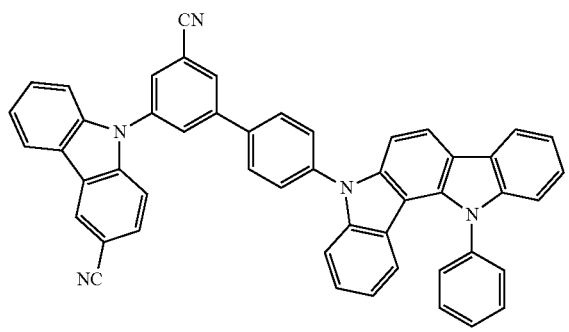
523 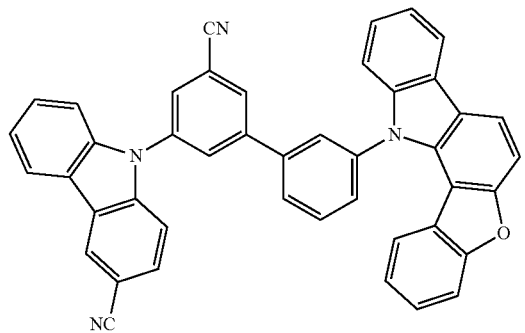

524
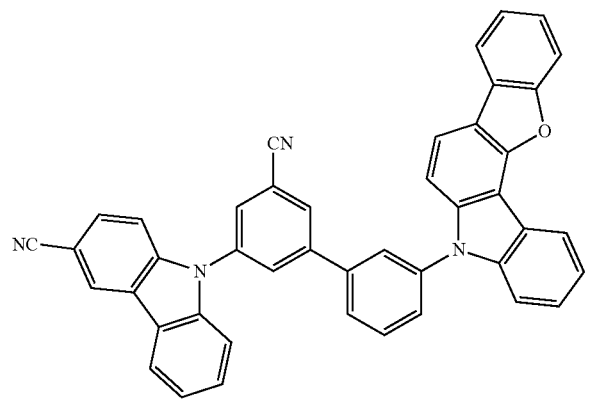
525
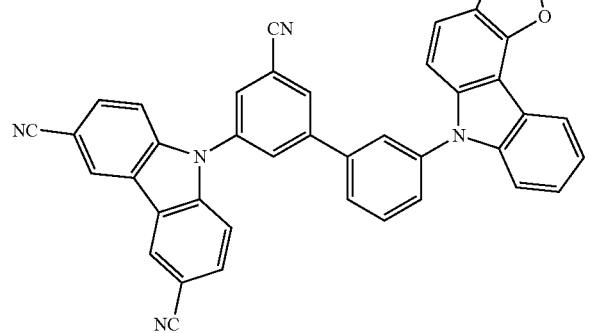
526
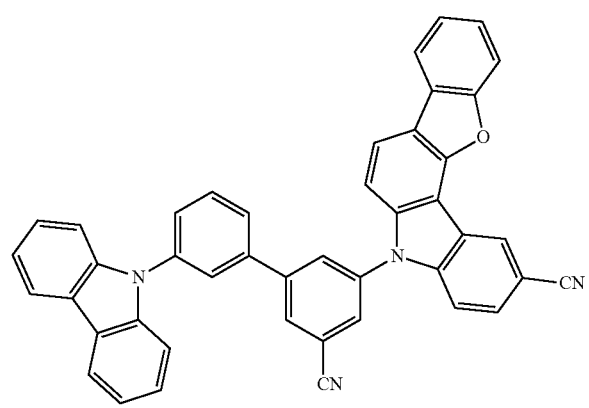
527
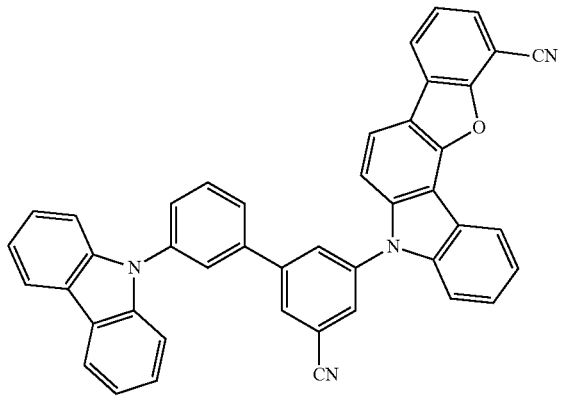
528
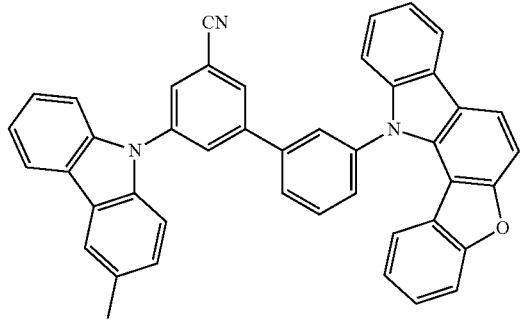
529
530
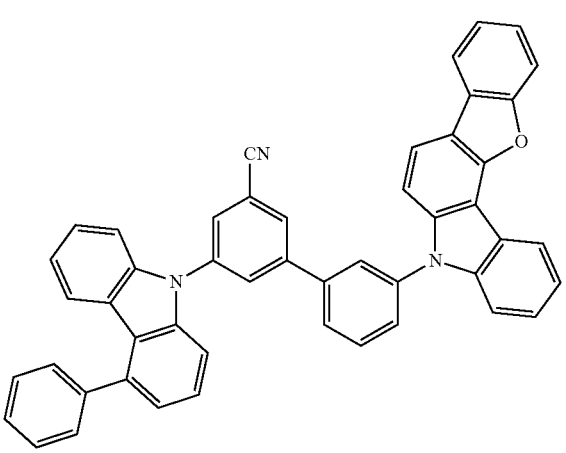

-continued
531
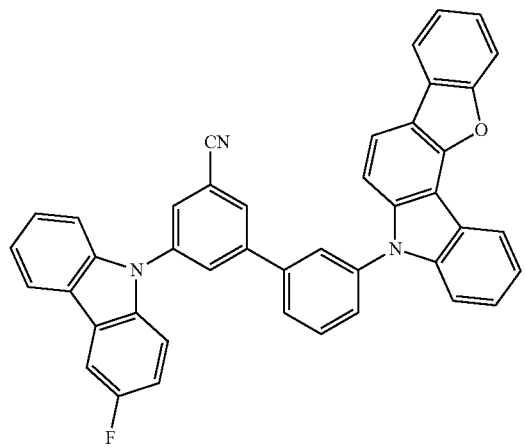
532
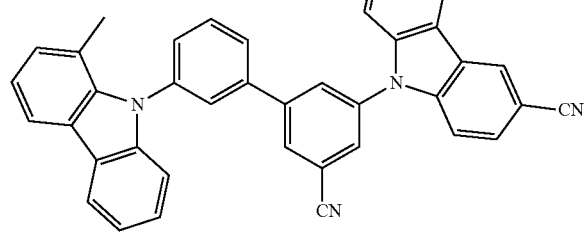
533
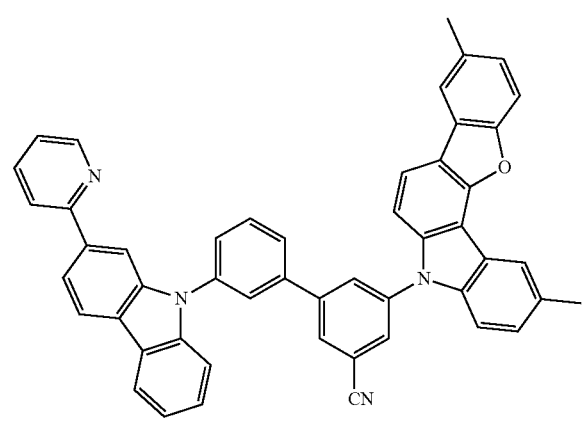
-continued
534
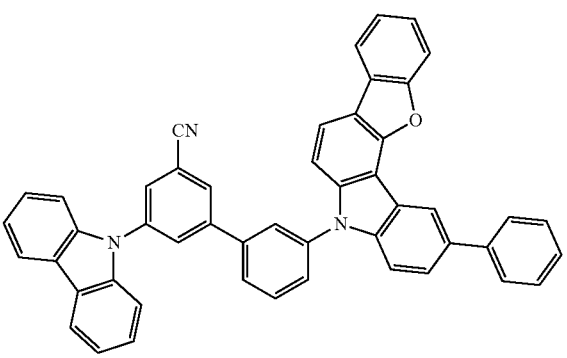
535
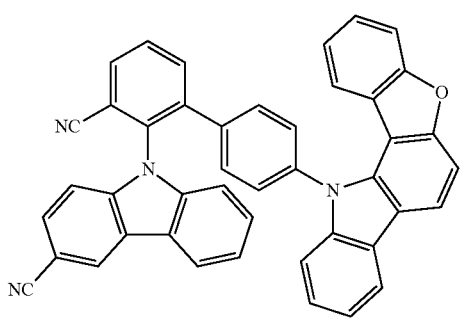
536
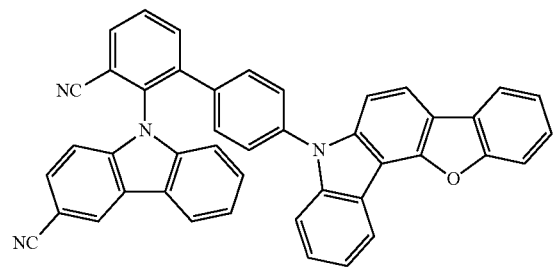
537
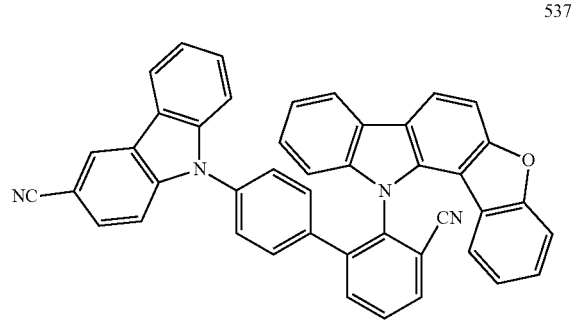

538
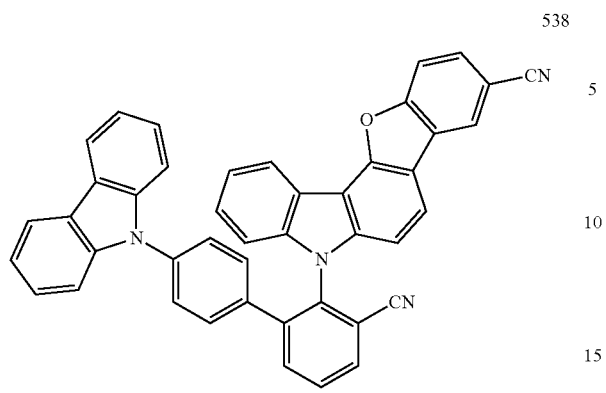
539
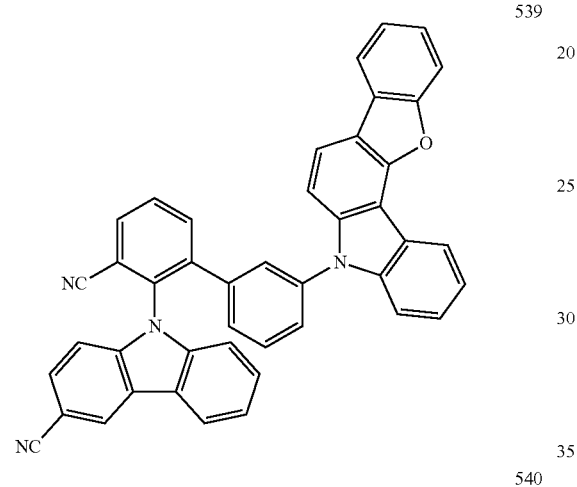
540
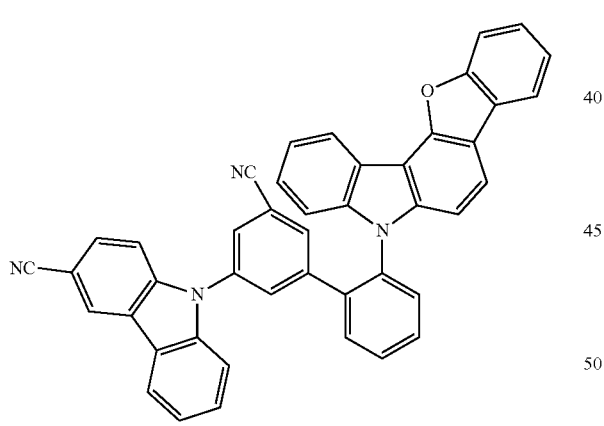
541
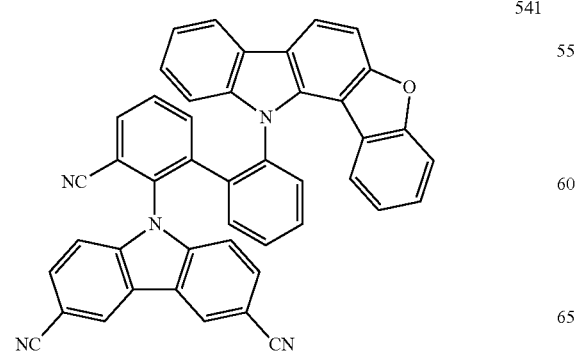
542
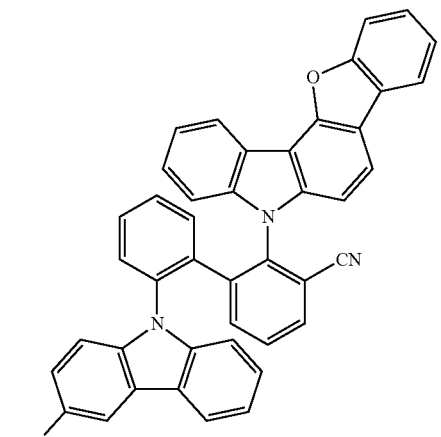
543
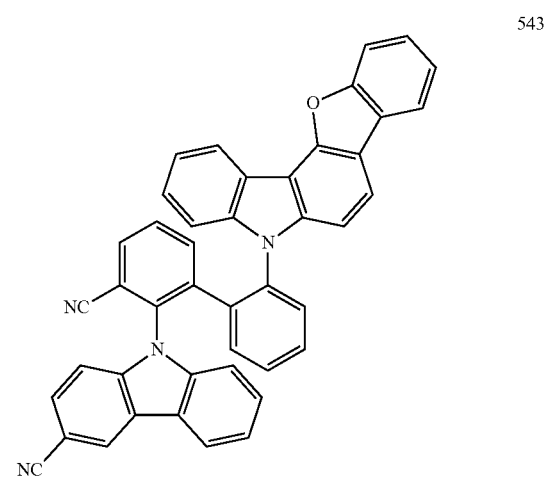
544
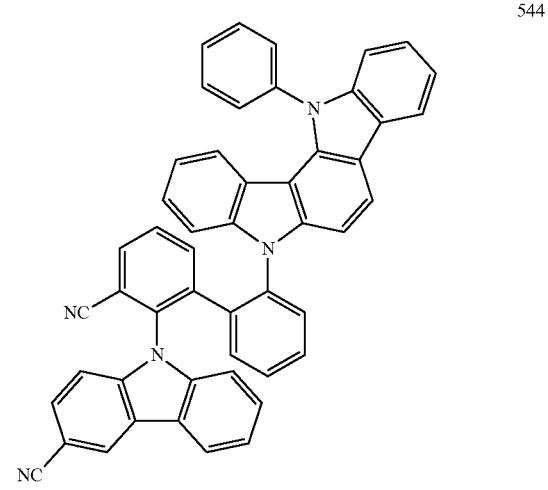

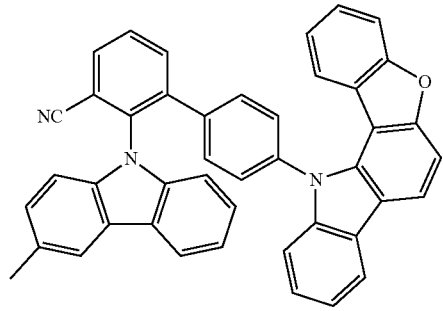
545
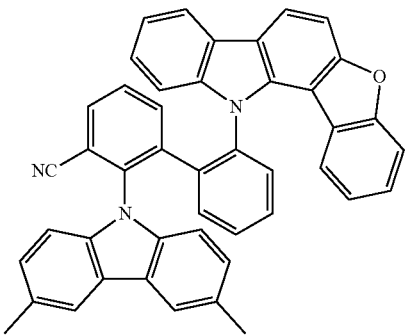
549
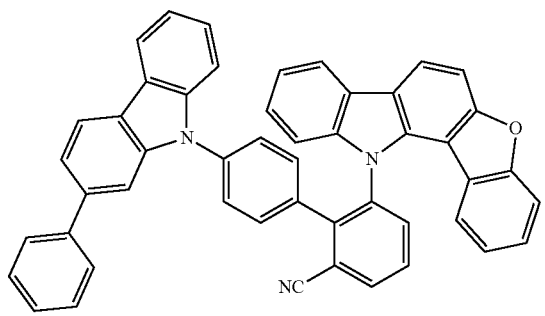
546
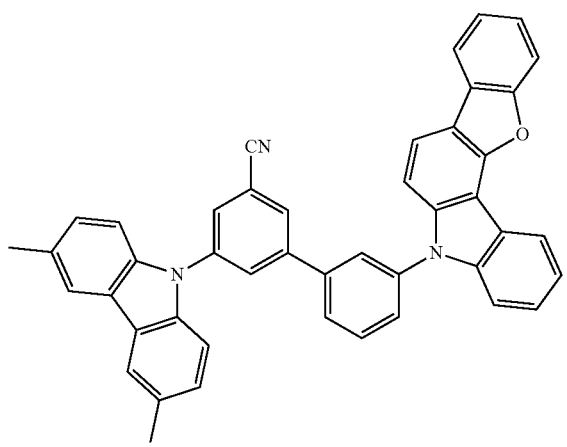
550
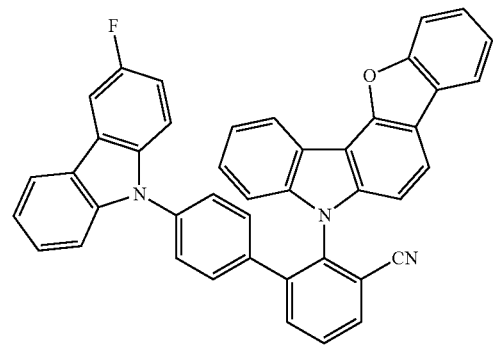
547
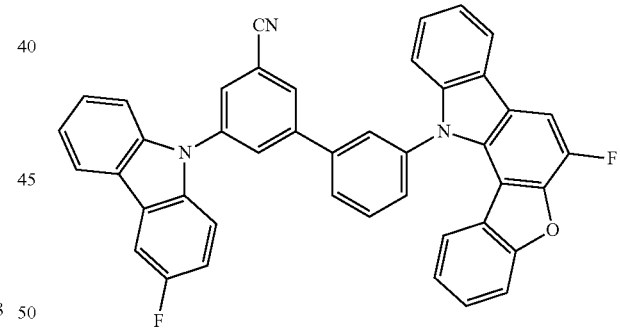
551
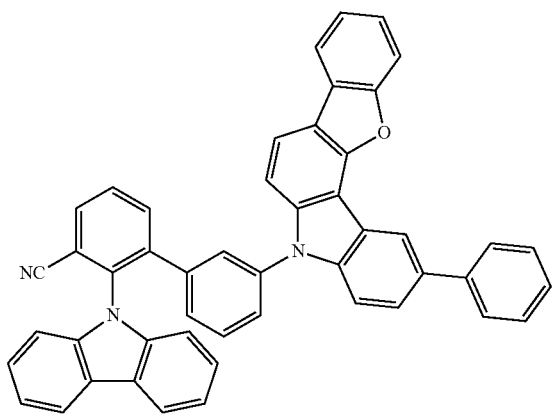
548
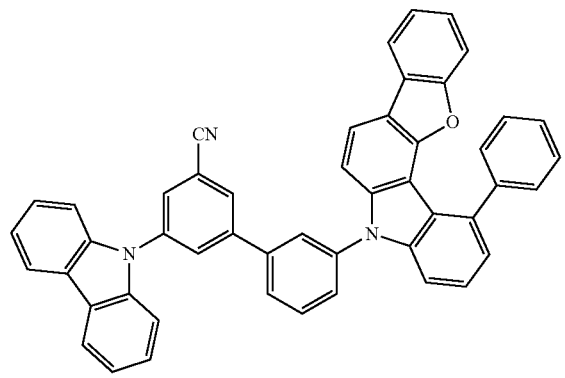
552

553
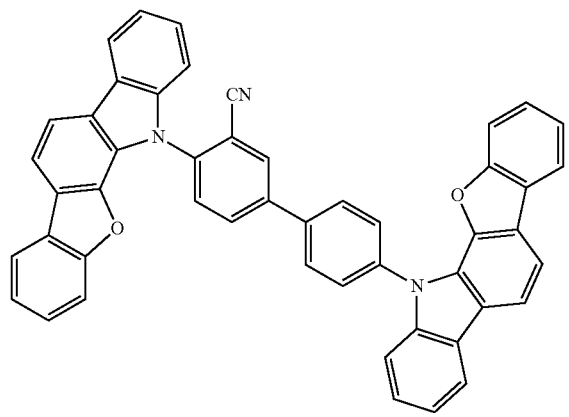
554
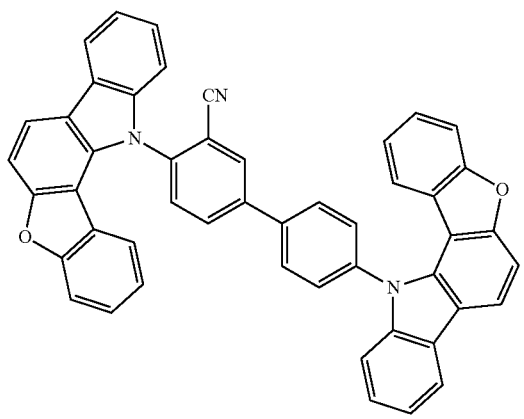
555
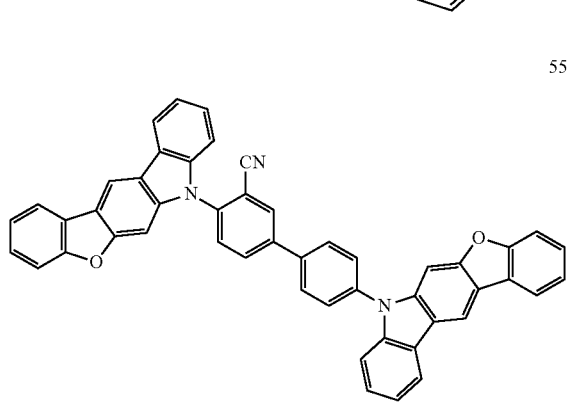
556
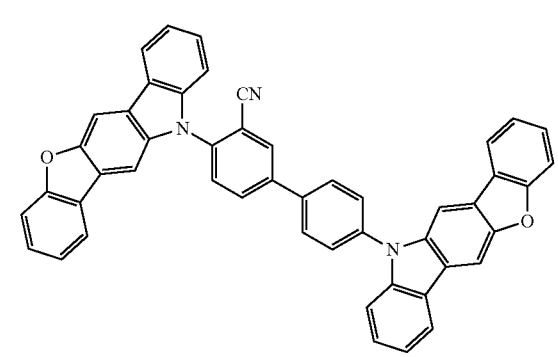
557
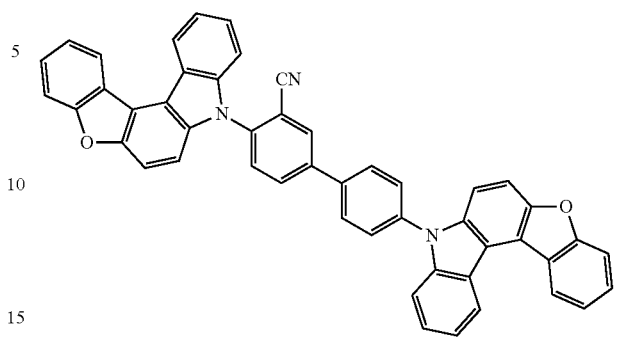
558
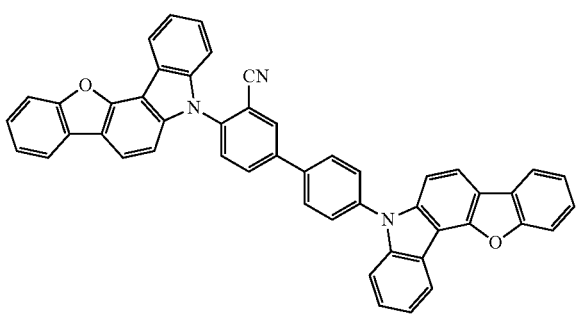
559
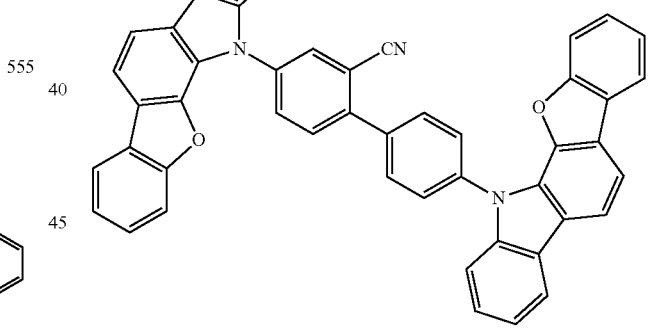
560
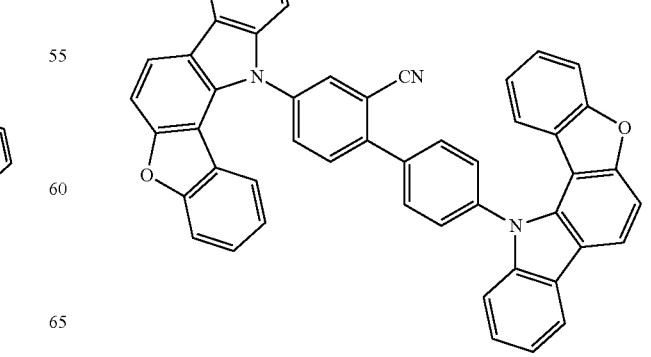

561
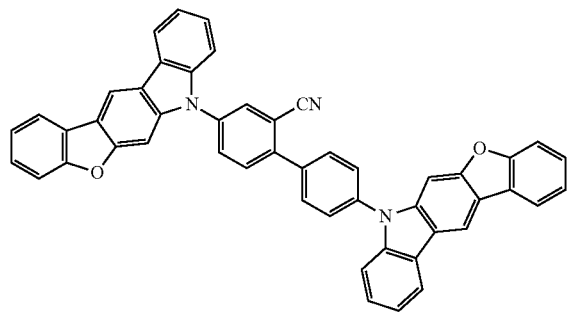
562
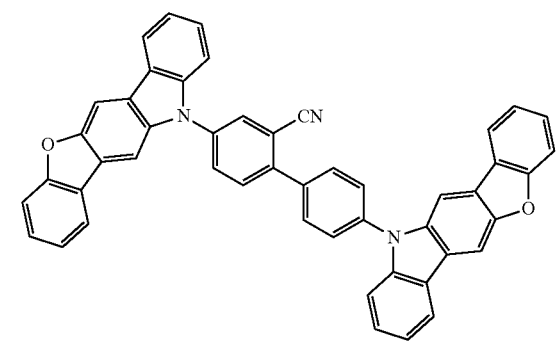
563
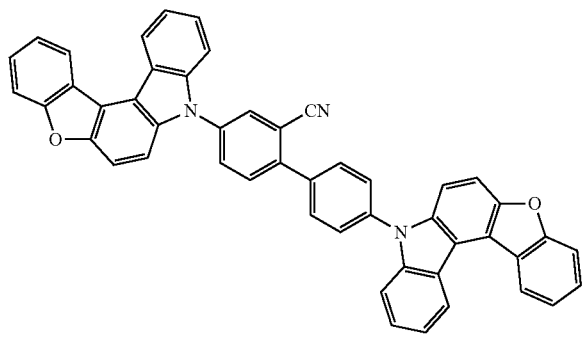
564
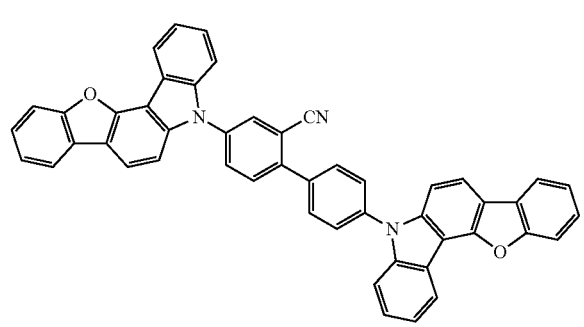
565
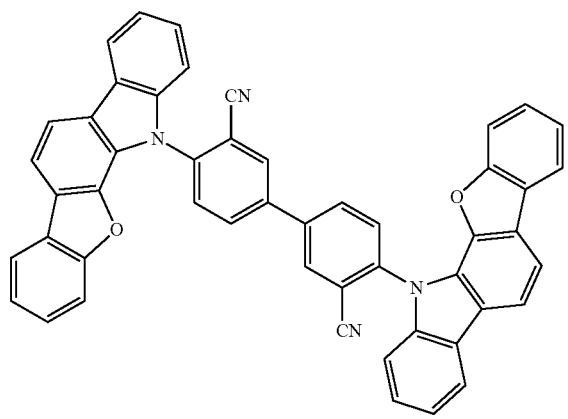
566
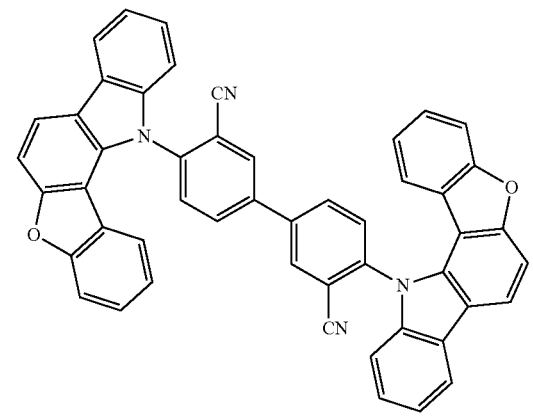
567
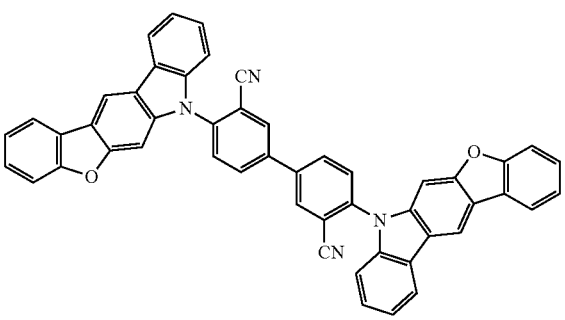
568
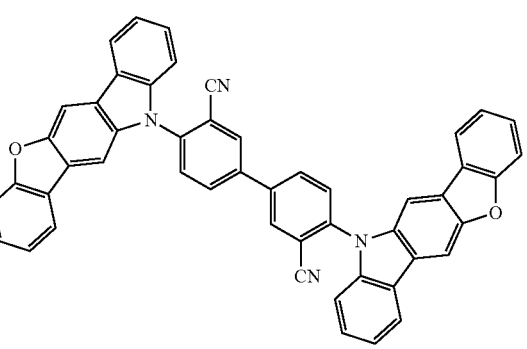

157
-continued
569
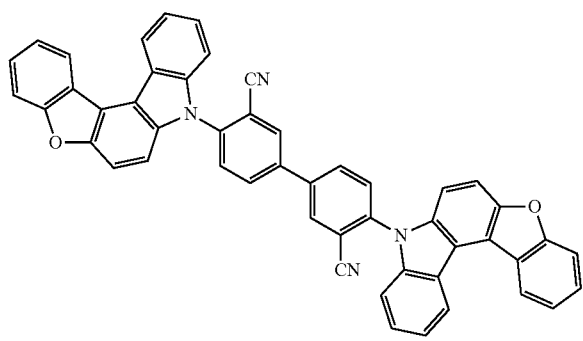
670
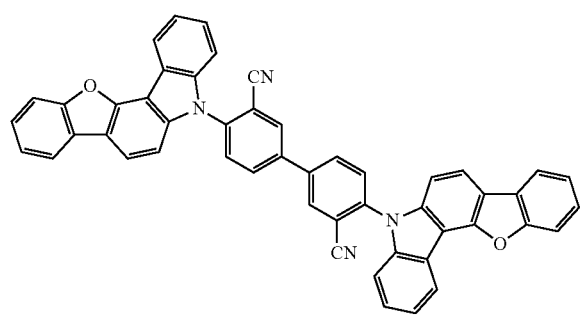
571
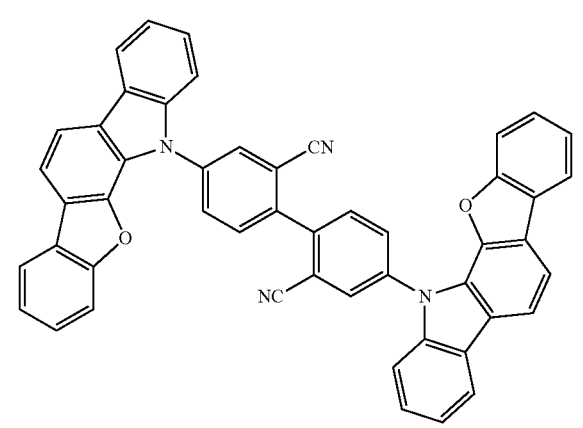
572
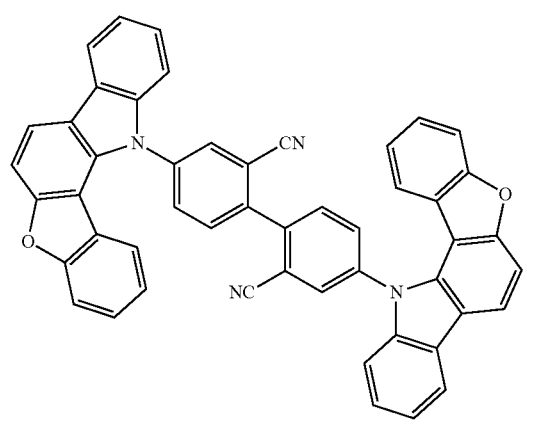
158
-continued
573
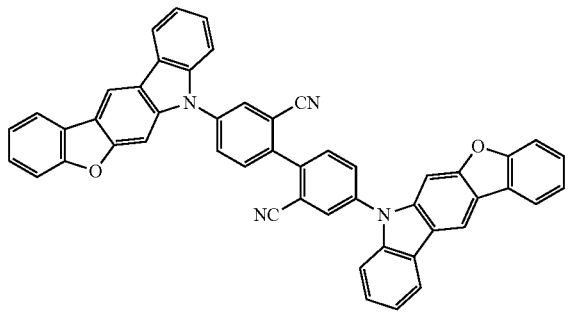
574
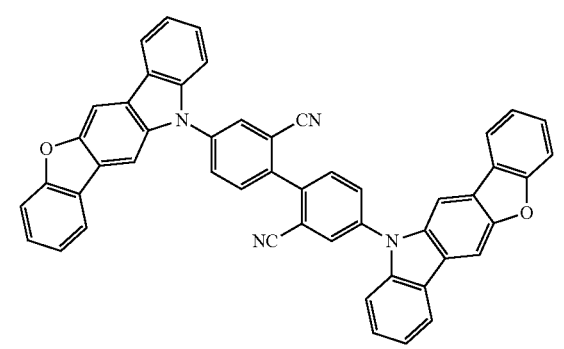
575
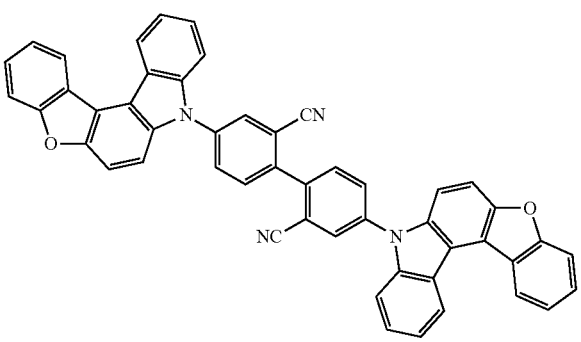
576
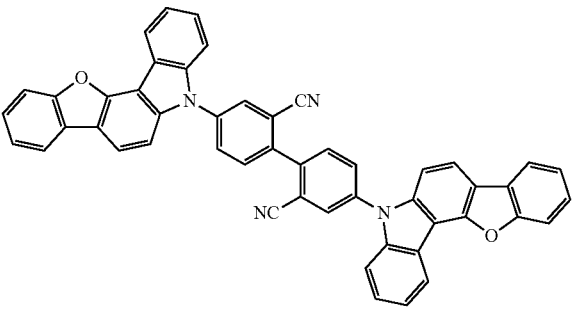

577
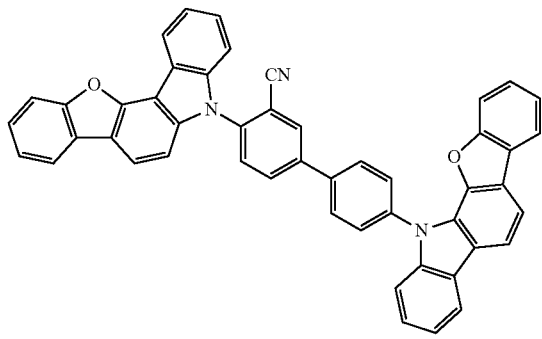
578
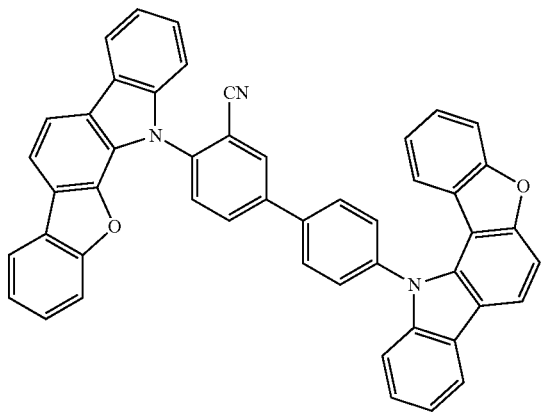
579
580
581
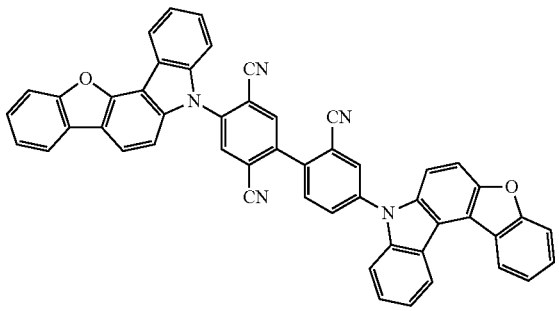
582
583
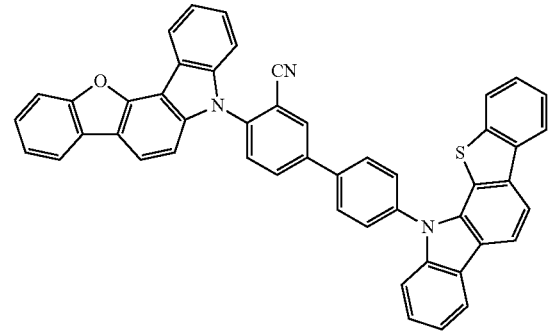
584
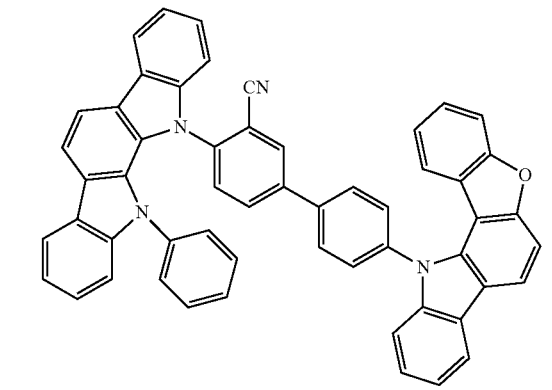
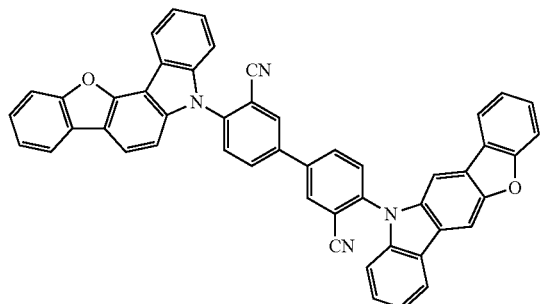

-continued
585
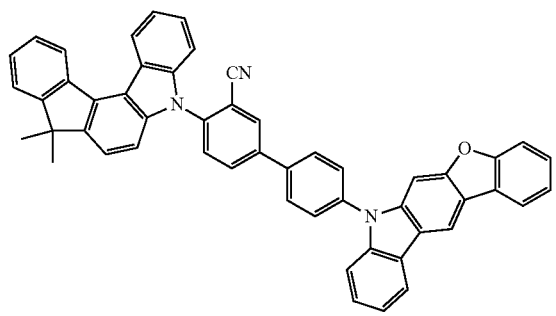
586
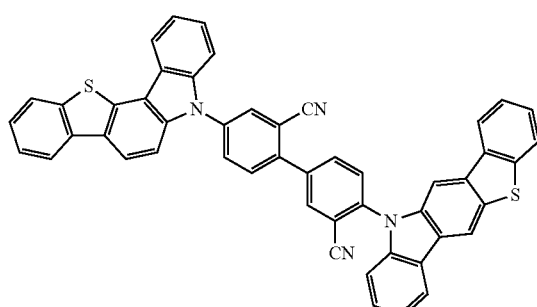
587
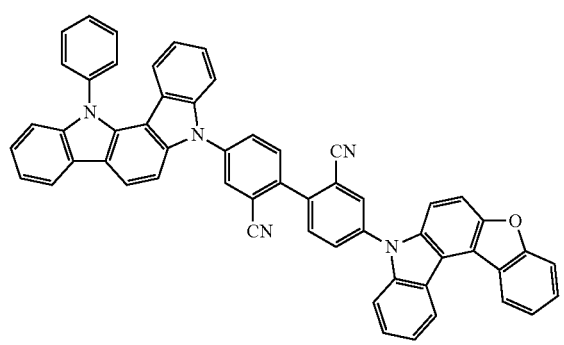
588
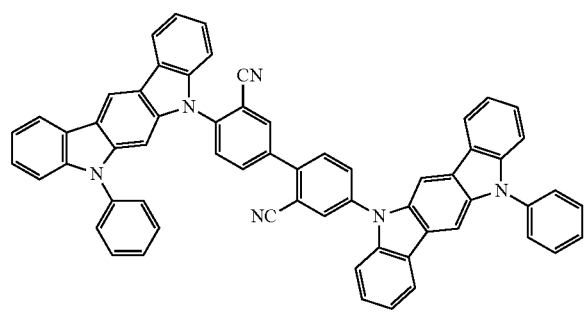
-continued
589
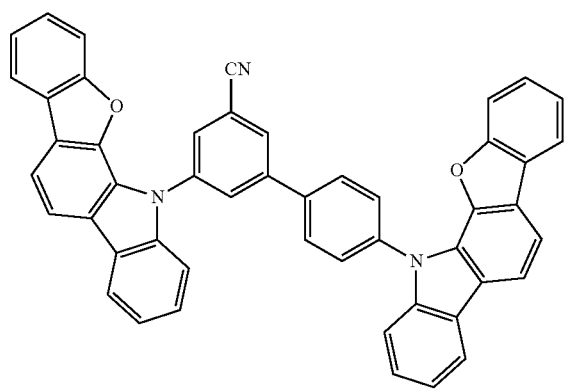
590
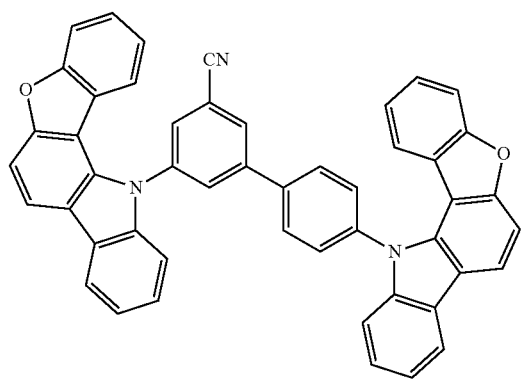
591
592
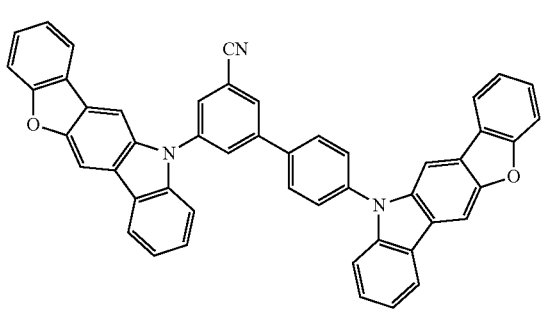

-continued
593
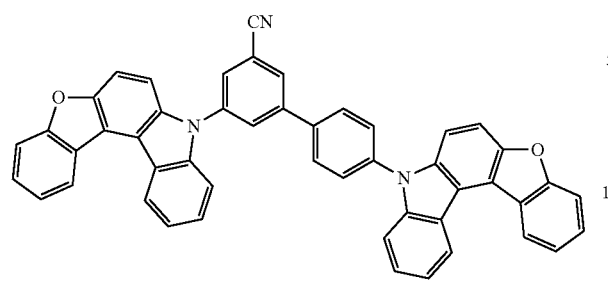
594
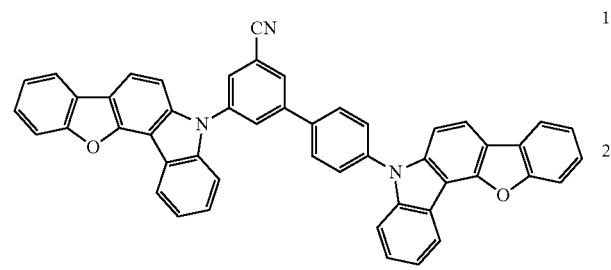
595
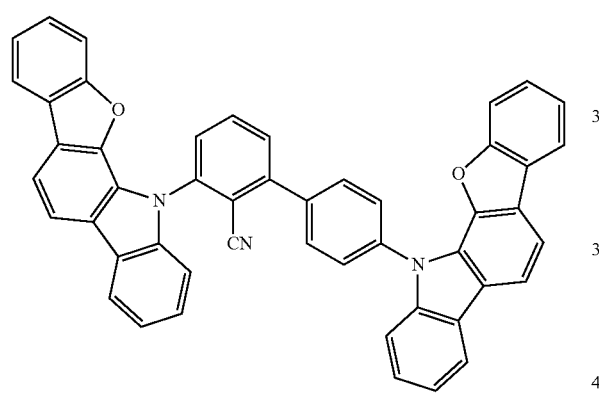
596
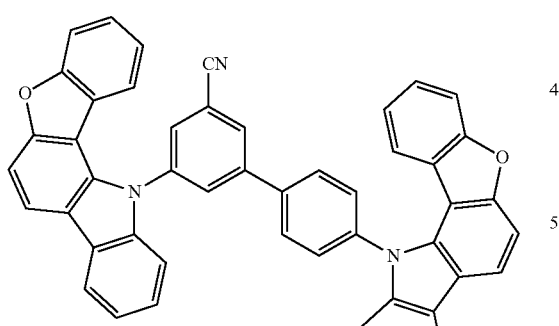
597
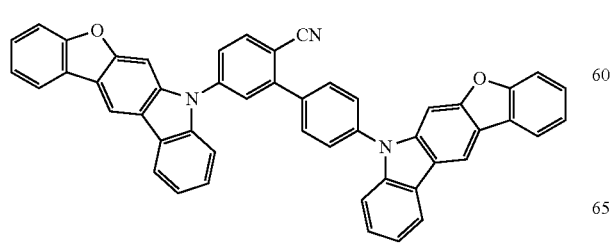
-continued
598
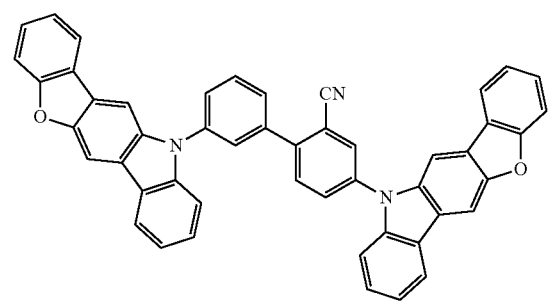
599
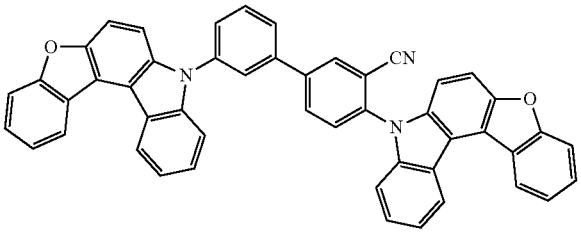
600
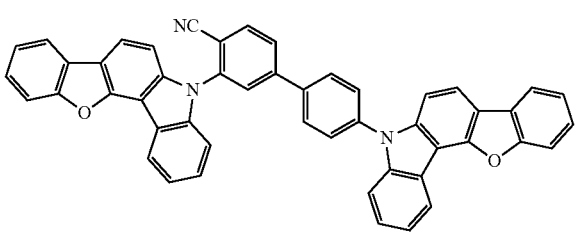
601
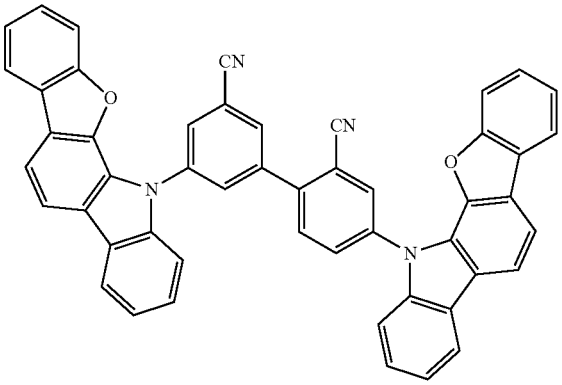
602
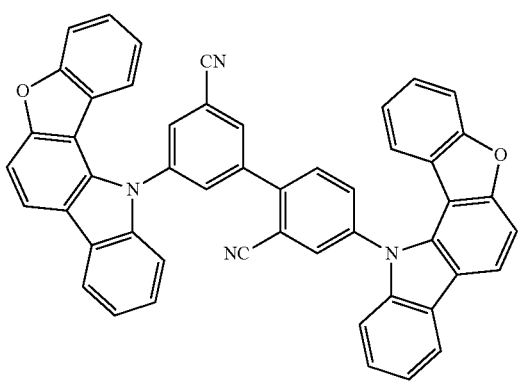

165
-continued
603
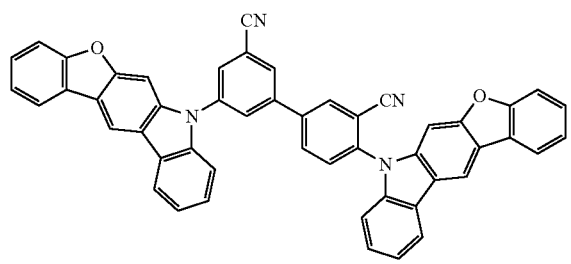
604
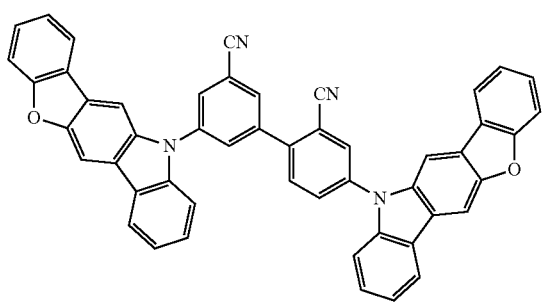
605
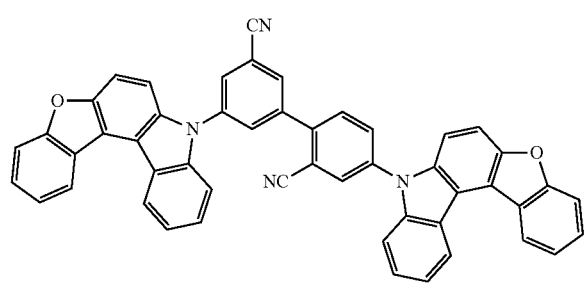
606
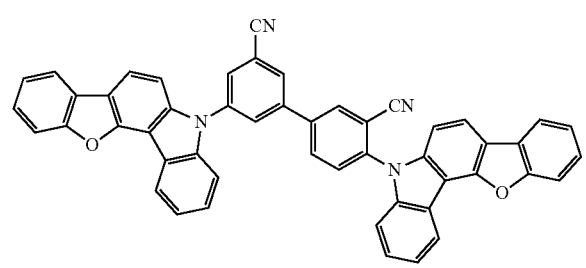
607
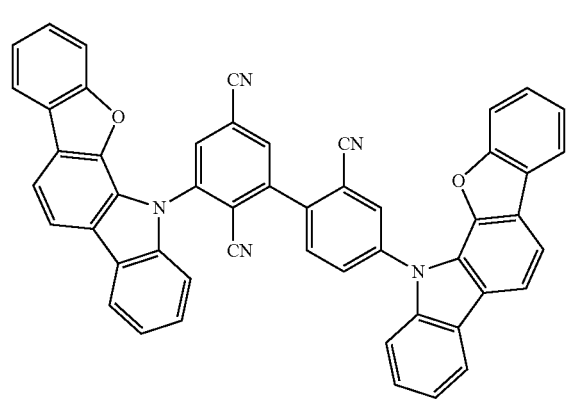
166
-continued
608
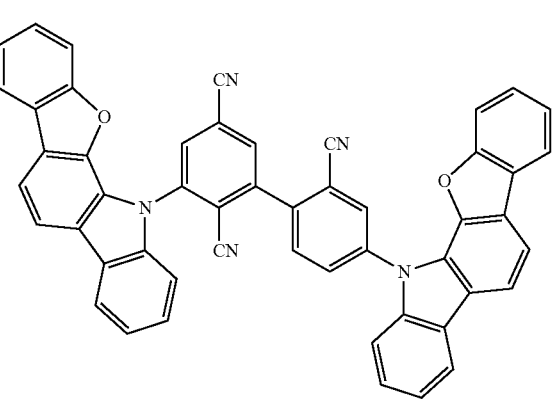
609
610
611
612

613
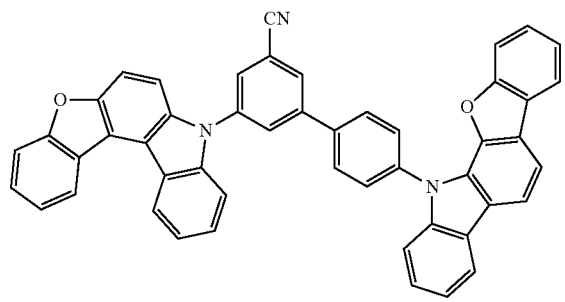
614
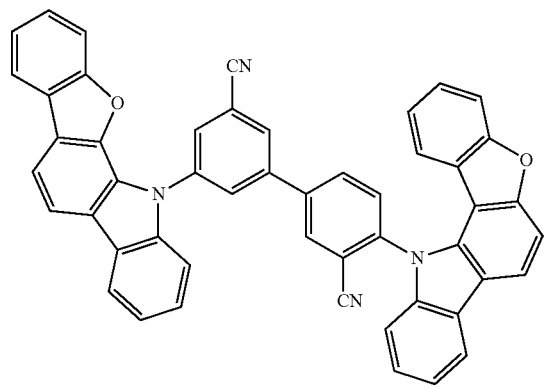
615
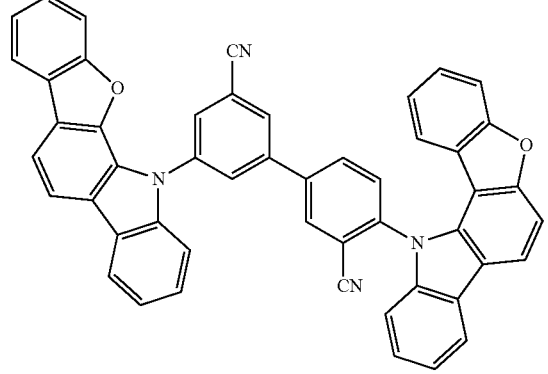
616
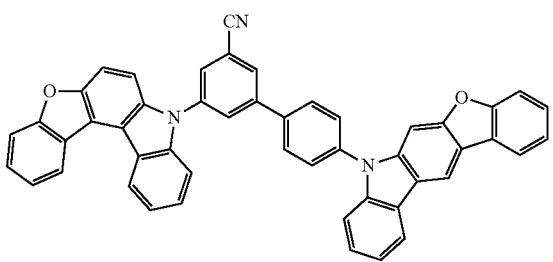
617
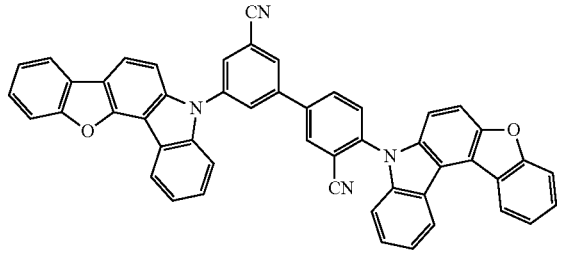
618
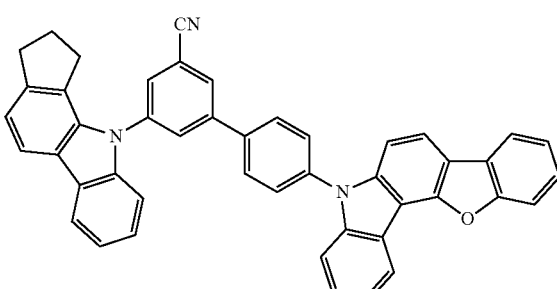
619
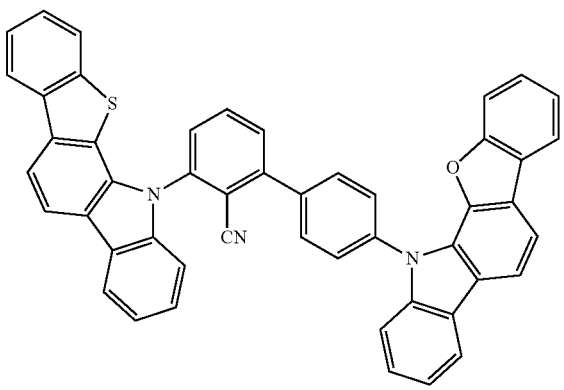
620
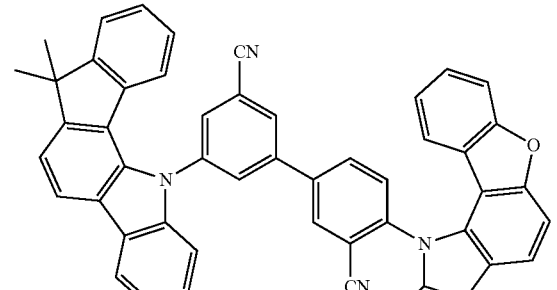
621
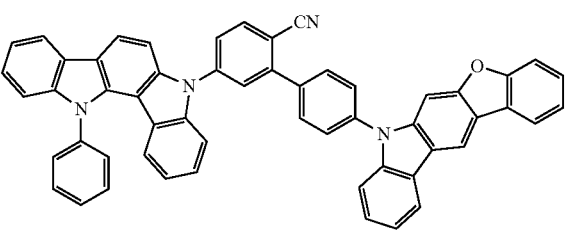

622
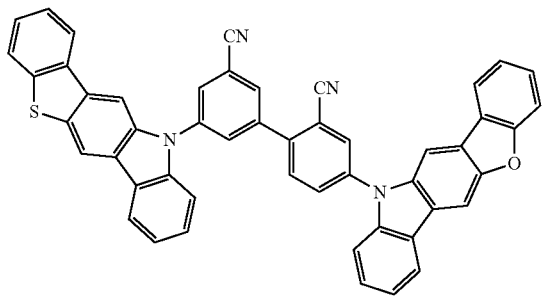
623
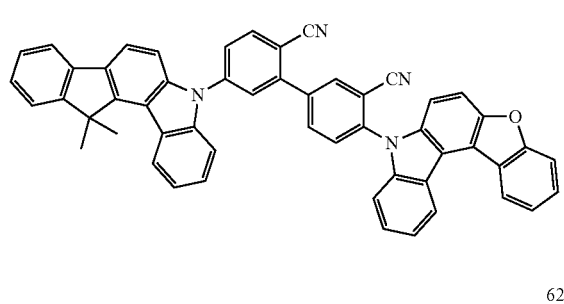
624
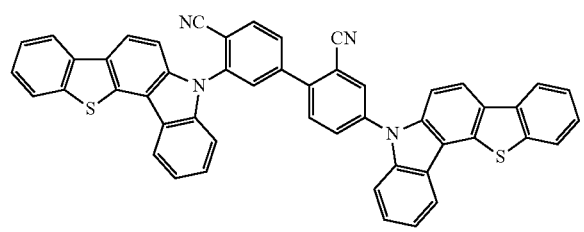
625
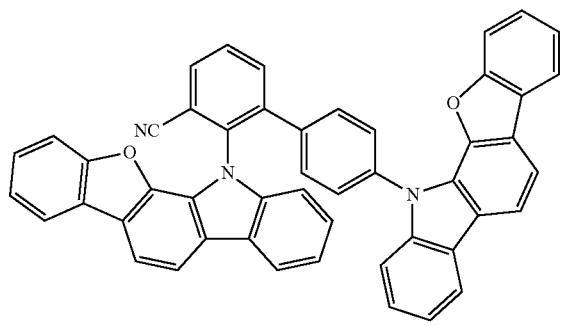
626
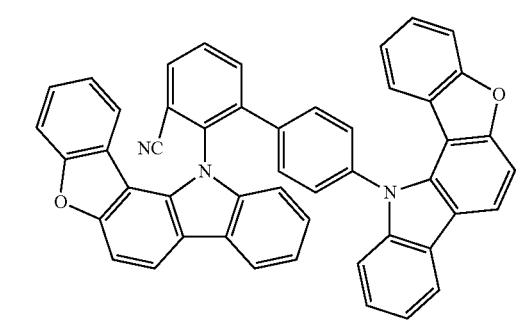
627
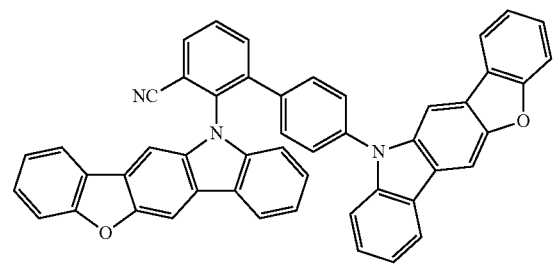
628
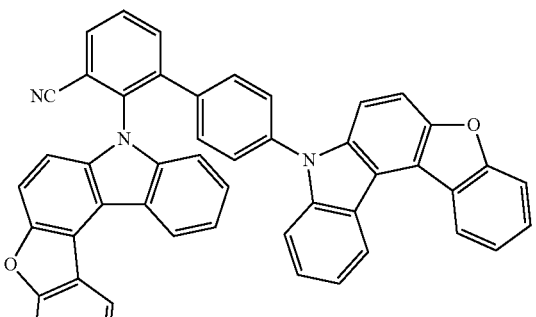
629
630
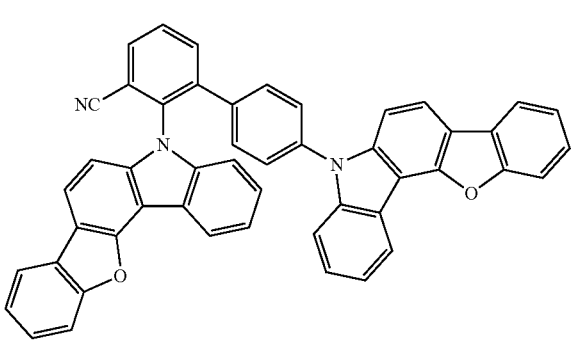

631
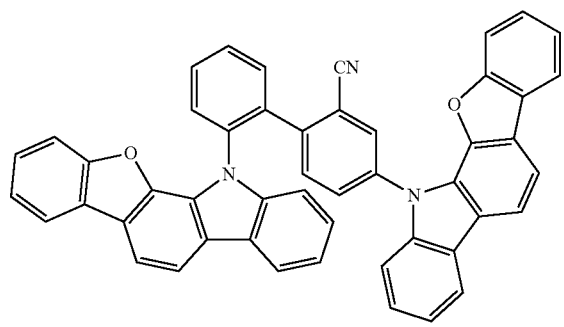
632
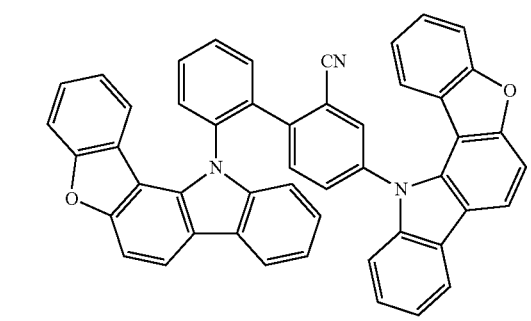
633
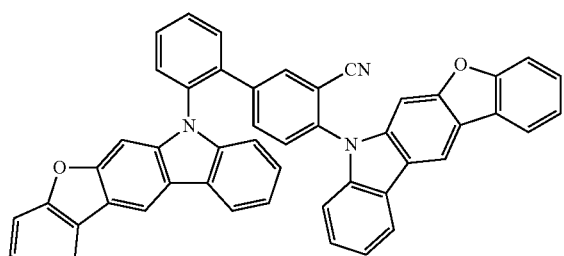
634
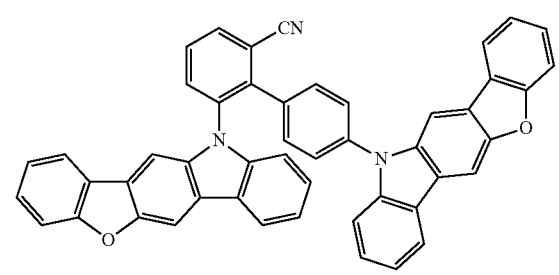
635
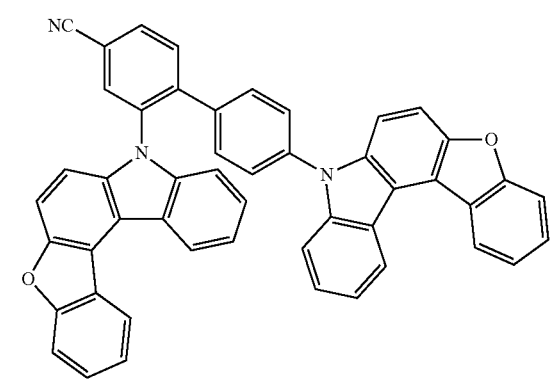
636
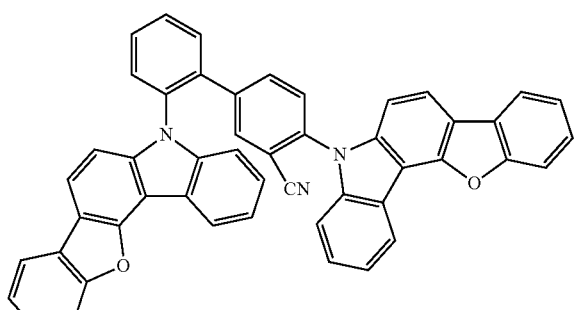
637
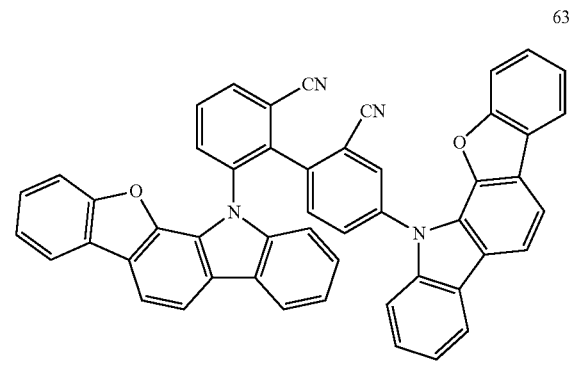
638
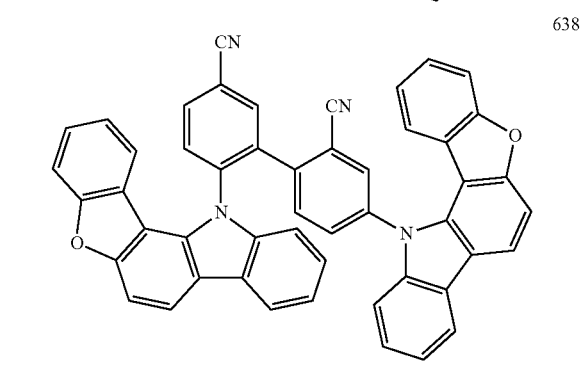
639
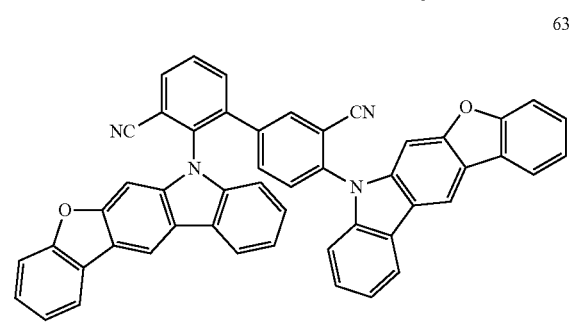
640
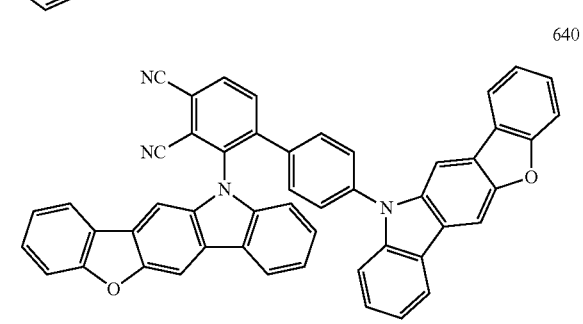

-continued
641
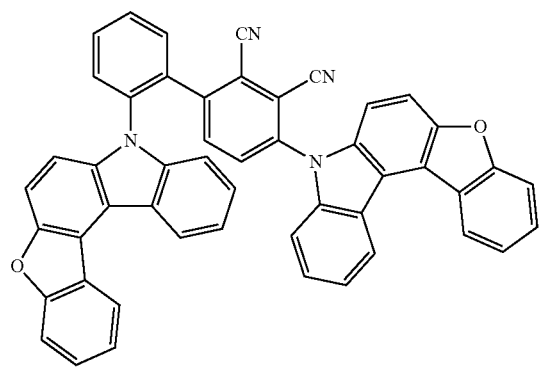
642
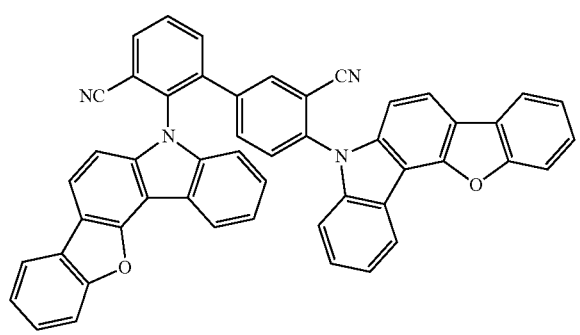
643
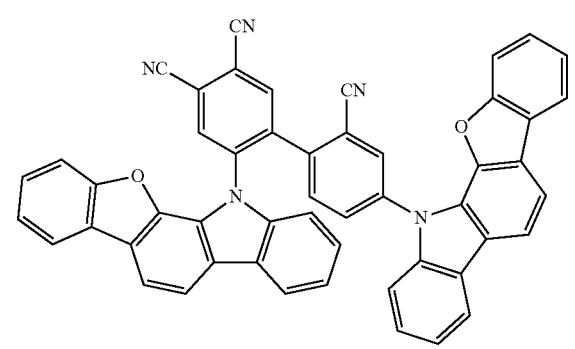
644
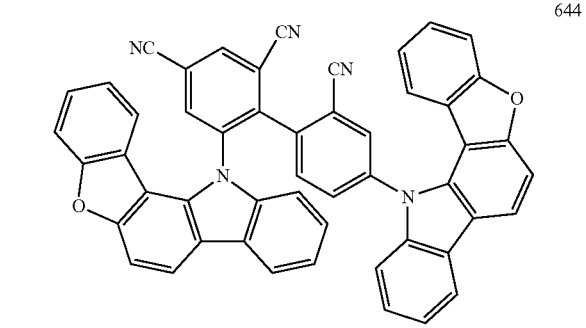
-continued
645
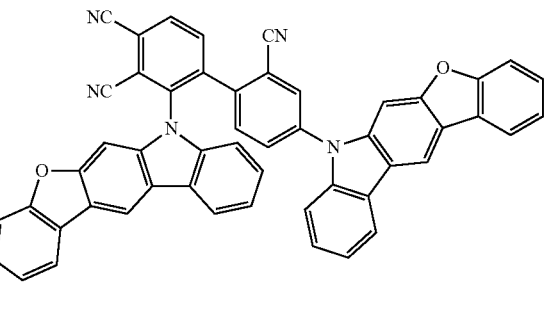
646
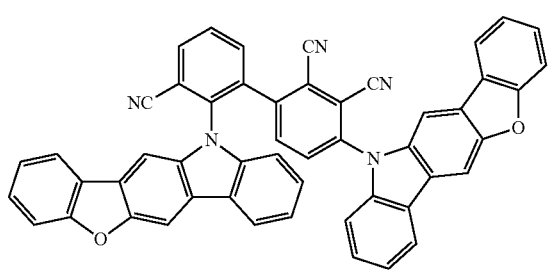
647
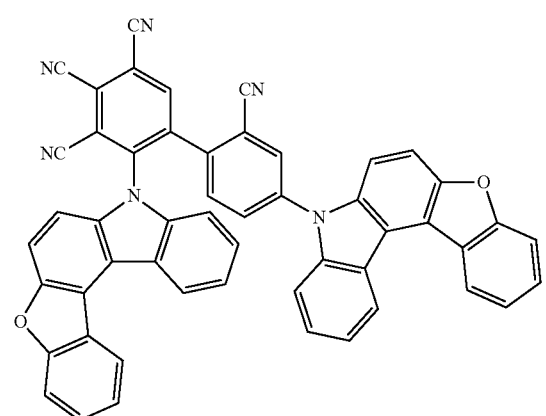
648
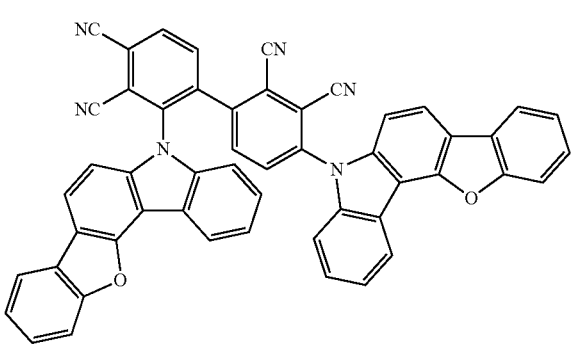

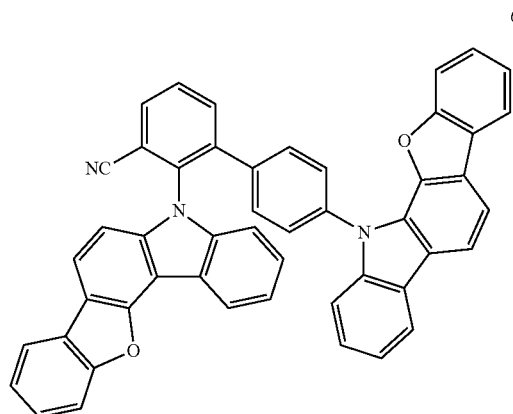
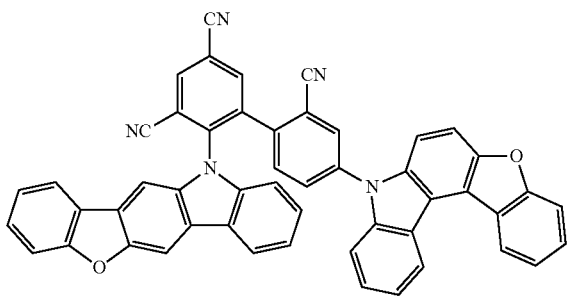
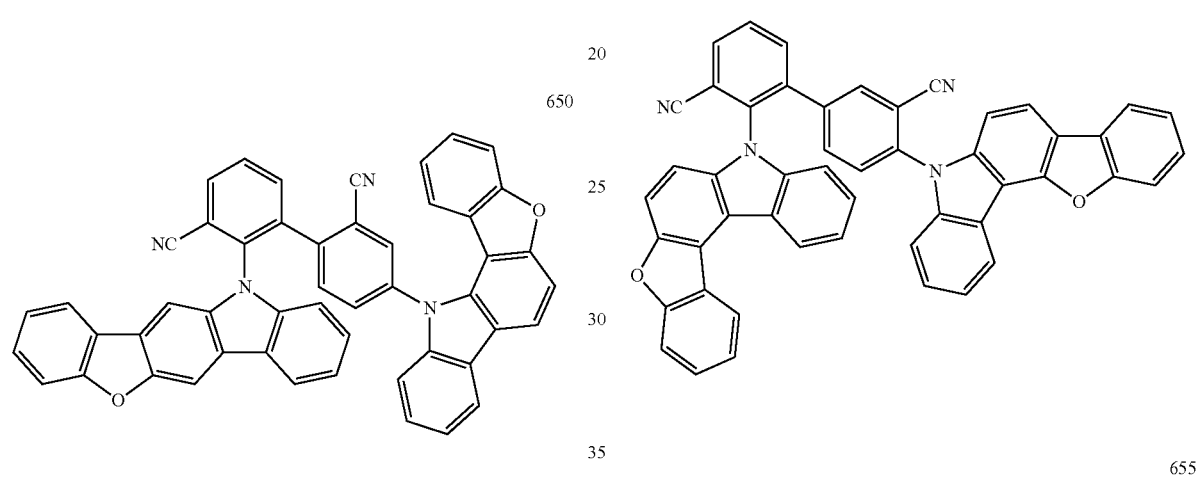
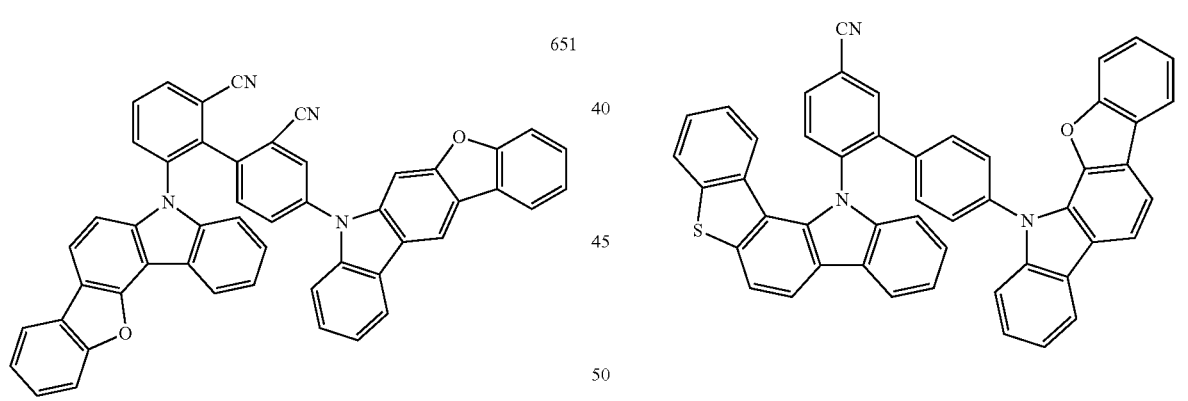
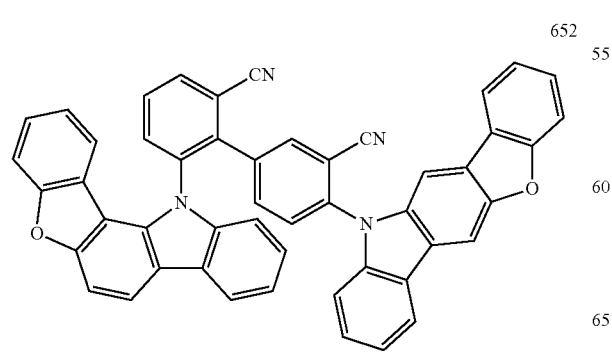
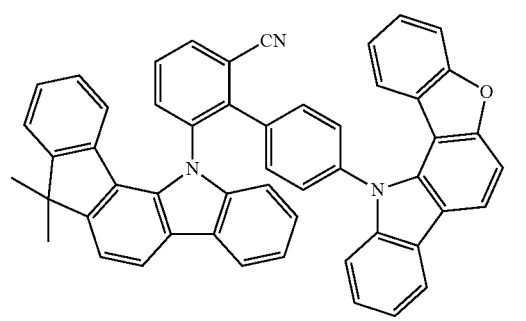

-continued
657
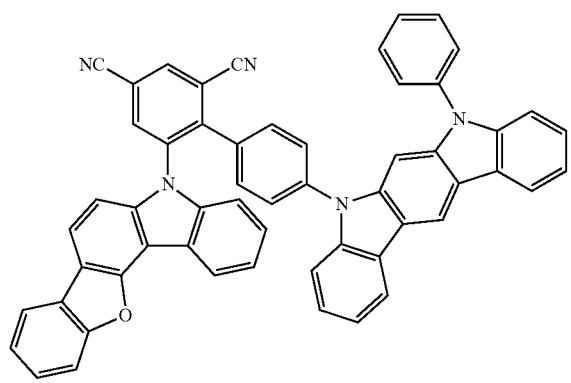
658
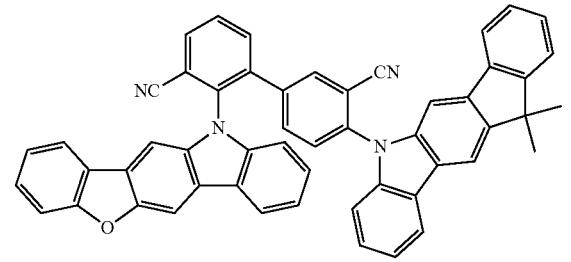
659
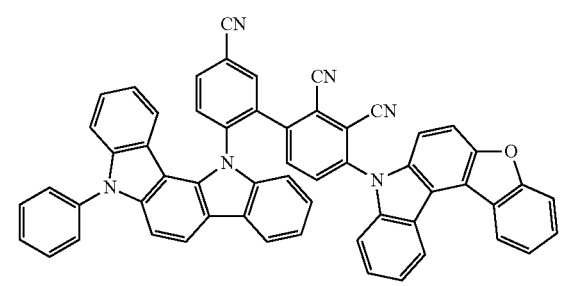
660
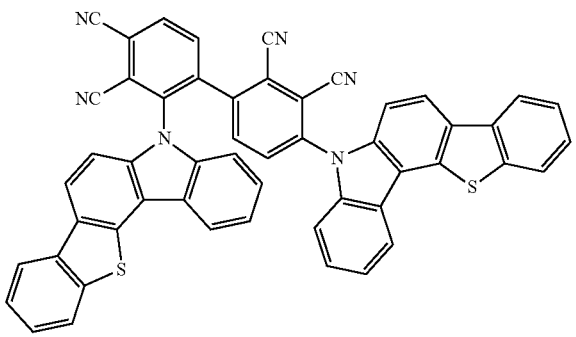
-continued
661
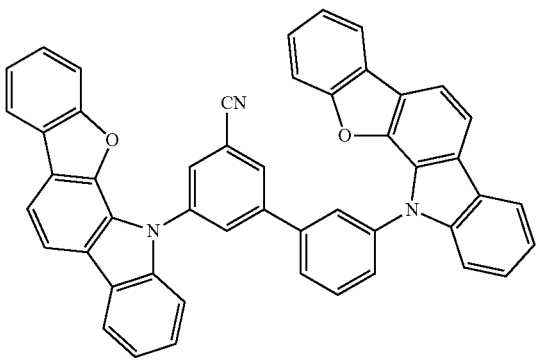
662
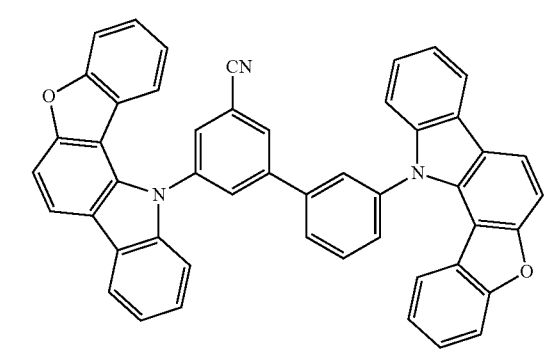
663
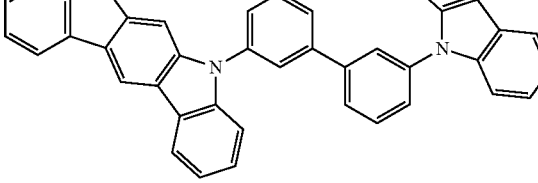
664
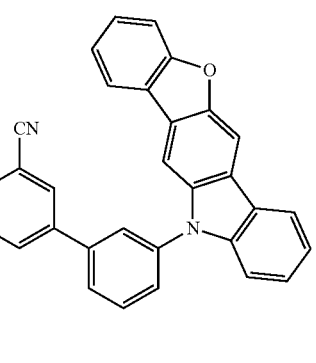

665
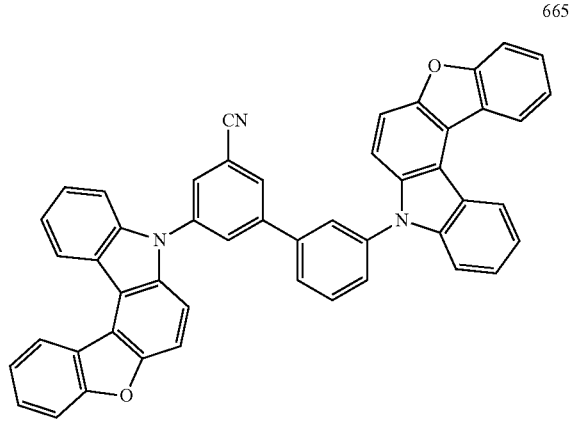
668
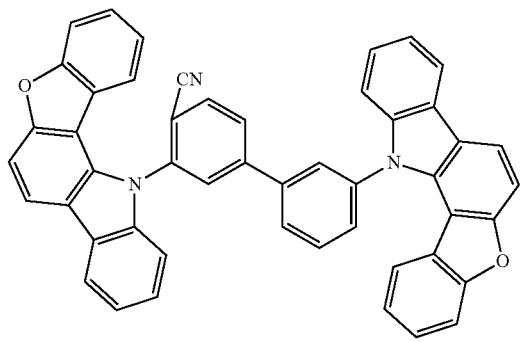
666
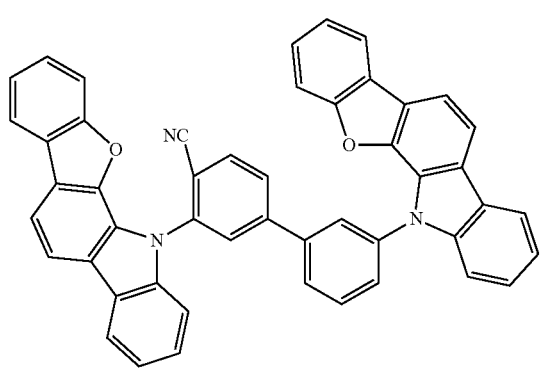
669
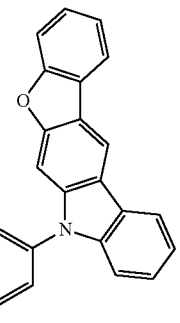
670
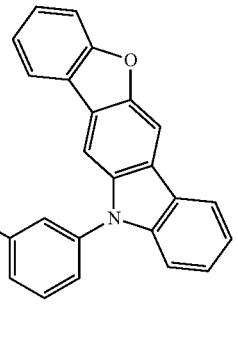
667
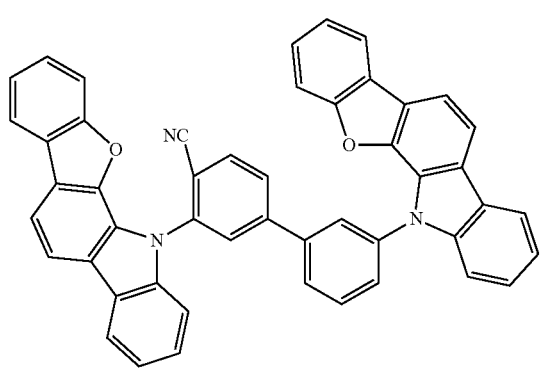
671
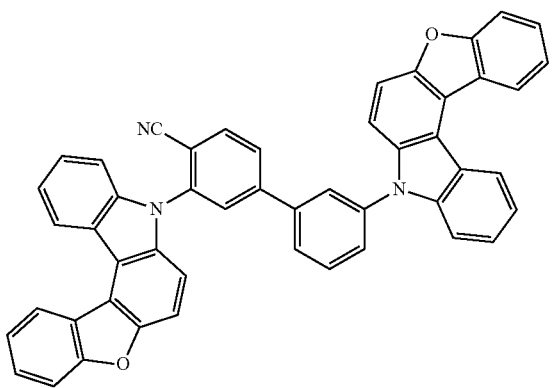

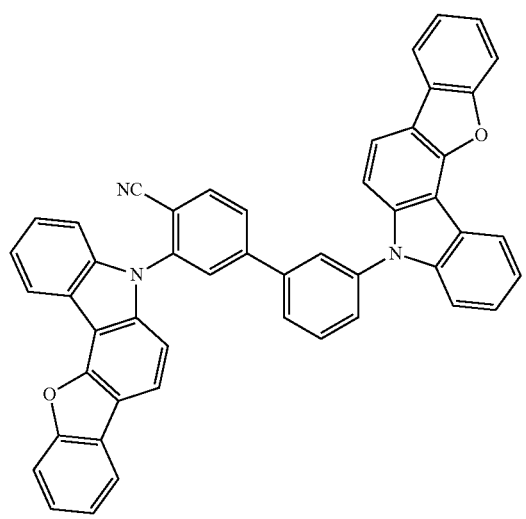
672
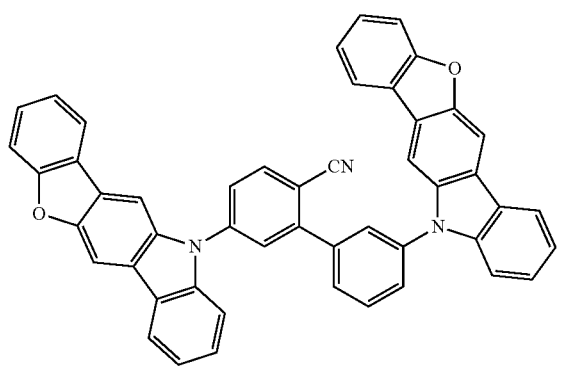
676
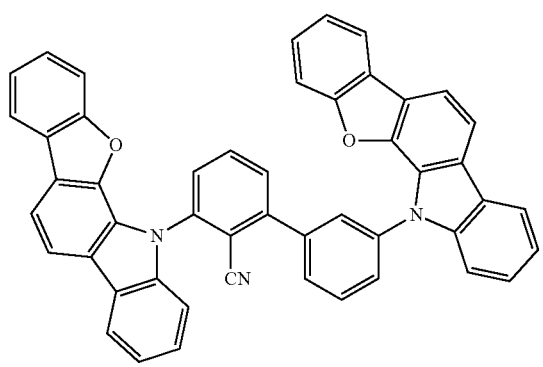
673
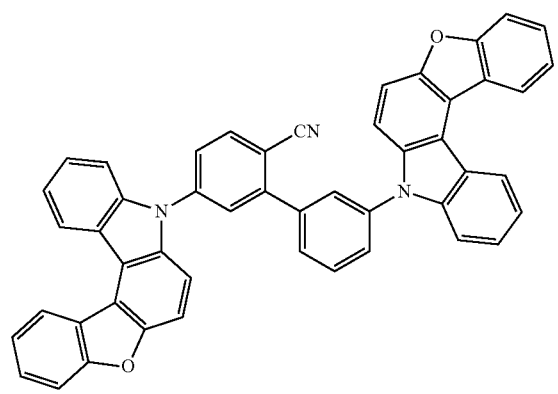
677
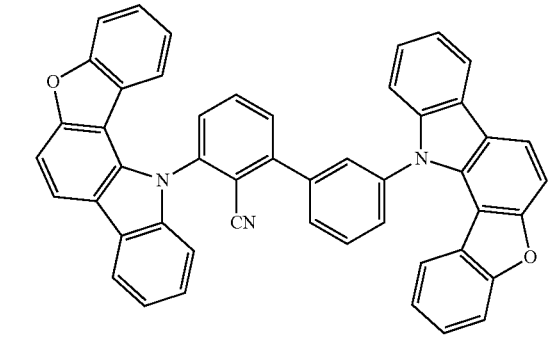
674
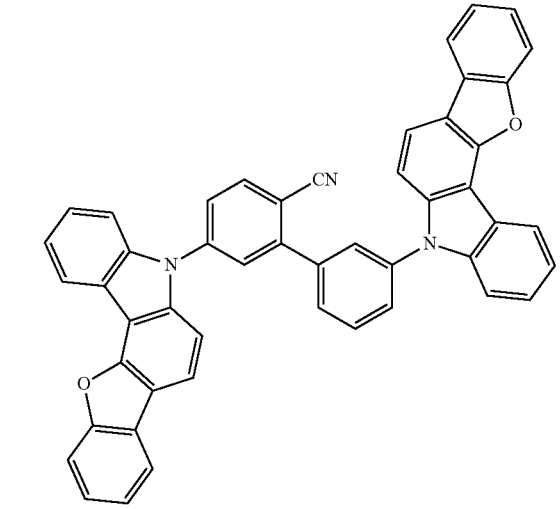
678
675

-continued
679
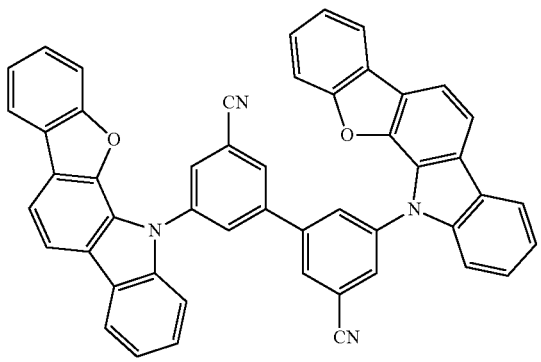
680
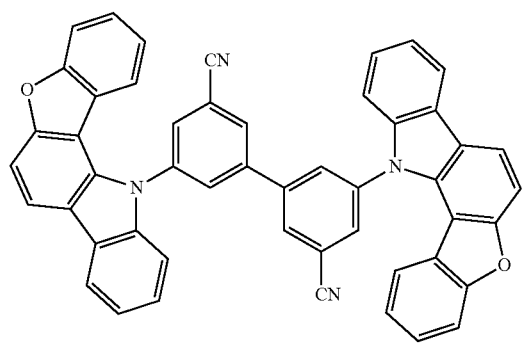
681
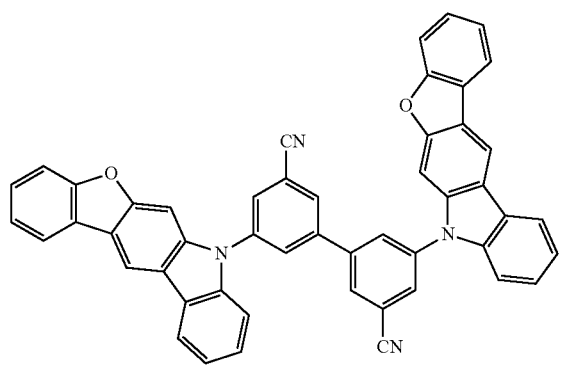
682
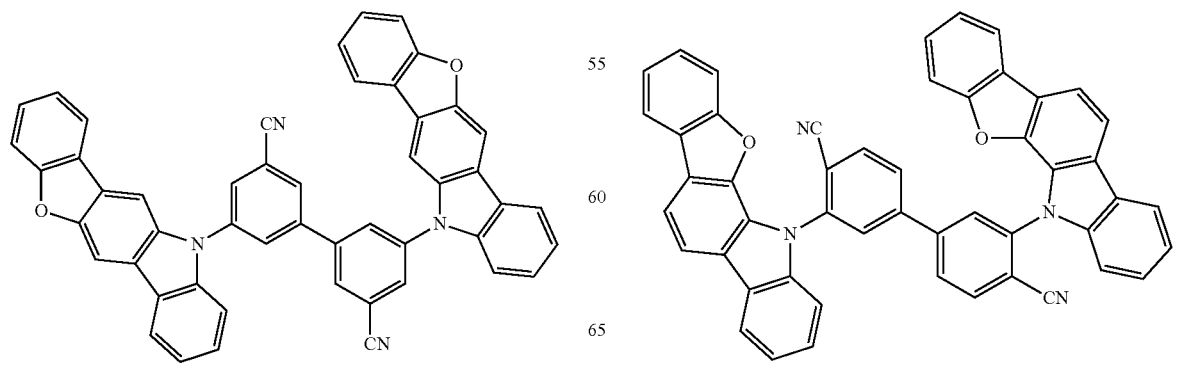
-continued
683
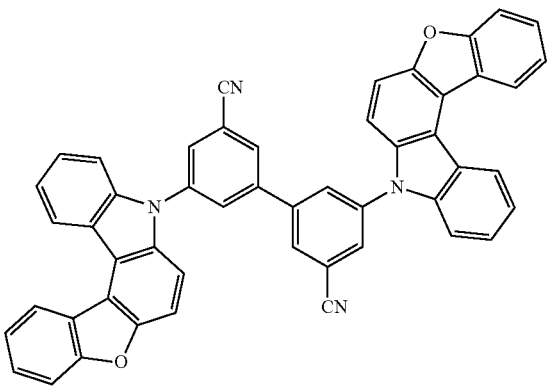
684
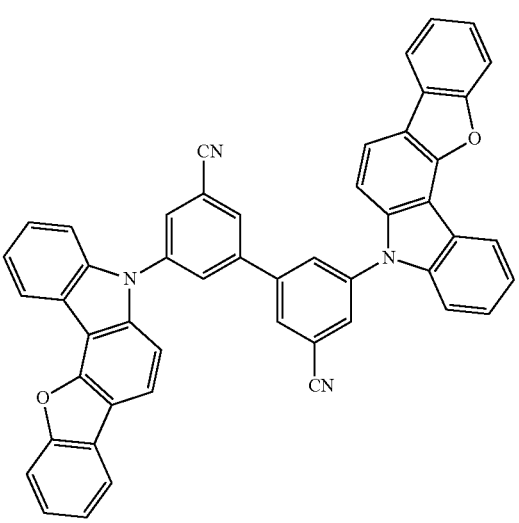
685

686
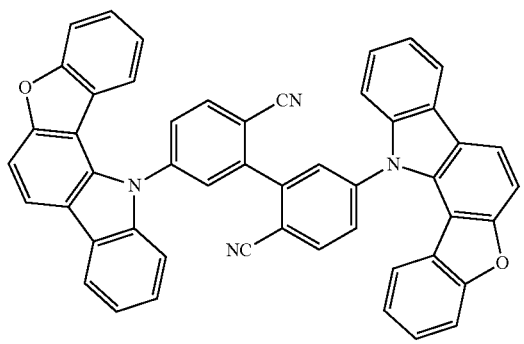
687
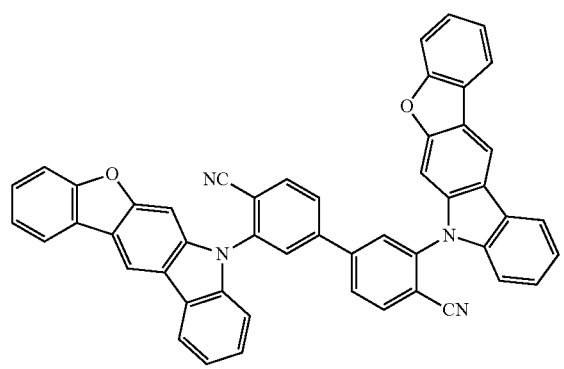
688
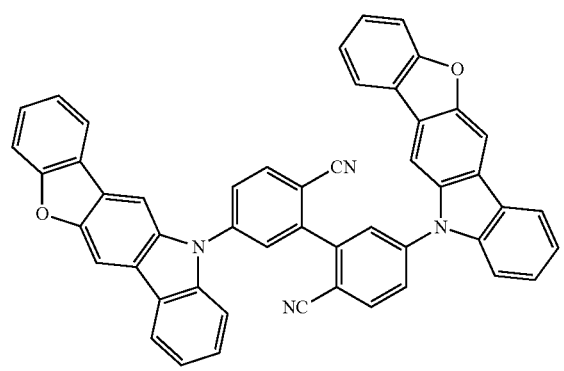
689
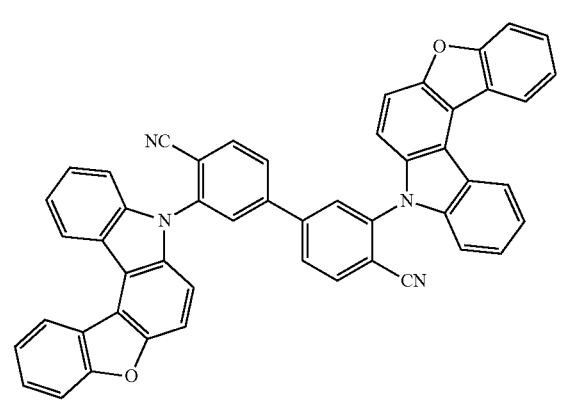
690
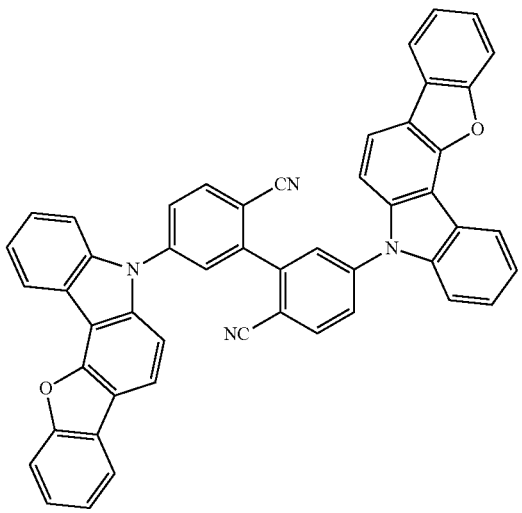
691
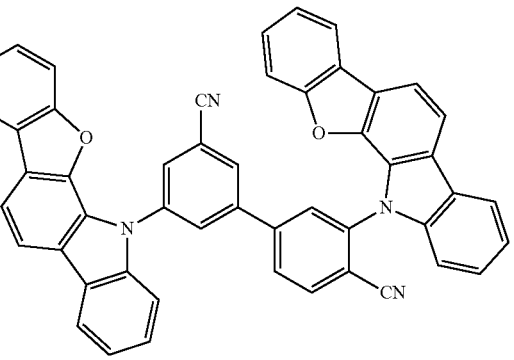
692
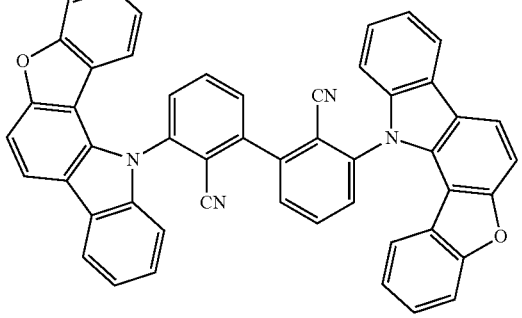

-continued
693
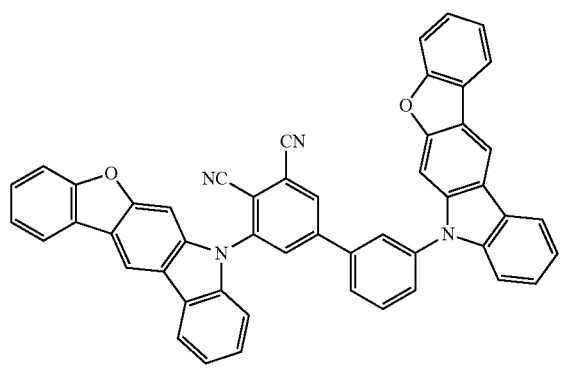
694
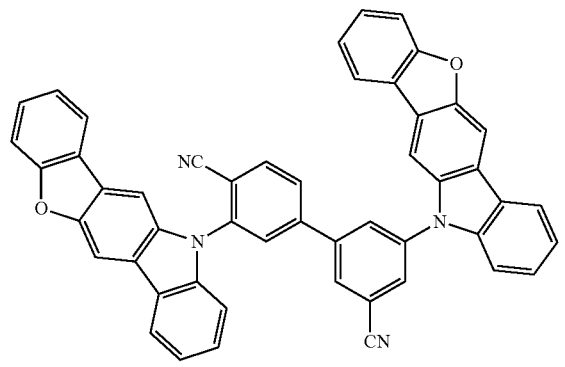
695
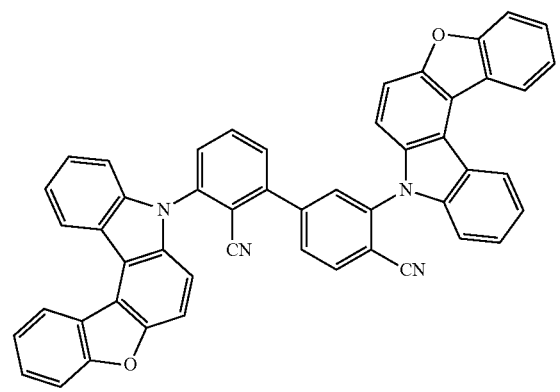
-continued
696
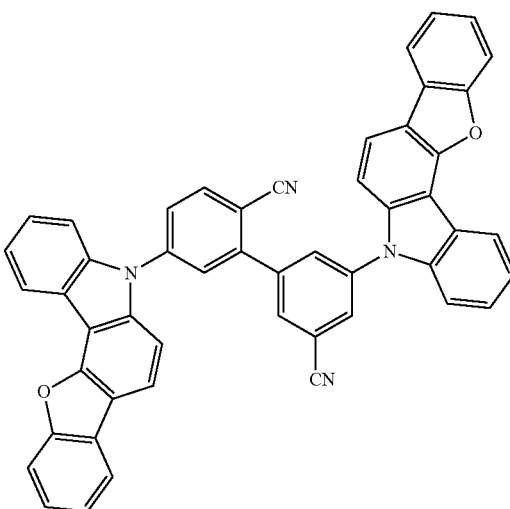
697
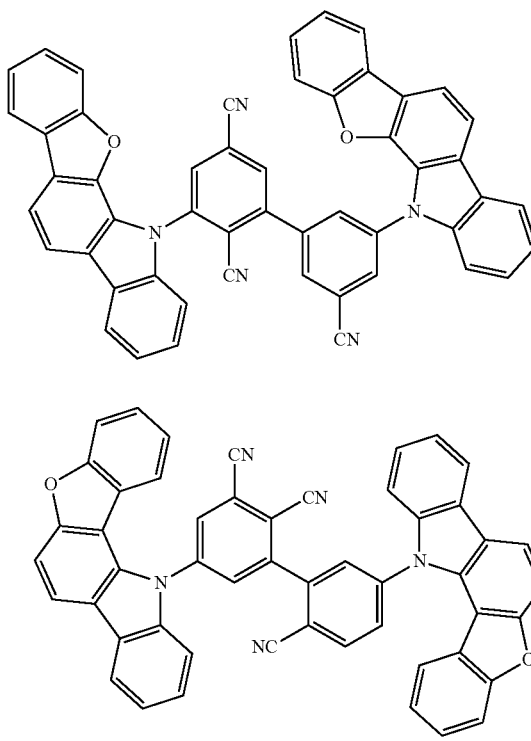
698
699
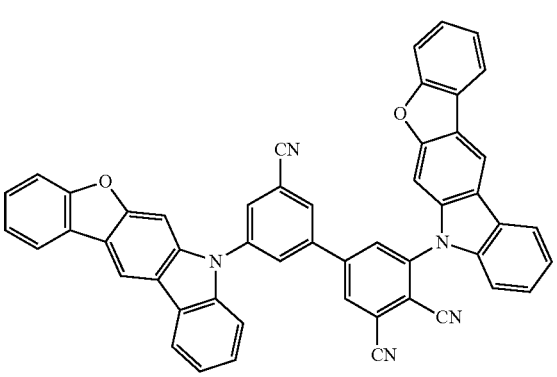

-continued
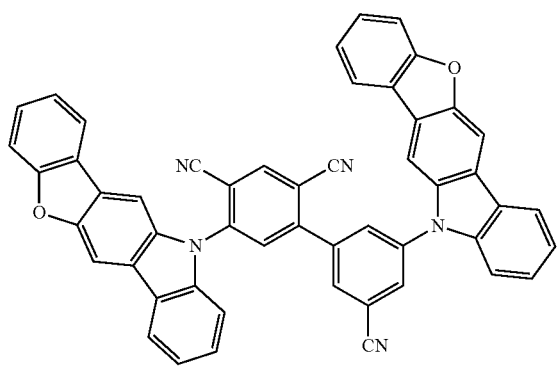
700
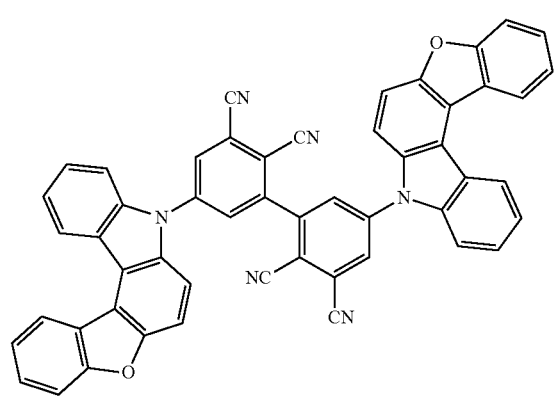
701
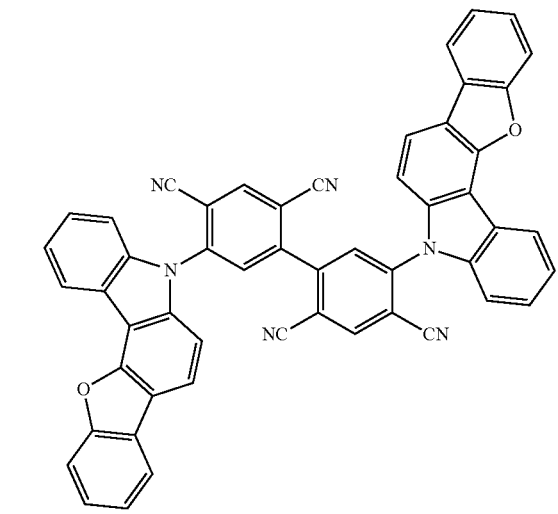
702
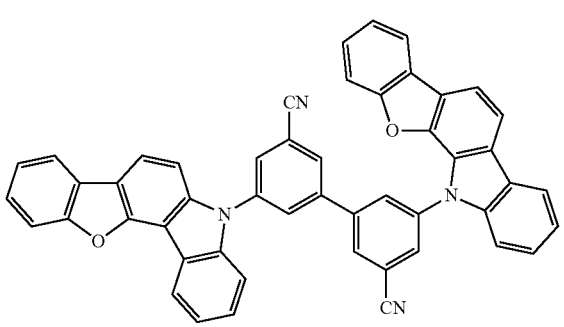
703
-continued
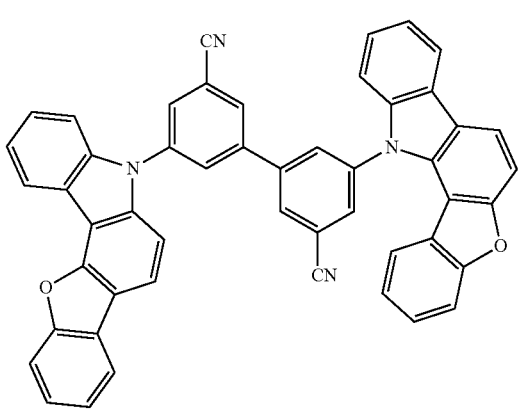
704
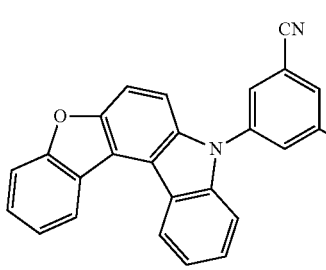
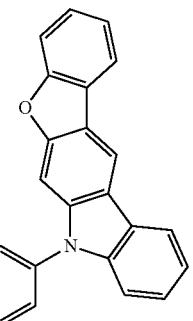
705
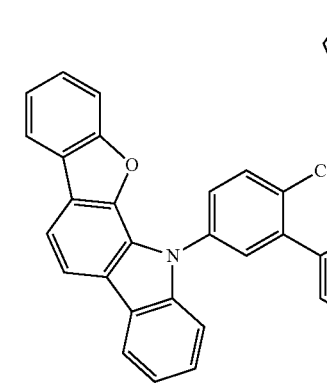
706
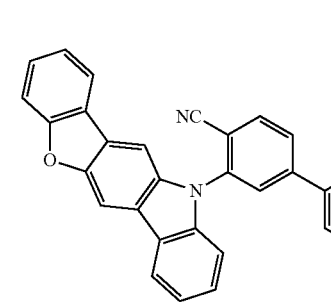
707

191
-continued
708
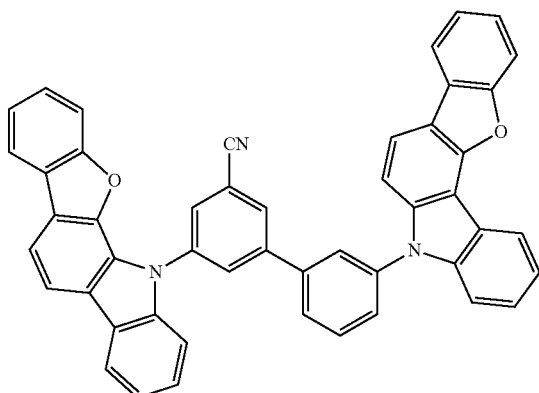
709
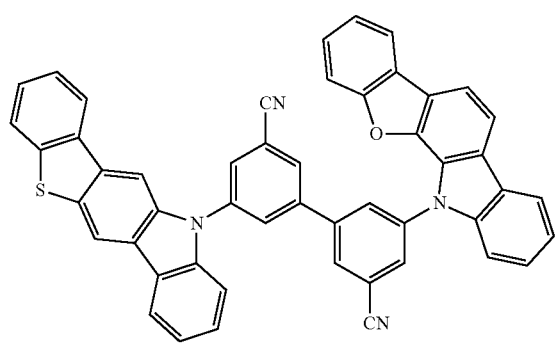
710
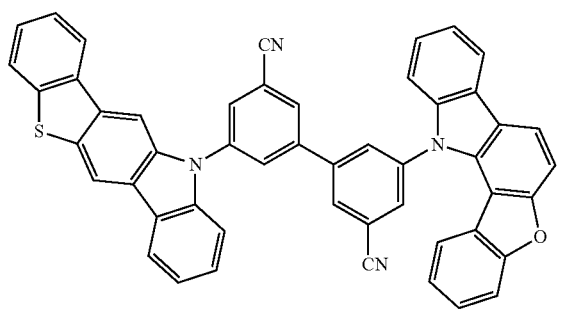
711
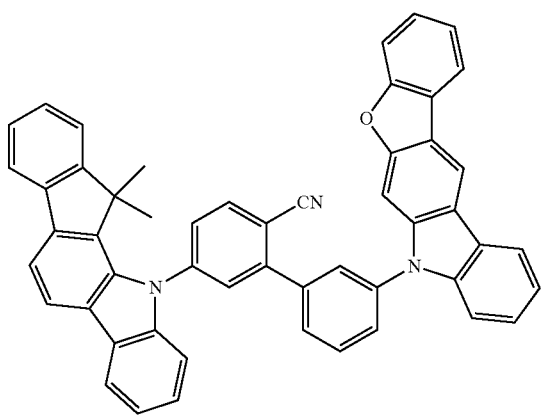
192
-continued
712
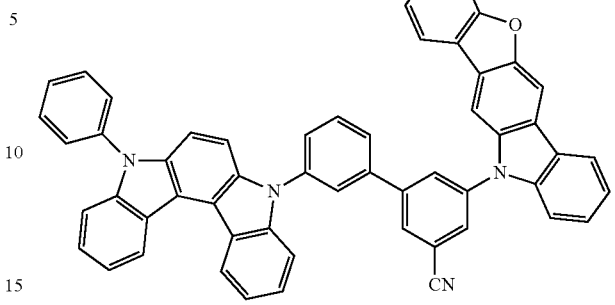
713
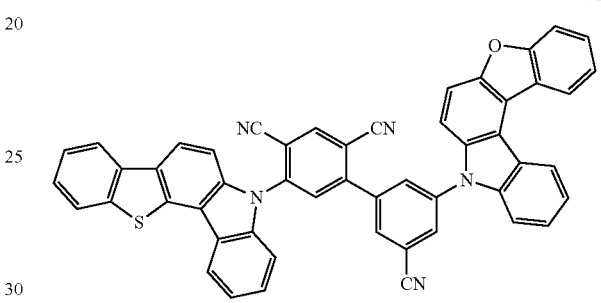
714
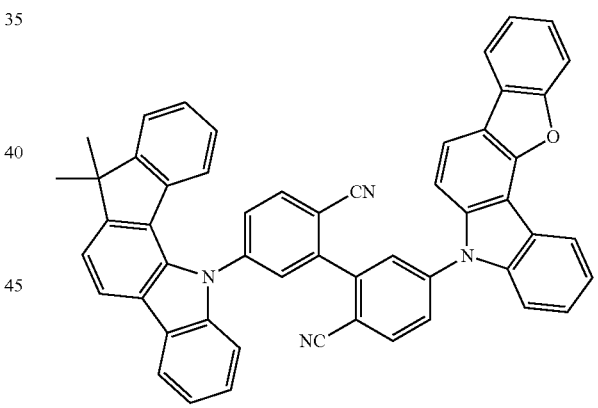
715
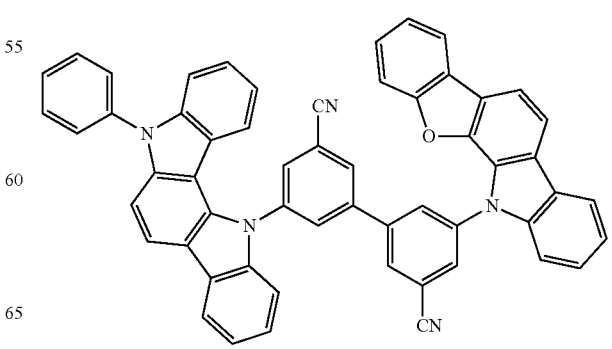

716
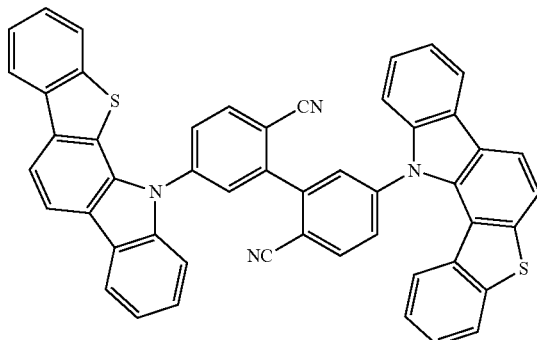
720
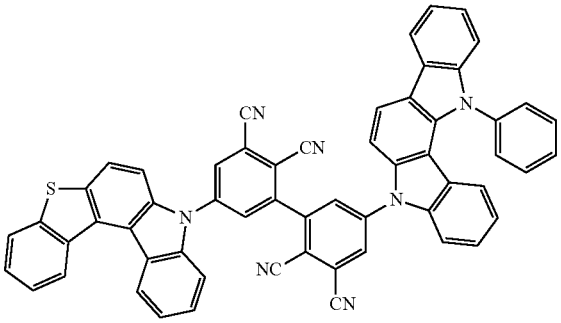
717
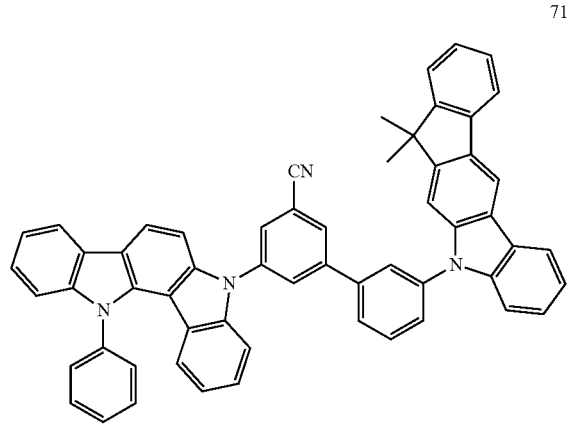
721
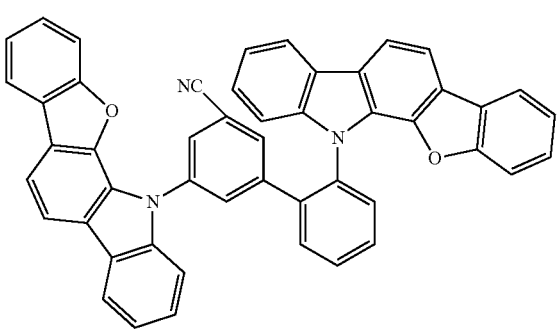
718
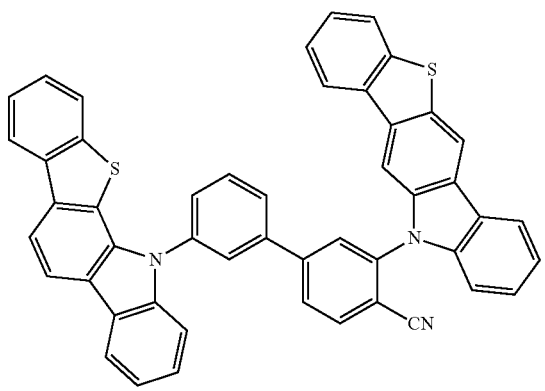
722
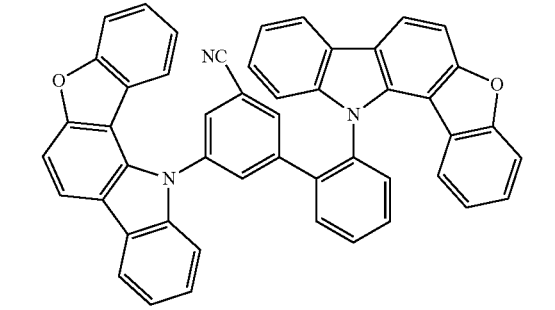
719
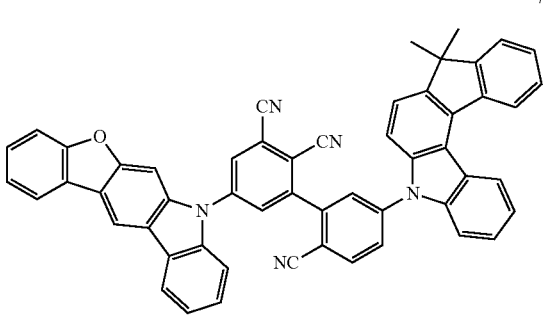
723
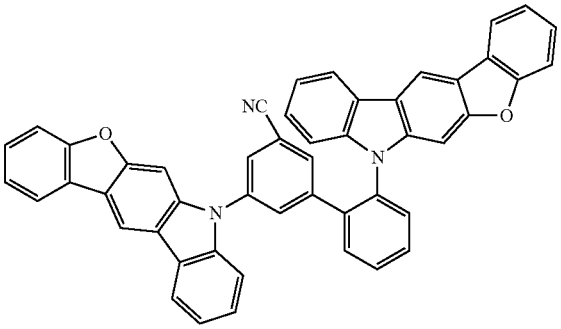

724
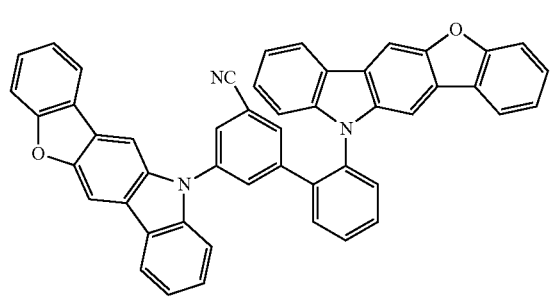
725
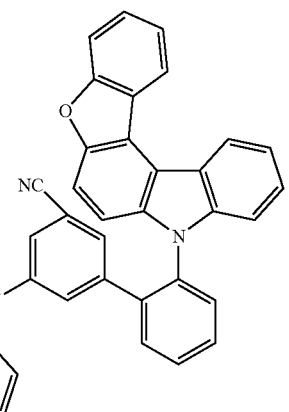
726
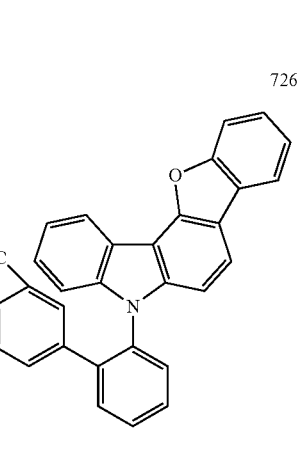
727
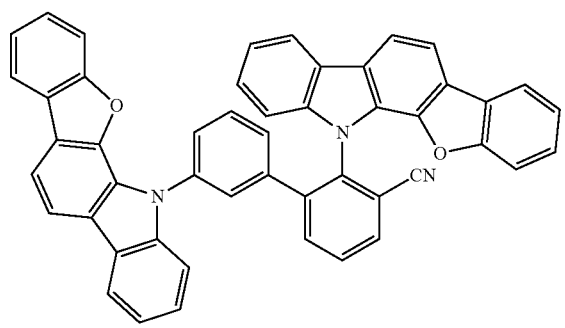
728
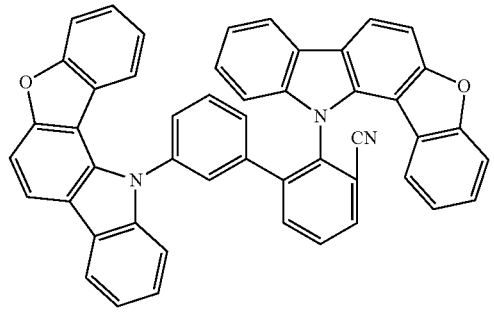
729
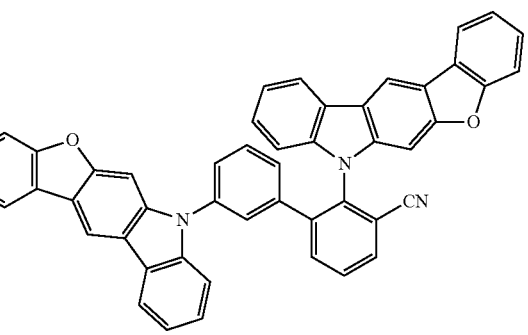
730
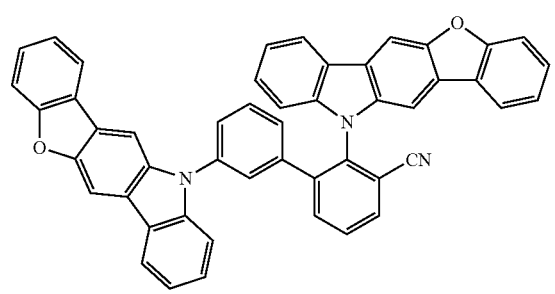
731
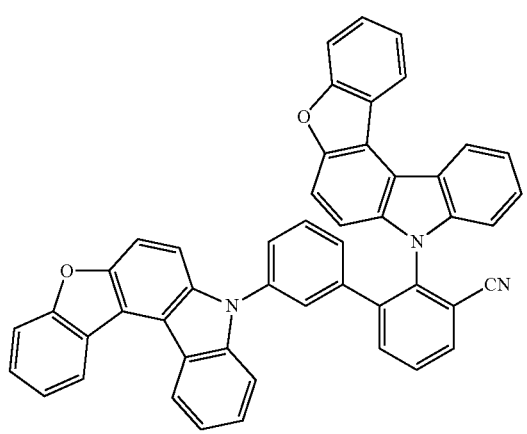

732
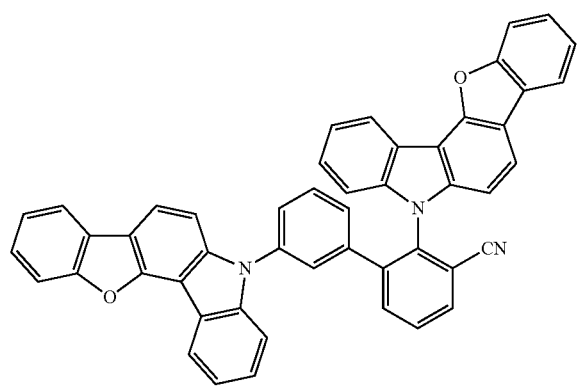
733
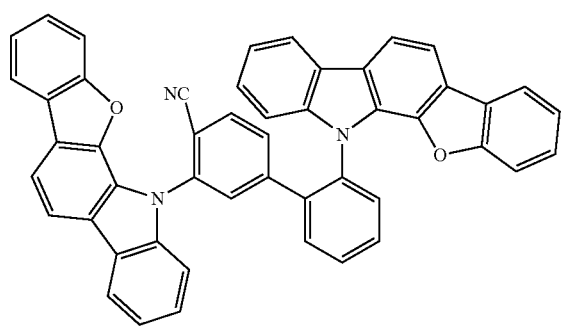
734
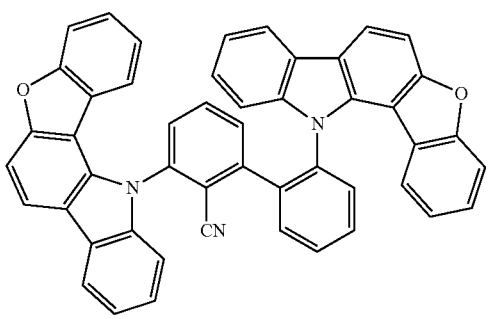
735
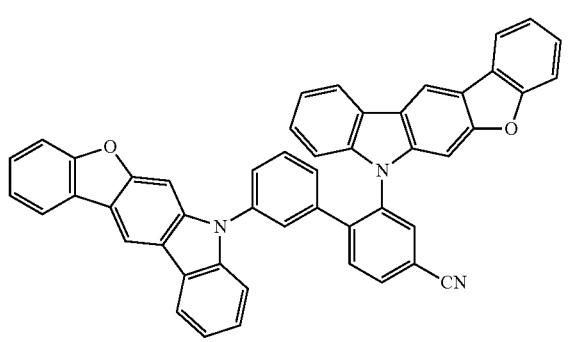
736
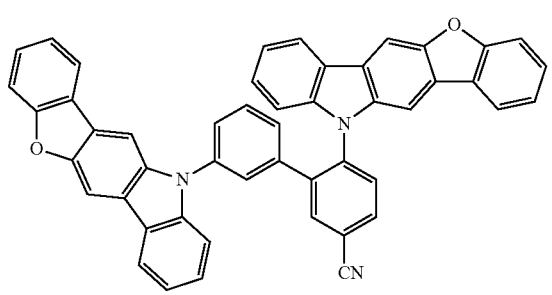
737
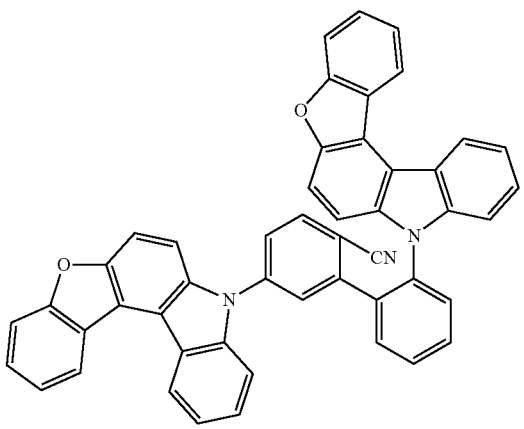
738
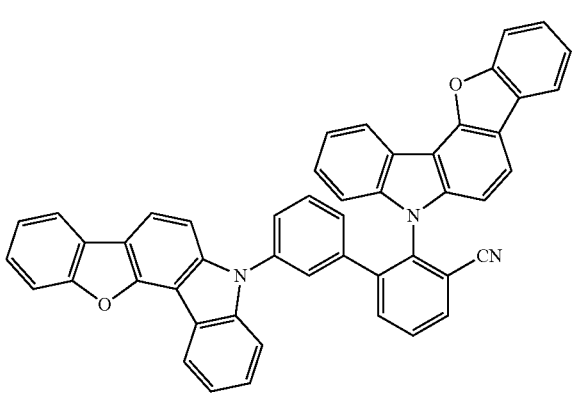
739
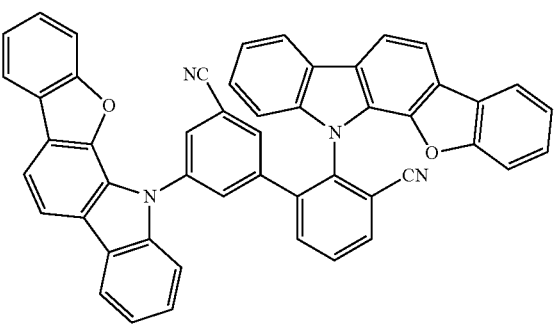

740
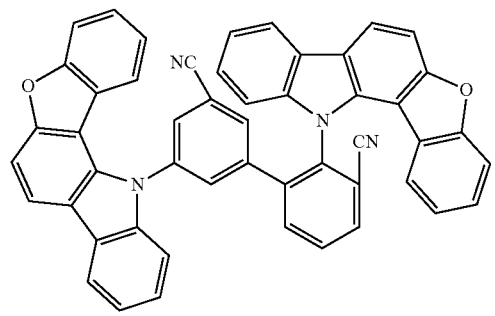
741
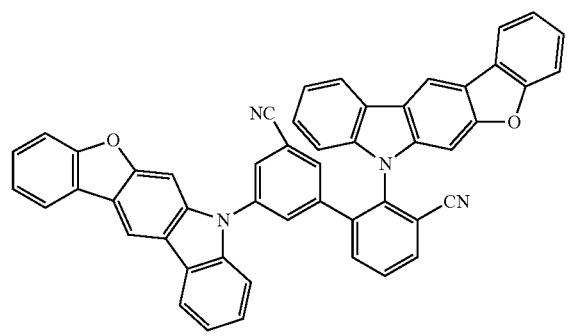
742
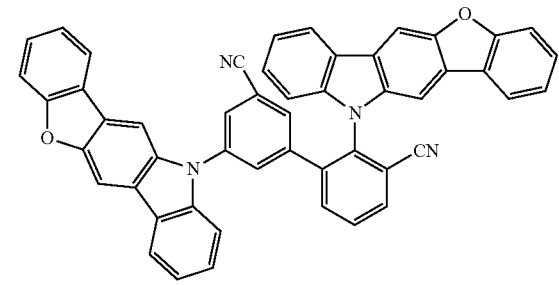
743
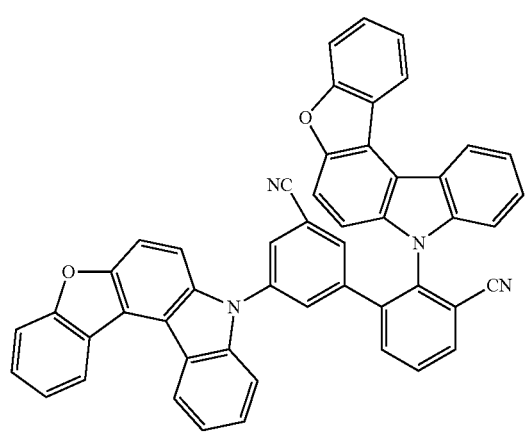
744
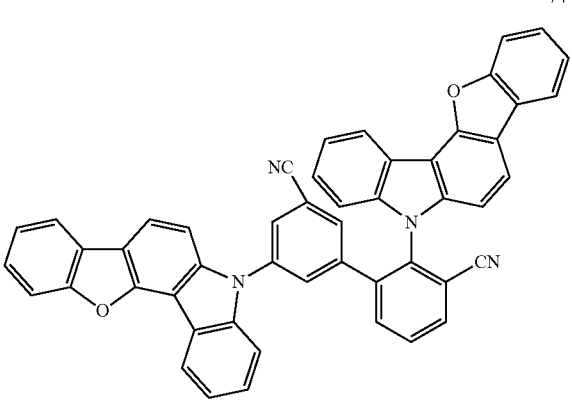
745
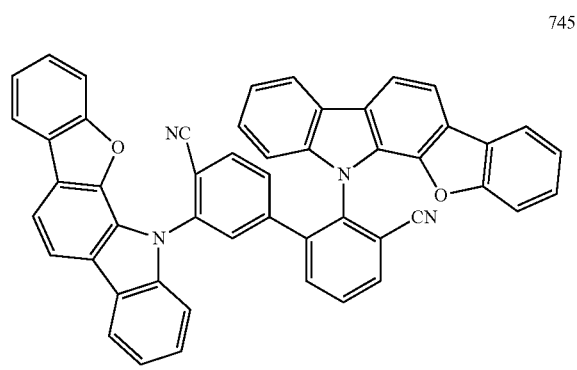
746
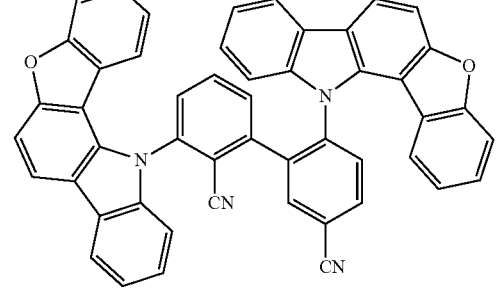
747
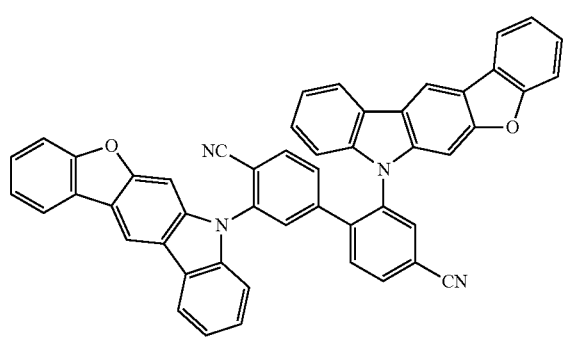

201
-continued
748
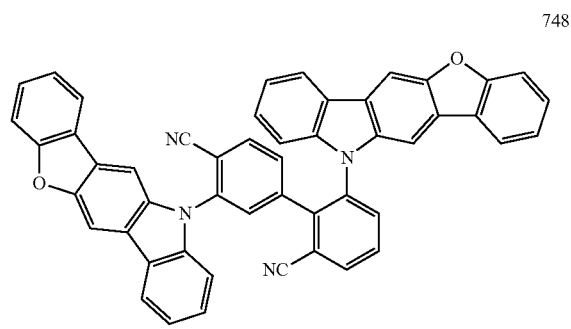
749
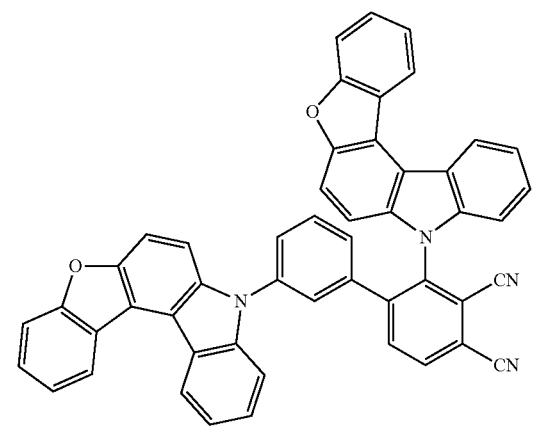
750
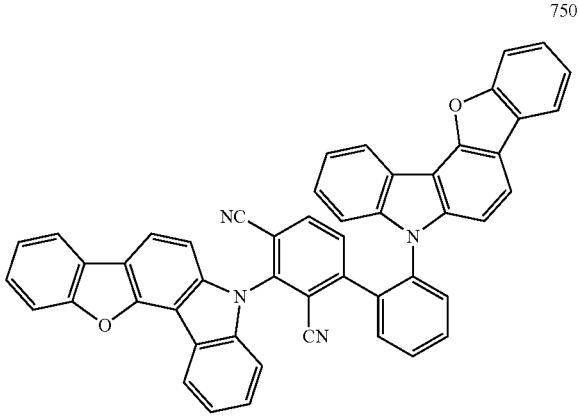
751
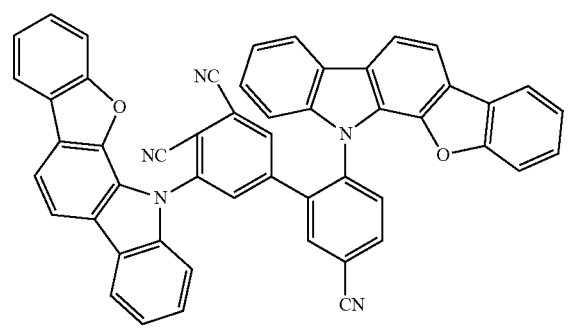
202
-continued
752
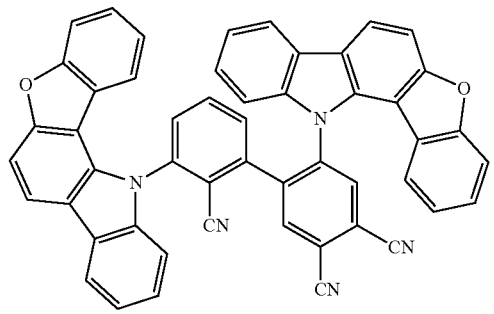
753
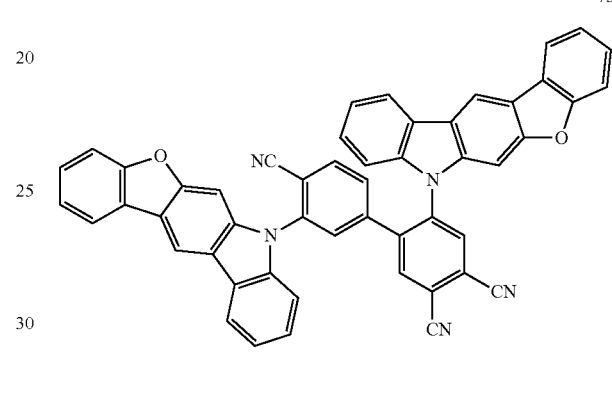
754
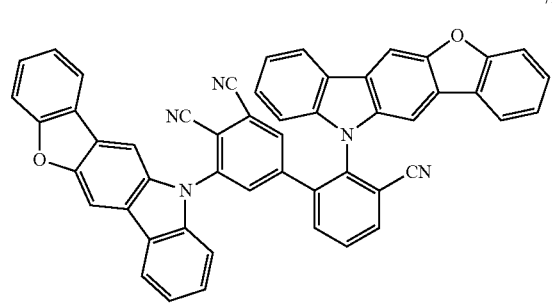
755
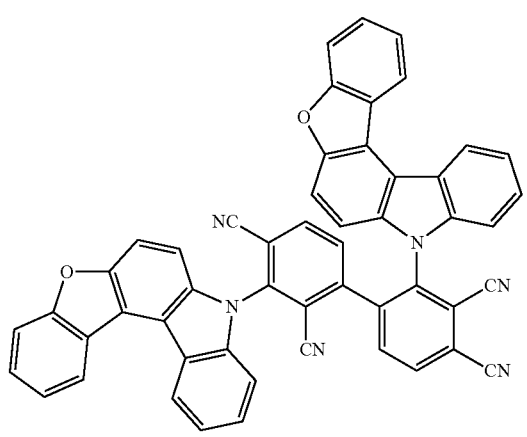

-continued
756
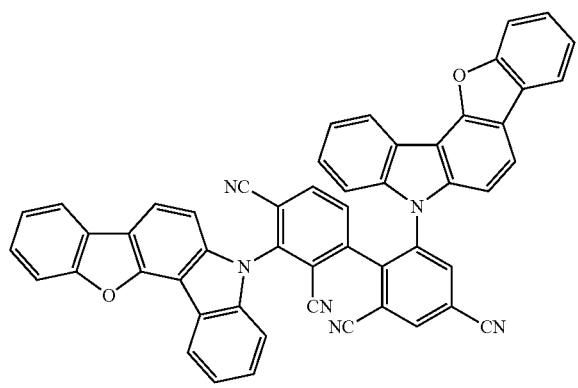
757
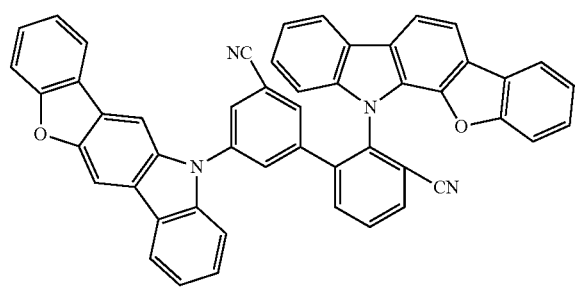
758
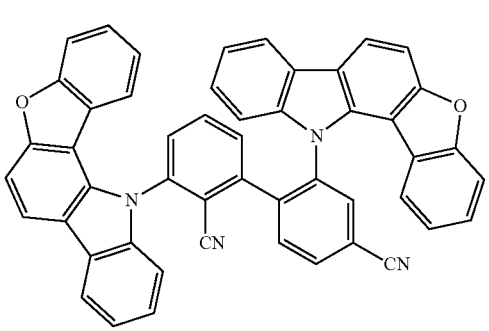
759
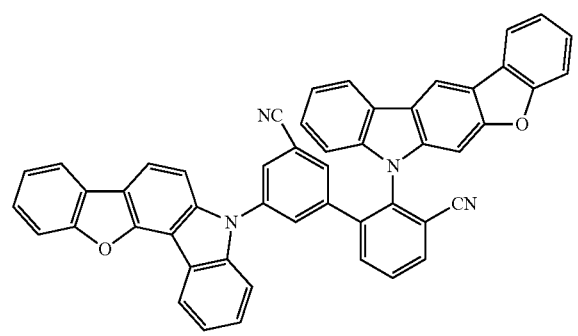
-continued
760
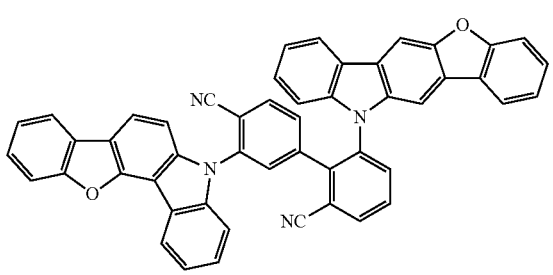
761
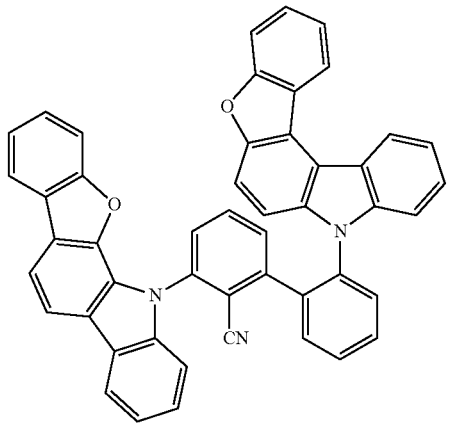
762
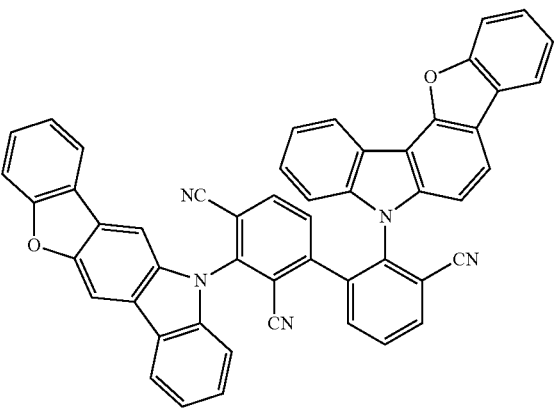
763
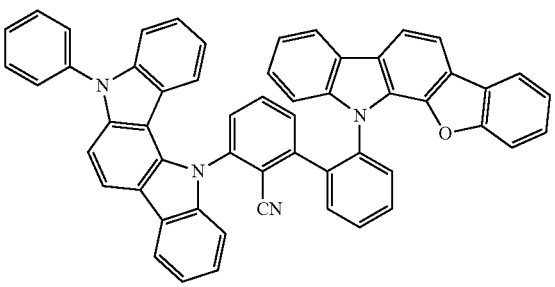

205
-continued
764
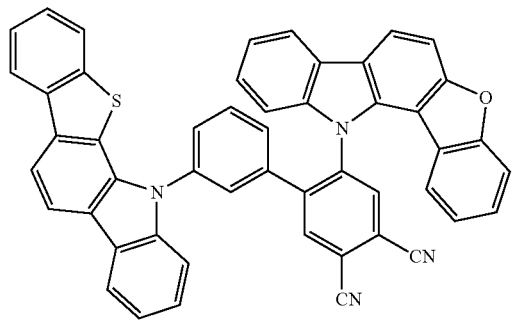
765
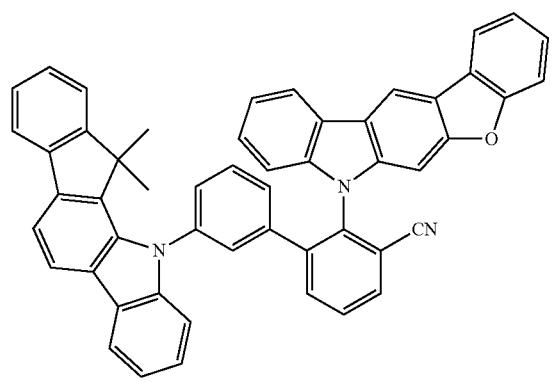
766
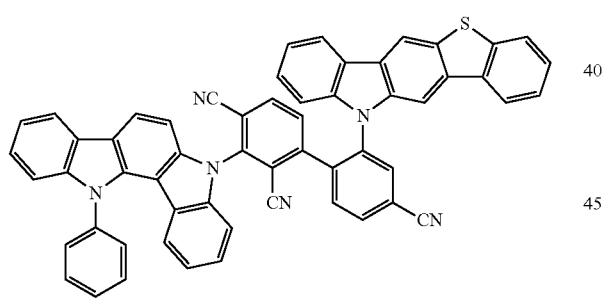
767
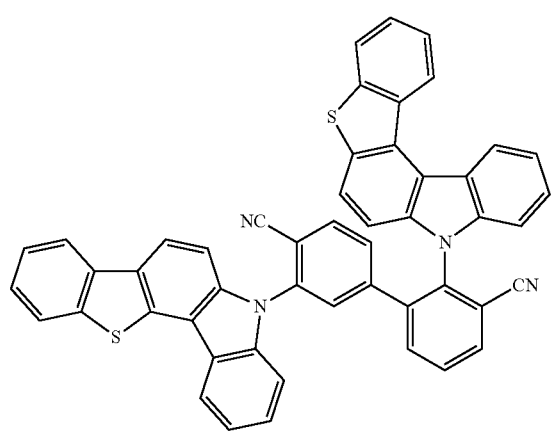
206
-continued
768
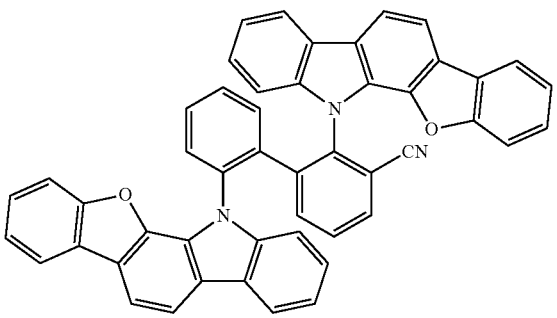
769
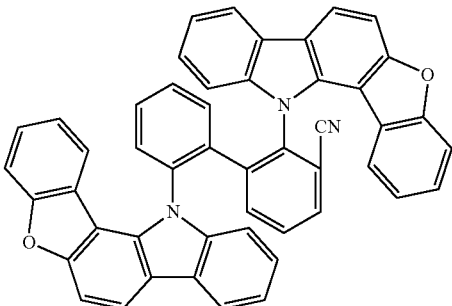
770
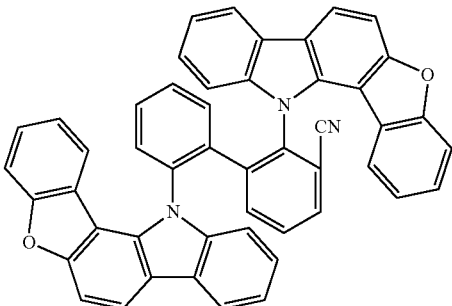
771
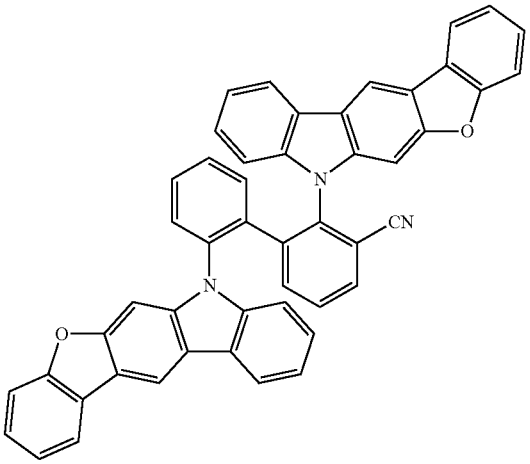

-continued
772
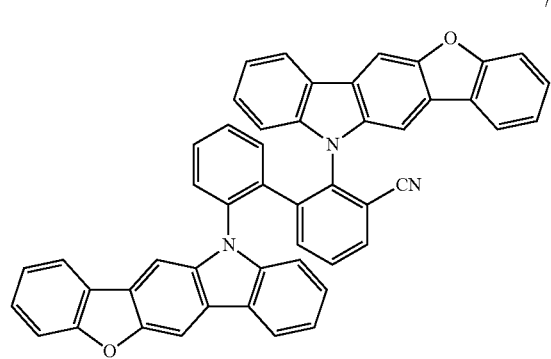
773
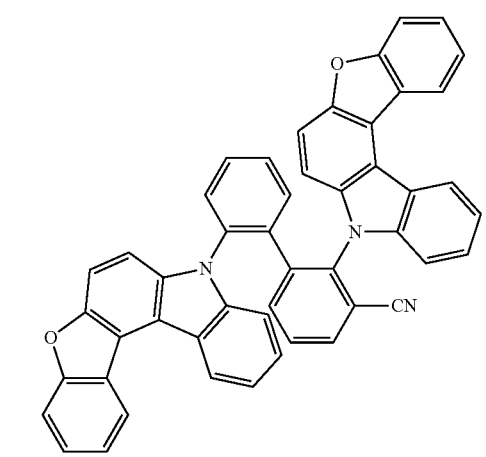
774
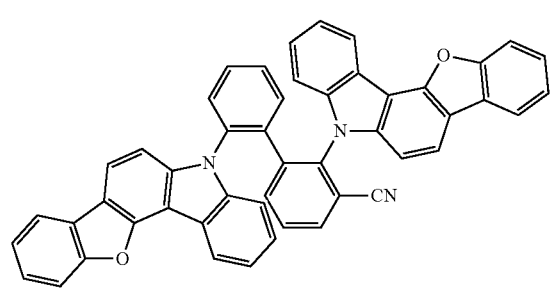
775
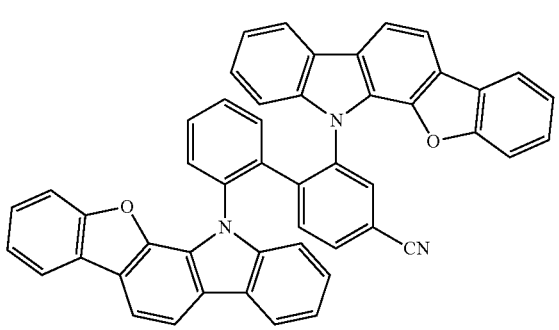
-continued
776
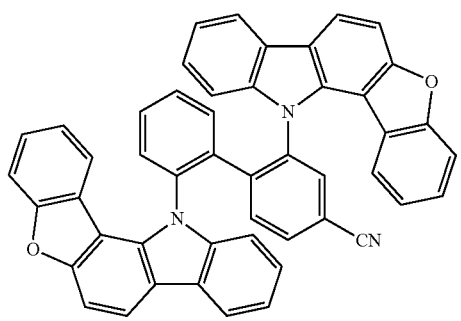
777
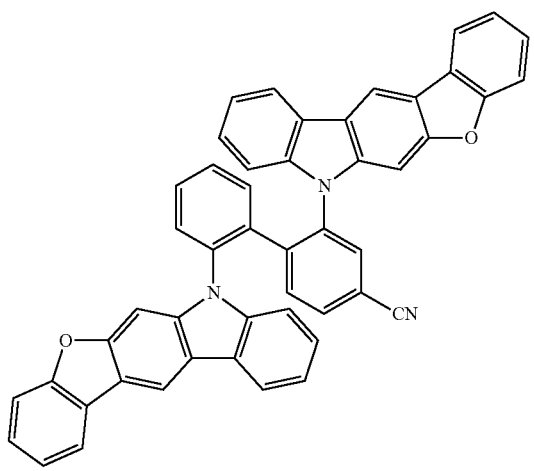
778
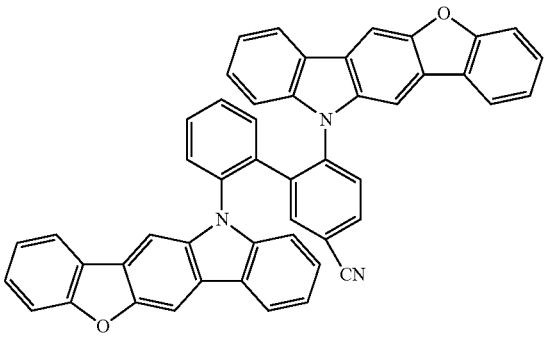
779
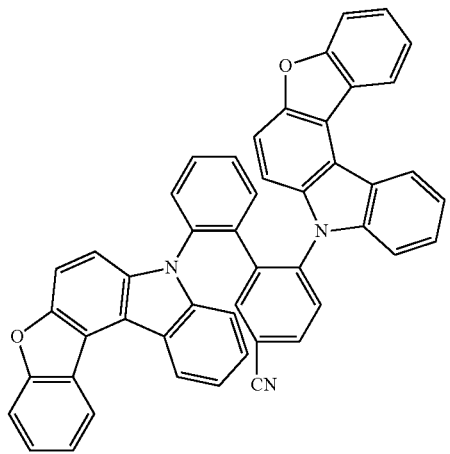

780
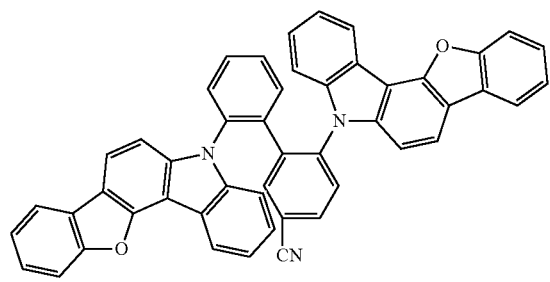
781
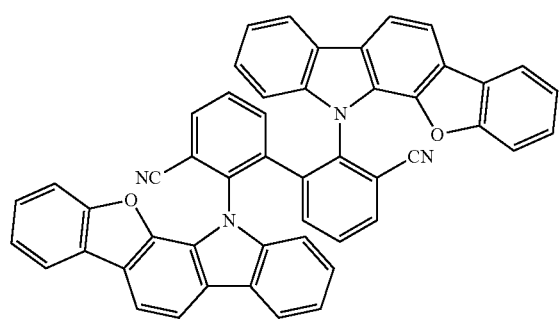
782
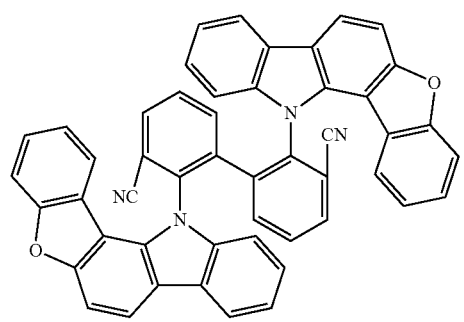
783
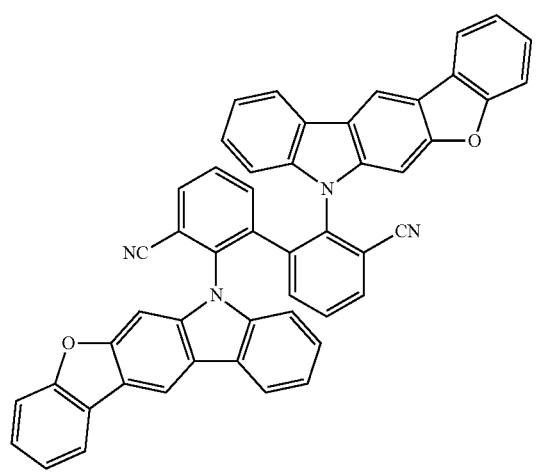
784
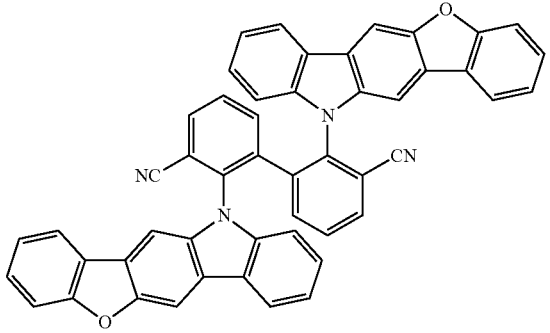
785
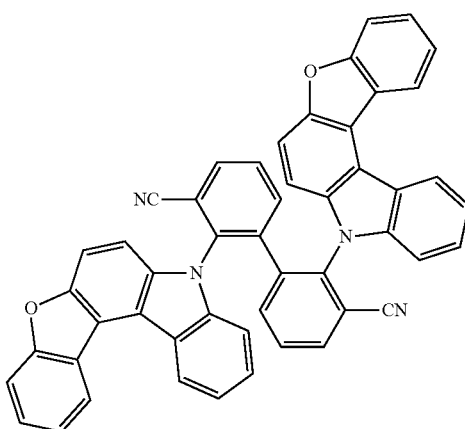
786
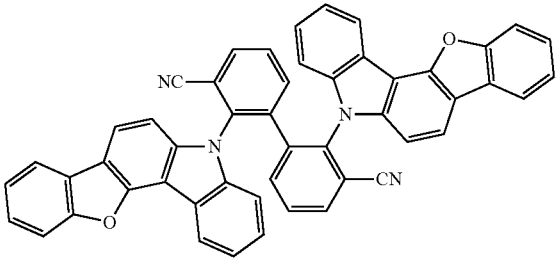
787
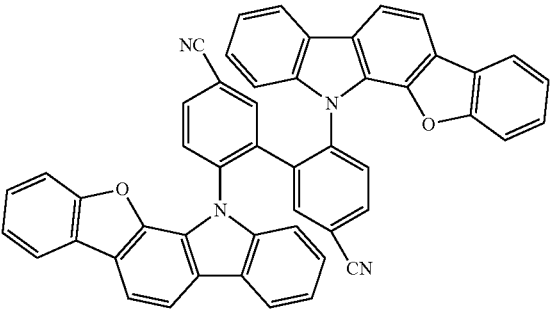

211
-continued
788
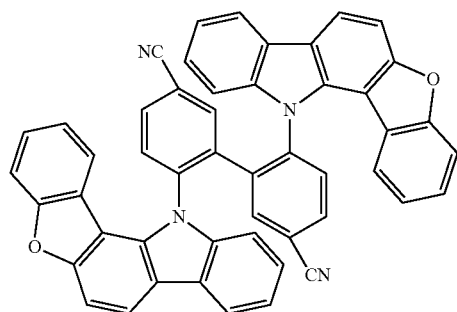
789
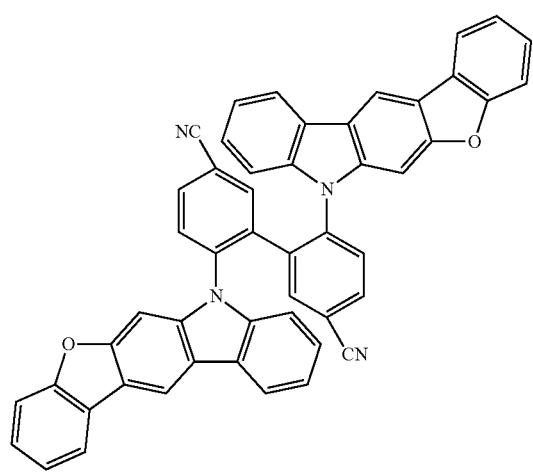
790
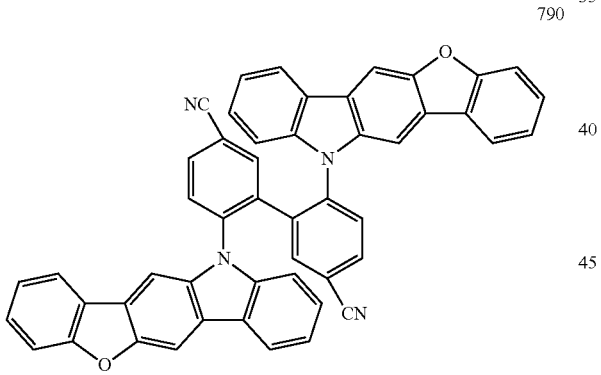
791
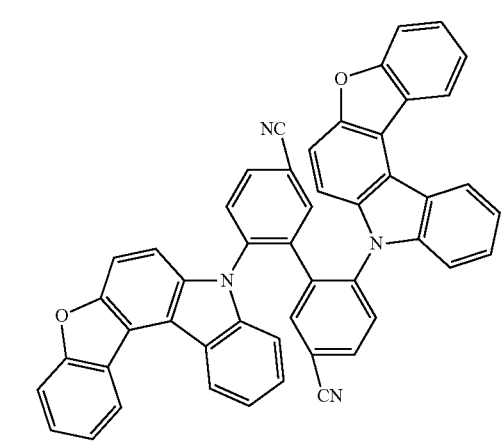
212
-continued
792
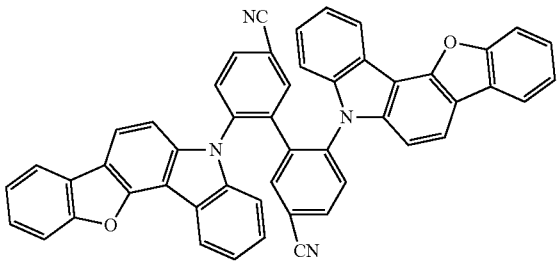
793
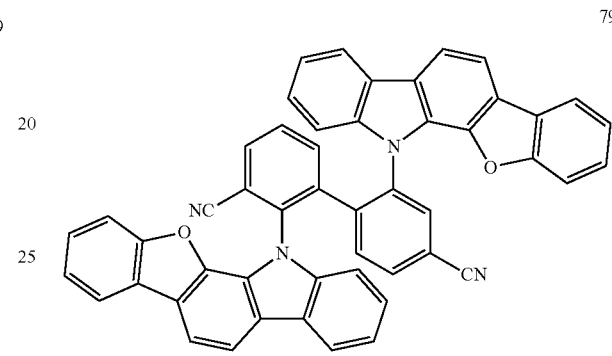
794
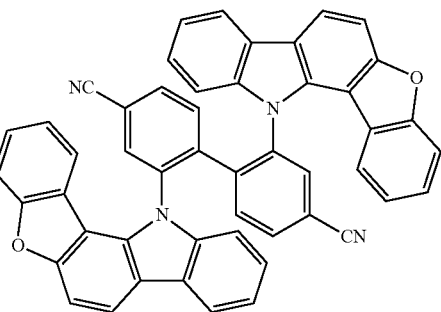
795
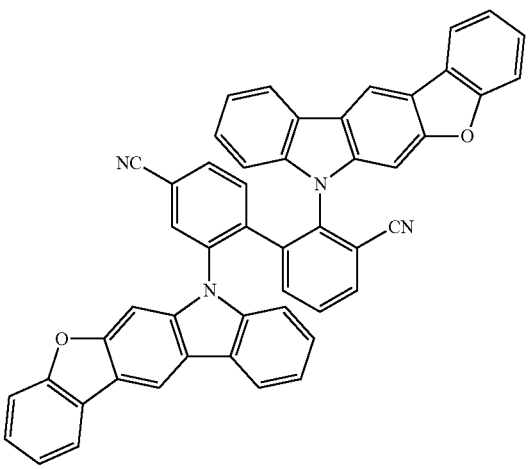

796
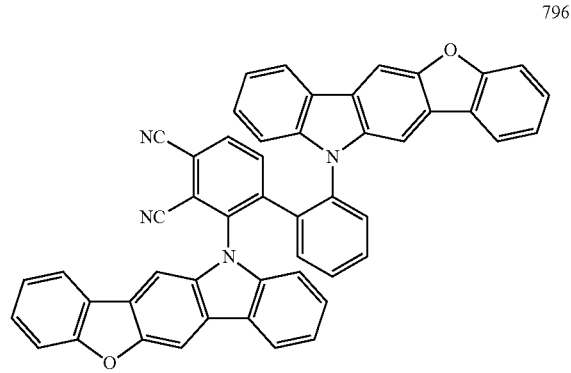
797
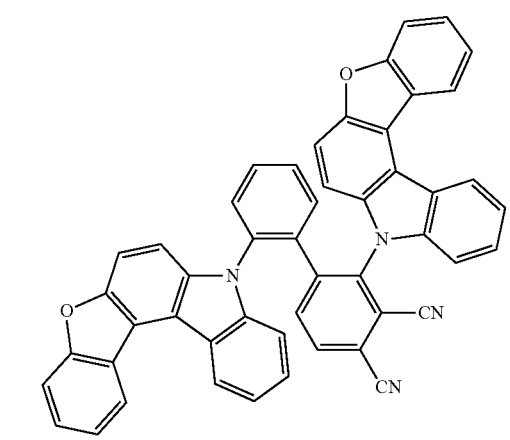
798
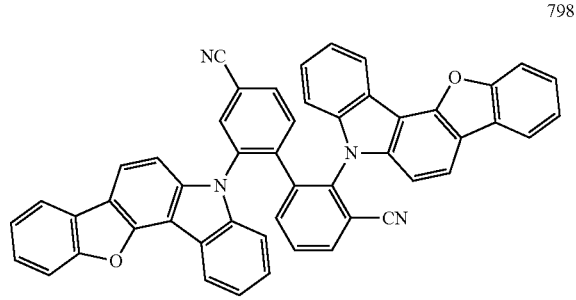
799
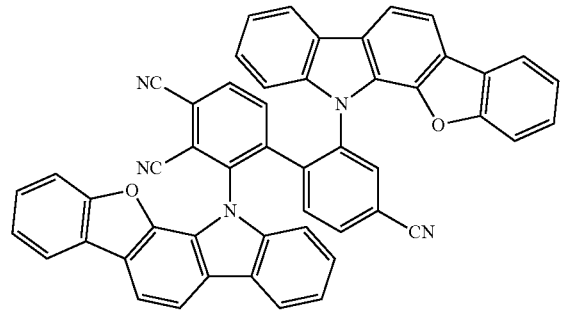
800
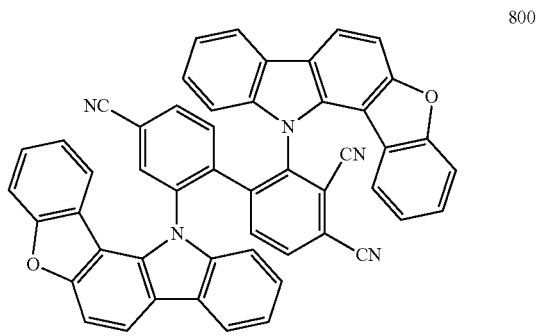
801
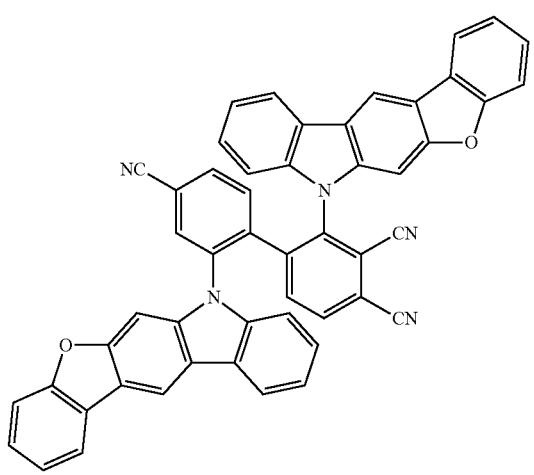
802
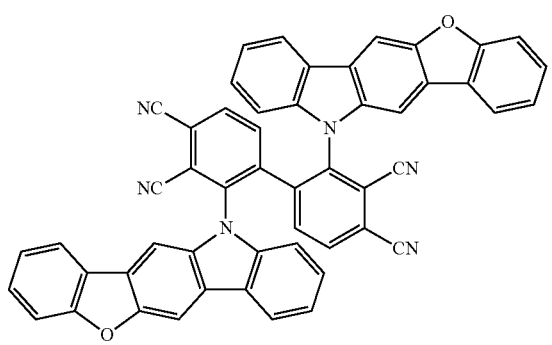
803
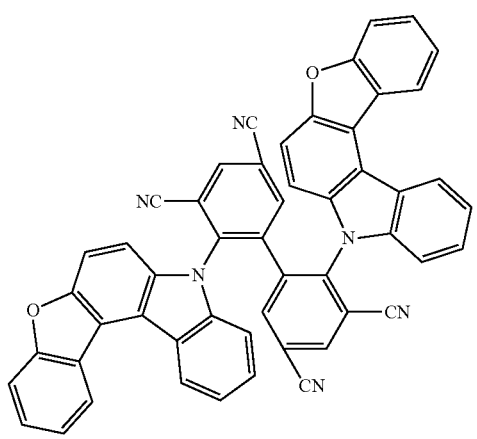

215
-continued
804
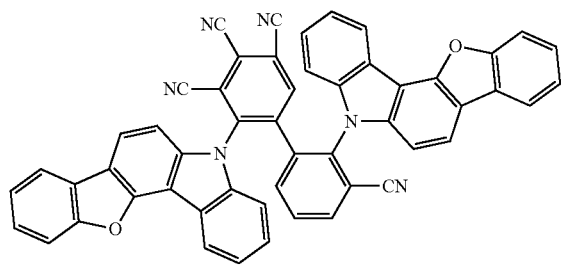
805
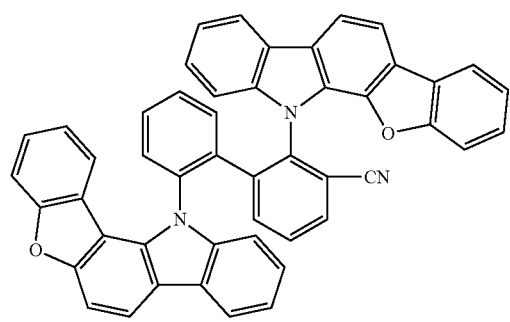
806
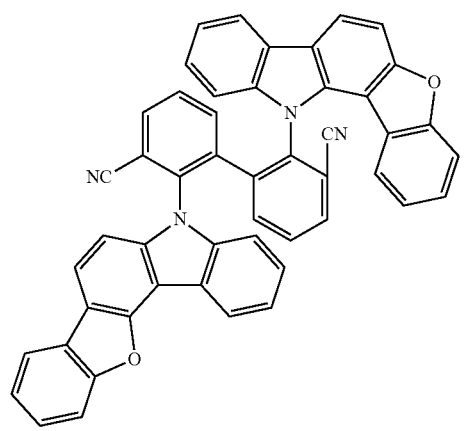
807
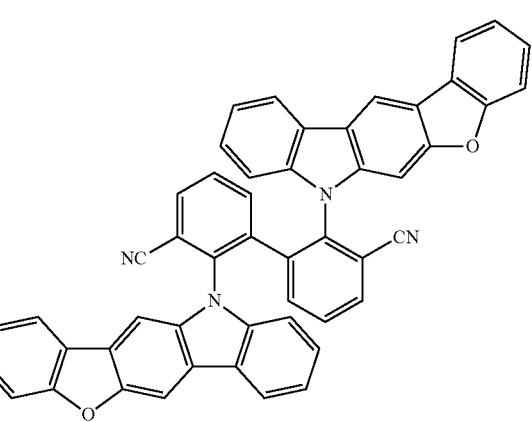
216
-continued
808
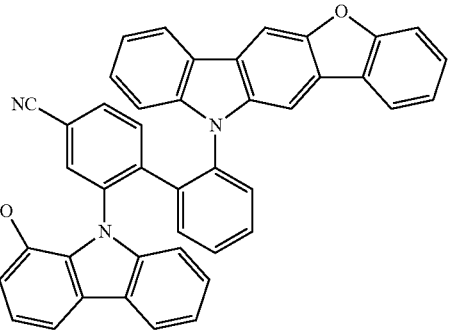
809
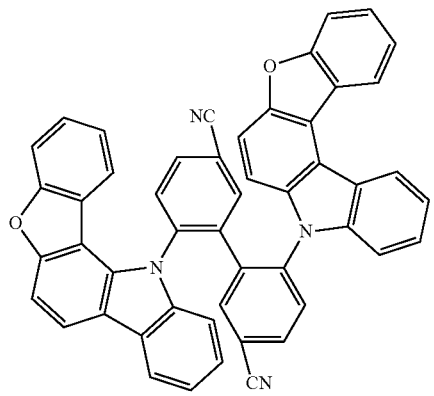
810
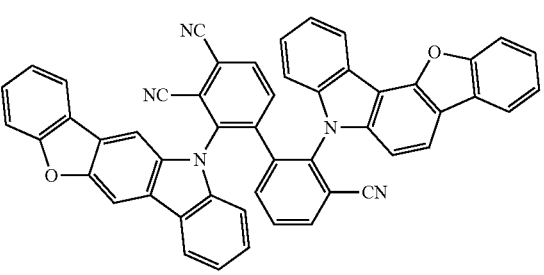
811
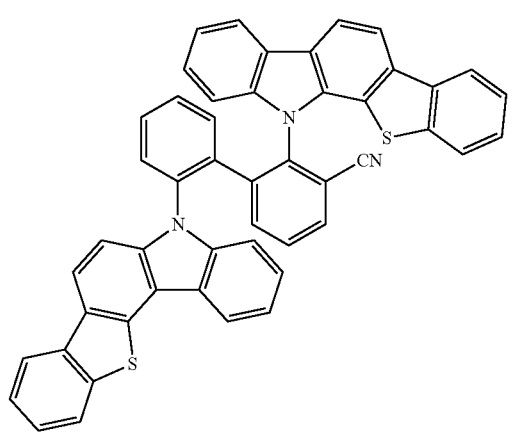

217
-continued
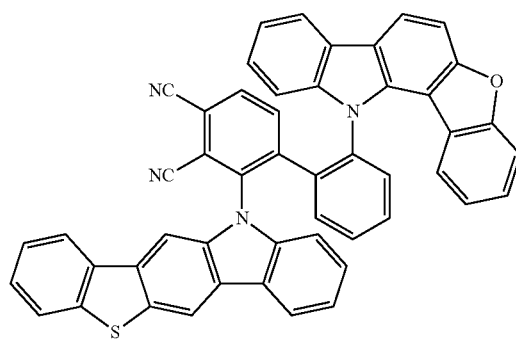
812
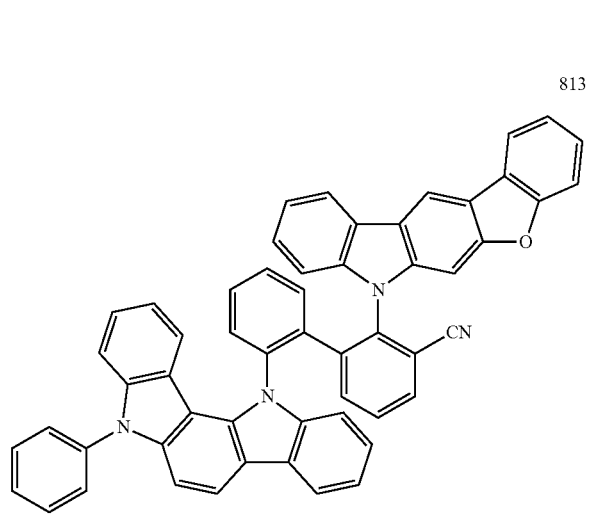
813
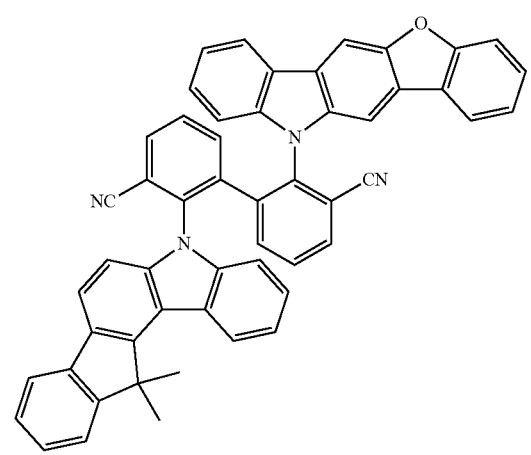
814
218
-continued
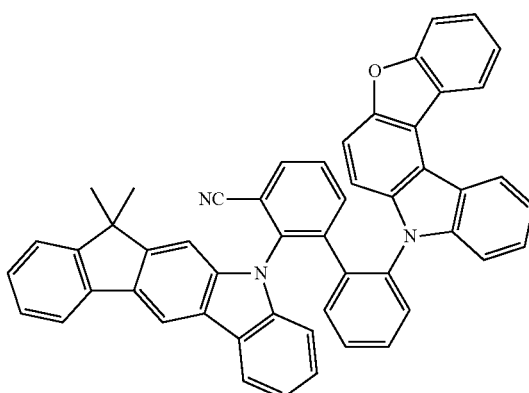
815
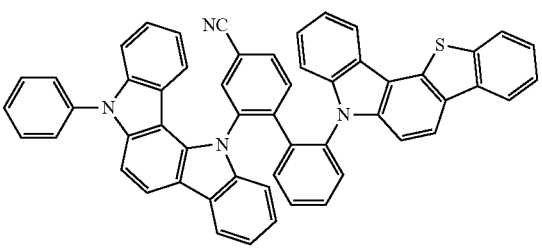
816
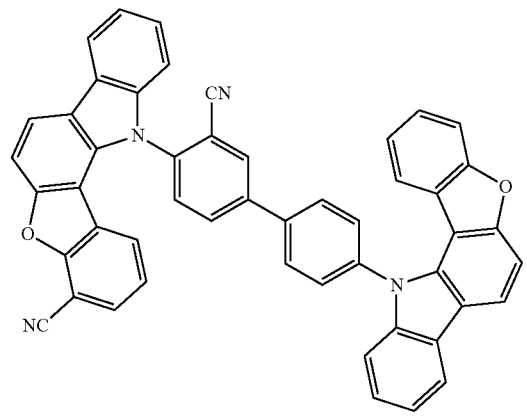
817
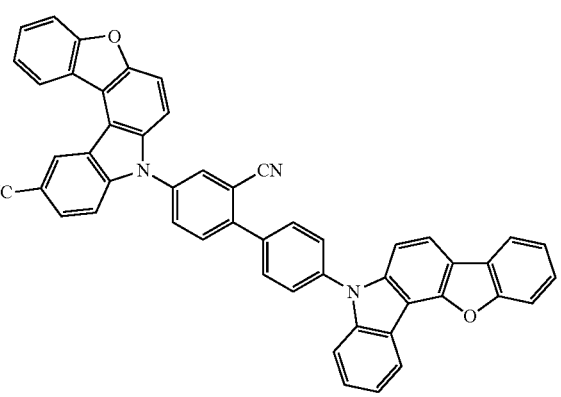
818

819
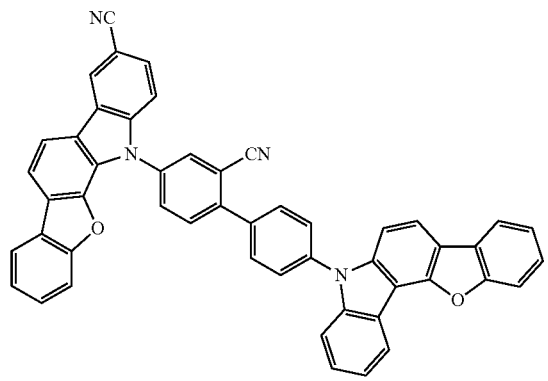
820
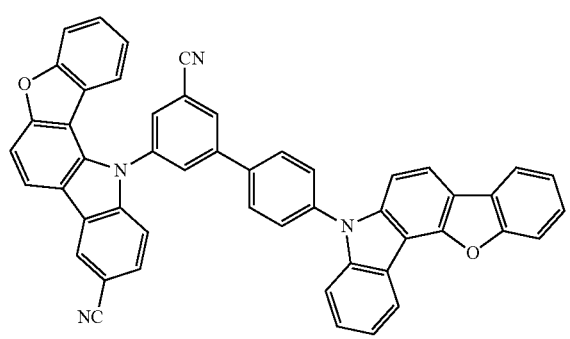
821
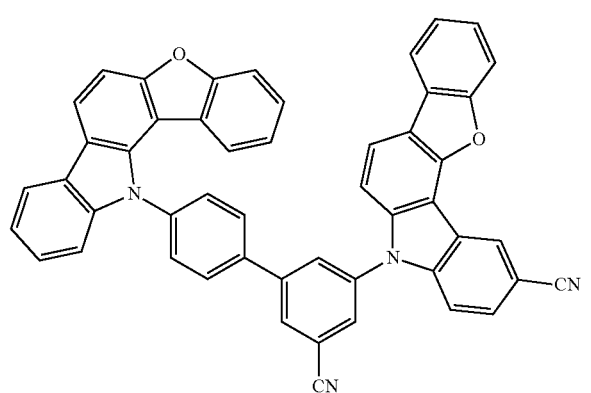
822
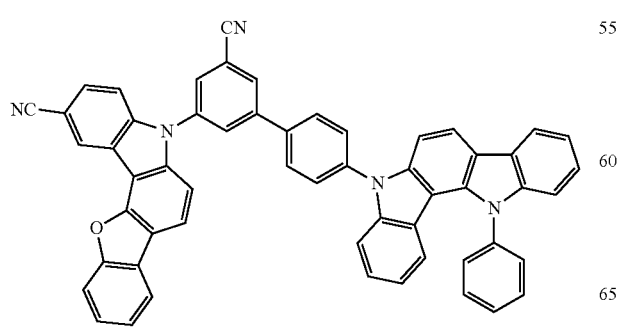
823
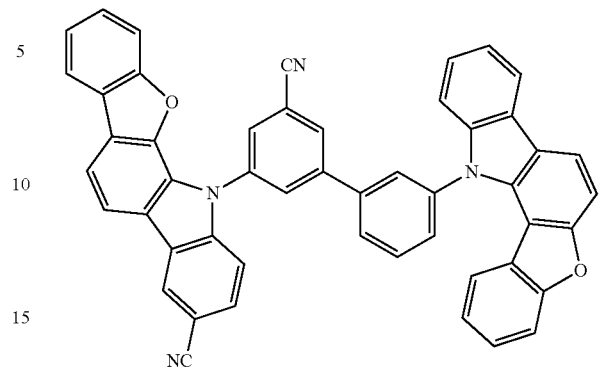
824
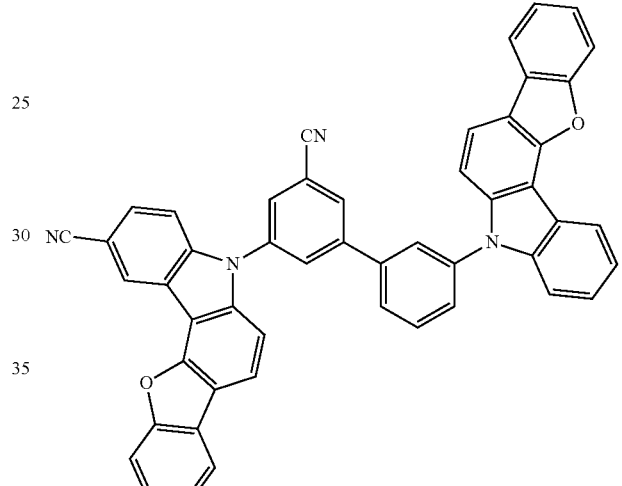
825
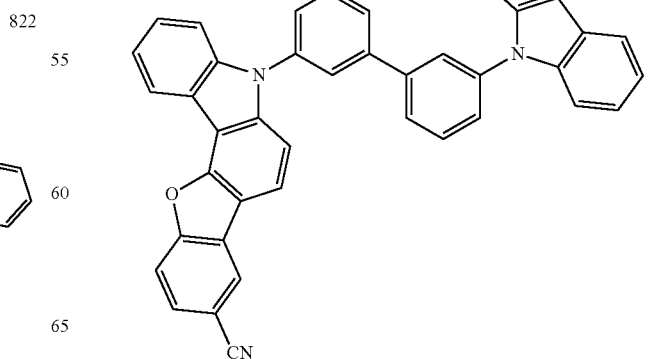

221
-continued
222
-continued
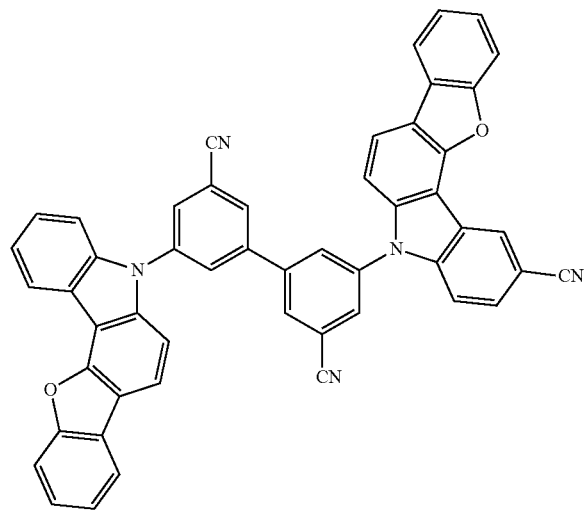
826
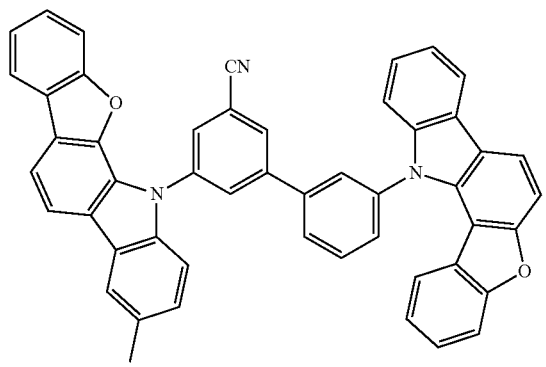
829
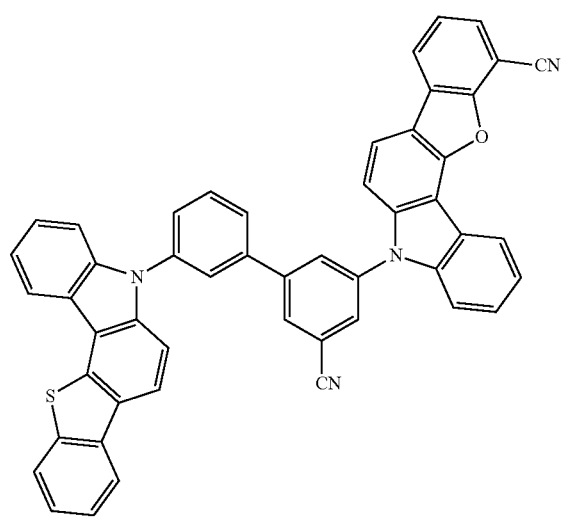
827
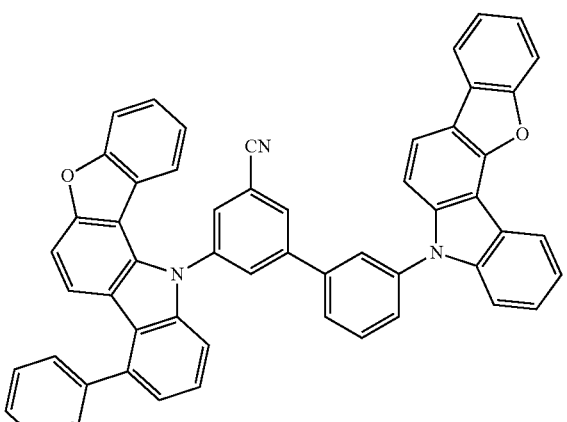
830
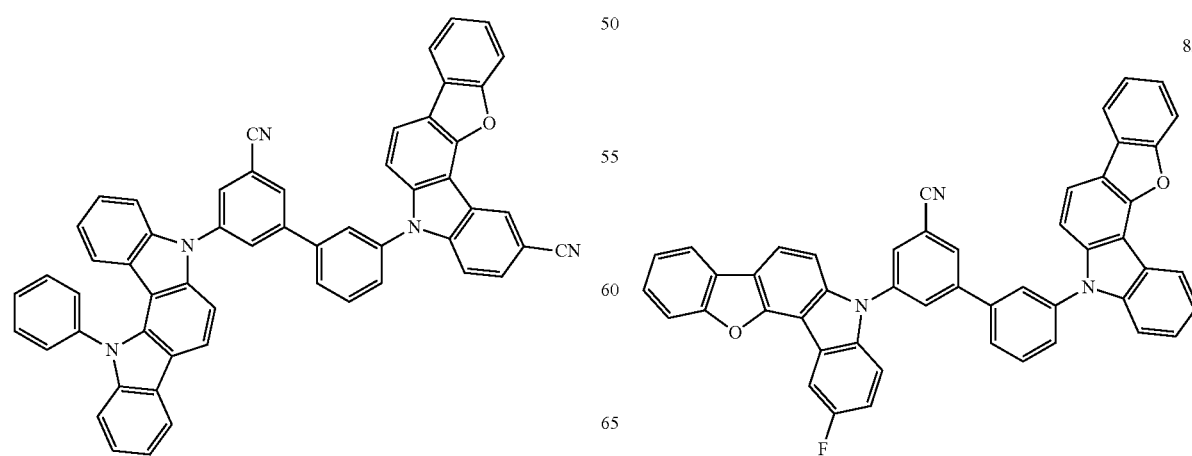

223
-continued
832
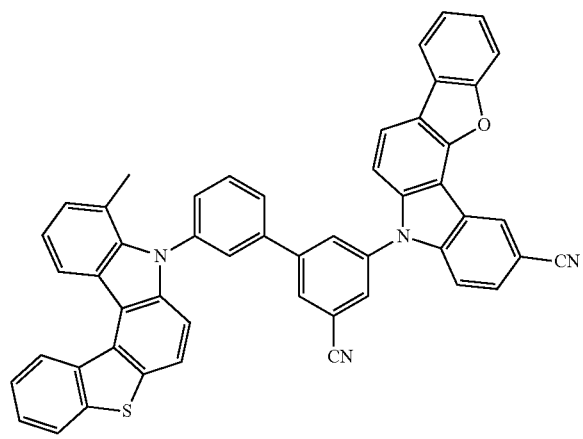
833
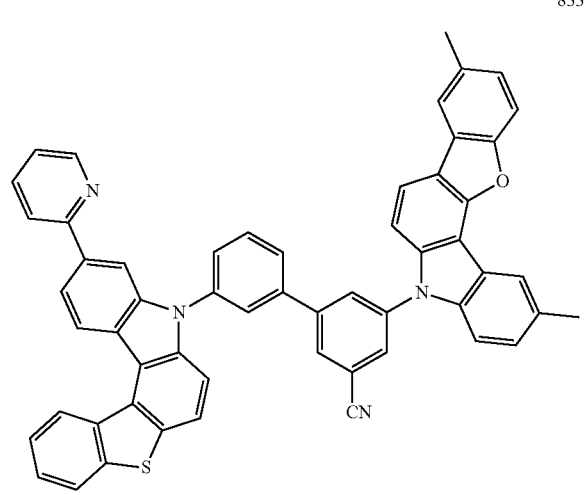
834
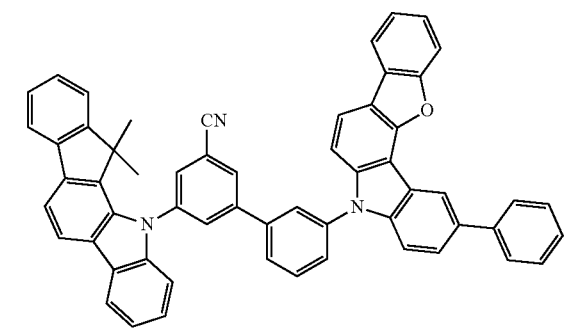
835
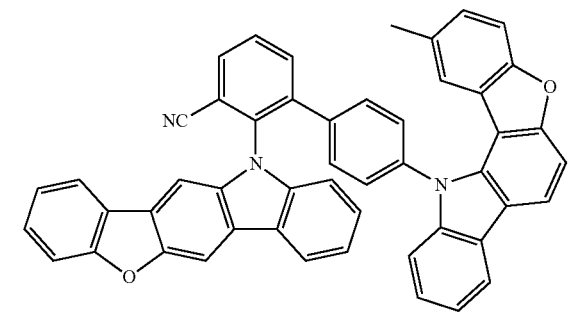
224
-continued
836
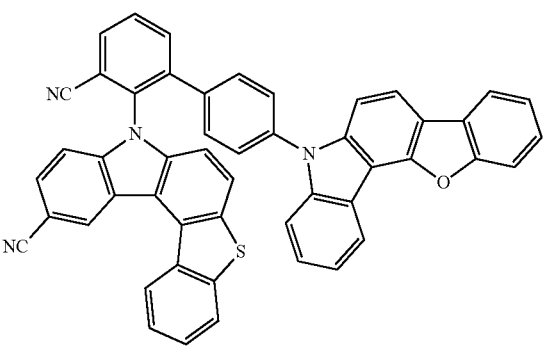
837
838
839
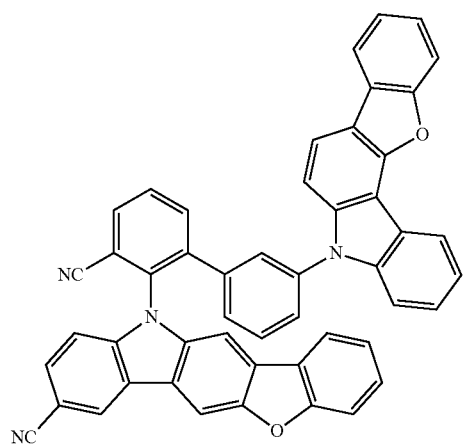

-continued
840
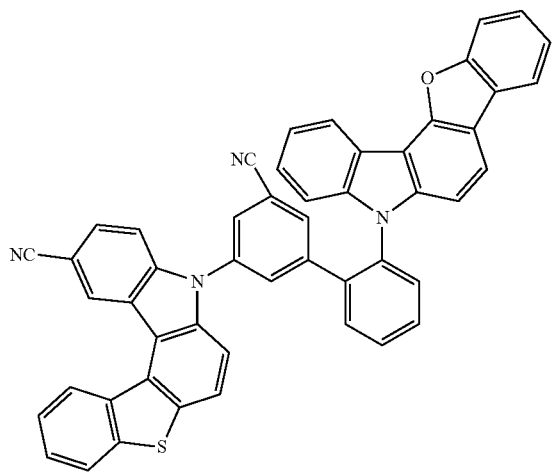
841
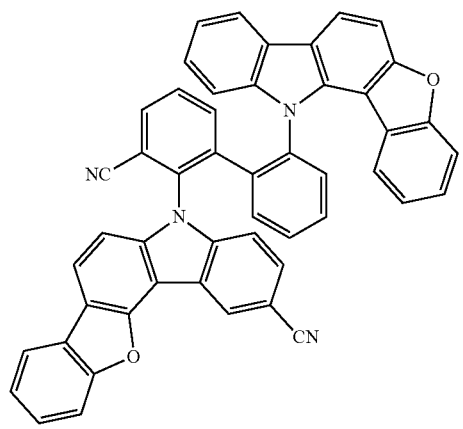
842
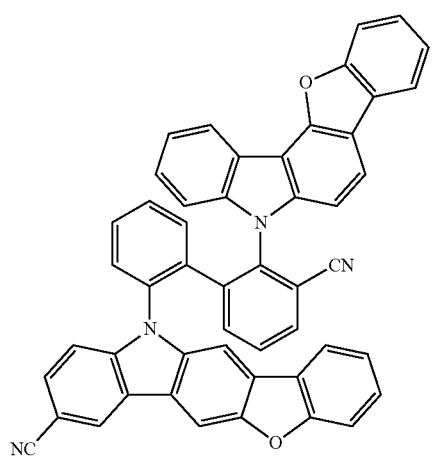
-continued
843
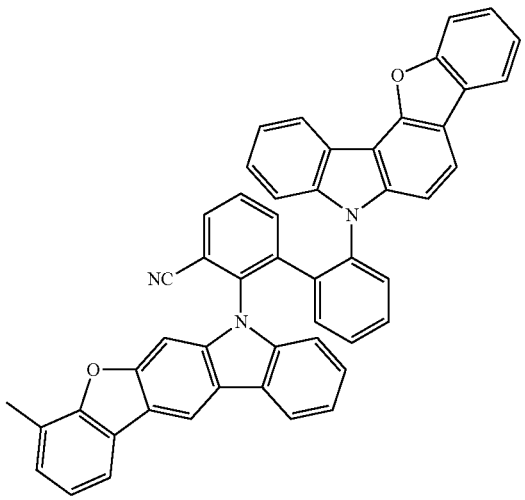
844
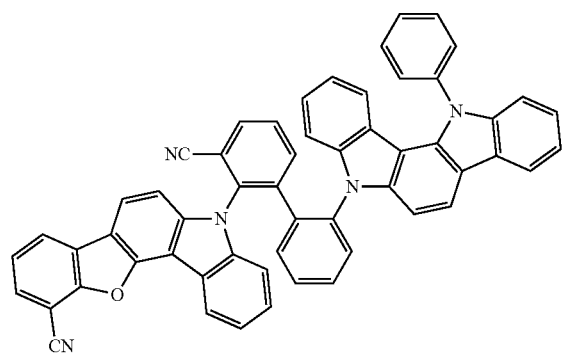
845
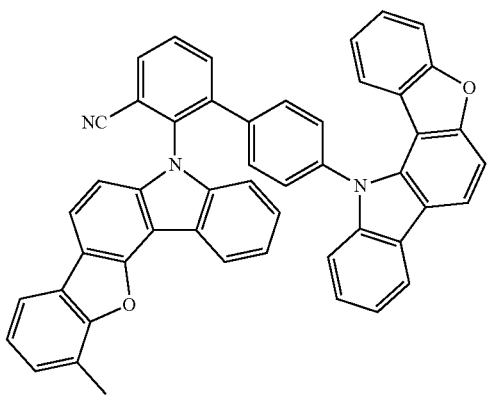

-continued
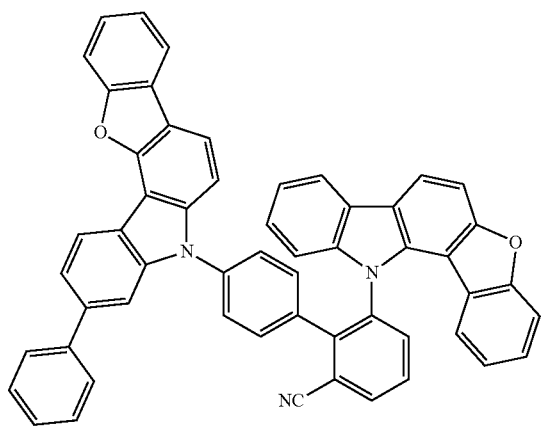
846
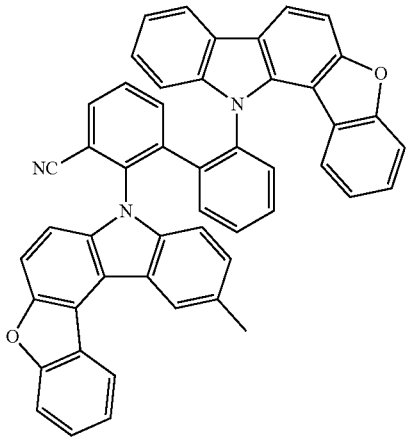
849
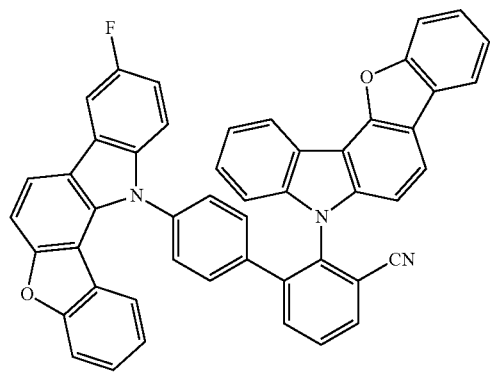
847
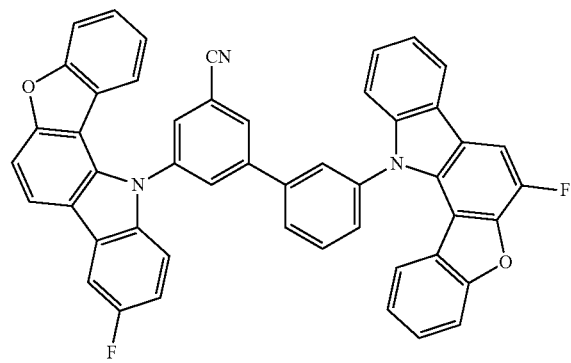
850
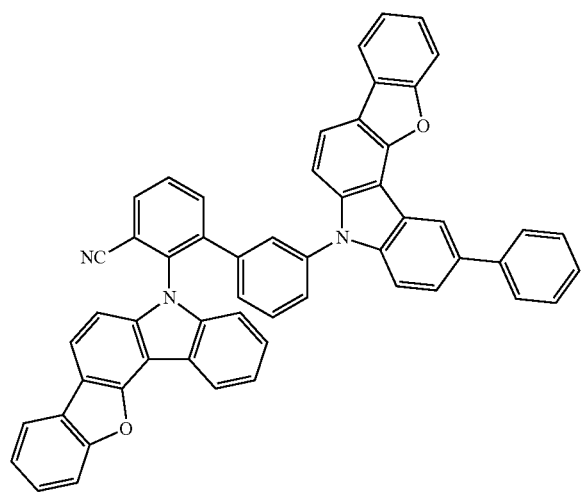
848
851

-continued

852

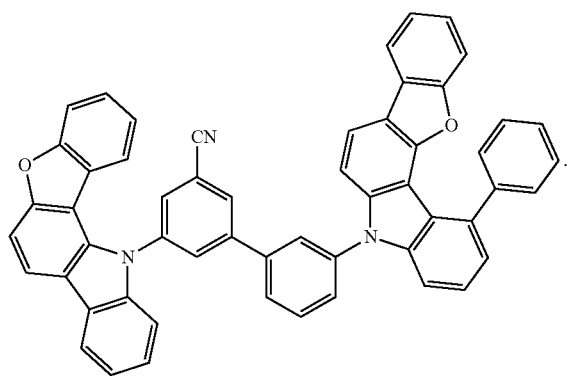

Ar₁ in Formula 1 may be the group represented by Formula 2, and Ar₂ in Formula 1 may be the group represented by Formula 3. That is, Ar₁ and Ar₂ in Formula 1 may each independently and simultaneously not be "a substituted or unsubstituted carbazole". In this regard, the condensed cyclic compound represented by Formula 1 may have a high glass transition temperature (Tg) and a high thermal decomposition temperature (Td), thereby exhibiting excellent thermal stability. Based on excellent hole mobility characteristics and a relatively high level of the highest occupied molecular orbital (HOMO) energy (that is, an absolute value of the relatively low HOMO energy) that the condensed cyclic compound represented by Formula 1 may have, an organic light-emitting device including the condensed cyclic compound represented by Formula 1 may have high efficiency and long lifespan. In addition, at least one of two rings that are each condensed with sides of the pyrrole ring of Formula 2 and with sides of the pyrrole ring of Formula 3 may be "a benzene" (refer to the structures of Formulae 2 and 3). Accordingly, the condensed cyclic compound represented by Formula 1 and including Ar₁ and Ar₂, which are each the group represented by Formula 2 and the group represented by Formula 3, may have a suitable triplet energy T₁ (which is relatively high) for a material of an organic light-emitting device, for example, a host included in an emission layer of an organic light-emitting device.

In addition, the group represented by *-L₁-L₂-*' in Formula 1 may include 1, 2, 3, or 4 cyano groups. In this regard, the condensed cyclic compound represented by Formula 1 may have a relatively low level of the lowest occupied molecular orbital (LUMO) (that is, an absolute value of the relatively high LUMO energy) and excellent electron mobility characteristics. Thus, the condensed cyclic compound represented by Formula 1 may have suitable electric characteristics for a material of an organic light-emitting device, for example, a host included in an emission layer of an organic light-emitting device. Accordingly, an organic light-emitting device including the condensed cyclic compound represented by Formula 1 may have high efficiency and long lifespan.

For example, HOMO, LUMO, S₁, and T₁ energy levels of Compounds 1, 36, 102, 108, 122, 126, 132, 146, 150, 218, 330, 366, 378, 474, 523, 524, 525, 666, 684, 704, and 786, and Compounds A and B were each measured and evaluated according to the Density Functional Theory (EFT) calculations using Gaussian software (structurally optimized at levels of B3LYP and 6-31G(d,p)), and the results are shown in Table 1.

TABLE 1

| Compound No. | HOMO (eV) | LUMO (eV) | T₁ (eV) | S₁ (eV) |
|---|---|---|---|---|
| 1 | −5.486 | −1.784 | 2.818 | 3.131 |
| 36 | −5.513 | −2.196 | 2.635 | 2.813 |
| 102 | −5.398 | −1.843 | 2.874 | 3.170 |
| 108 | −5.513 | −1.849 | 2.895 | 3.122 |
| 122 | −5.512 | −1.875 | 2.985 | 3.200 |
| 126 | −5.391 | −1.836 | 2.993 | 3.146 |
| 132 | −5.496 | −1.848 | 2.938 | 3.102 |
| 146 | −5.732 | −2.190 | 2.907 | 3.001 |
| 150 | −5.620 | −2.181 | 2.832 | 2.941 |
| 218 | −5.414 | −1.804 | 2.981 | 3.167 |
| 330 | −5.269 | −1.751 | 3.006 | 3.120 |
| 366 | −5.399 | −1.664 | 3.001 | 3.208 |
| 378 | −5.543 | −1.982 | 2.949 | 3.077 |
| 474 | −5.564 | −1.907 | 2.996 | 3.096 |
| 523 | −5.661 | −2.044 | 2.978 | 3.172 |
| 524 | −5.475 | −2.083 | 2.924 | 2.993 |
| 525 | −5.559 | −2.317 | 2.801 | 2.850 |
| 666 | −5.401 | −1.875 | 2.928 | 3.086 |
| 684 | −5.624 | −2.208 | 2.813 | 2.919 |
| 704 | −5.634 | −2.220 | 2.813 | 2.920 |
| 786 | −5.555 | −1.933 | 2.988 | 3.069 |
| A | −5.799 | −2.144 | 2.936 | 3.098 |
| B | −5.299 | −1.288 | 3.005 | 3.516 |

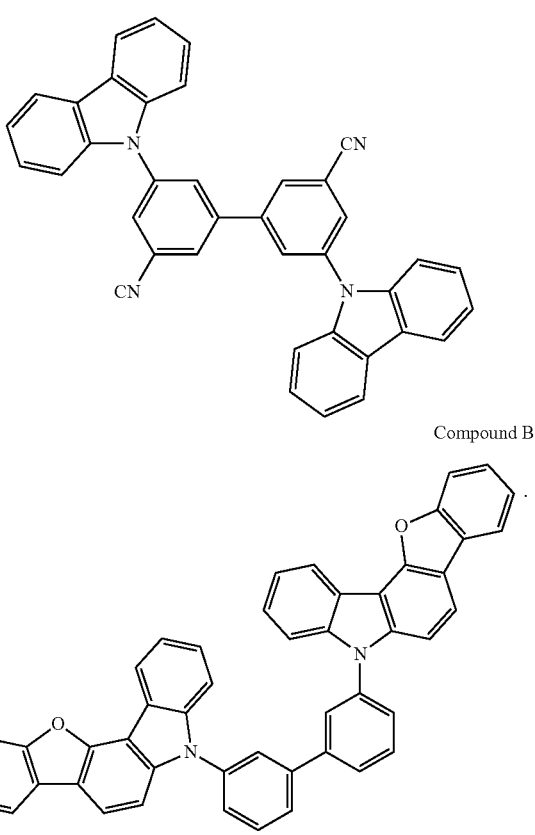

Compound A

Compound B

Referring to Table 1, it was determined that the condensed cyclic compound represented by Formula 1 may have excellent electric characteristics, for example, high T₁ energy levels.

A method of synthesizing the condensed cyclic compound represented by Formula 1 may be understood by those of ordinary skill in the art based on Synthesis Examples described below.

Therefore, the condensed cyclic compound represented by Formula 1 may be suitable as a material for the organic layer of an organic light-emitting device, and for example, may be suitable as a material for an emission layer and/or an electron transport region included in an organic layer.

Another aspect of the present disclosure includes an organic light-emitting device including:
a first electrode;
a second electrode; and
an organic layer disposed between the first electrode and the second electrode,
wherein the organic layer includes an emission layer and at least one of the condensed cyclic compounds represented by Formula 1.

The organic light-emitting device includes the organic layer including the condensed cyclic compound represented by Formula 1, thereby exhibiting low driving voltage, high efficiency, high brightness, high quantum efficiency, and long lifespan.

For example, the emission layer may include the condensed cyclic compound represented by Formula 1.

In various embodiments, the emission layer may include the condensed cyclic compound represented by Formula 1, wherein the condensed cyclic compound represented by Formula 1 is suitable as a delayed fluorescent material.

In various embodiments, the emission layer may include a host and a dopant (wherein an amount of the host is greater than an amount of the dopant), and the host may include the condensed cyclic compound represented by Formula 1. The condensed cyclic compound represented by Formula 1 having a role of the host may deliver energy to the dopant according to the emission mechanisms for the delayed fluorescence. The dopant used may include at least one of a fluorescent dopant and a phosphorescent dopant. The dopant may be selected from dopants known in the art. The host may further include at least one material selected from known materials in the art which can be used as a host.

In various embodiments, the emission layer may include a host and a dopant (wherein an amount of the host is greater than an amount of the dopant), and the dopant may include the condensed cyclic compound represented by Formula 1. The condensed cyclic compound represented by Formula 1 having a role of the dopant may emit delayed fluorescence according to the emission mechanisms for the delayed fluorescence. The host may be selected from the materials known in the art.

The emission layer may emit green light or blue light.

In an embodiment, the emission layer may include a blue emission layer including a phosphorescent dopant, but is not limited thereto.

In various embodiments, an electron transport region may include the condensed cyclic compound represented by Formula 1.

For example, an electron transport region included in the organic light-emitting device may include at least one selected from a hole blocking layer and an electron transport layer, and at least one selected from a hole blocking layer, and an electron transport layer may include the condensed cyclic compound represented by Formula 1.

In an embodiment, an electron transport region included in the organic light-emitting device may include a hole blocking layer, and the hole blocking layer may include the condensed cyclic compound represented by Formula 1. The hole blocking layer may directly contact the emission layer.

As used herein, the expression "(an organic layer) may include at least one of the condensed cyclic compounds" may refer to "(an organic layer) may include one condensed cyclic compound represented by Formula 1 or at least two different condensed cyclic compounds represented by Formula 1".

For example, the organic layer may include, as the condensed cyclic compound represented by Formula 1, only Compound 1. Here, Compound 1 may be included in the emission layer of the organic light-emitting device. In various embodiments, the organic layer may include, as the condensed cyclic compound represented by Formula 1, Compound 1 and Compound 2. Here, Compound 1 and Compound 2 may both be in the same layer (for example, both Compound 1 and Compound 2 may be in the emission layer), or Compound 1 and Compound 2 may be in different layers (for example, Compound 1 may be in the emission layer and Compound 2 may be in the hole blocking layer).

The first electrode may be an anode that is a hole injection electrode, and the second electrode may be a cathode that is an electron injection electrode. Alternatively, the first electrode may be a cathode that is an electron injection electrode and the second electrode may be an anode that is a hole injection electrode.

For example, in the organic light-emitting device,
the first electrode may be an anode,
the second electrode may be a cathode, and
the organic layer may include a hole transport region disposed between the first electrode and the emission layer and an electron transport region disposed between the emission layer and the second electrode,
wherein the hole transport region may include at least one selected from a hole injection layer, a hole transport layer, and an electron blocking layer, and
the electron transport region may include at least one selected from a hole blocking layer, an electron transport layer, and an electron injection layer.

As used herein, the term "organic layer" may refer to a single layer and/or a plurality of layers disposed between the first electrode and the second electrode of the organic light-emitting device. A material included in the "organic layer" is not limited to just an organic material.

FIG. 1 is a schematic cross-sectional view of a structure of an organic light-emitting device 10 according to an exemplary embodiment. Hereinafter, a structure of an organic light-emitting device according to an exemplary embodiment and a method of manufacturing an organic light-emitting device, according to an exemplary embodiment, will be described in connection with FIG. 1. The organic light-emitting device 10 may have a structure in which a first electrode 11, an organic layer 15, and a second electrode 19 are sequentially stacked in this stated order.

A substrate may be additionally disposed under the first electrode 11 or above the second electrode 19. The substrate may be any substrate generally used for organic light-emitting device in the art, but in an embodiment, may be a glass substrate or a transparent plastic substrate, each with excellent mechanical strength, thermal stability, transparency, surface smoothness, ease of handling, and/or water-resistance.

The first electrode 11 may be formed by, for example, depositing and/or sputtering a material for forming the first electrode 11 on the substrate. When the first electrode 11 is an anode, the material for forming the first electrode 11 may be selected from materials having a high work function so as to facilitate hole injection. The first electrode 11 may be a reflective electrode, a semi-transmissive electrode, or a transmissive electrode. The material for forming the first electrode 11 may be indium tin oxide (ITO), indium zinc oxide (IZO), tin oxide, ($SnO_2$), and zinc oxide (ZnO). In various embodiment, a metal, such as magnesium (Mg), aluminum (Al), aluminum-lithium (Al—Li), calcium (Ca), magnesium-indium (Mg—In), and/or magnesium-silver (Mg—Ag), may be used as the material for forming the first electrode 11.

The first electrode 11 may have a single-layer structure, or a multi-layer structure including two or more layers. For example, the first electrode 11 may have a triple-layered structure of ITO/Ag/ITO, but the structure of the first electrode 11 is not limited thereto.

The organic layer 15 may be disposed on the first electrode 11.

The organic layer 15 may include a hole transport region, an emission layer, and an electron transport region.

The hole transport region may be disposed between the first electrode 11 and the emission layer.

The hole transport region may include at least one selected from a hole injection layer, a hole transport layer, an electron blocking layer, and a buffer layer.

The hole transport region may include only a hole injection layer, or only a hole transport layer. In various embodiments, the hole transport region may include a structure of hole injection layer/hole transport layer or a structure of hole injection layer/hole transport layer/electron blocking layer, wherein for each structure, constituting layers are sequentially stacked on the first electrode 11.

When the hole transport region includes a hole injection layer, the hole injection layer may be formed on the first electrode 11 by using various suitable methods, such as vacuum deposition, spin coating, casting, and/or Langmuir-Blodgett (LB) deposition.

When a hole injection layer is formed by vacuum deposition, the vacuum deposition may be, for example, performed at a deposition temperature of about 100° C. to about 500° C., at a vacuum degree of about $10^{-8}$ to about $10^{-3}$ torr, and at a deposition rate of about 0.01 to about 100 Angstroms per second (Å/sec) by taking into account a compound for a hole injection layer to be deposited, a structure of a hole injection layer to be formed, and thermal properties of a hole injection to be formed, but the vacuum deposition conditions are not limited thereto.

When a hole injection layer is formed by spin coating, the spin coating may be performed at a coating rate of about 2,000 revolutions per minute (rpm) to about 5,000 rpm, and at a temperature of about 80° C. to 200° C. for the removal of a solvent after being coated by taking into account a compound for a hole injection layer to be deposited, a structure of a hole injection to be formed, and thermal properties of a hole injection to be formed, but the spin coating conditions are not limited thereto.

The hole transport layer and the electron blocking layer may each be formed by referring to the method used to form the hole injection layer.

The hole transport region may include at least one selected from m-MTDATA, TDATA, 2-TNATA, NPB, β-NPB, TPD, Spiro-TPD, Spiro-NPB, methylated-NPB, TAPC, HMTPD, 4,4',4"-tris(N-carbazolyl)tnphenylamine) (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphorsulfonic acid (Pani/CSA), polyaniline/poly(4-styrene sulfonate):polyaniline (Pani/PSS), a compound represented by Formula 201, and a compound represented by Formula 202:

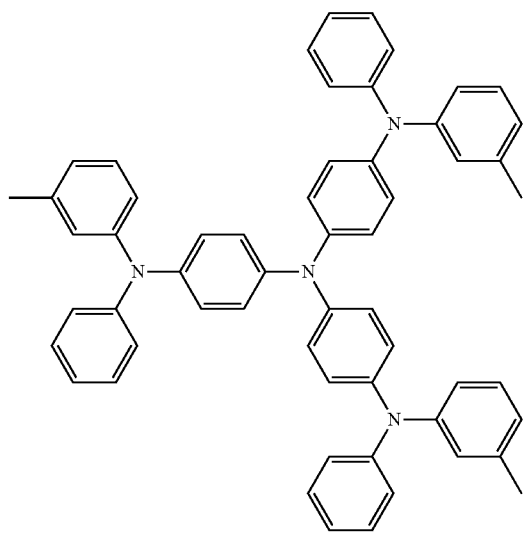

m-MTDATA

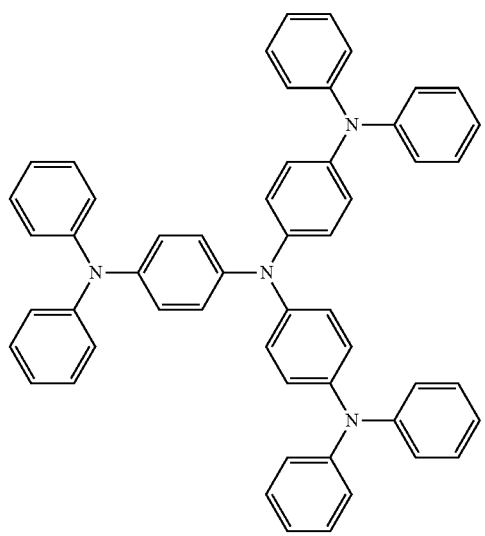

TDATA

-continued
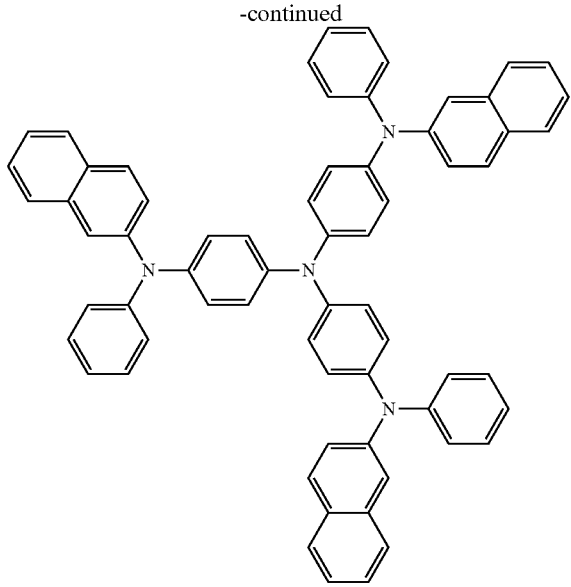
2-TNATA
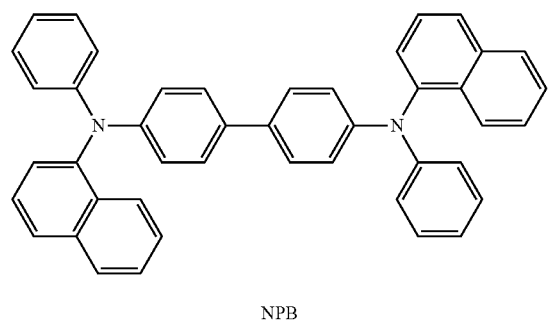
NPB
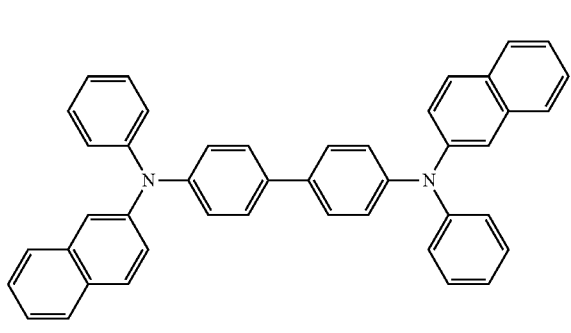
β-NPB
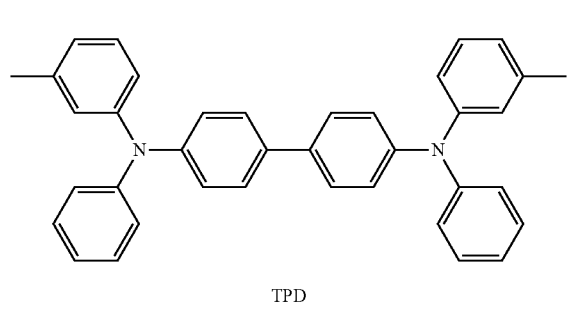
TPD
-continued
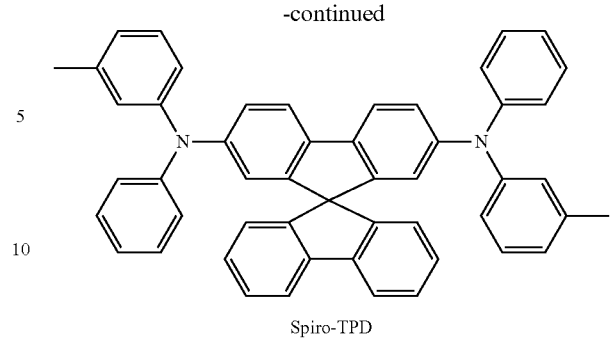
Spiro-TPD
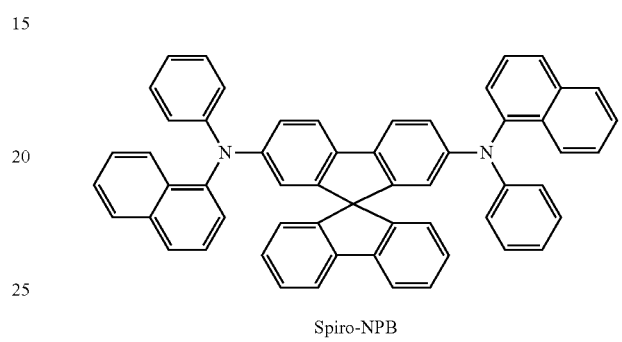
Spiro-NPB
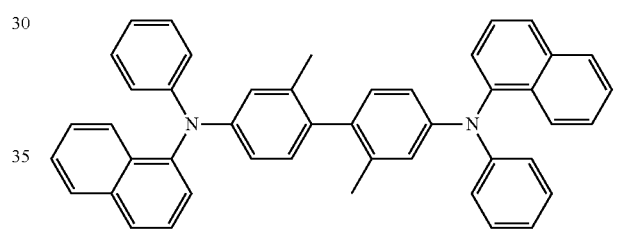
methylated NPB
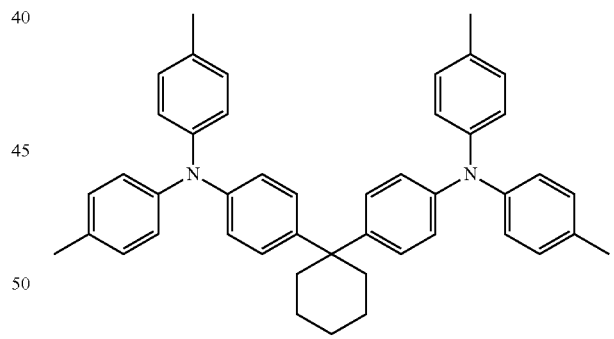
TAPC
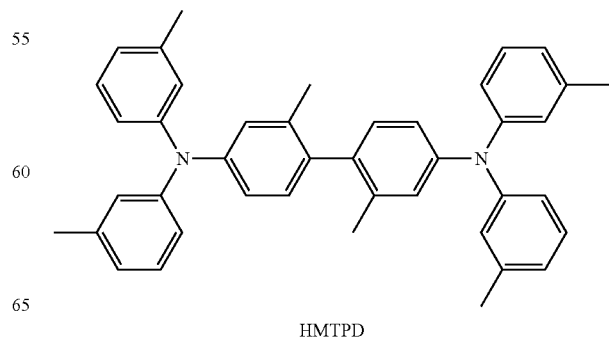
HMTPD Formula 201

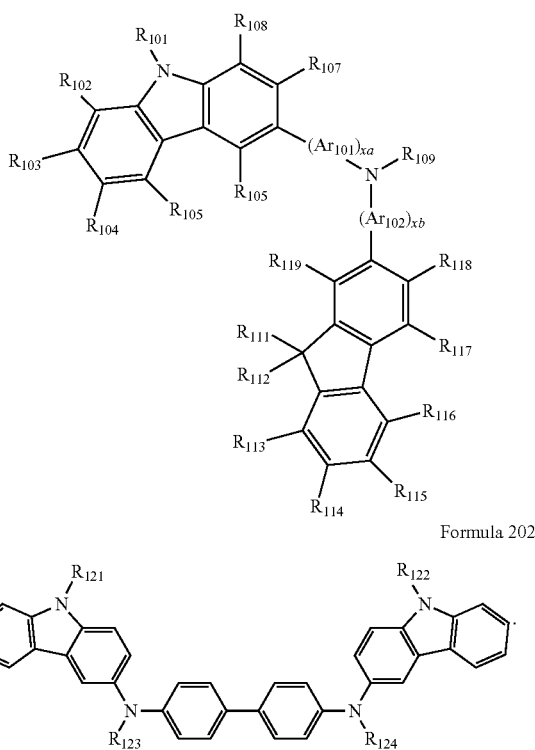

Formula 202

In Formula 201, $Ar_{101}$ and $Ar_{102}$ may each independently be selected from:

a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from deuterium, —F, —Cl, —Br, —I, a hydroxy group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

In Formula 201, xa and xb may each independently be an integer selected from 0 to 5, or may each independently be 0, 1, or 2. For example, xa may be 1 and xb may be 0, but xa and xb are not limited thereto.

In Formulae 201 and 202, $R_{101}$ to $R_{108}$, $R_{111}$ to $R_{119}$, and $R_{121}$ to $R_{124}$ may each independently be selected from:

hydrogen, deuterium, —F, —Cl, —Br, —I, a hydroxy group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, a pentyl group, and a hexyl group), and a $C_1$-$C_{10}$ alkoxy group (for example, a methoxy group, an ethoxy group, a propoxy group, a butoxy group, and a pentoxy group);

a $C_1$-$C_{10}$ alkyl group and a $C_1$-$C_{10}$ alkoxy group, each substituted with at least one selected from deuterium, —F, —Cl, —Br, —I, a hydroxy group, a cyano group, a nitro group, an amino group, an amidino group, a hydrazine group, a hydrazone group, a carboxylic acid group or a salt thereof, a sulfonic acid group or a salt thereof and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from deuterium, —F, —Cl, —Br, —I, a hydroxy group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but embodiments are not limited thereto.

In Formula 201, $R_{109}$ may be selected from:

a phenyl group, a naphthyl group, an anthracenyl group, and a pyridinyl group; and a phenyl group, a naphthyl group, an anthracenyl group, and a pyridinyl group, each substituted with at least one selected from deuterium, —F, —Cl, —Br, —I, a hydroxy group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, and a pyridinyl group.

In an embodiment, the compound represented by Formula 201 may be represented by Formula 201A, but is not limited thereto:

Formula 201A

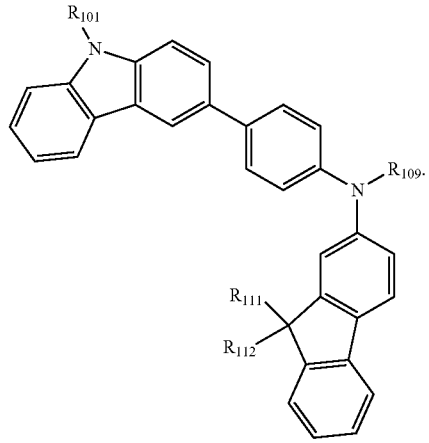

In Formula 201A, descriptions of $R_{101}$, $R_{111}$, $R_{112}$, and $R_{109}$ may each be understood by referring to the descriptions thereof provided above.

For example, the compound represented by Formula 201 and the compound represented by Formula 202 may each include Compounds HT1 to HT20, but embodiments are not limited thereto:
HT1
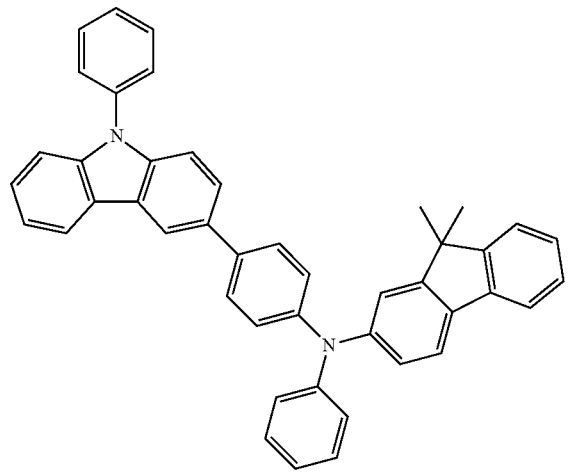
HT2
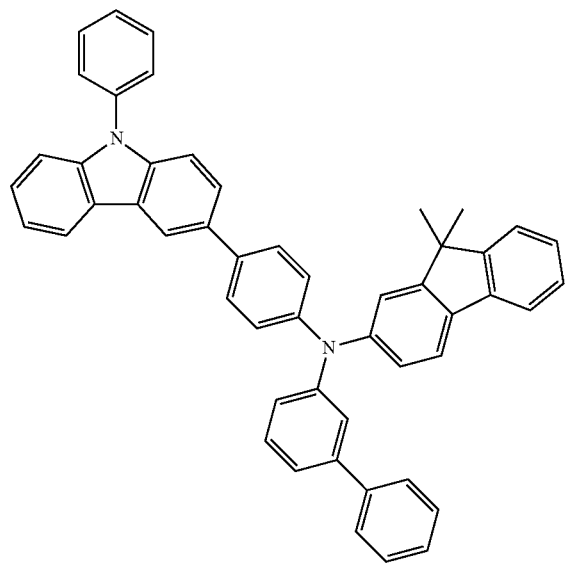
HT3
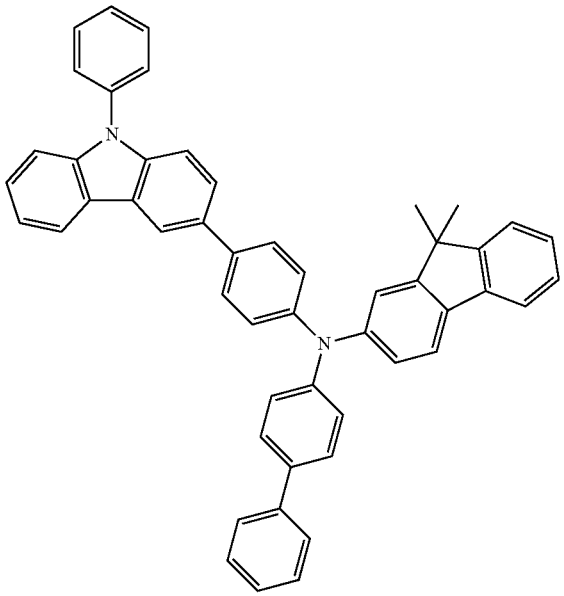
HT4

-continued
HT5
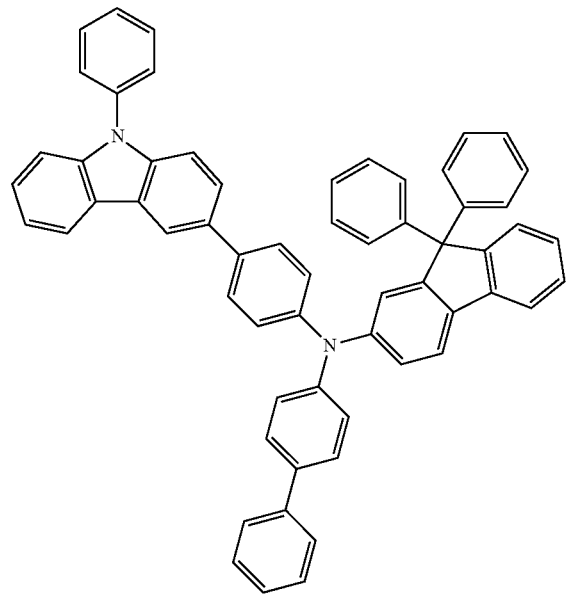
HT7
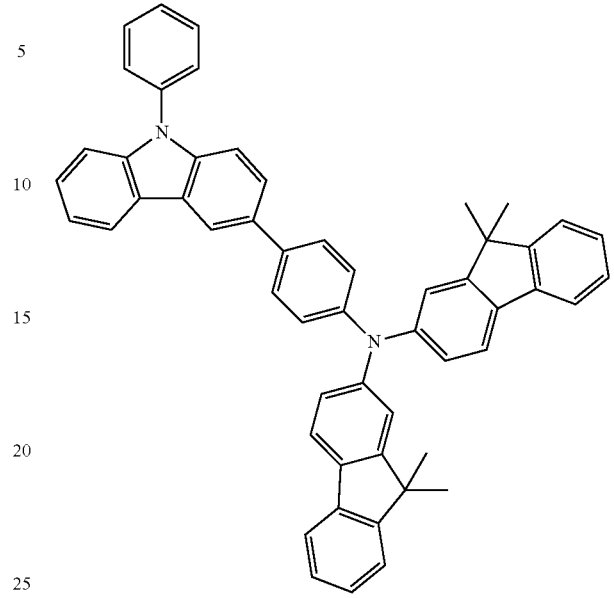
HT6
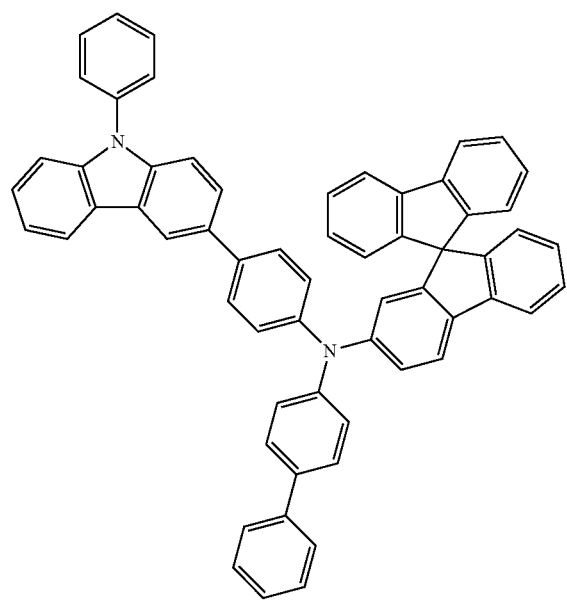
HT8
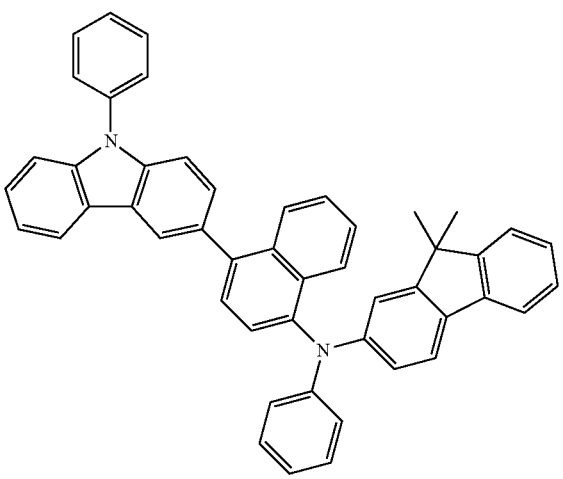

HT9
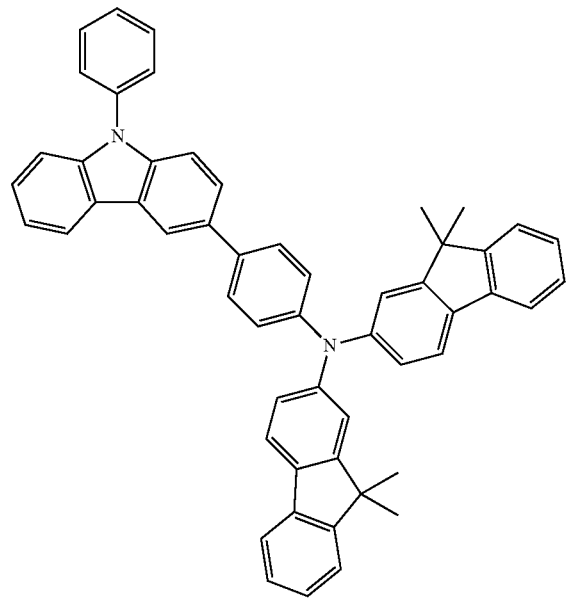
HT11
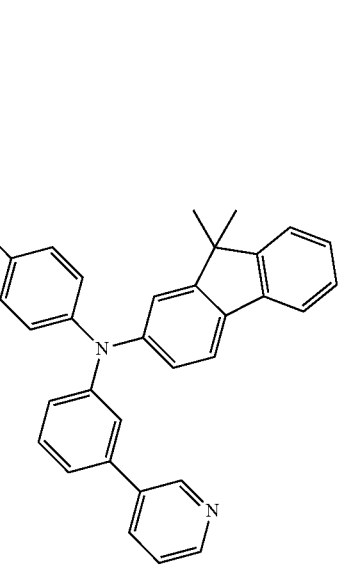
HT12
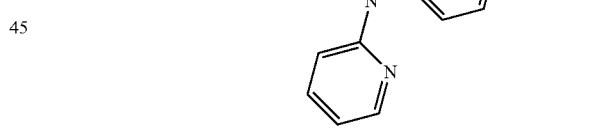
HT10
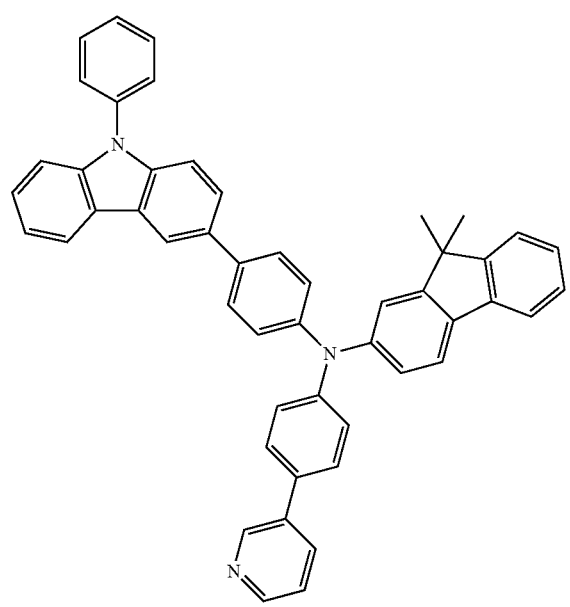
HT13
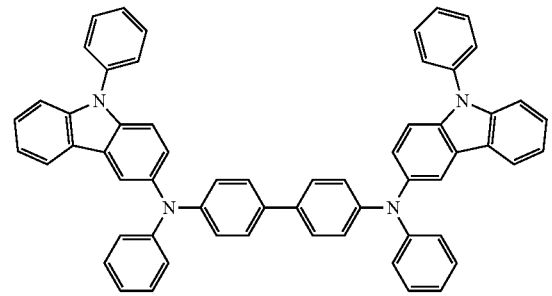

HT14
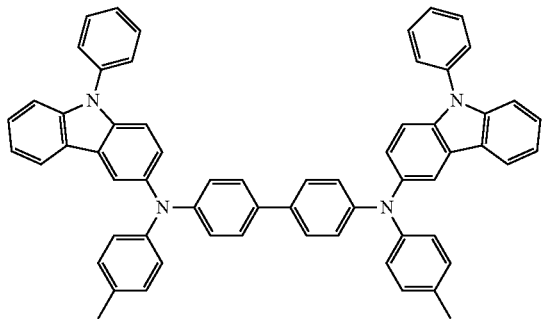

HT15
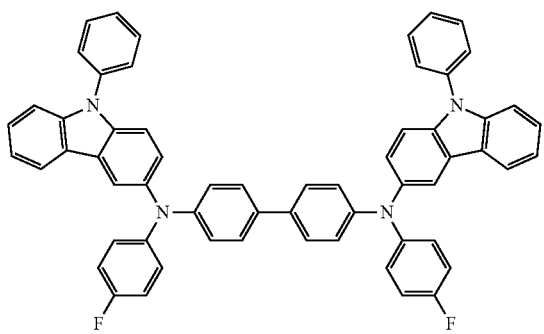

HT16
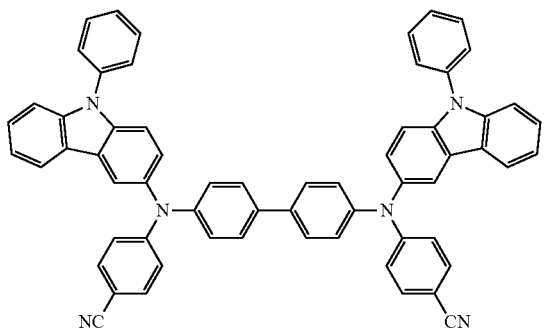

HT17
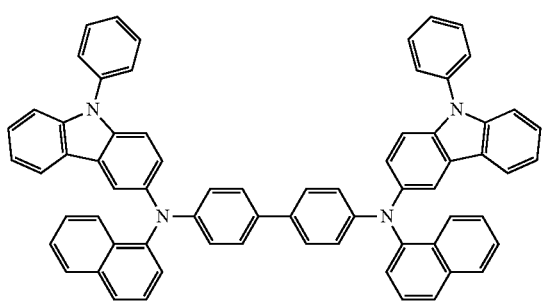

HT18
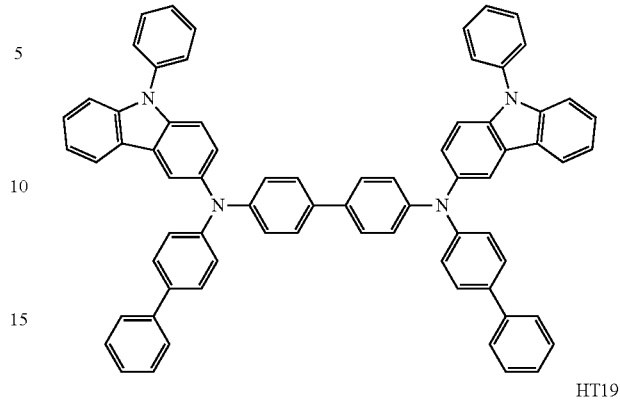

HT19
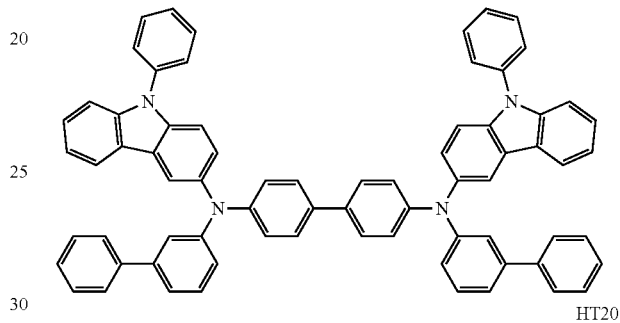

HT20
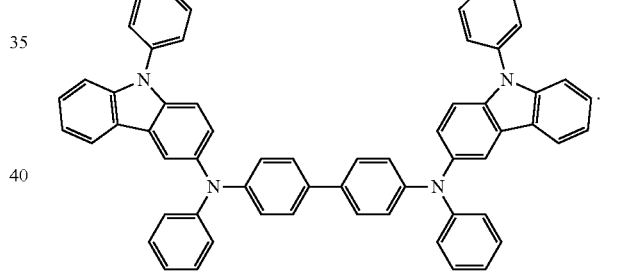

The thickness of the hole transport region may be in a range of about 100 Å to about 10,000 Å, for example, about 100 Å to about 1,000 Å. When the hole transport region includes at least one selected from a hole injection layer and a hole transport layer, a thickness of the hole injection layer may be in a range of about 100 Å to about 10,000 Å, for example, about 100 Å to about 1,000 Å, and a thickness of the hole transport layer may be in a range of about 50 Å to about 2,000 Å, for example, about 100 Å to about 1,500 Å. While not wishing to be bound by theory, it is understood that when the thicknesses of the hole transport region, the hole injection layer, and the hole transport layer are within any of these ranges, satisfactory hole transporting characteristics may be obtained without a substantial increase in driving voltage.

The hole transport region may further include, in addition to the materials described above, a charge-generation material for the improvement of conductive properties. The charge-generation material may be homogeneously or non-homogeneously dispersed in the hole transport region.

The charge-generation material may be, for example, a p-dopant. The p-dopant may be one selected from a quinone derivative, a metal oxide, and a cyano group-containing compound, but embodiments are not limited thereto. Examples of the p-dopant include quinone derivatives, such as tetracyanoquinonedimethane (TCNQ) and/or 2,3,5,6-tetrafluoro-tetracyano-1,4-benzoquinonedimethane (F4-TCNQ); metal oxides, such as tungsten oxide and/or molybdenum oxide; and Compounds HT-D1 and HP-1, but embodiments are not limited thereto:

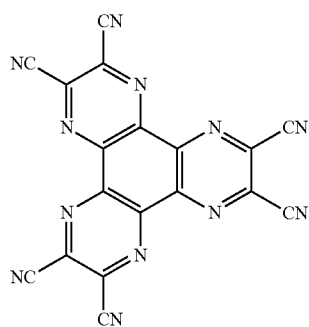

Compound HT-D1

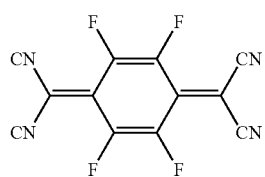

F4-TCNQ

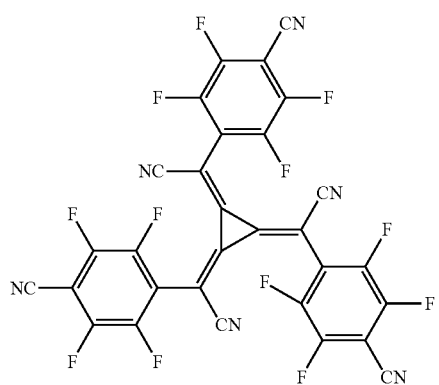

Compound HP-1

The hole transport region may further include a buffer layer.

The buffer layer may compensate for an optical resonance distance according to a wavelength of light emitted from the emission layer.

The emission layer may be disposed on the hole transport region by using various suitable methods, such as vacuum deposition, spin coating, casting and/or an LB deposition. When the emission layer is formed by vacuum deposition and spin coating, the deposition and coating conditions for forming the emission layer may be determined by referring to the deposition and coating conditions for forming the hole injection layer.

The hole transport region may further include an electron blocking layer. The electron blocking layer may include a material known in the art, and for example, may include mCP, but embodiments are not limited thereto:

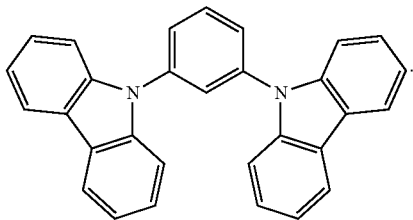

mCP

A thickness of the electron blocking layer may be in a range of about 50 Å to about 1,000 Å, for example, about 70 Å to about 500 Å. While not wishing to be bound by theory, it is understood that when the thickness of the electron blocking layer is within any of these ranges, satisfactory electron blocking characteristics may be obtained without a substantial increase in driving voltage.

When the organic light-emitting device 10 is a full-color organic light-emitting device, the emission layer may be patterned into a red emission layer, a green emission layer, and a blue emission layer. In various embodiments, the emission layer may have a multi-layer structure in which a red emission layer, a green emission layer, and/or a blue emission layer are stacked on each other, to thereby emit white light.

The emission layer may include the condensed cyclic compound represented by Formula 1. For example, the emission layer may include only the condensed cyclic compound represented by Formula 1. In various embodiments, the emission layer may include a host and a dopant, wherein the host includes the condensed cyclic compound represented by Formula 1. In various embodiments, the emission layer may include a host and a dopant, wherein the dopant includes the condensed cyclic compound represented by Formula 1.

In an embodiment, the dopant included in the emission layer may be a phosphorescent dopant, wherein the phosphorescent dopant includes an organometallic compound represented by Formula 81:

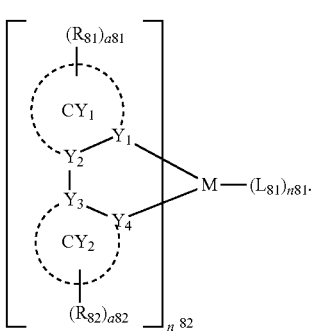

Formula 81

In Formula 81

M may be selected from iridium (Ir), platinum (Pt), osmium (Os), titanium (Ti), zirconium (Zr), hafnium (Hf), europium (Eu), terbium (Tb), and thulium (Tm), $Y_1$ to $Y_4$ may each independently be carbon (C) or nitrogen (N), $Y_1$ and $Y_2$ may be linked with each other via a single bond or a double bond, and $Y_3$ and $Y_4$ may be linked with each other via a single bond or a double bond, $CY_1$ and $CY_2$ may each independently be a benzene group, a naphthalene group, a fluorene group, a spirofluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzoimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, or a dibenzothiophene group, wherein $CY_1$ and $CY_2$ may optionally be linked with each other via a single bond or an organic linking group, $R_{81}$ and $R_{82}$ may each independently be selected from hydrogen, deuterium, —F, —Cl, —Br, —I, a hydroxy group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —$SF_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycydic group, a substituted or unsubstituted monovalent non-aromatic condensed heteropolycyclic group, —$N(Q_1)(Q_2)$, —$Si(Q_3)(Q_4)(Q_5)$, and —$B(Q_6)(Q_7)$, a81 and a82 may each independently be an integer selected from 1 to 5, n81 may be an integer selected from 0 to 4, n82 may be 1, 2, or 3, and $L_{81}$ may be a monovalent organic ligand, a divalent organic ligand, or a trivalent organic ligand.

Descriptions of $R_{81}$ and $R_{82}$ may each be understood by referring to the description provided herein in connection with $R_{11}$.

The phosphorescent dopant may include at least one selected from Compounds PD1 to PD78 and Fire, but is not limited thereto:

PD1

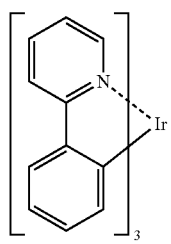

PD2

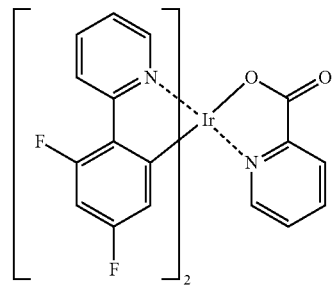

PD3

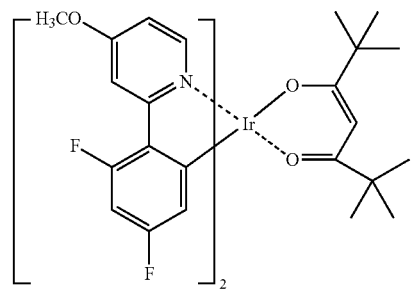

PD4

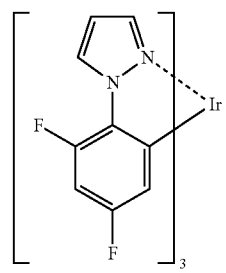

PD5

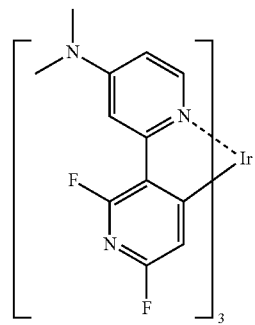

PD6

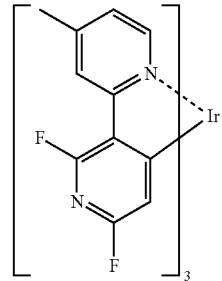

PD7 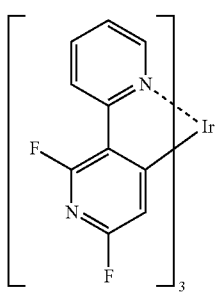
PD8 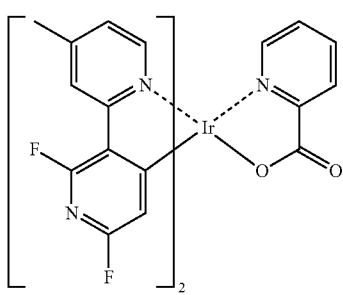
PD9 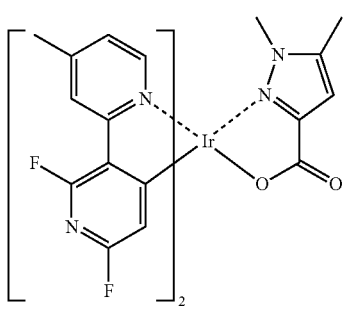
PD10 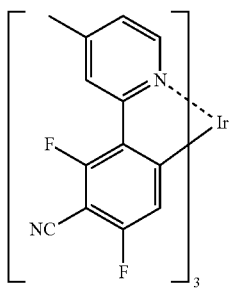
PD11 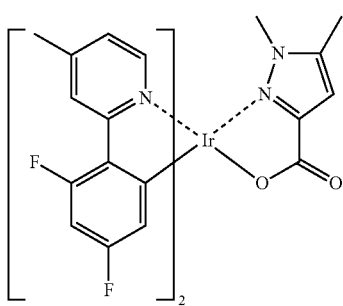
PD12 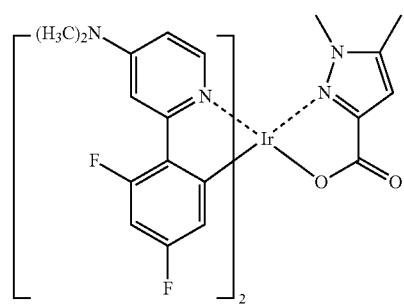
PD13 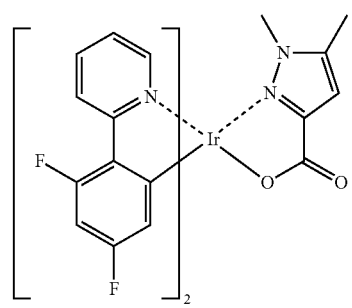
PD14 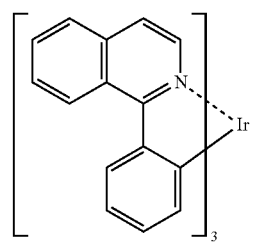
PD15 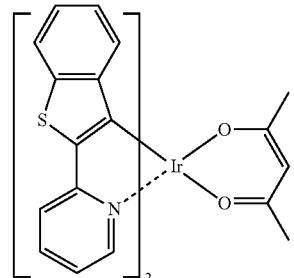
PD16 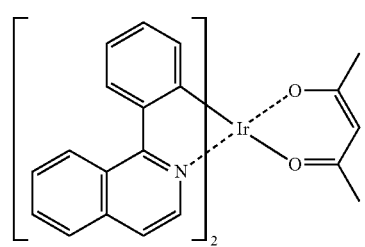

PD17
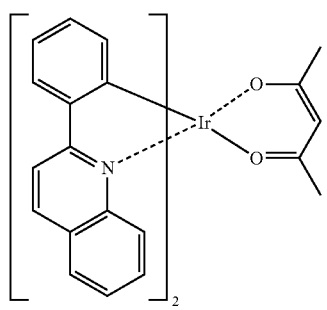
PD18
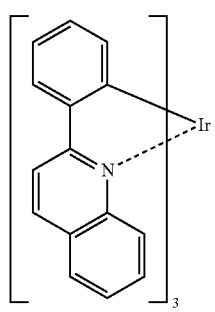
PD19
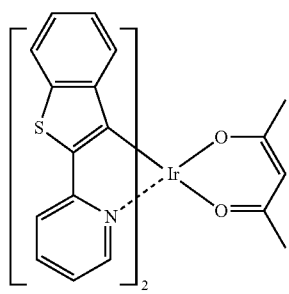
PD20
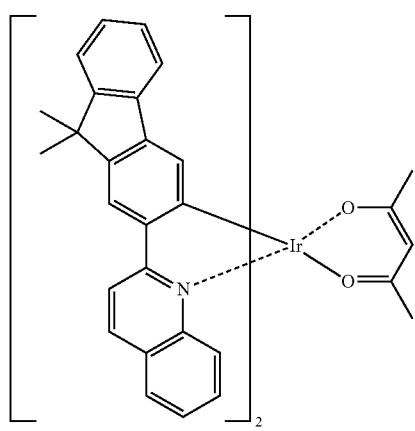
PD21
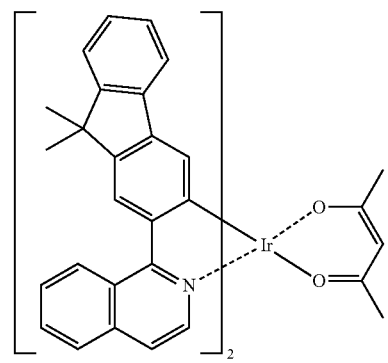
PD22
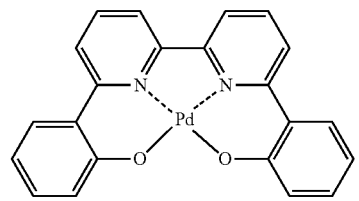
PD23
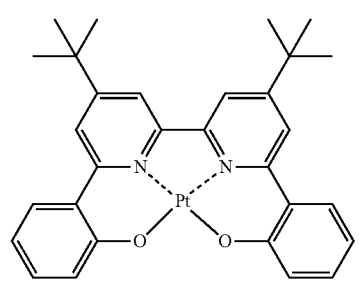
PD24
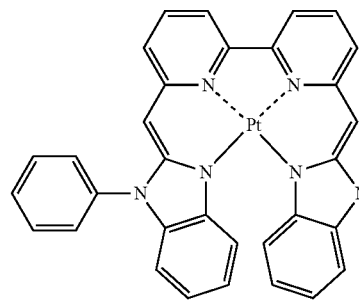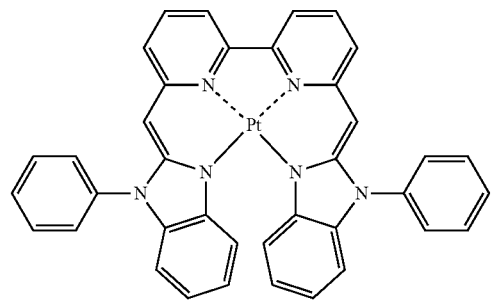
PD25
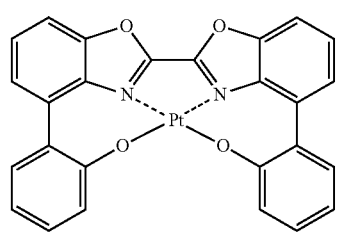
PD26
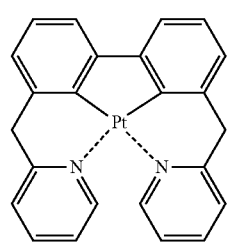

-continued
PD27 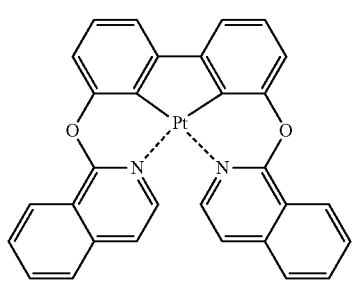
PD28 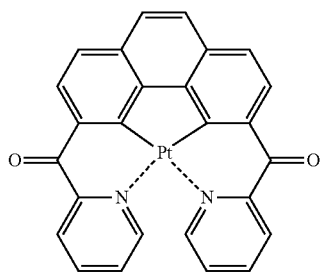
PD29 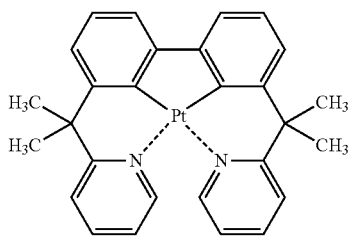
PD30 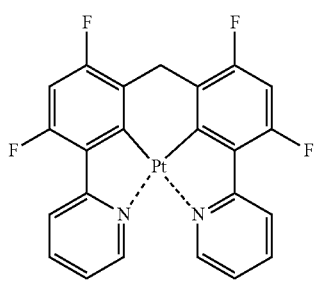
PD31 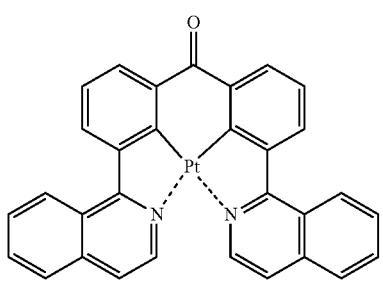
PD32 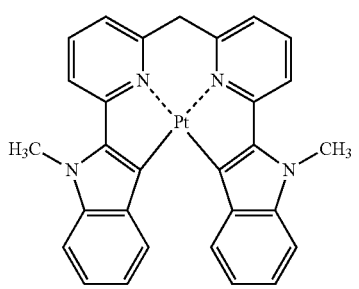
-continued
PD33 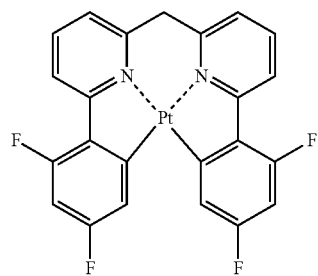
PD34 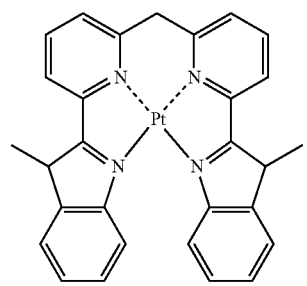
PD35 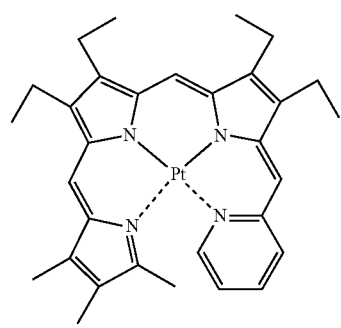
PD36 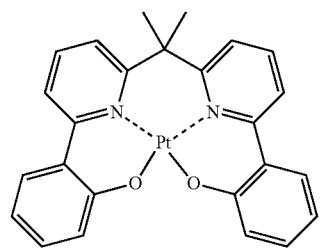
PD37 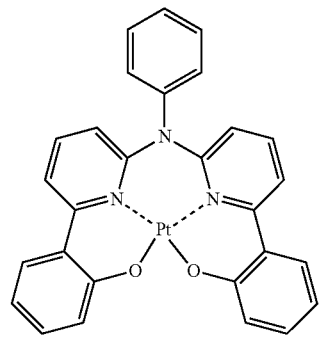

PD38
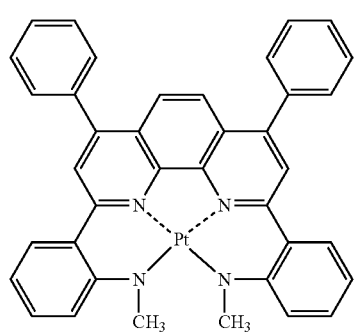
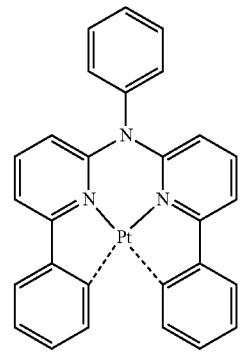
PD43
PD39
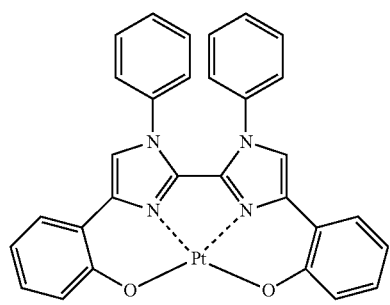
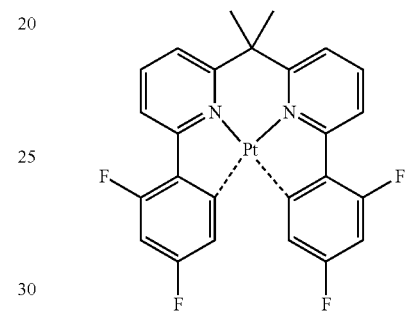
PD44
PD40
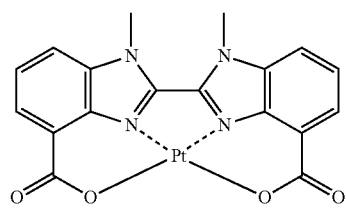
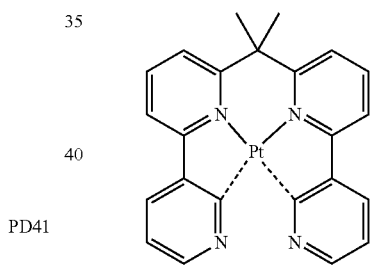
PD45
PD41
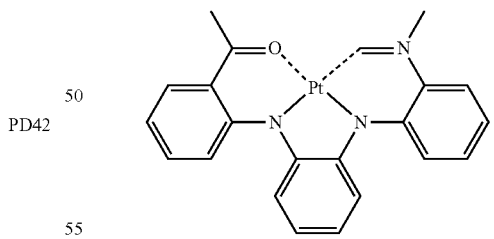
PD46
PD42
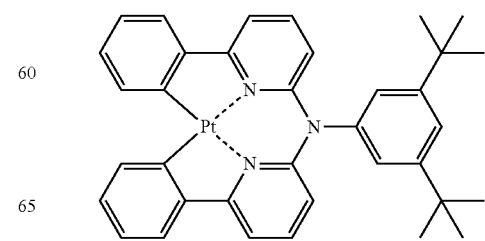
PD47

-continued
PD48
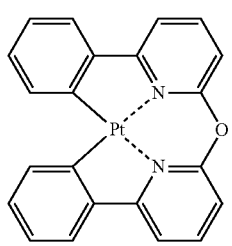
PD49
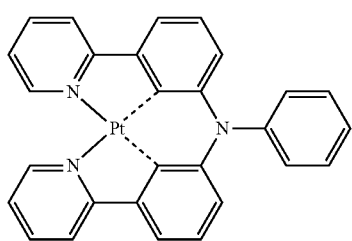
PD50
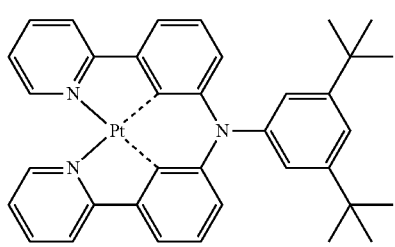
PD51
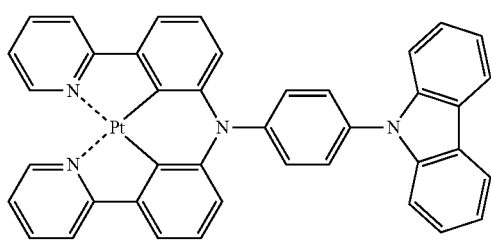
PD52
PD53
PD54
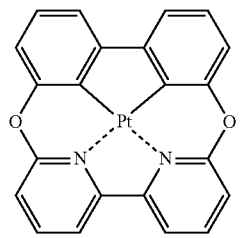
PD55
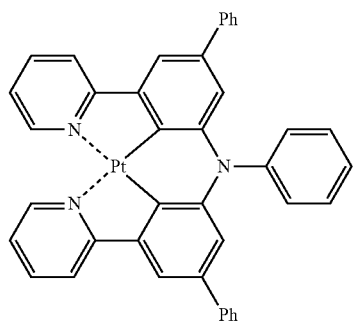
PD56
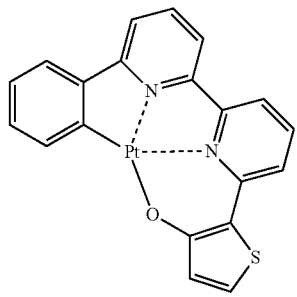
PD57
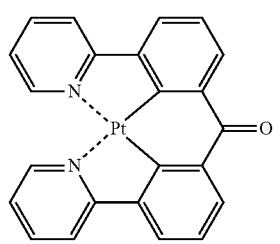
PD58
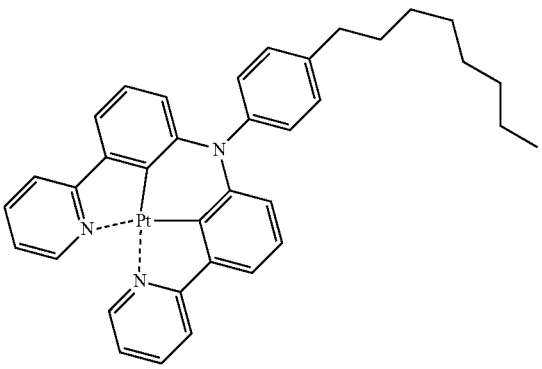

PD59 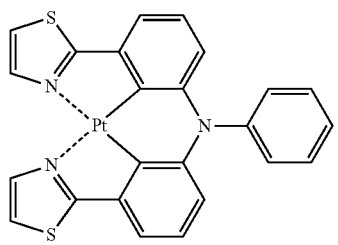
PD60 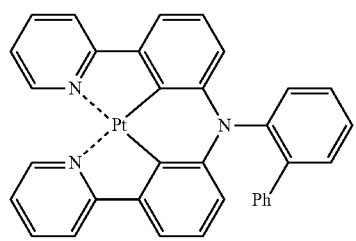
PD61 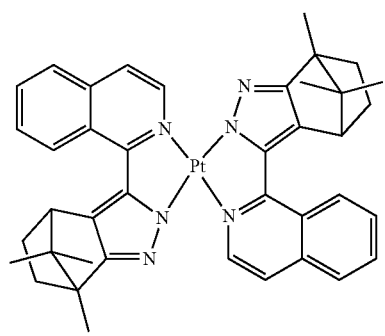
PD62 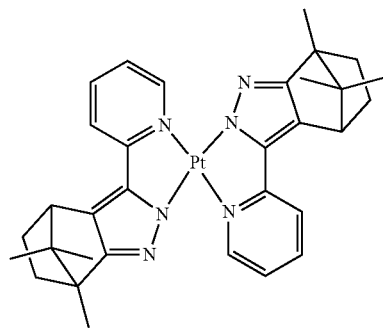
PD63 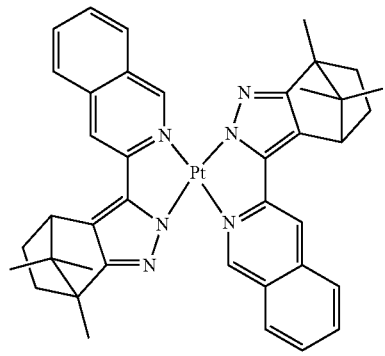
PD64 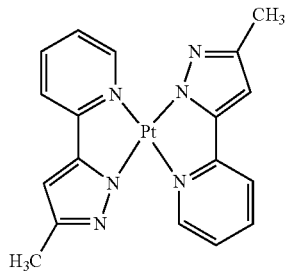
PD65 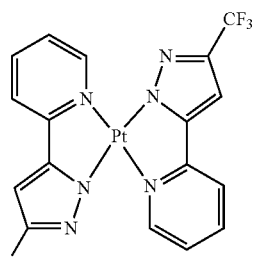
PD66 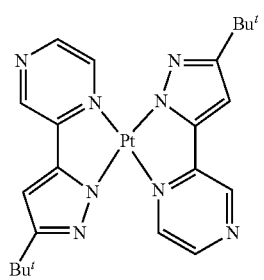
PD67 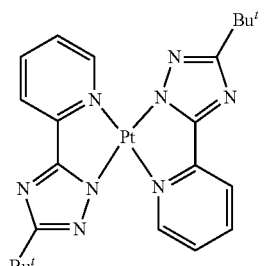
PD68 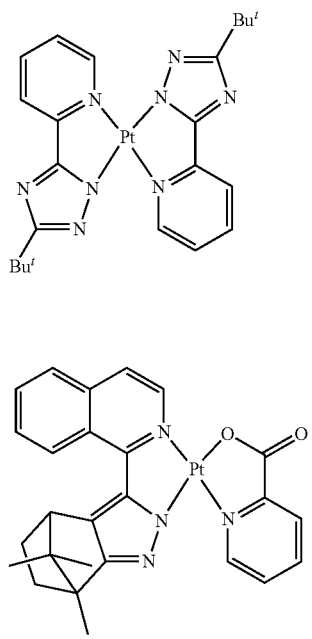

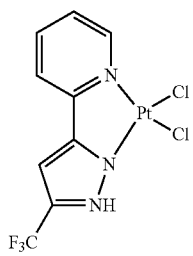
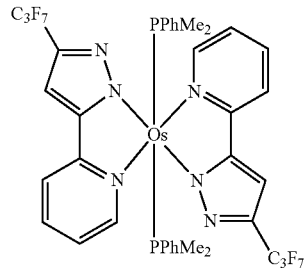
PD69
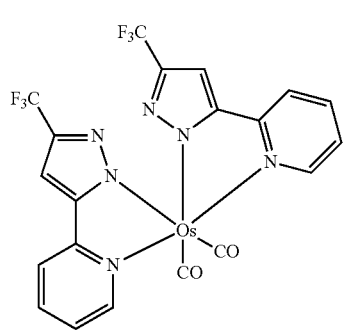
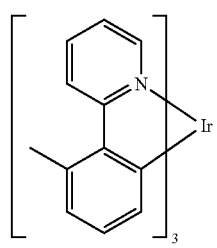
PD70
PD75
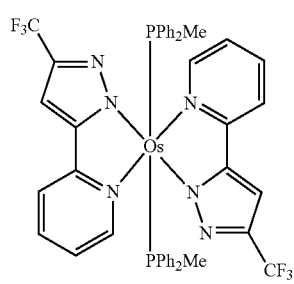
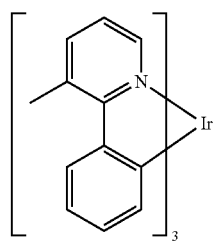
PD71
PD76
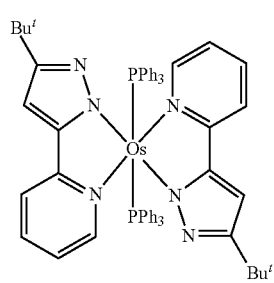
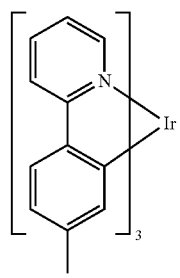
PD72
PD77
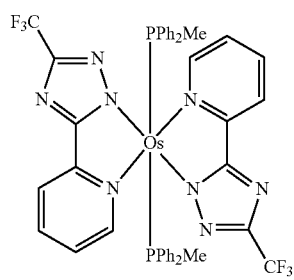
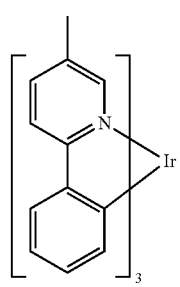
PD73
PD78

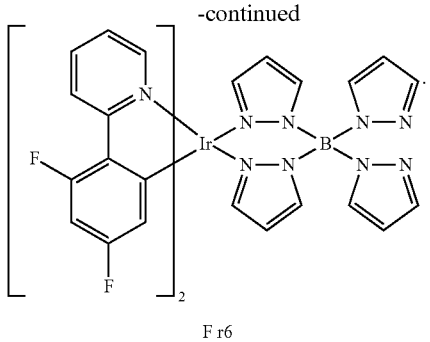

F r6

In various embodiments, the phosphorescent dopant may include PtOEP:

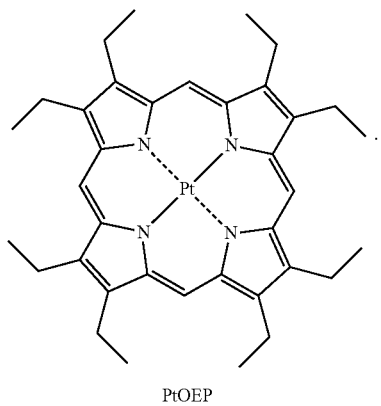

PtOEP

When the emission layer includes a host and a dopant, an amount of the dopant may be in a range of about 0.01 parts by weight to about 20 parts by weight based on 100 parts by weight of the host, but the amount of the dopant is not limited thereto.

A thickness of the emission layer may be in a range of about 100 Å to about 1,000 Å, for example, about 200 Å to about 600 Å. While not wishing to be bound by theory, it is understood that when the thickness of the emission layer is within any of these ranges, the emission layer may have excellent light-emitting characteristics without a substantial increase in driving voltage.

Next, the electron transport region may be disposed on the emission layer.

The electron transport region may include at least one selected from a hole blocking layer, an electron transport layer, and an electron injection layer.

For example, the electron transport region may have a structure of hole blocking layer/electron transport layer/electron injection layer or a structure of electron transport layer/electron injection layer, but the structure of the electron transport region is not limited thereto. The electron transport layer may have a single-layer structure, or a multi-layer structure including two or more layers.

The hole blocking layer, the electron transport layer, and the electron injection layer included in the electron transport region may each be formed by referring to the method used to form the hole injection layer.

When the electron transport region includes a hole blocking layer, the hole blocking layer may include, for example, at least one selected from BCP and Bphen, but embodiments are not limited thereto:

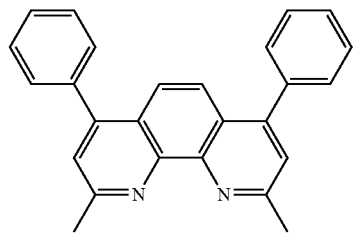

BCP

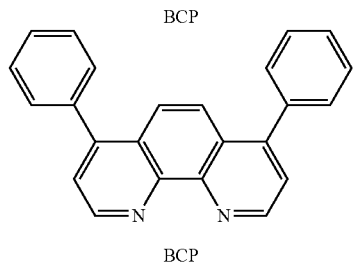

BCP

In various embodiments, the hole blocking layer may include the condensed cyclic compound represented by Formula 1.

A thickness of the hole blocking layer may be in a range of about 20 Å to about 1,000 Å, for example, about 30 Å to about 300 Å. While not wishing to be bound by theory, it is understood that when the thickness of the hole blocking layer is within any of these ranges, satisfactory hole blocking characteristics may be obtained without a substantial increase in driving voltage.

The electron transport layer may further include at least one selected from BCP, Bphen, Alq$_3$, BAlq, TAZ, and NTAZ:

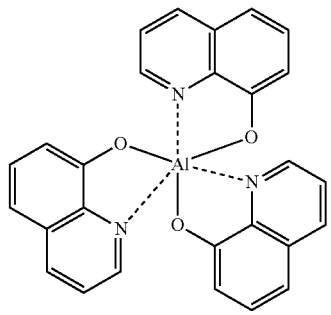

Alq$_3$

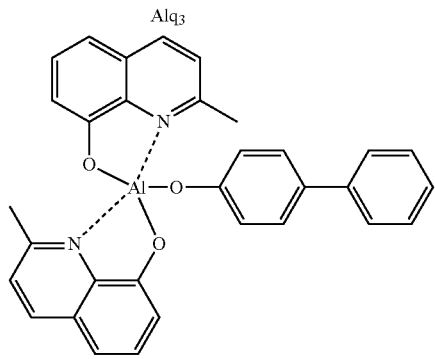

BAlq

-continued

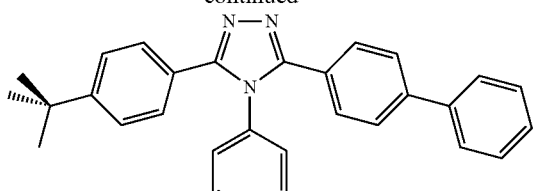

TAZ

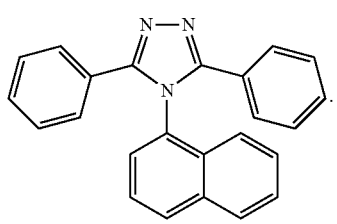

NTAZ

In various embodiments, the electron transport layer may include at least one selected from Compounds ET1, ET2, and ET3, but embodiments are not limited thereto:

ET1

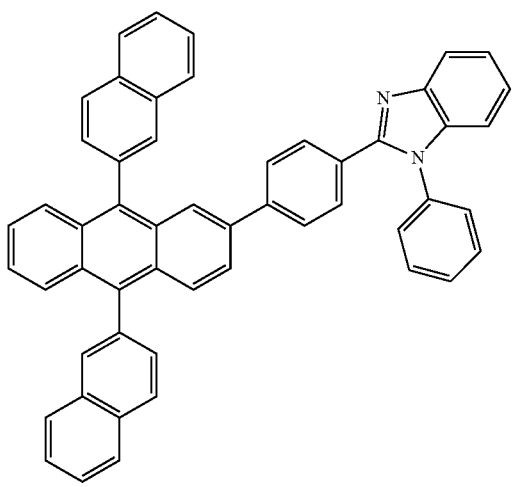

ET2

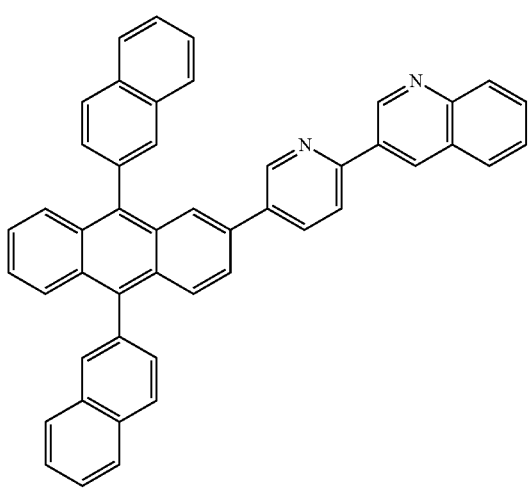

-continued

ET3

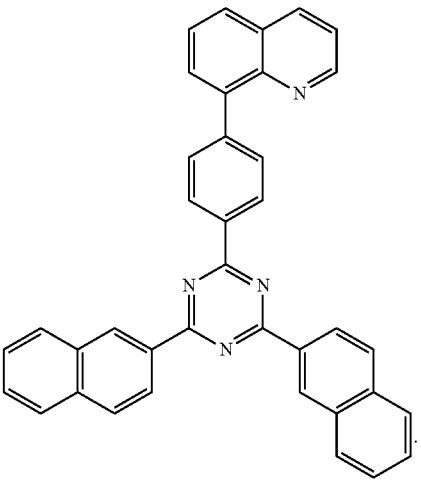

A thickness of the electron transport layer may be in a range of about 100 Å to about 1,000 Å, for example, about 150 Å to about 500 Å. While not wishing to be bound by theory, it is understood that when the thickness of the electron transport layer is within any of these ranges, satisfactory electron transporting characteristics may be obtained without a substantial increase in driving voltage.

The electron transport layer may further include, in addition to the materials described above, a metal-containing compound.

The metal-containing compound may include a Li complex. The Li complex may include, for example, Compounds ET-D1 (lithium quinolate (LiQ)) or ET-D2:

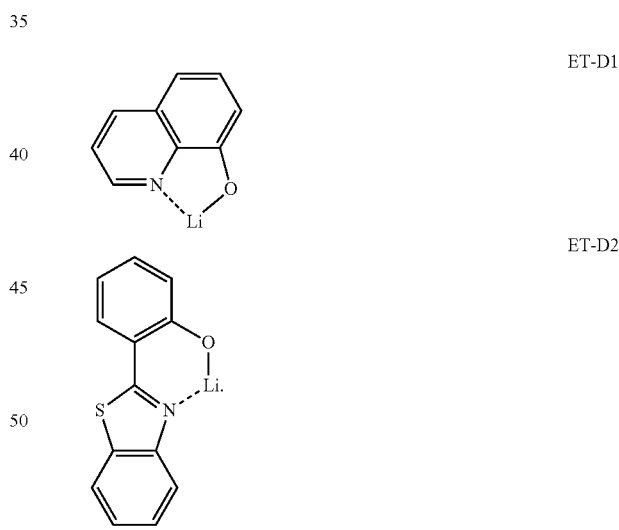

In addition, the electron transport region may include an electron injection layer that facilitates electron injection from the second electrode 19.

The electron injection layer may include at least one selected from LiQ, LiF, NaCl, CsF, $Li_2O$, and BaO.

A thickness of the electron injection layer may be in a range of about 1 Å to about 100 Å, for example, about 3 Å to about 90 Å. While not wishing to be bound by theory, it is understood that when the thickness of the electron injection layer is within any of these ranges, satisfactory electron injecting characteristics may be obtained without a substantial increase in driving voltage.

The second electrode 19 may be disposed on the organic layer 15. When the second electrode 19 is a cathode, a material for forming the second electrode 19 may be a material having a low work function, and non-limiting examples thereof include a metal, an alloy, an electrically conductive compound, and a combination (for example, mixture) thereof, each with a low work function. For example, Li, Mg, Al, Al—Li, Ca, Mg—In, and/or Mg—Ag may be used as the material for forming the second electrode 19. In various embodiments, to form a top-emission device, ITO or IZO may be used to form a transmissive second electrode 19.

Hereinbefore, the organic light-emitting device 10 has been described with reference to FIG. 1, but is not limited thereto.

A $C_1$-$C_{60}$ alkyl group as used herein may refer to a linear or branched aliphatic saturated hydrocarbon monovalent group having 1 to 60 carbon atoms, and non-limiting examples thereof include a methyl group, an ethyl group, a propyl group, an iso-butyl group, a sec-butyl group, a tert-butyl group, a pentyl group, an iso-amyl group, and a hexyl group. A $C_1$-$C_{60}$ alkylene group as used herein may refer to a divalent group having the same structure as the $C_1$-$C_{60}$ alkyl group.

A $C_1$-$C_{60}$ alkoxy group as used herein may refer to a monovalent group represented by —$OA_{101}$ (wherein $A_{101}$ is the $C_1$-$C_{60}$ alkyl group), and non-limiting examples thereof include a methoxy group, an ethoxy group, and an iso-propoxy group.

A $C_2$-$C_{60}$ alkenyl group as used herein may refer to a hydrocarbon group having at least one carbon-carbon double bond in the middle or at either terminal end of the $C_2$-$C_{60}$ alkyl group, and non-limiting examples thereof include an ethenyl group, a propenyl group, and a butenyl group. A $C_2$-$C_{60}$ alkenylene group as used herein may refer to a divalent group having the same structure as the $C_2$-$C_{60}$ alkenyl group.

A $C_2$-$C_{60}$ alkynyl group as used herein may refer to a hydrocarbon group having at least one carton-carbon triple bond in the middle or at either terminal end of the $C_2$-$C_{60}$ alkyl group, and non-limiting examples thereof include an ethynyl group and a propynyl group. A $C_2$-$C_{60}$ alkynylene group as used herein may refer to a divalent group having the same structure as the $C_2$-$C_{60}$ alkynyl group.

A $C_3$-$C_{10}$ cycloalkyl group as used herein may refer to a monovalent saturated hydrocarbon monocyclic saturated group having 3 to 10 carbon atoms, and non-limiting examples thereof include a cyclopropyl group, a cyclobutyl group, a cydopentyl group, a cyclohexyl group, and a cycloheptyl group. A $C_3$-$C_{10}$ cycloalkylene group as used herein may refer to a divalent group having the same structure as the $C_3$-$C_{10}$ cycloalkyl group.

A $C_1$-$C_{10}$ heterocycloalkyl group as used herein may refer to a monovalent saturated monocyclic group having at least one heteroatom selected from N, O, P, Si and S as a ring-forming atom and 1 to 10 carbon atoms, and non-limiting examples thereof include a tetrahydrofuranyl group and a tetrahydrothiophenyl group. A $C_1$-$C_{10}$ heterocycloalkylene group as used herein may refer to a divalent group having the same structure as the $C_1$-$C_{10}$ heterocycloalkyl group.

A $C_3$-$C_{10}$ cycloalkenyl group carbon as used herein may refer to a monovalent monocyclic group that has 3 to 10 carbon atoms and at least one carbon-carbon double bond in the ring thereof and does not have aromaticity, and non-limiting examples thereof include a cyclopentenyl group, a cyclohexenyl group, and a cycloheptenyl group. A $C_3$-$C_{10}$ cycloalkenylene group as used herein may refer to a divalent group having the same structure as the $C_3$-$C_{10}$ cycloalkenyl group.

A $C_1$-$C_{10}$ heterocycloalkenyl group as used herein may refer to a monovalent monocyclic group that has at least one heteroatom selected from N, O, P, Si, and S as a ring-forming atom, 1 to 10 carbon atoms, and at least one double bond in the ring. Non-limiting examples of the $C_2$-$C_{10}$ heterocycloalkenyl group include 2,3-dihydrofuranyl group and a 2,3-dihydrothiophenyl group. A $C_1$-$C_{10}$ heterocycloalkenylene group as used herein may refer to a divalent group having the same structure as the $C_1$-$C_{10}$ heterocycloalkenyl group.

A $C_6$-$C_{60}$ aryl group as used herein may refer to a monovalent group having an aromatic system having 6 to 60 carbon atoms, and a $C_6$-$C_{60}$ arylene group as used herein may refer to a divalent group having an aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each independently include two or more rings, the respective rings may be fused to each other or may be linked with each other.

A $C_6$-$C_{60}$ heteroaryl group as used herein may refer to a monovalent group having a heterocyclic aromatic system that has at least one heteroatom selected from N, O, P, and S as a ring-forming atom, and 1 to 60 carbon atoms. A $C_1$-$C_{60}$ heteroarylene group as used herein may refer to a divalent group having a heterocyclic aromatic system that has at least one heteroatom selected from N, O, P, and S as a ring-forming atom, and 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each independently include two or more rings, the respective rings may be fused to each other or may be linked with each other.

A $C_6$-$C_{60}$ aryloxy group as used herein may refer to a monovalent group represented by —$OA_{102}$ (wherein $A_{102}$ is the $C_6$-$C_{60}$ aryl group), and a $C_6$-$C_{60}$ arylthio group as used herein may refer to a monovalent group represented by —$SA_{103}$ (wherein $A_{103}$ is the $C_6$-$C_{60}$ aryl group).

A monovalent non-aromatic condensed polycyclic group (as used herein may refer to a monovalent group that has two or more rings condensed to each other, has only carbon atoms as ring-forming atoms (for example, 8 to 60 carbon atoms), and is non-aromatic in the entire molecular structure. A non-limiting example of the monovalent non-aromatic condensed polycyclic group includes a fluorenyl group. A divalent non-aromatic condensed polycyclic group as used herein may refer to a divalent group having the same structure as the monovalent non-aromatic condensed polycyclic group.

A monovalent non-aromatic condensed heteropolycyclic group as used herein may refer to a monovalent group that has two or more rings condensed to each other, has at least one heteroatom selected from N, O, Si, P, and S as a ring-forming atom, in addition to carbon atoms (for example, 1 to 60 carbon atoms), and which is non-aromatic in the entire molecular structure. An example of the monovalent non-aromatic condensed heteropolycyclic group includes a carbazolyl group. A divalent non-aromatic condensed heteropolycyclic group as used herein may refer to a divalent group having the same structure as the monovalent non-aromatic condensed heteropolycyclic group.

In the present specification, in Formula 1, at least one substituent of the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —$CD_3$, —$CD_2H$, —$CDH_2$, —F, —Cl, —Br, —I, a hydroxy group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —$CD_3$, —$CD_2H$, —$CDH_2$, —F, —Cl, —Br, —I, a hydroxy group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{14})(Q_{15})$, and —$B(Q_{16})(Q_{17})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —$CD_3$, —$CD_2H$, —$CDH_2$, —F, —Cl, —Br, —I, a hydroxy group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{21})(Q_{22})(Q_{23})$, —$N(Q_{24})(Q_{25})$, and —$B(Q_{26})(Q_{27})$; and —$Si(Q_{31})(Q_{32})(Q_{33})$, —$N(Q_{34})(Q_{35})$, and —$B(Q_{36})(Q_{37})$, wherein $Q_{11}$ to $Q_{17}$, $Q_{21}$ to $Q_{27}$, and $Q_{31}$ to $Q_{37}$ may each independently be selected from hydrogen, deuterium, —F, —Cl, —Br, —I, a hydroxy group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

When a group containing a specified number of carbon atoms is substituted with any of the groups listed in the preceding paragraph, the number of carbon atoms in the resulting "substituted" group is defined as the sum of the carbon atoms contained in the original (unsubstituted) group and the carbon atoms (if any) contained in the substituent. For example, when the term "substituted $C_1$-$C_{30}$ alkyl" refers to a $C_1$-$C_3$ alkyl group substituted with $C_6$-$C_{30}$ aryl group, the total number of carbon atoms in the resulting aryl substituted alkyl group is $C_7$-$C_{60}$.

The term "biphenyl group" as used herein may refer to a monovalent group in which two benzene rings are linked together via a single bond.

The term "terphenyl group" as used herein may refer to a monovalent group in which three benzene rings are linked together via a single bond.

Symbols * and *' used herein, unless defined otherwise, refer to a binding site to a neighboring atom in a corresponding formula.

Hereinafter, an organic light-emitting device according to an embodiment will be described in detail with reference to Synthesis Examples and Examples. The wording "B was used instead of A" used in describing Synthesis Examples means that an identical number of molar equivalents of A was used in place of molar equivalents of B.

EXAMPLES

Synthesis Example 1: Synthesis of Compound 1

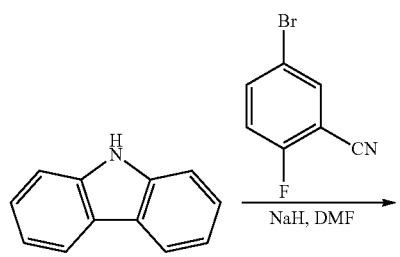

-continued

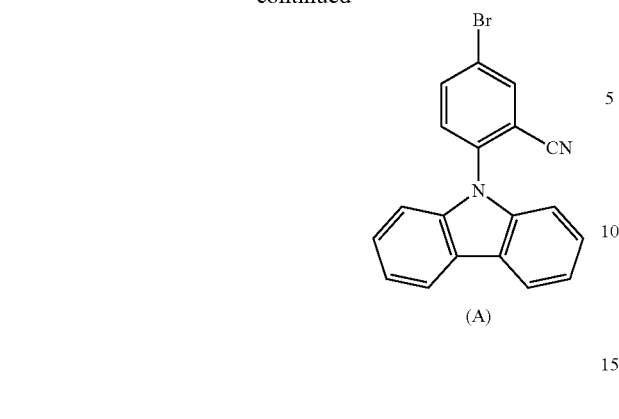

(A)

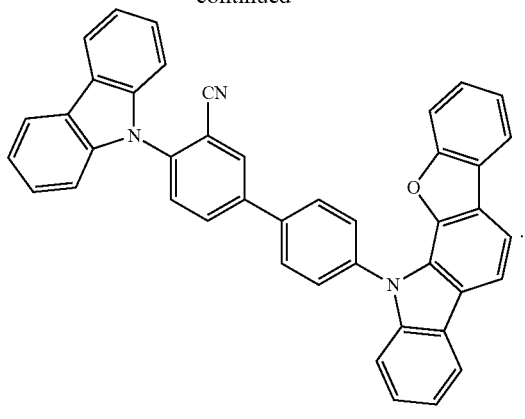

Compound 1

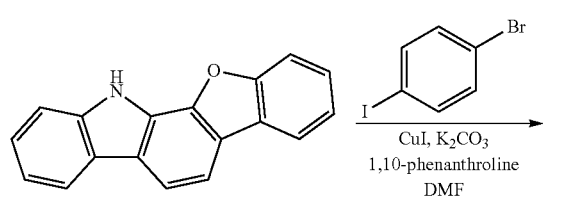

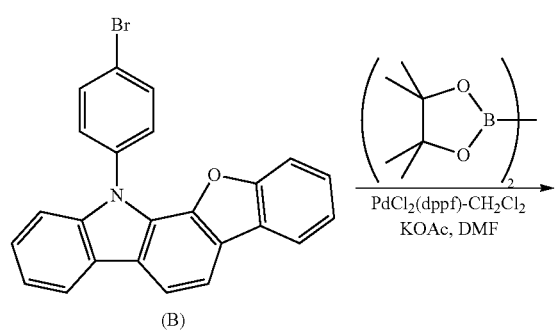

(B)

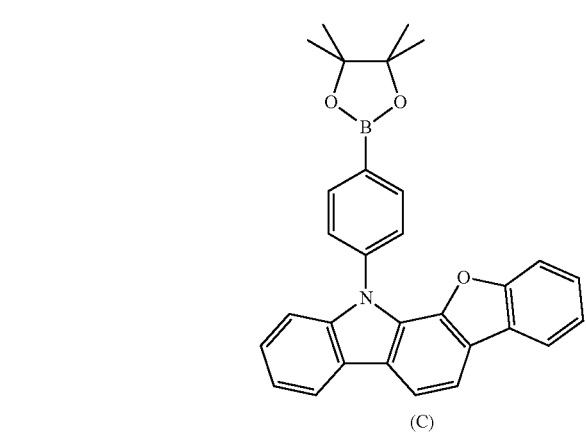

(C)

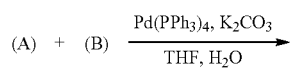

Synthesis of Intermediate (A)

15.0 grams (g) (89.7 millimoles, mmol) of carbazole was dissolved in 200 milliliters (mL) of dimethylformamide (DMF), and the mixed solution was cooled to 0° C. 3.77 g (94.19 mmol) of sodium hydride (NaH, 60% dispersion in mineral oil) was slowly added thereto, and the mixed solution was stirred for 30 minutes at a temperature of 0° C. A solution, in which 23.3 g (117 mmol) of 5-bromo-2-fluorobenzonitrile was diluted with 50 mL of DMF, was added slowly over 10 minutes to the mixed solution. When a temperature for the reaction was raised up to about 150° C., the reaction solution was stirred for an additional 18 hours. After the completion of the reaction, the reaction solution was cooled to room temperature, and a saturated ammonium chloride ($NH_4Cl$) aqueous solution was added thereto to extract an organic layer therefrom by using dichloromethane (DCM). A solvent, that is water, was removed from the organic layer by using anhydrous magnesium sulfate ($MgSO_4$). The filtrate obtained by filtering the reaction solution was concentrated under reduced pressure, and the resulting product obtained therefrom was separated by silica gel column chromatography, thereby obtaining 21.2 g (yield: 68%) of the desired compound, Intermediate (A).

LC-Mass (calculated: 346.01 g/mol, found: M+1=347 g/mol).

Synthesis of Intermediate (B)

10.0 g (38.9 mmol) of 12H-benzofuro[2,3-a]carbazole, 13.2 g (46.6 mmol) of 1-bromo-4-iodobenzene, 1.48 g (7.77 mmol) of copper iodide (CuI), 16.1 g (117 mmol) of potassium carbonate ($K_2CO_3$), and 2.80 g (15.6 mmol) of 1,10-phenanthroline were dissolved in 130 mL of DMF, and the mixed solution was stirred under reflux for 24 hours. After the completion of the reaction, the reaction solution was cooled to room temperature and filtered by passing through a silica gel column under reduced pressure, and the filtrate was concentrated under reduced pressure. The resulting product obtained therefrom was separated by silica gel column chromatography, thereby obtaining 8.81 g (yield: 55%) of the desired compound, Intermediate (B).

LC-Mass (calculated: 411.03 g/mol, found: M+1=412 g/mol).

Synthesis of Intermediate (C)

8.81 g (21.4 mmol) of Intermediate (B), 6.51 g (25.6 mmol) of bis(pinacolato)diboron, 6.51 g (25.6 mmol) of $PdCl_2(dppf) \cdot CH_2Cl_2$, and 6.29 g (64.1 mmol) of potassium acetate were dissolved in 70 mL of DMF, and the mixed solution was stirred for 24 hours at a temperature of 100° C. After the completion of the reaction, the reaction solution was cooled to room temperature, and filtered by passing through a silica gel column under reduced pressure. The resulting product obtained therefrom was separated by silica gel column chromatography, and recrystallized under a DCM/n-hexane condition, thereby obtaining 8.05 g (yield: 82%) of the desired compound, Intermediate (C).

LC-Mass (calculated: 459.20 g/mol, found: M+1=460 g/mol).

Synthesis of Compound 1

5.50 g (15.8 mmol) of Intermediate (A), 7.64 g (16.6 mmol) of Intermediate (C), 3.66 g (3.17 mmol) of tetrakis(triphenylphosphine)palladium(0) (Pd(PPh$_3$)$_4$), and 8.76 g (63.4 mmol) of potassium carbonate were dissolved in a mixture including 35 mL of THF and 18 mL of water, and the mixed solution was stirred under reflux. After the completion of the reaction, the reaction solution was cooled to room temperature, and an extraction process was performed thereon to separate an organic layer and remove an aqueous layer. The filtrate obtained by passing through a silica gel column under reduced pressure was concentrated under reduced pressure. The resulting product obtained therefrom was separated by silica gel column chromatography, and recrystallized under a DCM/n-hexane condition, thereby obtaining 4.27 g (yield: 45%) of the desired compound, Compound 1.

LC-Mass (calculated: 599.20 g/mol, found: M+1=600 g/mol).

Synthesis Example 2: Synthesis of Compound 36

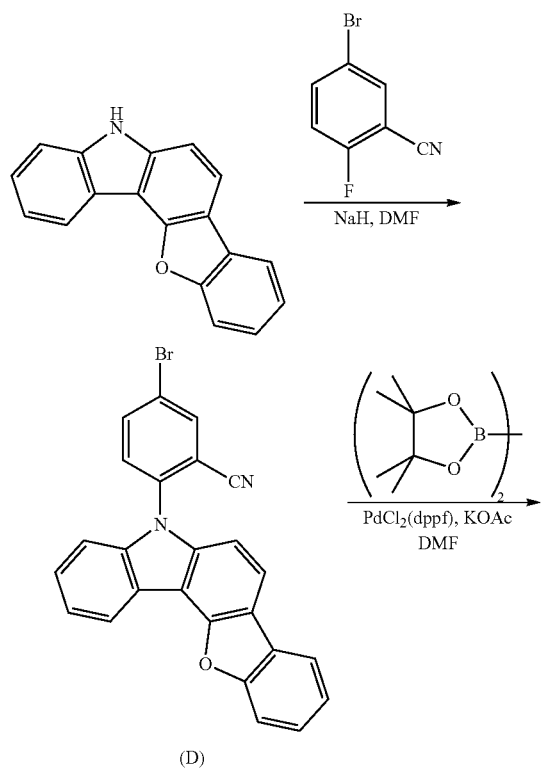

(D)

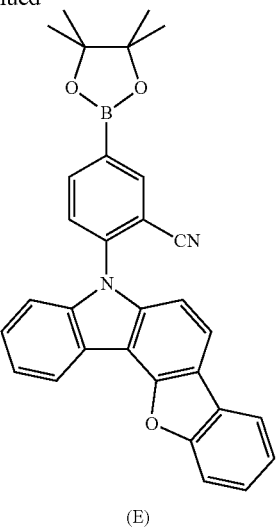

(E)

(A) + (E) $\xrightarrow{\text{Pd(PPh}_3)_4, \text{K}_2\text{CO}_3}{\text{THF, H}_2\text{O}}$

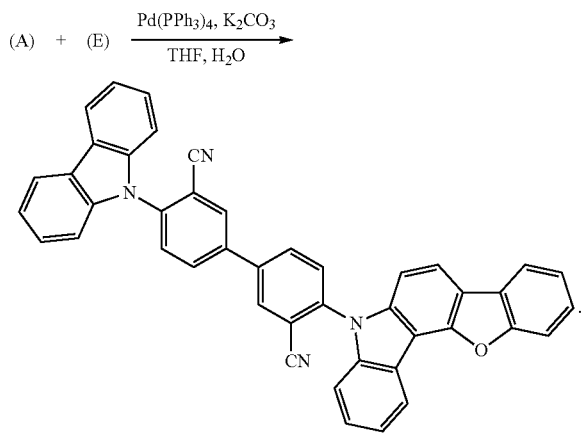

Compound 36

Synthesis of Intermediate (D)

8.84 g (yield: 52%) of the desired compound, Intermediate (D), was obtained in the same manner as Intermediate (A) of Synthesis Example 1, except that 10.0 g (38.9 mmol) of 5H-benzofuro[3,2-c]carbazole was used instead of carbazole.

LC-Mass (calculated: 436.02 g/mol, found: M+1=437 g/mol).

Synthesis of Intermediate (E)

7.25 g (yield: 74%) of the desired compound, Intermediate (E), was obtained in the same manner as Intermediate (C) of Synthesis of Example 1, except that 8.84 g (20.2 mmol) of Intermediate (D) was used instead of Intermediate (B).

LC-Mass (calculated: 484.20 g/mol, found: M+1=485 g/mol).

Synthesis of Compound 36

5.24 g (yield: 53%) of the desired compound, Compound 36, was obtained in the same manner as Compound 1 of Intermediate Synthesis Example 1, except that 8.06 g (16.6 mmol) of Intermediate (E) was used instead of Intermediate (C).

LC-Mass (calculated: 624.20 g/mol, found: M+1=625 g/mol).

Synthesis Example 3: Synthesis of Compound 102

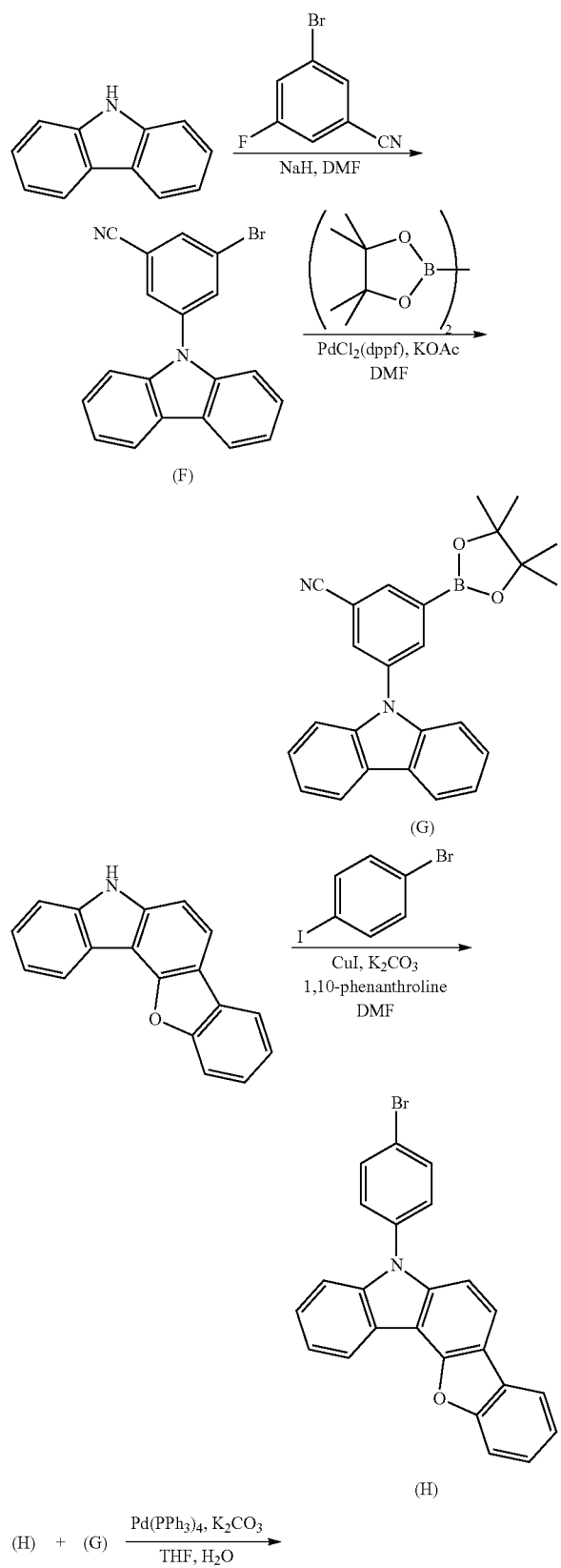

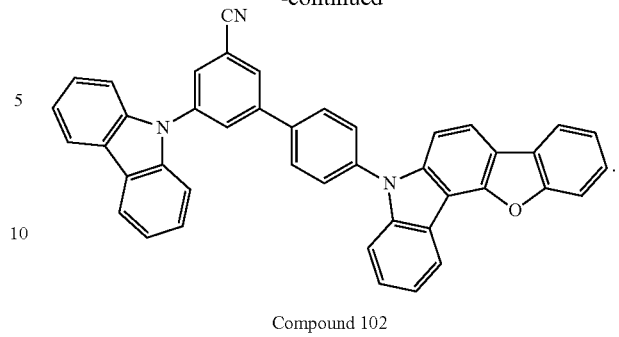

Compound 102

Synthesis of Intermediate (F)

16.0 g (yield: 77%) of the desired compound, Intermediate (F), was obtained in the same manner as Intermediate (A) of Synthesis Example 1, except that 15.6 g (77.8 mmol) of 3-bromo-5-fluorobenzonitrile was used instead of 5-bromo-2-fluorobenzonitrile.

LC-Mass (calculated: 346.01 g/mol, found: M+1=347 g/mol).

Synthesis of Intermediate (G)

9.42 g (yield: 83%) of the desired compound, Intermediate (G), was obtained in the same manner as Intermediate (C) of Synthesis Example 1, except that 10.0 g (28.8 mmol) of Intermediate (F) was used instead of Intermediate (B).

LC-Mass (calculated: 394.19 g/mol, found: M+1=395 g/mol).

Synthesis of Intermediate (H)

7.37 g (yield: 46%) of the desired compound, Intermediate (H), was obtained in the same manner as Intermediate (B), except that 5H-benzofuro[3,2-c]carbazole was used instead of 12H-benzofuro[2,3-a]carbazole.

LC-Mass (calculated: 411.03 g/mol, found: M+1=412 g/mol).

Synthesis of Compound 102

5.32 g (yield: 61%) of the desired compound, Compound 102, was obtained in the same manner as Compound 1 of Synthesis Example 1, except that 6.00 g (14.6 mmol) of Intermediate (H) and 6.03 g (15.3 mmol) of Intermediate (G) were used instead of Intermediate (A) and Intermediate (C), respectively.

LC-Mass (calculated: 599.20 g/mol, found: M+1=600 g/mol).

Synthesis Example 4: Synthesis of Compound 108

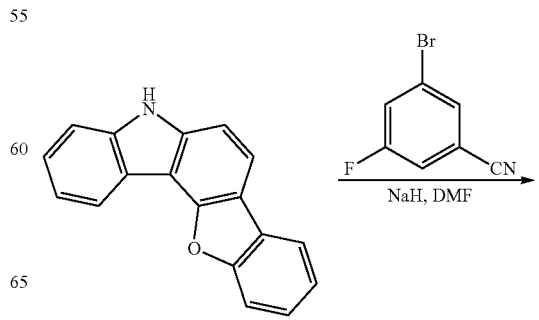

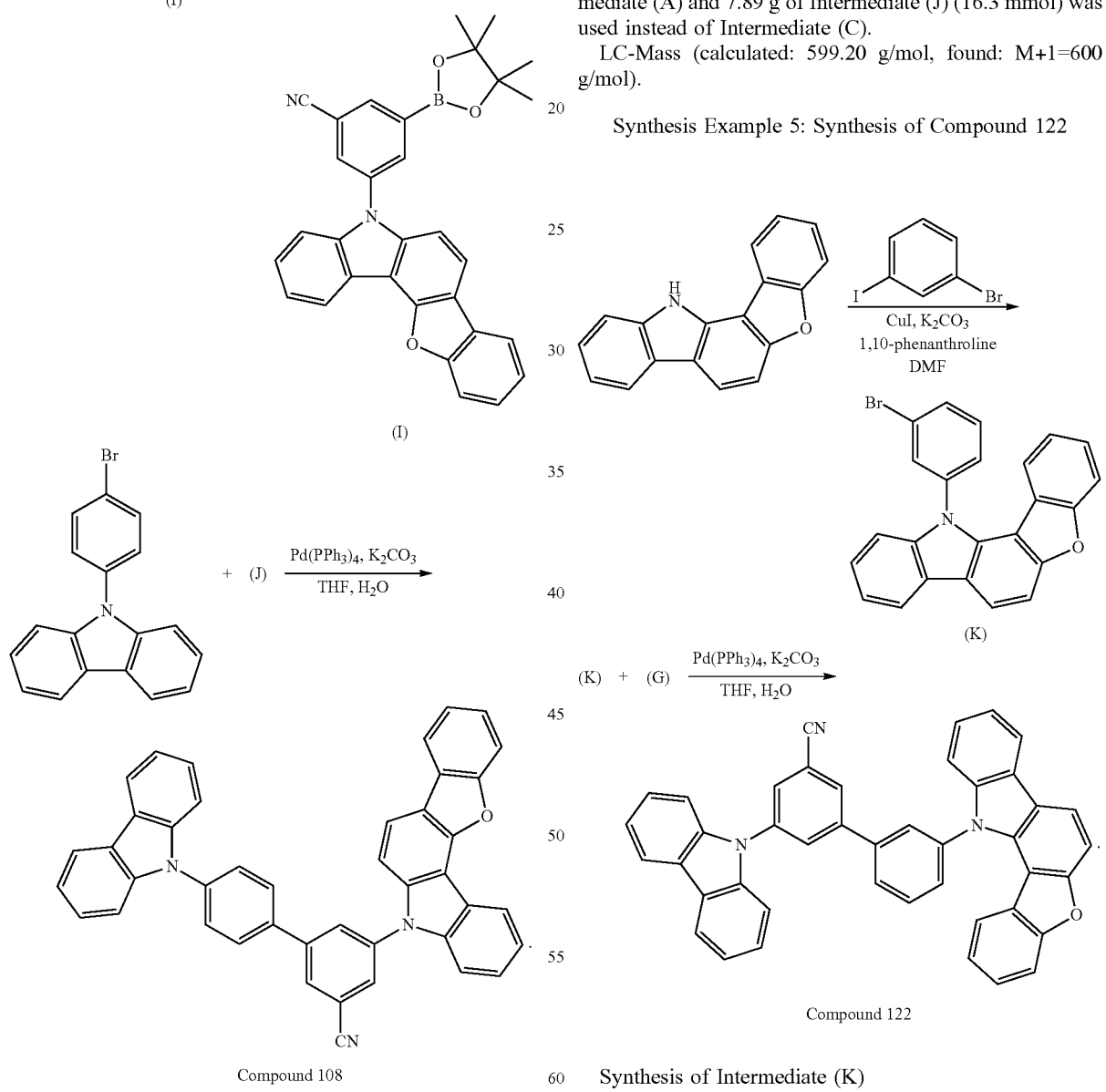

LC-Mass (calculated: 436.02 g/mol, found: M+1=437 g/mol).

Synthesis of Intermediate (J)

9.55 g (yield: 77%) of the desired compound, Intermediate (K), was obtained in the same manner as Intermediate (C) of Synthesis Example 1, except that 11.2 g (25.6 mmol) of Intermediate (I) was used instead of Intermediate (B).

LC-Mass (calculated: 484.20 g/mol, found: M+1=485 g/mol).

Synthesis of Compound 108

5.12 g (yield: 55%) of the desired compound, Compound 108, was obtained in the same manner as Compound 1 of Synthesis Example 1, except that 5.00 g (15.5 mmol) of 9-(4-bromophenyl)-9H-carbazole was used instead of Intermediate (A) and 7.89 g of Intermediate (J) (16.3 mmol) was used instead of Intermediate (C).

LC-Mass (calculated: 599.20 g/mol, found: M+1=600 g/mol).

Synthesis Example 5: Synthesis of Compound 122

Compound 122

Synthesis of Intermediate (I)

11.2 g (yield: 66%) of the desired compound, Intermediate (I), was obtained in the same manner as Intermediate (F) of Synthesis Example 1, except that 5H-benzofuro[3,2-c]carbazole was used instead of carbazole.

Synthesis of Intermediate (K)

6.57 g (yield: 41%) of the desired compound, Intermediate (K), was obtained in the same manner as Intermediate (B) of Synthesis Example 1, except that 10.0 g (38.9 mmol) of 12H-benzofuro[3,2-a]carbazole was used instead of 12H-benzofuro[2,3-a]carbazole and 13.2 g (46.6 mmol) of 1-bromo-3-iodobenzene was used instead of 1-bromo-4-iodobenzene.

LC-Mass (calculated: 411.03 g/mol, found: M+1=412 g/mol).

Synthesis of Compound 122

4.28 g (yield: 49%) of the desired compound, Compound 108, was obtained in the same manner as Compound 102 of Synthesis Example 3, except that 6.00 g (14.6 mmol) of Intermediate (K) was used instead of Intermediate (H).

LC-Mass (calculated: 599.20 g/mol, measured: M+1=600 g/mol).

Synthesis Example 6: Synthesis of Compound 126

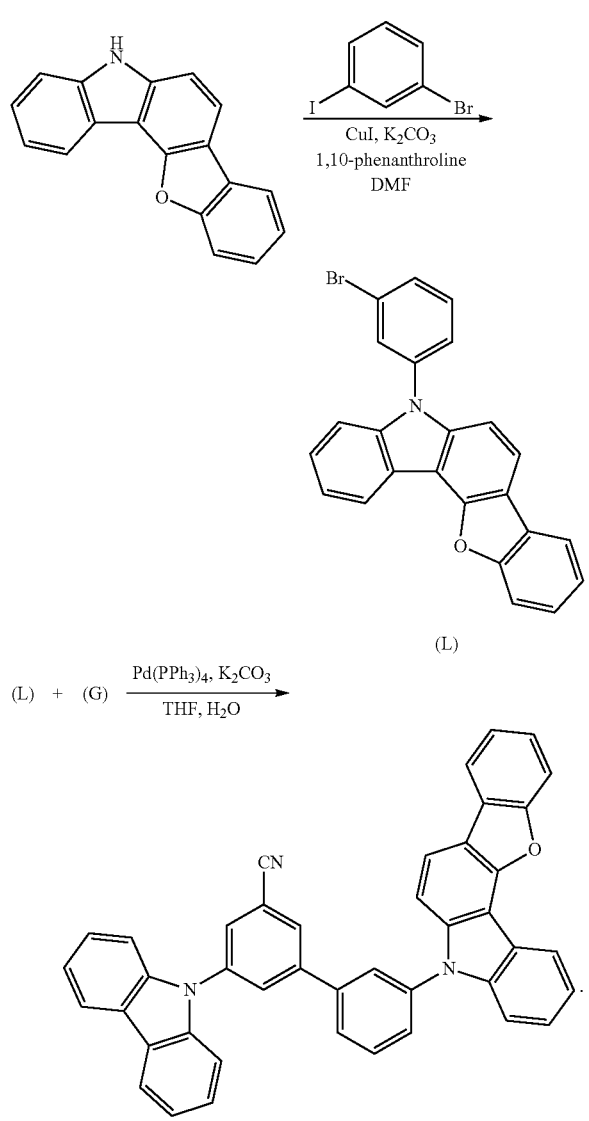

Compound 126

Synthesis of Intermediate (L)

9.13 g (yield: 57%) of the desired compound, Intermediate (L), was obtained in the same manner as Intermediate (K) of Synthesis Example 5, except that 10.0 g (38.9 mmol) of 5H-benzofuro[3,2-c]carbazole was used instead of 12H-benzofuro[3,2-a]carbazole.

LC-Mass (calculated: 411.03 g/mol, found: M+1=412 g/mol).

Synthesis of Compound 126

10.6 g (yield: 81%) of the desired compound, Compound 126, was obtained in the same manner as Compound 102 of Synthesis Example 3, except that 9.00 g (21.8 mmol) of Intermediate (L) was used instead of Intermediate (H).

LC-Mass (calculated: 599.20 g/mol, found: M+1=600 g/mol).

Synthesis Example 7: Synthesis of Compound 132

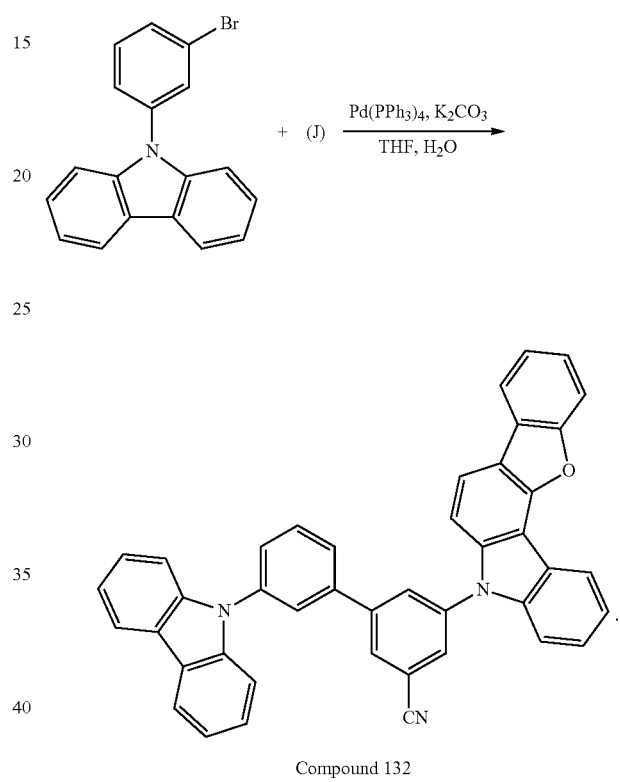

Compound 132

11.0 g (yield: 74%) of the desired compound, Compound 132, was obtained in the same manner as Compound 108 of Synthesis Example 4, except that 8.00 g (24.8 mmol) of 9-(3-bromophenyl)-9H-carbazole was used instead of 9-(4-bromophenyl)-9H-carbazole.

LC-Mass (calculated: 599.20 g/mol, found: M+1=600 g/mol).

Synthesis Example 8: Synthesis of Compound 146

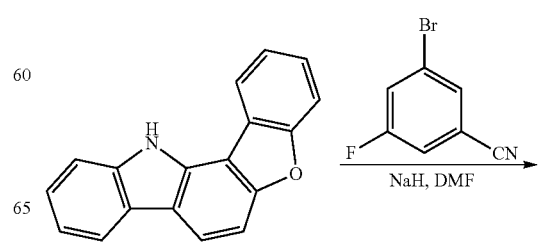

-continued

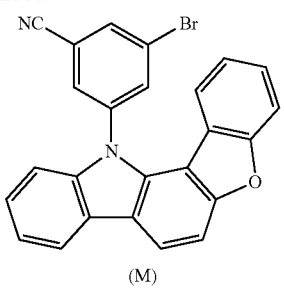
(M)

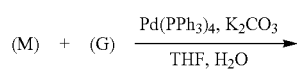

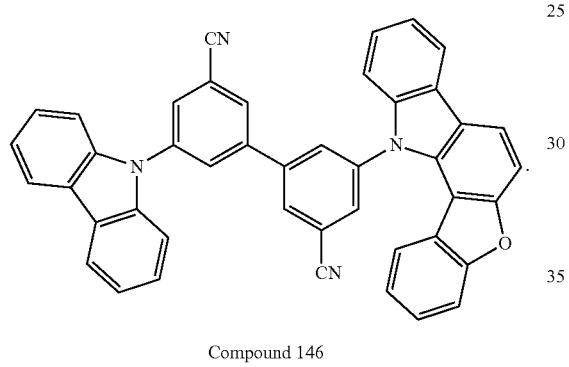
Compound 146

Synthesis of Intermediate (M)

9.69 g (yield: 38%) of the desired compound, Intermediate (M), was obtained in the same manner as Intermediate (F) of Synthesis Example 3, except that 15.0 g (58.3 mmol) of 12H-benzofuro[3,2-a]carbazole was used instead of carbazole.

LC-Mass (calculated: 436.02 g/mol, found: M+1=437 g/mol).

Synthesis of Compound 146

5.37 g (yield: 47%) of the desired compound, Compound 146, was obtained in the same manner as Compound 102 of Synthesis Example 3, except that 8.00 g (18.3 mmol) of Intermediate (M) was used instead of Intermediate (H).

LC-Mass (calculated: 624.20 g/mol, found: M+1=625 g/mol).

Synthesis Example 9: Synthesis of Compound 150

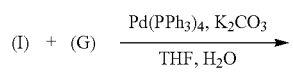

-continued

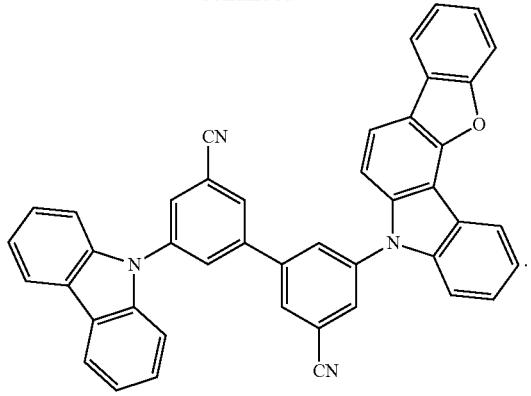
Compound 150

6.36 g (yield: 61%) of the desired compound, Compound 150, was obtained in the same manner as Compound 102 of Synthesis Example 3, except that 7.30 g (16.7 mmol) of Intermediate (I) 7 was used instead of Intermediate (H).

LC-Mass (calculated: 624.20 g/mol, found: M+1=625 g/mol).

Synthesis Example 10: Synthesis of Compound 218

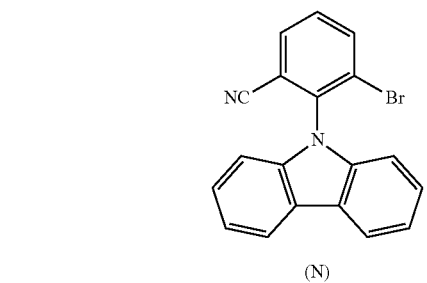

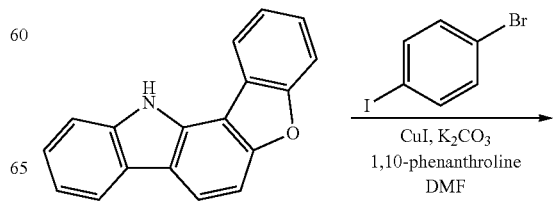
(N)

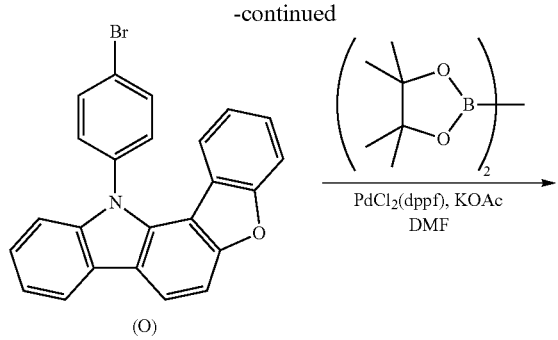

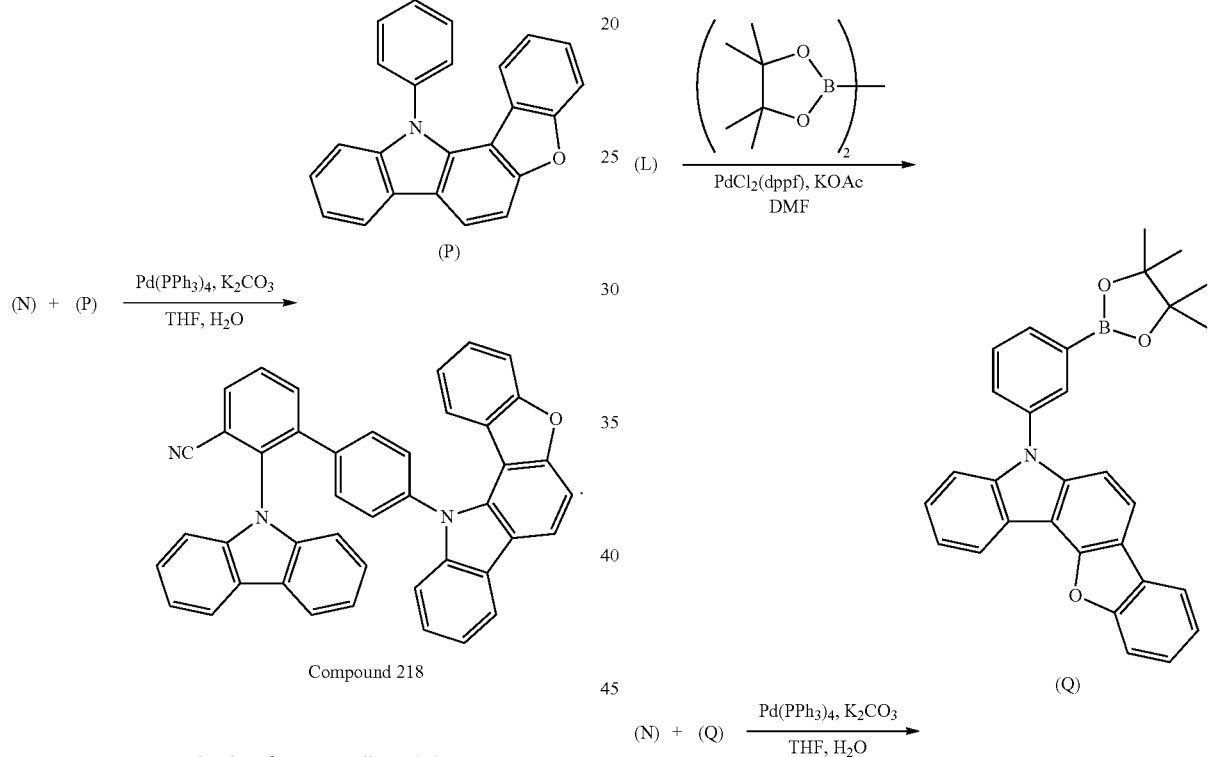

of Synthesis Example 1, except that 6.73 g (15.5 mmol) of Intermediate (O) was used instead of Intermediate (B).

LC-Mass (calculated: 459.20 g/mol, found: M+1=460 g/mol).

Synthesis of Compound 218

4.79 g (yield: 66%) of the desired compound, Compound 218, was obtained in the same manner as Compound 1 of Synthesis Example 1, except that 4.50 g (13.0 mmol) of Intermediate (N) was used instead of Intermediate (A) and 6.25 g (13.6 mmol) of Intermediate (P) was used instead of Intermediate (C).

LC-Mass (calculated: 599.20 g/mol, found: M+1=600 g/mol).

Synthesis Example 11: Synthesis of Compound 330

Synthesis of Intermediate (N)

15.0 g (yield: 72%) of the desired compound, Intermediate (N), was obtained in the same manner as Intermediate (A) of Synthesis Example 1, except that 15.6 g (77.8 mmol) of 3-bromo-2-fluorobenzonitrile was used instead of 5-bromo-2-fluorobenzonitrile.

LC-Mass (calculated: 346.01 g/mol, found: M+1=347 g/mol).

Synthesis of Intermediate (O)

6.73 g (yield: 42%) of the desired compound, Intermediate (O), was obtained in the same manner as Intermediate (B) of Synthesis Example 1, except that 10.0 g (28.8 mmol) of 12H-benzofuro[3,2-a]carbazole was used instead of 12H-benzofuro[2,3-a]carbazole.

LC-Mass (calculated: 411.03 g/mol, found: M+1=412 g/mol).

Synthesis of Intermediate (P)

4.97 g (yield: 70%) of the desired compound, Intermediate (P), was obtained in the same manner as Intermediate (C)

Synthesis of Intermediate (Q)

6.68 g (yield: 75%) of the desired compound, Intermediate (Q), was obtained in the same manner as Intermediate (C) of Synthesis Example 1, except that 8.00 g (19.4 mmol) of Intermediate (L) was used instead of Intermediate (B).

LC-Mass (calculated: 459.20 g/mol, found: M+1=460 g/mol).

Synthesis of Compound 330

4.07 g (yield: 54%) of the desired compound, Compound 330, was obtained in the same manner as Compound 218 of Synthesis Example 10, except that 6.50 g (13.5 mmol) of Intermediate (Q) was used instead of Intermediate (P).

LC-Mass (calculated: 599.20 g/mol, found: M+1=600 g/mol).

Synthesis Example 12: Synthesis of Compound 366 of Synthesis Example 6, except that 13.2 g (46.6 mmol) of 1-bromo-2-iodobenzene was used instead of 1-bromo-3-iodobenzene.

LC-Mass (calculated: 411.03 g/mol, found: M+1=412 g/mol).

Synthesis of Compound 366

4.75 g (yield: 50%) of the desired compound, Compound 366, was obtained in the same manner as Compound 102 of Synthesis Example 3, except that 7.00 g (17.0 mmol) of Intermediate (R) was used instead of Intermediate (H).

LC-Mass (calculated: 599.20 g/mol, found: M+1=600 g/mol).

Synthesis Example 13: Synthesis of Compound 378

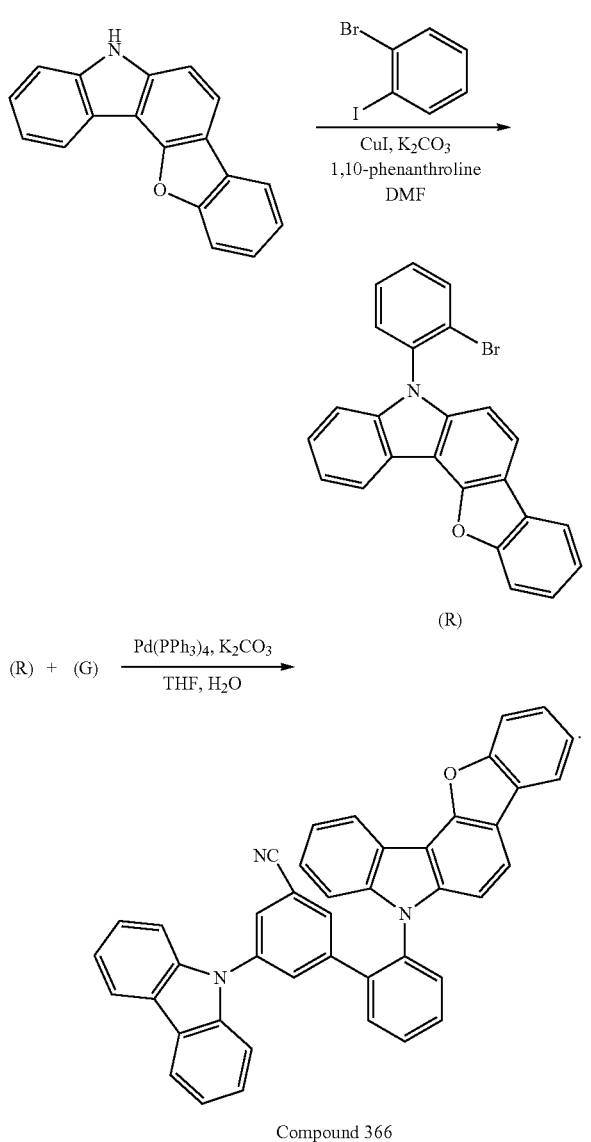

Compound 366

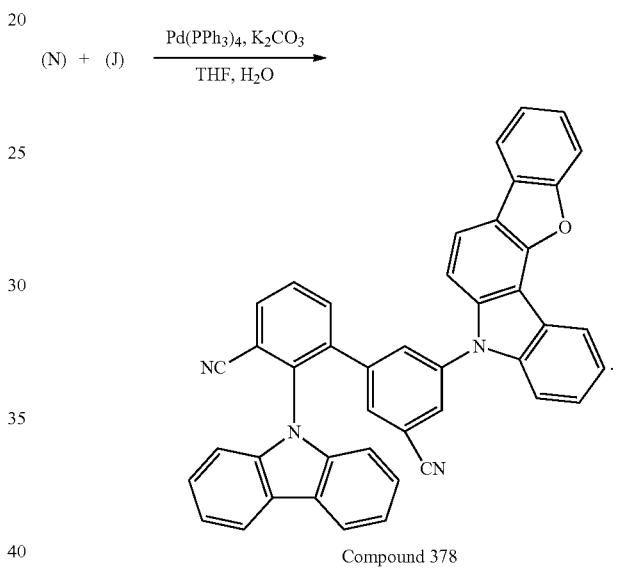

Compound 378

7.56 g (yield: 60%) of the desired compound, Compound 378, was obtained in the same manner as Compound 108 of Synthesis Example 4, except that 7.00 g (20.2 mmol) of Intermediate (N) was used instead of 9-(4-bromophenyl)-9H-carbazole.

LC-Mass (calculated: 624.20 g/mol, found: M+1=625 g/mol).

Synthesis Example 14: Synthesis of Compound 474

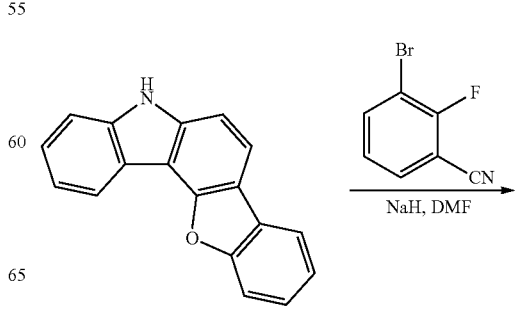

Synthesis of Intermediate (R)

7.85 g (yield: 49%) of the desired compound, Intermediate (R), was obtained in the same manner as Intermediate (L)

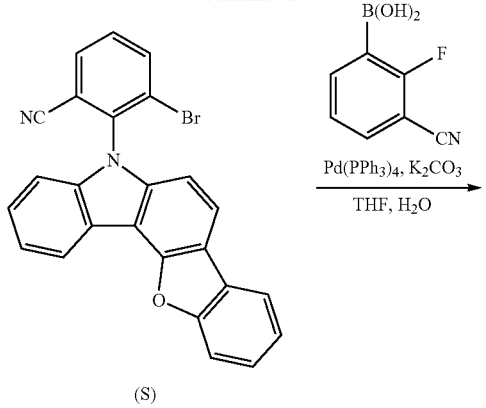

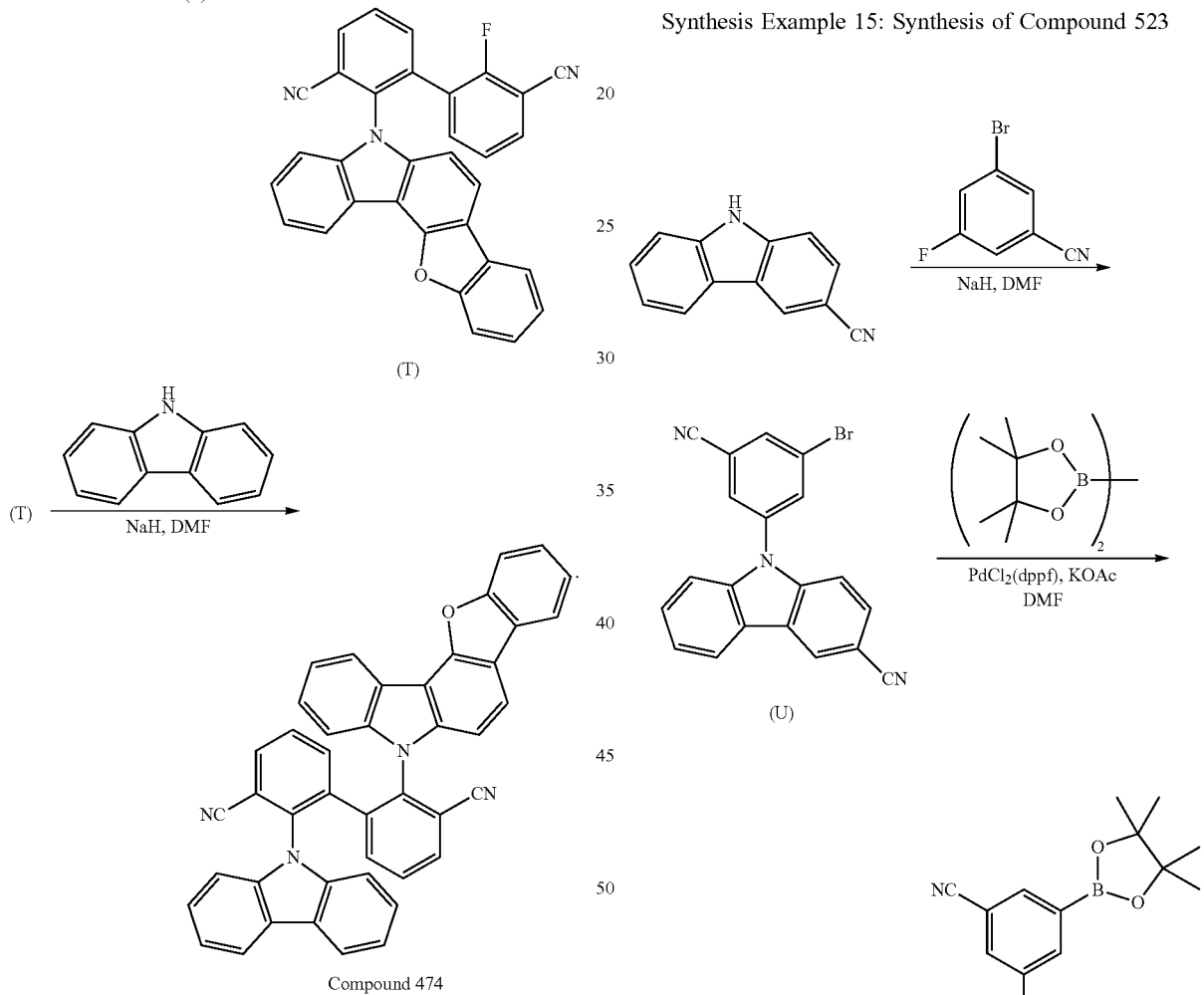

Synthesis of Intermediate (S)

11.5 g (yield: 45%) of the desired compound, Intermediate (S), was obtained in the same manner as Intermediate (N) of Synthesis Example 10, except that 15.0 g (75.8 mmol) of 5H-benzofuro[3,2-c]carbazole was used instead of carbazole.

LC-Mass (calculated: 346.02 g/mol, found: M+1=347 g/mol).

Synthesis of Intermediate (T)

7.75 g (yield: 71%) of the desired compound, Intermediate (T), was obtained in the same manner as Compound 1 of Synthesis Example 1, except that 10.0 g (22.9 mmol) of Intermediate (S) was used instead of Intermediate (A), and 3.96 g (24.0 mmol) of (3-cyano-2-fluorophenyl)boronic acid was used instead of Intermediate (C).

LC-Mass (calculated: 477.13 g/mol, found: M+1=478 g/mol).

Synthesis of Compound 474

3.51 g (yield: 47%) of the desired compound, Compound 474, was obtained in the same manner as Intermediate (A) of Synthesis Example 1, except that 7.43 g (15.6 mmol) of Intermediate (T) was used instead of 5-bromo-2-fluorobenzonitrile.

LC-Mass (calculated: 624.20 g/mol, found: M+1=625 g/mol).

Synthesis Example 15: Synthesis of Compound 523

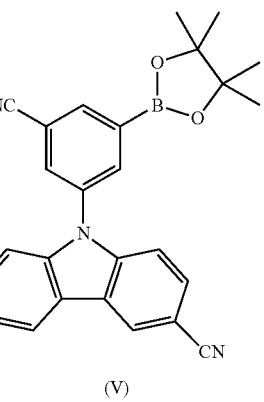

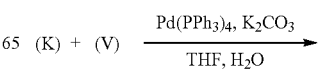

-continued

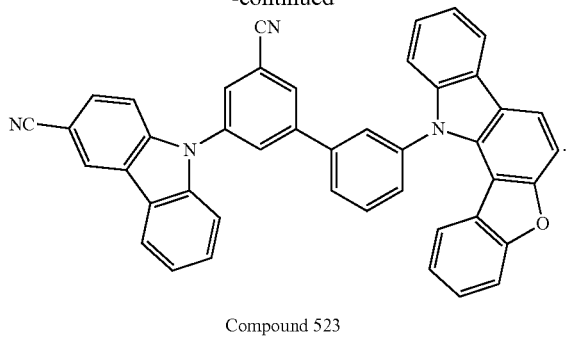

Compound 523

Synthesis of Intermediate (U)

16.0 g (yield: 55%) of the desired compound, Intermediate (U), was obtained in the same manner as Intermediate (F) of Synthesis Example 3, except that 15.0 g (78.0 mmol) of 9H-carbazole-3-carbonitrile was used instead of carbazole.

LC-Mass (calculated: 371.01 g/mol, found: M+1=372 g/mol).

Synthesis of Intermediate (V)

7.64 g (yield: 72%) of the desired compound, Intermediate (V), was obtained in the same manner as Intermediate (C) of Synthesis Example 1, except that 7.48 g (17.8 mmol) of Intermediate (U) was used instead of Intermediate (B).

LC-Mass (calculated: 419.18 g/mol, found: M+1=420 g/mol).

Synthesis of Compound 523

9.56 g (yield: 71%) of the desired compound, Compound 523, was obtained in the same manner as Compound 122 of Synthesis Example 5, except that 8.00 g (21.5 mmol) of Intermediate (V) was used instead of Intermediate (J).

LC-Mass (calculated: 624.20 g/mol, found: M+1=625 g/mol).

Synthesis Example 16: Synthesis of Compound 524

(U) + (Q) $\xrightarrow[\text{THF, H}_2\text{O}]{\text{Pd(PPh}_3)_4, \text{K}_2\text{CO}_3}$

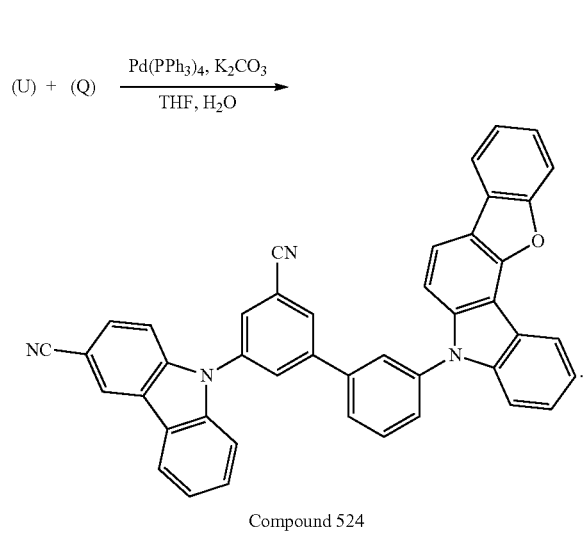

Compound 524

10.1 g (yield: 75%) of the desired compound, Compound 524, was obtained in the same manner as Compound 330 of Synthesis Example 11, except that 8.00 g (21.5 mmol) of Intermediate (U) was used instead of Intermediate (N).

LC-Mass (calculated: 624.20 g/mol, found: M+1=625 g/mol).

Synthesis Example 17: Synthesis of Compound 525

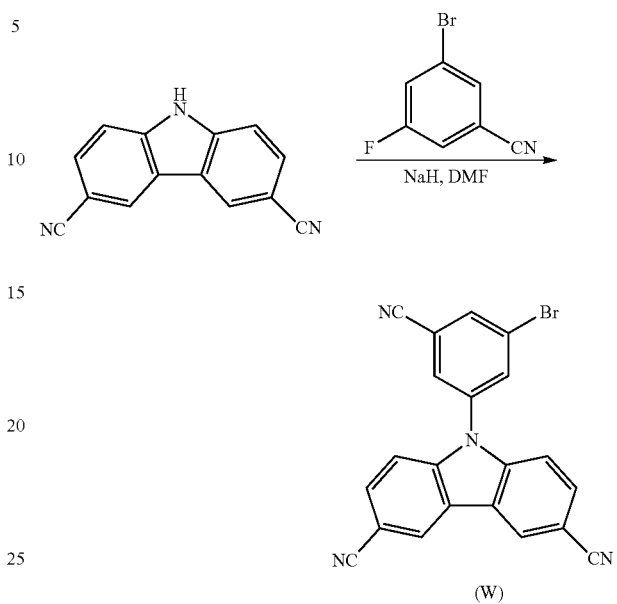

(W) + (Q) $\xrightarrow[\text{THF, H}_2\text{O}]{\text{Pd(PPh}_3)_4, \text{K}_2\text{CO}_3}$

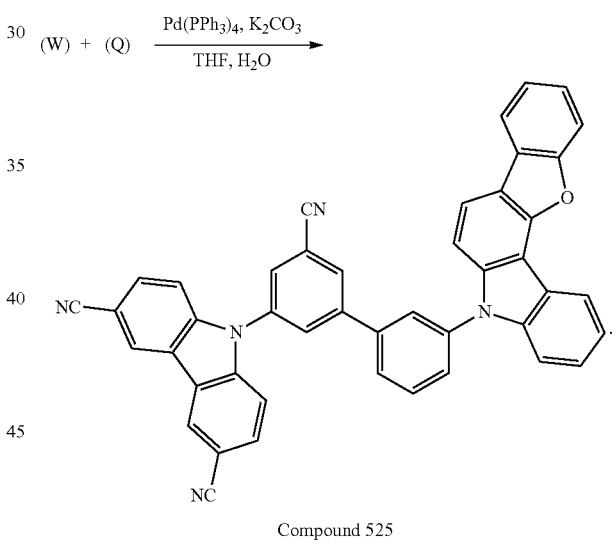

Compound 525

Synthesis of Intermediate (W)

8.50 g (yield: 31%) of the desired compound, Intermediate (W), was obtained in the same manner as Intermediate (F) of Synthesis Example 3, except that 15.0 g (69.1 mmol) of 9H-carbazole-3,6-dicarbonitrile was used instead of carbazole.

LC-Mass (calculated: 396.00 g/mol, found: M+1=397 g/mol).

Synthesis of Compound 525

8.76 g (yield: 63%) of the desired compound, Compound 525, was obtained in the same manner as Compound 330 of Synthesis Example 11, except that 8.50 g (21.4 mmol) of Intermediate (W) was used instead of Intermediate (N).

LC-Mass (calculated: 649.19 g/mol, found: M+1=650 g/mol).

Synthesis Example 18: Synthesis of Compound 666

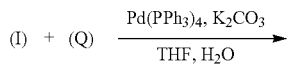

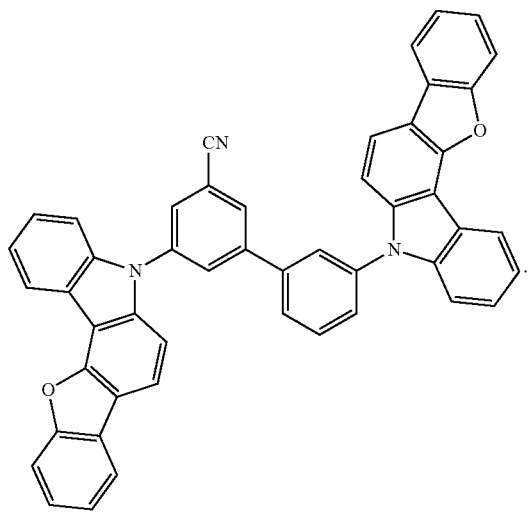

Compound 666

7.59 g (yield: 74%) of the desired compound, Compound 666, was obtained in the same manner as Compound 330 of Synthesis Example 11, except that 6.50 g (14.9 mmol) of Intermediate (I) was used instead of Intermediate (N).

LC-Mass (calculated: 689.21 g/mol, found: M+1=690 g/mol).

Synthesis Example 19: Synthesis of Compound 684

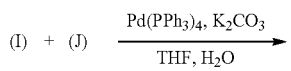

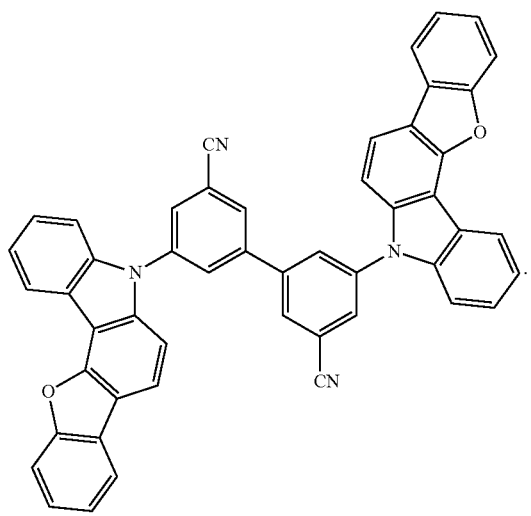

Compound 684

7.33 g (yield: 69%) of the desired compound, Compound 684, was obtained in the same manner as in Synthesis Example 18, except that 7.56 g (15.6 mmol) of Intermediate (J) was used instead of Intermediate (Q).

LC-Mass (calculated: 714.21 g/mol, found: M+1=715 g/mol).

Synthesis Example 20: Synthesis of Compound 704

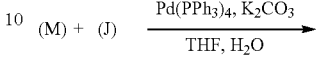

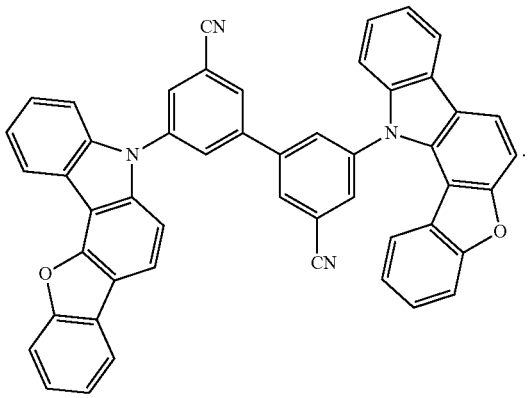

Compound 704

8.44 g (yield: 63%) of the desired compound, Compound 704, was obtained in the same manner as Compound 330 of Synthesis Example 11, except that 8.20 g (18.8 mmol) of Intermediate (M) was used instead of Intermediate (N).

LC-Mass (calculated: 714.21 g/mol, found: M+1=715 g/mol).

Synthesis Example 21: Synthesis of Compound 786

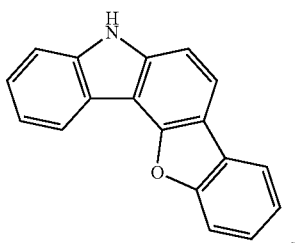

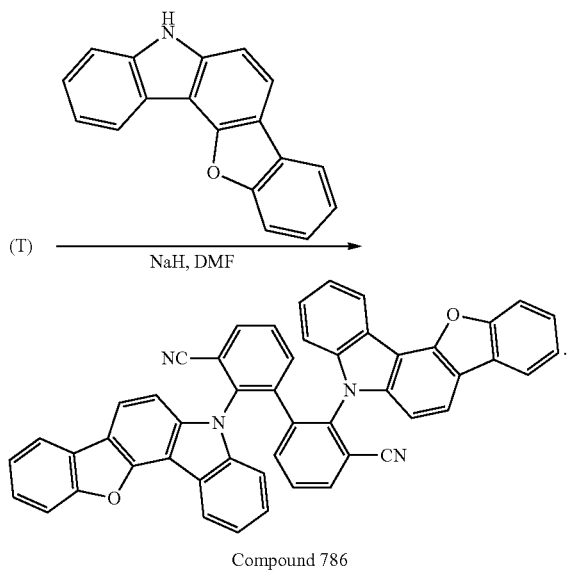

Compound 786

5.48 g (yield: 47%) of the desired compound, Compound 786, was obtained in the same manner as Compound 474 of Synthesis Example 14, except that 4.20 g (16.3 mmol) of 5H-benzofuro[3,2-c]carbazole was used instead of carbazole.

LC-Mass (calculated: 714.21 g/mol, found: M+1=715 g/mol).

Comparative Synthesis Example A: Synthesis of Compound A

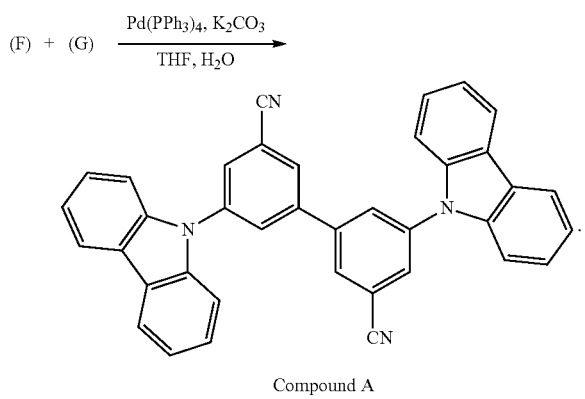

Compound A 9.27 g (yield: 86%) of the desired compound, Compound A, was obtained in the same manner as Compound 102 of Synthesis Example 3, except that 7.00 g (20.2 mmol) of Intermediate (F) was used instead of Intermediate (H).

LC-Mass (calculated: 534.18 g/mol, found: M+1=535 g/mol).

Comparative Synthesis Example B: Synthesis of Compound B

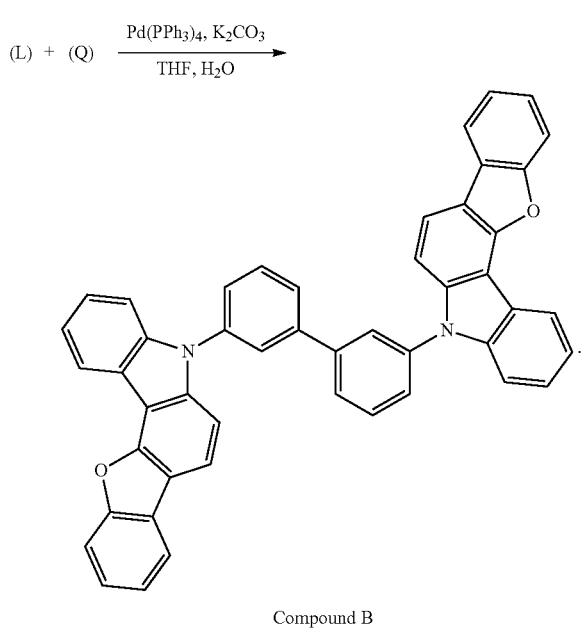

Compound B 8.46 g (yield: 75%) of the desired compound, Compound B, was obtained in the same manner as Compound 330 of Synthesis Example 11, except that 7.00 g (17.0 mmol) of Intermediate (L) was used instead of Intermediate (N).

LC-Mass (calculated: 664.22 g/mol, found: M+1=665 g/mol).

Example 1

A 1,500 Å glass substrate, on which an indium tin oxide (ITO) electrode (first electrode, anode) was ultrasonically washed with distilled water. After the completion of the washing process, the glass substrate was ultrasonically washed with a solvent, such as iso-propyl alcohol, acetone, and/or methanol, dried, and mounted on a plasma cleaner. The glass substrate was cleaned by using oxygen plasma for 5 minutes, and mounted on a vacuum depositor.

Compound HT3 and Compound HP-1 were co-deposited on the ITO electrode of the glass substrate to form a hole injection layer having a thickness of 100 Angstroms (Å). Compound HT3 was deposited on the hole injection layer to form a hole transport layer having a thickness of 1,300 Å, and mCP was deposited on the hole transport layer to form an electron blocking layer having a thickness of 100 Å, thereby forming a hole transport region.

Compound 1 (as a host) and Flr6 (as a dopant, 10 percent by weight, wt %) were co-deposited on the hole transport region to form an emission layer having a thickness of 400 Å.

BCP was vacuum deposited on the emission layer to form a hole blocking layer having a thickness of 100 Å, and Compound ET3 and Liq were co-deposited on the hole blocking layer to form an electron transport layer having a thickness of 300 Å. LiQ was deposited on the electron transport layer to form an electron injection layer having a thickness of 10 Å, and an Al second electrode (as a cathode) was formed on the electron injection layer, thereby manufacturing an organic light-emitting device.

Examples 2 to 21 and Comparative Examples 1 and 2

Organic light-emitting devices were manufactured in the same manner as in Example 1, except in forming the emission layer, compounds listed in Table 2 were respectively used as a host instead of Compound 1.

Evaluation Example 1: Evaluation of Characteristics of Organic Light-Emitting Devices The organic light-emitting devices of Examples 1 to 21 and Comparative Examples 1 and 2 were analyzed to measure changes in voltage-dependent current density, changes in brightness, and light-emission efficiency. Detailed methods for measuring such changes above are as follows, and the results are shown in Table 2.

(1) Measurement of Changes in Voltage-Dependent Current Density

The organic light-emitting devices manufactured above were each analyzed for current value flowing in unit devices in accordance with voltage increasing from 0 Volts (V) to 10 V using a current-voltage meter (Keithley 2400), and the measured current value was divided by an area to provide the result.

(2) Measurement of Changes in Voltage-Dependent Brightness

The organic light-emitting devices manufactured above were each analyzed for brightness in accordance with voltage increasing from 0 V to 10 V using a brightness meter (Minolta Cs-1000A) to provide the result.

(3) Measurement of Light-Emission Efficiency

On the basis of the brightness current density results provided according to Evaluation Examples 1(1) and to Evaluation Examples 1(2) and the use of voltage, the current efficiency (cd/A) of the organic light-emitting devices manufactured above were each measured in accordance with the same current density (10 milliAmperes per square centimeter, mA/cm$^2$).

(4) Measurement of Durability

The time at which the brightness of the organic light-emitting devices manufactured above was 95% of the initial brightness (100%) was measured for evaluation.

The driving voltage, the current efficiency, and the durability of the organic light-emitting devices shown in Table 2 were relative values based on 100% of the driving voltage, 100% of the current efficiency, and 100% of the durability of the organic light-emitting device of Comparative Example 1.

TABLE 2

| Host | Driving voltage (relative value) | Current efficiency (relative value) | Durability (relative value) | Color |
|---|---|---|---|---|
| Example 1 | Compound 1 | 97% | 101% | 121% | Blue |
| Example 2 | Compound 36 | 102% | 98% | 115% | Blue |
| Example 3 | Compound 102 | 92% | 116% | 120% | Blue |
| Example 4 | Compound 108 | 94% | 113% | 118% | Blue |
| Example 5 | Compound 122 | 97% | 108% | 107% | Blue |
| Example 6 | Compound 126 | 92% | 121% | 119% | Blue |
| Example 7 | Compound 132 | 91% | 128% | 122% | Blue |
| Example 8 | Compound 146 | 100% | 96% | 107% | Blue |
| Example 9 | Compound 150 | 93% | 124% | 119% | Blue |
| Example 10 | Compound 218 | 93% | 103% | 105% | Blue |
| Example 11 | Compound 330 | 94% | 102% | 104% | Blue |
| Example 12 | Compound 366 | 95% | 115% | 114% | Blue |
| Example 13 | Compound 378 | 95% | 104% | 116% | Blue |
| Example 14 | Compound 474 | 90% | 131% | 126% | Blue |
| Example 15 | Compound 523 | 89% | 126% | 131% | Blue |
| Example 18 | Compound 524 | 92% | 131% | 145% | Blue |
| Example 17 | Compound 525 | 97% | 114% | 109% | Blue |
| Example 18 | Compound 666 | 90% | 107% | 105% | Blue |
| Example 19 | Compound 684 | 101% | 102% | 113% | Blue |
| Example 20 | Compound 704 | 94% | 110% | 121% | Blue |
| Example 21 | Compound 786 | 89% | 125% | 118% | Blue |
| Comparative Example 1 | Compound A | 100% | 100% | 100% | Blue |
| Comparative Example 2 | Compound B | 140% | 77% | 22% | Blue |

Compound A

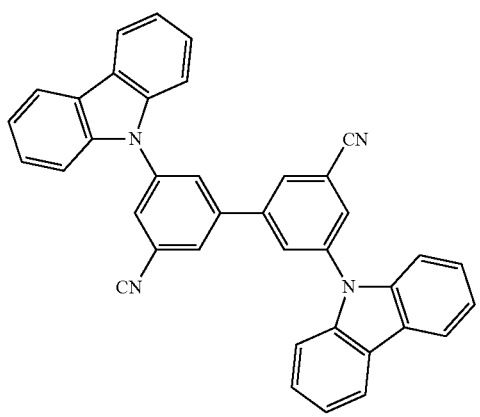

Compound B

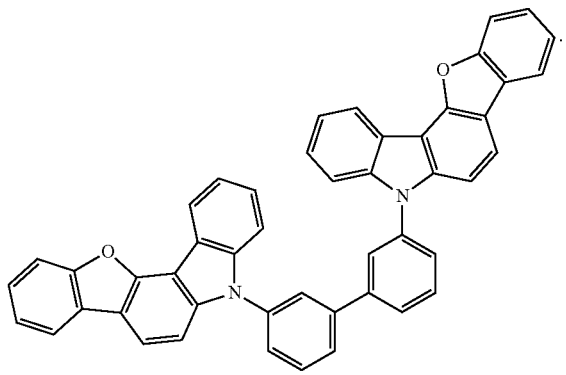

Referring to Table 2, it was determined that the organic light-emitting devices of Examples 1 to 21 had lower driving voltage, higher efficiency, and higher durability than those values of the organic light-emitting devices of Comparative Examples 1 and 2.

A condensed cyclic compound according to the one or more embodiments may have excellent electrical characteristics and thermal stability, and thus an organic light-emitting device including the condensed cyclic compound may have low driving voltage, high efficiency, and high durability characteristics.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the present disclosure as defined by the following claims.

What is claimed is:

1. A condensed cyclic compound represented by Formula 1:

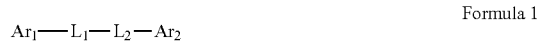

Formula 1

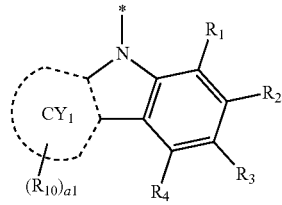

Formula 2

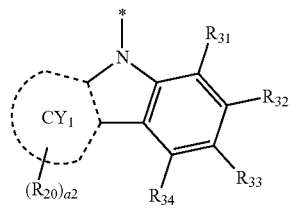

Formula 3

Formula 4

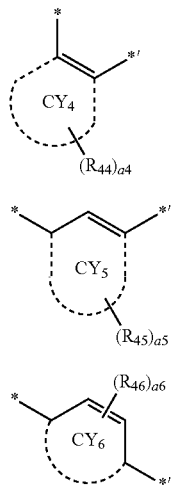

Formula 5

Formula 6 wherein, in Formulae 1 to 6,
Ar$_1$ is a group represented by Formula 2,
Ar$_2$ is a group represented by Formula 3,
CY$_1$ is selected from a fluorene group, a carbazole group, a dibenzofuran group, and a dibenzothiophene group,
CY$_2$ is selected from a benzene group, a fluorene group, a carbazole group, a dibenzofuran group, and a dibenzothiophene group,
L$_1$ and L$_2$ are each independently a group represented by Formula 4, a group represented by Formula 5, or a group represented by Formula 6,
CY$_4$ to CY$_e$ are each independently a C$_5$-C$_{30}$ carbocyclic group,
R$_1$ to R$_4$, R$_{10}$, R$_{20}$, R$_{31}$ to R$_{34}$, and R$_{44}$ to R$_{46}$ are each independently selected from hydrogen, deuterium, —F, —Cl, —Br, —I, a hydroxy group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_1$-C$_{60}$ heteroaryl group, a substituted or unsubstituted monovalent non-aromatic condensed polycyclic group, a substituted or unsubstituted monovalent non-aromatic condensed heteropolycyclic group, —Si(Q$_1$)(Q$_2$)(Q$_3$), —N(Q$_4$)(Q$_5$), and —B(Q$_6$)(Q$_7$),
provided that a group represented by *-L$_1$-L$_2$-*' in Formula 1 comprises at least one cyano group, wherein the number of the cyano groups comprised in a group represented by *-L$_1$-L$_2$-*' in Formula 1 is 1, 2, 3, or 4,
a1, a2, and a4 to a6 are each independently an integer selected from 0 to 10,
* and *' each indicate a binding site to a neighboring atom, and at least one substituent of the substituted C$_1$-C$_{60}$ alkyl group, the substituted C$_2$-C$_{60}$ alkenyl group, the substituted C$_2$-C$_{60}$ alkynyl group, the substituted C$_3$-C$_{10}$ cycloalkyl group, the substituted C$_1$-C$_{10}$ heterocycloalkyl group, the substituted C$_3$-C$_{10}$ cycloalkenyl group, the substituted C$_1$-C$_{10}$ heterocycloalkenyl group, the substituted C$_6$-C$_{60}$ aryl group, the substituted C$_6$-C$_{60}$ aryloxy group, the substituted C$_6$-C$_{60}$ arylthio group, the substituted C$_1$-C$_{60}$ heteroaryl group, the substituted monovalent non-aromatic condensed polycyclic group, and the substituted monovalent non-aromatic condensed heteropolycyclic group is selected from:
deuterium, —CD$_3$, —CD$_2$H, —CDH$_2$, —F, —Cl, —Br, —I, a hydroxy group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, and a C$_1$-C$_{60}$ alkoxy group;
a C$_1$-C$_{60}$ alkyl group, a C$_2$-C$_{60}$ alkenyl group, a C$_2$-C$_{60}$ alkynyl group, and a C$_1$-C$_{60}$ alkoxy group, each substituted with at least one selected from deuterium, —CD$_3$, —CD$_2$H, —CDH$_2$, —F, —Cl, —Br, —I, a hydroxy group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycydic group, a monovalent non-aromatic condensed heteropolycyclic group, —Si(Q$_{11}$)(Q$_{12}$)(Q$_{13}$), —N(Q$_{14}$)(Q$_{15}$), and —B(Q$_{16}$)(Q$_{17}$);
a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, and a monovalent non-aromatic condensed heteropolycyclic group;
a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, and a monovalent non-aromatic condensed heteropolycyclic group, each substituted with at least one selected from deuterium, —CD$_3$, —CD$_2$H, —CDH$_2$, —F, —Cl, —Br, —I, a hydroxy group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, a monovalent non-aromatic condensed heteropolycyclic group, —Si(Q$_{21}$)(Q$_{22}$)(Q$_{23}$), —N(Q$_{24}$)(Q$_{25}$), and —B(Q$_{26}$)(Q$_{27}$); and —Si(Q$_{31}$)(Q$_{32}$)(Q$_{33}$), —N(Q$_{34}$)(Q$_{35}$), and —B(Q$_{36}$)(Q$_{37}$), wherein Q$_1$ to Q$_7$, Q$_{11}$ to Q$_{17}$, Q$_{21}$ to Q$_{27}$, and Q$_{31}$ to Q$_{37}$ are each independently selected from hydrogen, deuterium, —F, —Cl, —Br, —I, a hydroxy group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_1$-C$_{60}$ heteroaryl group, a substituted or unsubstituted monovalent non-aromatic condensed polycyclic group, and a substituted or unsubstituted monovalent non-aromatic condensed heteropolycyclic group.

2. The condensed cyclic compound of claim 1, wherein Ar$_1$ is selected from groups represented by Formulae 2-1 to 2-6, and Ar$_2$ is selected from groups represented by Formulae 3-1 to 3-7:

Formula 2-1

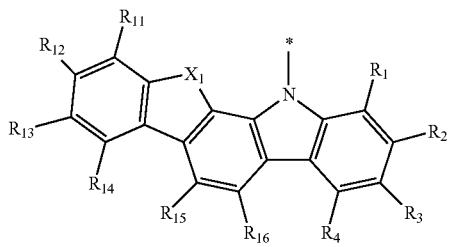

Formula 2-2

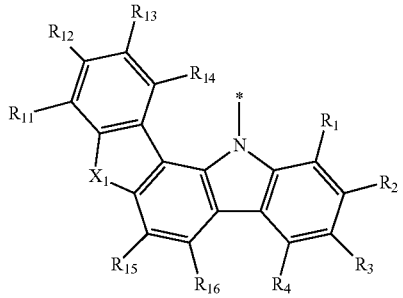

Formula 2-3

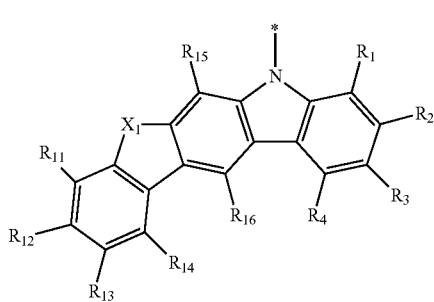

Formula 2-4

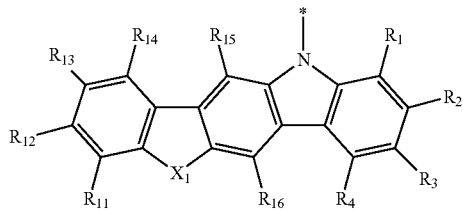

Formula 2-5

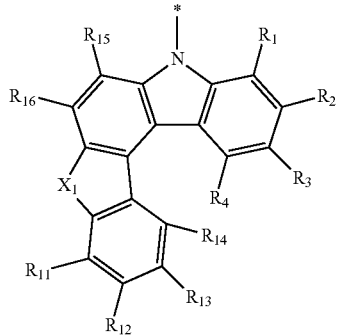

Formula 2-6

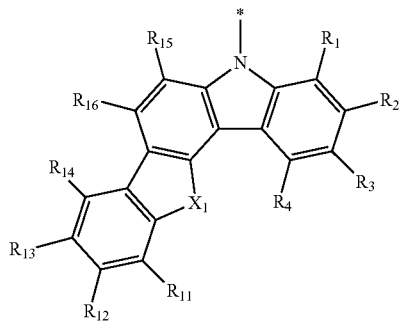

Formula 3-1

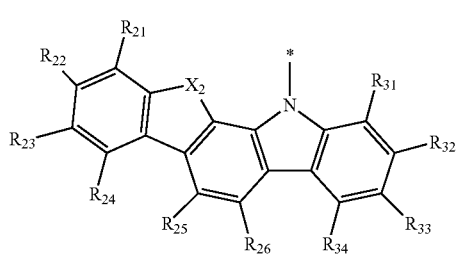

Formula 3-2

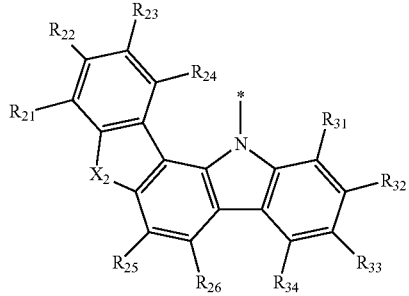

Formula 3-3

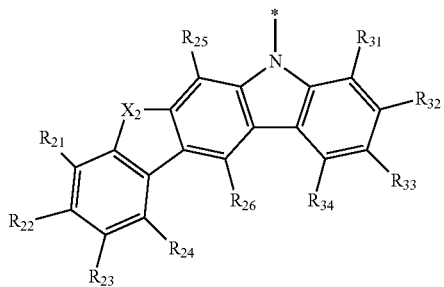

Formula 3-4

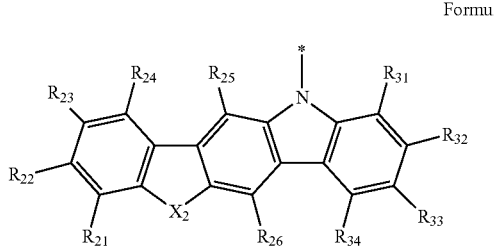

Formula 3-5

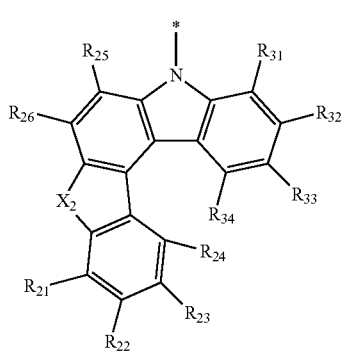

Formula 3-6

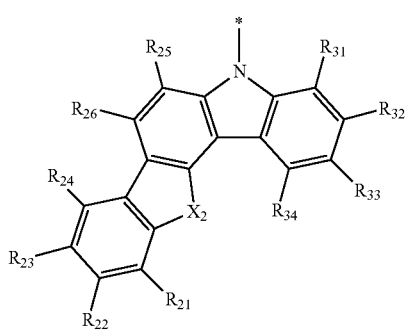

Formula 3-7

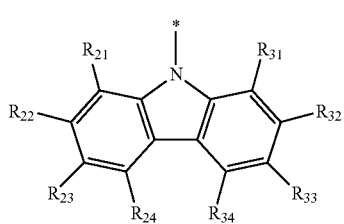

wherein, in Formulae 2-1 to 2-6 and Formulae 3-1 to 3-7,
$X_1$ is $C(R_{17})(R_{18})$, $N(R_{19})$, O, or S,
$X_2$ is $C(R_{27})(R_{28})$, $N(R_{29})$, O, or S,
$R_1$ to $R_4$, $R_{11}$ to $R_{19}$, $R_{21}$ to $R_{29}$, and $R_{31}$ to $R_{34}$ are each independently selected from:
hydrogen, deuterium, —F, —Cl, —Br, —I, a hydroxy group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxy group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a biphenyl group, a terphenyl group, and a naphthyl group;

a cyclopentyl group, a cyclohexyl group, a cyclopentenyl group, a cyclohexenyl group, a cycloheptenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, an imidazopyridinyl group, a pyridoindolyl group, a benzofuropyridinyl group, a benzothienopyridinyl group, a pyrimidoindolyl group, a benzopyrimidinyl group, a benzothienopyrimidinyl group, a phenoxazinyl group, a pyridobenzooxazinyl group, and a pyridobenzothiazinyl group;

a cyclopentyl group, a cyclohexyl group, a cyclopentenyl group, a cyclohexenyl group, a cycloheptenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, an imidazopyridinyl group, a pyridoindolyl group, a benzofuropyridinyl group, a benzothienopyridinyl group, a pyrimidoindolyl group, a benzopyrimidinyl group, a benzothienopyrimidinyl group, a phenoxazinyl group, a pyridobenzoxazinyl group, and a pyridobenzothiazinyl group, each substituted with at least one selected from deuterium, —F, —Cl, —Br, —I, a hydroxy group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_2$ alkenyl group, a $C_2$-$C_{20}$ alkynyl group, a $C_1$-$C_{20}$ alkoxy group, a phenyl group, a biphenyl group, a terphenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, a quinazolinyl group, —Si($Q_{31}$)($Q_{32}$)($Q_{33}$), —N($Q_{34}$)($Q_{35}$), and —B($Q_{36}$)($Q_{37}$); and —Si($Q_1$)($Q_2$)($Q_3$), —N($Q_4$)($Q_5$), and —B($Q_6$)($Q_7$), wherein $Q_1$ to $Q_7$ and $Q_{31}$ to $Q_{37}$ are each independently selected from hydrogen, a $C_1$-$C_{20}$ alkyl group, a $C_1$-$C_{20}$ alkoxy group, a phenyl group, a biphenyl group, a terphenyl group, a naphthyl group, a fluorenyl group, a carbazolyl group, a dibenzofuranyl group, and a dibenzothiophenyl group, and

* indicates a binding site to a neighboring atom.

3. The condensed cyclic compound of claim 2, wherein $R_1$ to $R_4$, $R_{11}$ to $R_{19}$, $R_{21}$ to $R_{29}$, and $R_{31}$ to $R_{34}$ are each independently selected from:

hydrogen, deuterium, a cyano group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, a cyano group, a phenyl group, a biphenyl group, a terphenyl group, and a naphthyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, and a dibenzothiophenyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, and a dibenzothiophenyl group, each substituted with at least one selected from deuterium, a cyano group, $C_1$-$C_{20}$ alkyl group, a $C_1$-$C_{20}$ alkoxy group, a phenyl group, a biphenyl group, a terphenyl group, a naphthyl group, and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ are each independently selected from hydrogen, a $C_1$-$C_{20}$ alkyl group, a $C_1$-$C_{20}$ alkoxy group, a phenyl group, a biphenyl group, a terphenyl group, and a naphthyl group.

4. The condensed cyclic compound of claim 2, wherein at least one of $R_3$, $R_{13}$, $R_{23}$, and $R_{33}$ in Formula 1 is a cyano group.

5. The condensed cyclic compound of claim 1, wherein $CY_4$ to $CY_6$ in Formulae 4 to 6 are each independently selected from a benzene group, a naphthalene group, a fluorene group, a carbazole group, a dibenzofuran group, and a dibenzothiophene group.

6. The condensed cyclic compound of claim 1, wherein at least one of $L_1$ and $L_2$ in Formula 1 is the group represented by Formula 4 or the group represented by Formula 5.

7. The condensed cyclic compound of claim 1, wherein $L_1$ and $L_2$ in Formula 1 are each independently the group represented by Formula 4 or the group represented by Formula 5.

8. The condensed cyclic compound of claim 1, wherein, one, two, three, or four substituents of *-$L_1$-L-*" in Formula 1 are each independently selected from:

a cyano group; and a $C_1$-$C_{10}$ alkyl group, a $C_1$-$C_{10}$ alkoxy group, a phenyl group, a biphenyl group, and a terphenyl group, each substituted with at least one cyano group.

9. The condensed cyclic compound of claim 1, wherein the condensed cyclic compound is represented by one of Formulae 1-1 to 1-9:

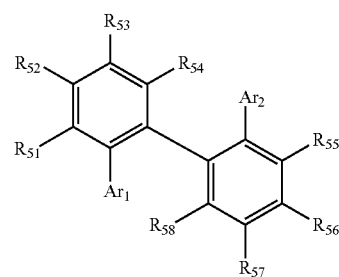

Formula 1-1

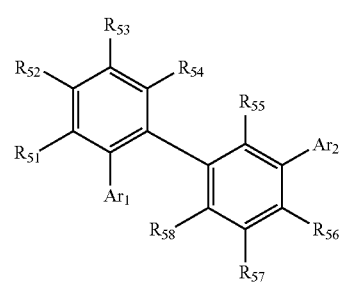

Formula 1-2

-continued

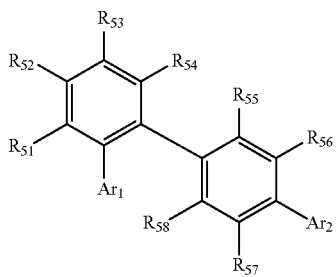
Formula 1-3

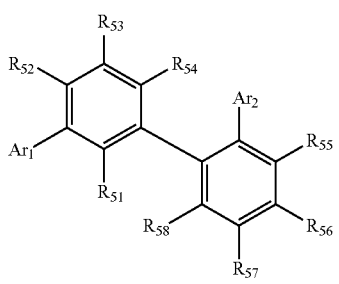
Formula 1-4

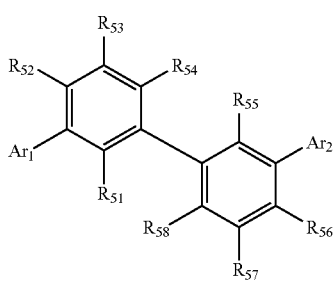
Formula 1-5

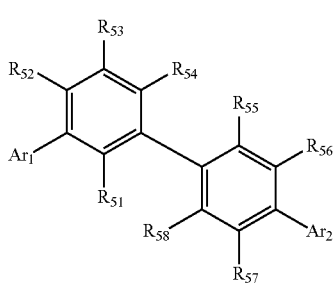
Formula 1-6

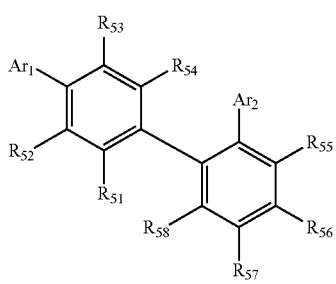
Formula 1-7

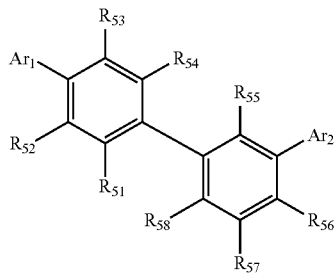
Formula 1-8

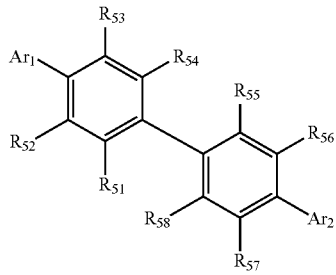
Formula 1-9 wherein, in Formulae 1-1 to 1-9,
$Ar_1$ and $Ar_2$ are the same as $Ar_1$ and $Ar_2$ in claim 1,
$R_{51}$ to $R_{58}$ are the same as $R_{44}$ in claim 1, and
the total number of the cyano groups comprised in $R_{51}$ to $R_{58}$ is 1, 2, 3, or 4.

10. The condensed cyclic compound of claim 9, wherein $R_{51}$ to $R_{58}$ are each independently selected from:
hydrogen, deuterium, a cyano group, a $C_1$-$C_{20}$ alkyl group, and a $C_1$-$C_{20}$ alkoxy group;
a $C_1$-$C_{20}$ alkyl group and a $C_1$-$C_{20}$ alkoxy group, each substituted with at least one selected from deuterium, a cyano group, a phenyl group, a biphenyl group, a terphenyl group, and a naphthyl group;
a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, and a dibenzothiophenyl group;
a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, and a dibenzothiophenyl group, each substituted with at least one selected from deuterium, a cyano group, $C_1$-$C_{20}$ alkyl group, a $C_1$-$C_{20}$ alkoxy group, a phenyl group, a biphenyl group, a terphenyl group, a naphthyl group, and —Si($Q_{31}$)($Q_{32}$)($Q_{33}$); and
—Si($Q_1$)($Q_2$)($Q_3$),
wherein $Q_1$ to $Q_3$ and $Q_{31}$ to $Q_{33}$ are each independently selected from hydrogen, a $C_1$-$C_{20}$ alkyl group, a $C_1$-$C_{20}$ alkoxy group, a phenyl group, a biphenyl group, a terphenyl group, and a naphthyl group.

11. The condensed cyclic compound of claim 9, wherein one, two, three, or four substituents of $R_{51}$ to $R_{58}$ are each independently selected from:
a cyano group; and
a $C_1$-$C_{10}$ alkyl group, a $C_1$-$C_{10}$ alkoxy group, a phenyl group, a biphenyl group, and a terphenyl group, each substituted with at least one cyano group.

12. The condensed cyclic compound of claim 9, wherein one or two of $R_{51}$ to $R_{58}$ are each independently a cyano group.
13. The condensed cyclic compound of claim 9, wherein the condensed cyclic compound is represented by Formula 1-1, 1-2, 1-4, or 1-5.
14. The condensed cyclic compound of claim 1, wherein the condensed cyclic compound is selected from Compounds 1 to 852:
1
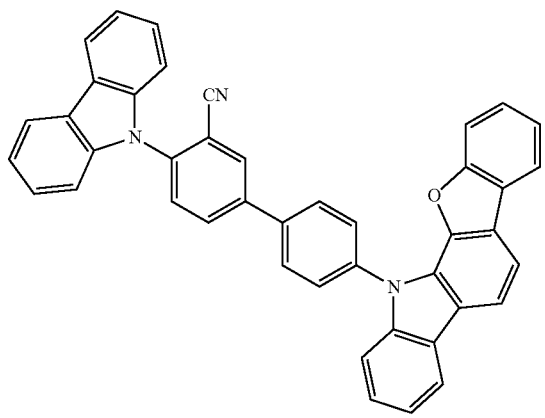
2
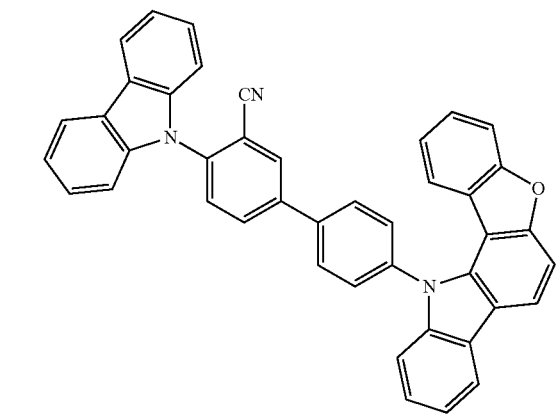
3
-continued
4
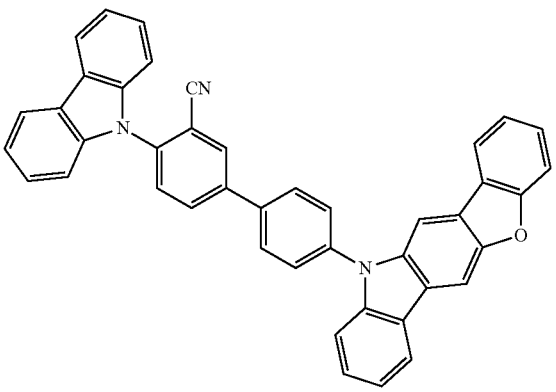
5
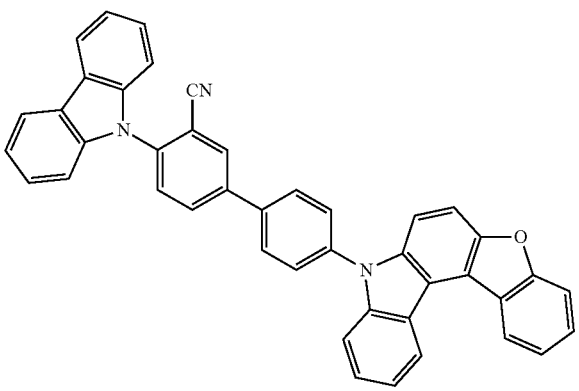
6
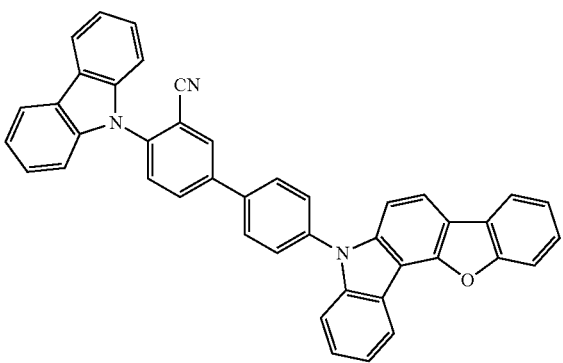
7
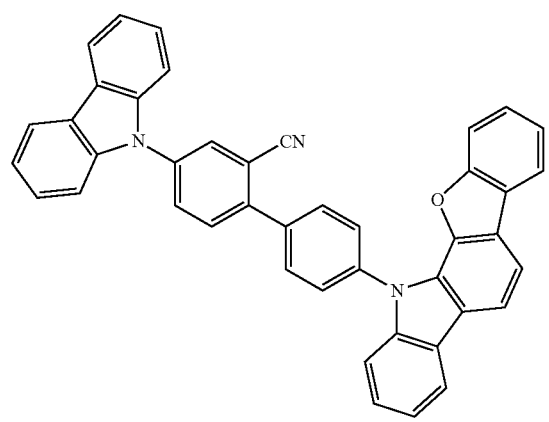

311
-continued
8
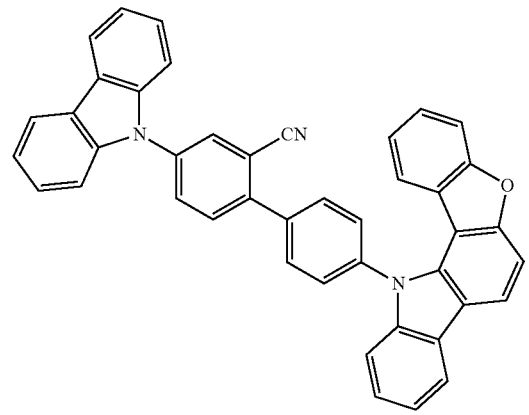
9
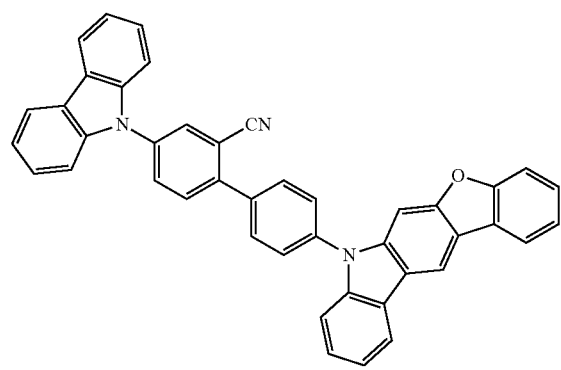
10
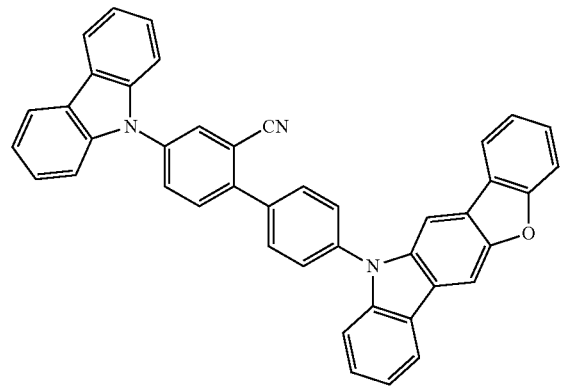
11
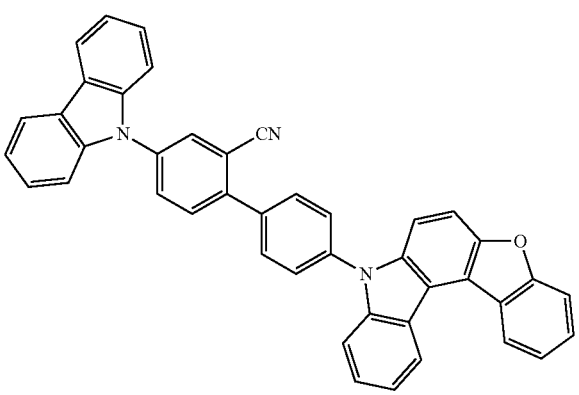
312
-continued
12
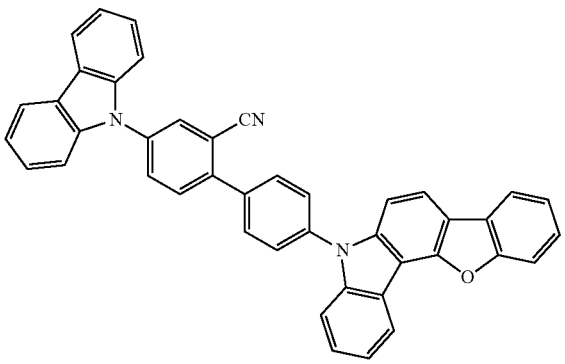
13
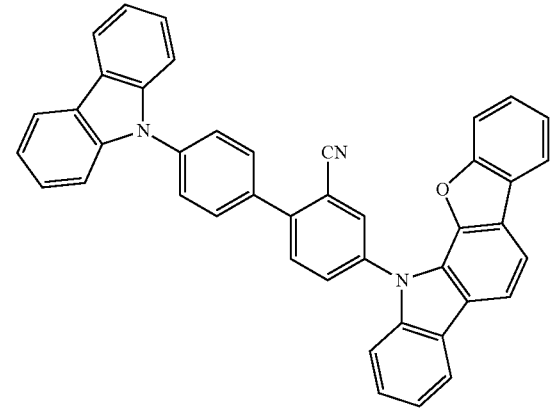
14
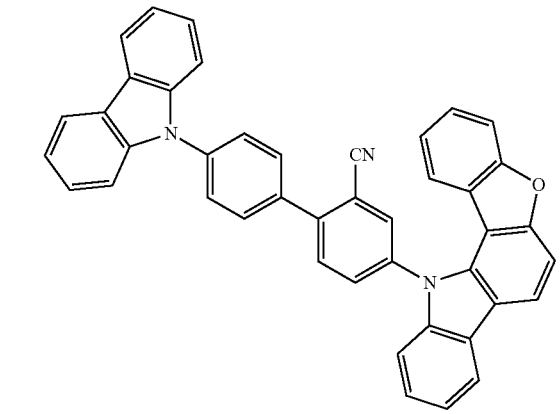
15
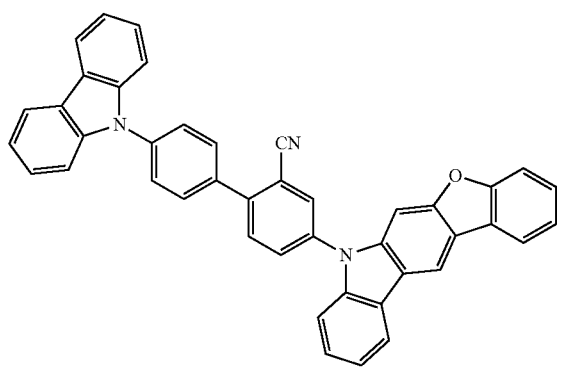

-continued
16
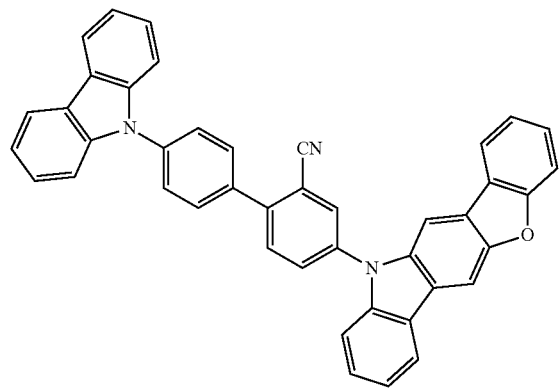
17
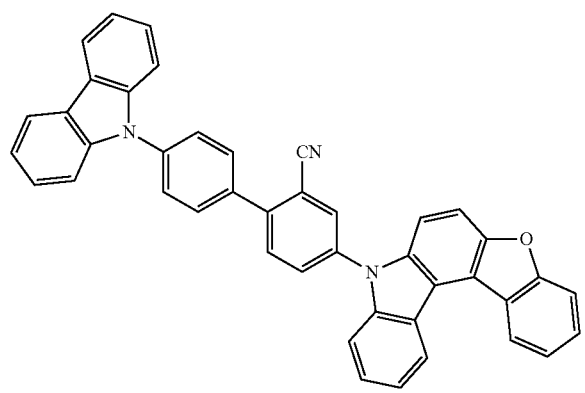
18
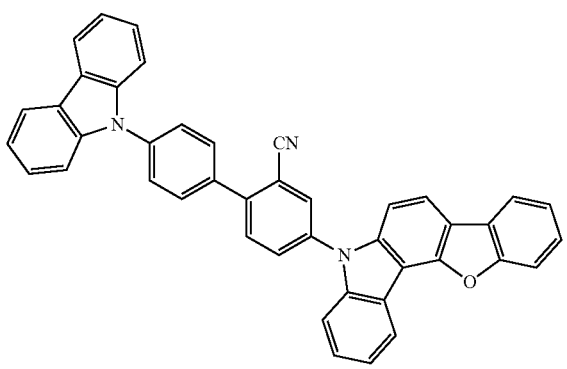
19
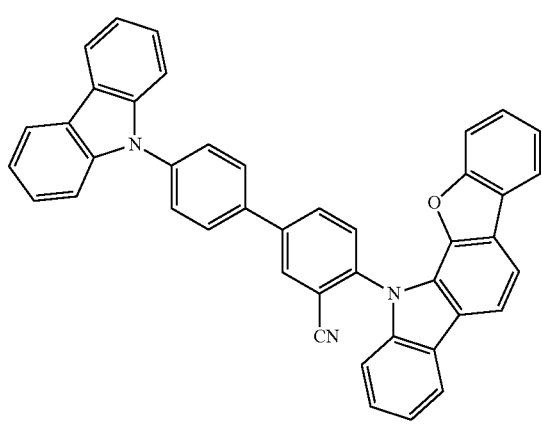
-continued
20
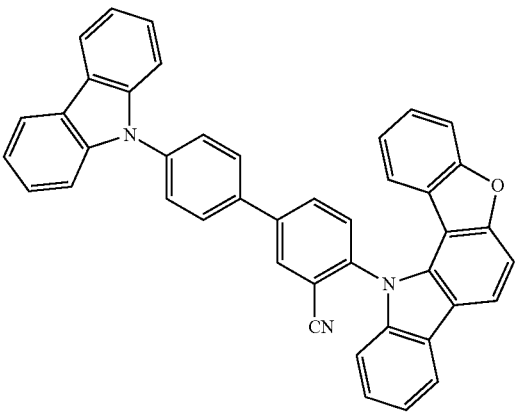
21
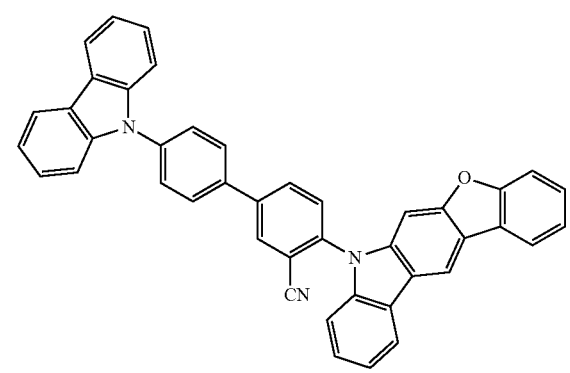
22
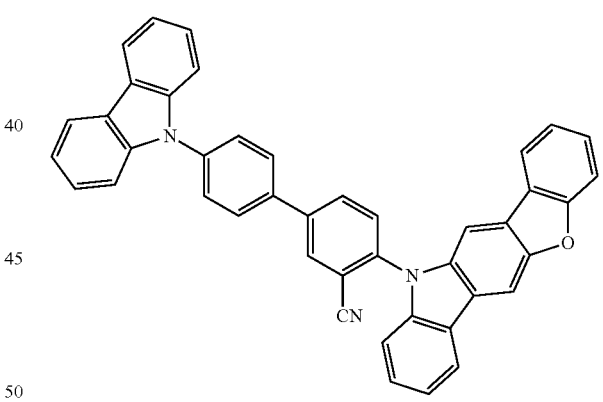
23
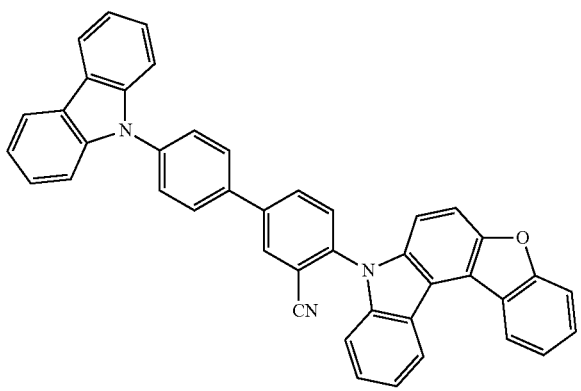

-continued
24
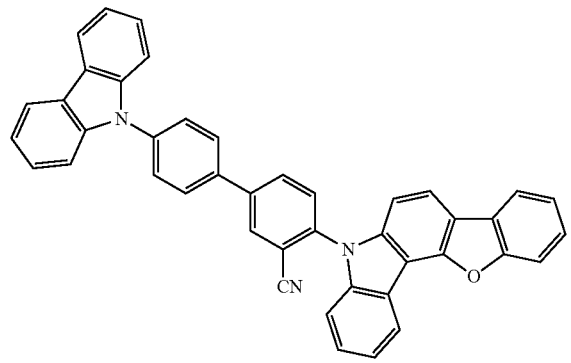
25
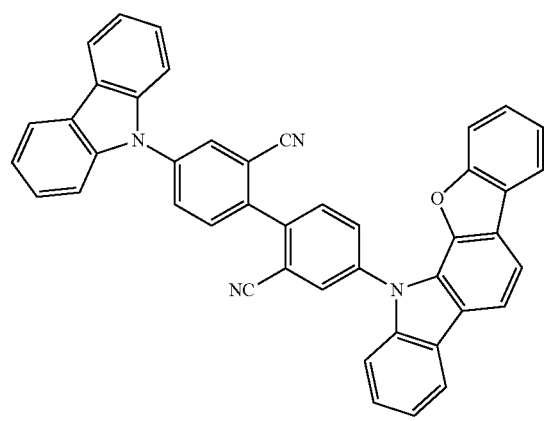
26
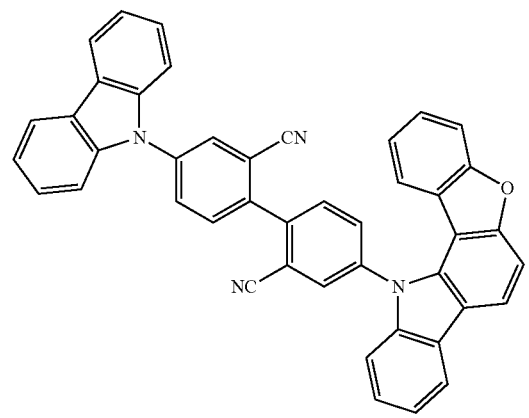
27
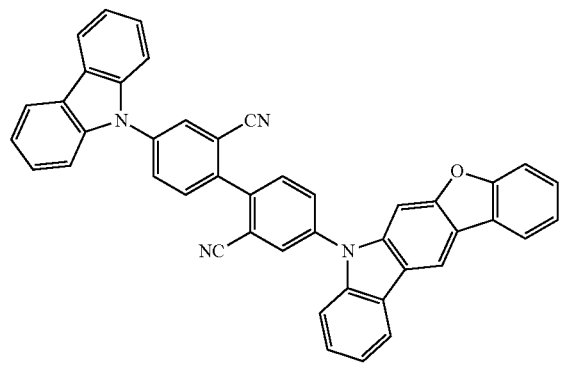
-continued
28
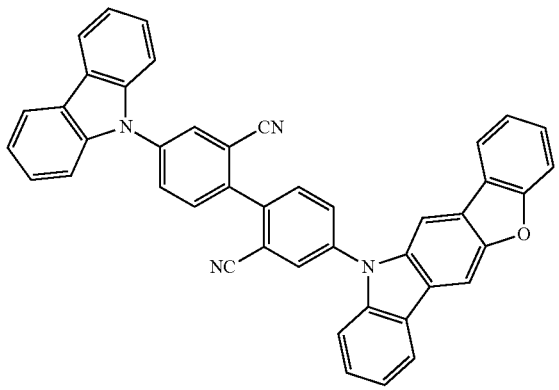
29
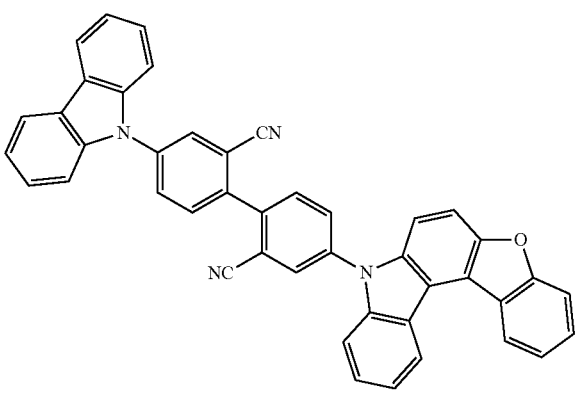
30
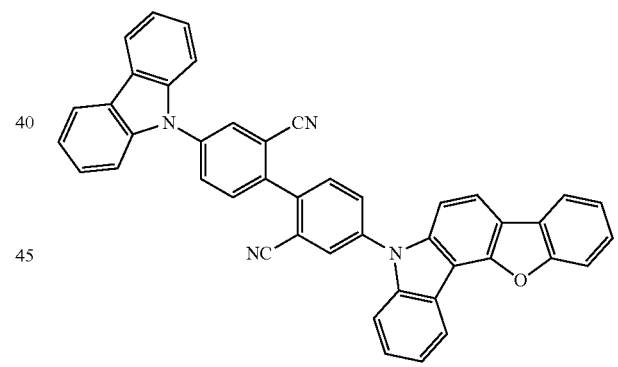
31
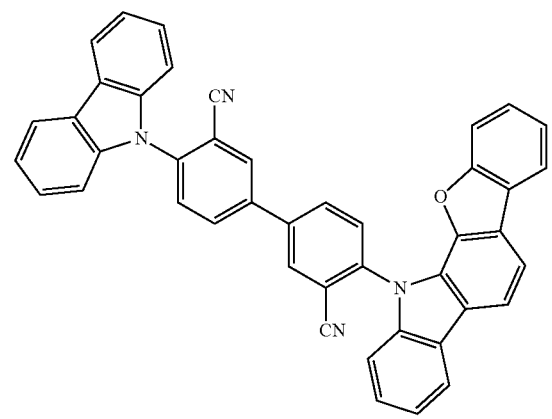

-continued
32
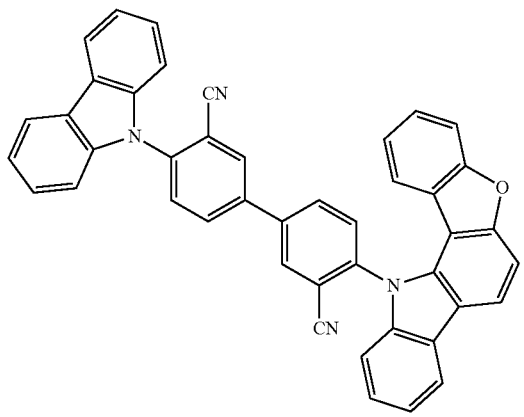
33
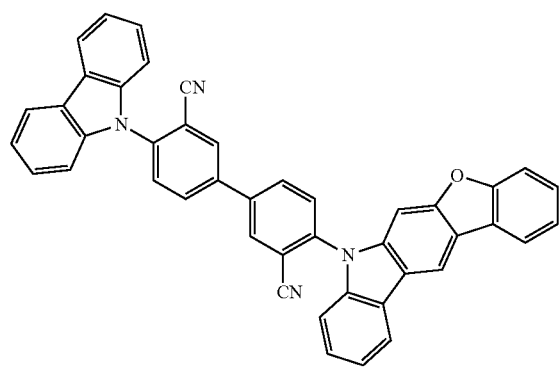
34
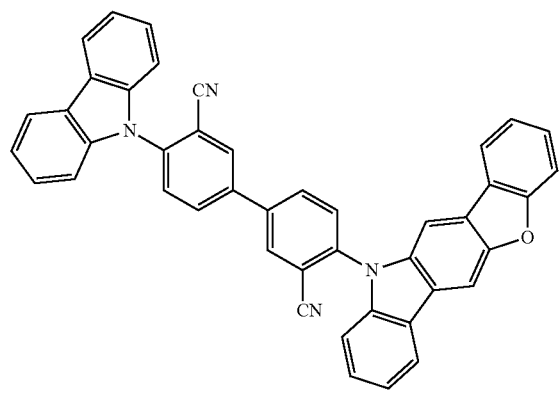
35
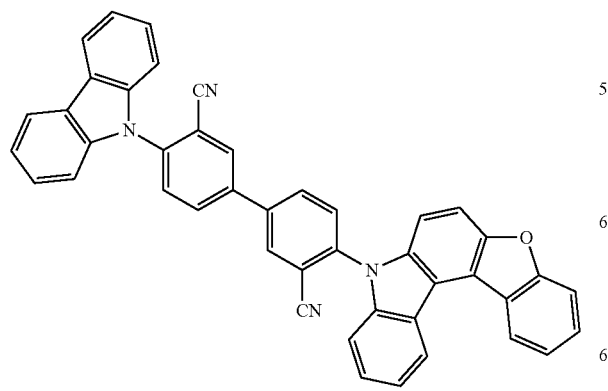
-continued
36
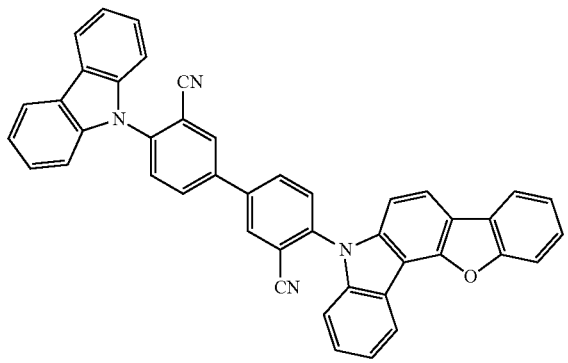
37
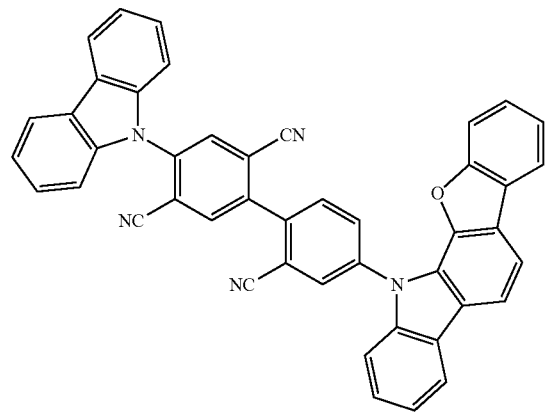
38
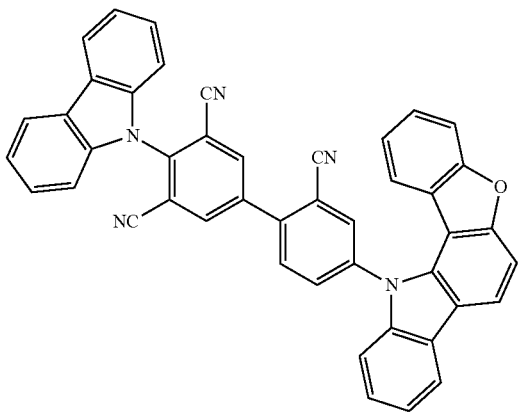
39
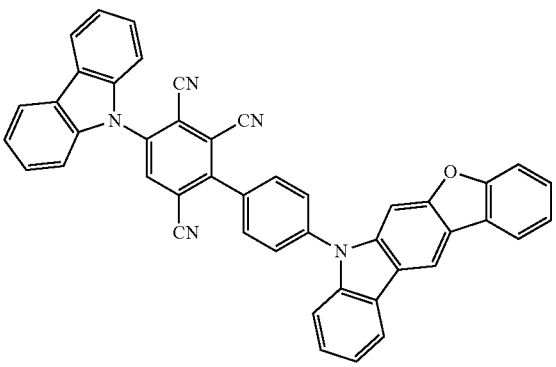

40
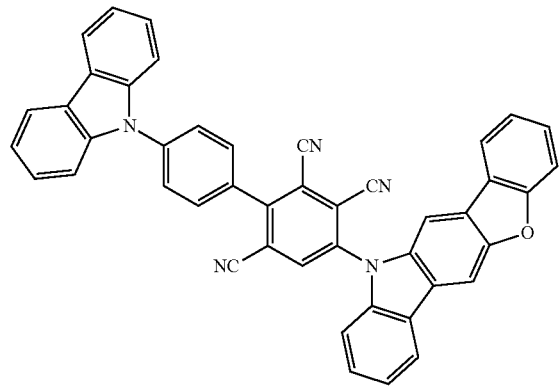
41
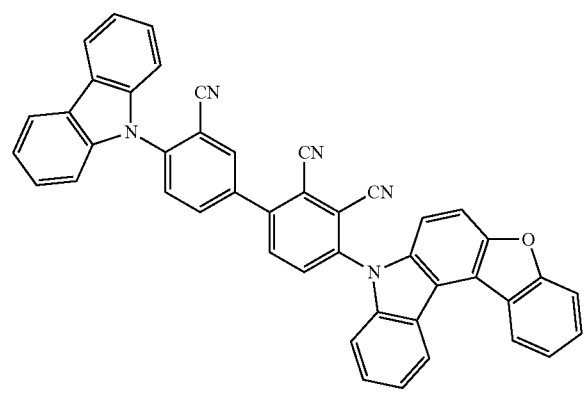
42
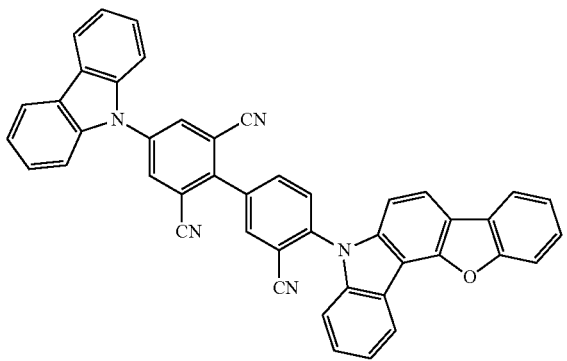
43
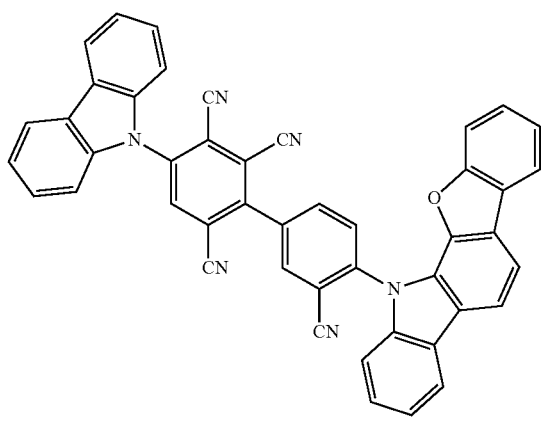
44
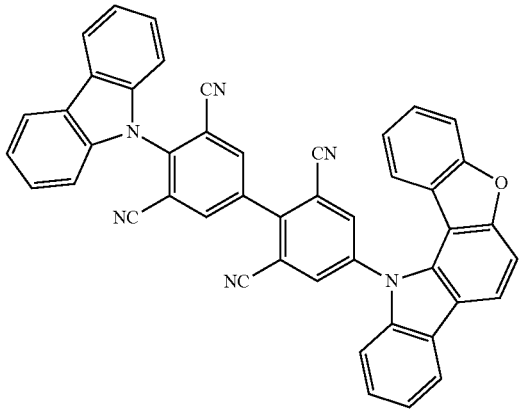
45
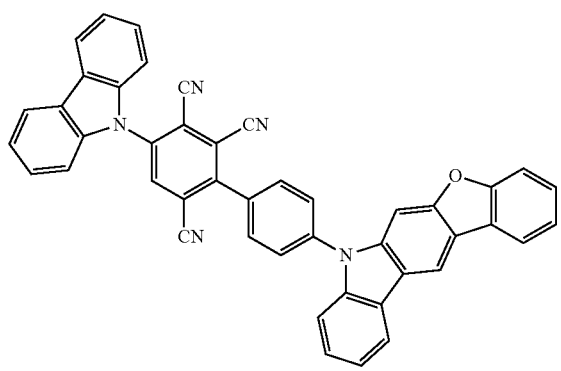
46
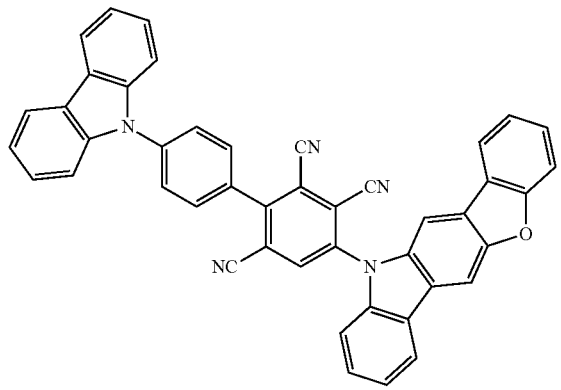
47
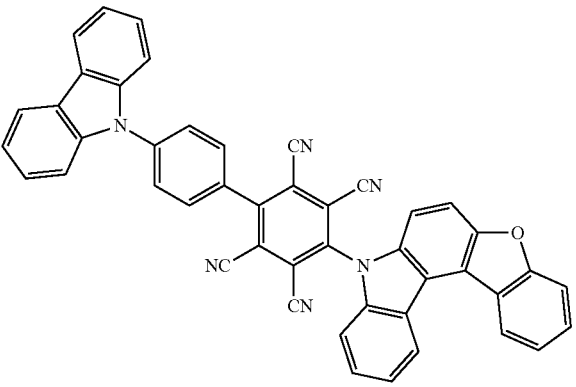

321
-continued
48
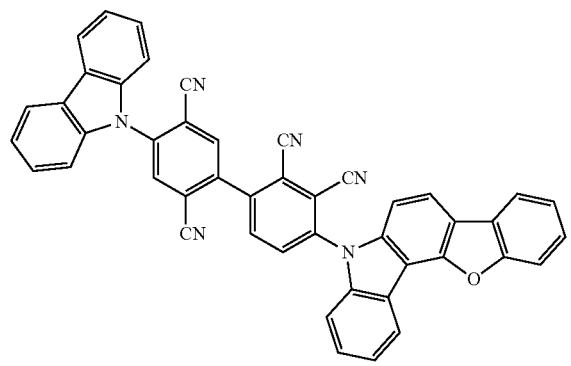
49
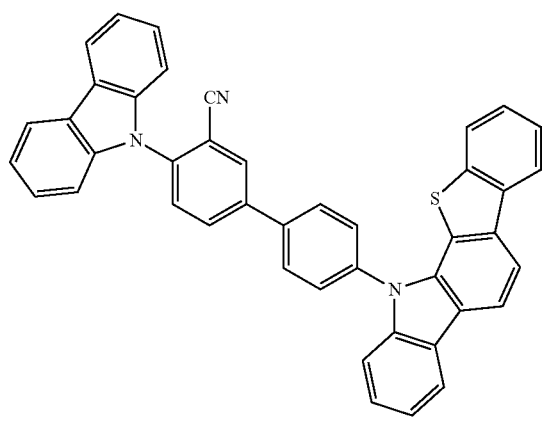
50
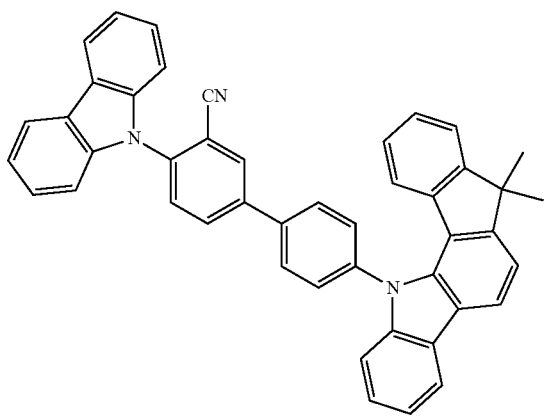
51
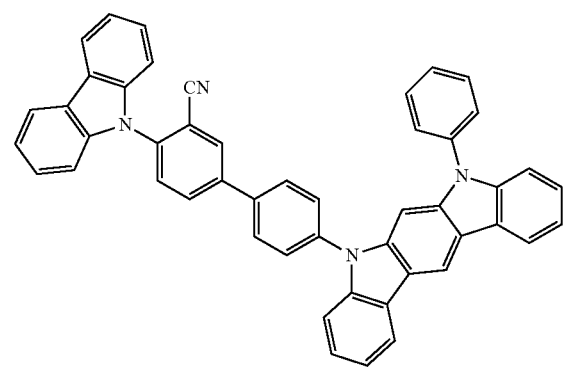
322
-continued
52
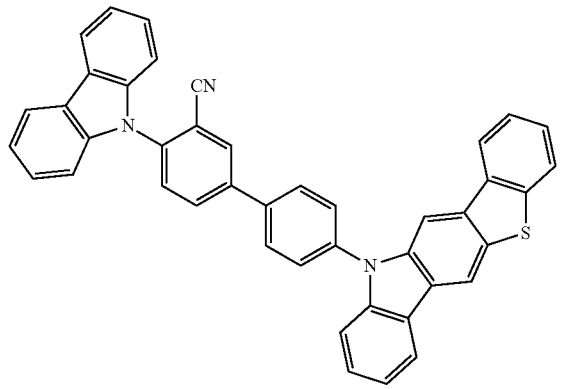
53
54
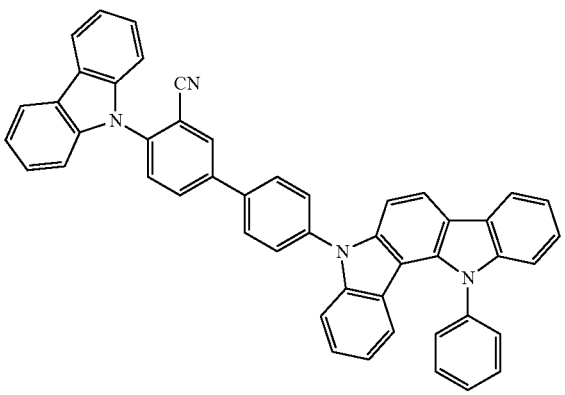

55
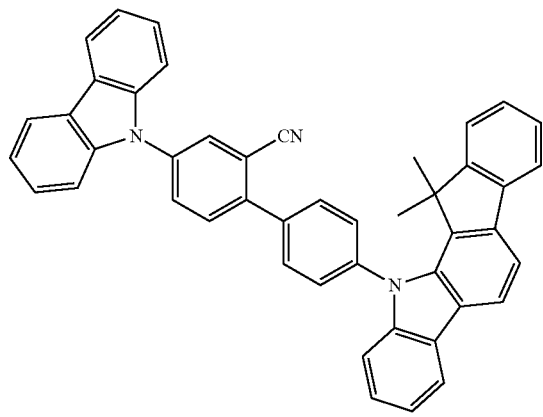
56
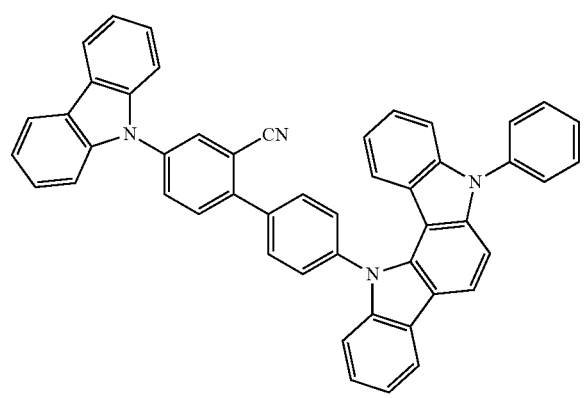
57
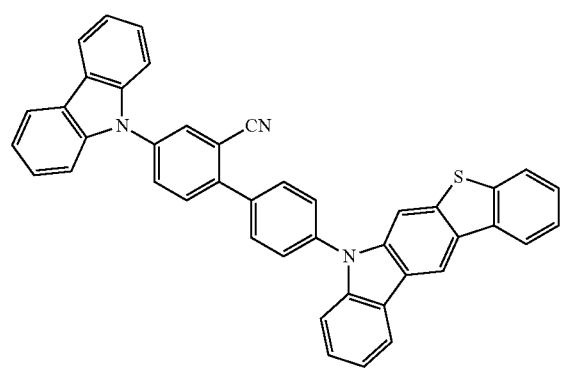
58
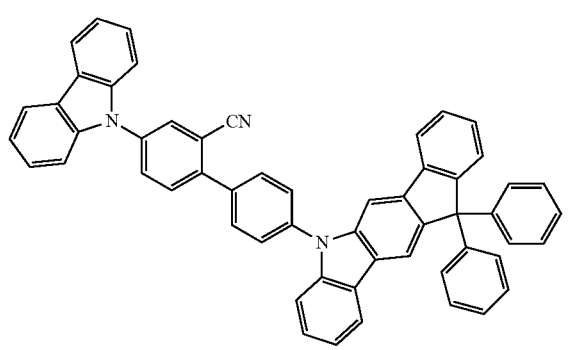
59
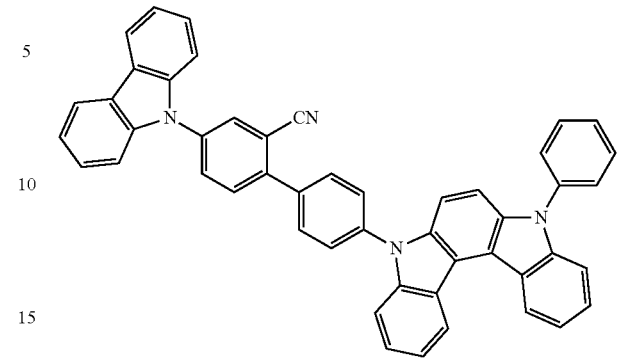
60
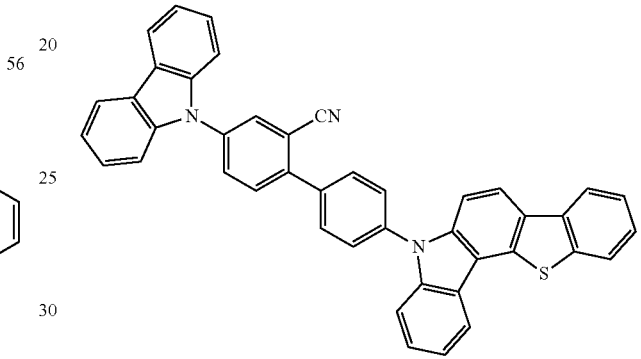
61
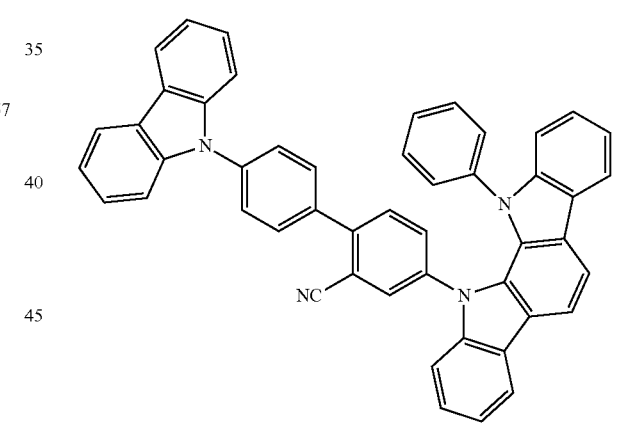
62
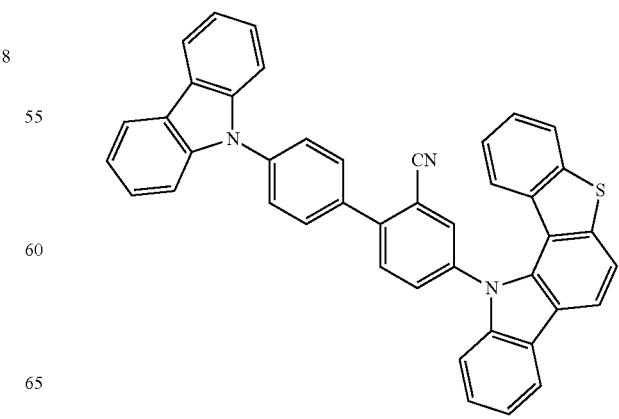

325
-continued
326
-continued
63
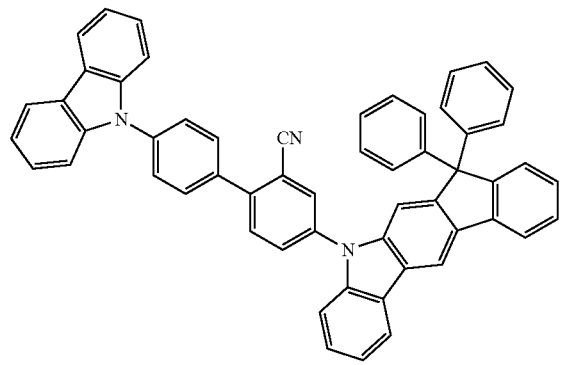
64
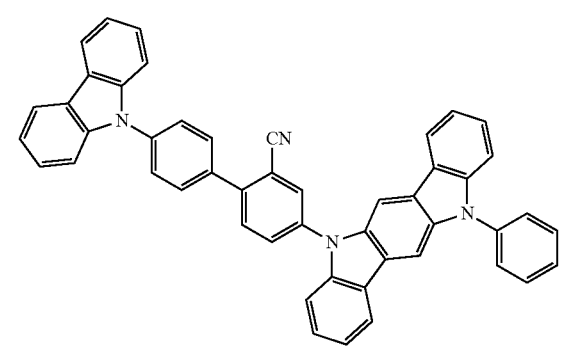
65
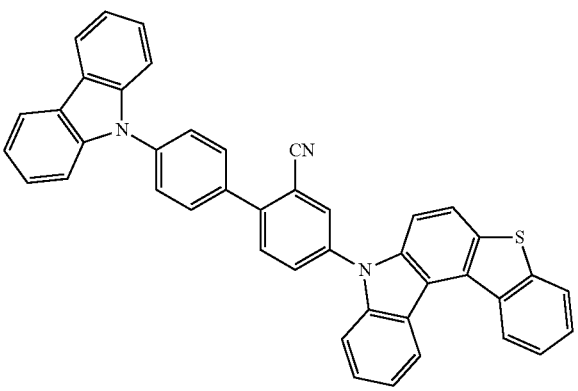
66
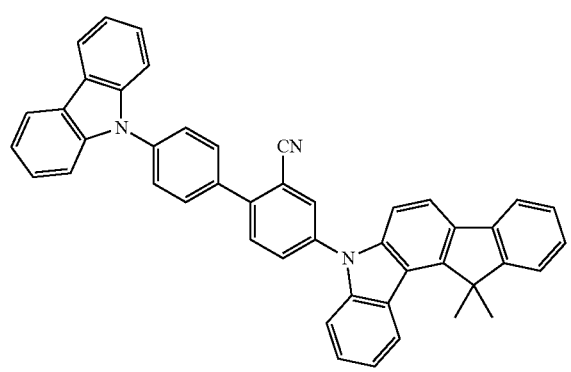
67
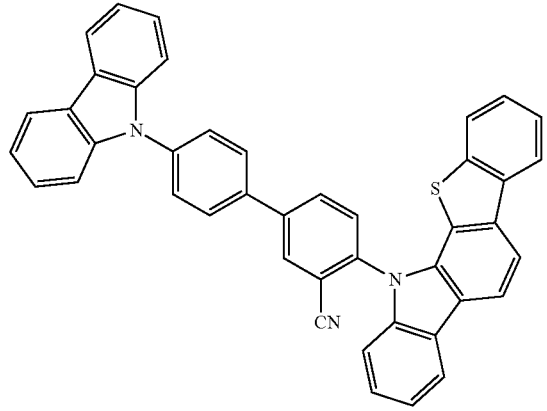
68
69
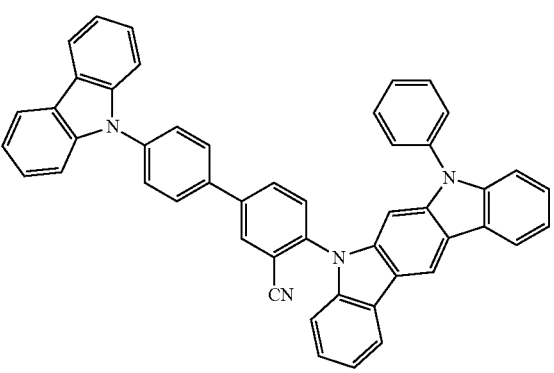

327
-continued
328
-continued
70
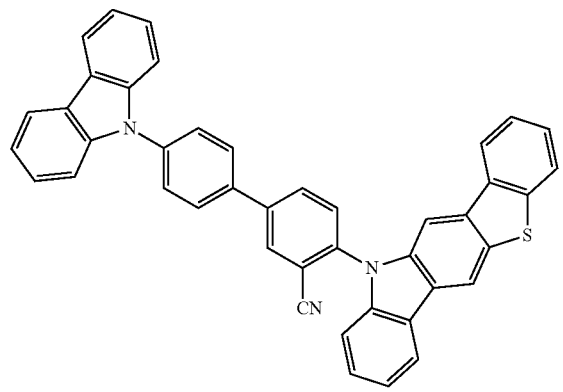
71
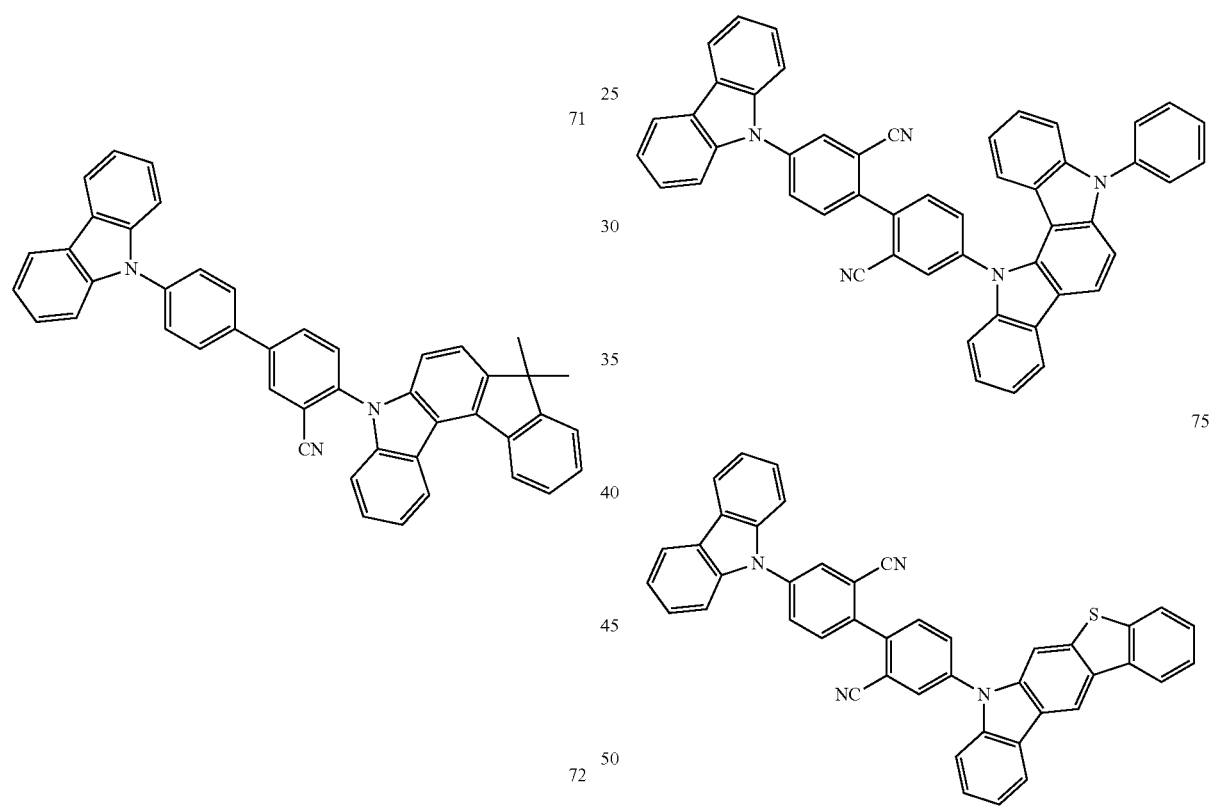
72
73
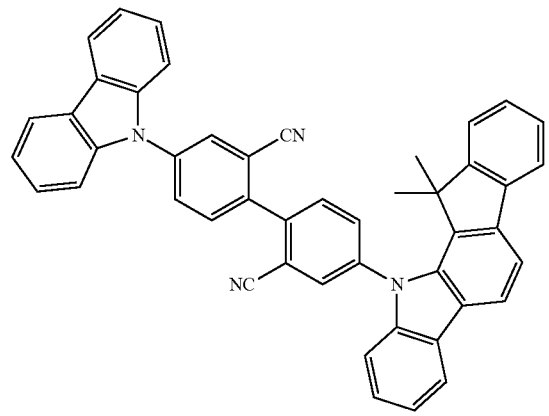
74
75
76
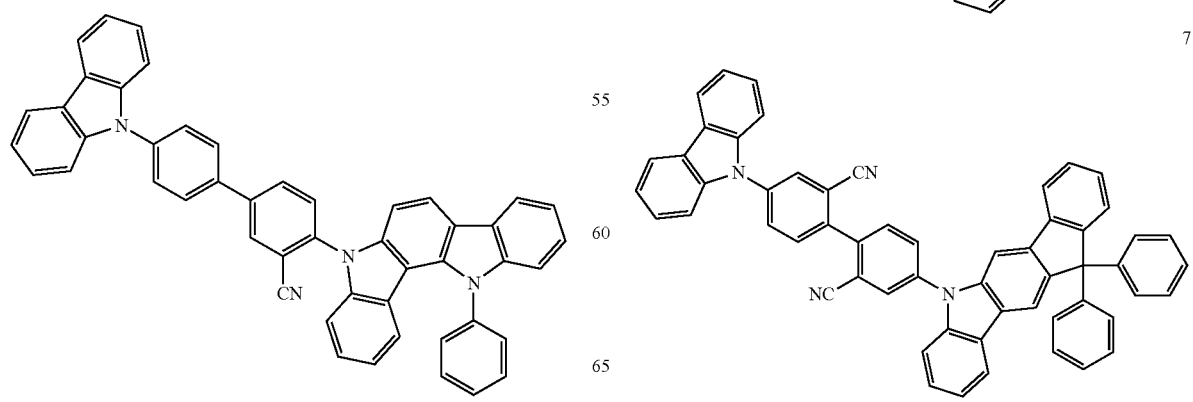

77
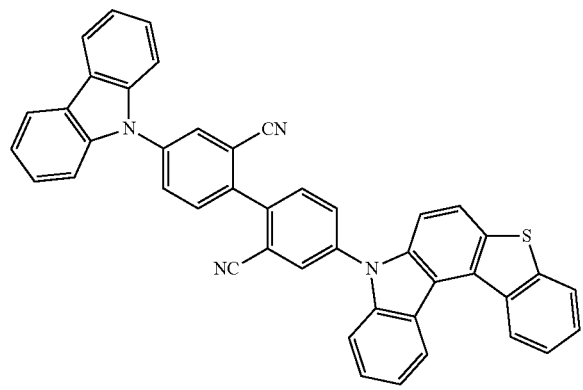
78
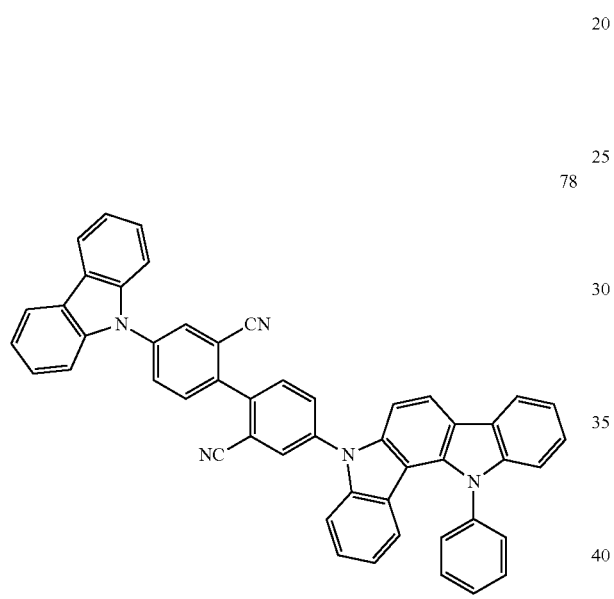
79
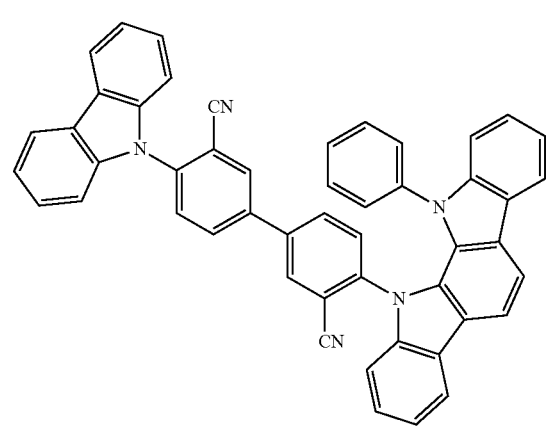
80
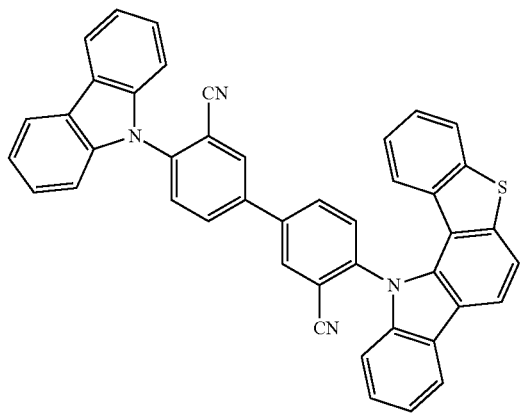
81
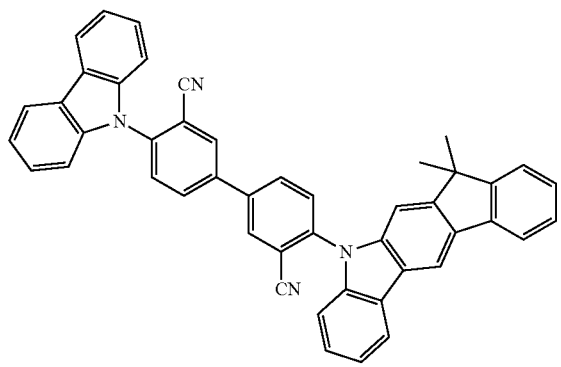
82
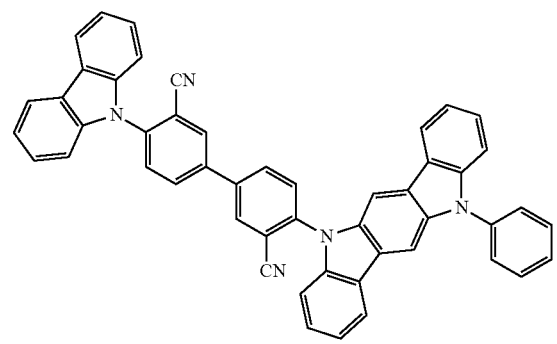
83
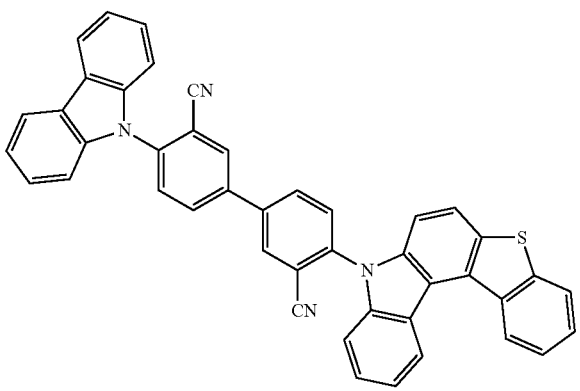

84
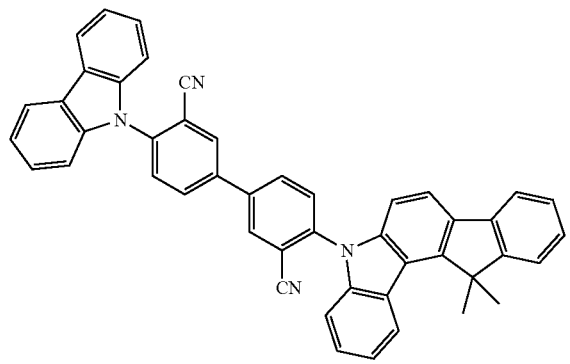
85
88
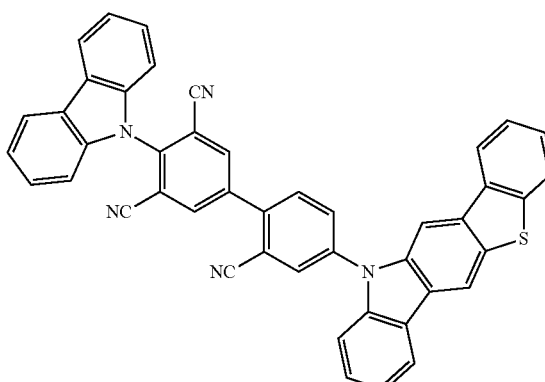
89
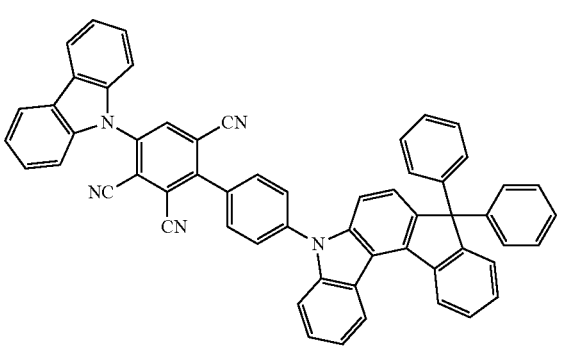
86
90
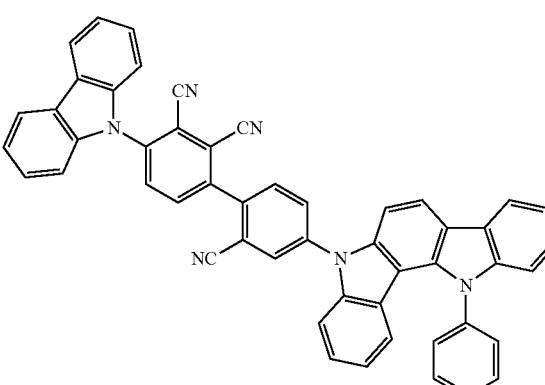
87
91
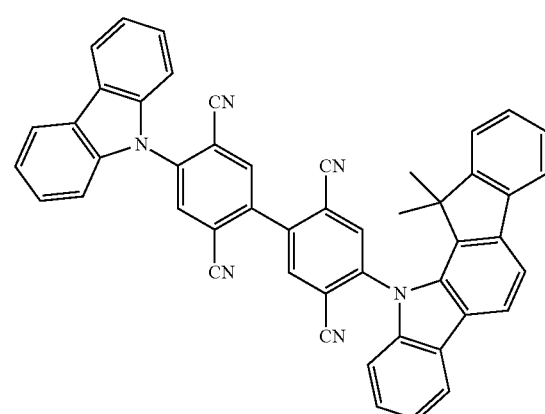

333
-continued
92
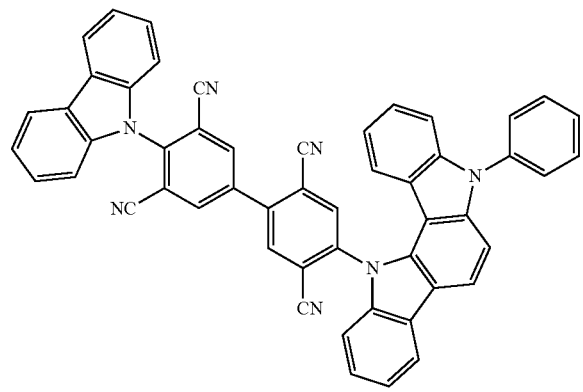
93
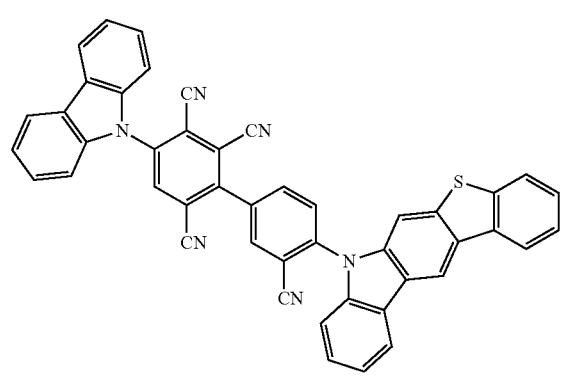
94
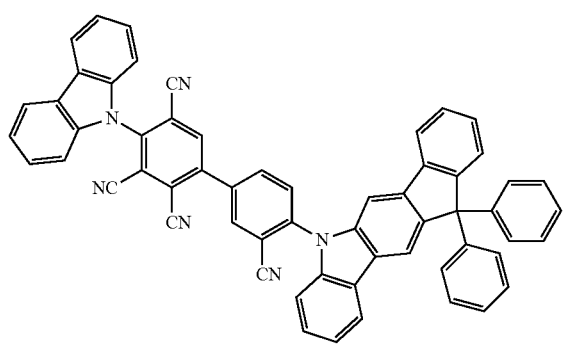
95
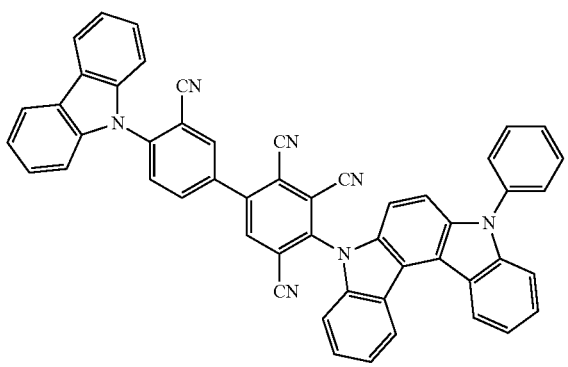
334
-continued
96
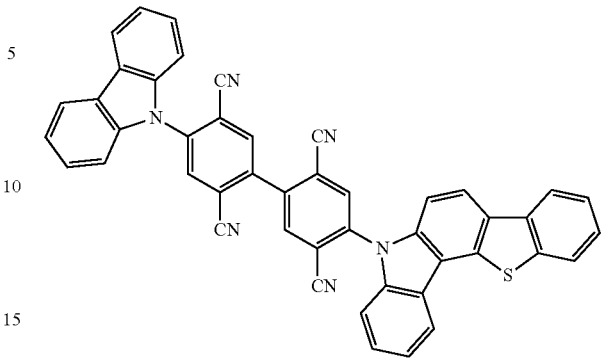
97
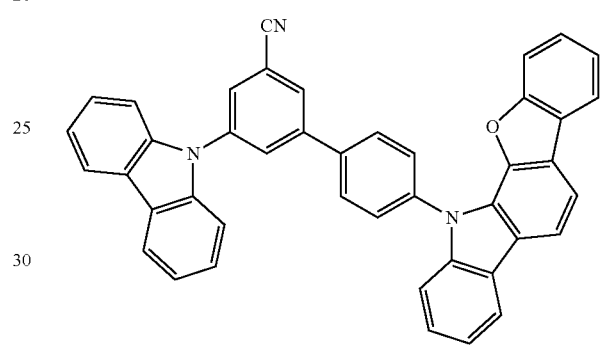
98
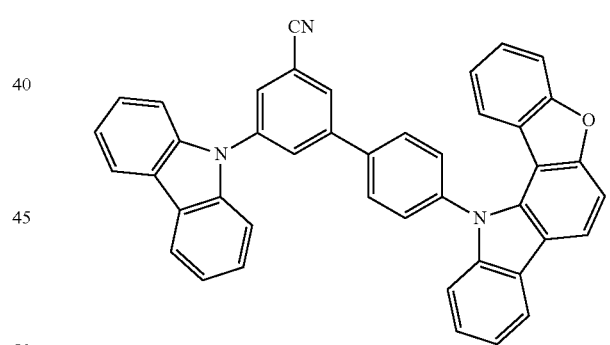
99
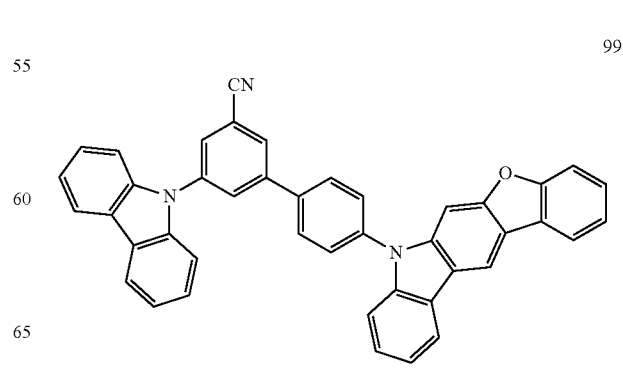

-continued
100
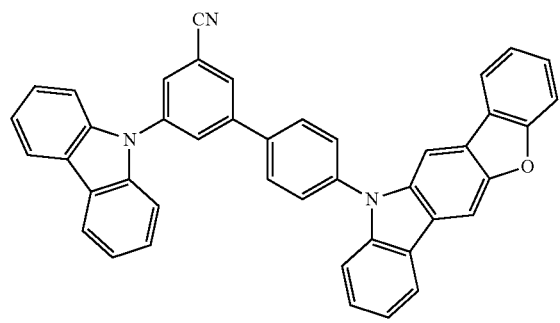
101
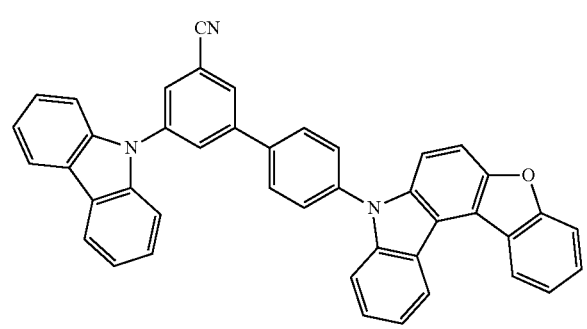
102
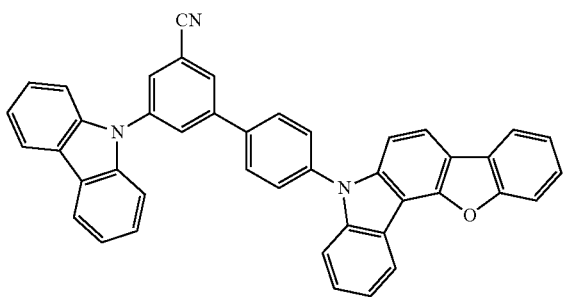
103
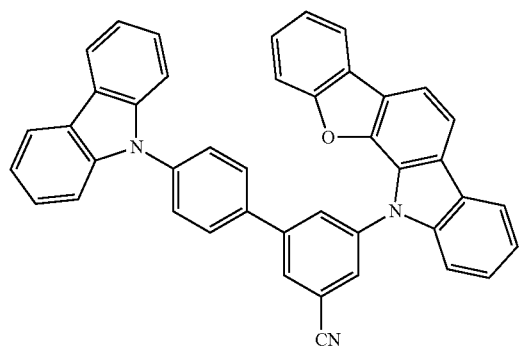
104
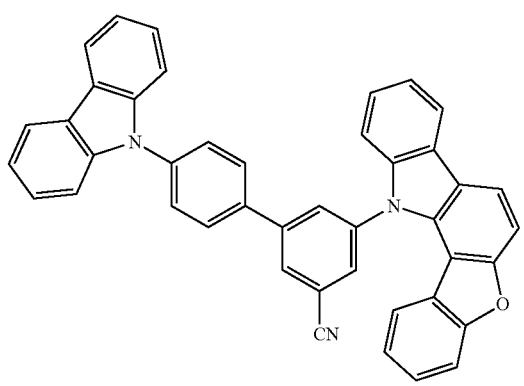
105
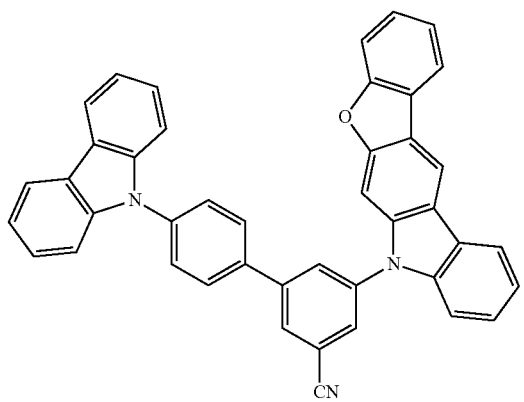
106
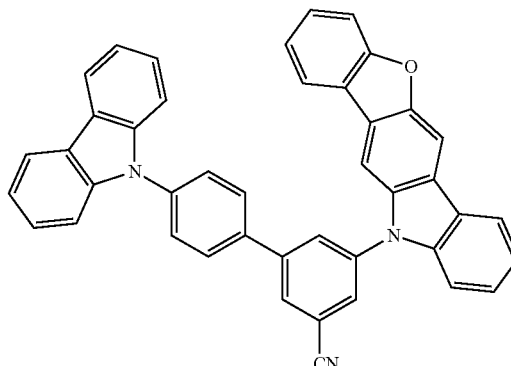
107
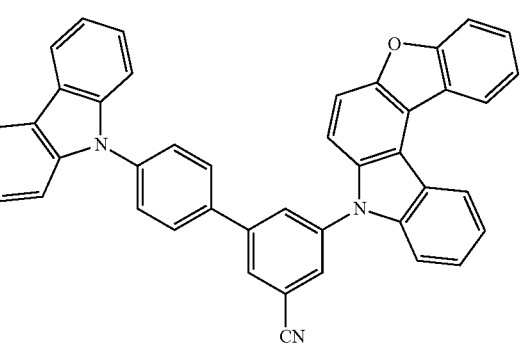

108
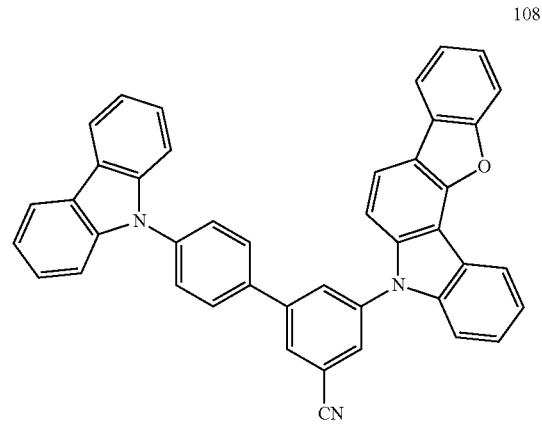
112
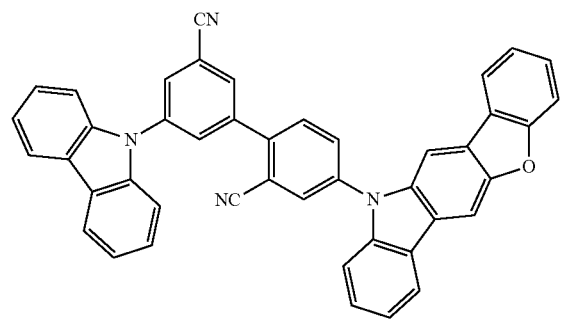
109
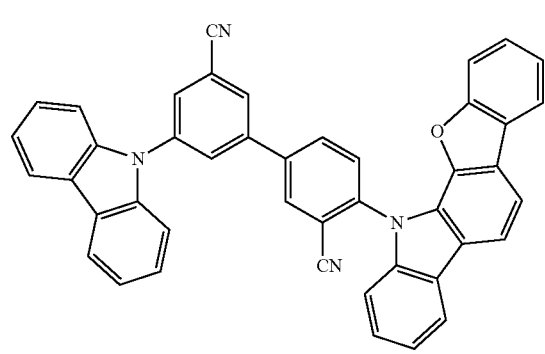
113
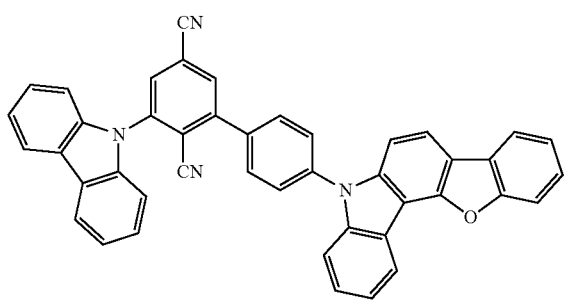
110
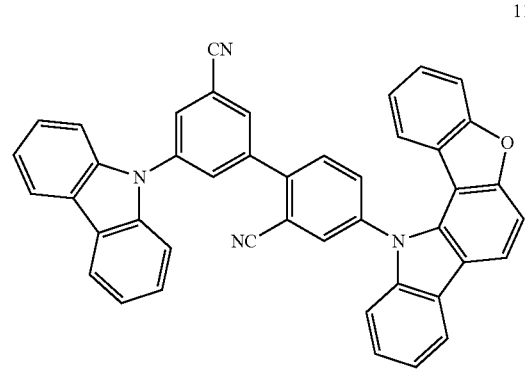
114
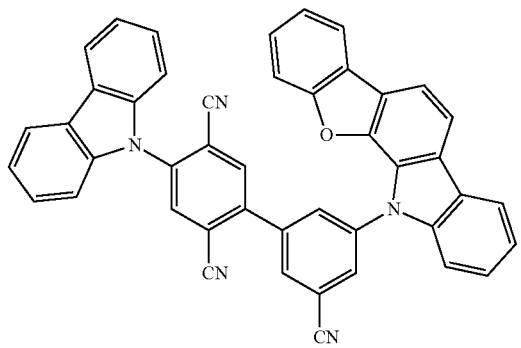
111
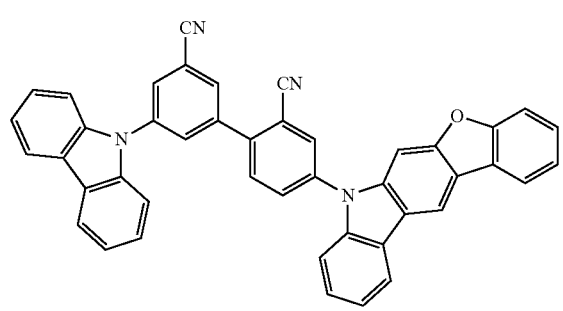
115

116
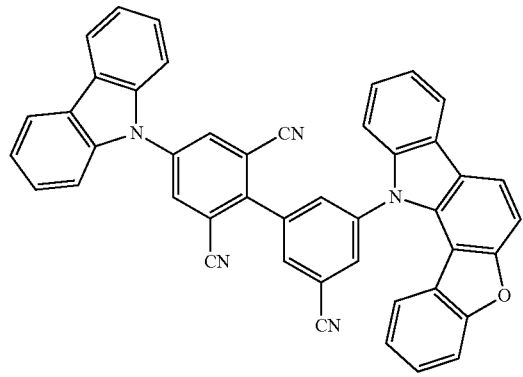
117
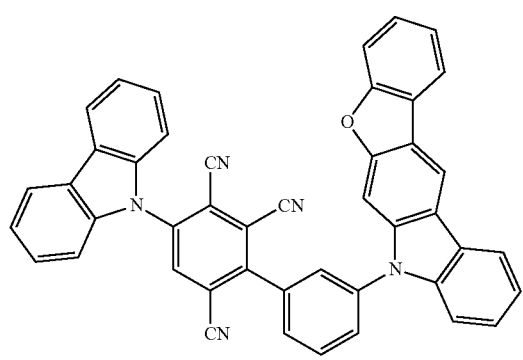
118
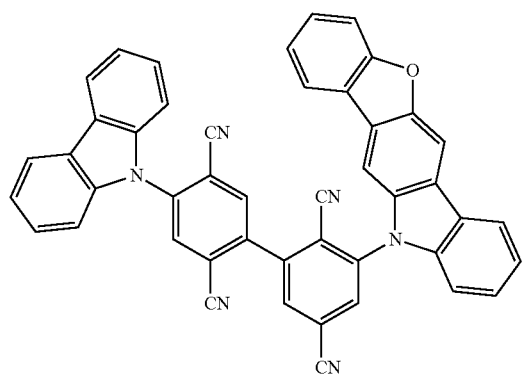
119
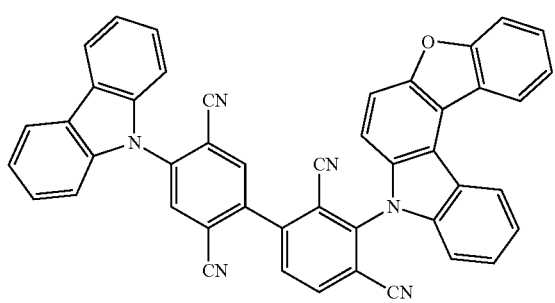
120
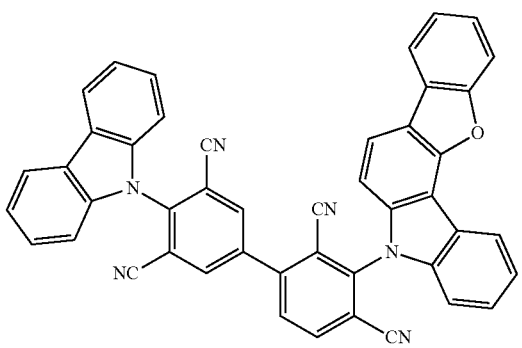
121
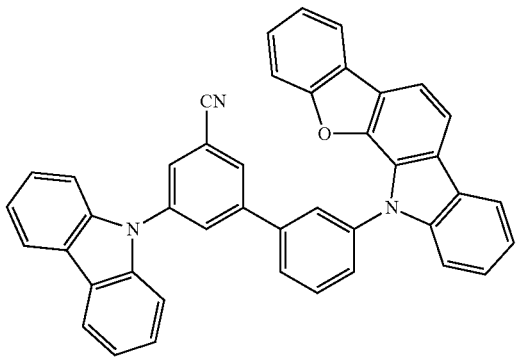
122
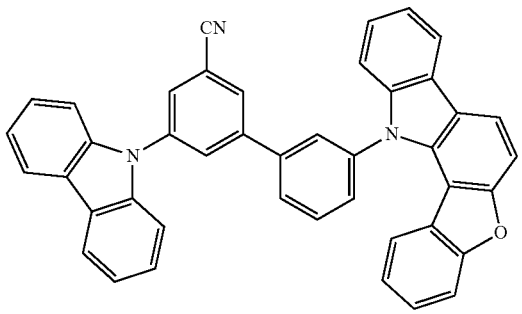
123
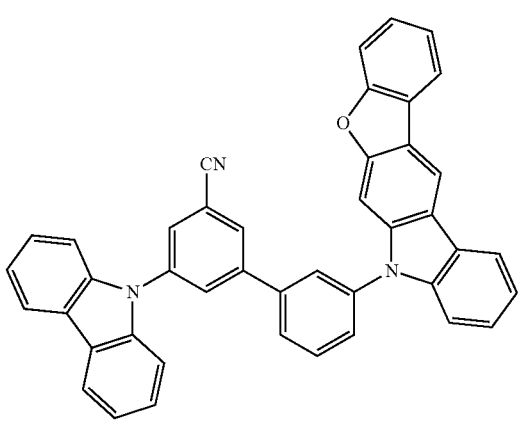

124
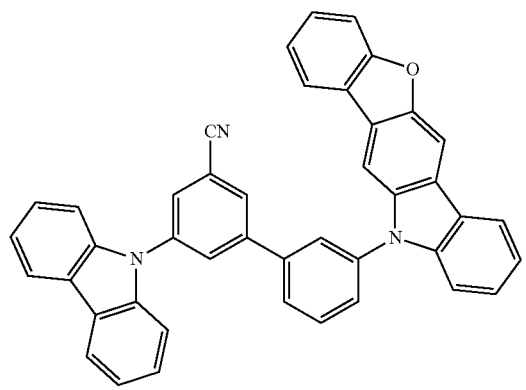
125
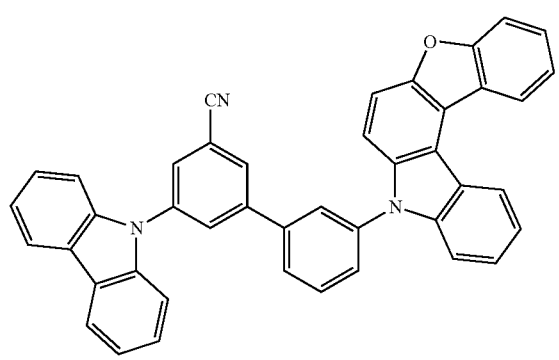
126
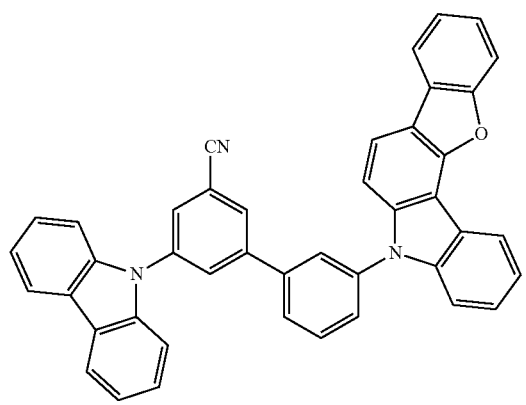
127
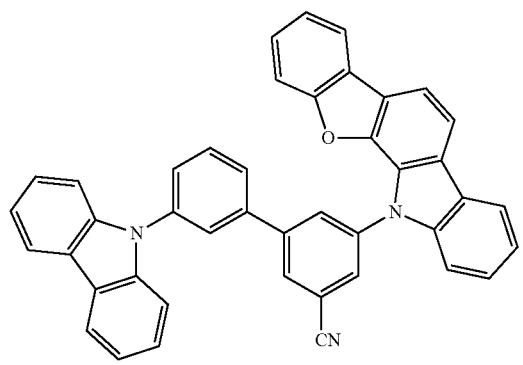
128
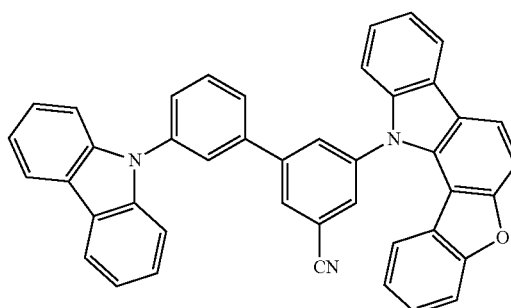
129
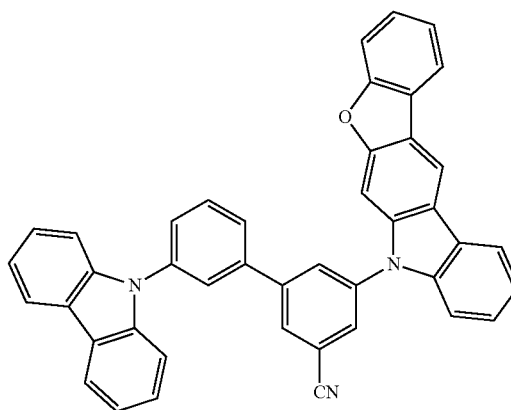
130
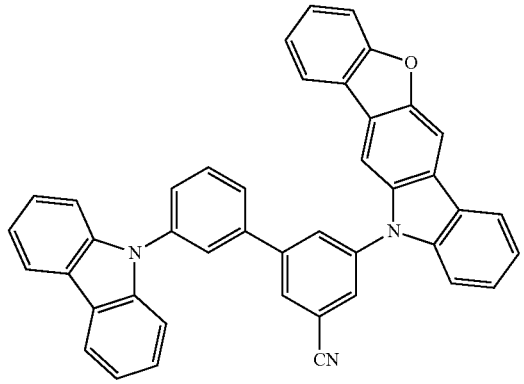
131
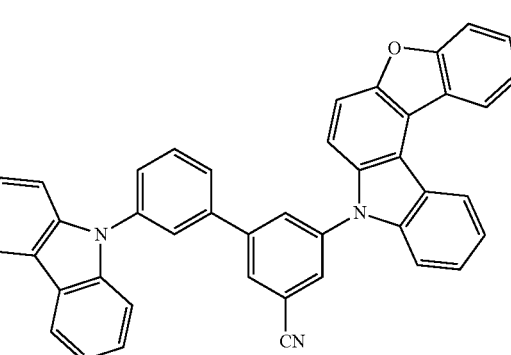

132
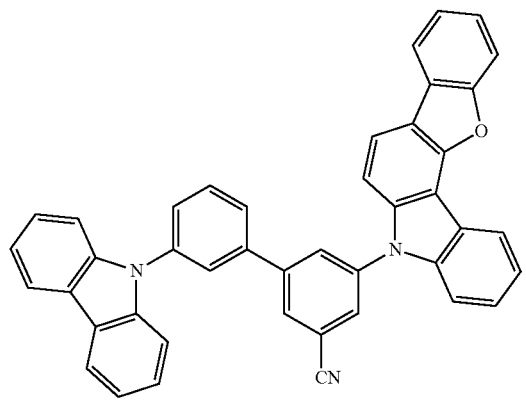
133
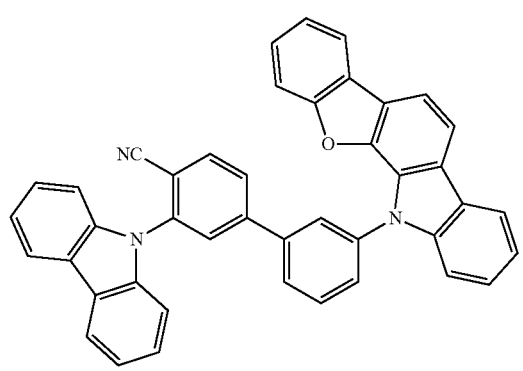
134
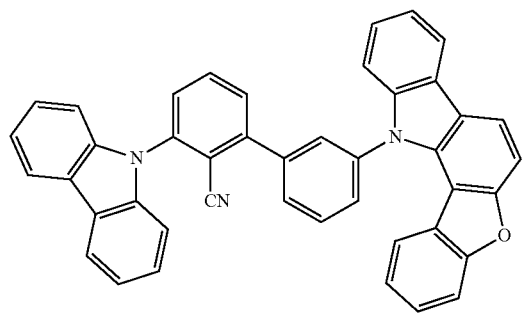
135
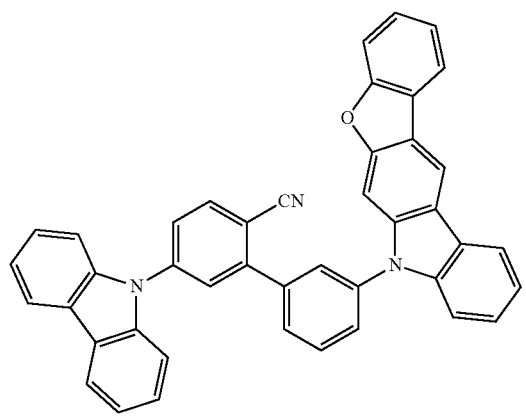
136
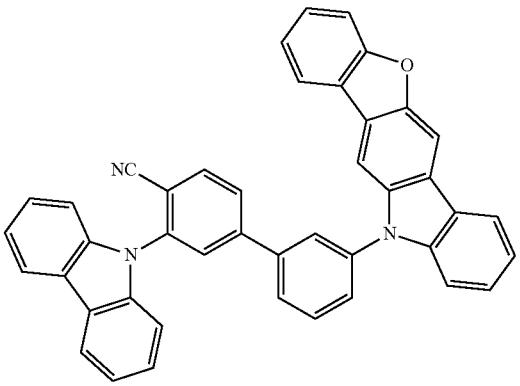
137
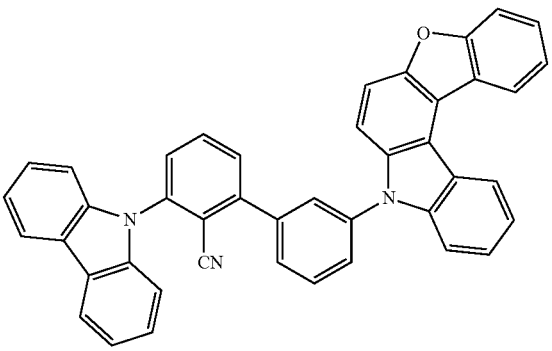
138
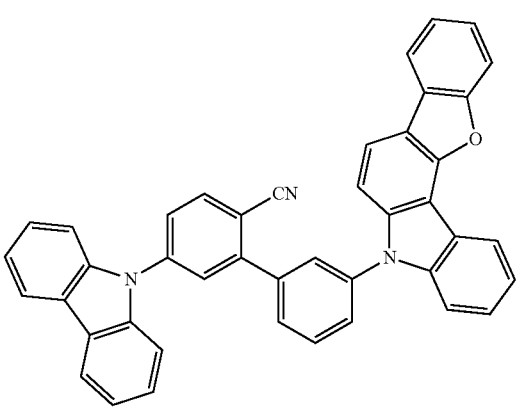
139
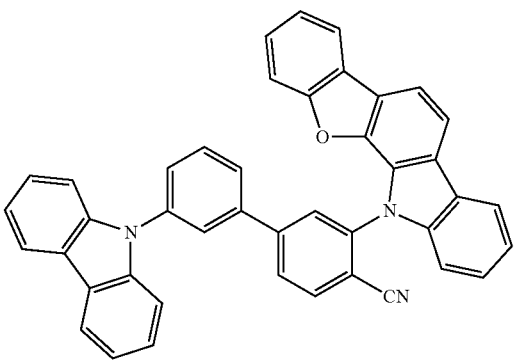

140
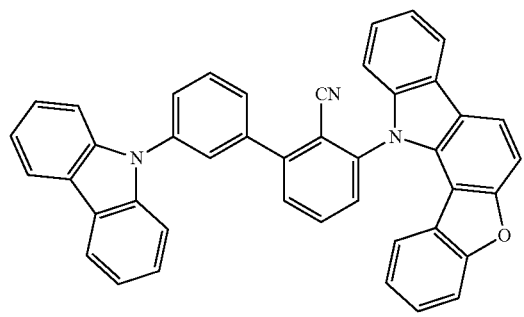
141
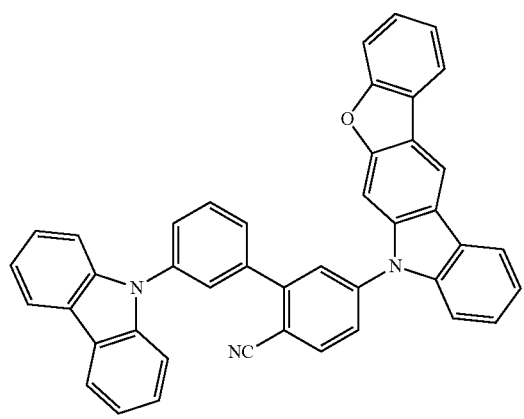
142
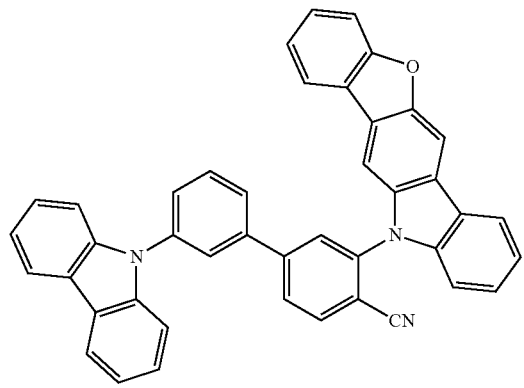
143
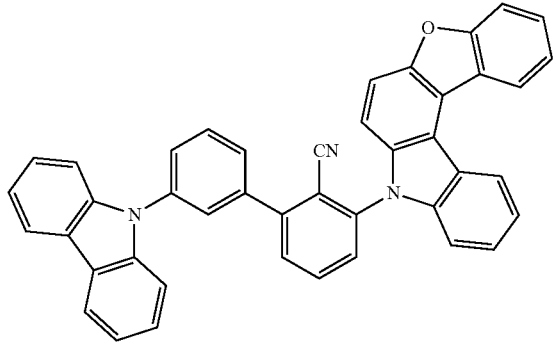
144
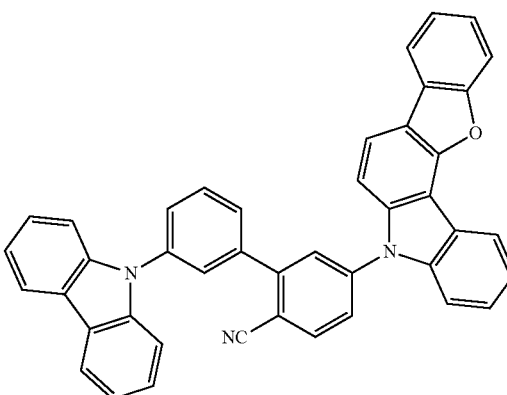
145
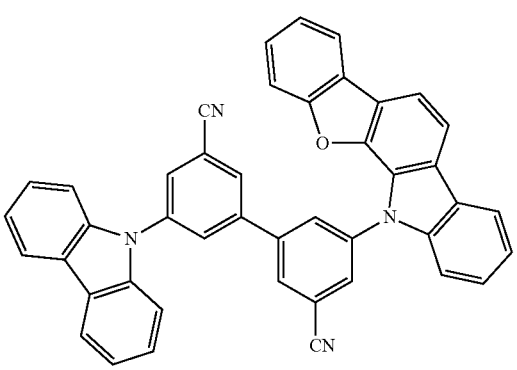
146
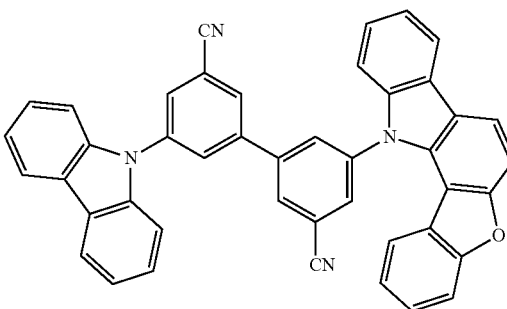
147
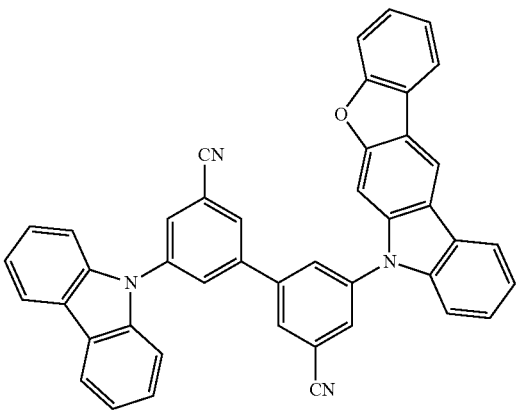

148
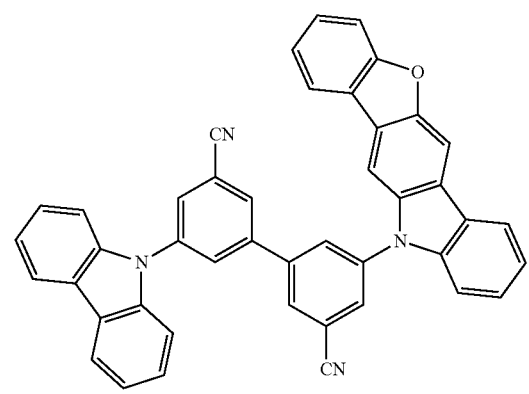
149
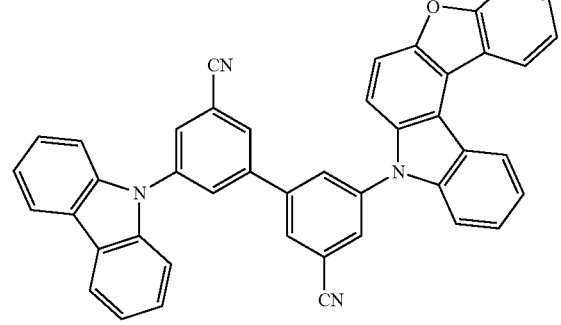
150
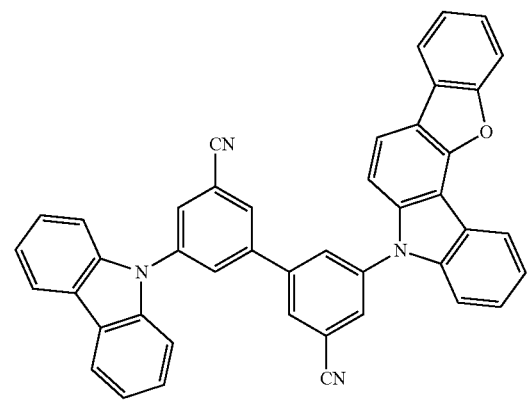
151
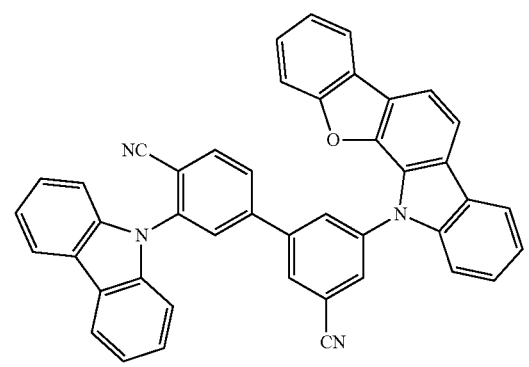
152
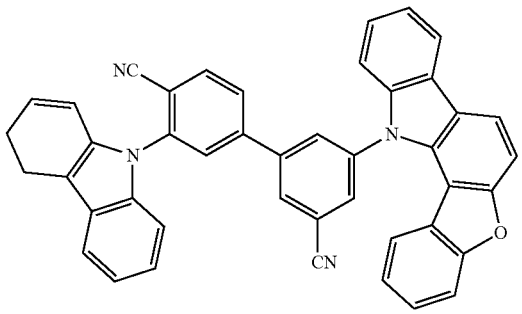
153
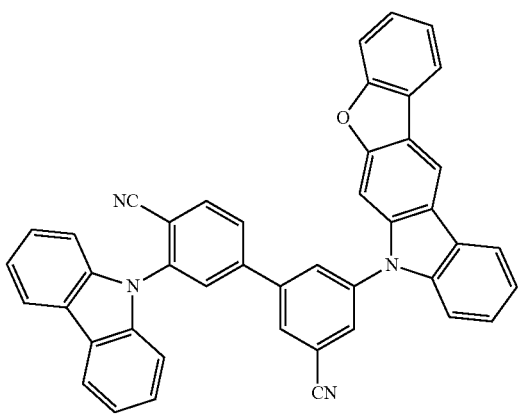
154
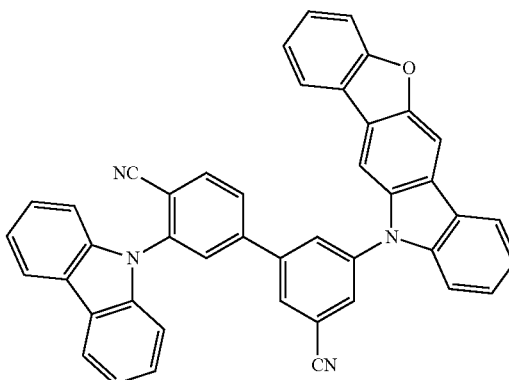
155
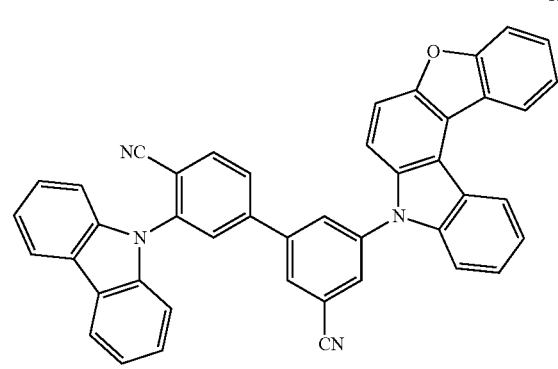

156
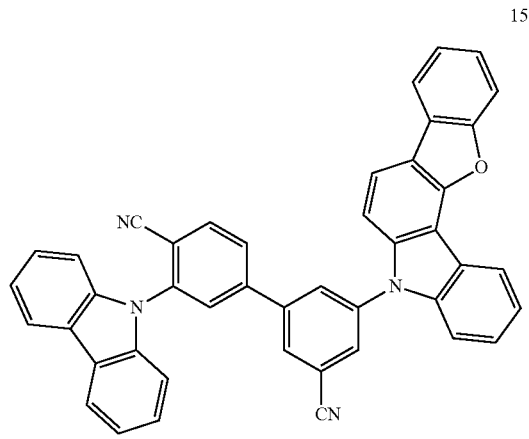
157
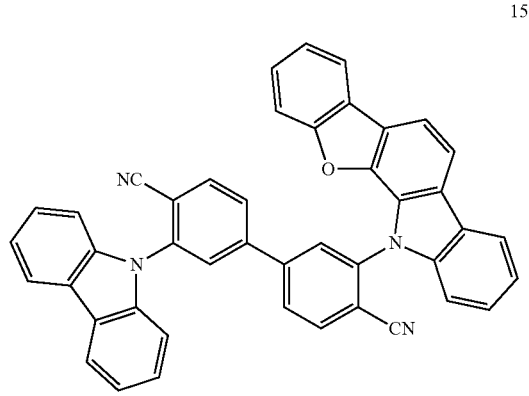
158
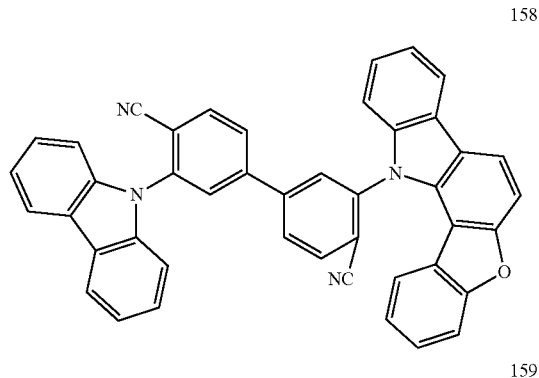
159
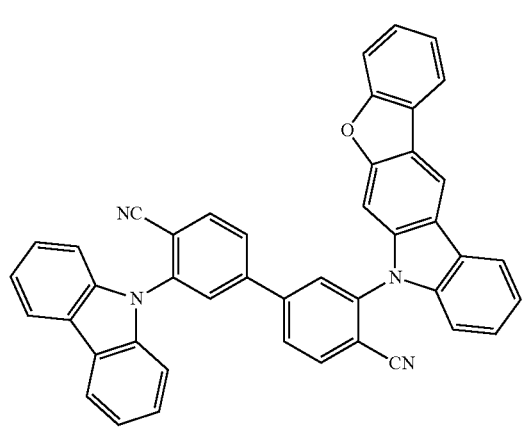
160
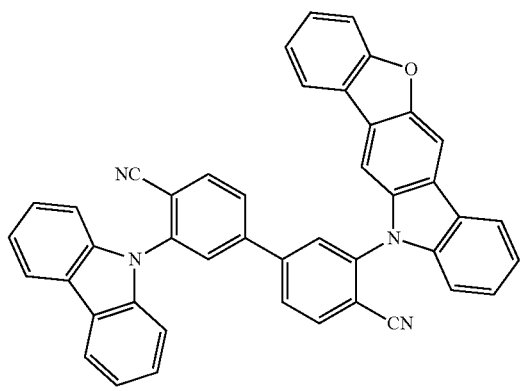
161
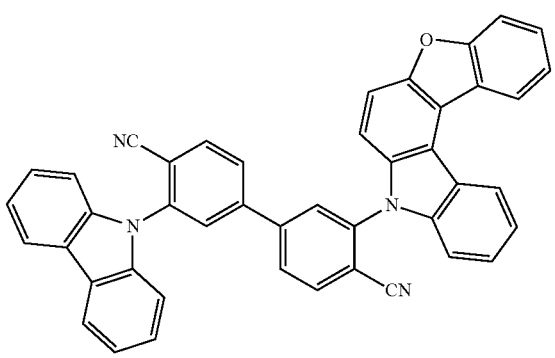
162
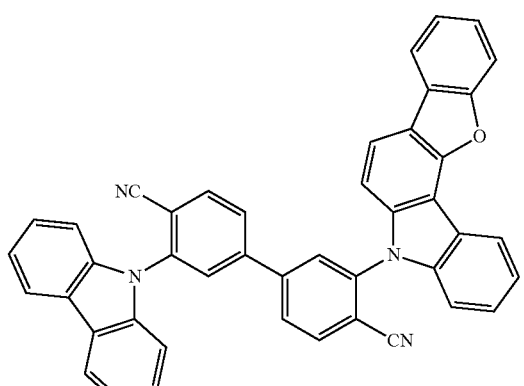
163
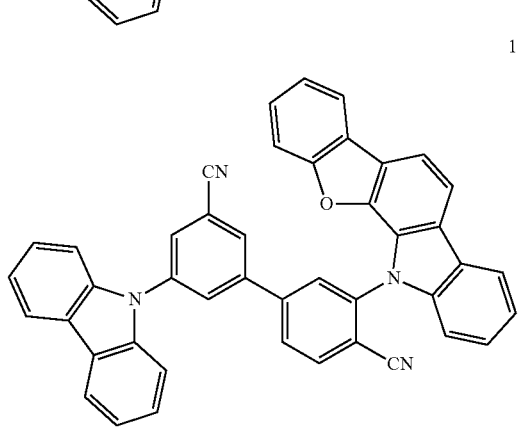

-continued
164
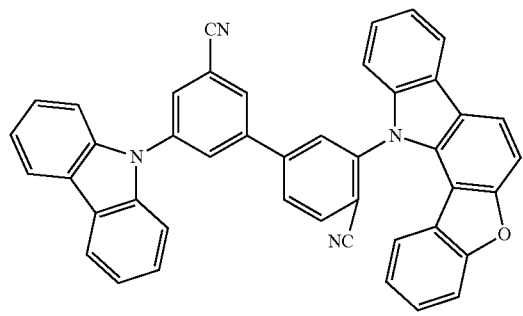
165
166
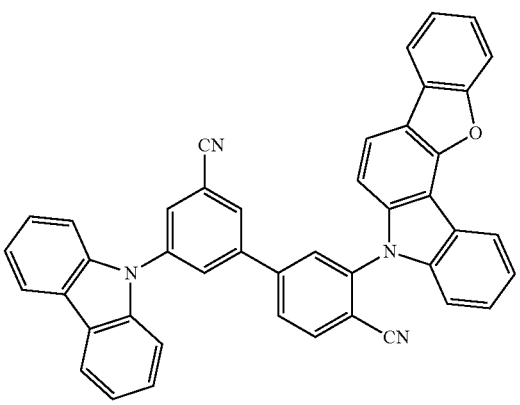
167
168
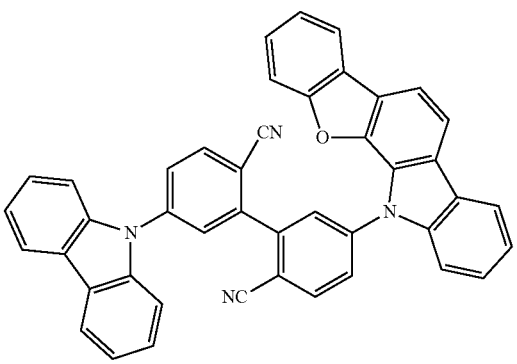
169
170
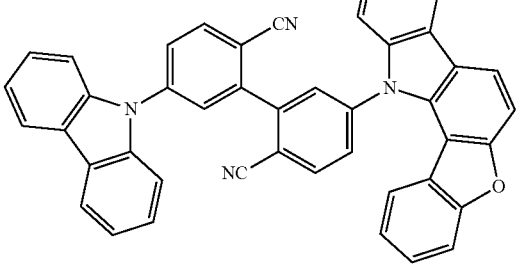
171
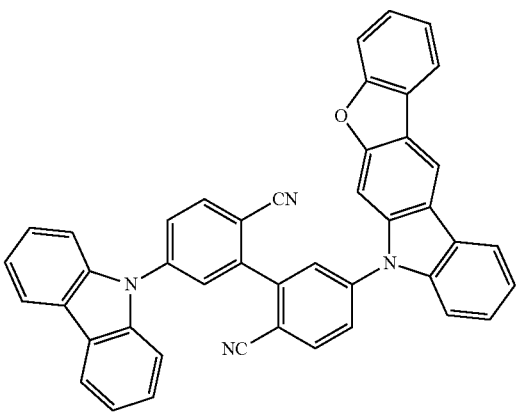

-continued
172
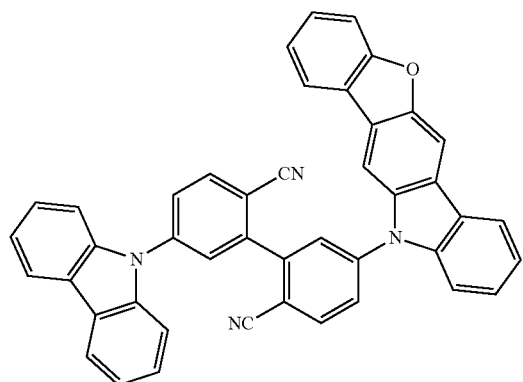
173
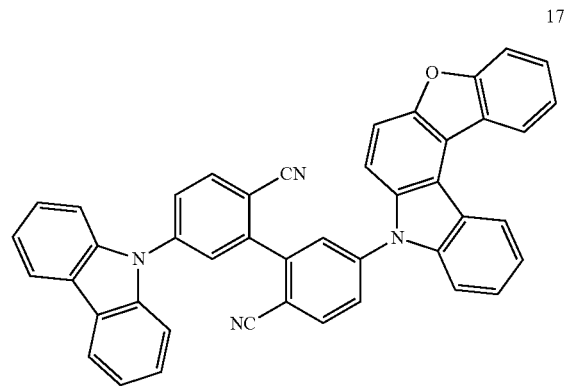
174
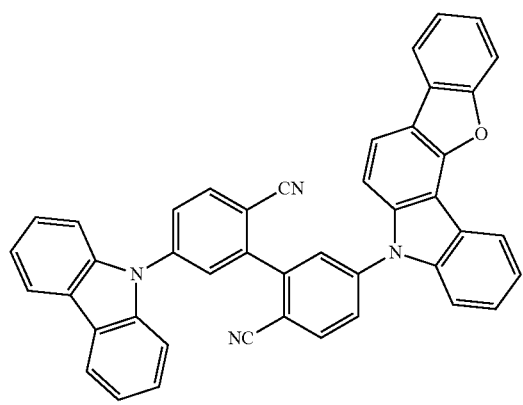
175
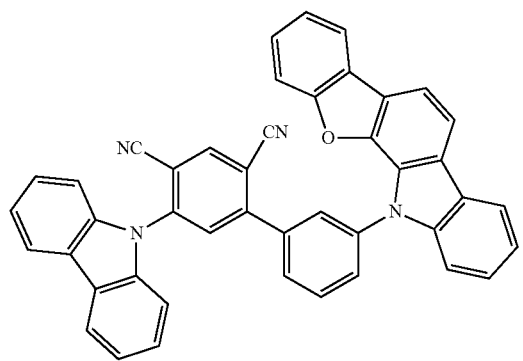
-continued
176
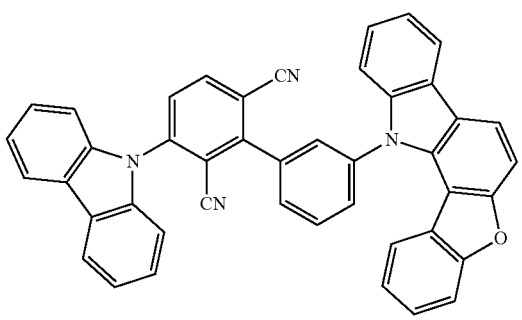
177
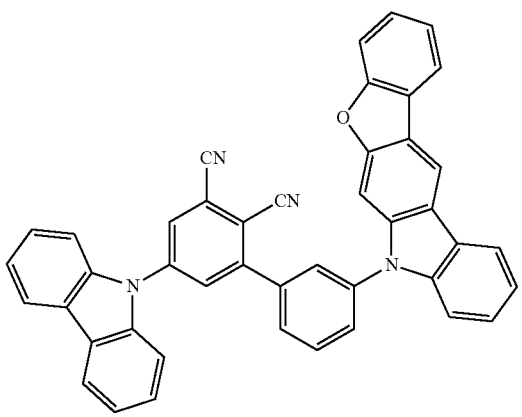
178
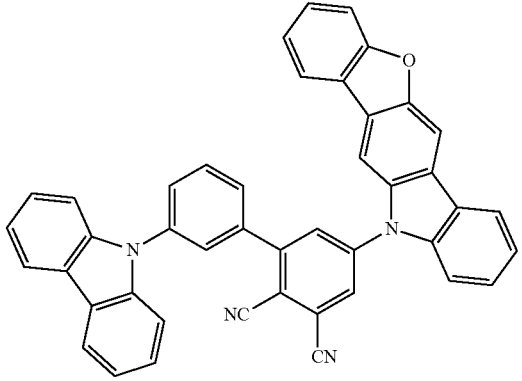
179
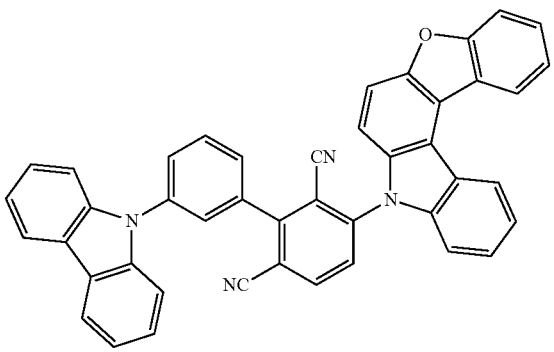

180
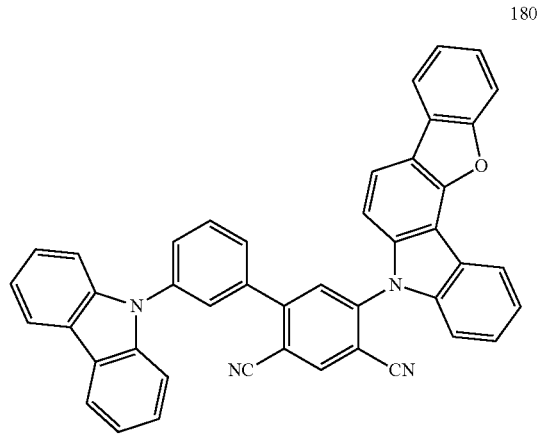
181
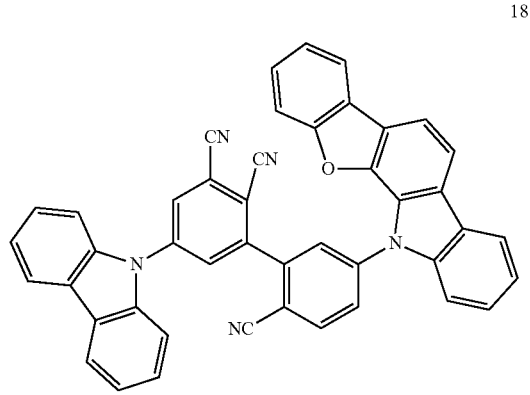
182
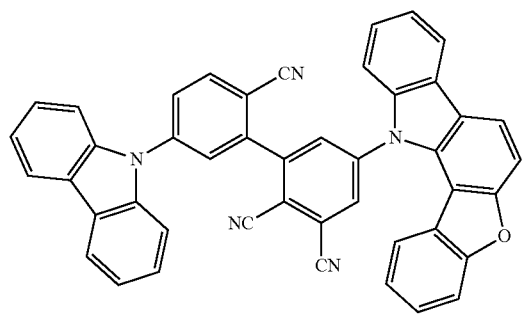
183
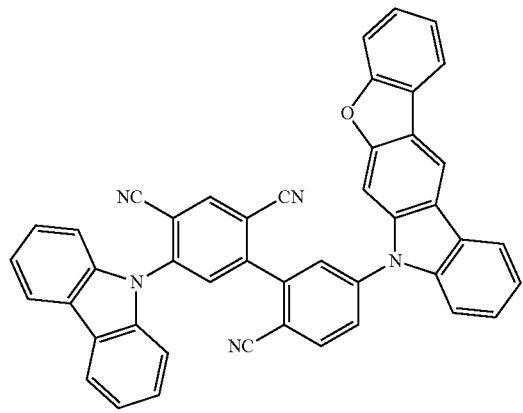
184
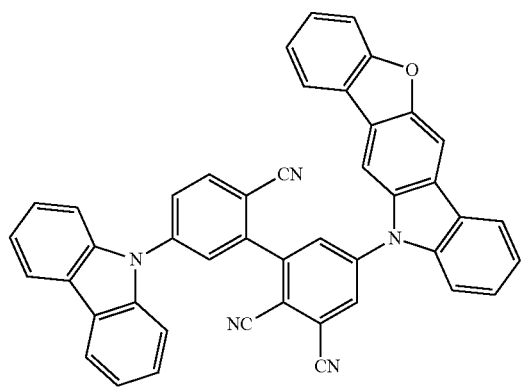
185
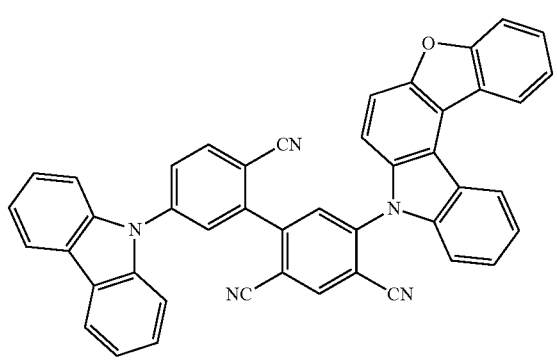
186
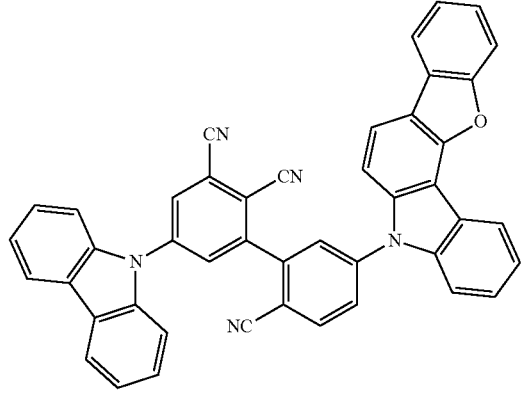
187
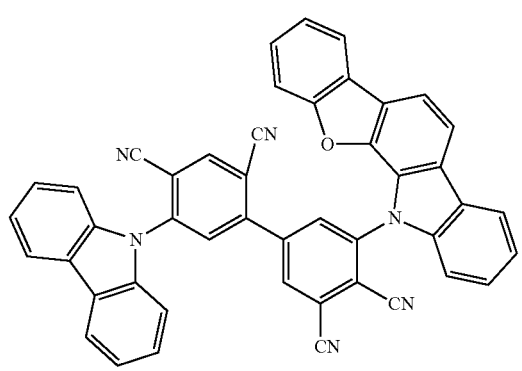

188
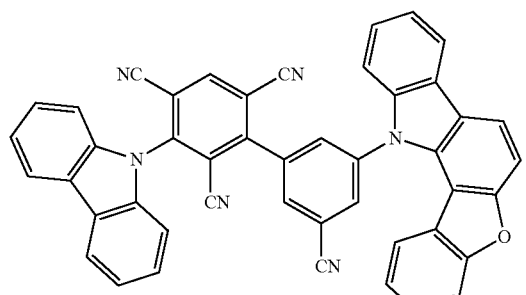
189
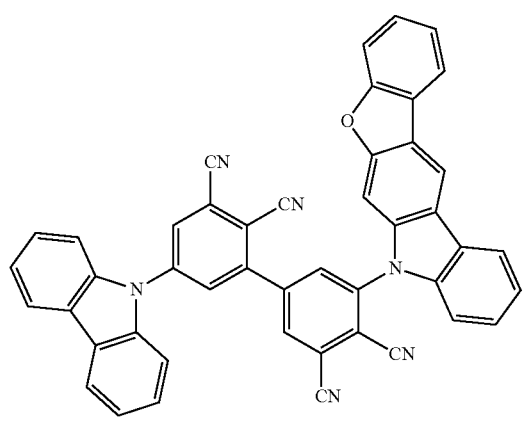
190
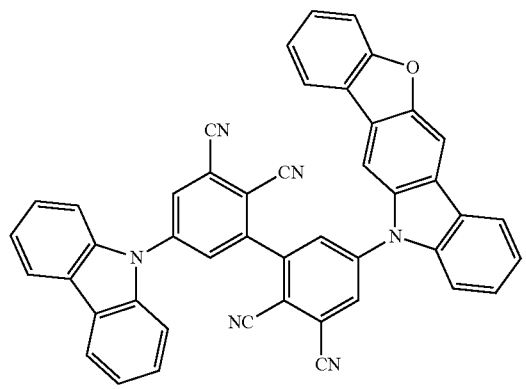
191
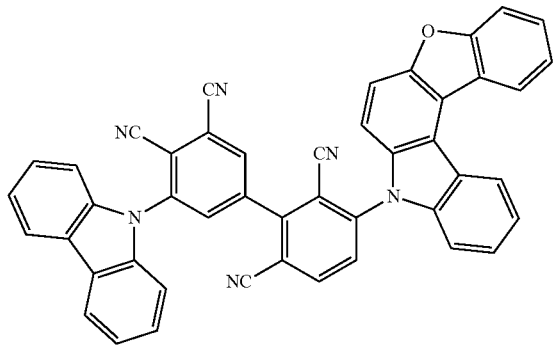
192
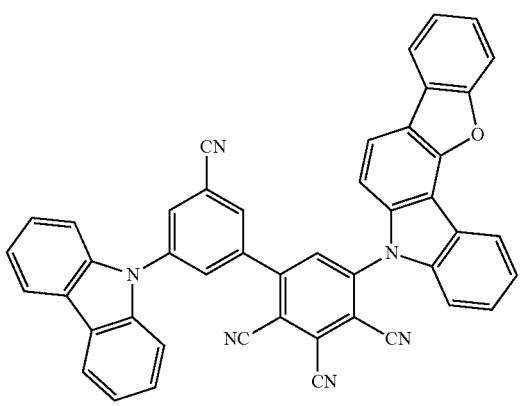
193
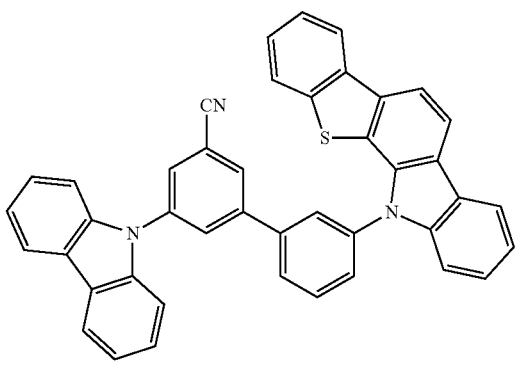
194
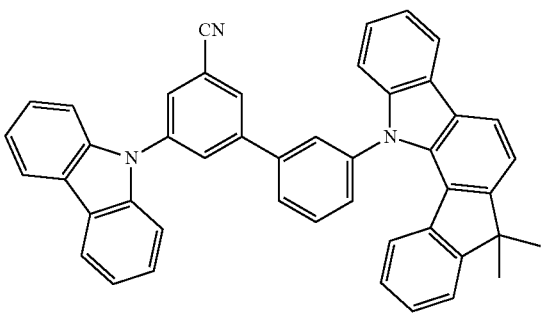
195
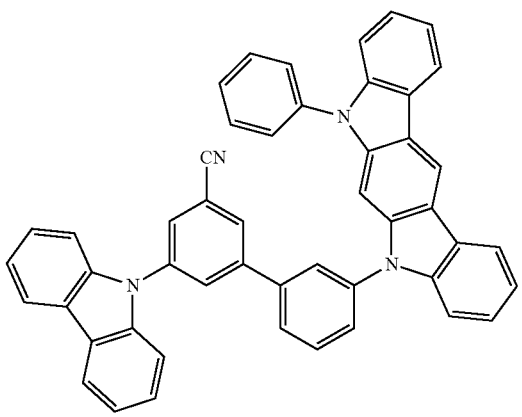

-continued
196
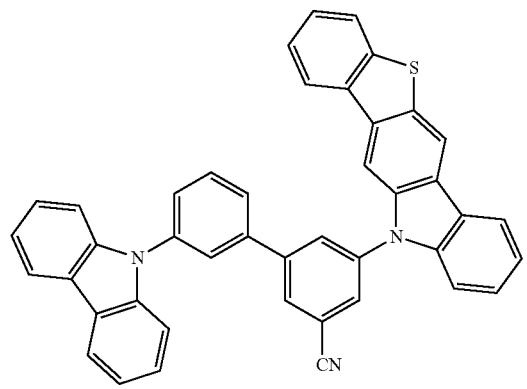
197
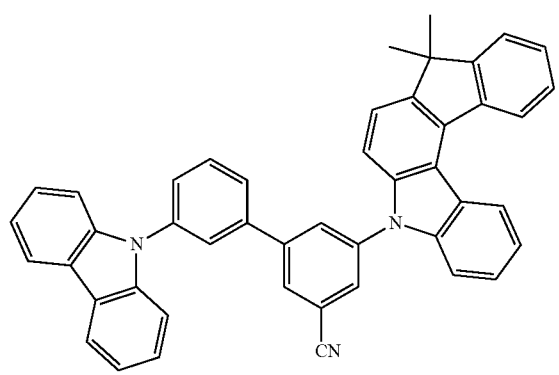
198
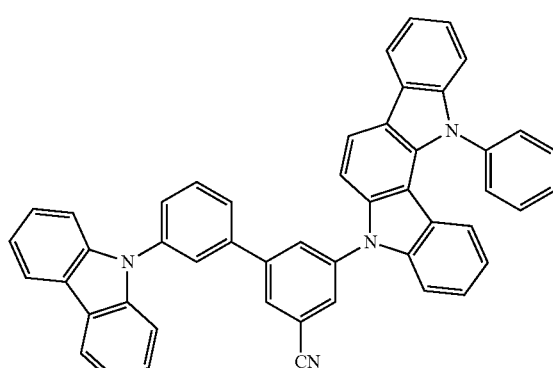
199
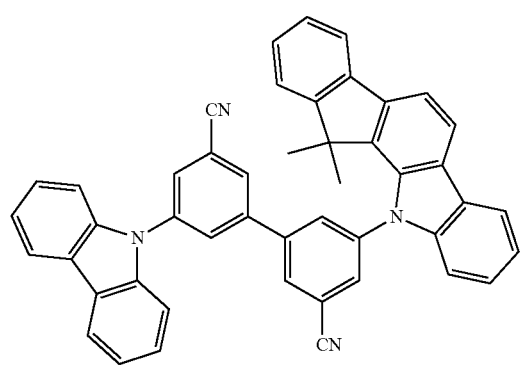
-continued
200
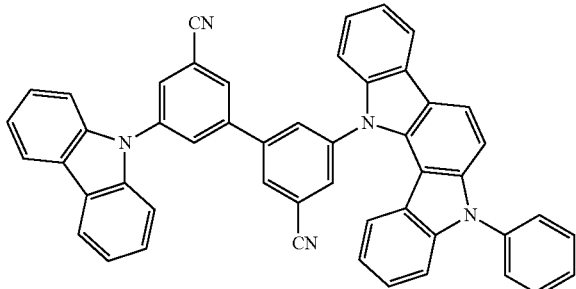
201
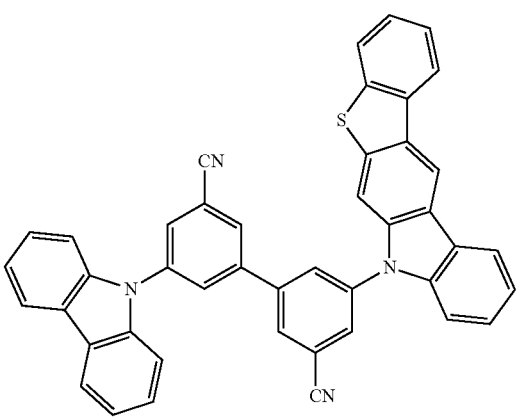
202
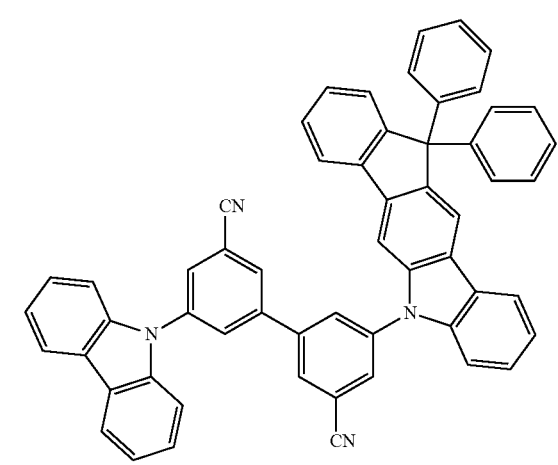

-continued
203
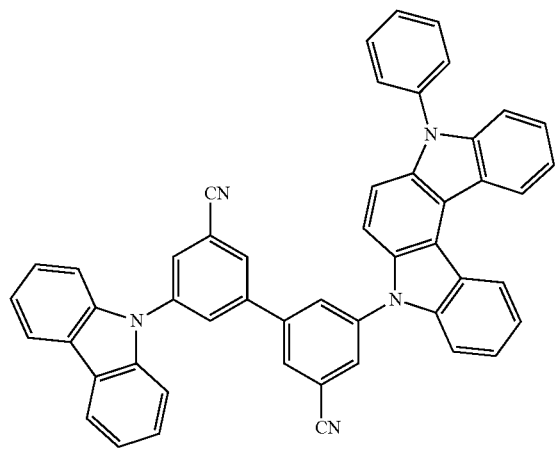
204
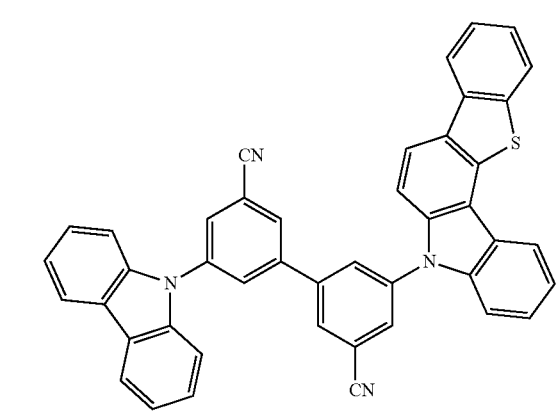
205
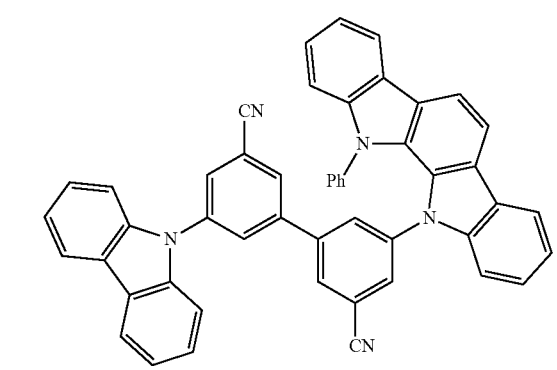
206
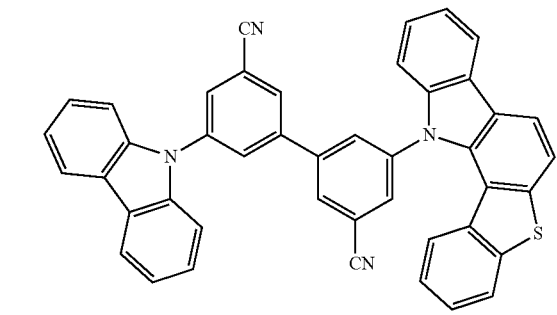
-continued
207
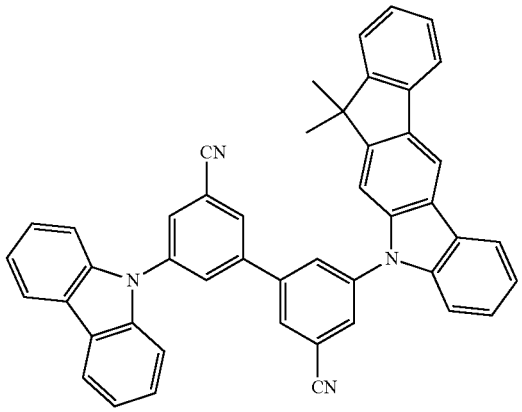
208
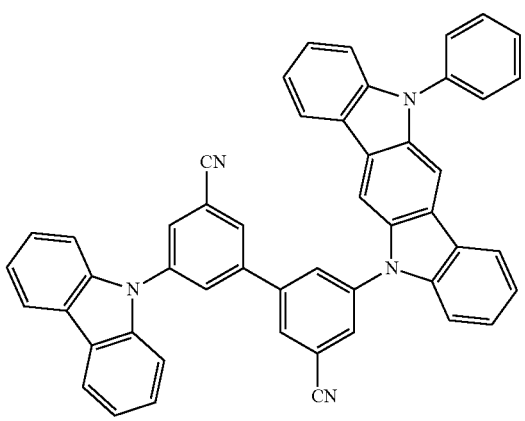
209
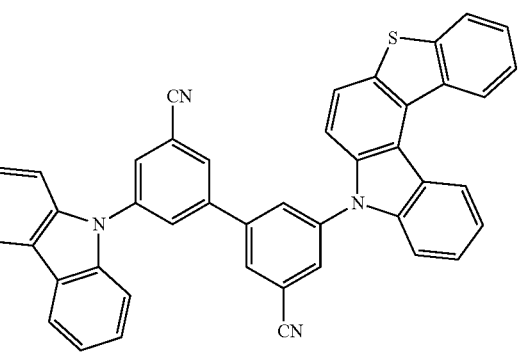
210
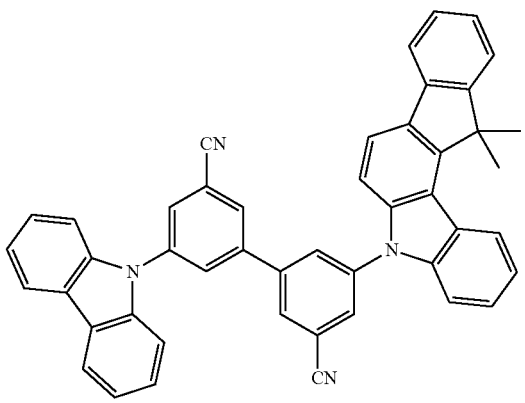

211 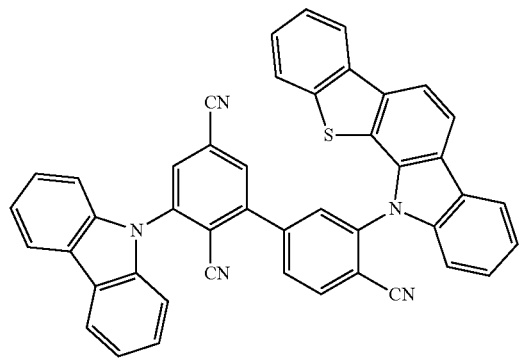
212 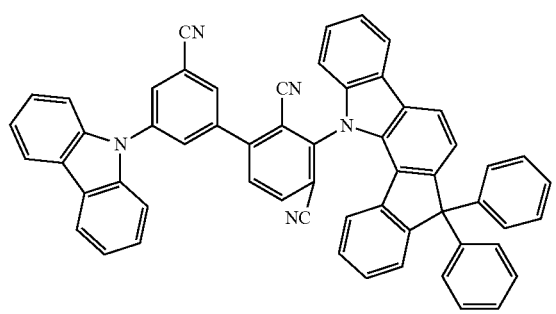
213 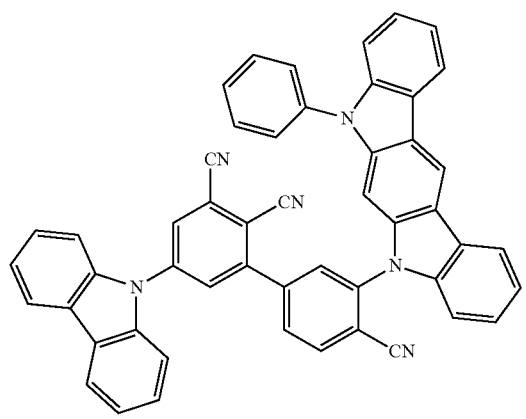
214 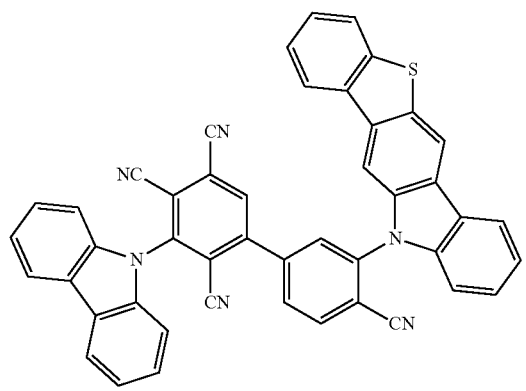
215 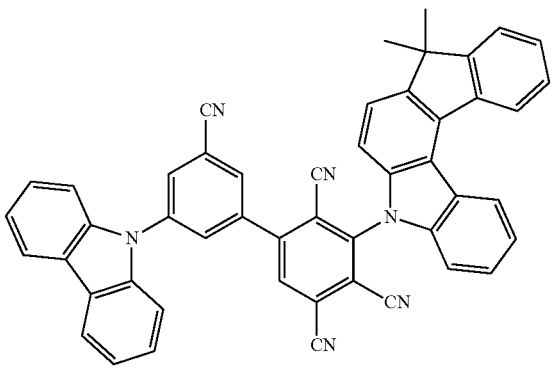
216 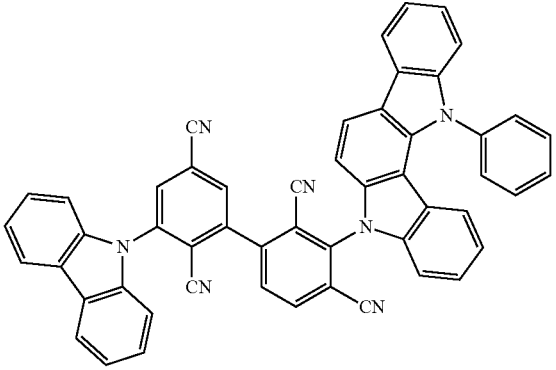
217 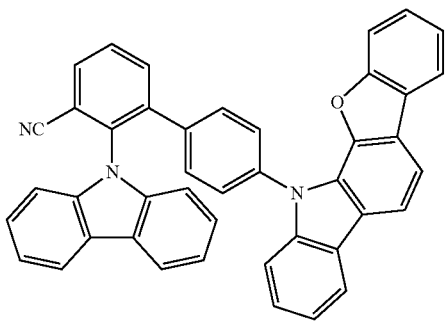
218 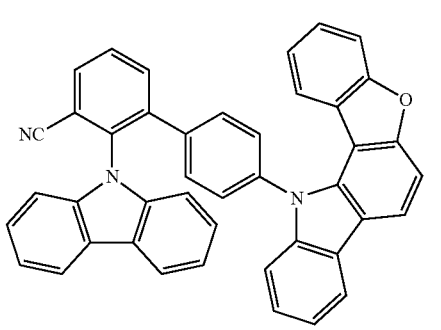

365
-continued
219
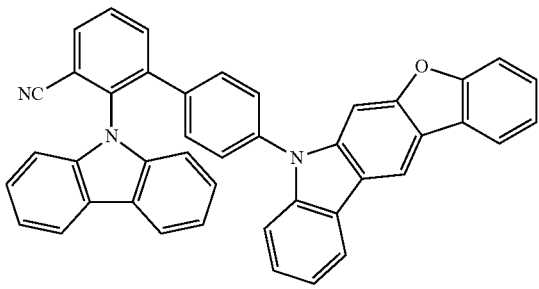
220
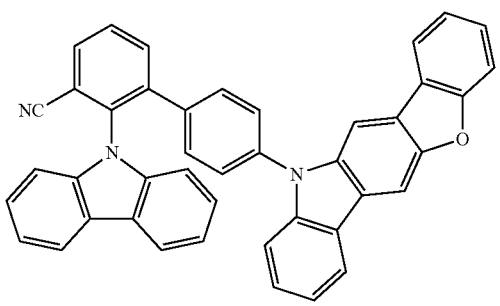
221
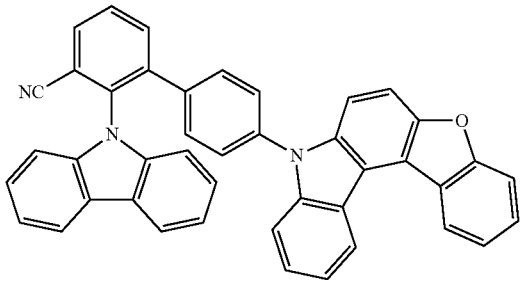
222
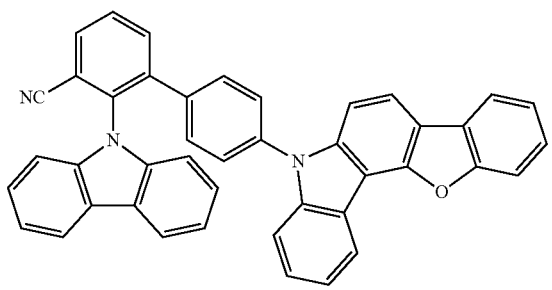
223
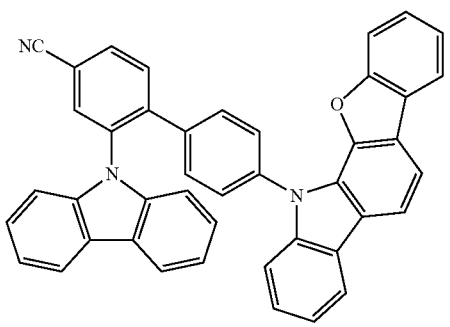
366
-continued
224
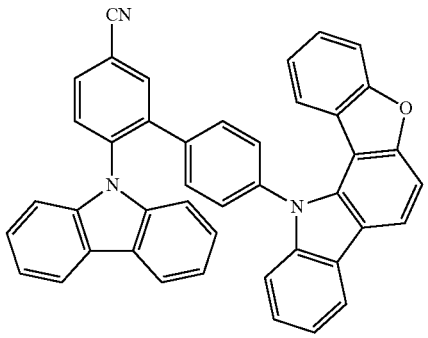
225
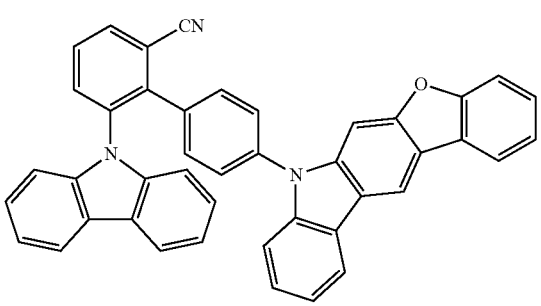
226
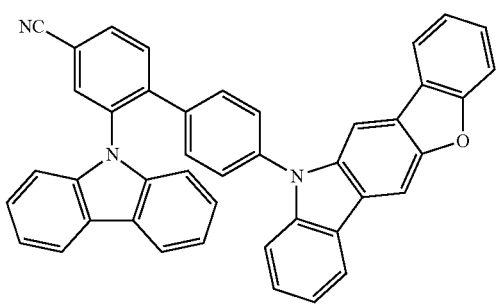
227
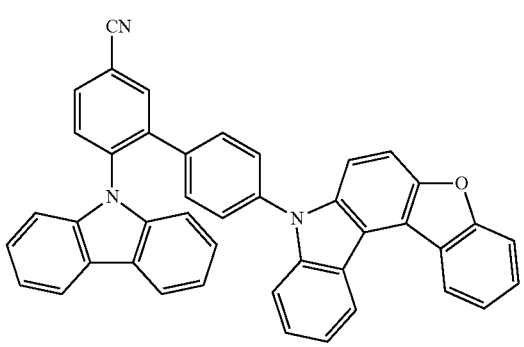
228
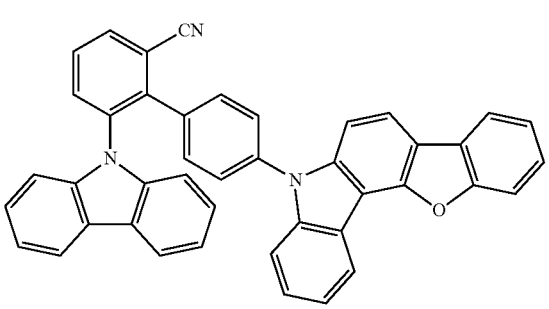

229
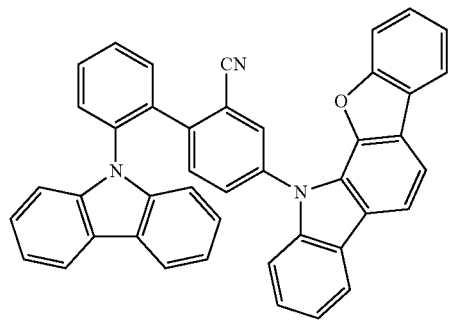
230
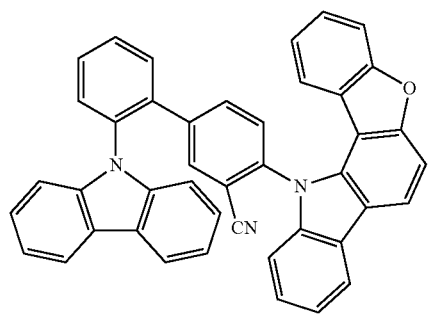
231
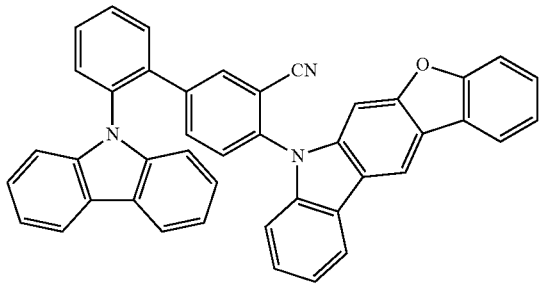
232
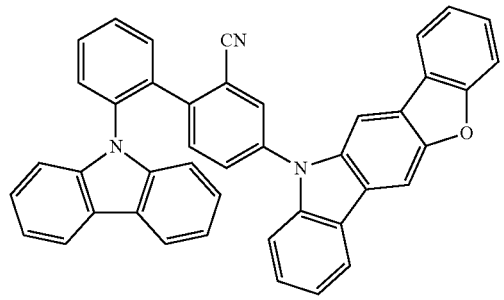
233
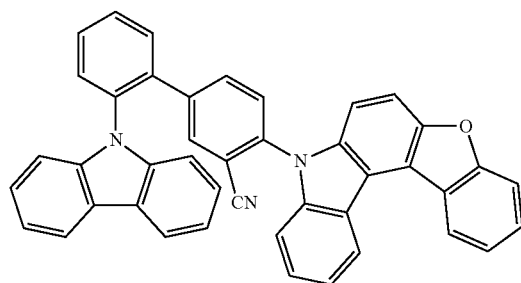
234
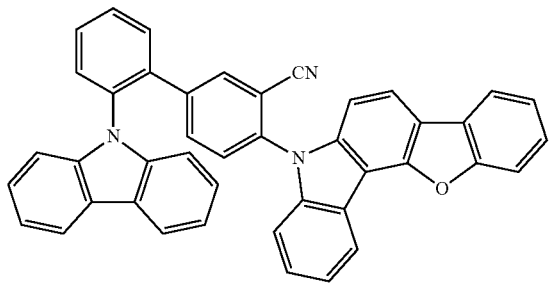
235
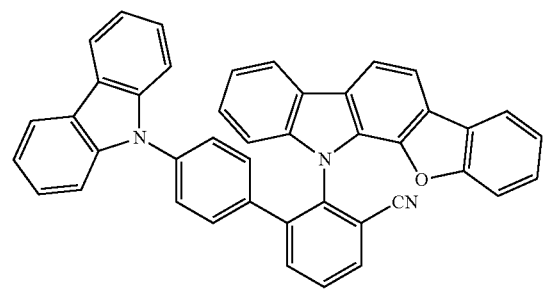
236
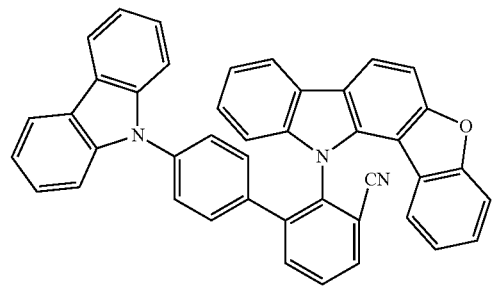
237
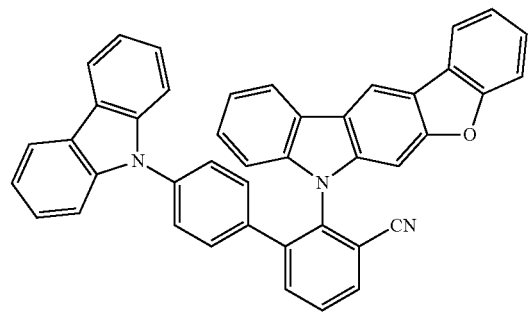
238
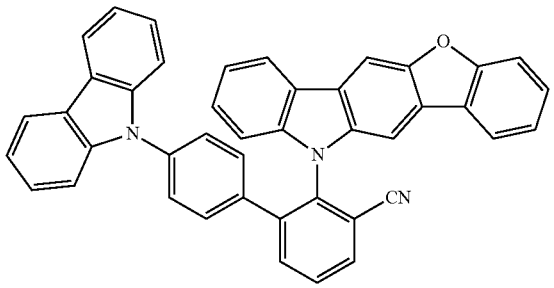

239 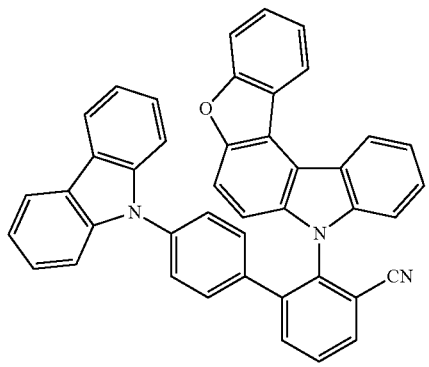
243 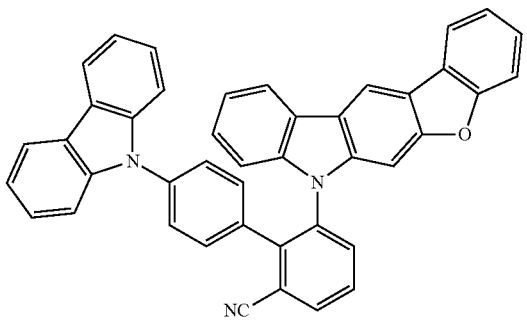
240 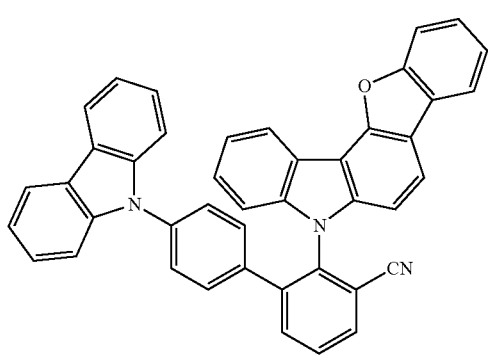
244 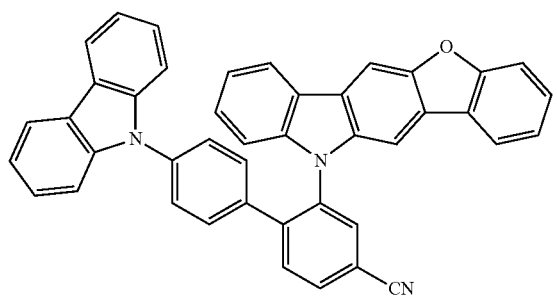
241 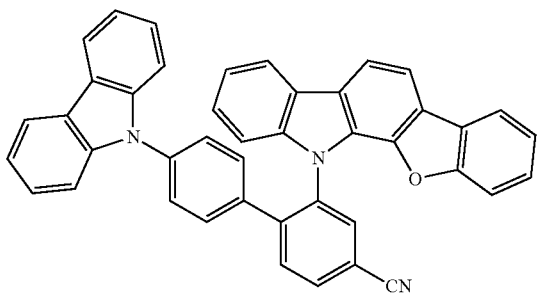
245 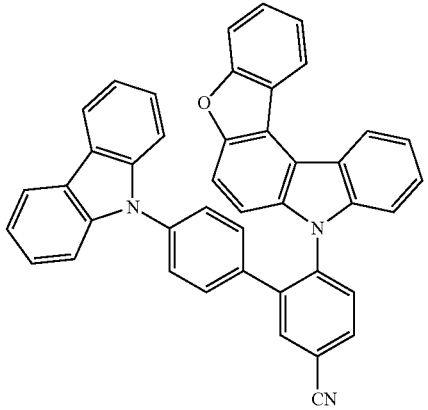
242 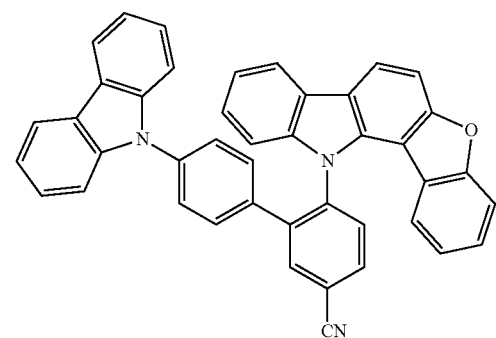
246 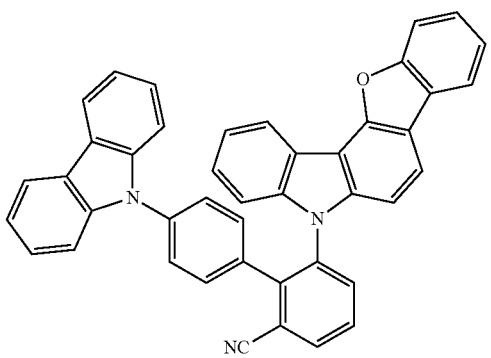

247
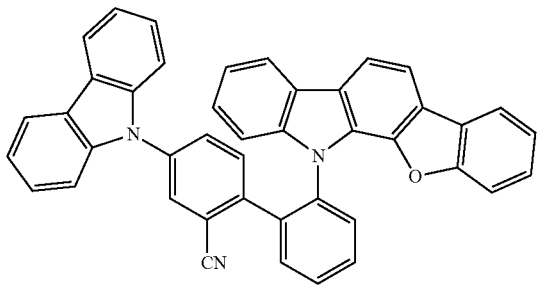
248
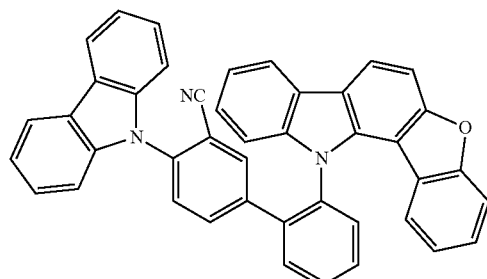
249
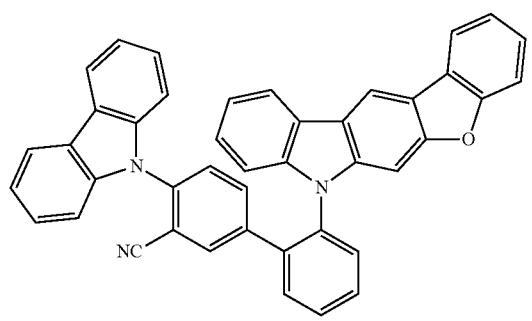
250
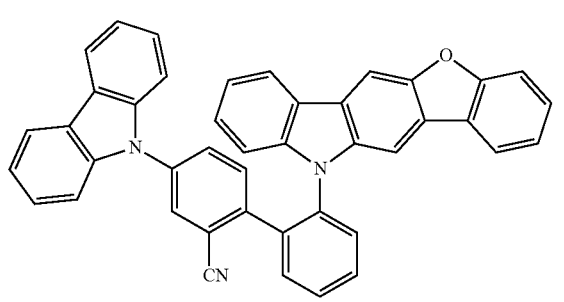
251
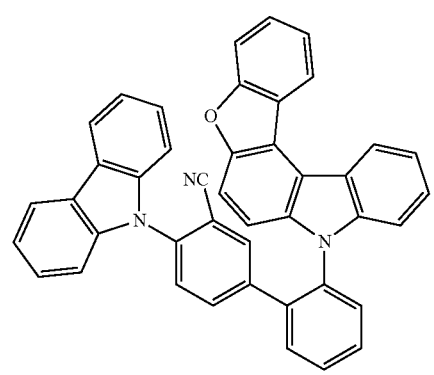
252
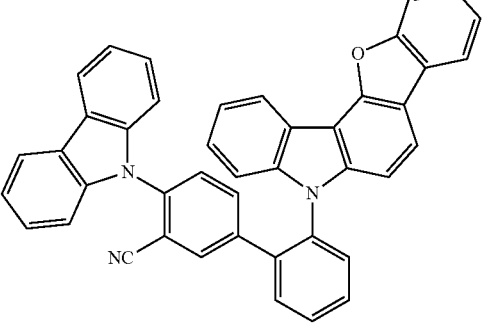
253
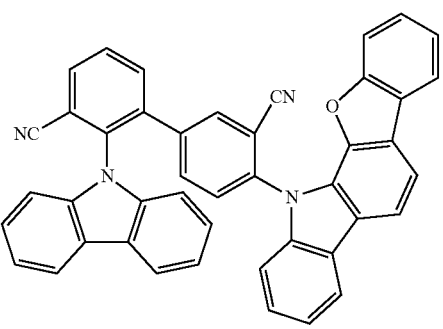
254
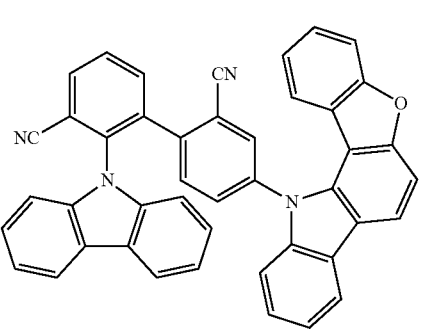
255
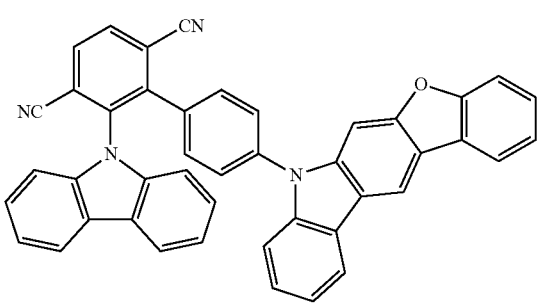
256
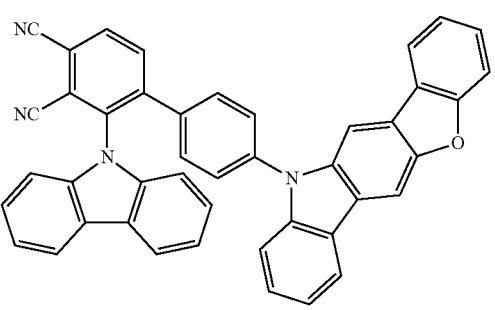

257
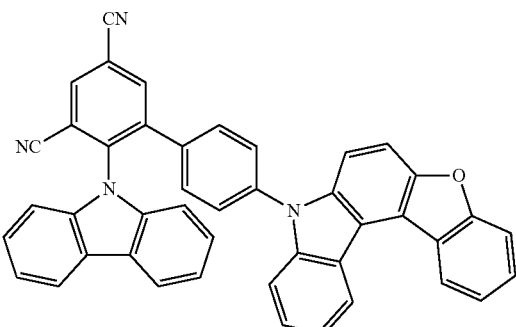
258
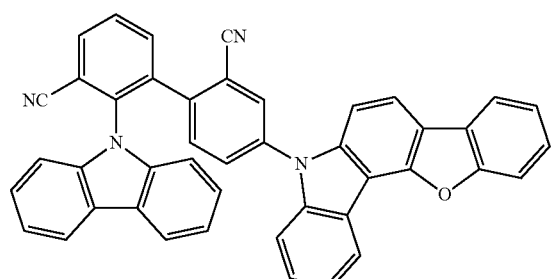
259
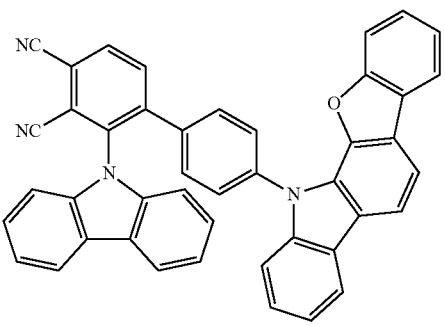
260
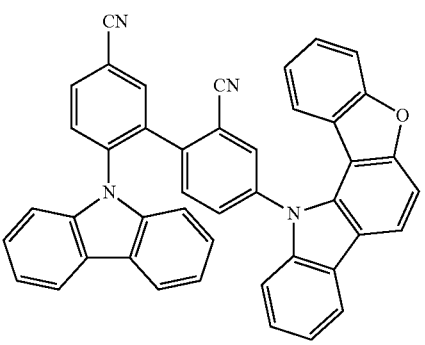
261
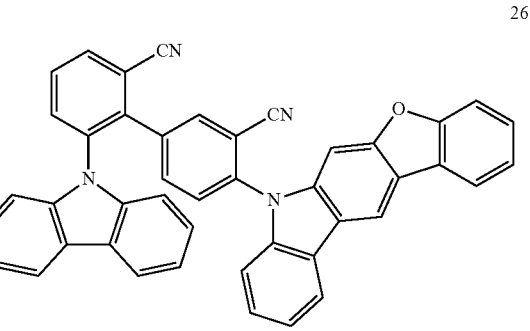
262
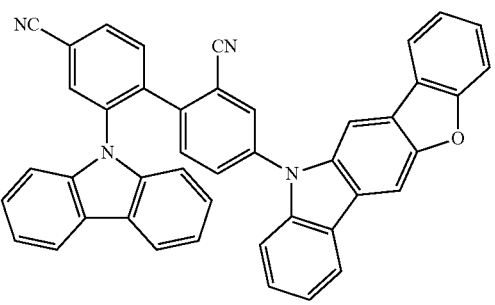
263
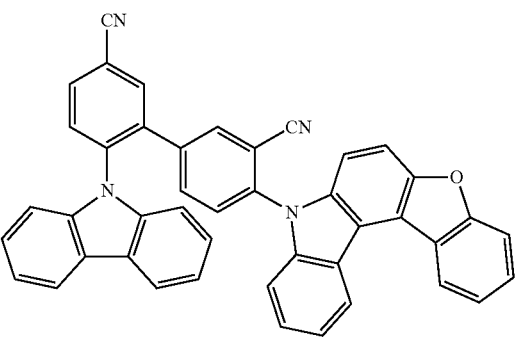
264
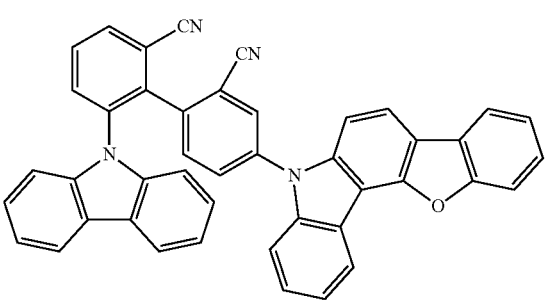
265
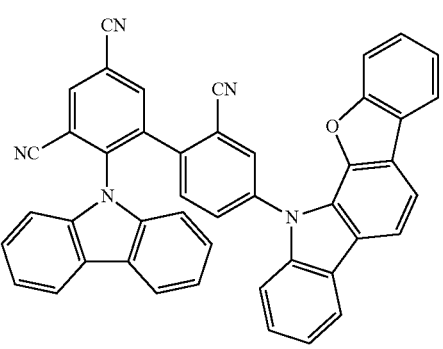
266
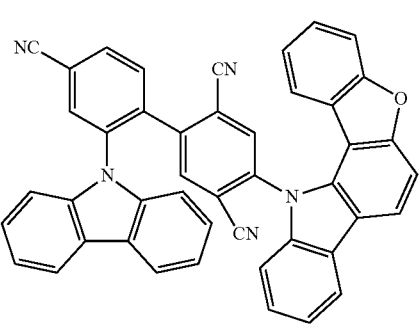

| 375 -continued | 376 -continued |
|---|---|
| 267 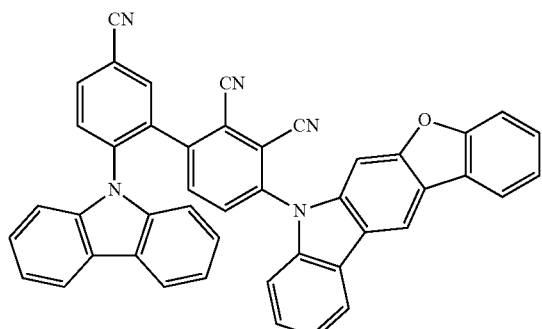 | 271 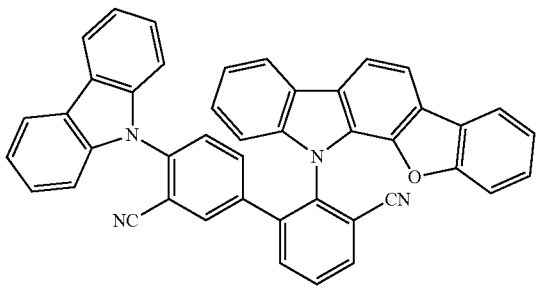 |
| 268 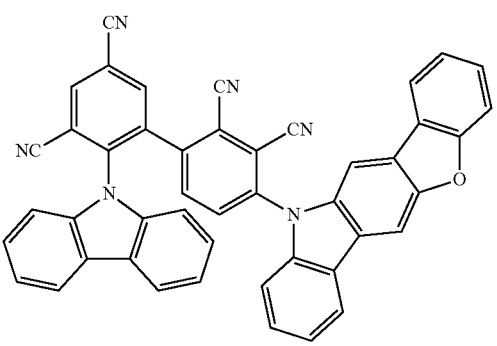 | 272 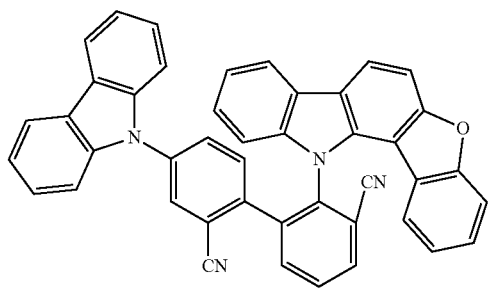 |
| 269 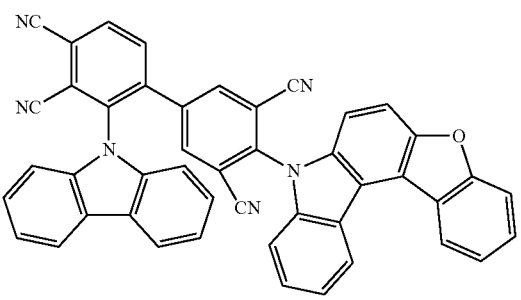 | 273 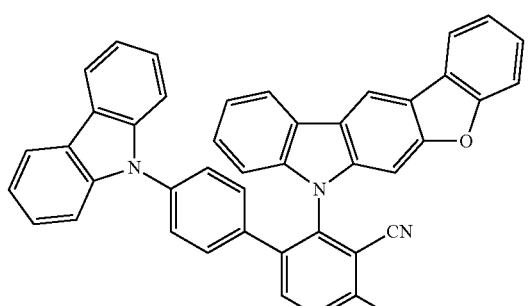 |
| 270 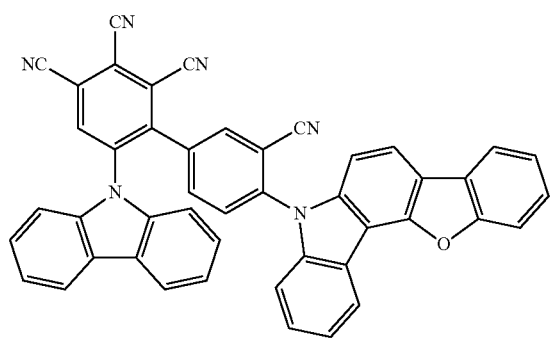 | 274 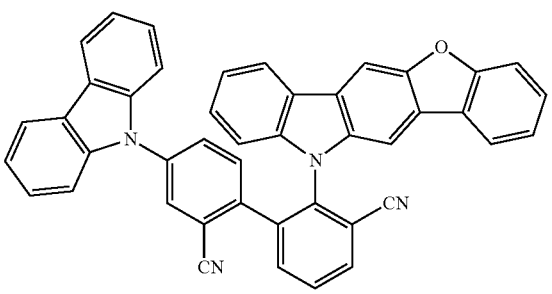 |
| | 275 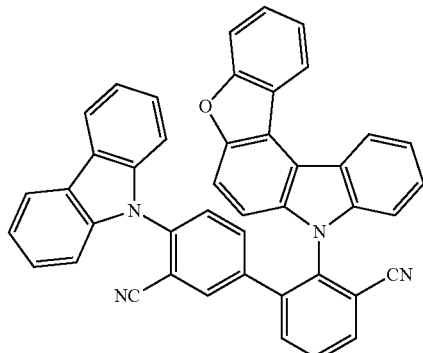 |

-continued
276
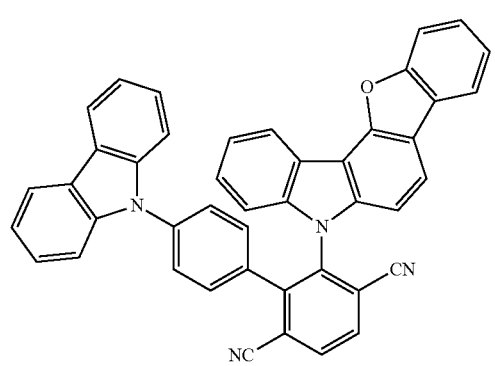
277
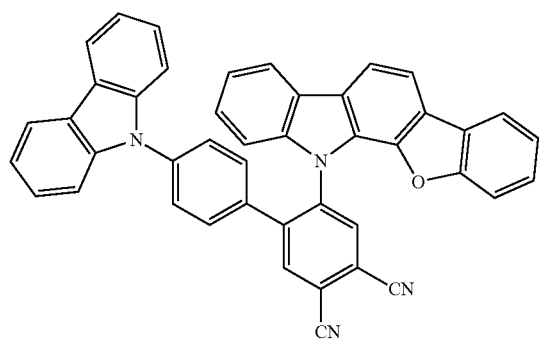
278
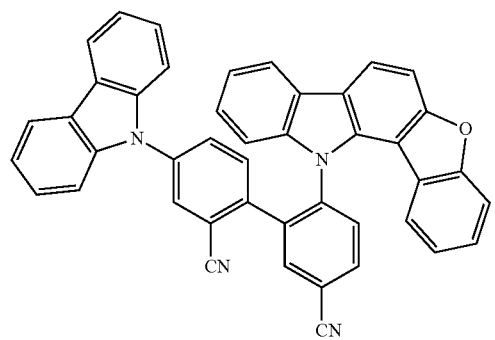
279
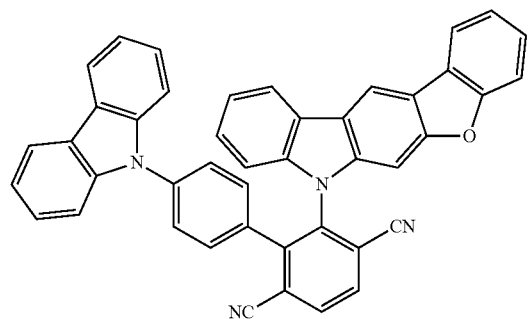
-continued
280
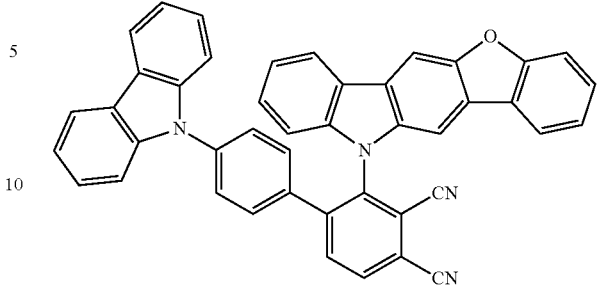
281
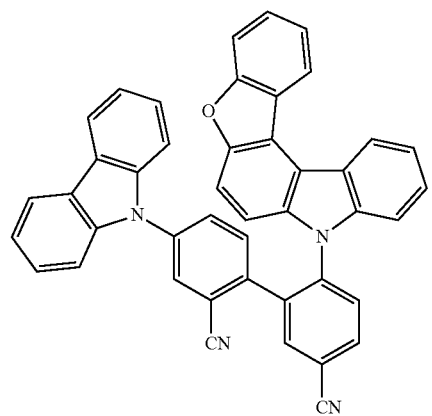
282
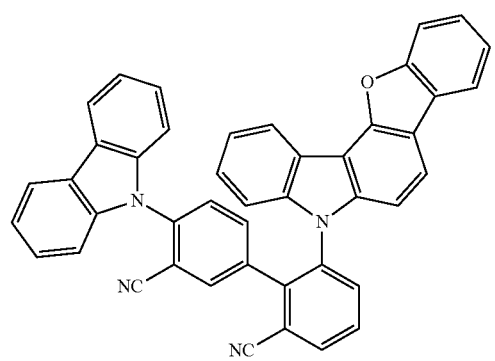
283
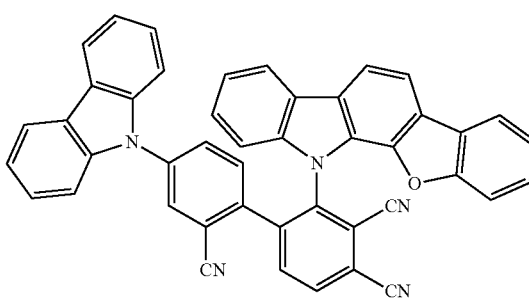

284
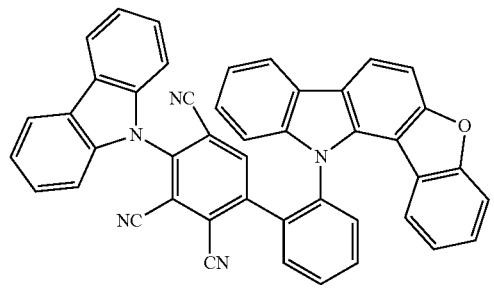
285
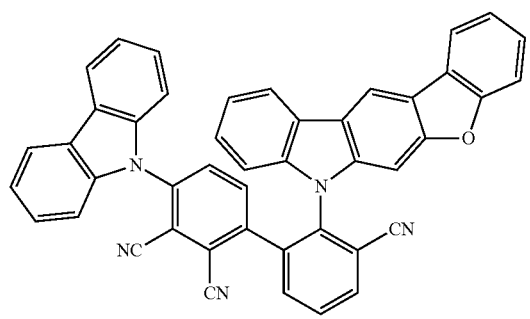
286
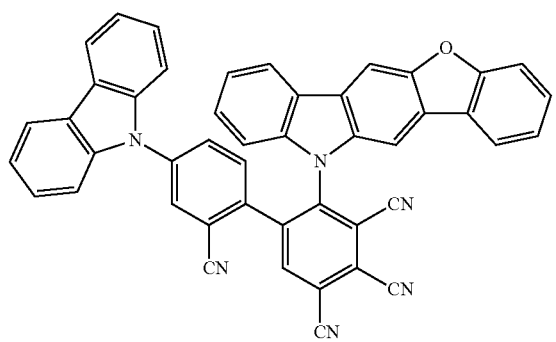
287
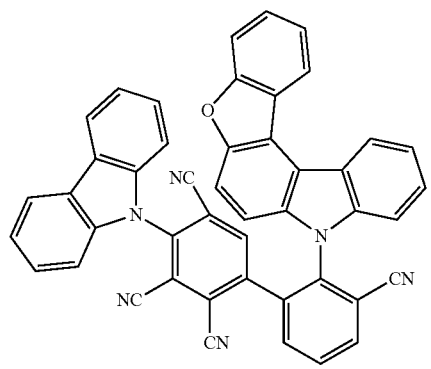
288
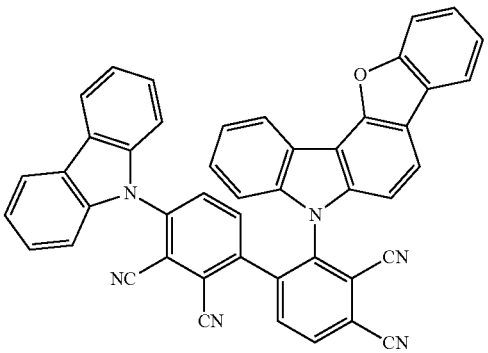
289
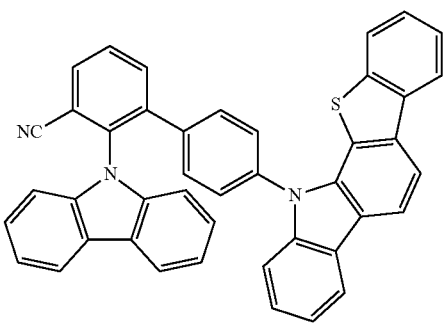
290
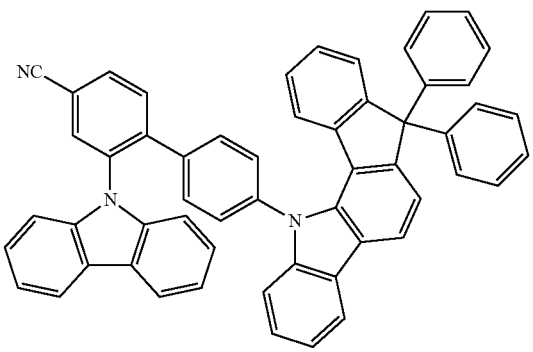
291
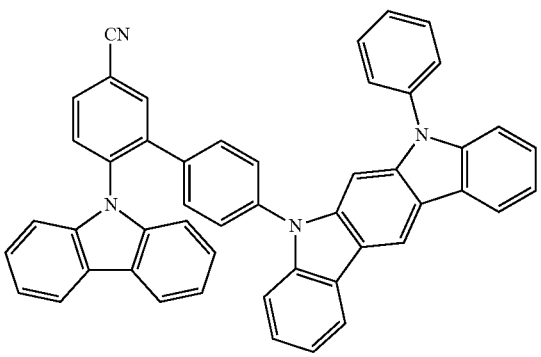

-continued
292
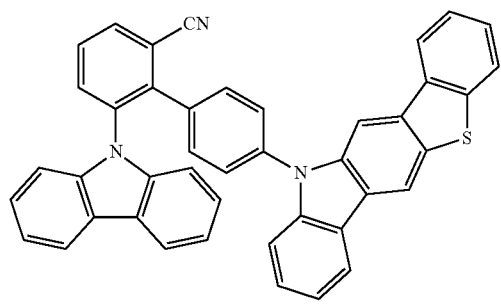
293
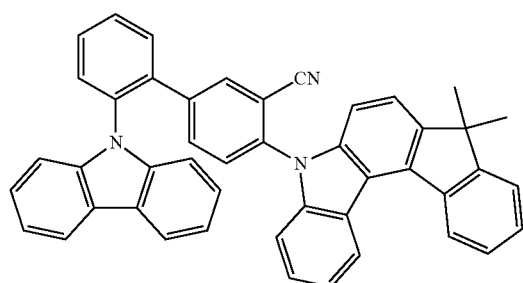
294
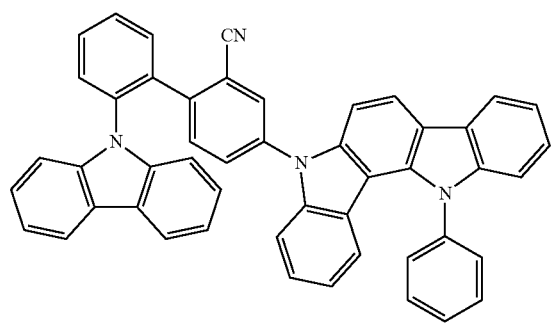
295
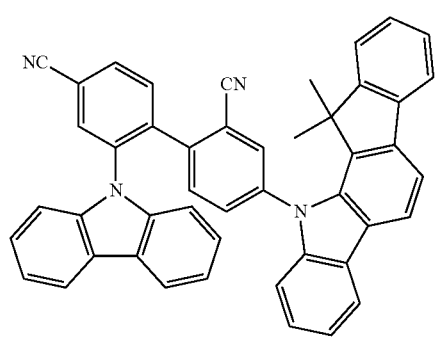
-continued
296
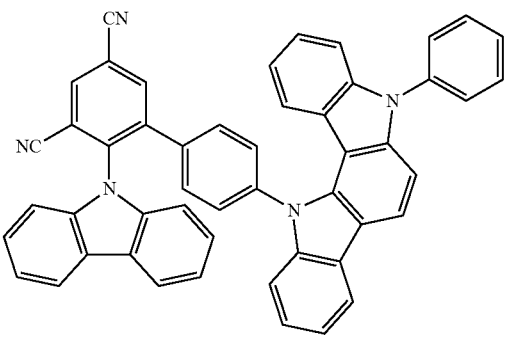
297
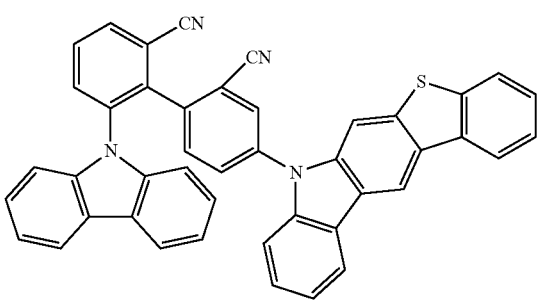
298
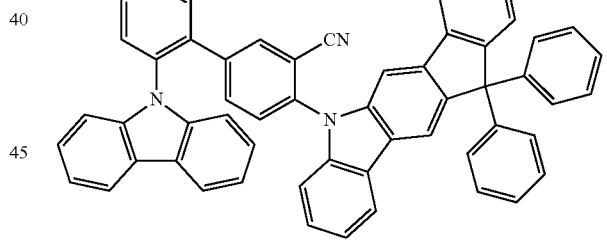
299
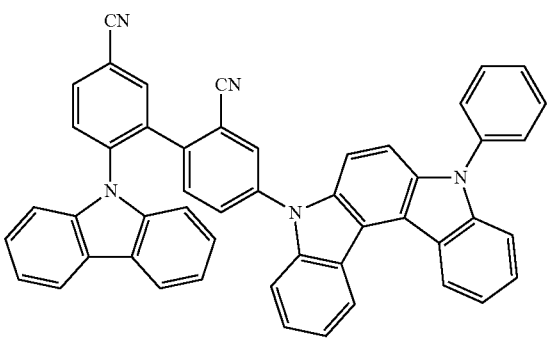

300
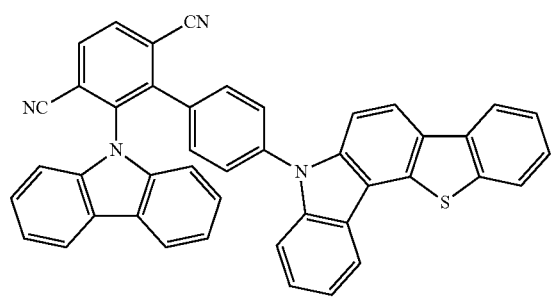
301
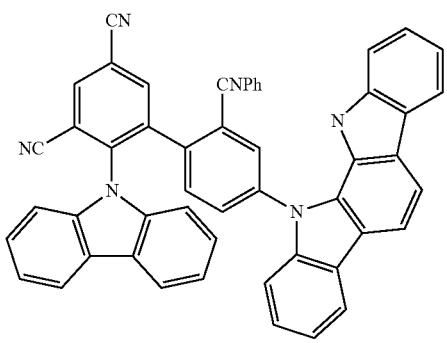
302
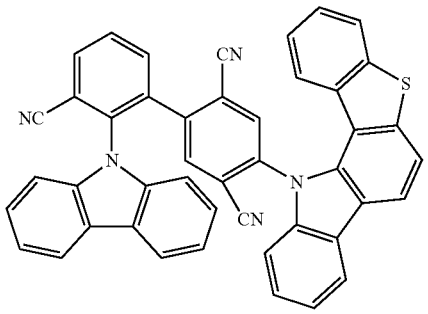
303
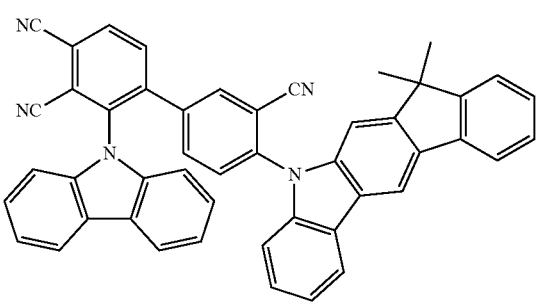
304
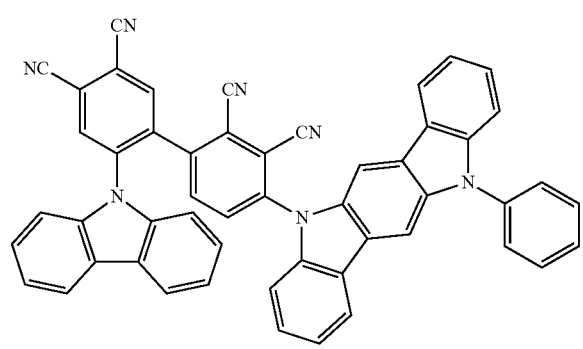
305
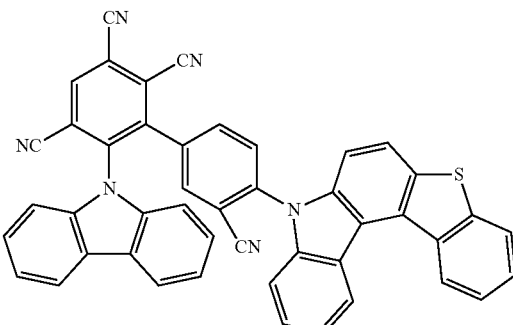
306
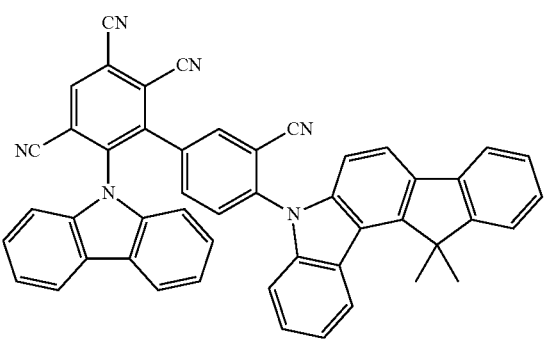
307
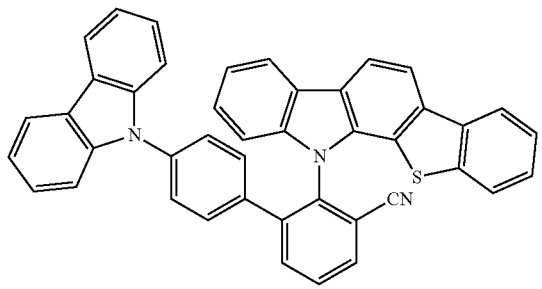
308
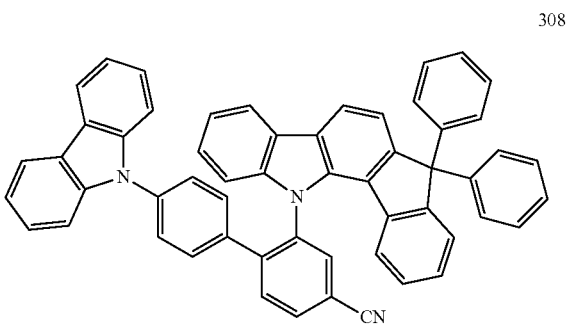

-continued
309
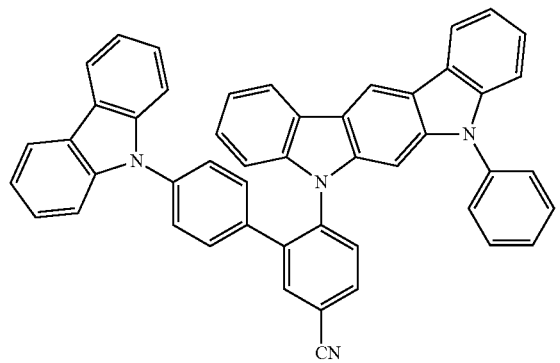
310
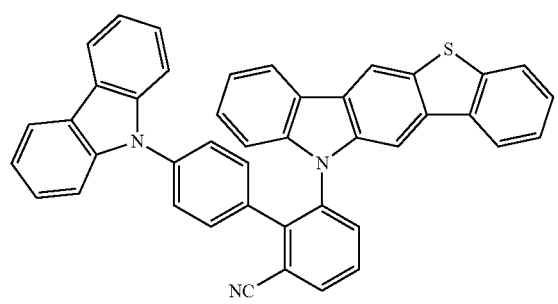
311
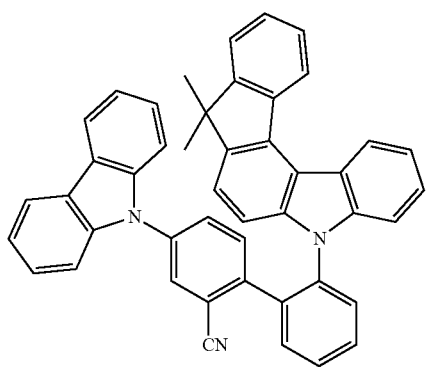
312
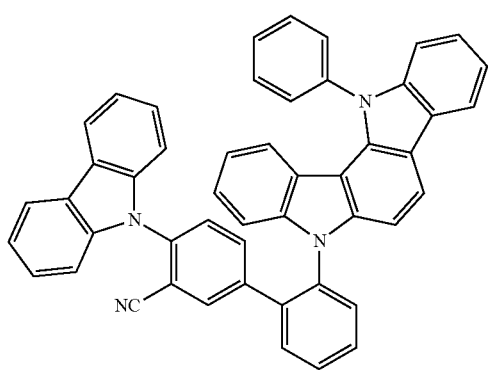
-continued
313
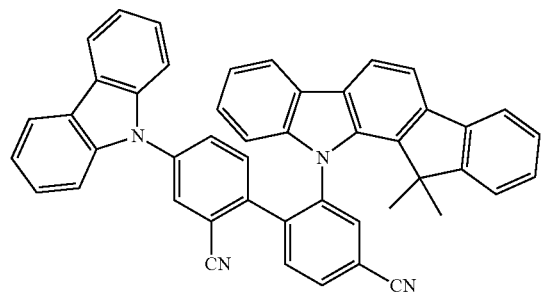
314
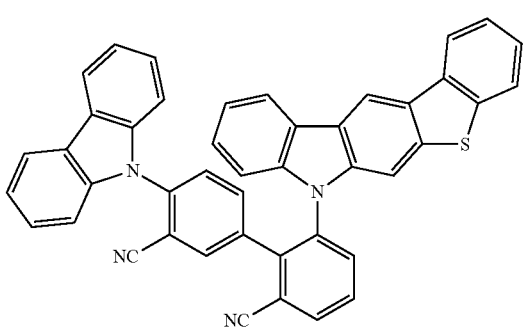
315
316
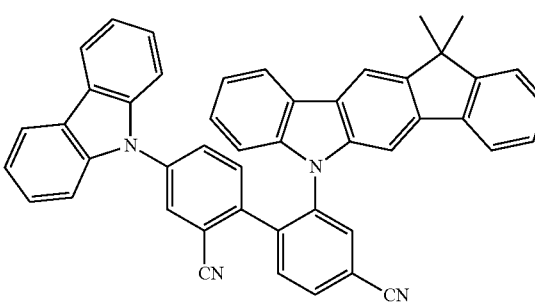

317
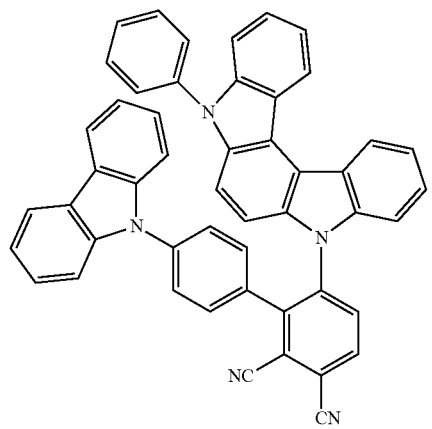
321
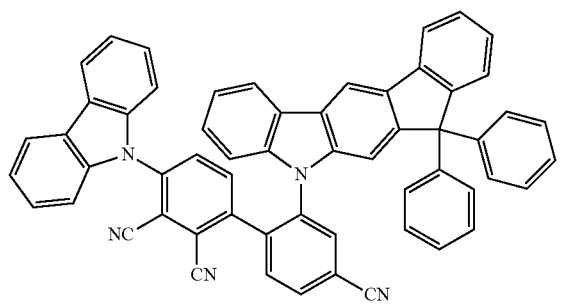
318
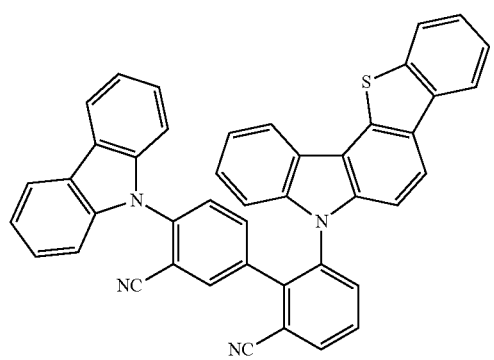
322
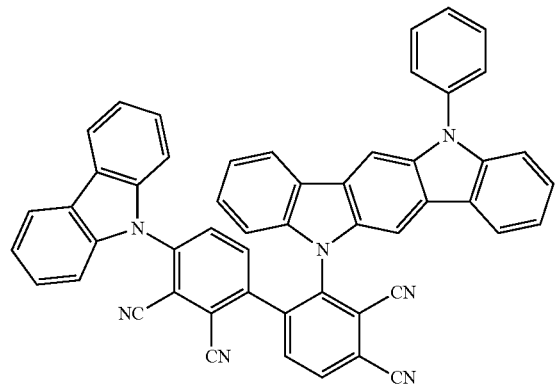
319
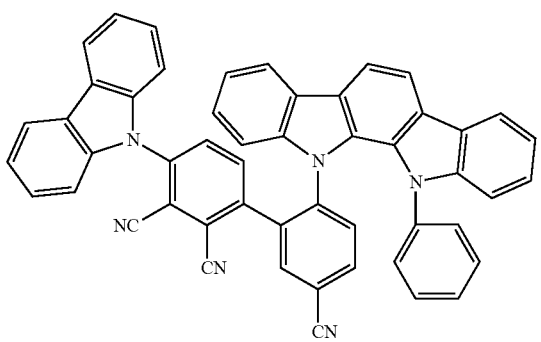
323
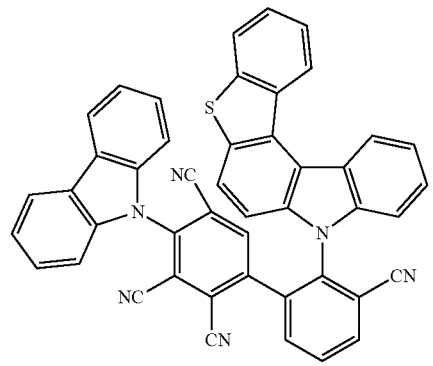
320
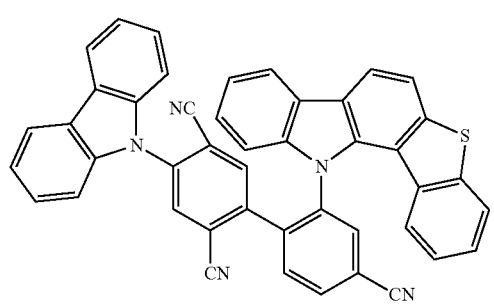
324
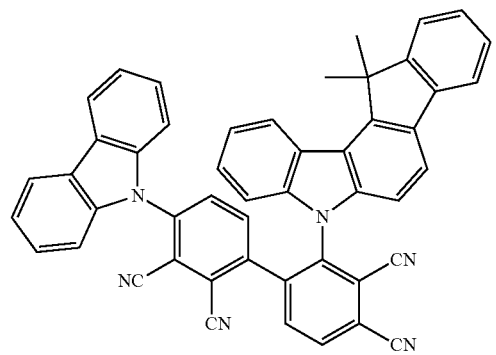

325 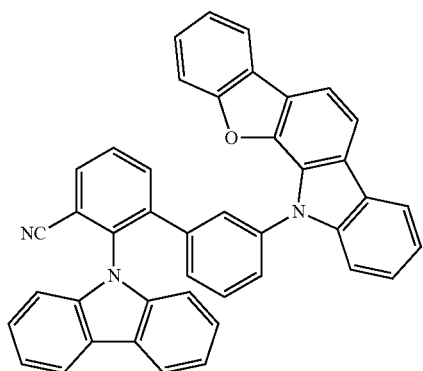
326 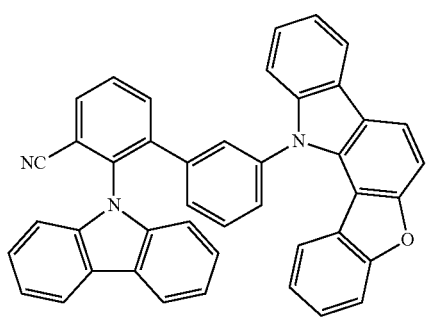
327 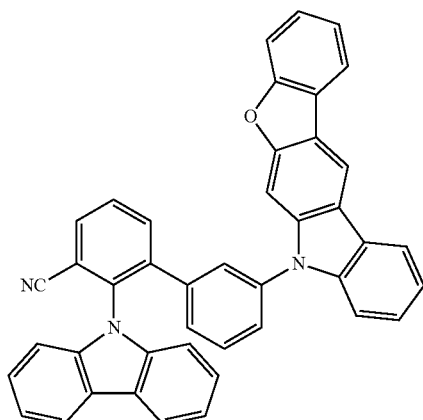
328 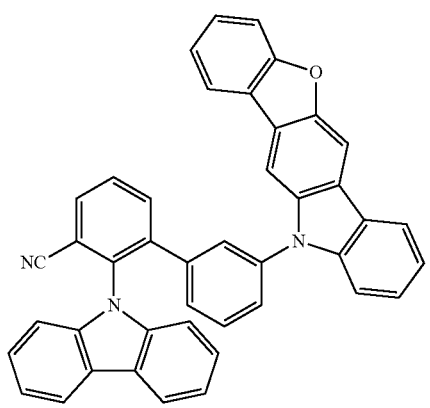
329 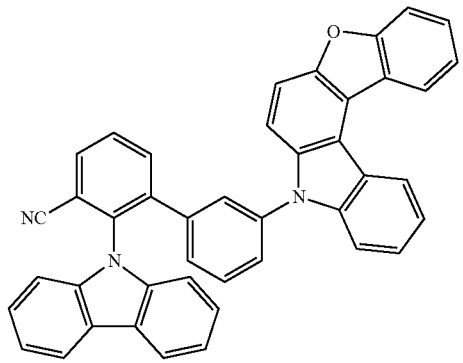
330 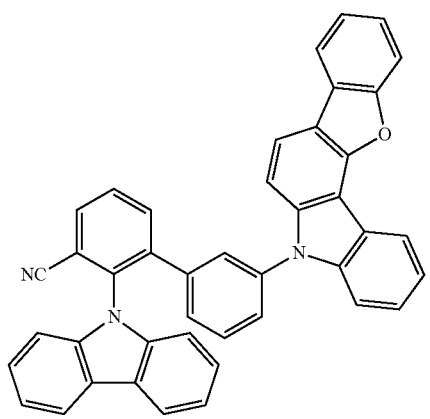
331 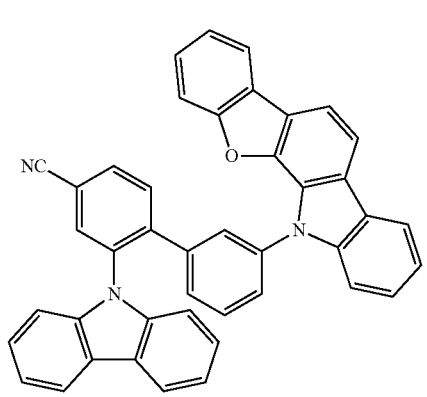
332 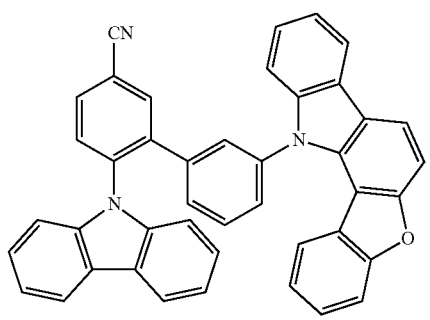

-continued
333
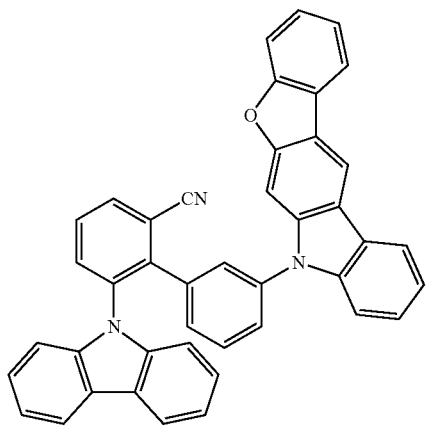
334
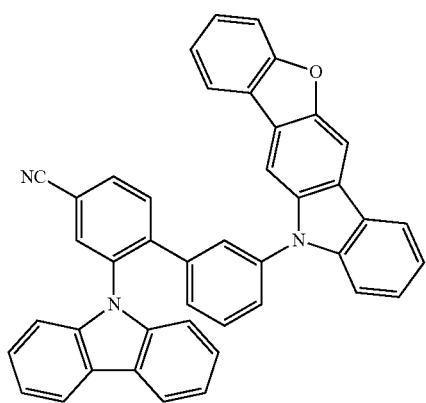
335
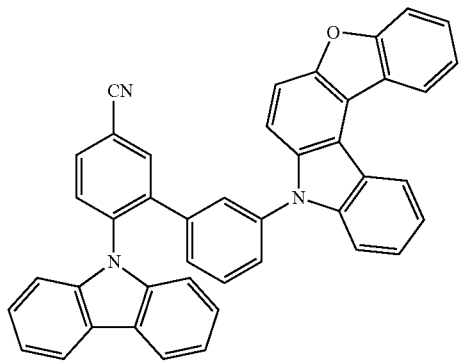
336
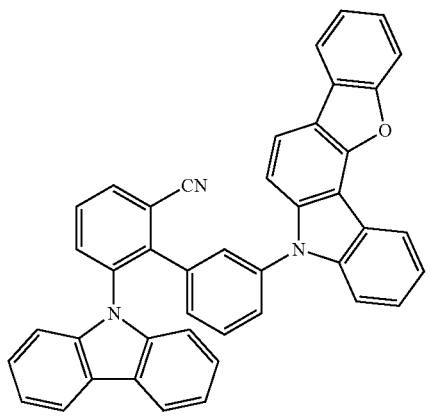
-continued
337
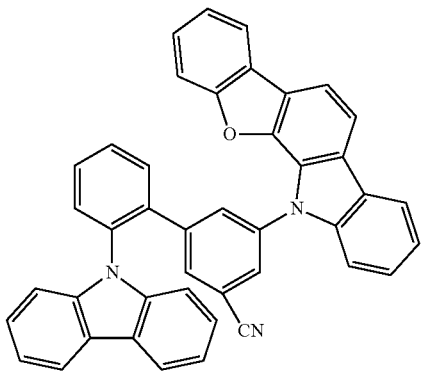
338
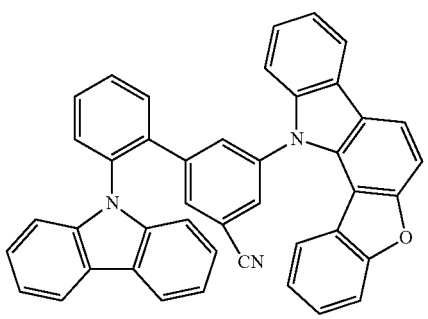
339
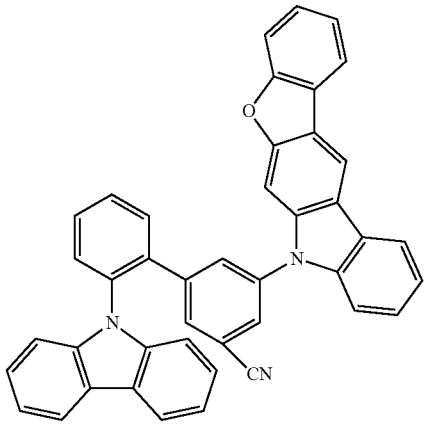
340
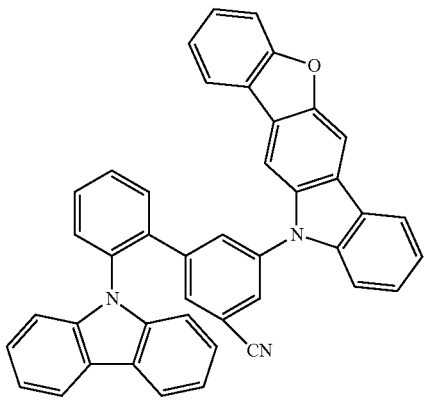

| 393 | 394 |
|---|---|
| -continued | -continued |
341
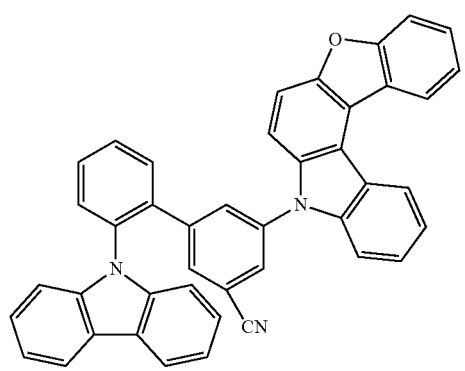
345
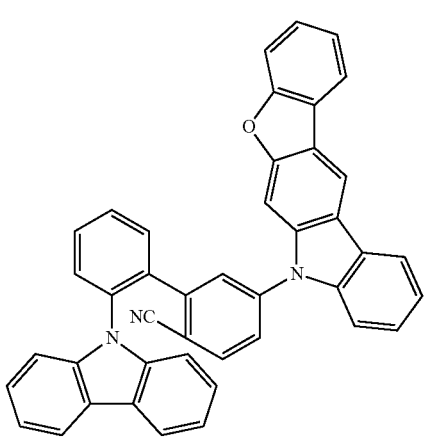
342
346
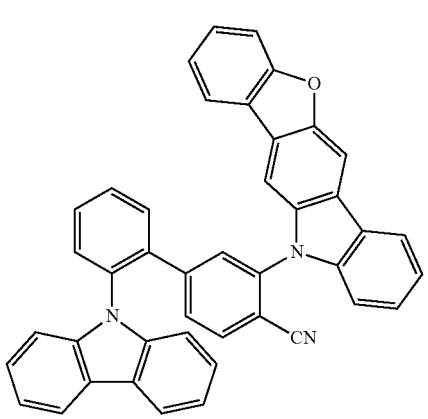
343
347
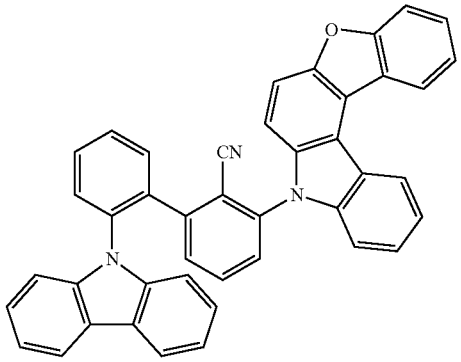
344
348
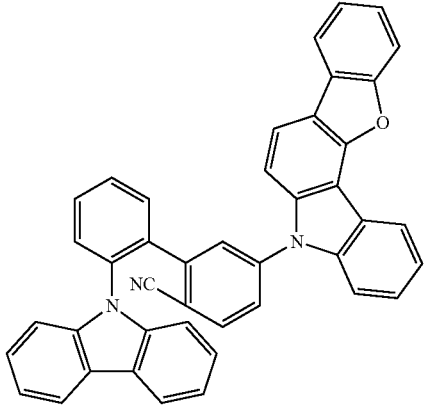

349
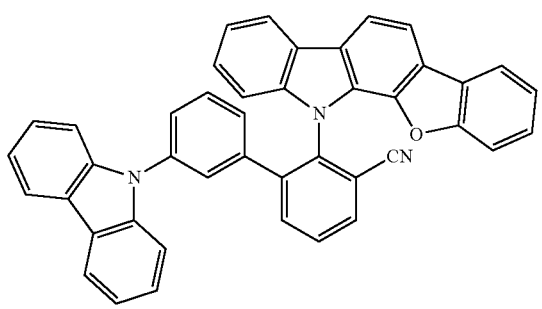
350
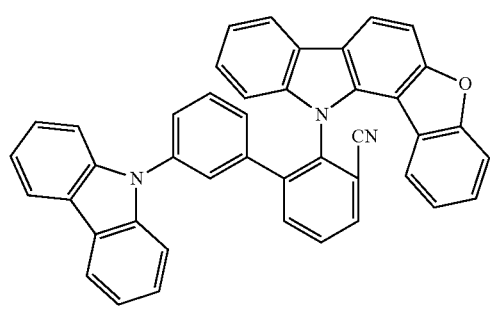
351
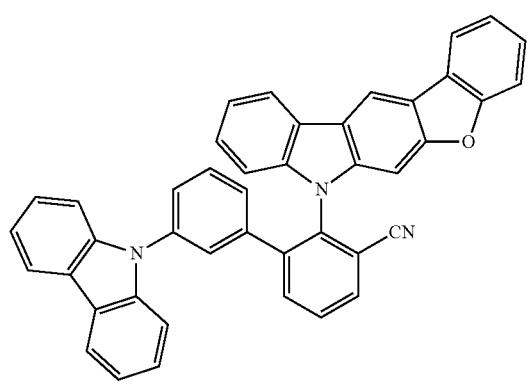
352
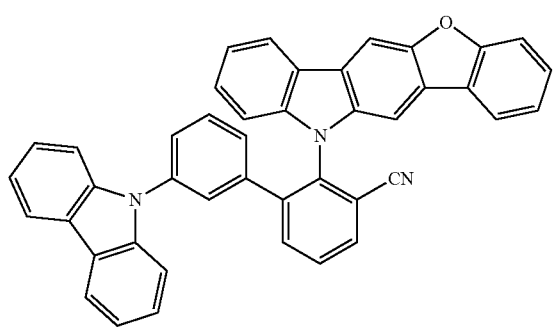
353
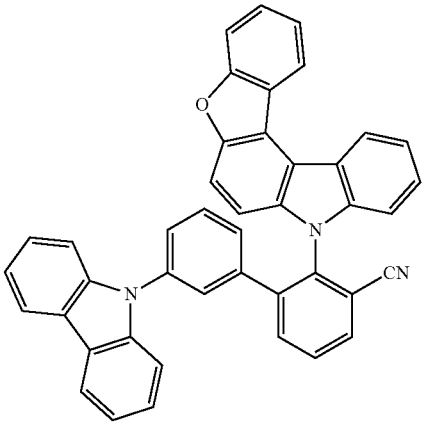
354
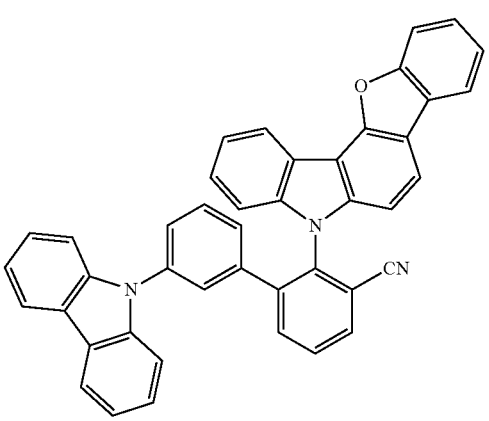
355
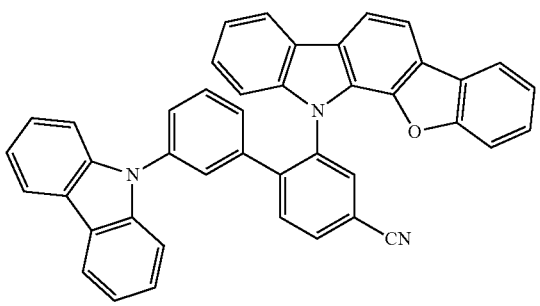
356
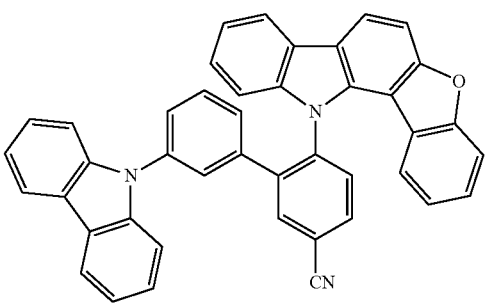

397
-continued
357
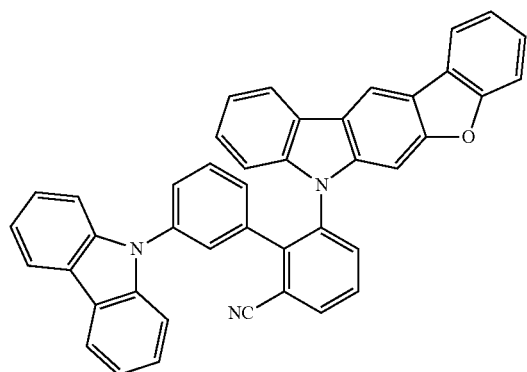
358
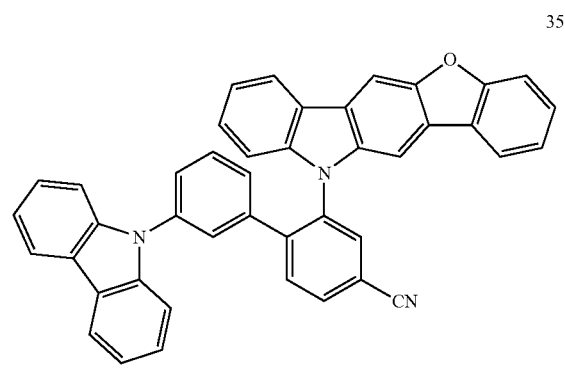
359
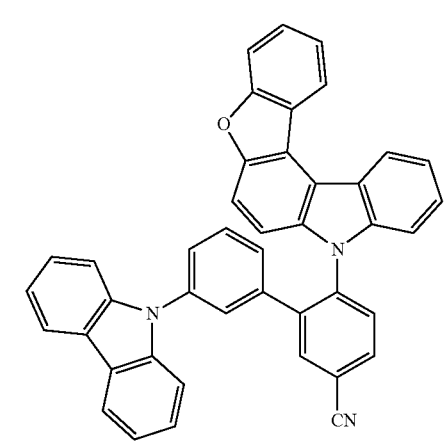
360
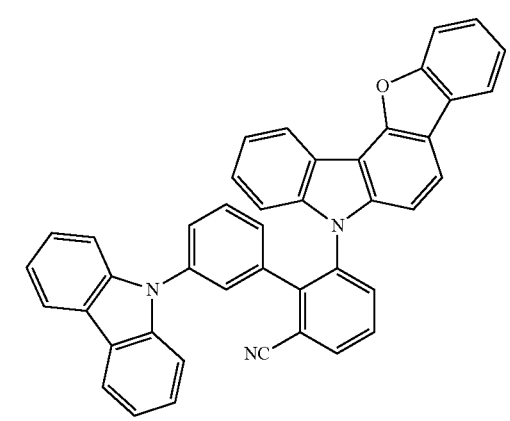
398
-continued
361
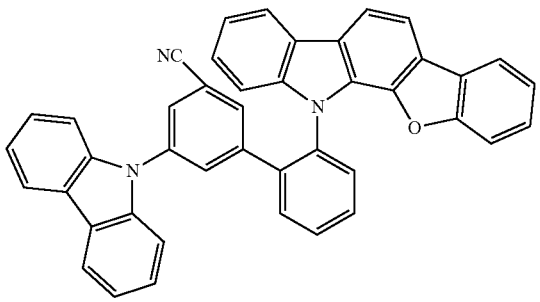
362
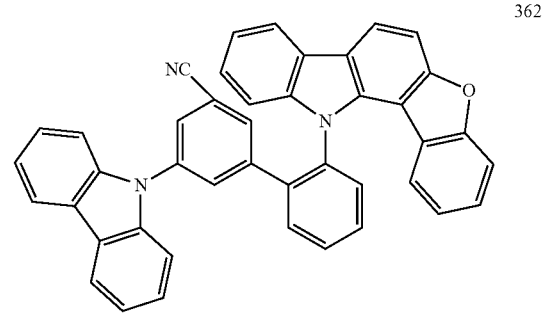
363
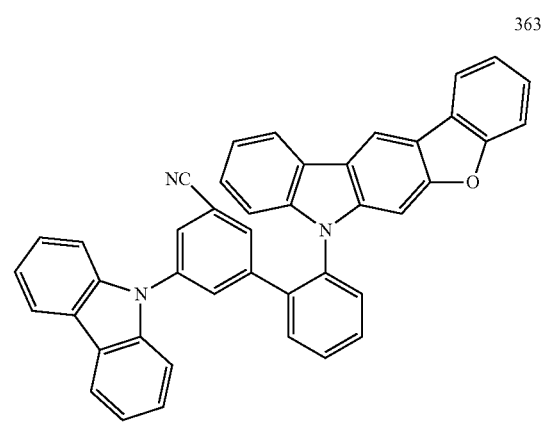
364
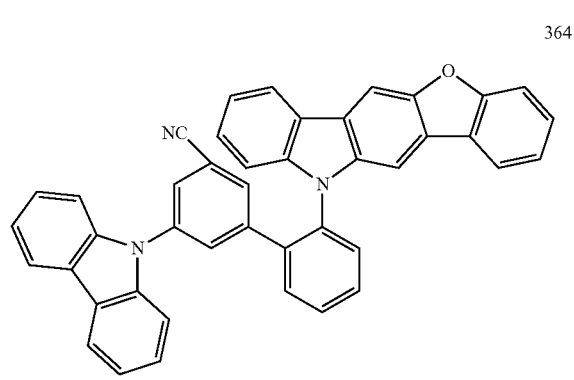

365 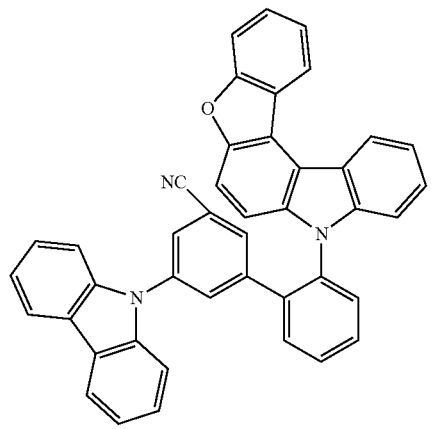
366 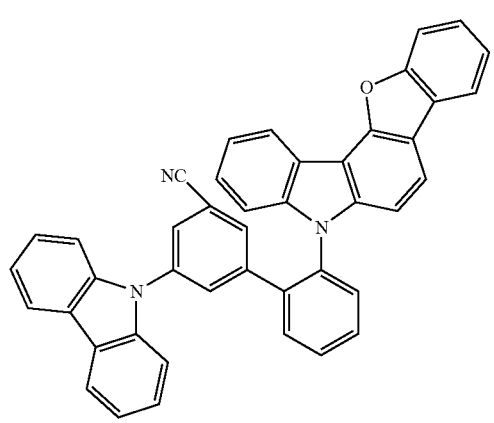
367 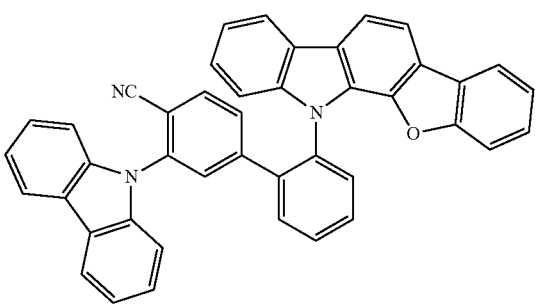
368 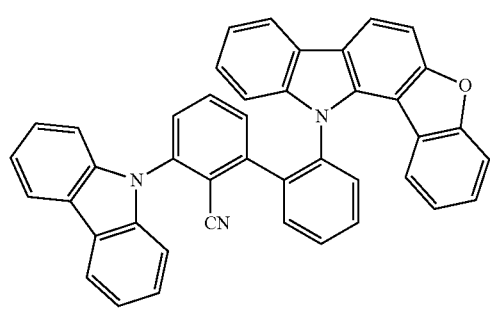
369 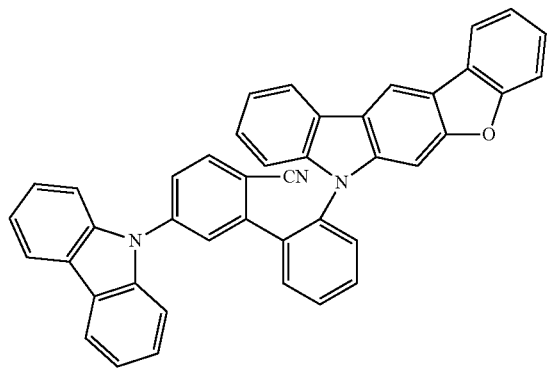
370 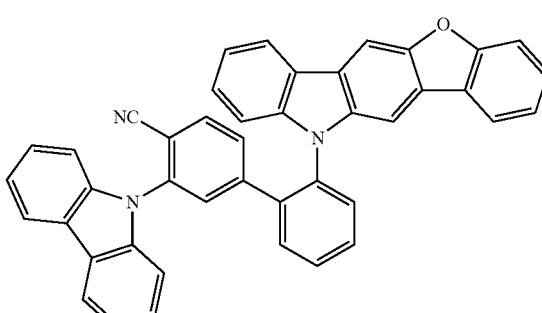
371 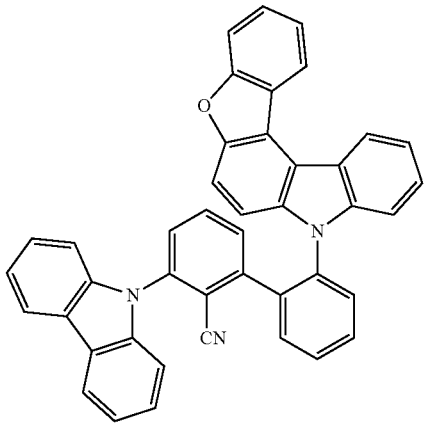
372 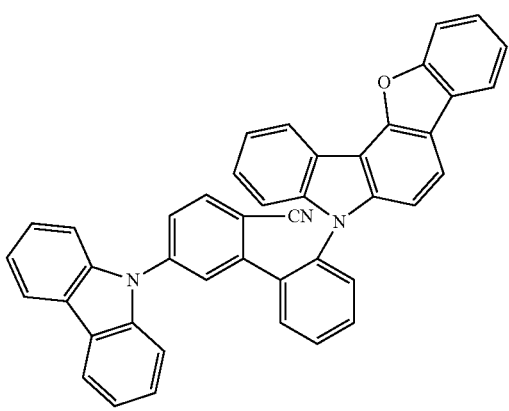

373
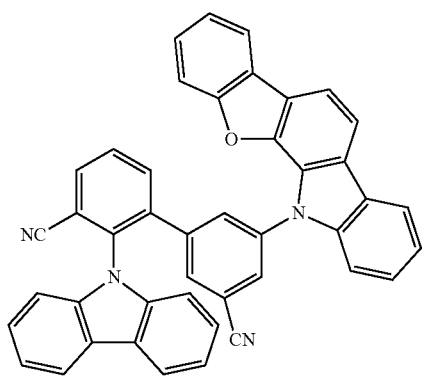
377
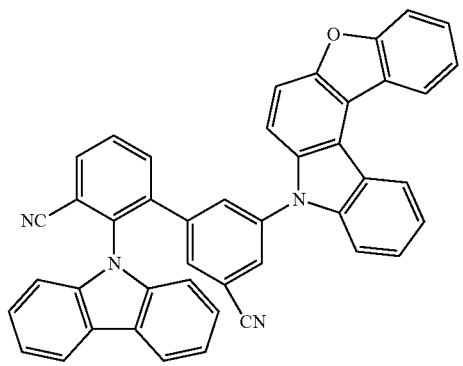
374
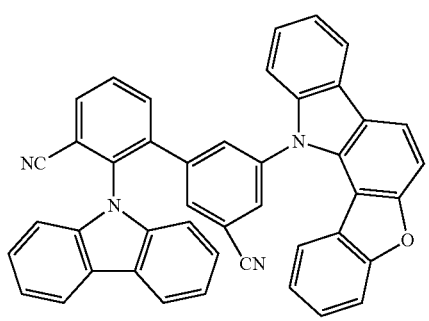
378
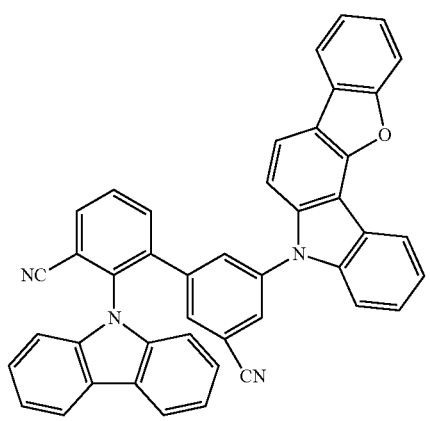
375
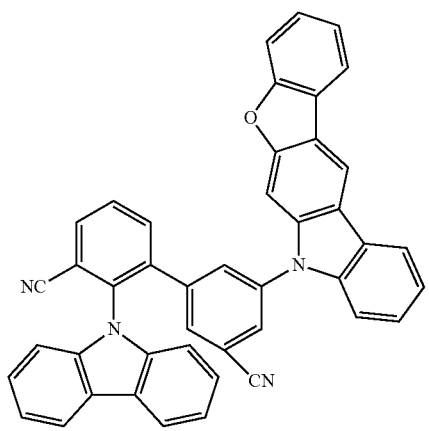
379
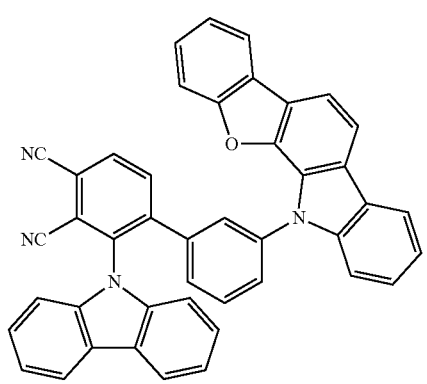
376
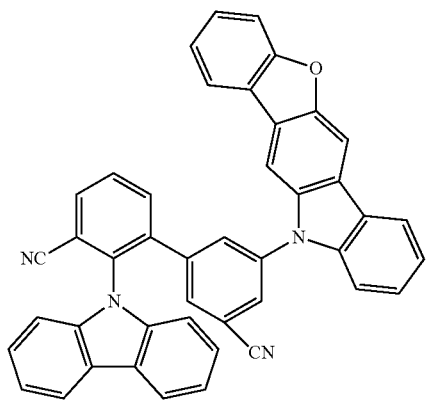
380
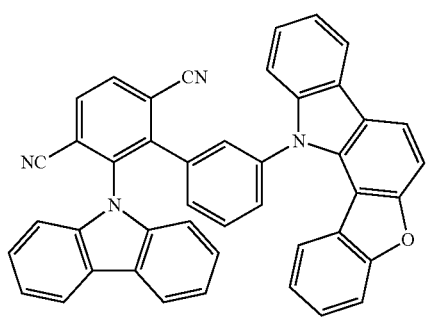

381 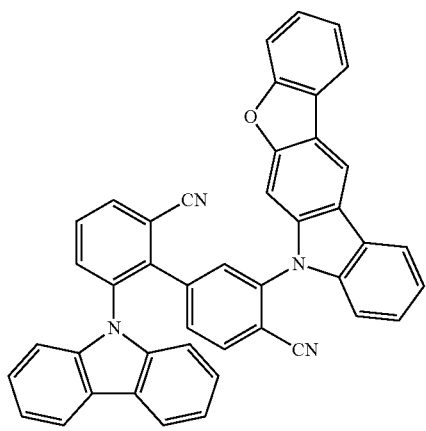
382 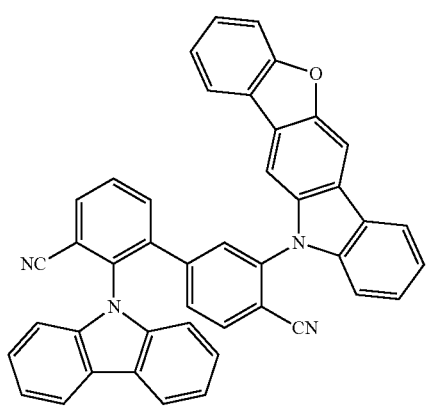
383 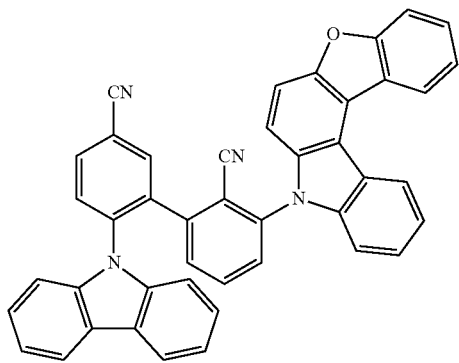
384 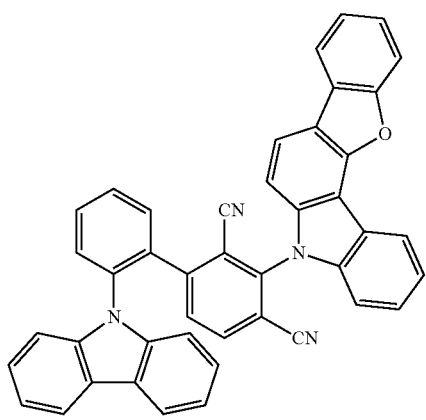
385 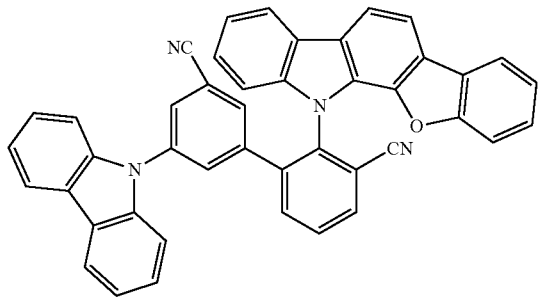
386 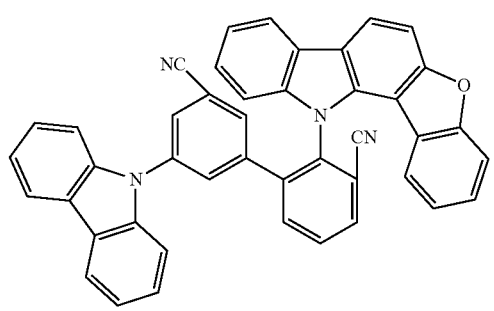
387 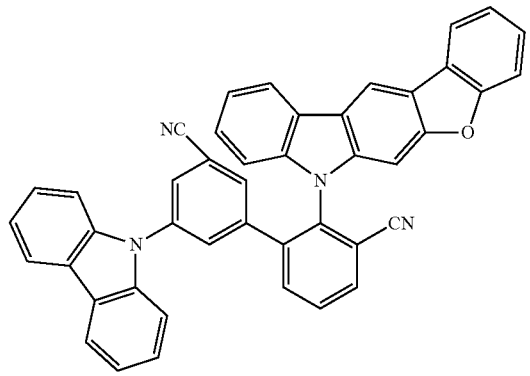
388 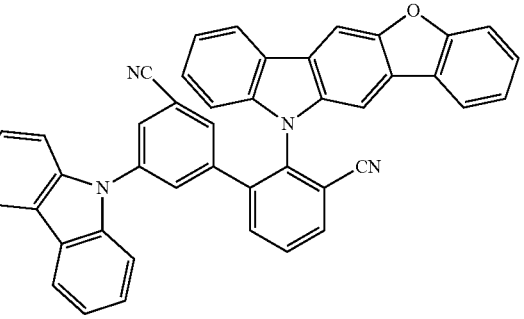

389
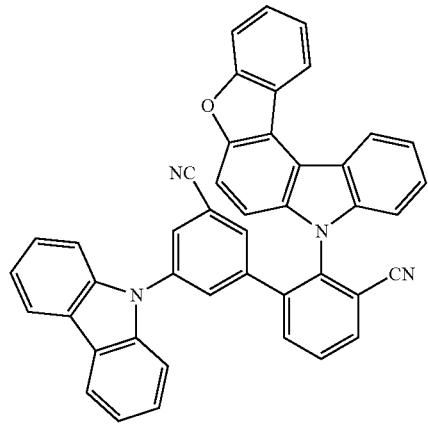
390
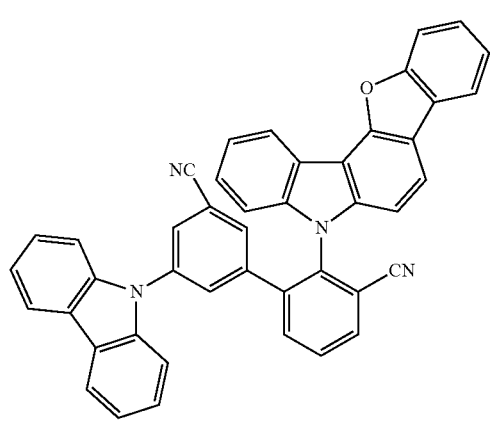
391
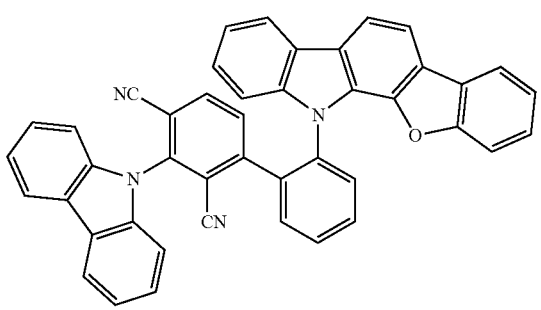
392
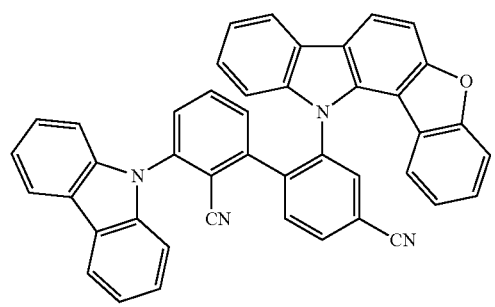
393
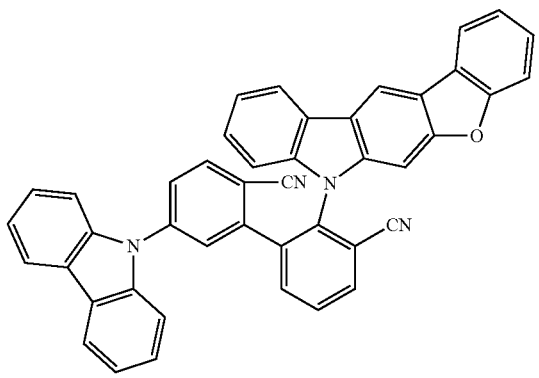
394
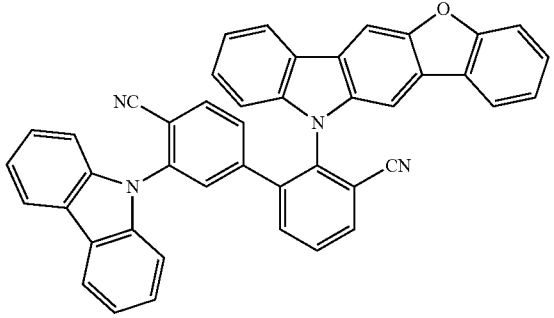
395
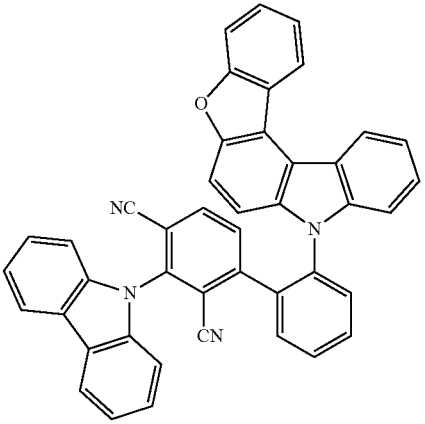
396
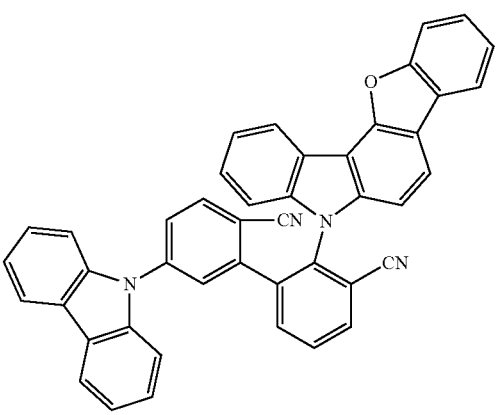

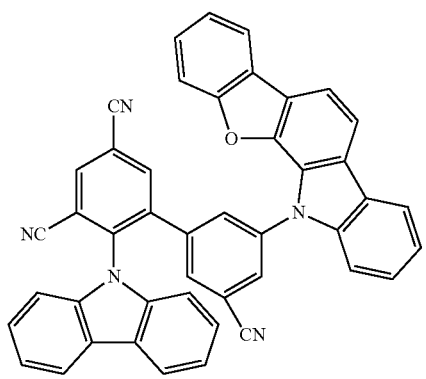
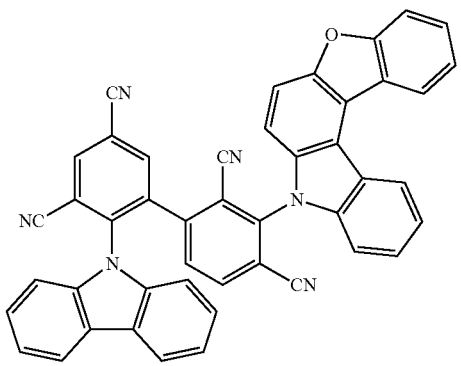
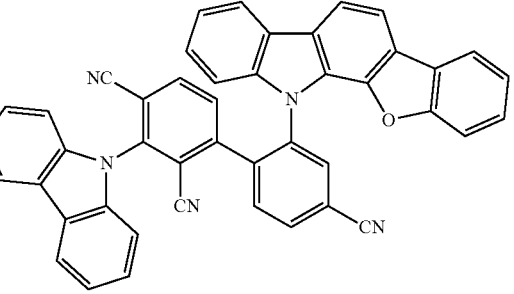
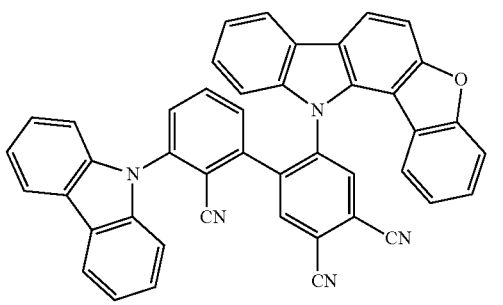

405
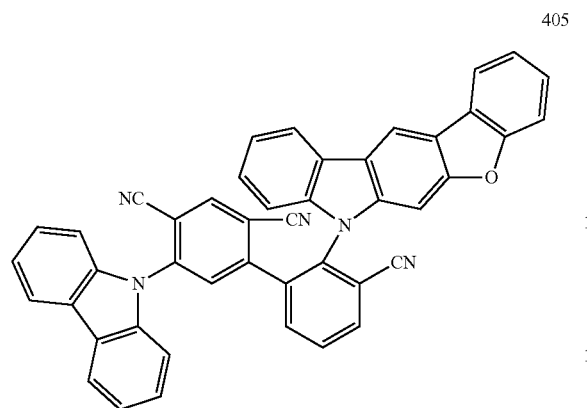
409
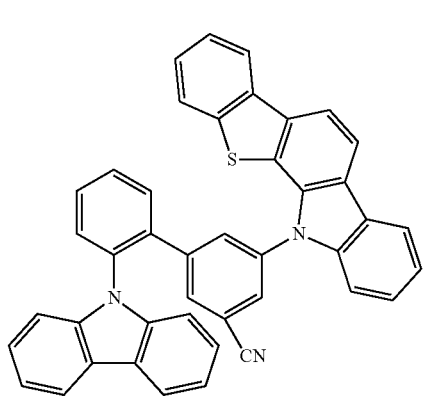
406
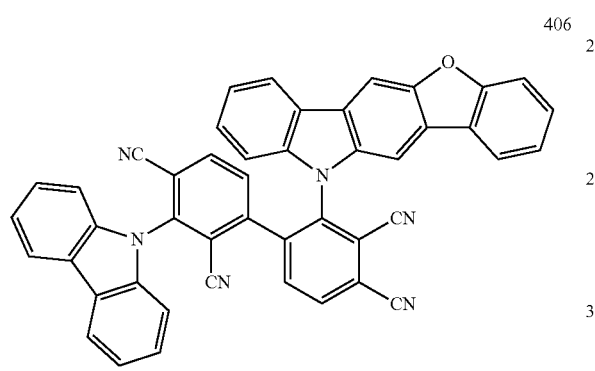
410
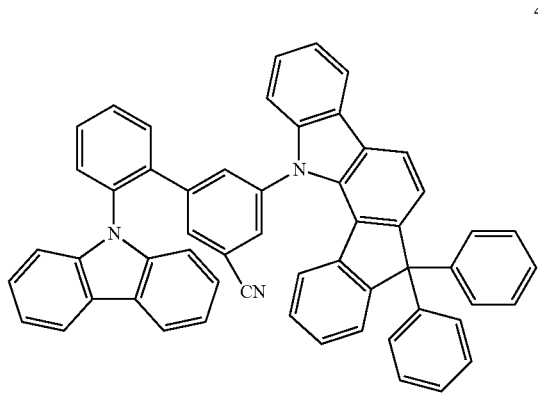
407
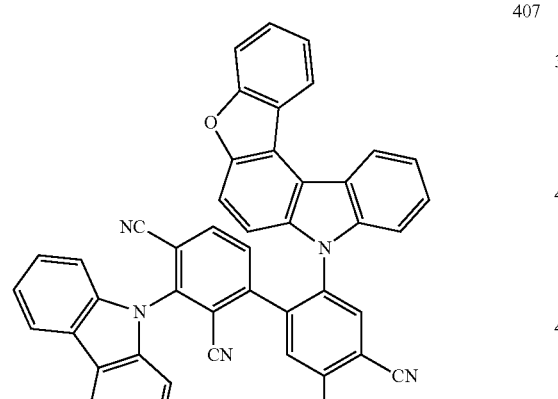
411
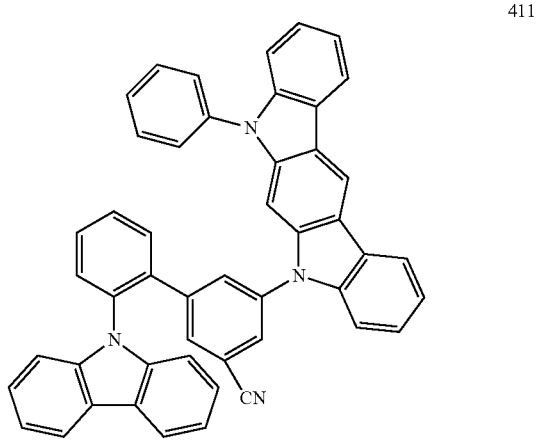
408
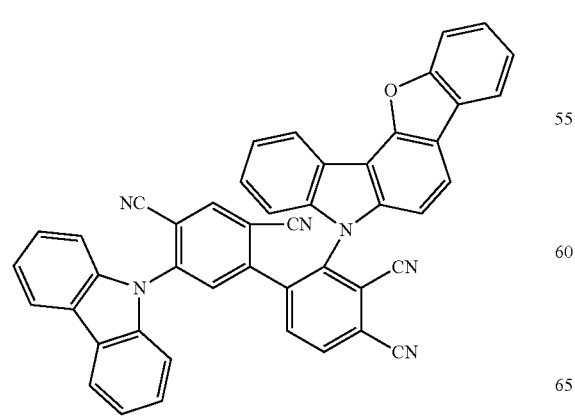
412
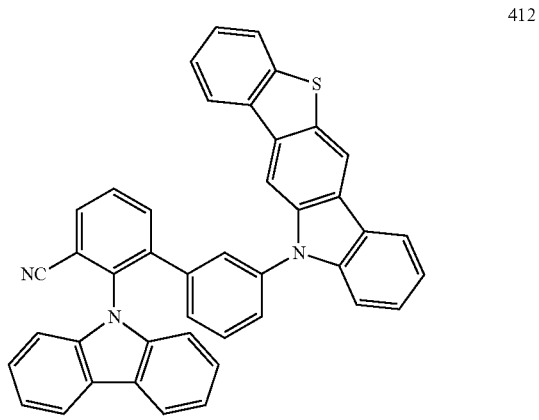

411
-continued
412
-continued
413
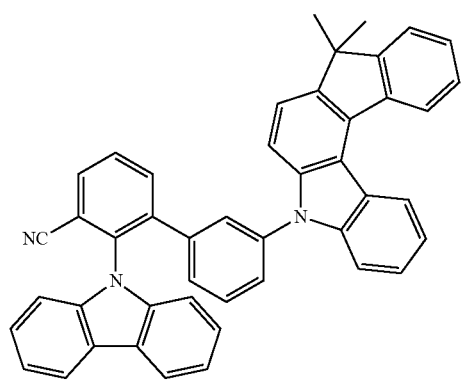
414
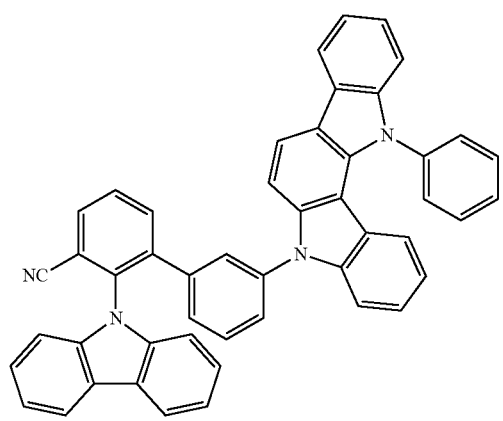
415
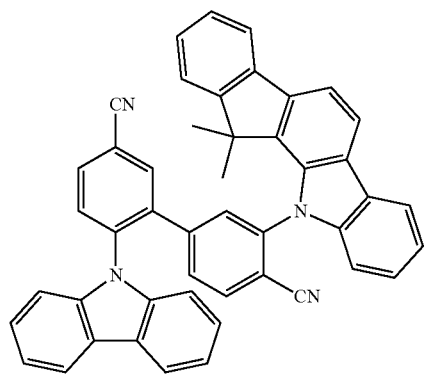
416
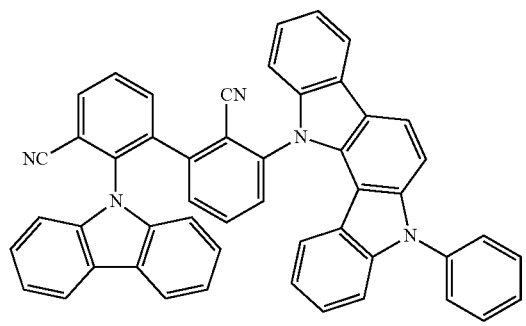
417
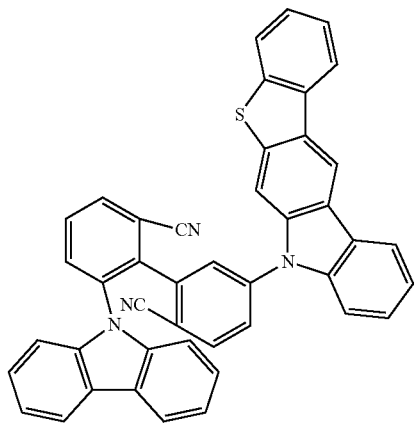
418
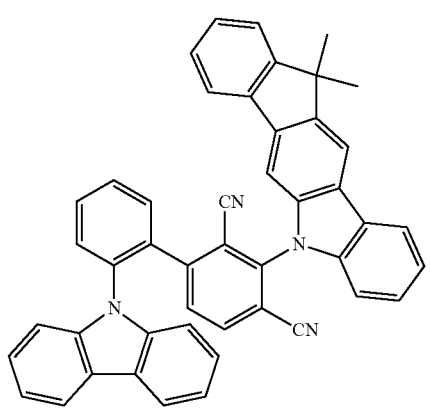
419
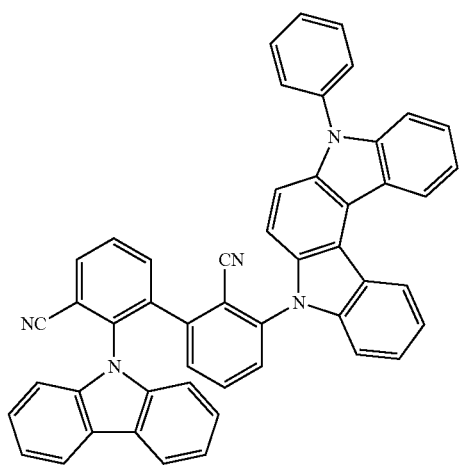

-continued
420
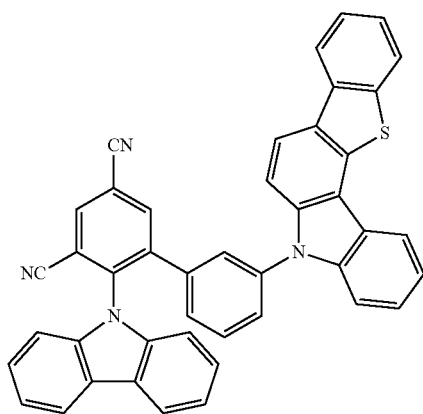
421
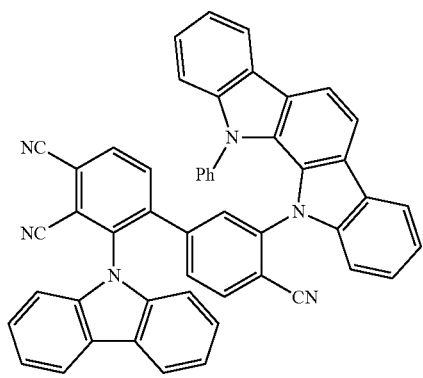
422
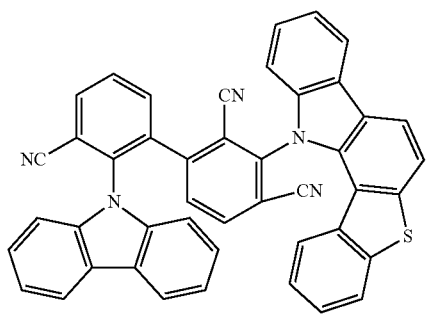
423
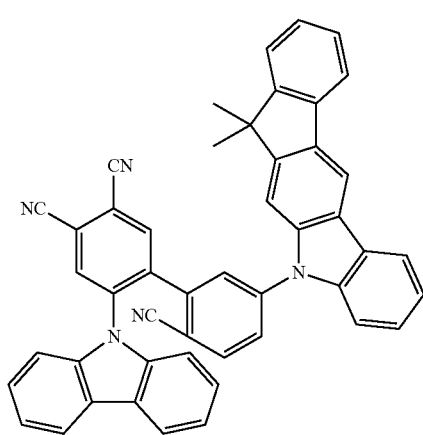
-continued
424
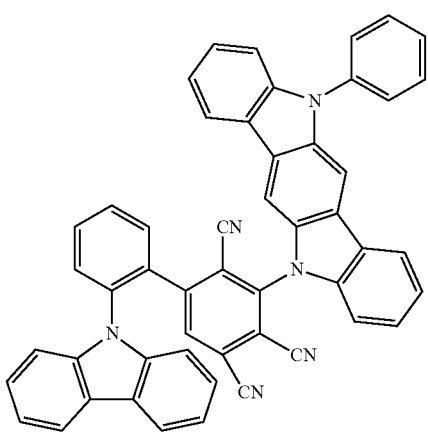
425
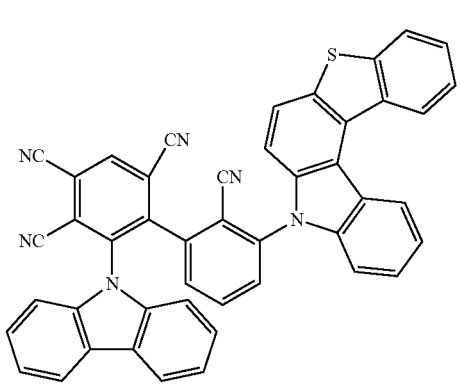
426
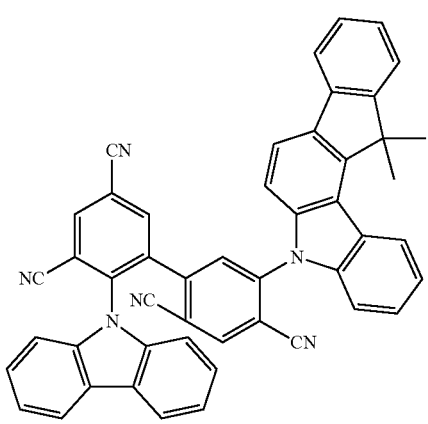
427
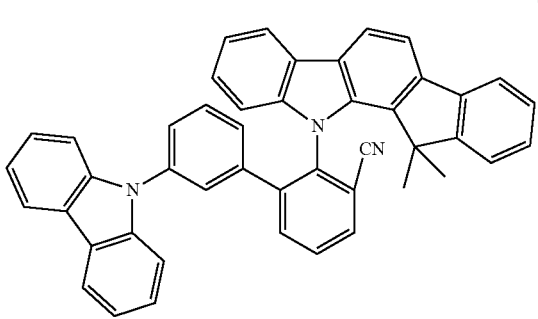

-continued
428
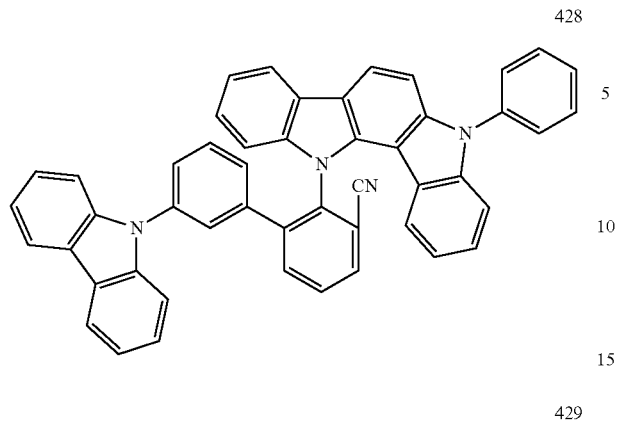
429
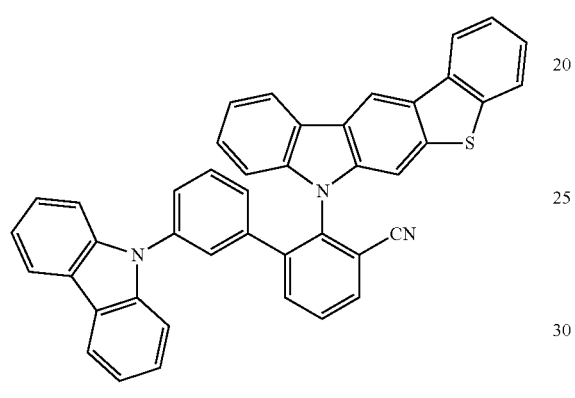
430
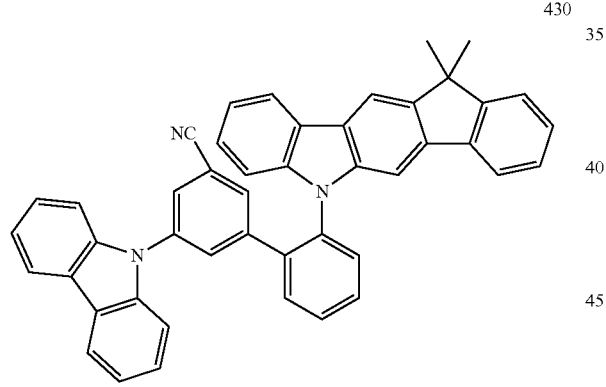
431
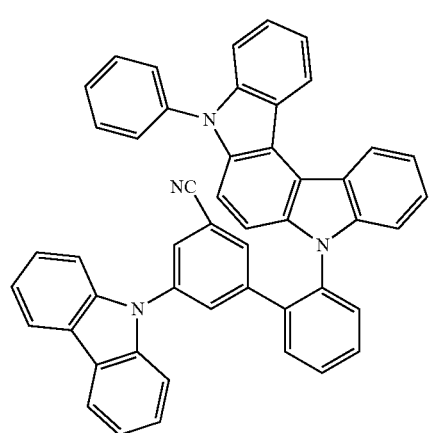
-continued
432
433
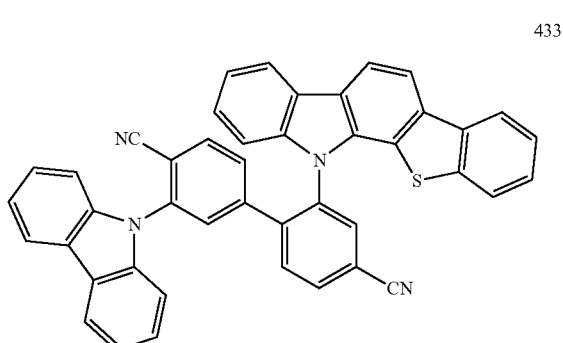
434
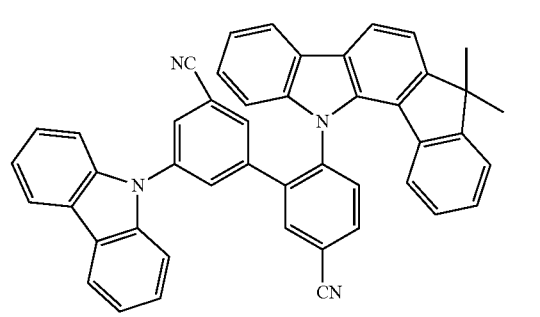
435
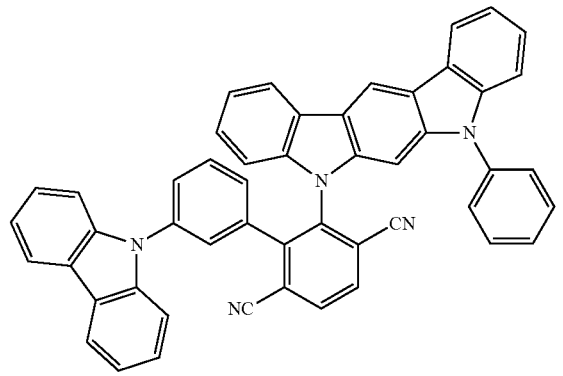

436
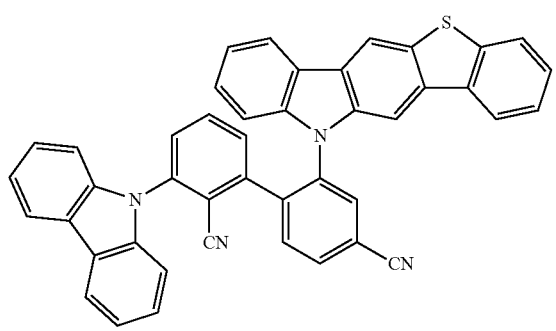
437
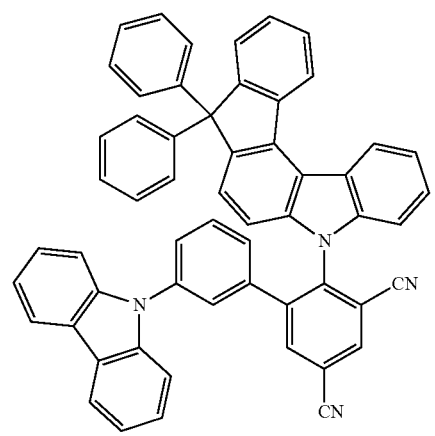
438
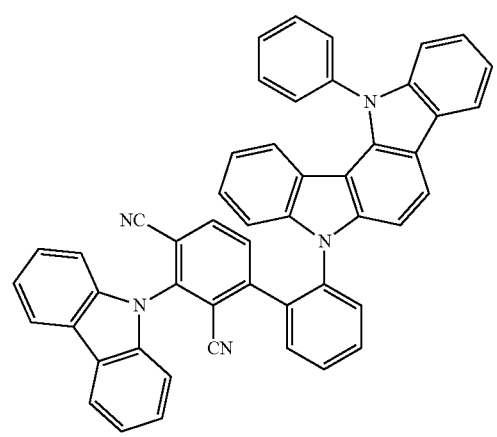
439
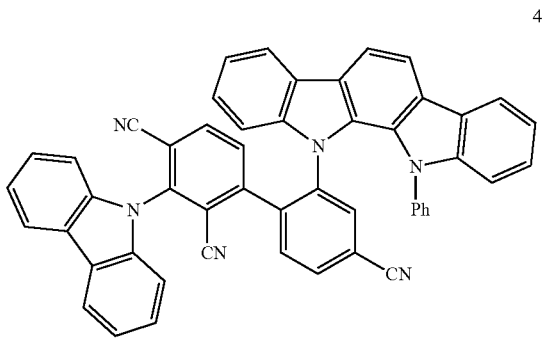
440
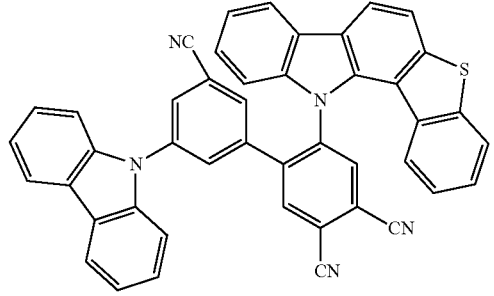
441
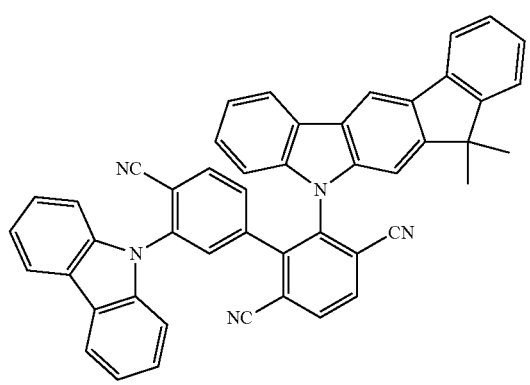
442
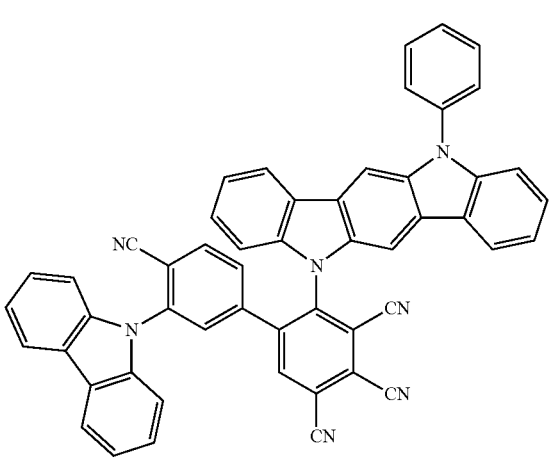
443
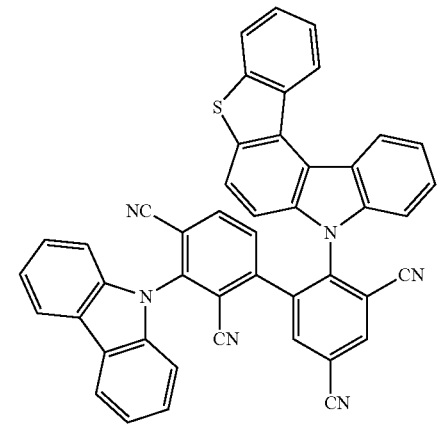

444
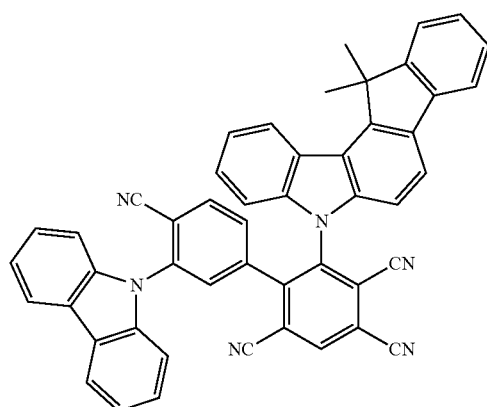
445
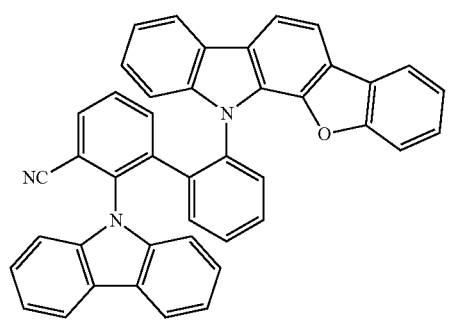
446
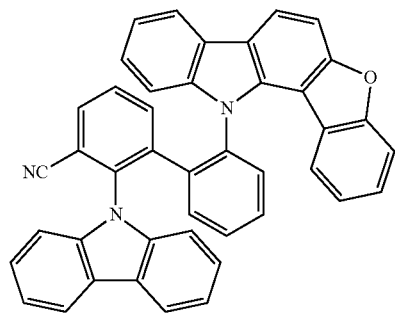
447
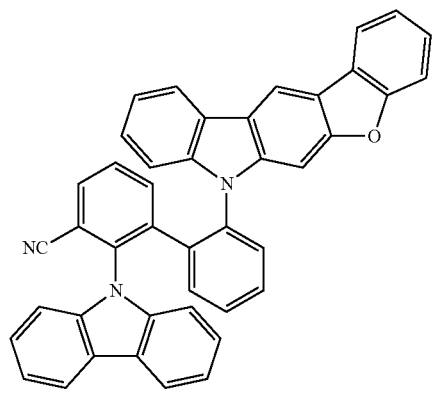
448
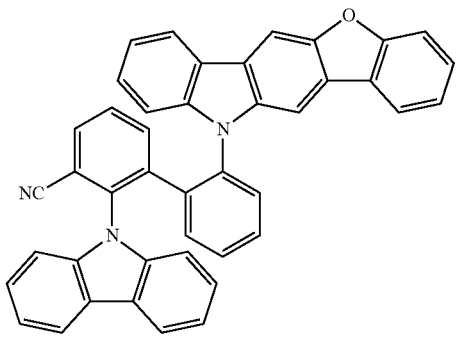
449
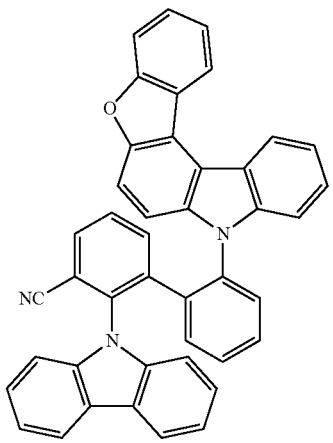
450
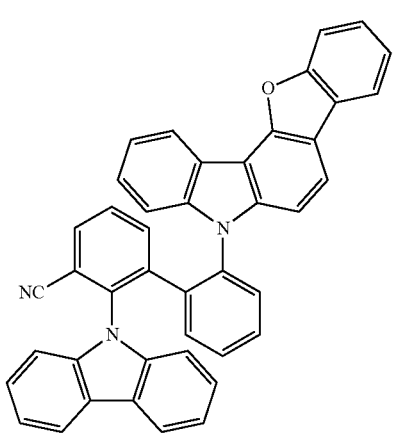
451
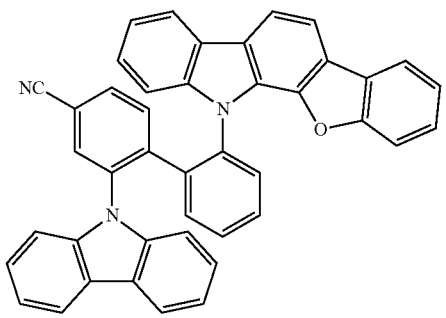

421
-continued
452
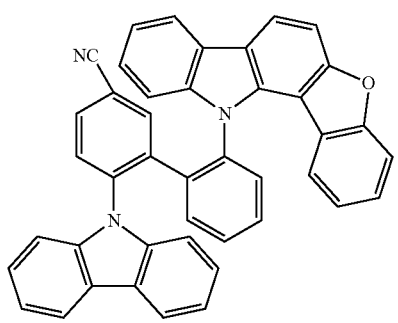
453
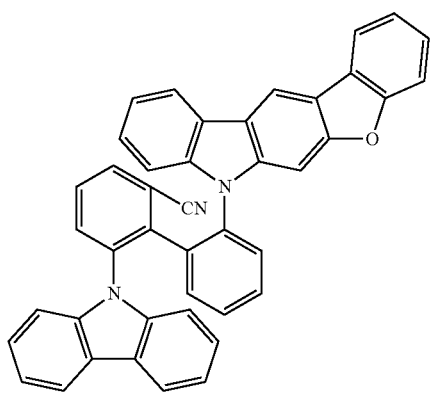
454
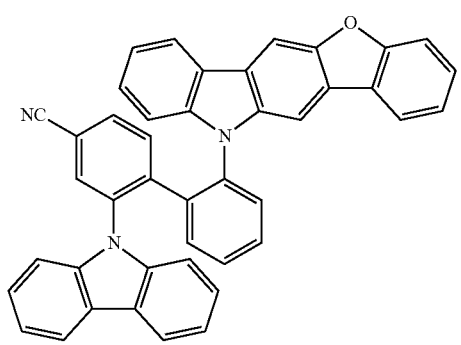
455
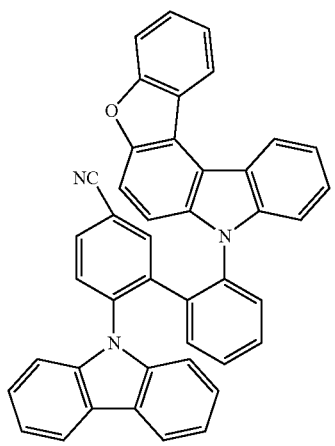
422
-continued
456
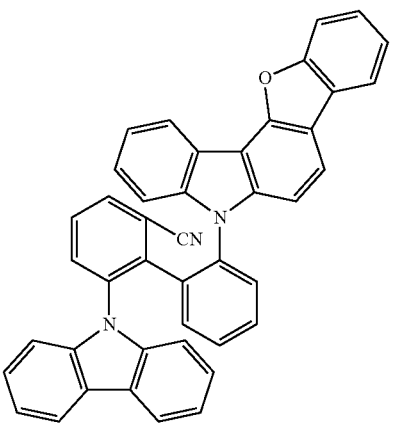
457
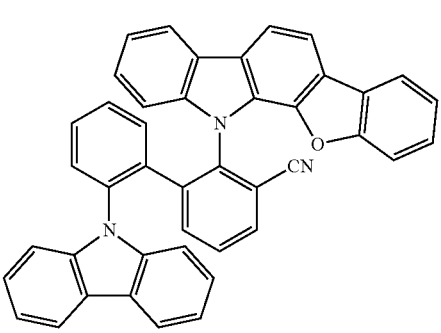
458
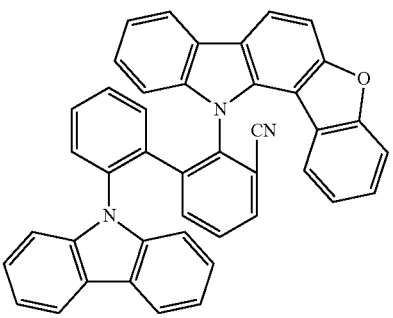
459
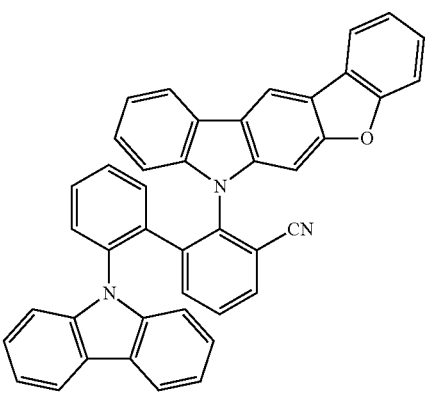

-continued
460
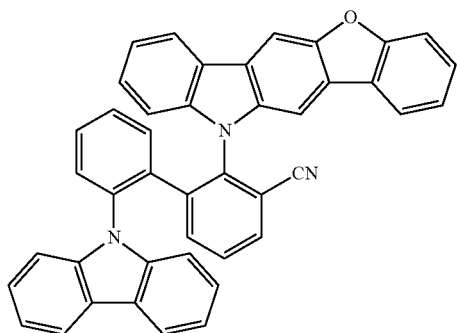
461
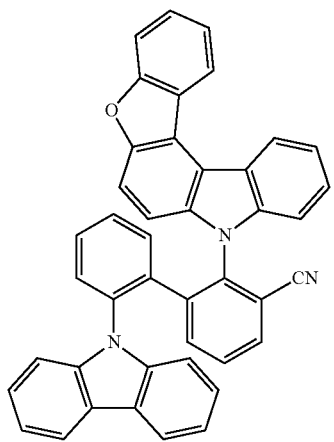
462
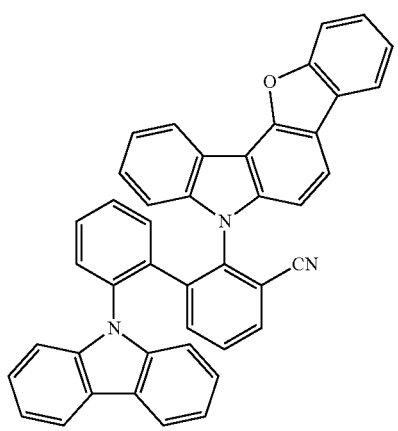
463
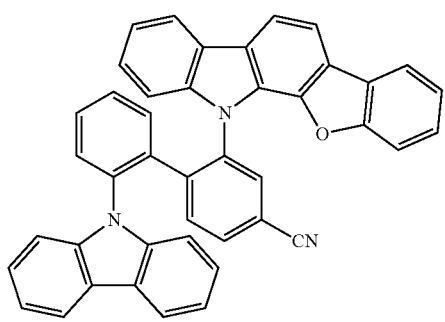
-continued
464
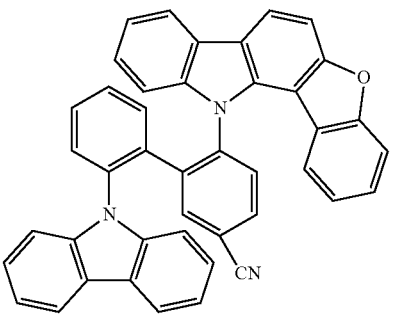
465
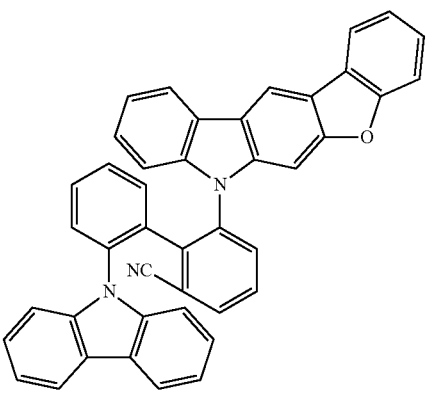
466
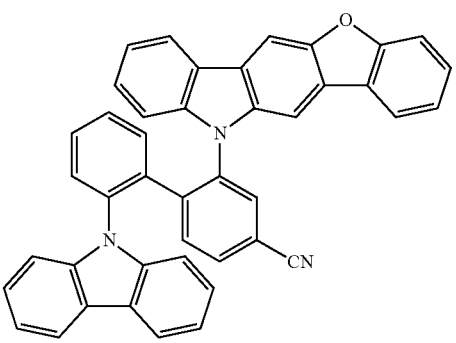
467
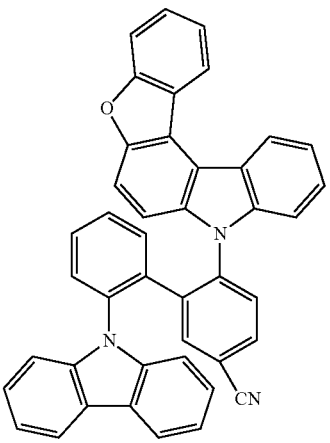

468
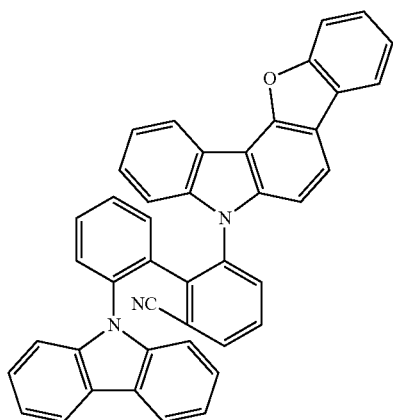
469
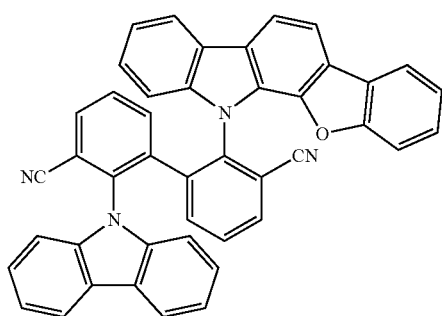
470
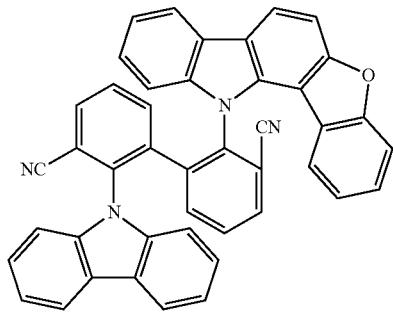
471
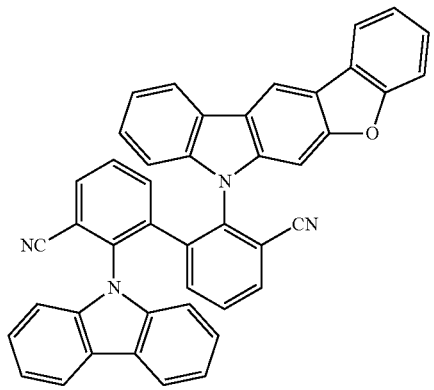
472
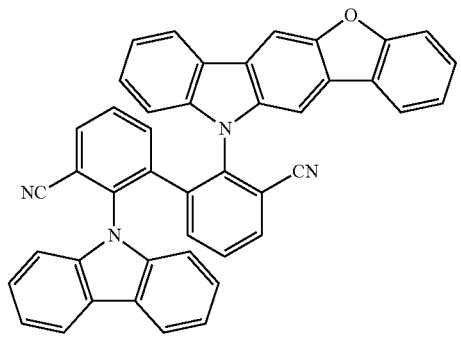
473
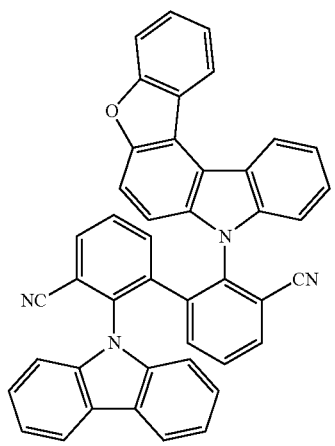
474
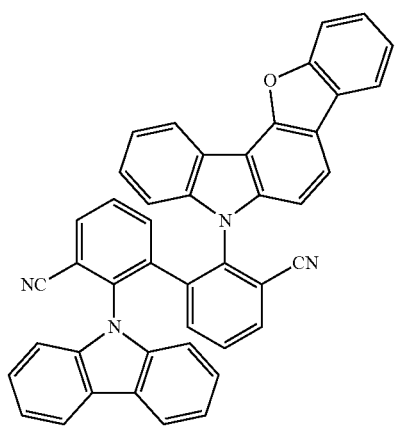
475
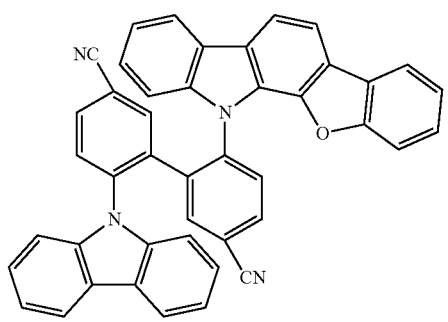

476
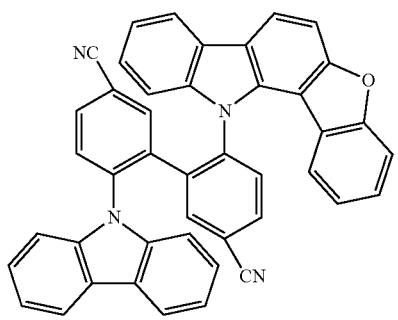
477
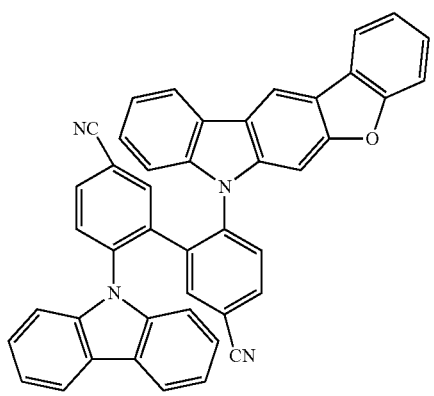
478
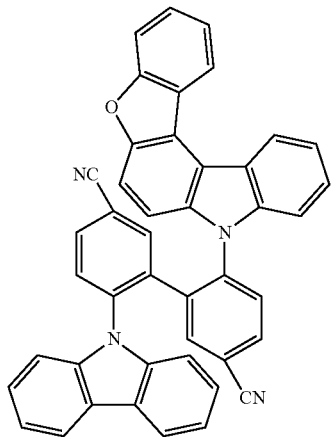
479
480
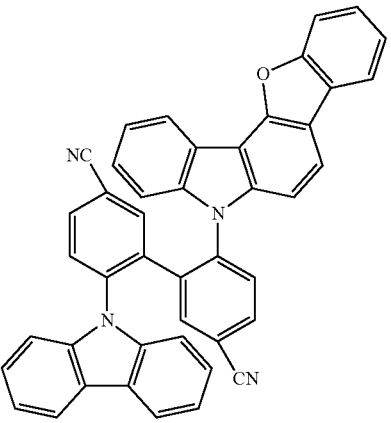
481
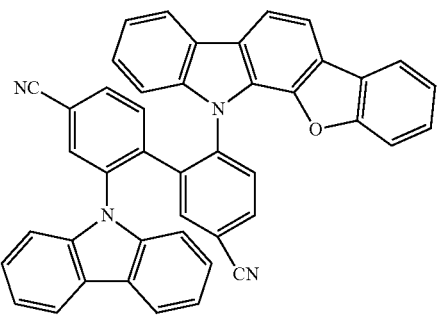
482
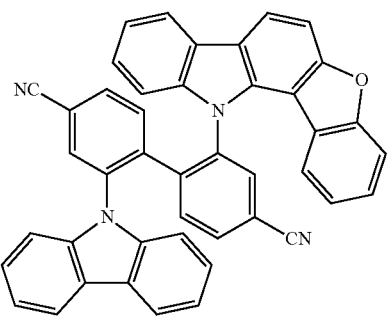
483
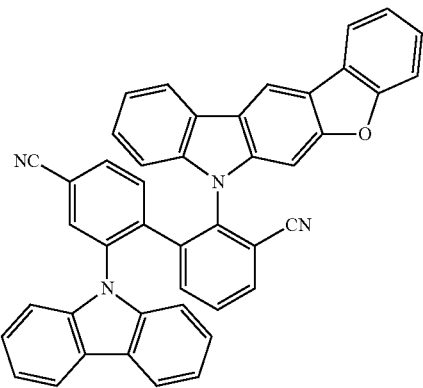

| 484 | 488 |
|---|---|
| 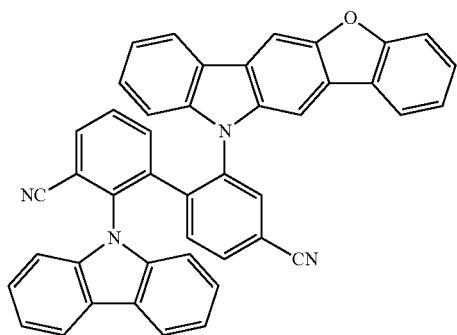 | 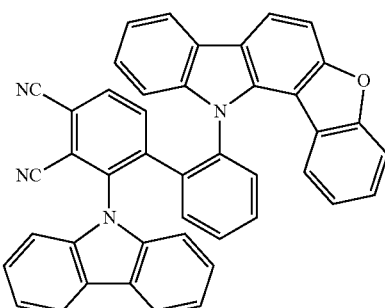 |
| 485 | 489 |
|---|---|
| 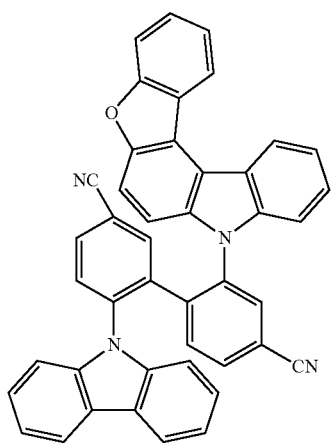 | 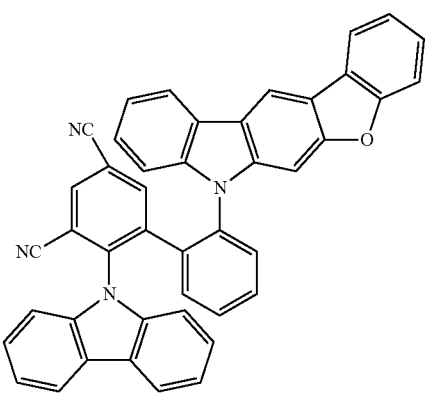 |
| 486 | 490 |
|---|---|
| 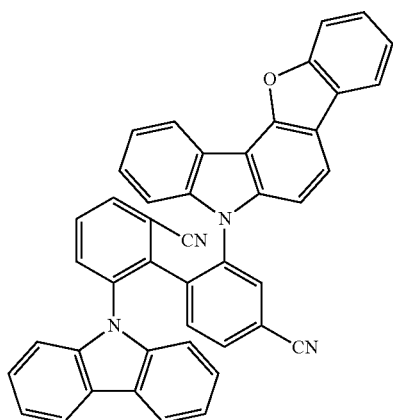 | 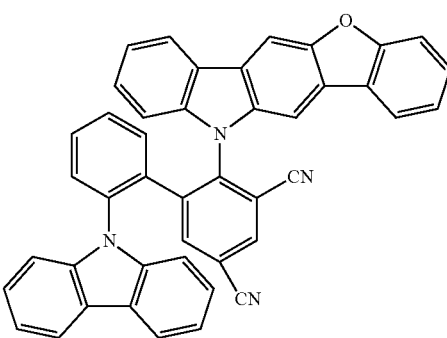 |
| 487 | 491 |
|---|---|
| 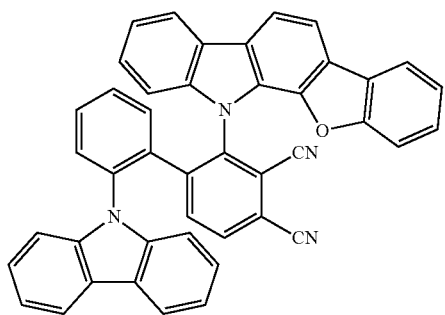 | 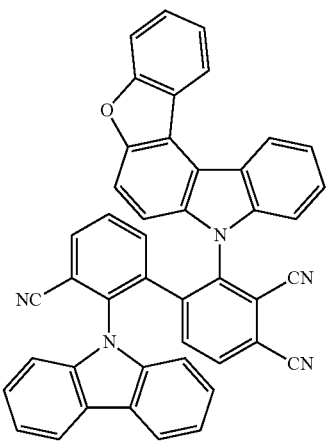 |

431
-continued
492
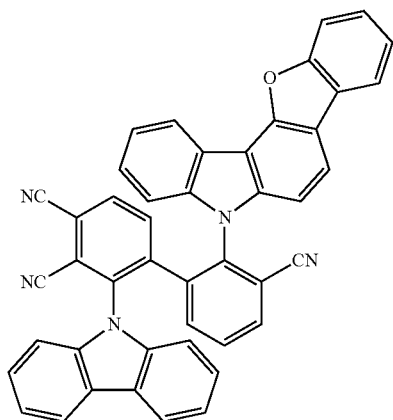
493
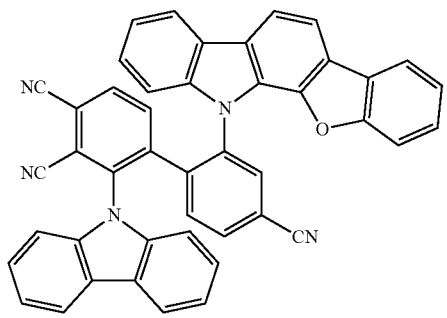
494
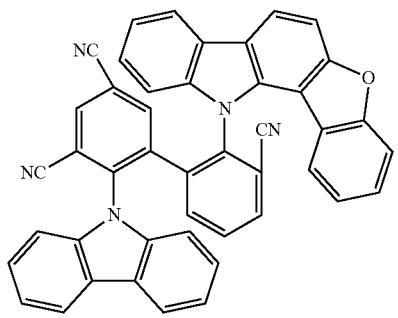
495
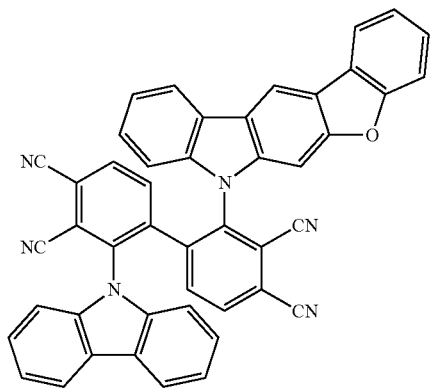
432
-continued
496
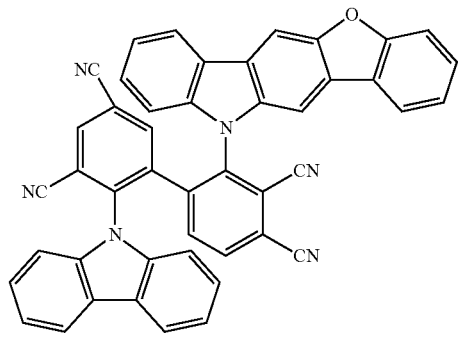
497
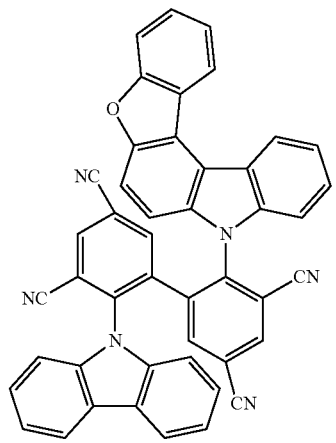
498
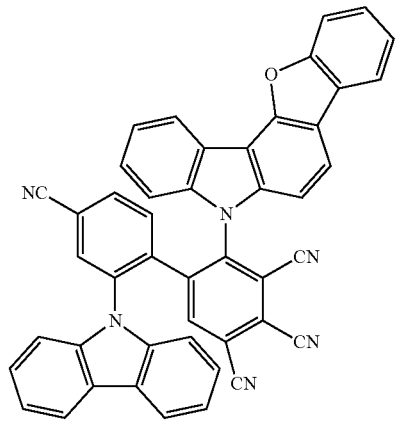
499
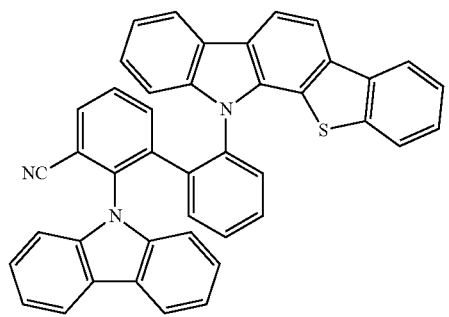

-continued
500
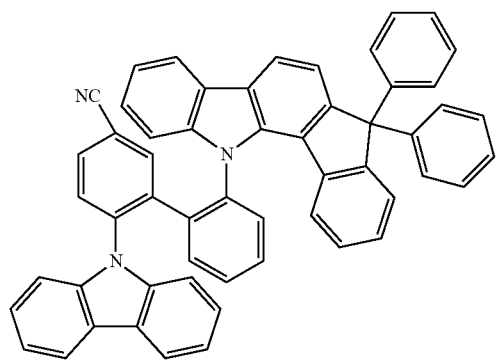
501
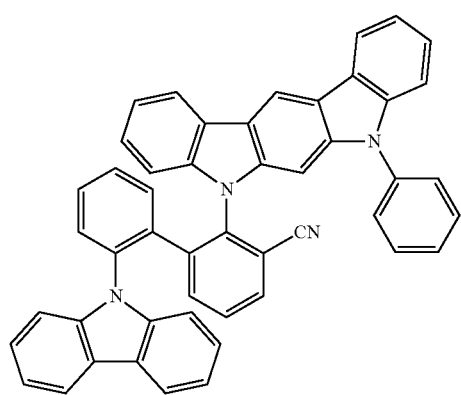
502
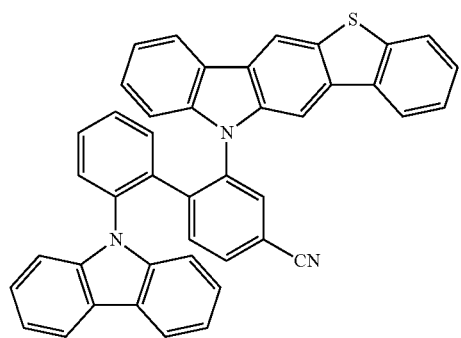
503
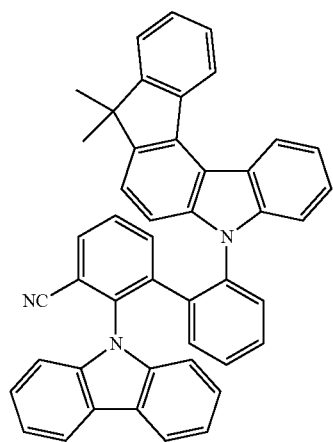
-continued
504
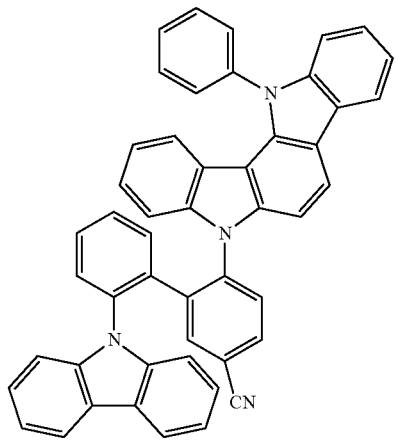
505
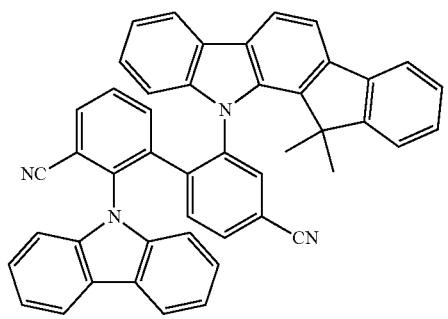
506
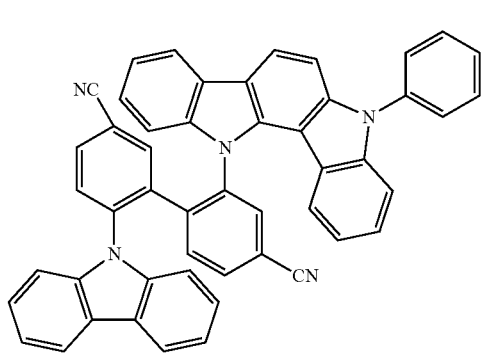
507
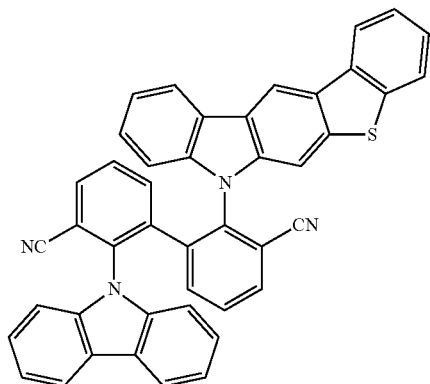

-continued
508
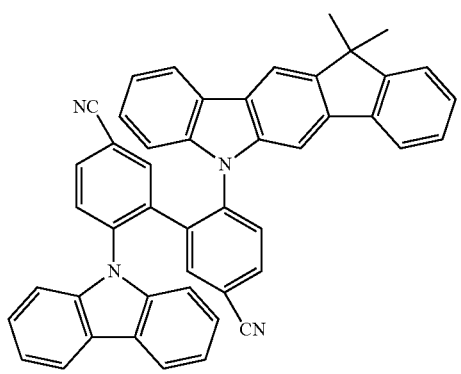
509
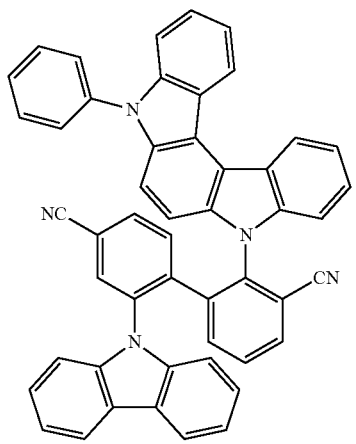
510
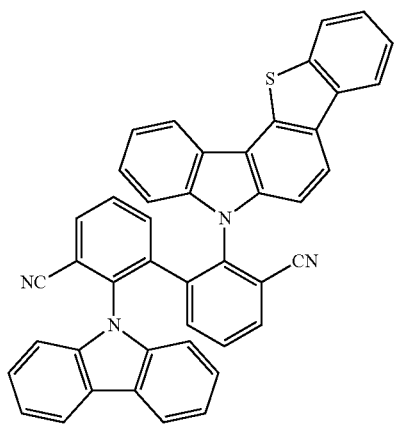
511
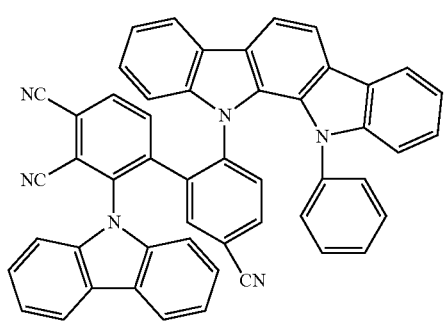
-continued
512
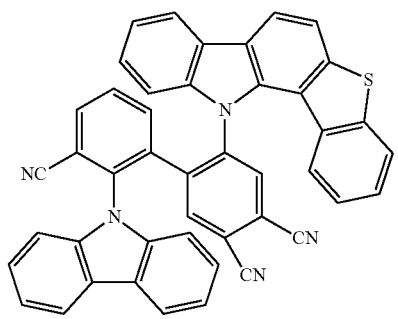
513
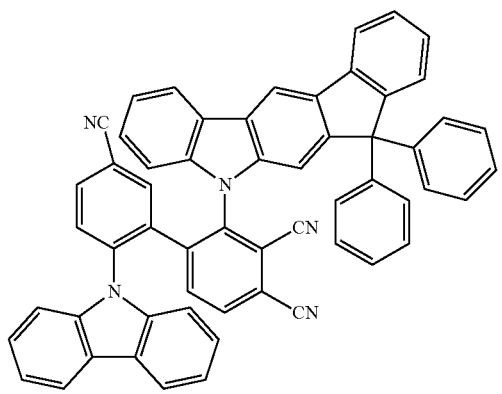
514
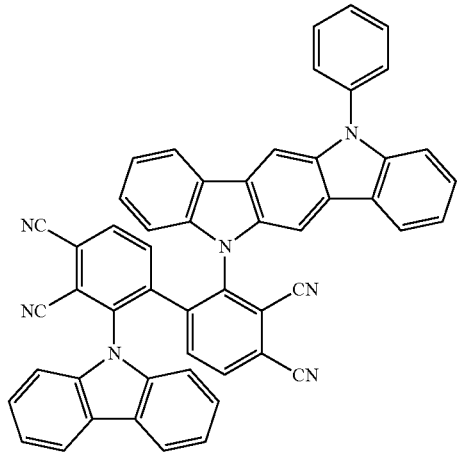
515
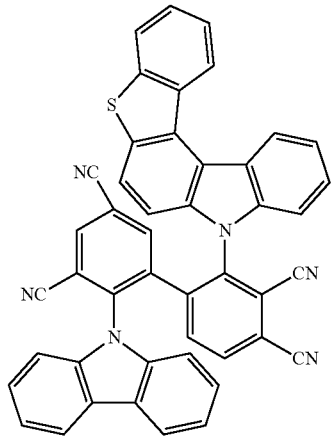

516
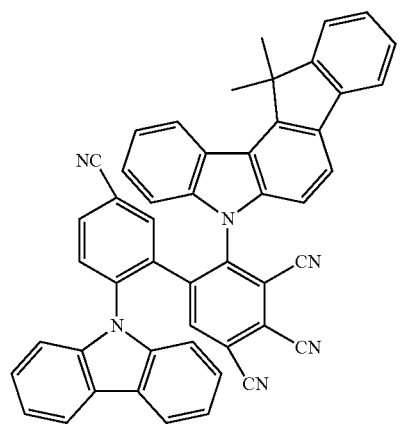
517
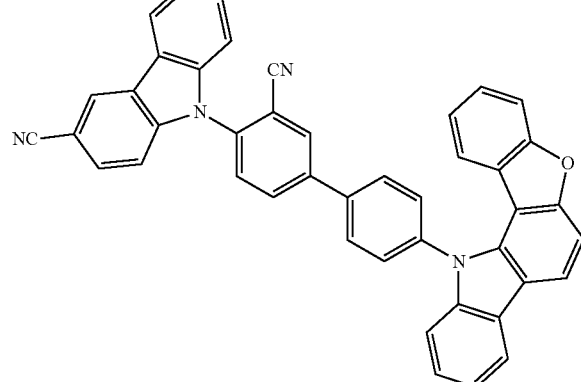
518
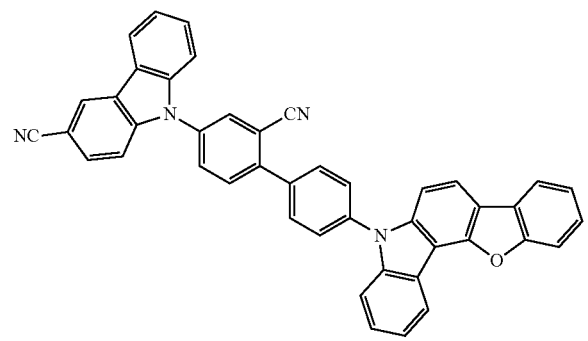
519
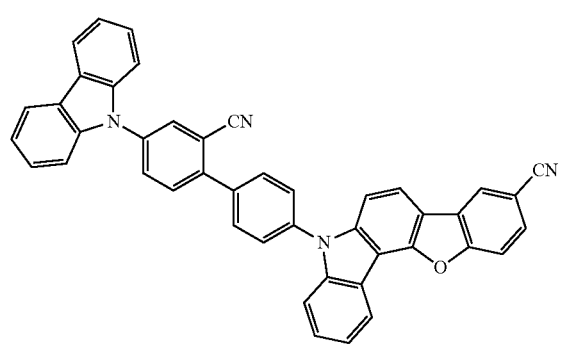
520
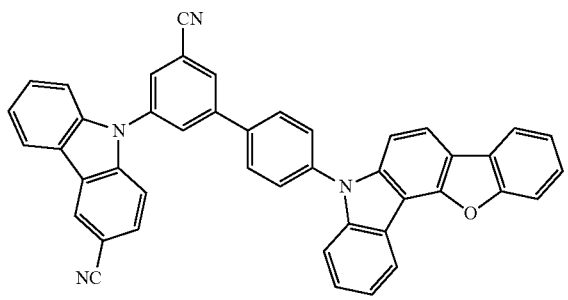
521
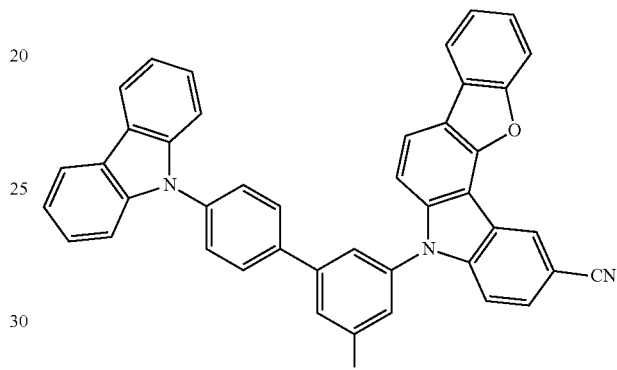
522
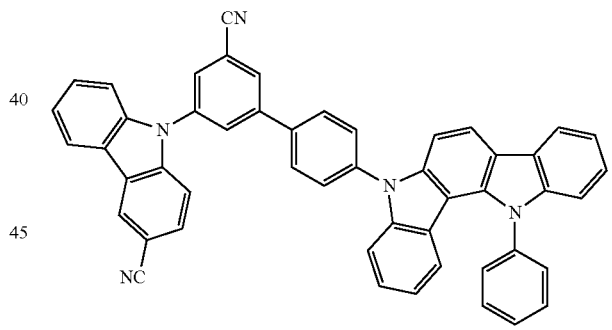
523
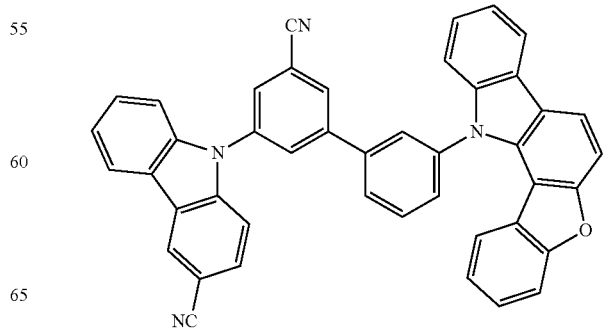

-continued
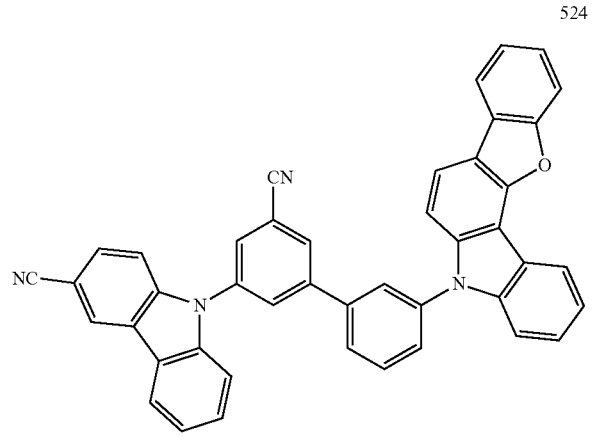
524
525
526
-continued
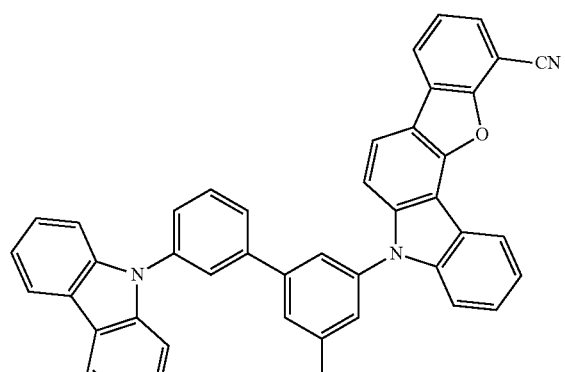
527
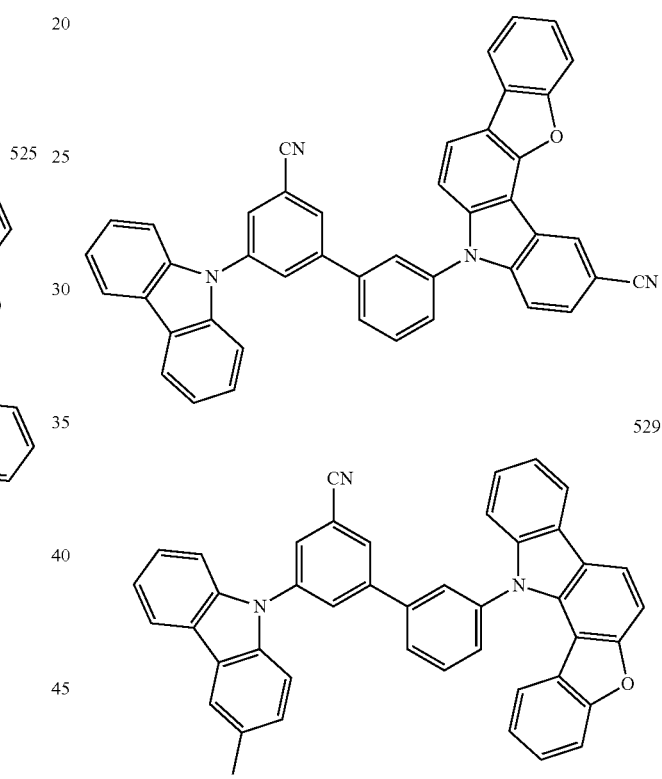
528
529
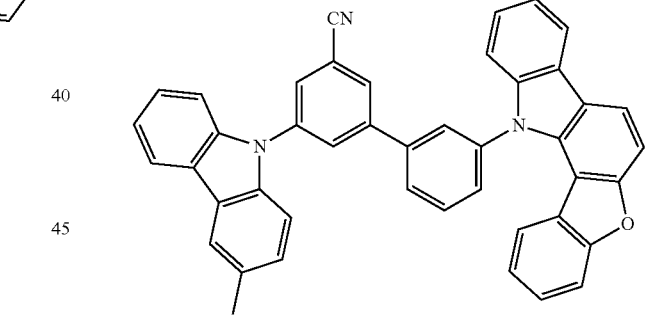
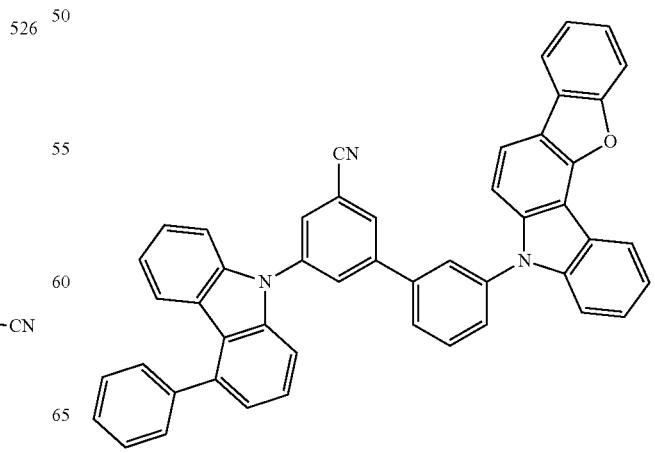
530

531
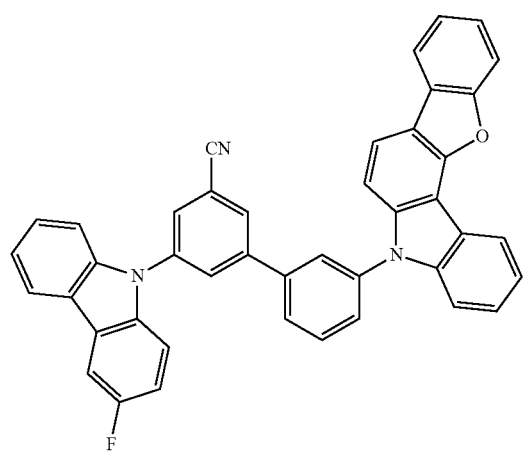
532
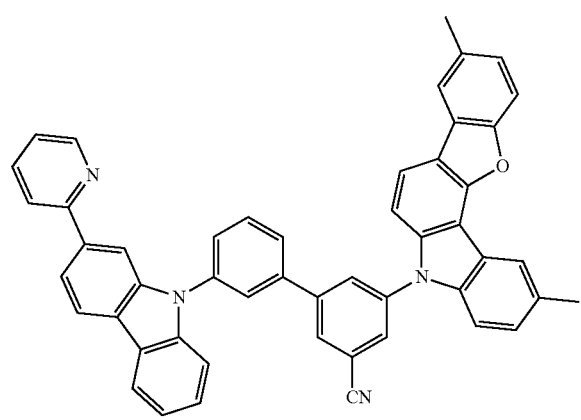
533
534
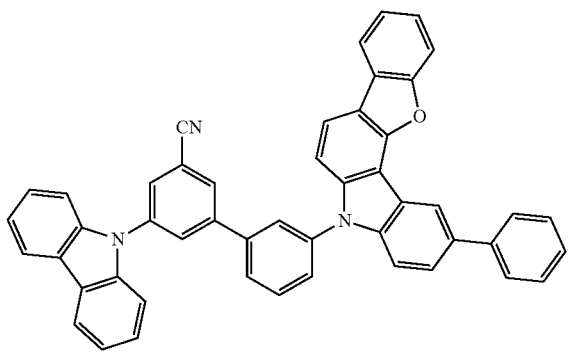
535
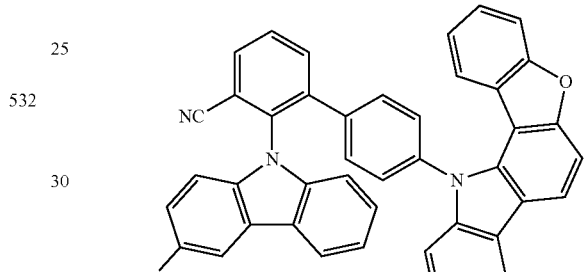
536
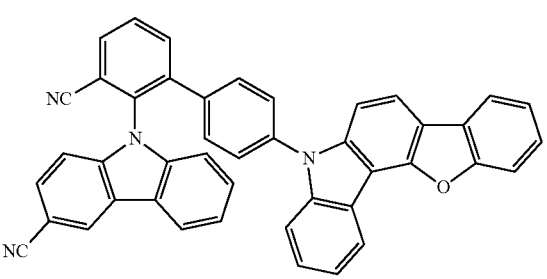
537

443
-continued
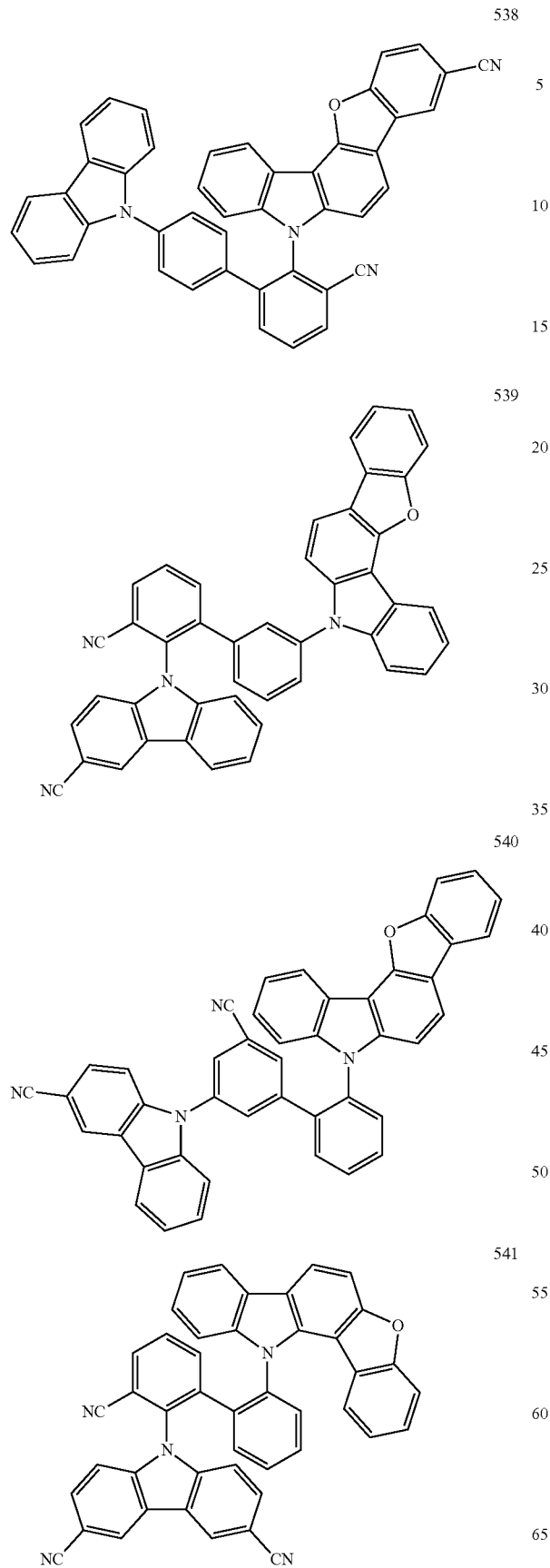
444
-continued
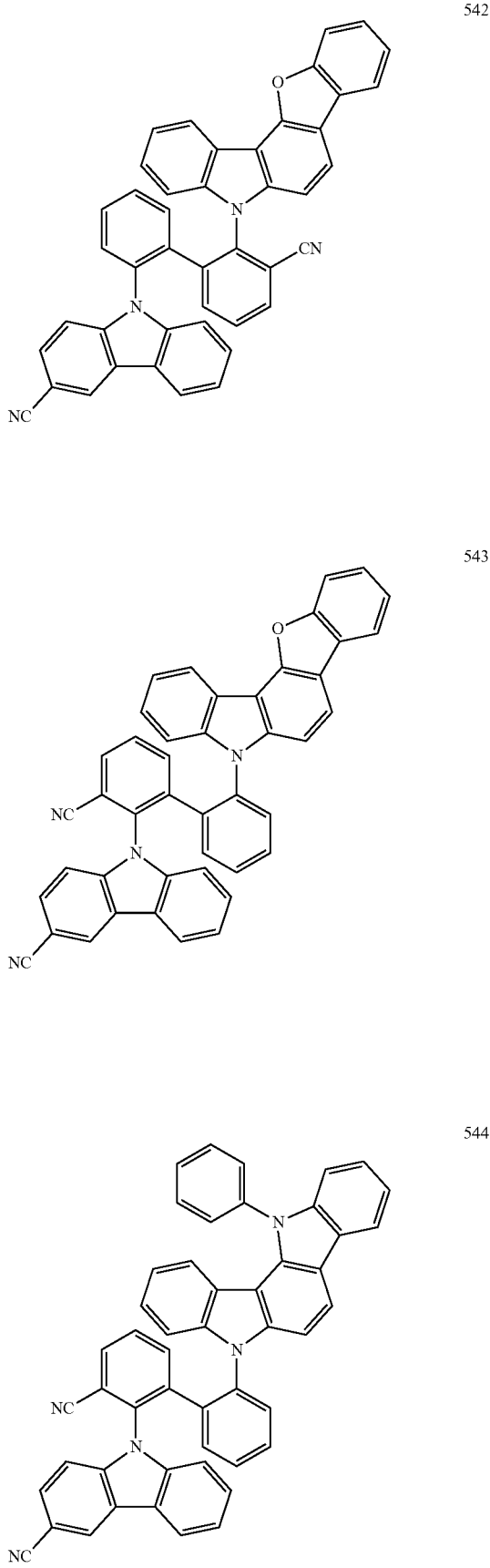

445  
-continued
546
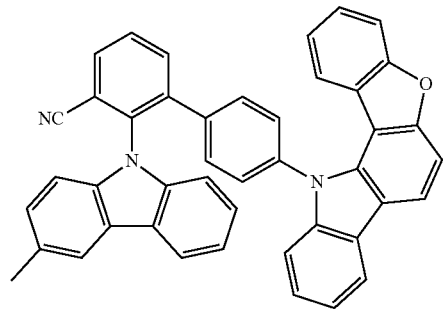
547
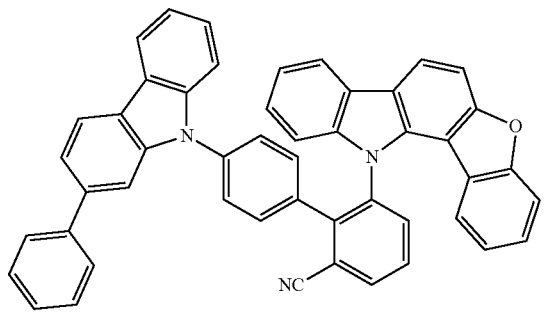
548
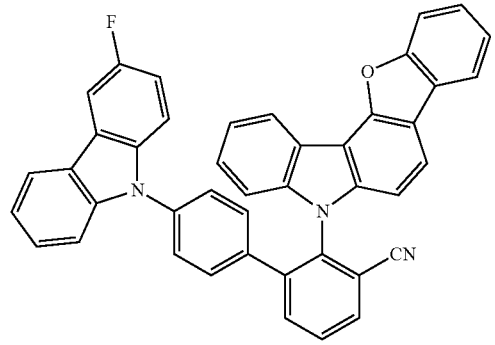
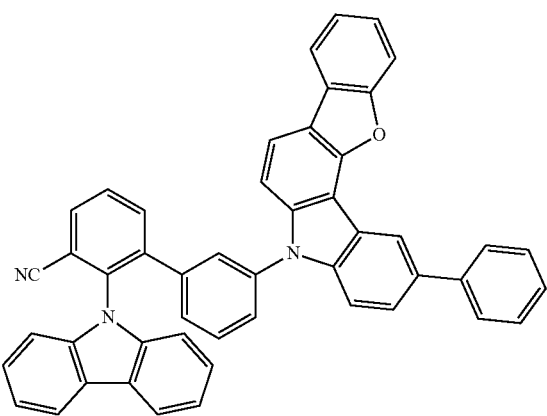
446  
-continued
549
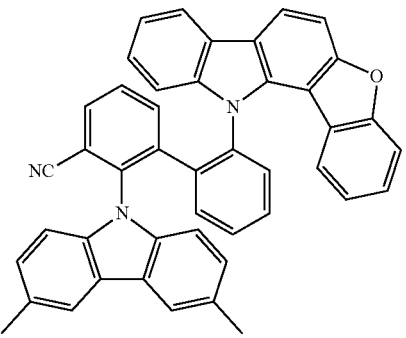
550
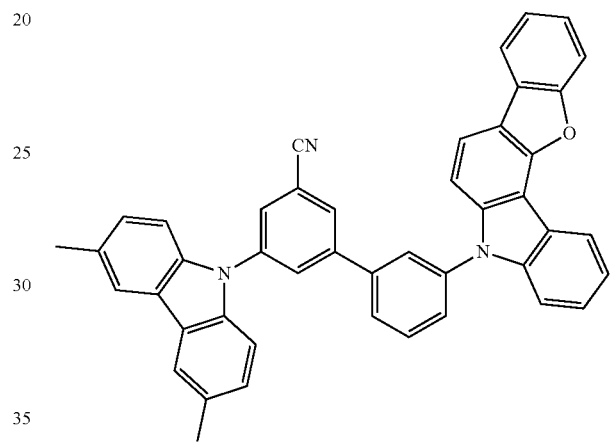
551
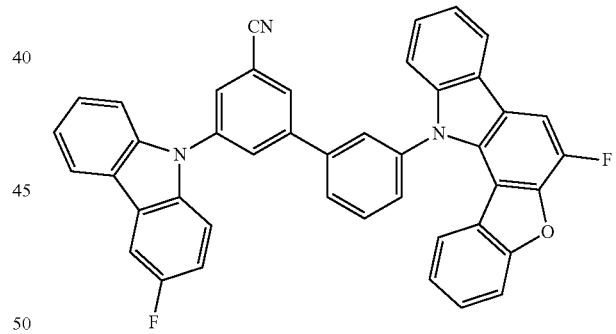
552
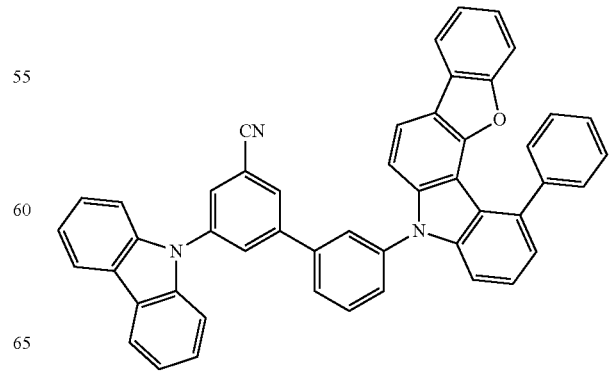

-continued
553
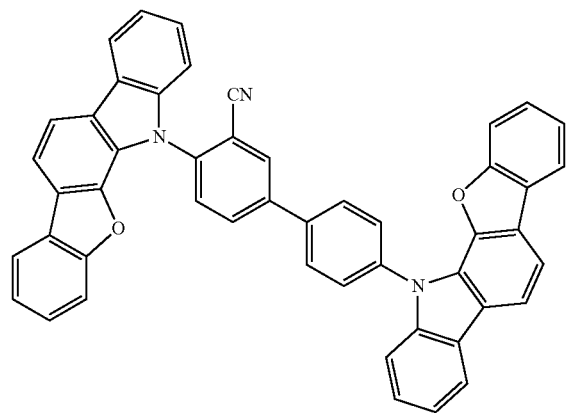
554
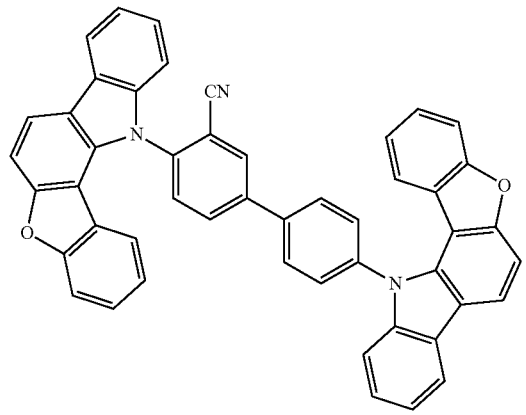
555
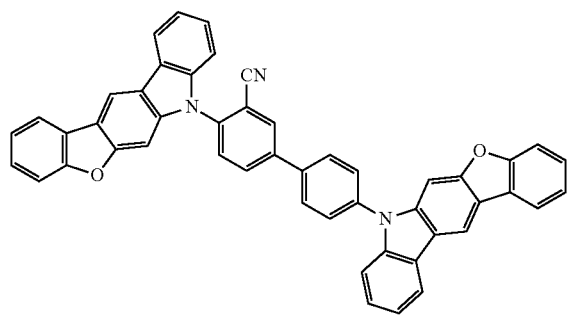
556
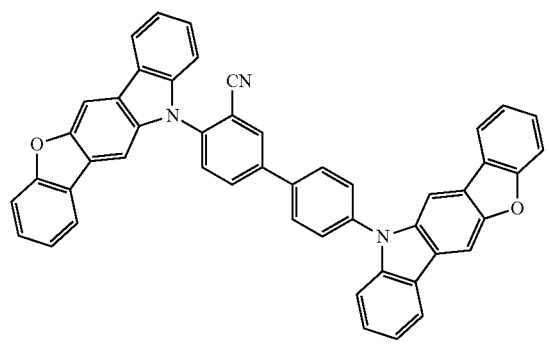
-continued
557
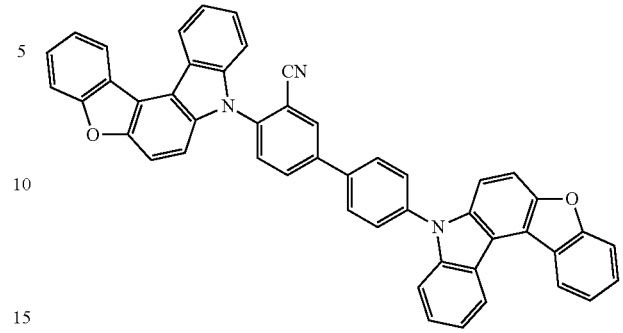
558
559
560
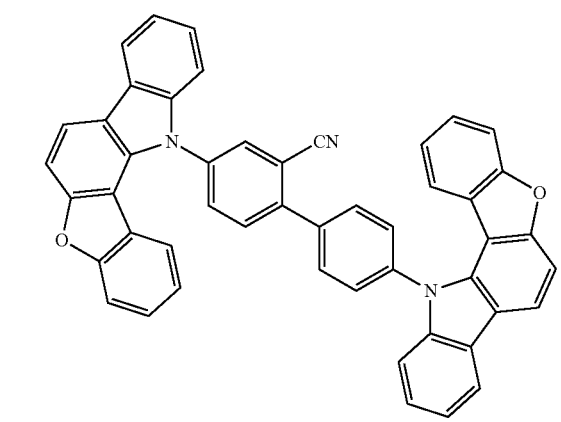

-continued
561
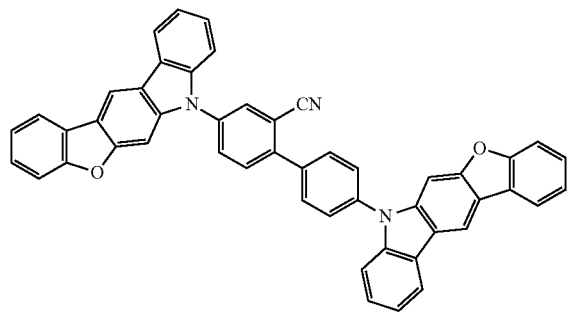
562
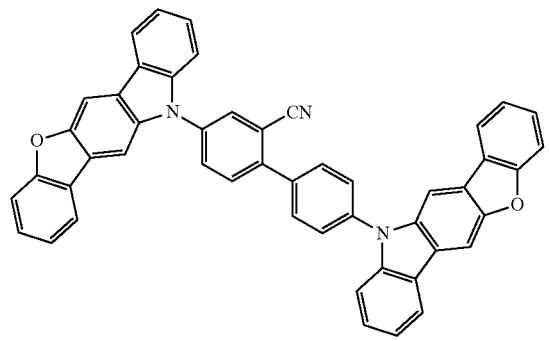
563
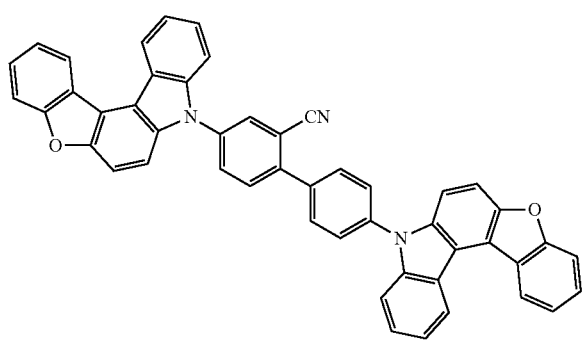
564
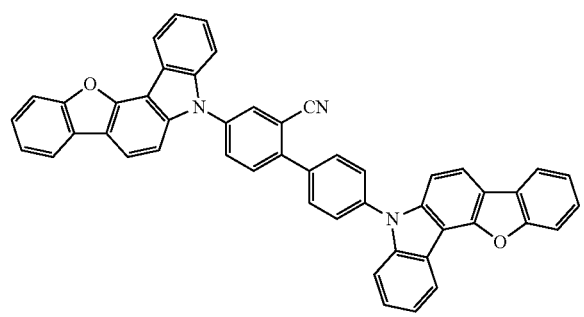
-continued
565
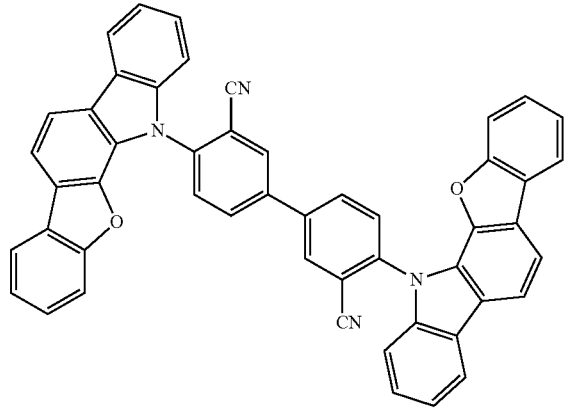
566
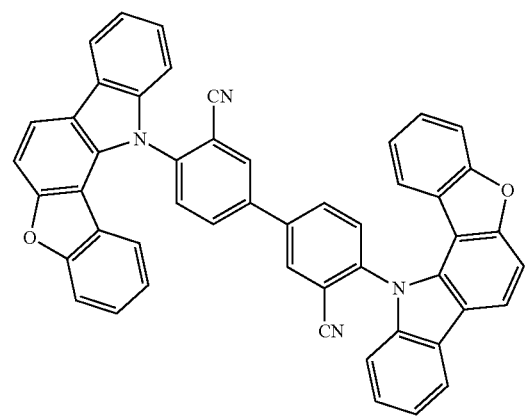
567
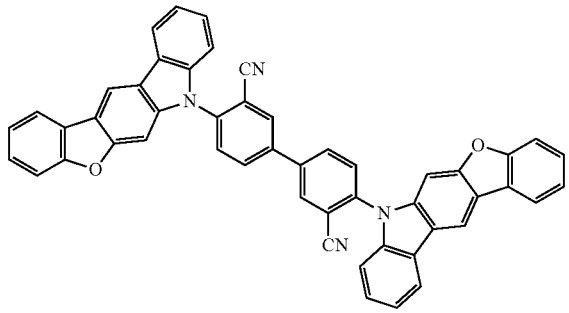
568
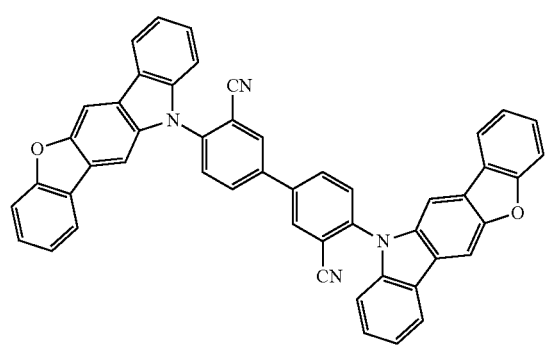

569
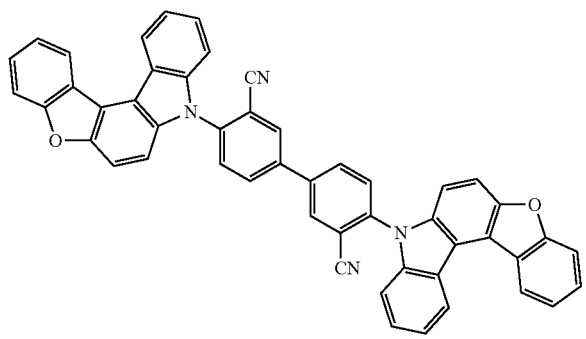
670
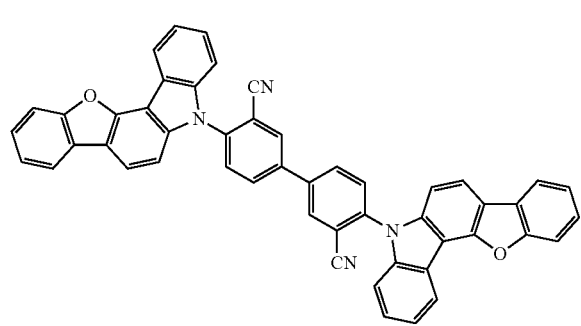
571
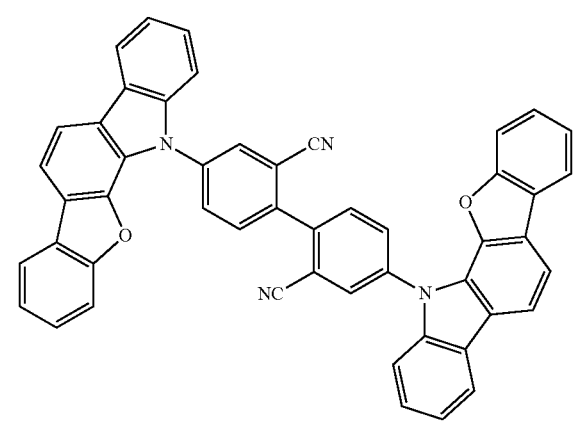
572
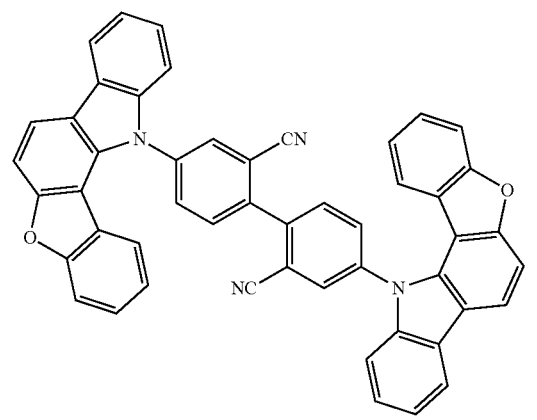
573
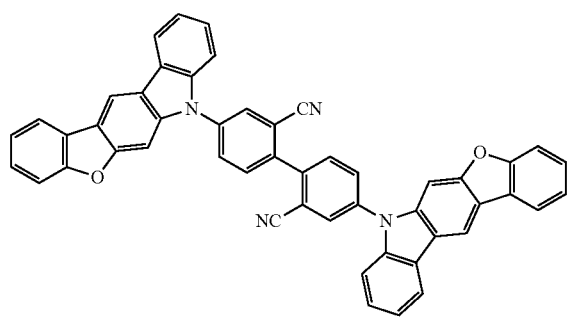
574
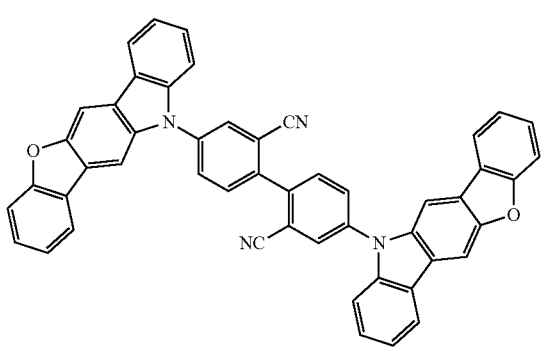
575
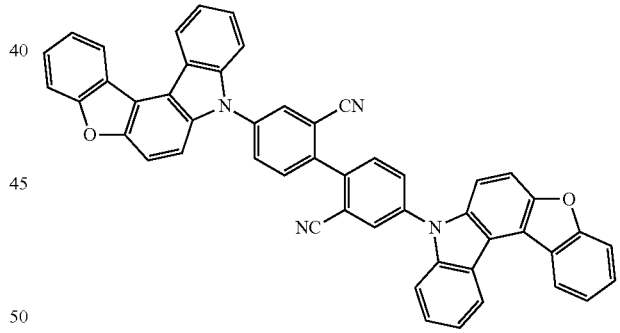
576
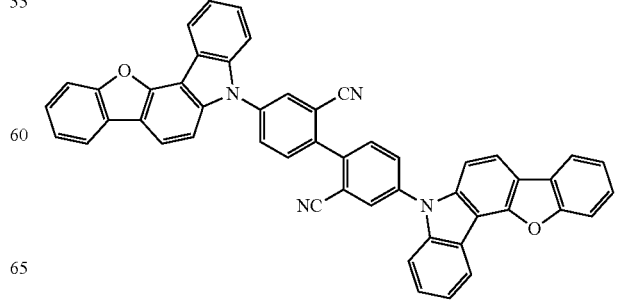

453
-continued
577
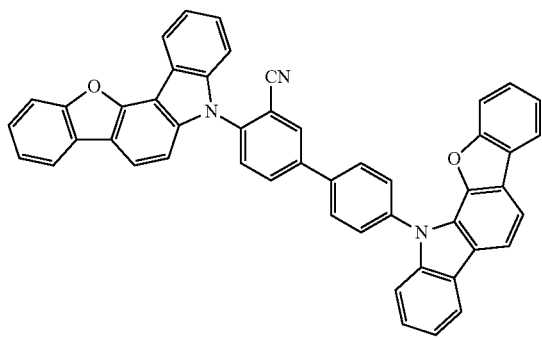
578
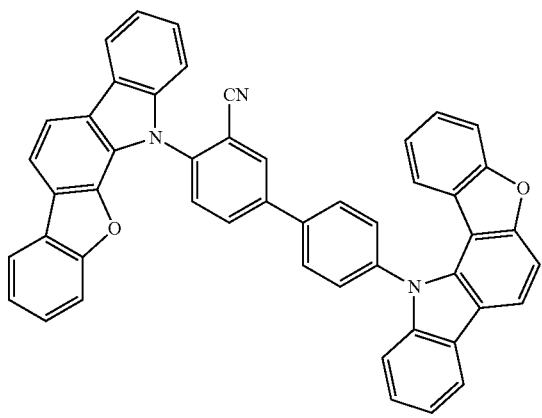
579
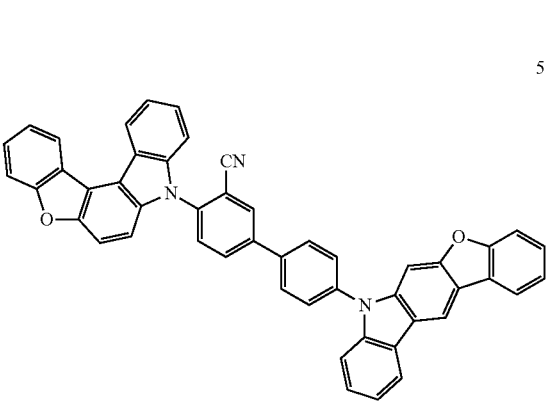
580
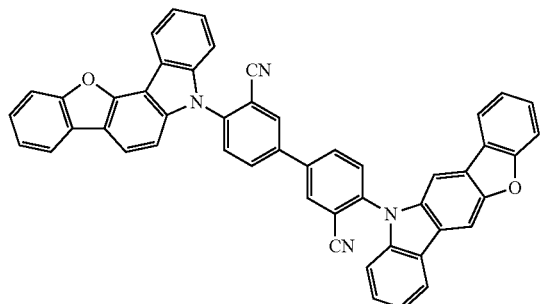
454
-continued
581
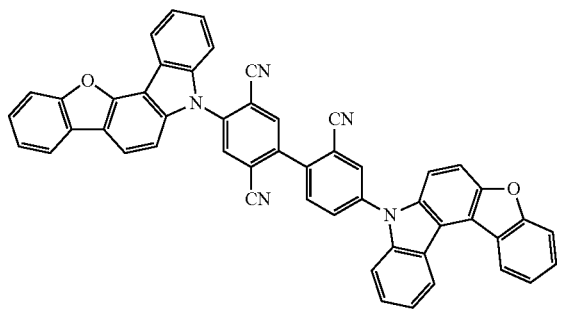
582
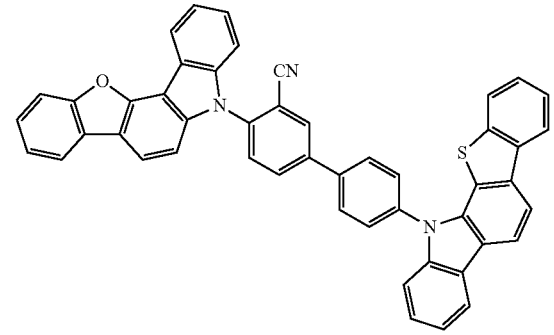
583
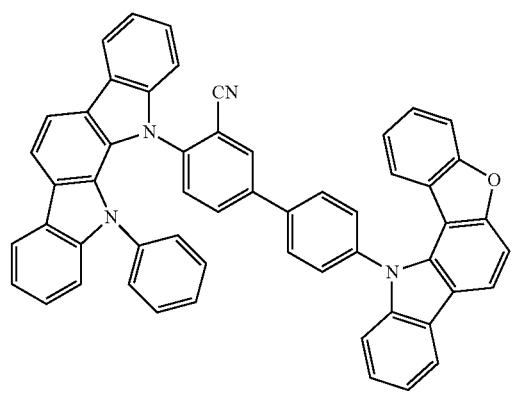
584

-continued
585
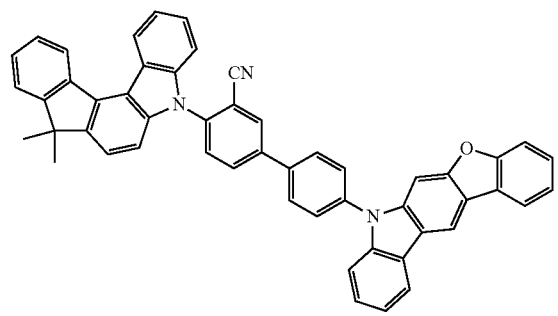
586
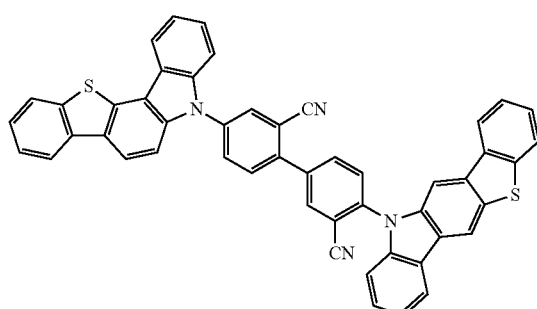
587
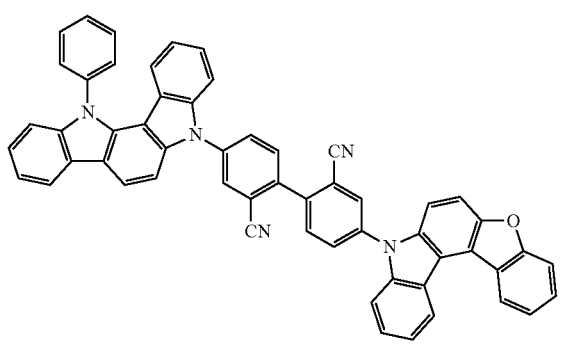
588
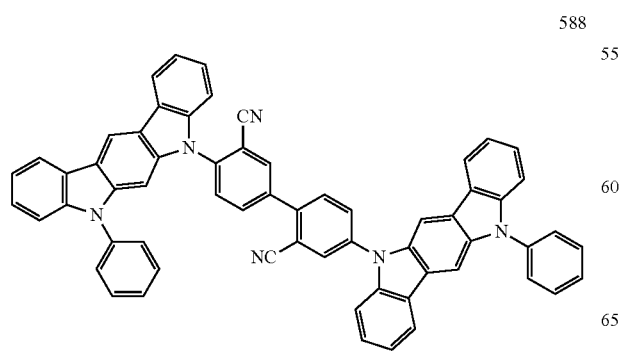
-continued
589
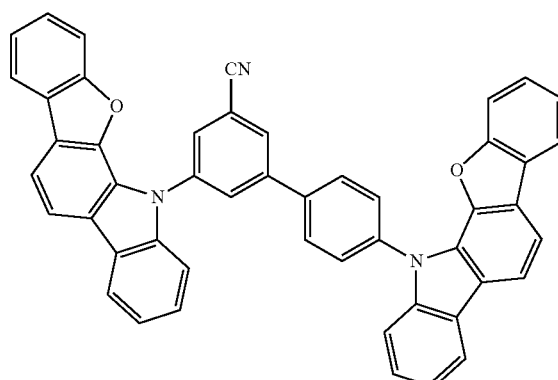
590
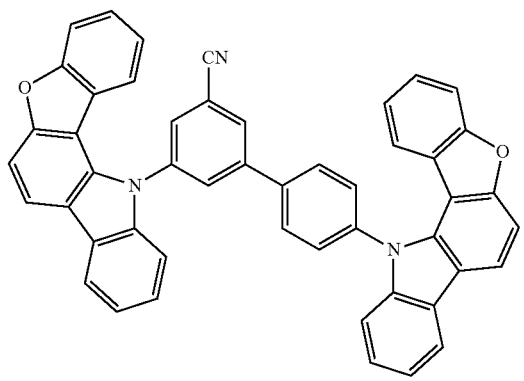
591
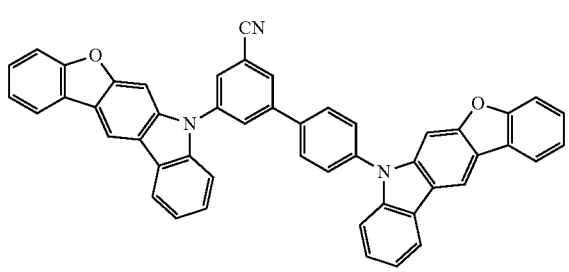
592
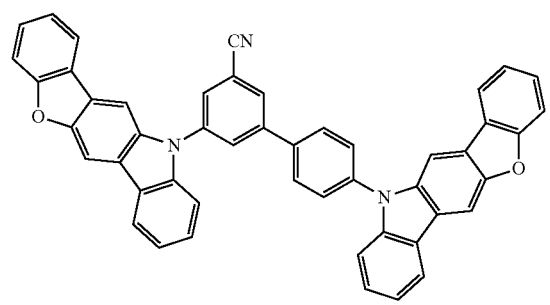

593
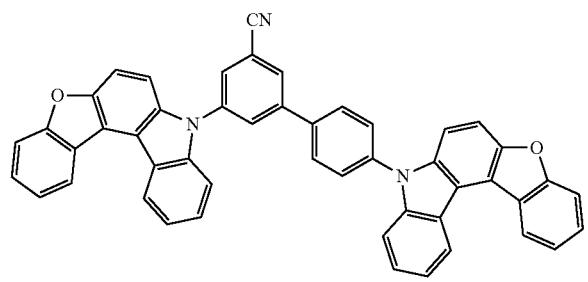
594
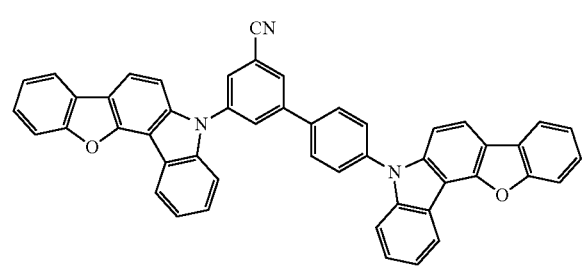
595
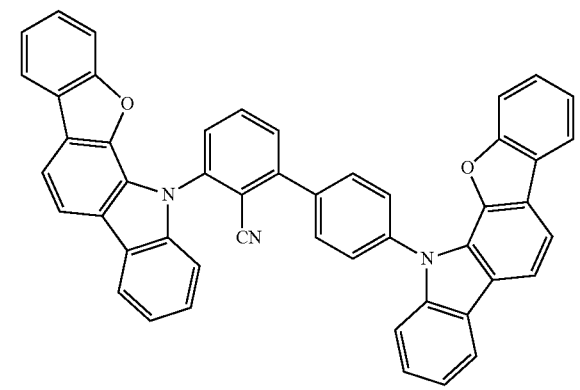
596
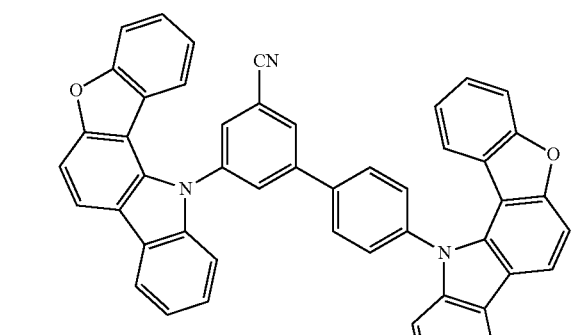
597
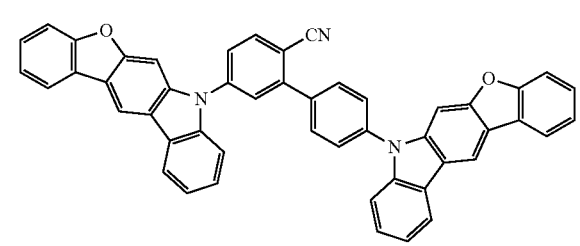
598
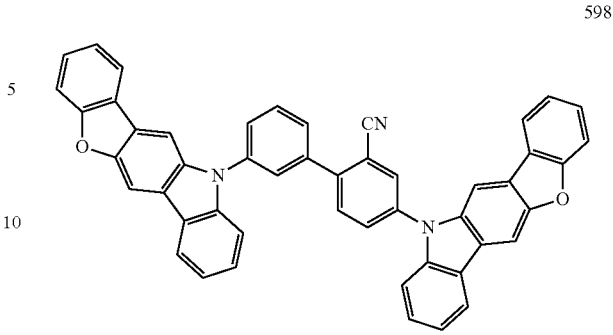
599
600
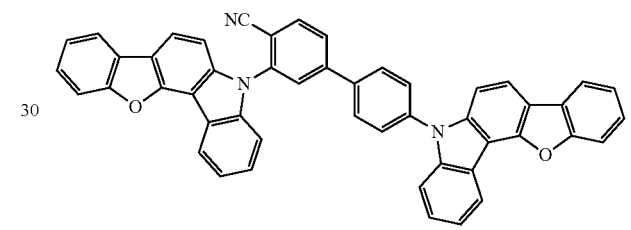
601
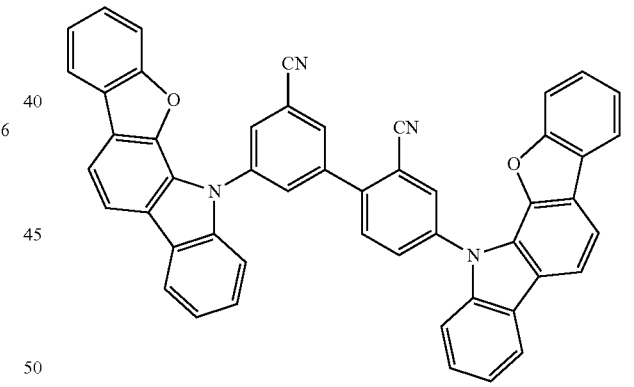
602
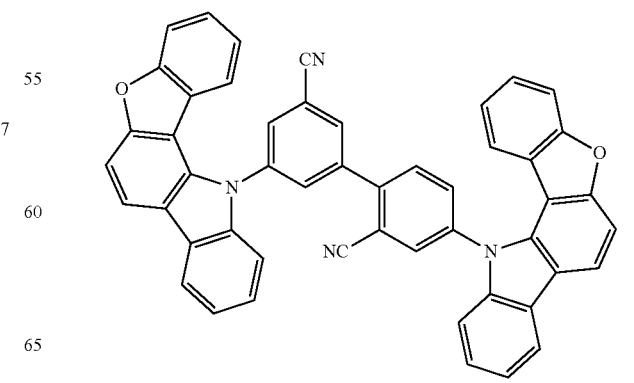

-continued
603
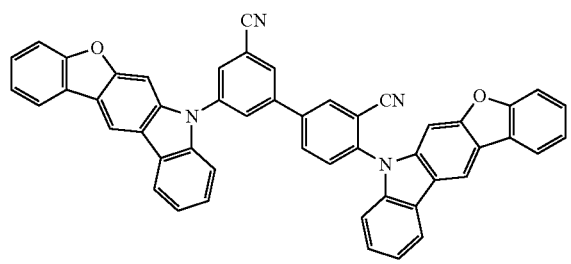
604
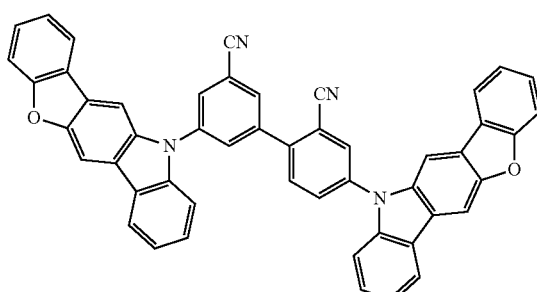
605
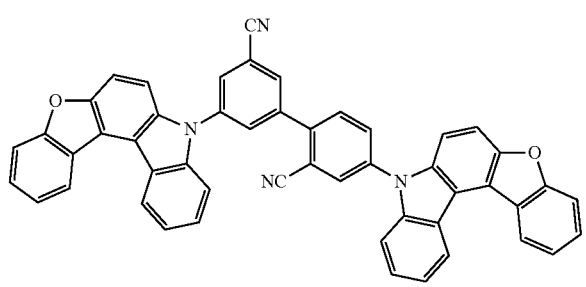
606
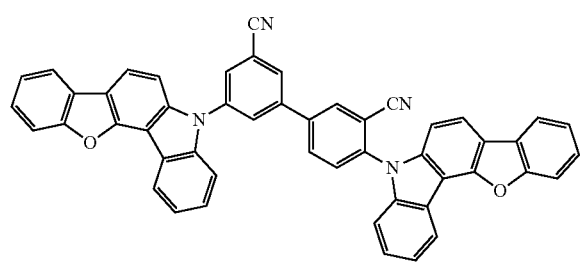
607
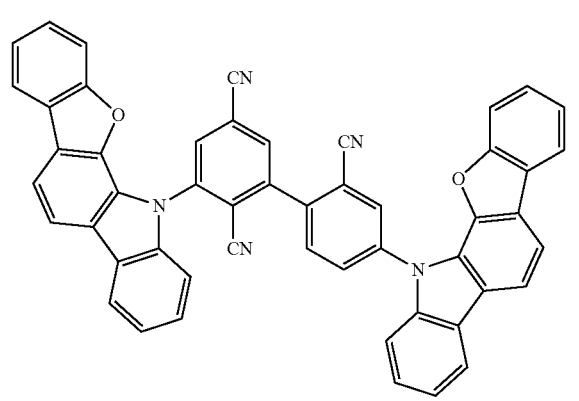
-continued
608
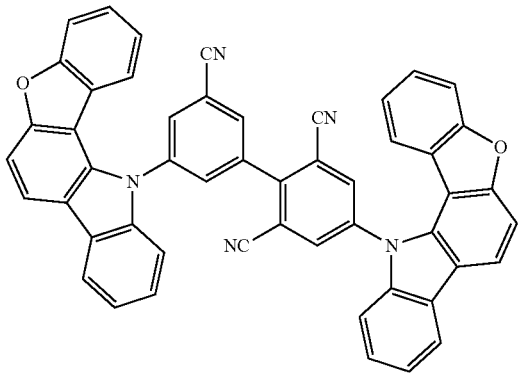
609
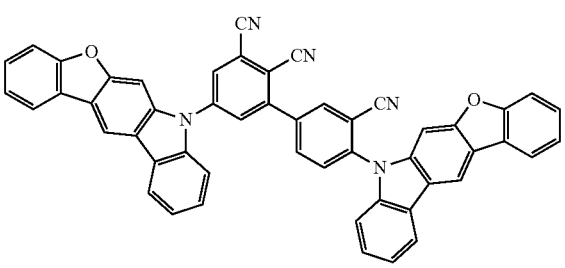
610
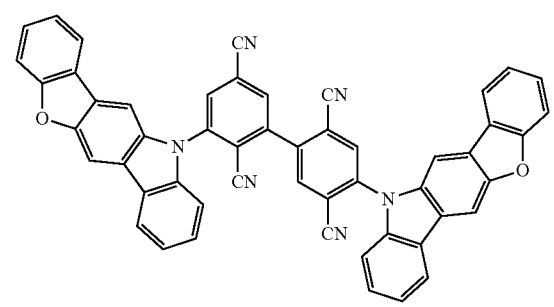
611
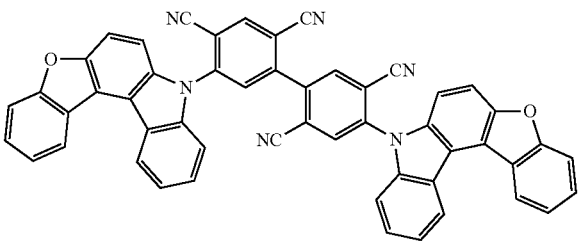
612
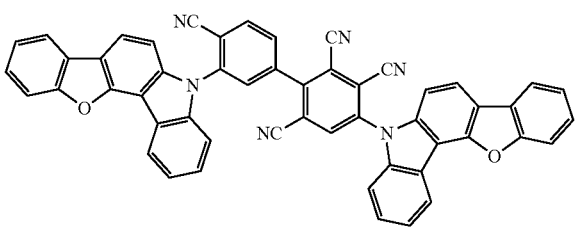

461
-continued
613
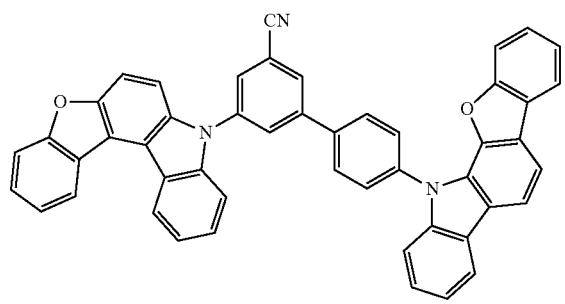
614
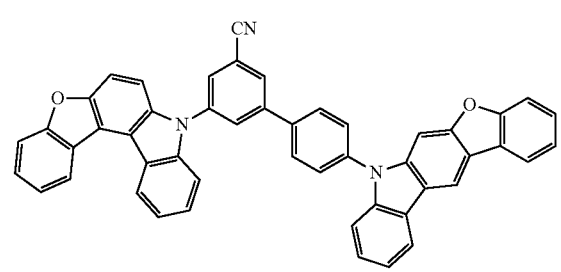
615
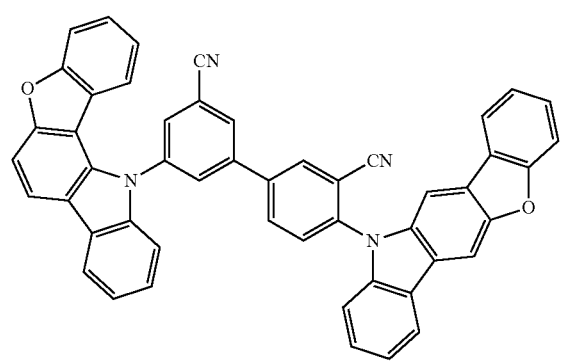
616
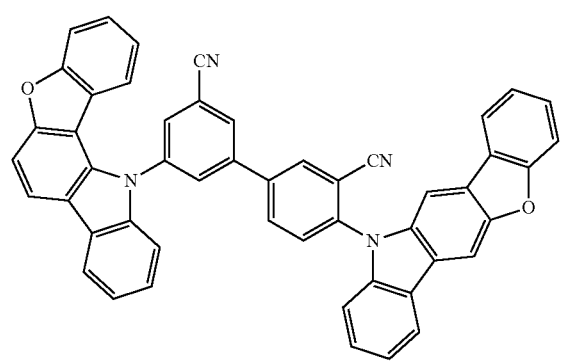
462
-continued
617
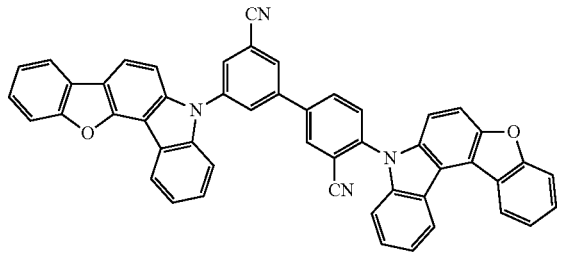
618
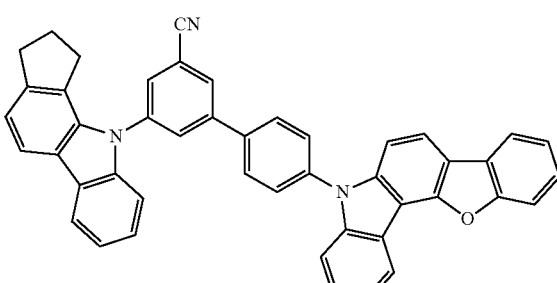
619
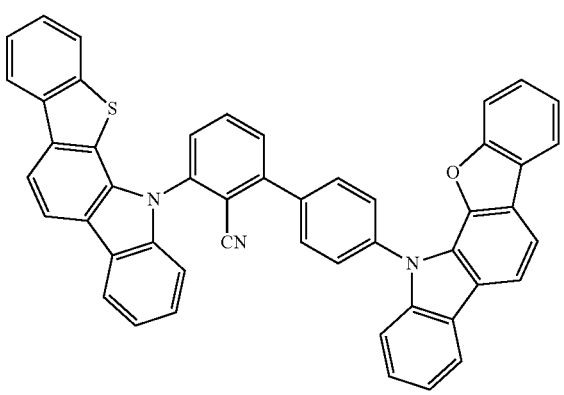
620
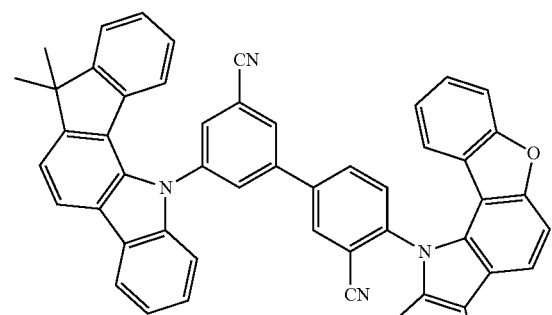
621
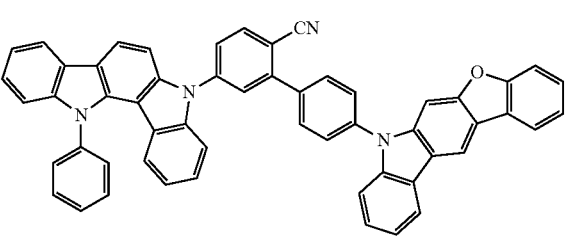

463
-continued
622
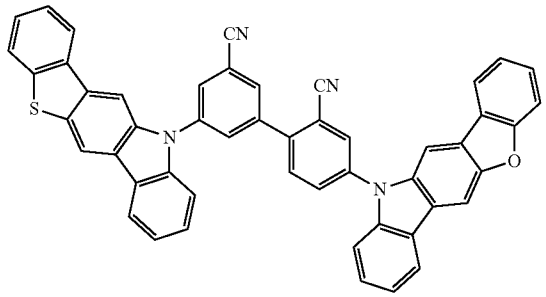
623
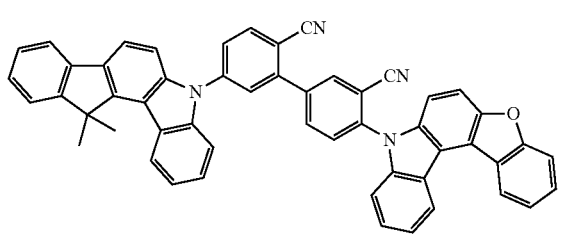
624
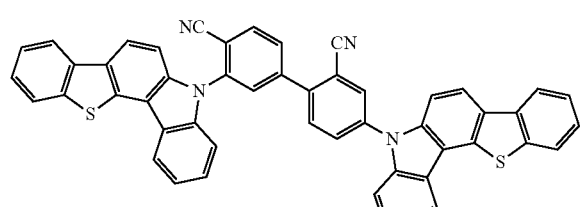
625
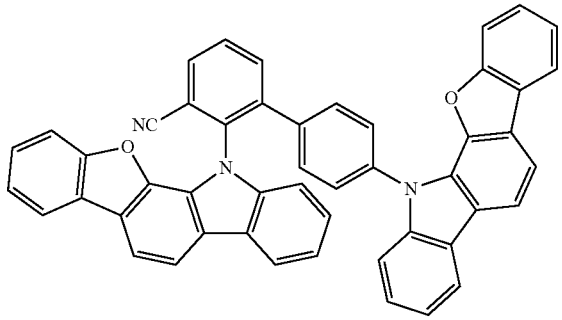
626
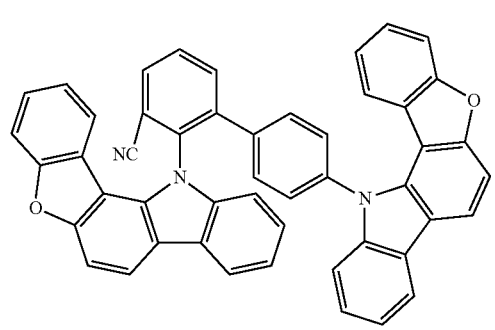
464
-continued
627
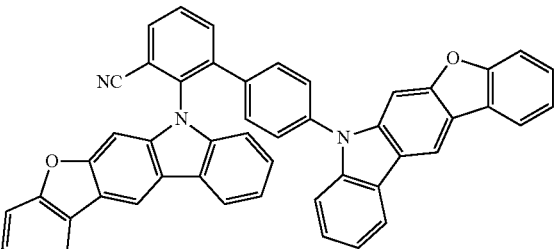
628
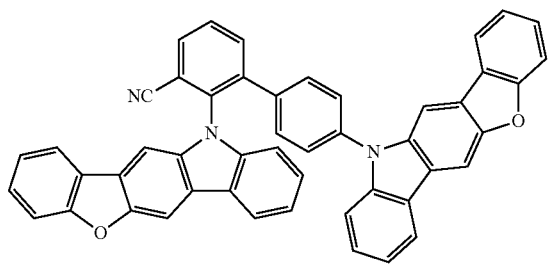
629
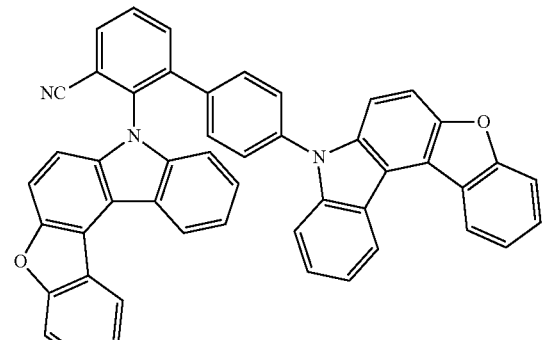
630
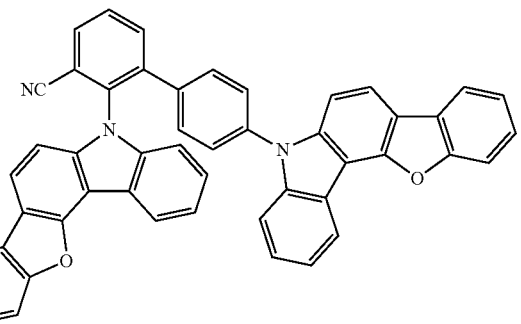

-continued
631
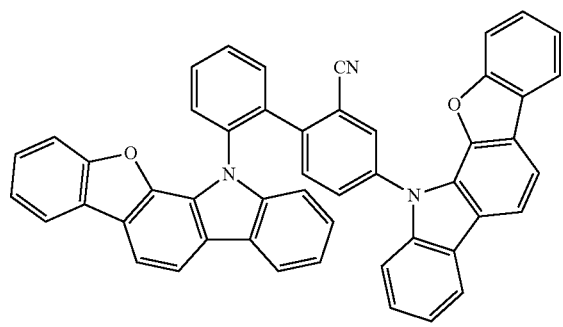
632
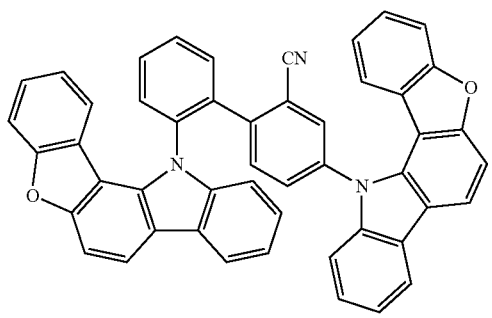
633
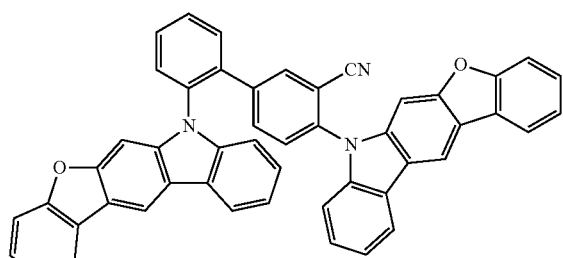
634
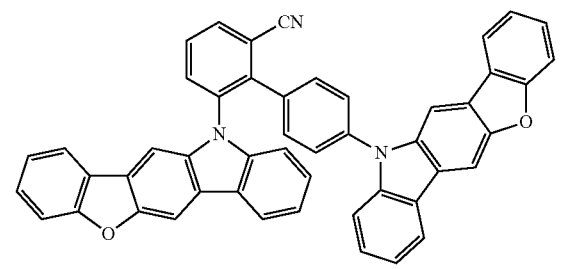
635
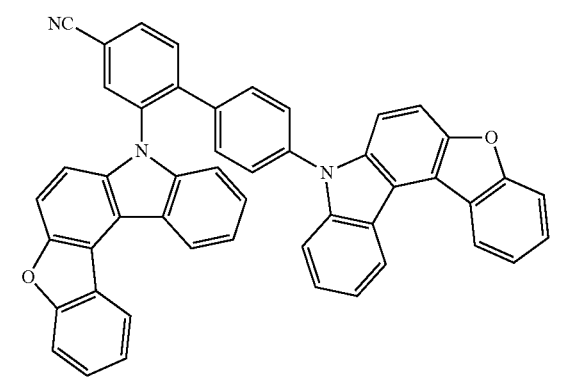
636
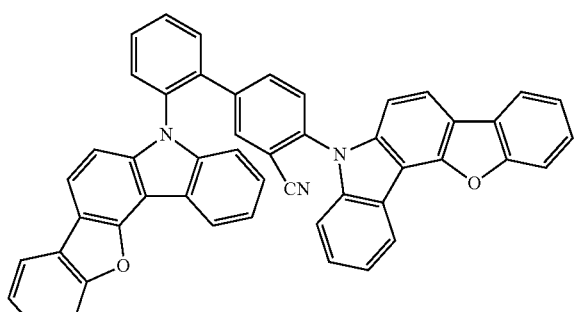
637
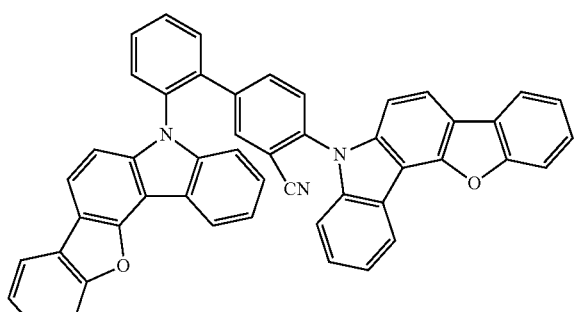
638
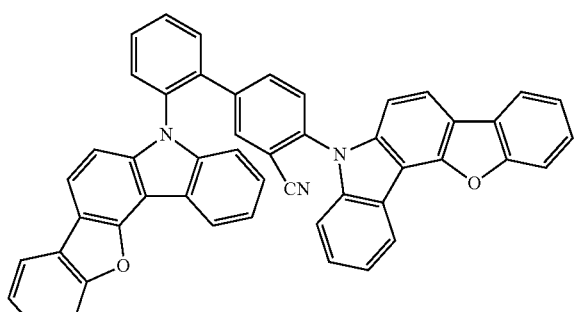
639
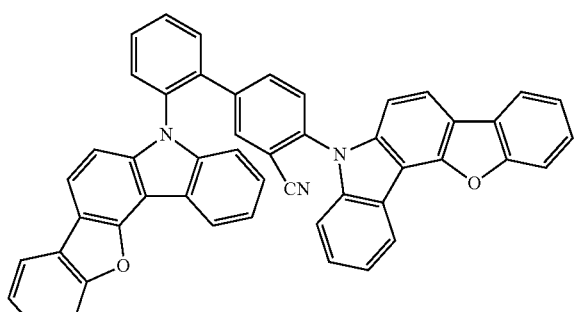
640
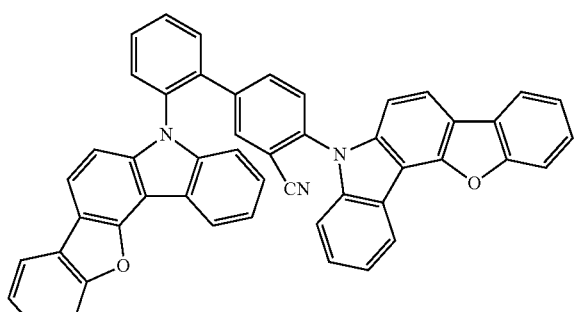

467
-continued
468
-continued
641
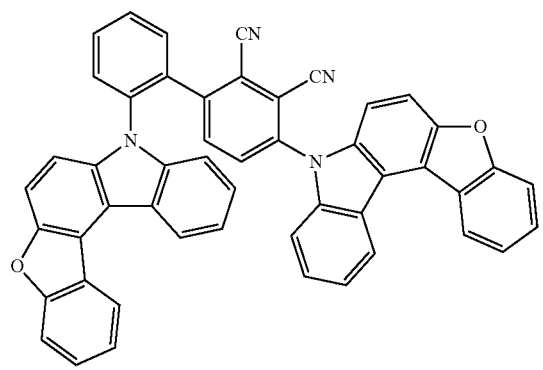
645
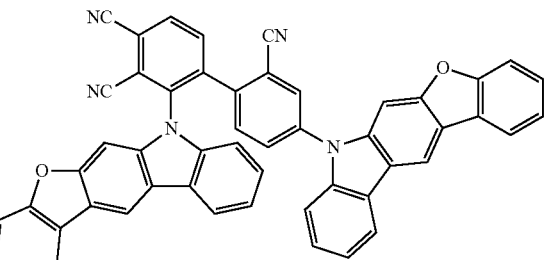
642
646
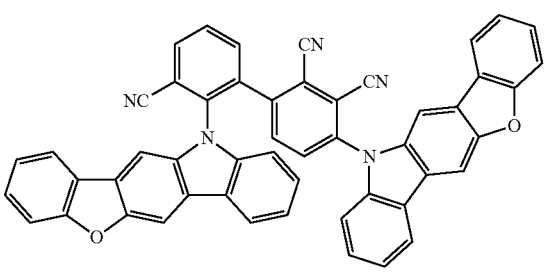
643
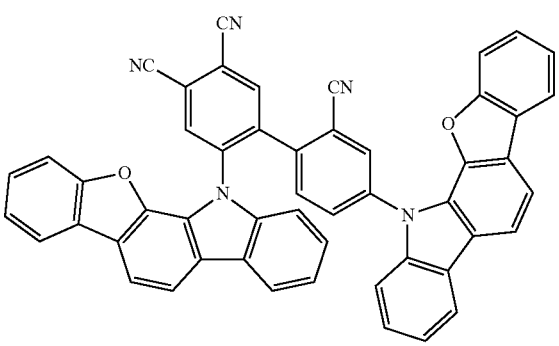
647
644
648
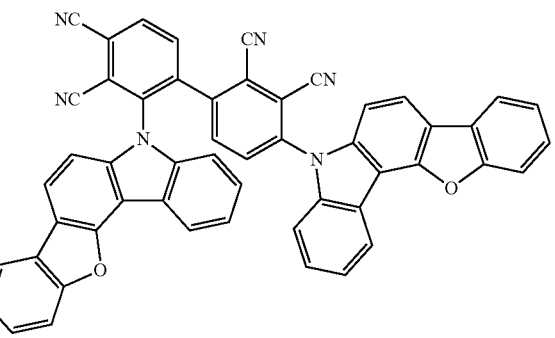

469
-continued
470
-continued
649
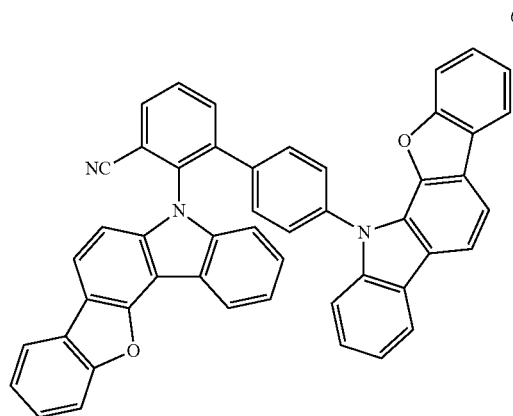
653
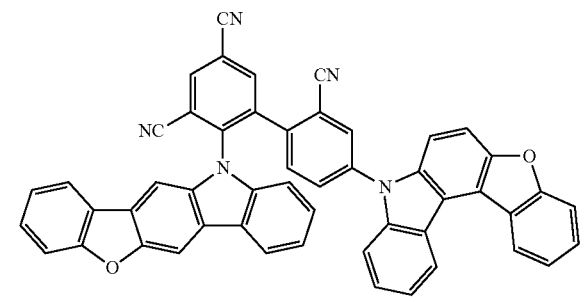
650
654
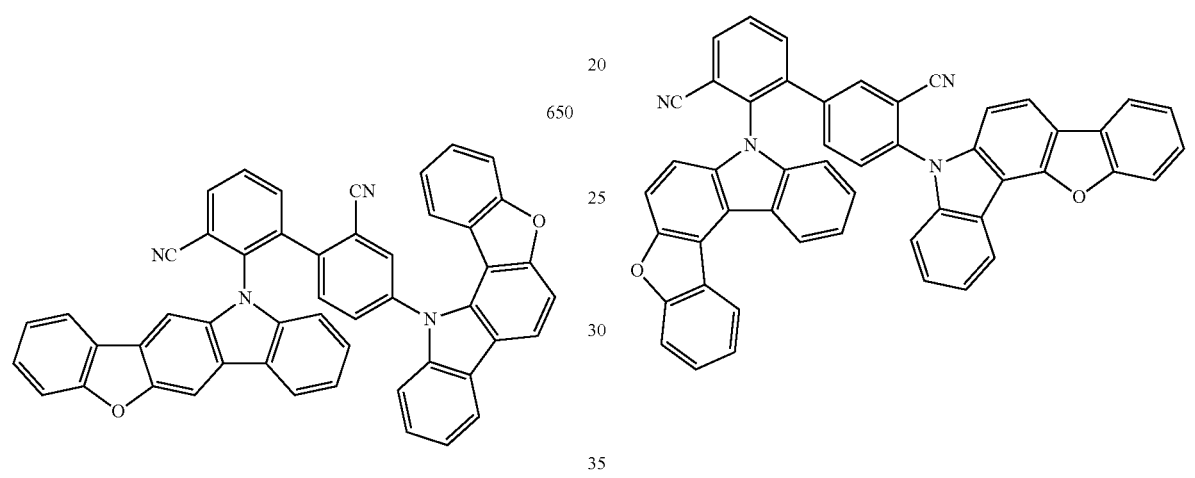
651
655
652
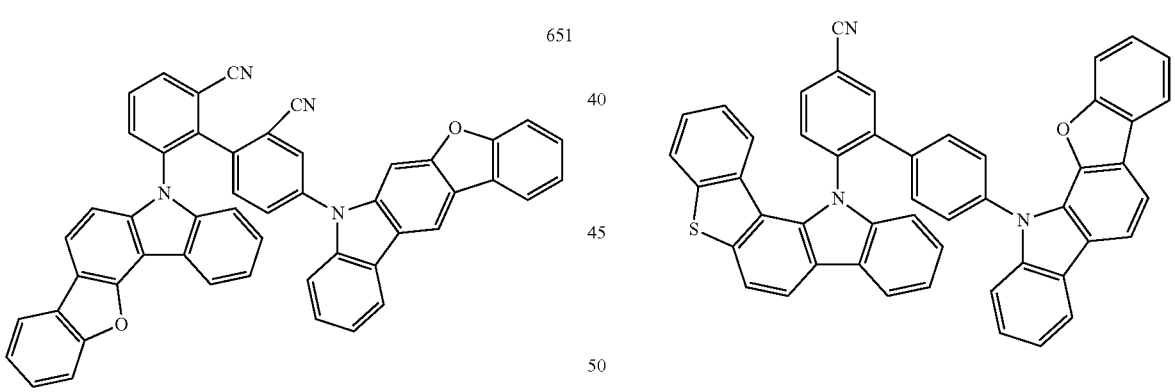
656
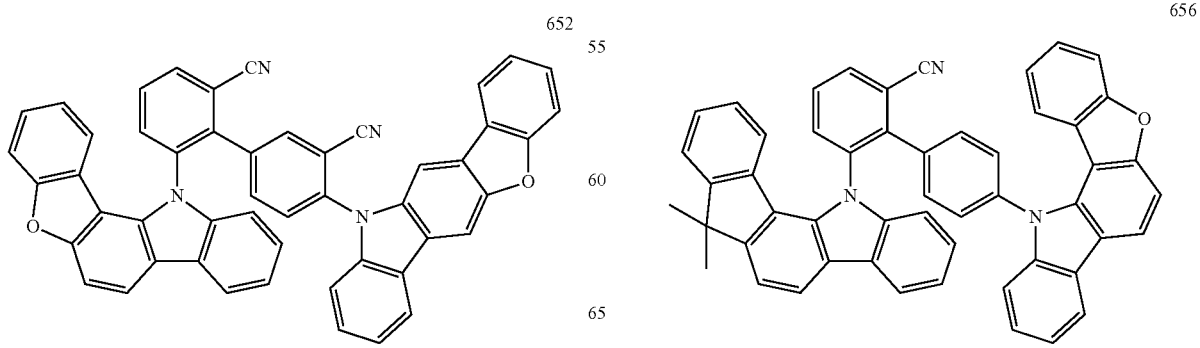

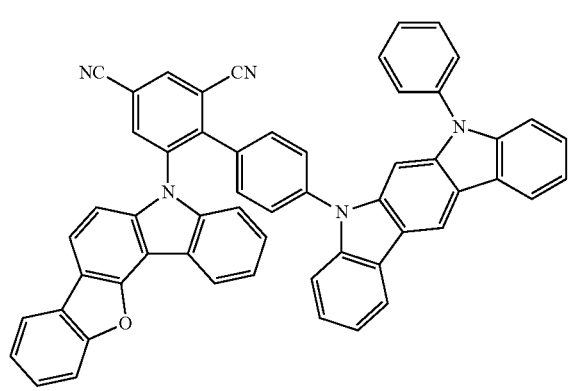
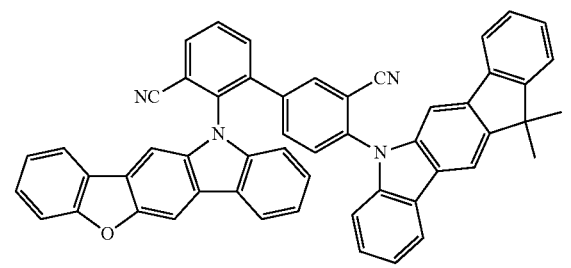
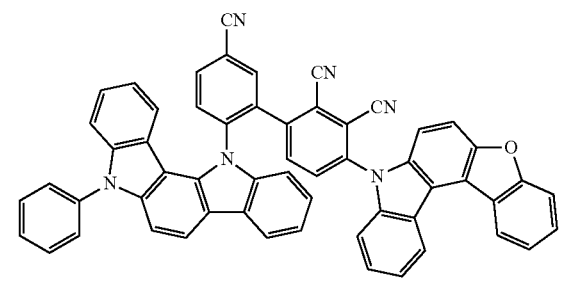
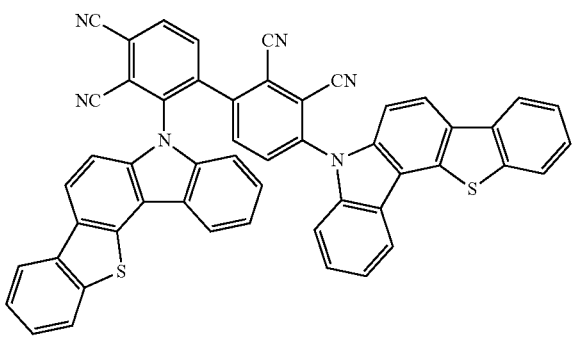

665
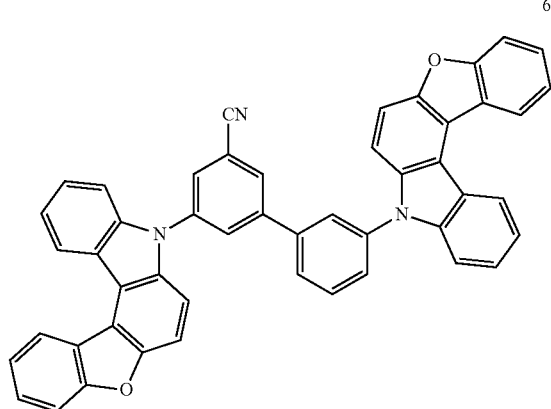
666
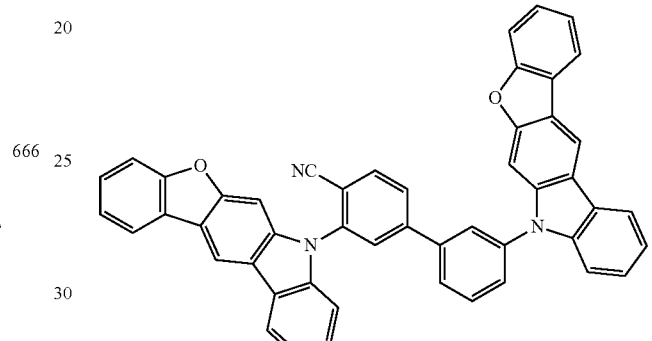
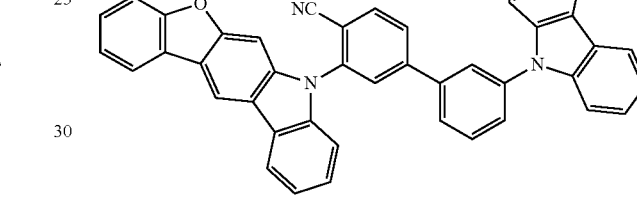
667
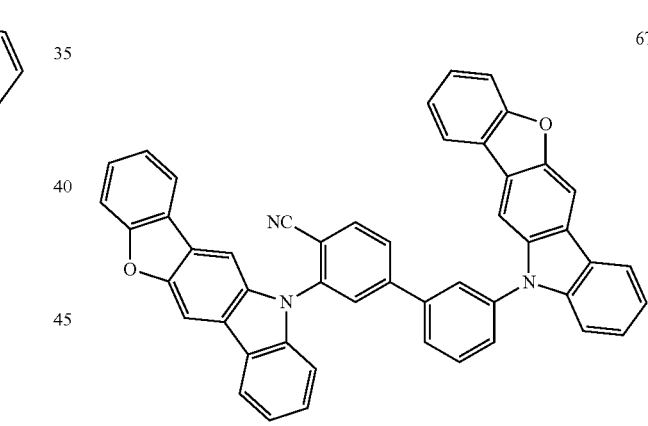
668
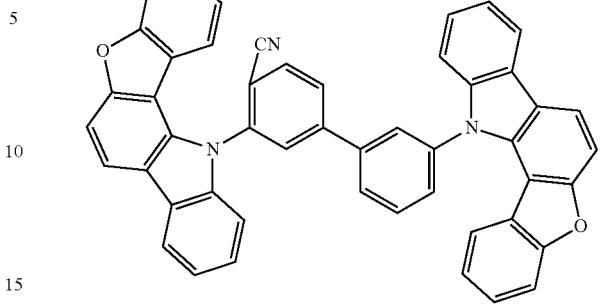
669
670
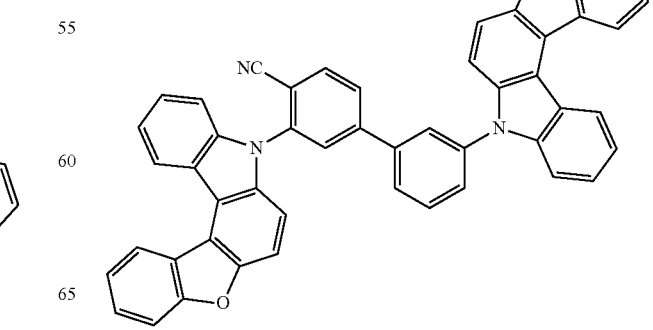
671

475
-continued
672
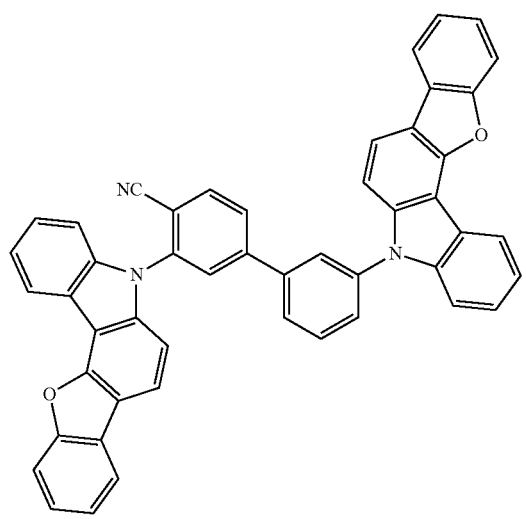
673
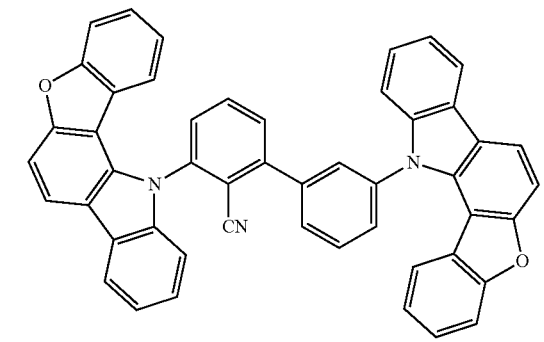
674
675
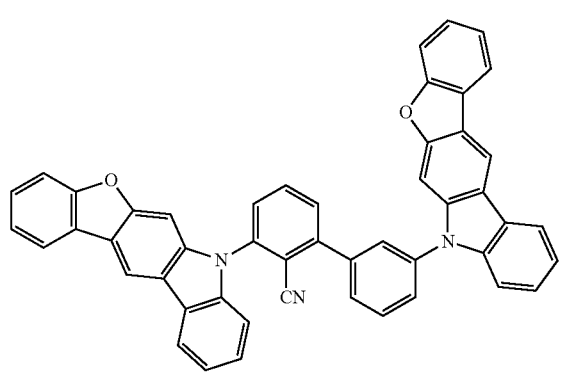
476
-continued
676
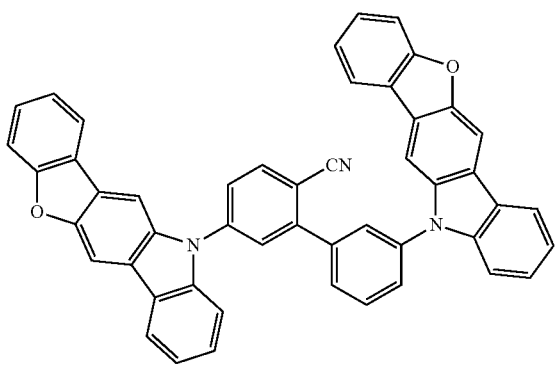
677
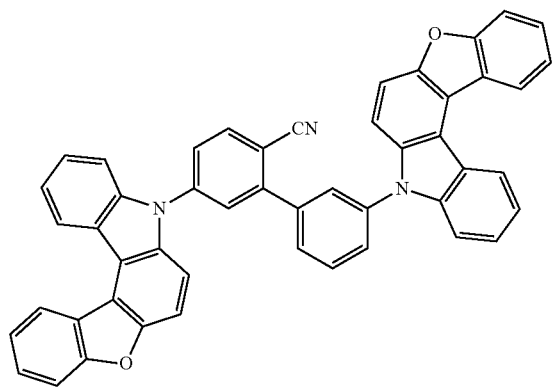
678
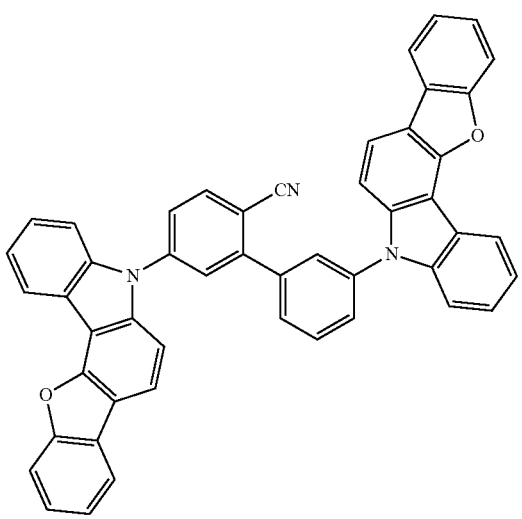

-continued
679
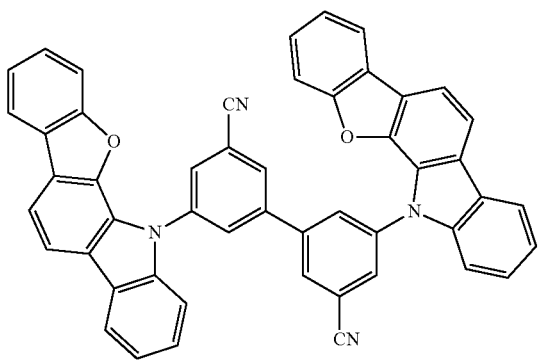
680
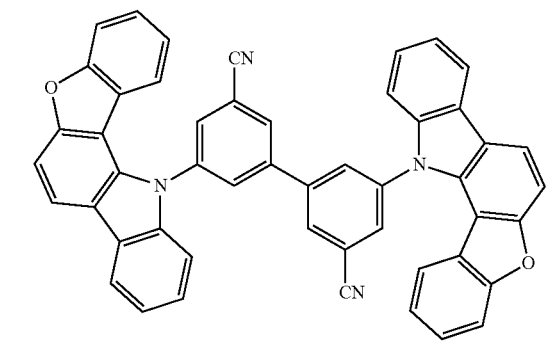
681
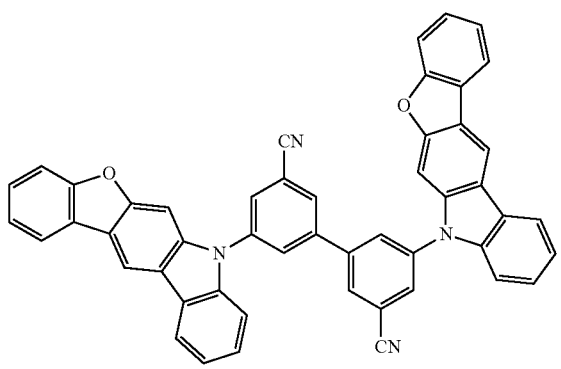
682
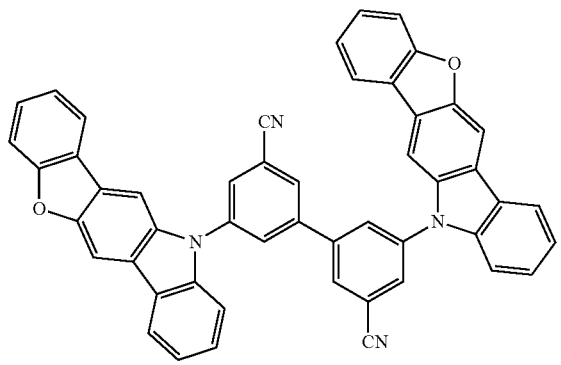
-continued
683
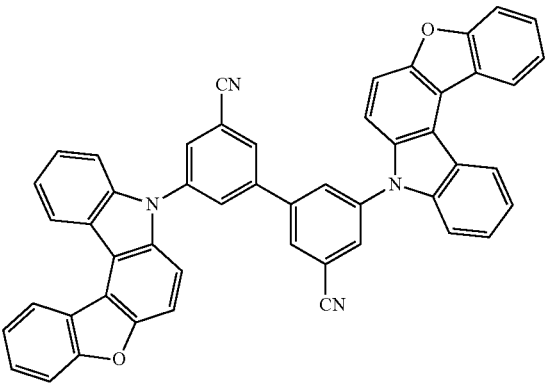
684
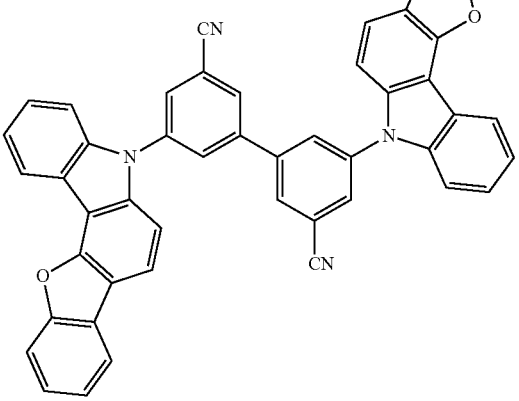
685
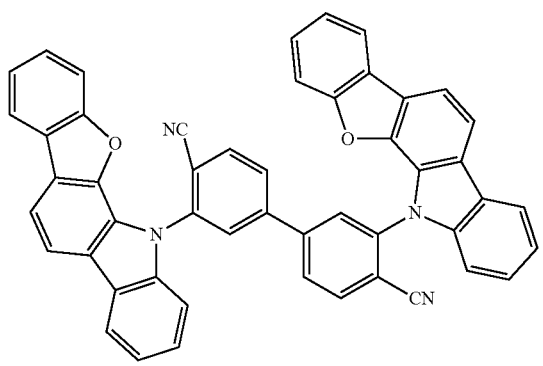

479
-continued
686
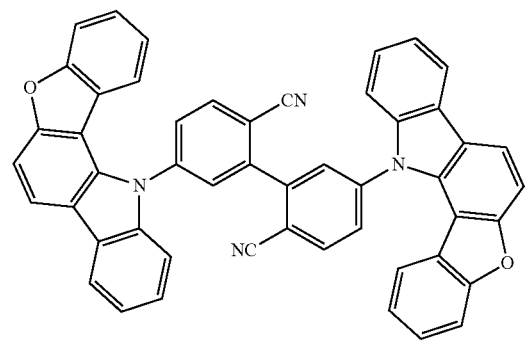
687
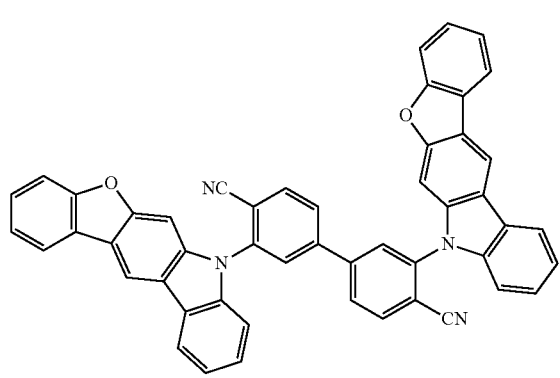
688
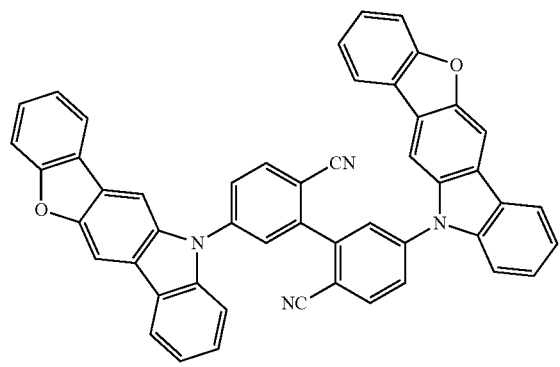
689
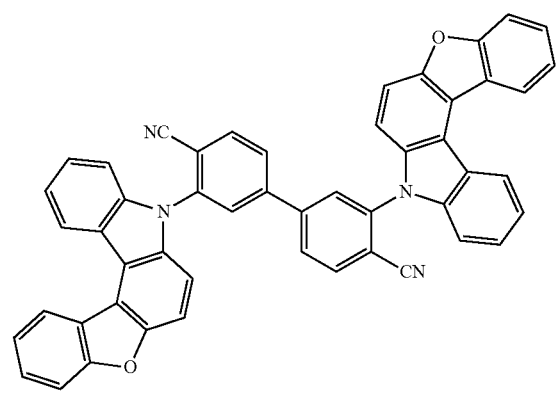
480
-continued
690
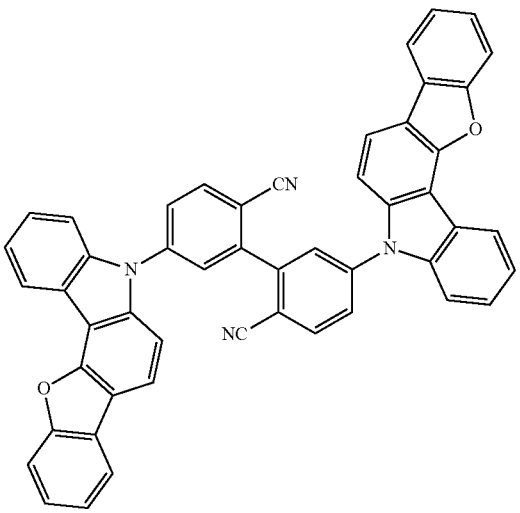
691
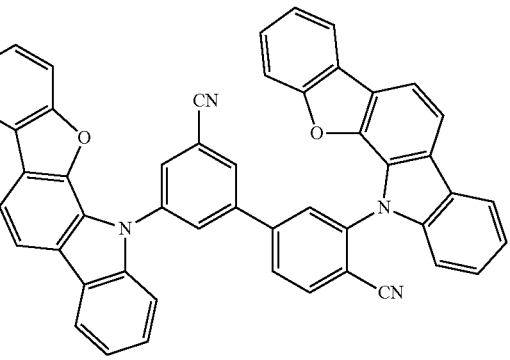
692
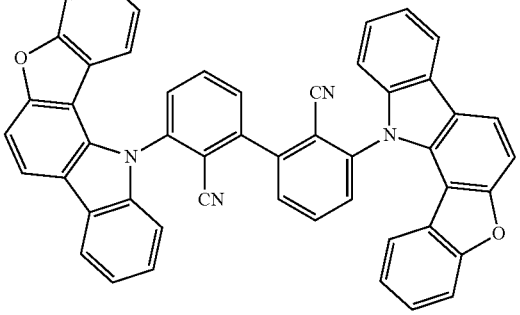

693
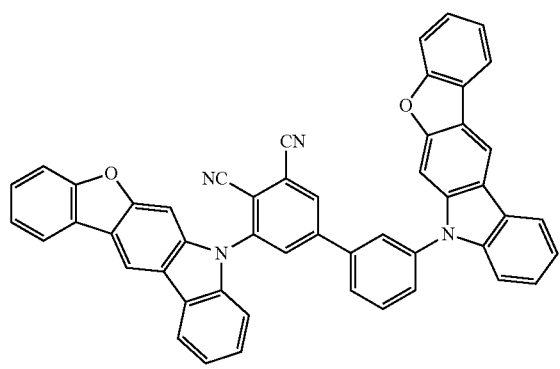
694
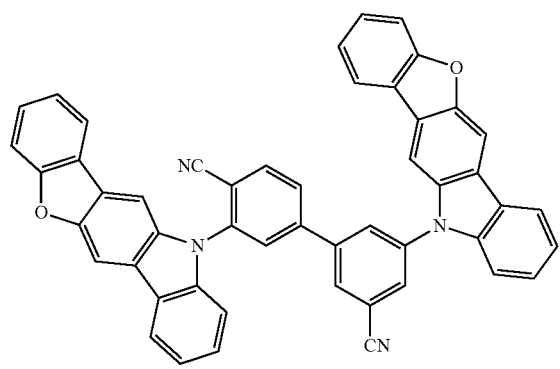
695
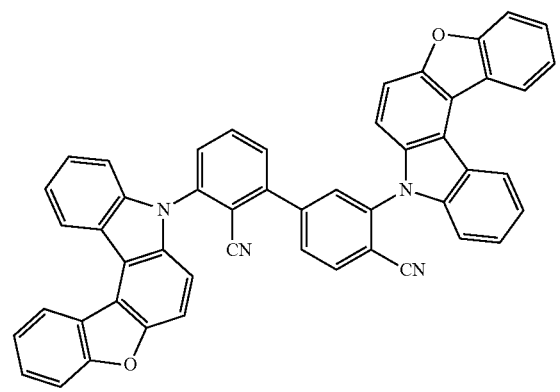
696
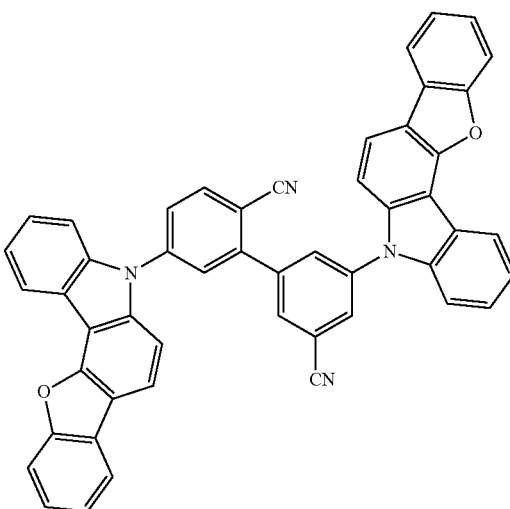
697
698
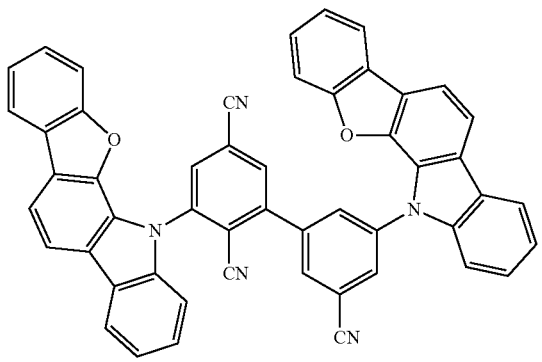
699
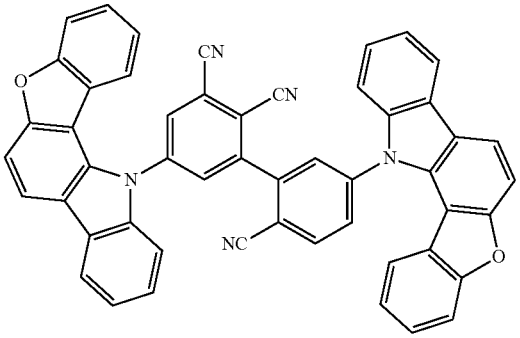

-continued
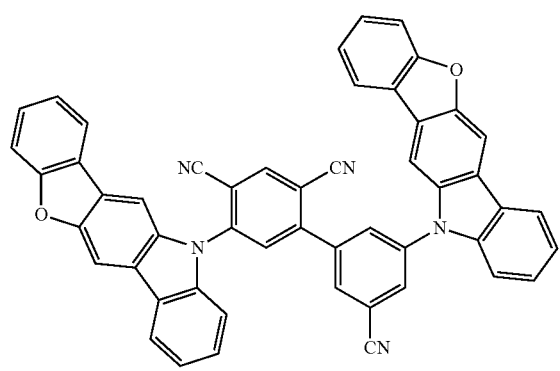
700
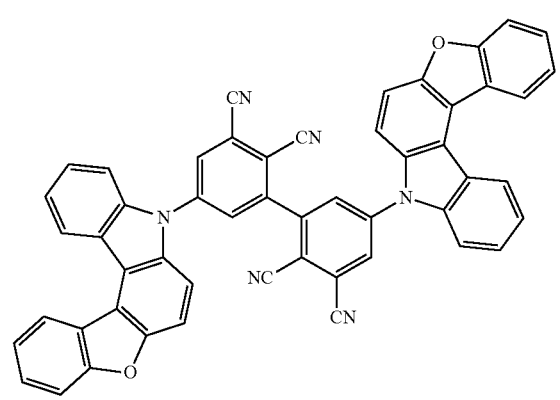
701
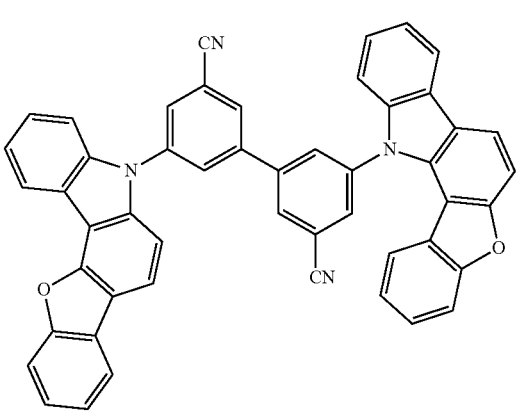
704
-continued
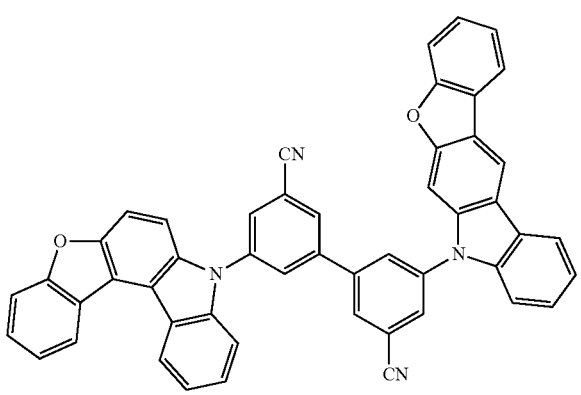
705
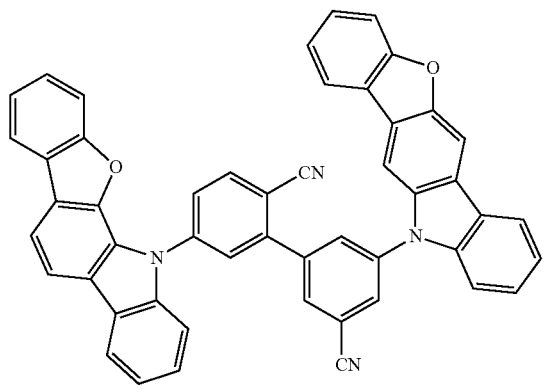
706
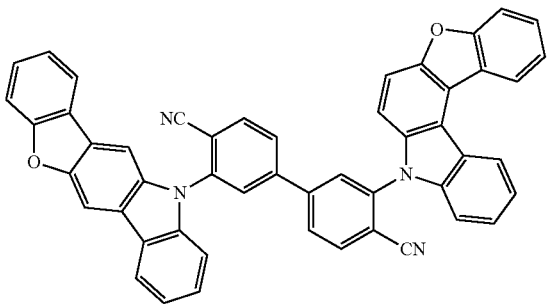
707

485
-continued
708
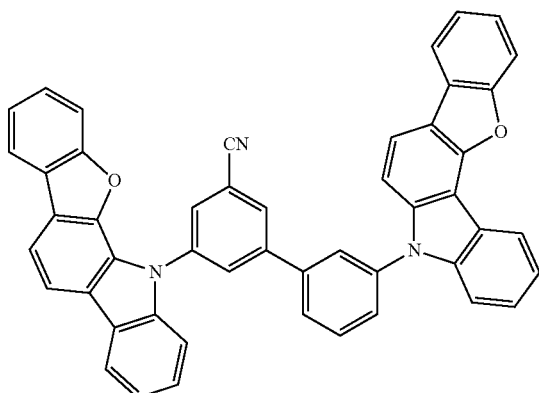
709
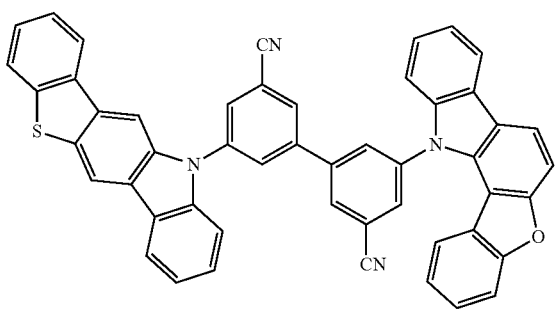
710
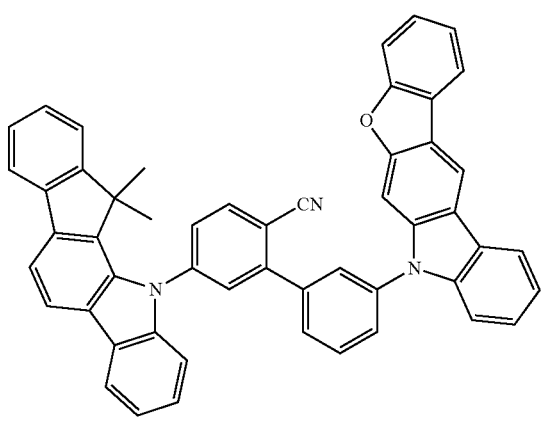
711
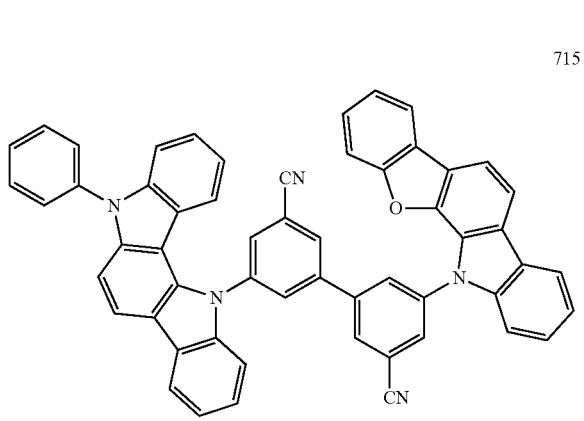
486
-continued
712
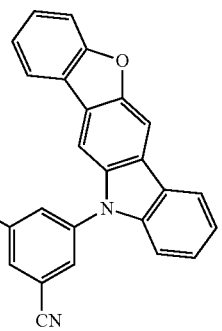
713
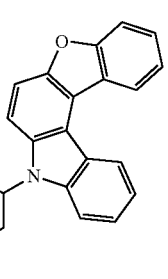
714
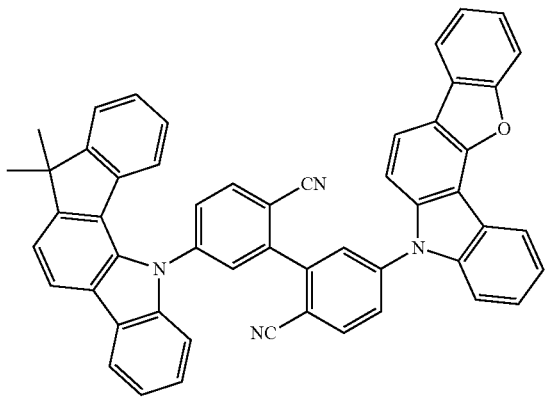
715

487
-continued
716
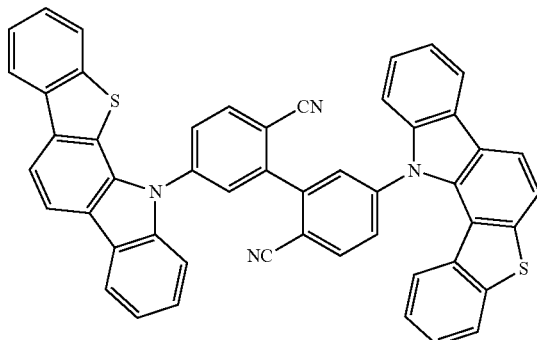
717
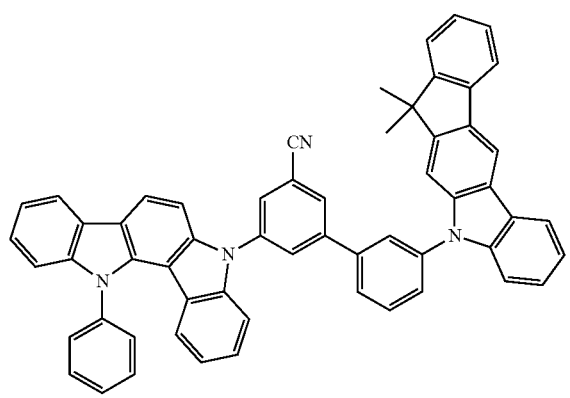
718
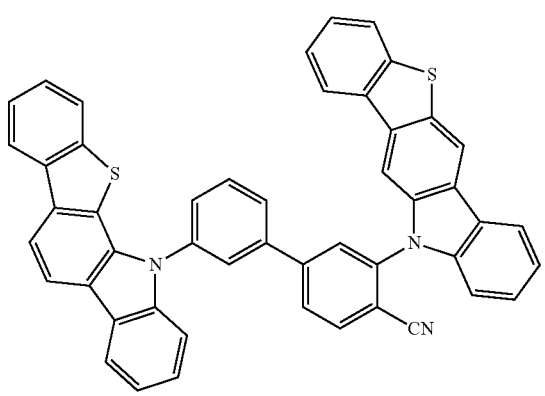
719
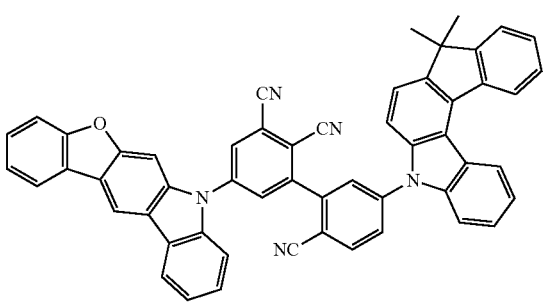
488
-continued
720
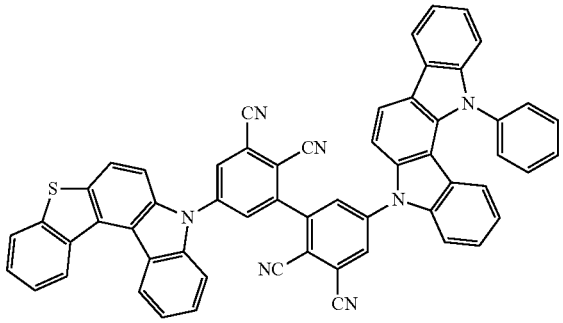
721
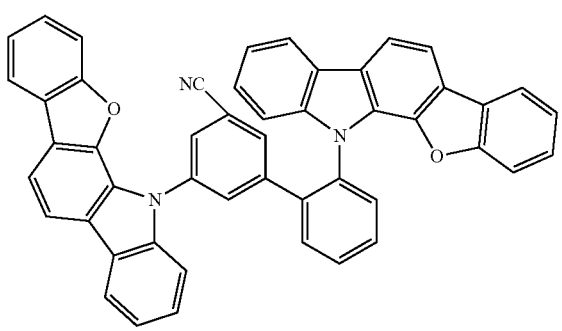
722
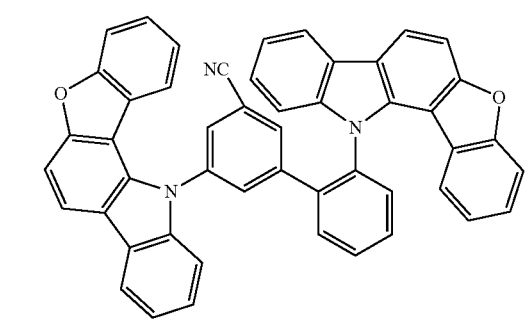
723
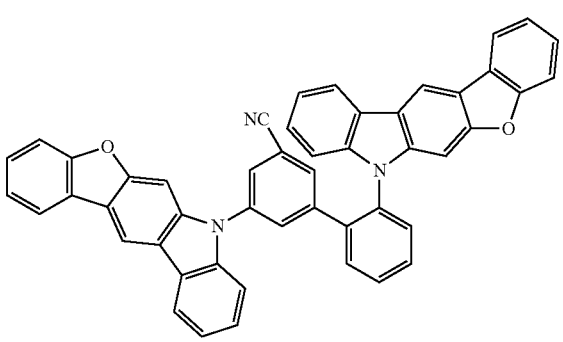

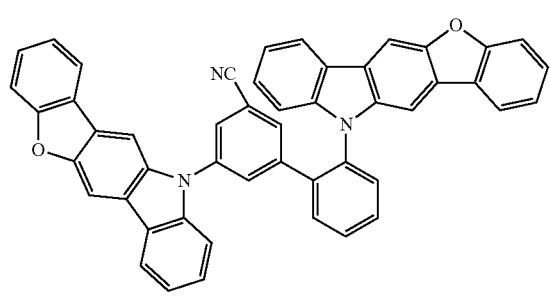
724
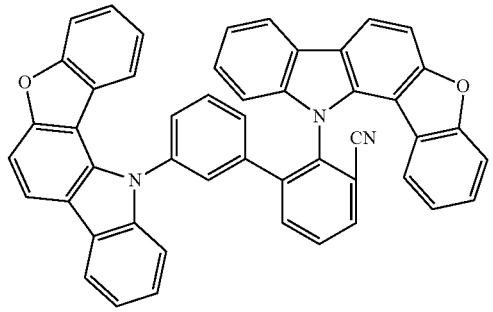
728
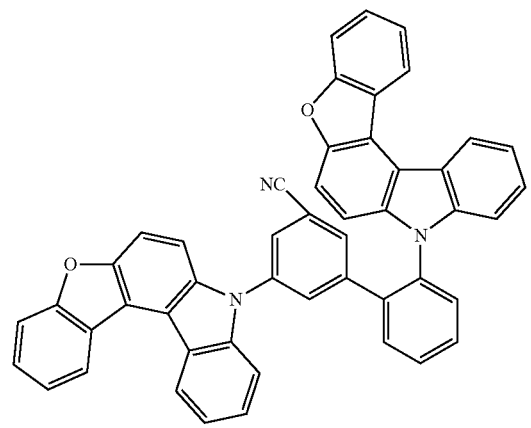
725
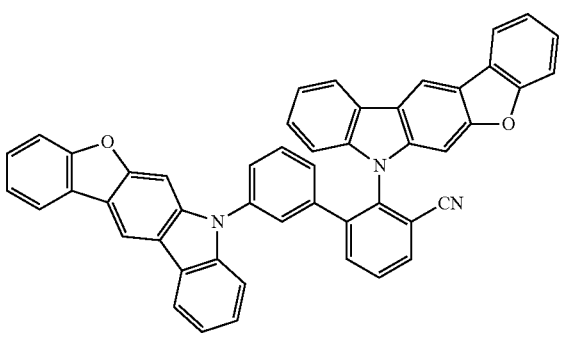
729
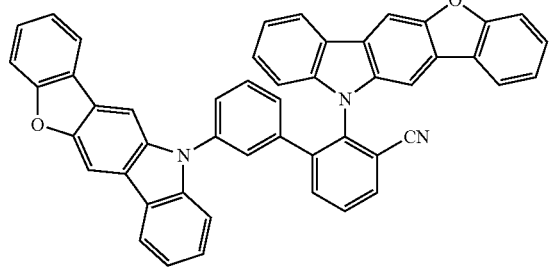
730
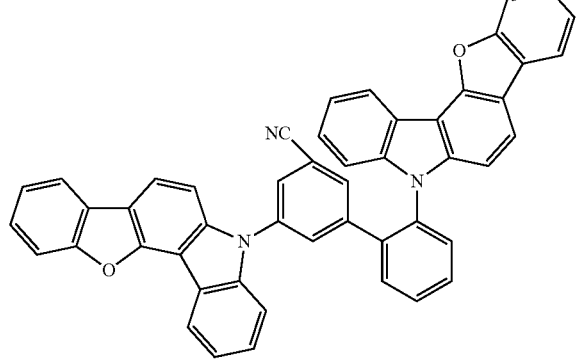
726
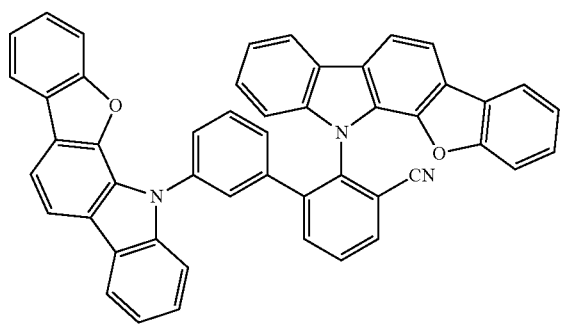
727
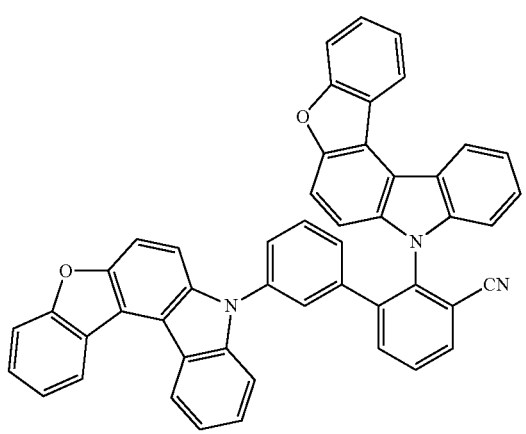
731

491
-continued
732
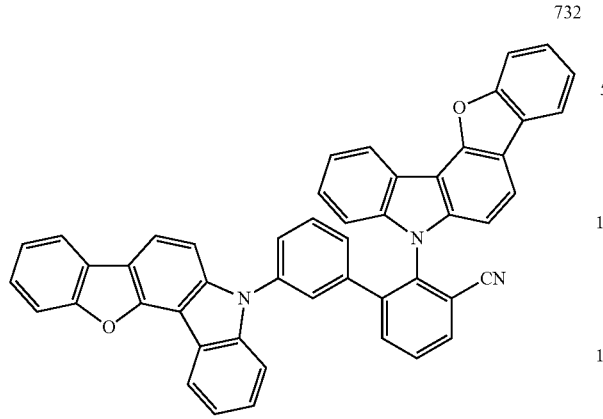
733
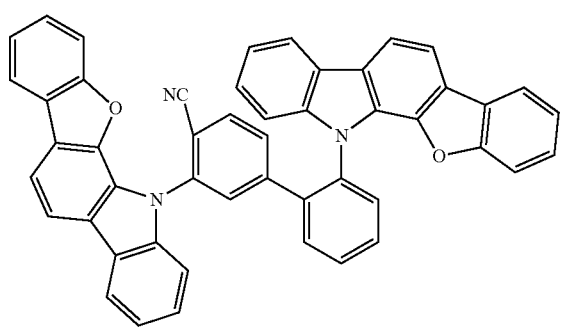
734
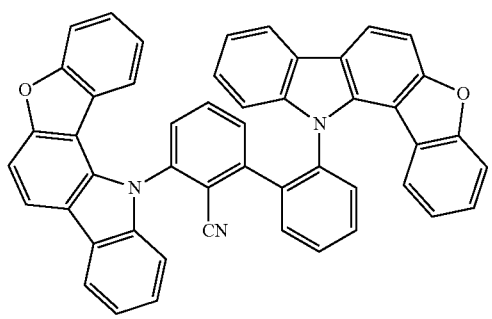
735
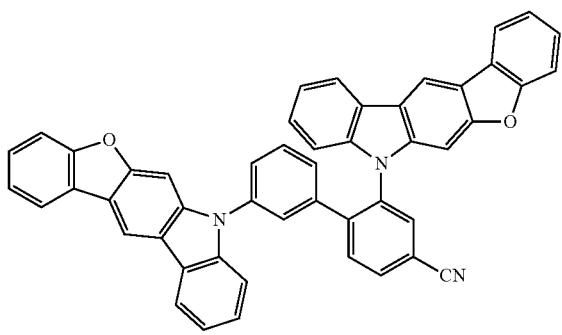
492
-continued
736
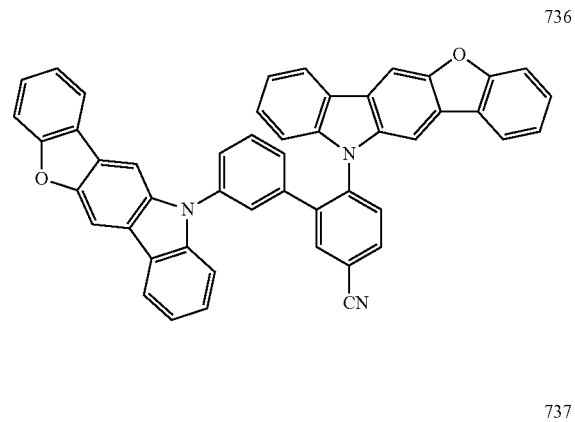
737
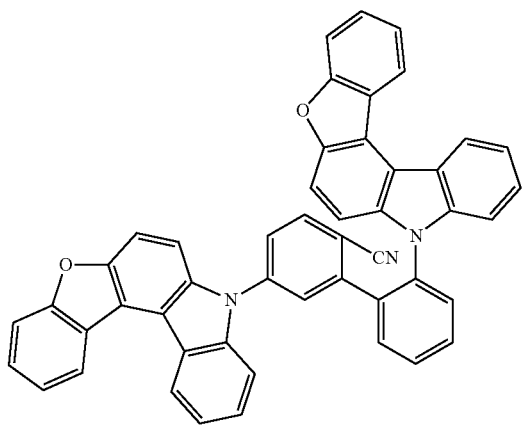
738
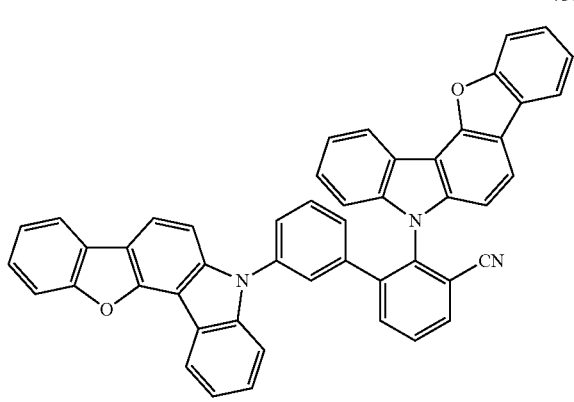
739
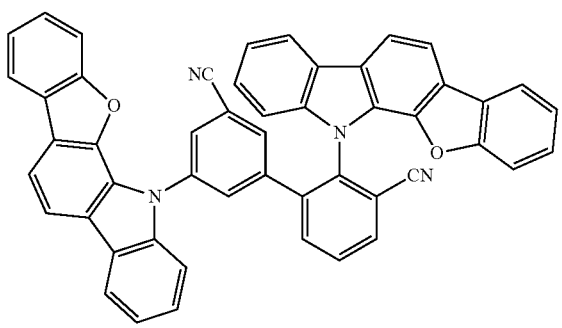

-continued
740
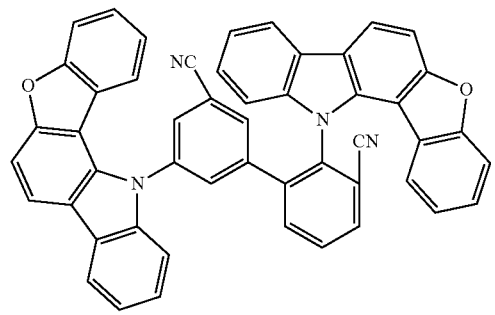
741
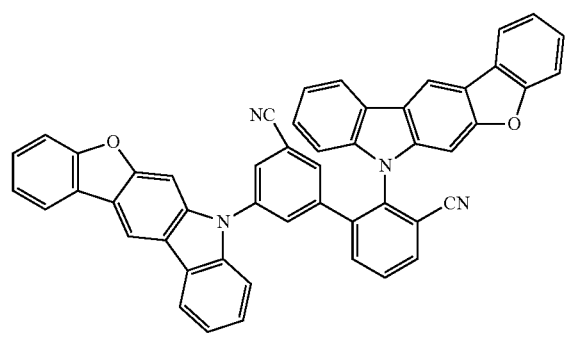
742
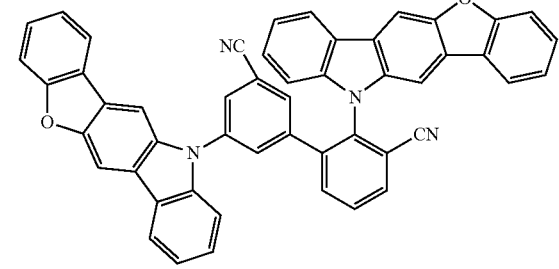
743
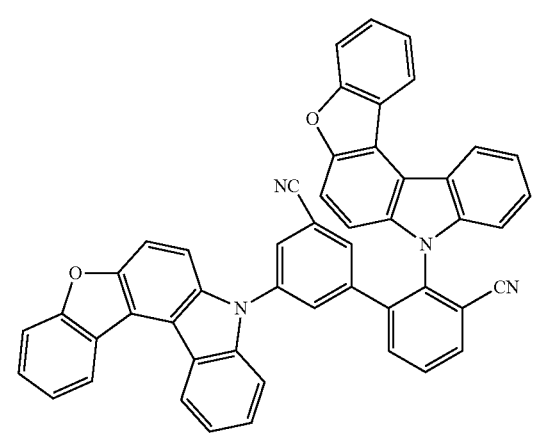
-continued
744
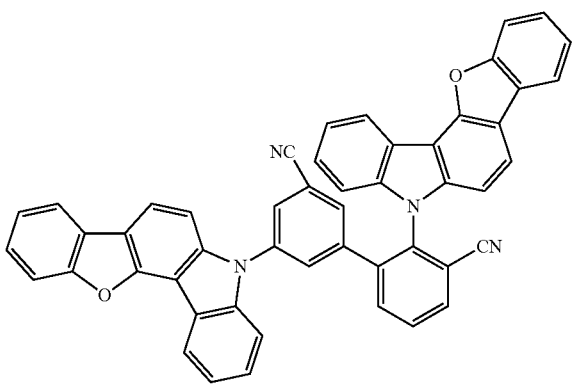
745
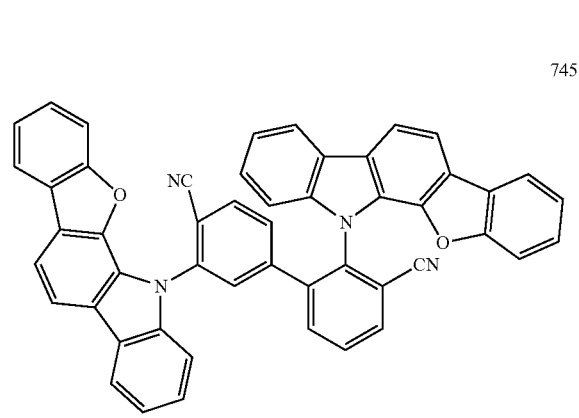
746
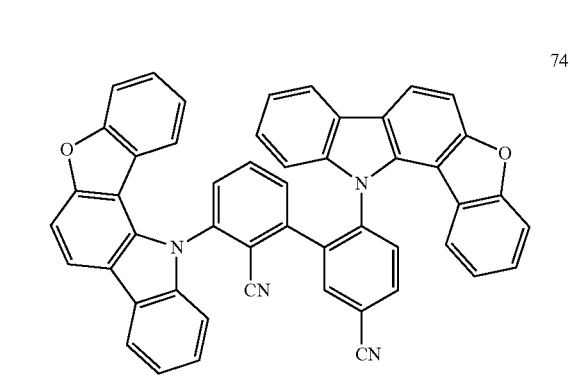
747
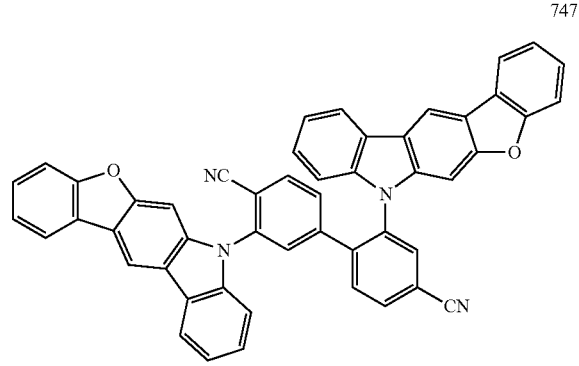

495
-continued
748
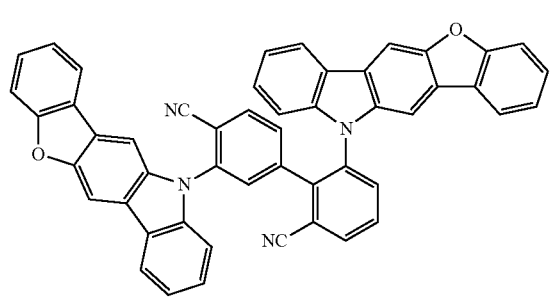
749
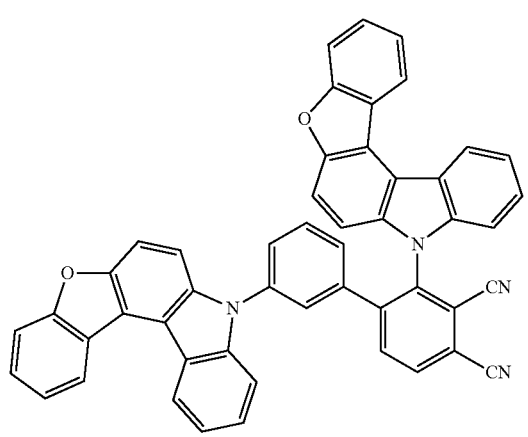
750
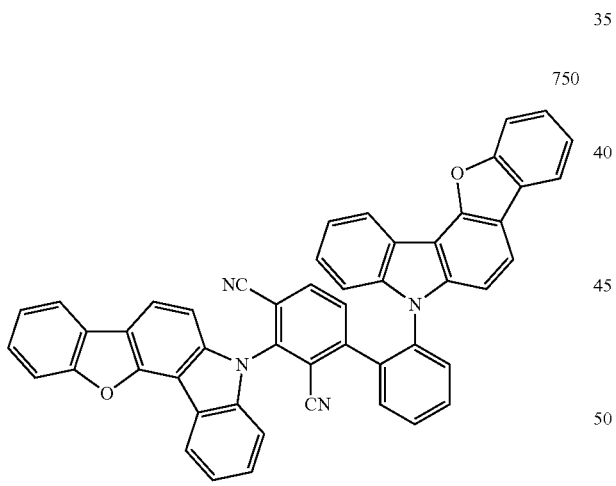
751
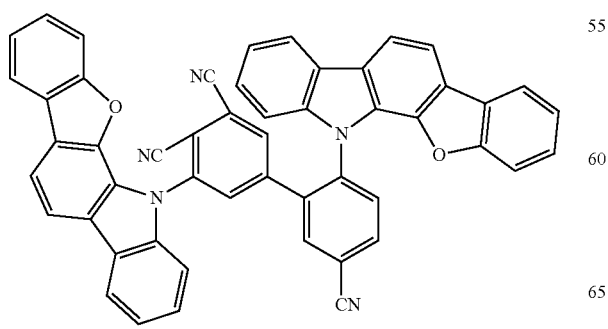
496
-continued
752
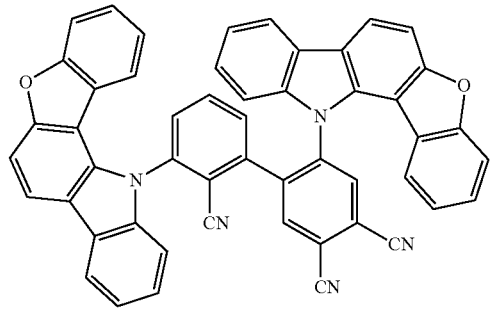
753
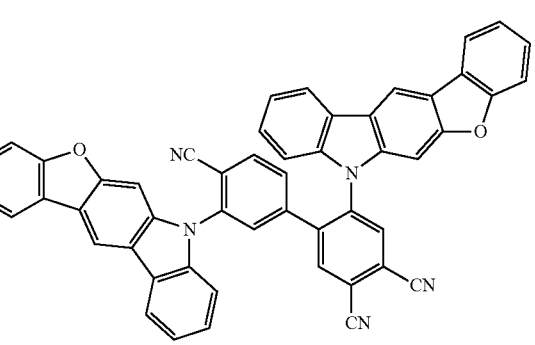
754
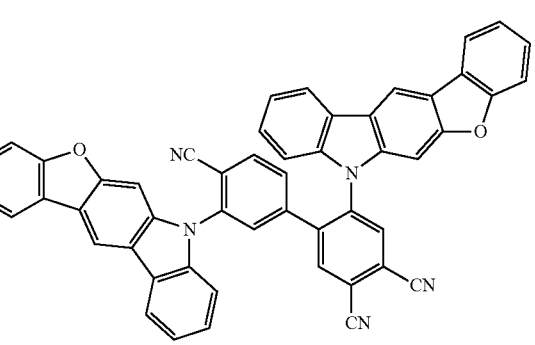
755
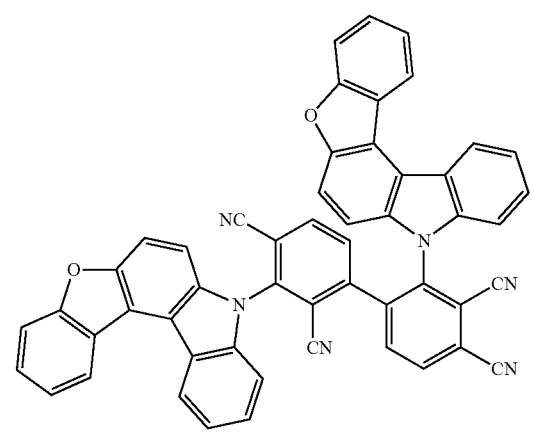

497
-continued
756
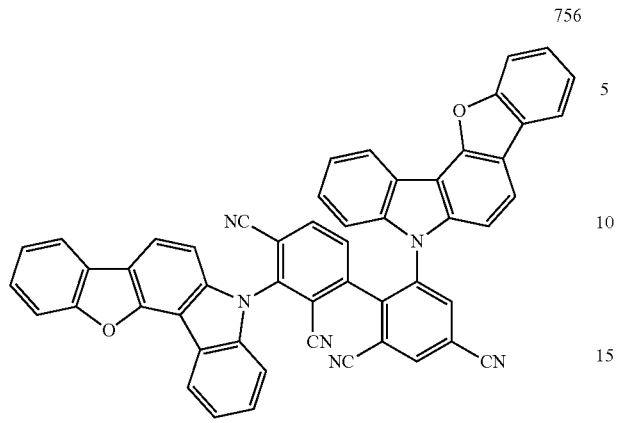
757
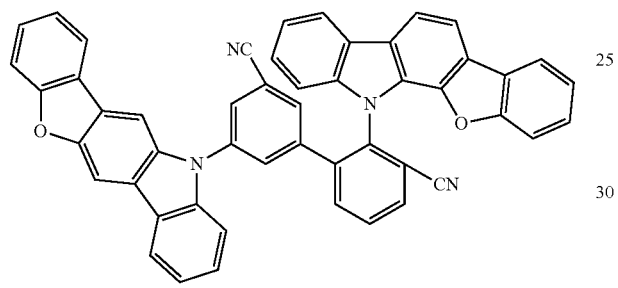
758
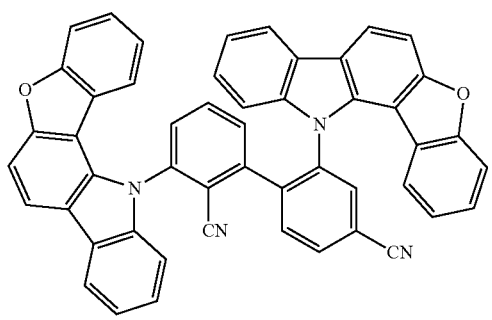
759
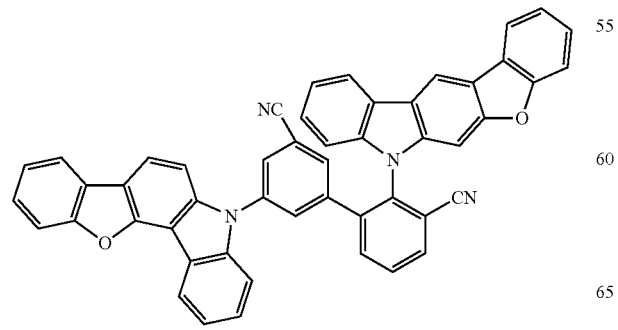
498
-continued
760
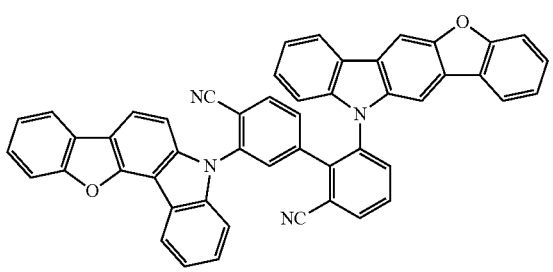
761
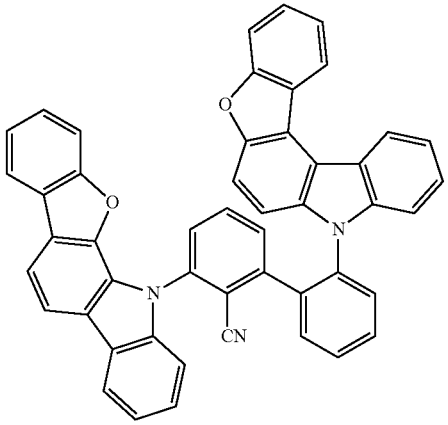
762
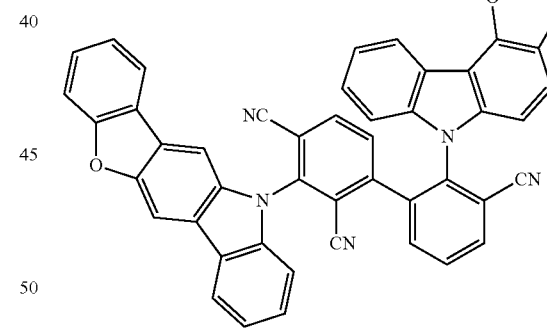
763
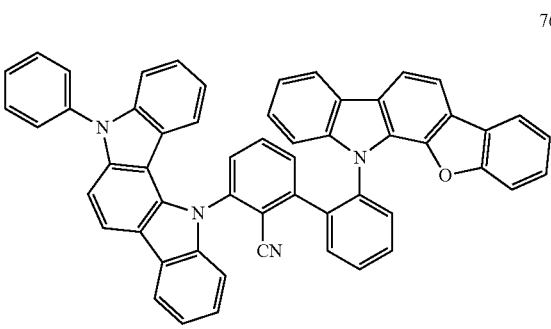

499 -continued
764
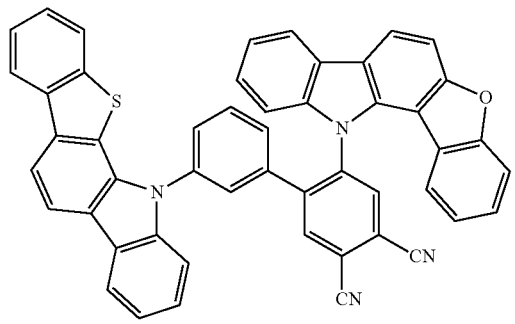
765
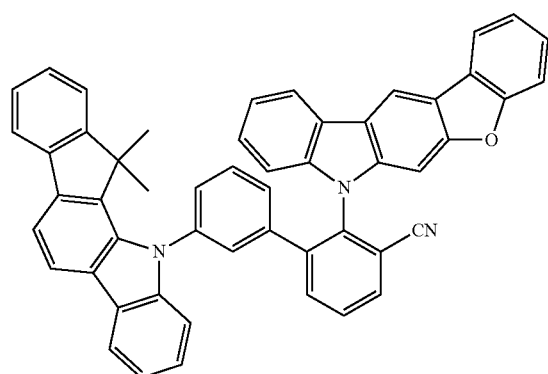
766
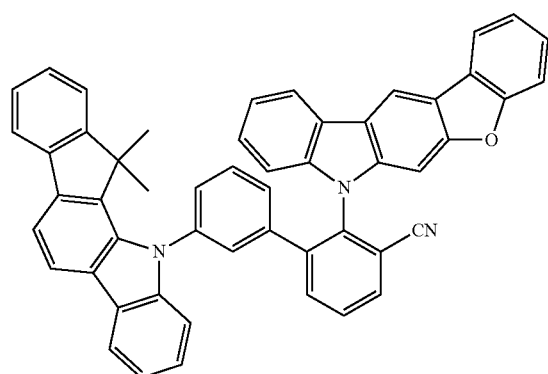
767
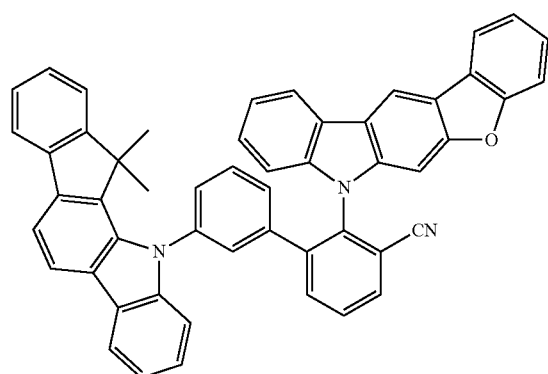
500 -continued
768
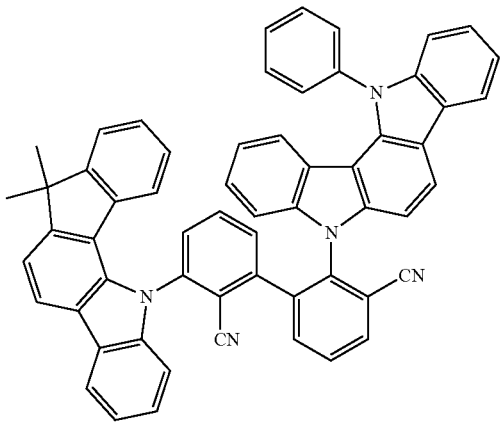
769
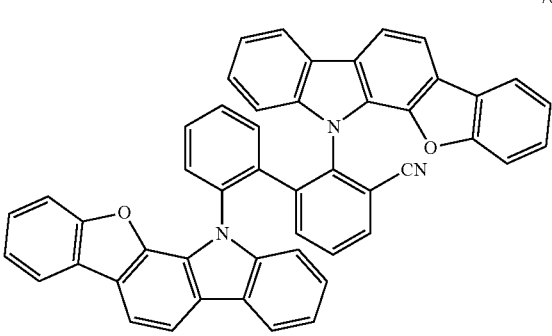
770
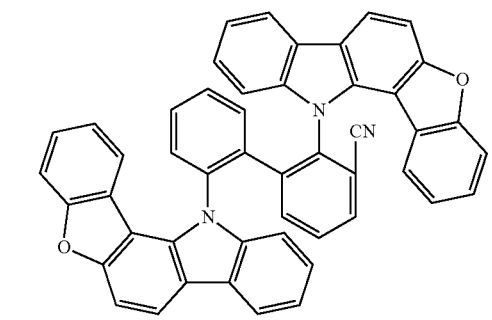
771
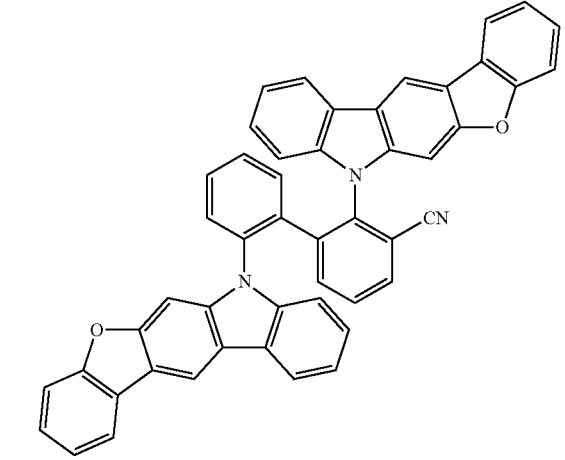

501
-continued
772
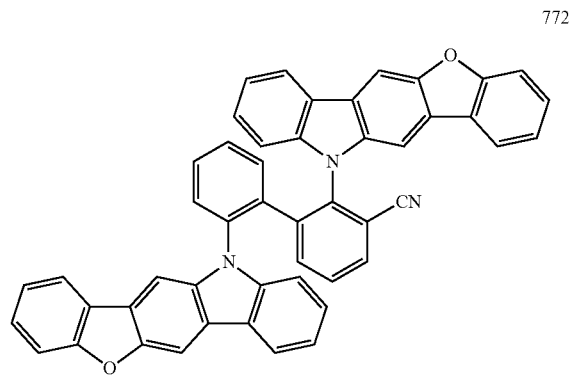
773
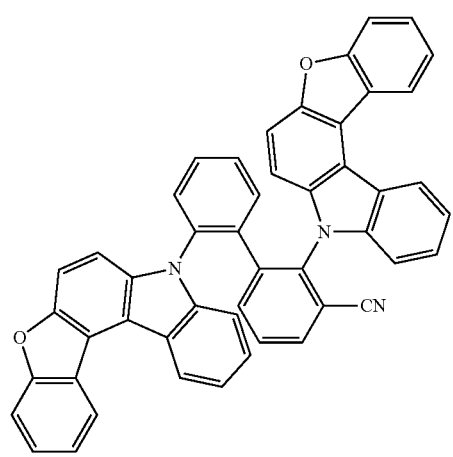
774
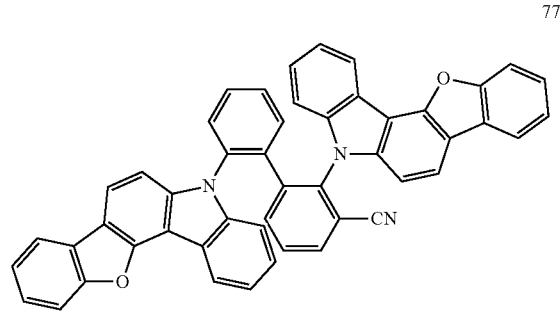
775
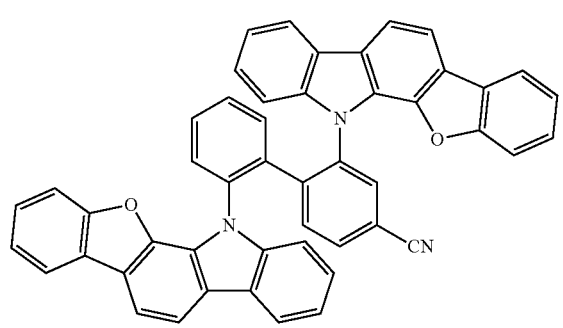
502
-continued
776
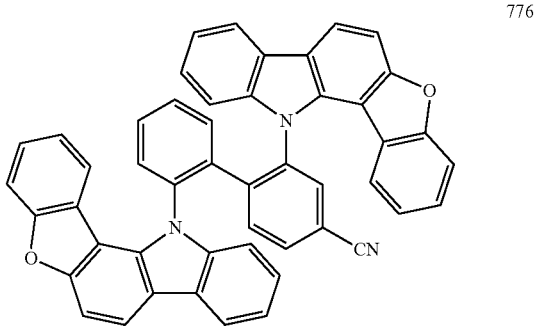
777
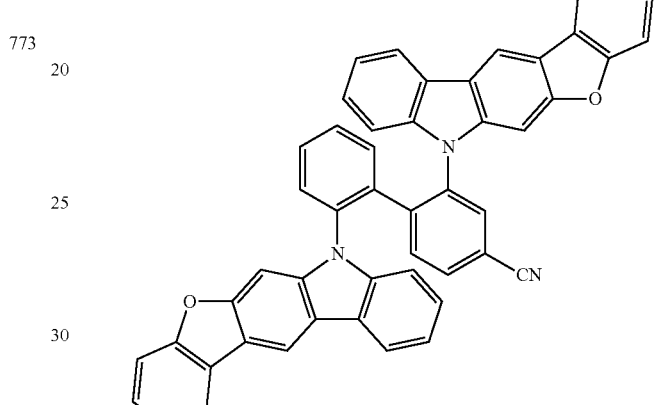
778
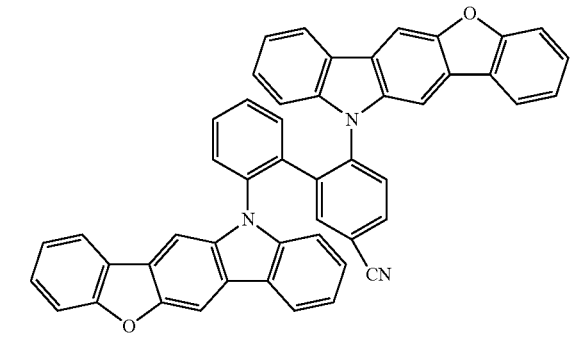
779
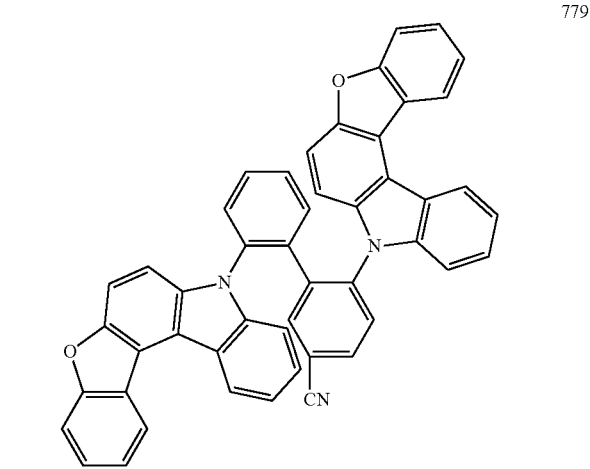

780
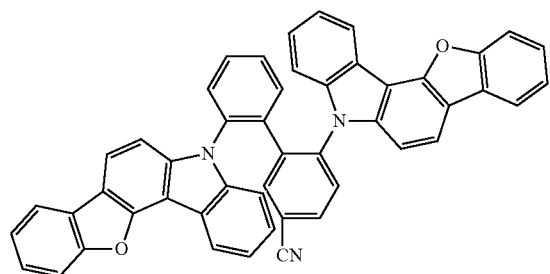
781
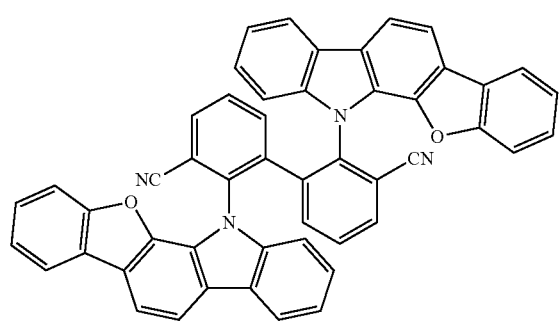
782
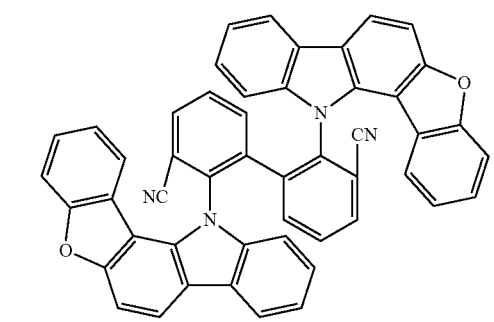
783
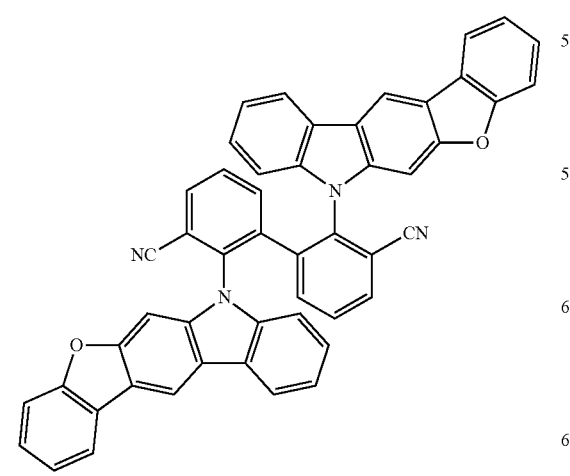
784
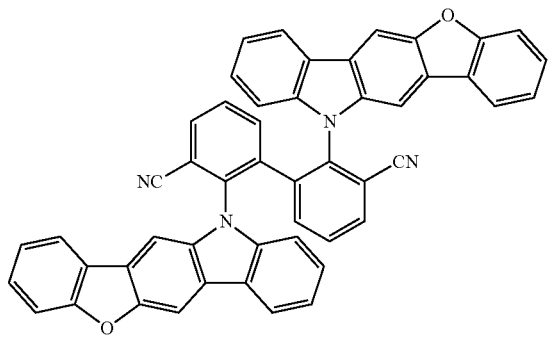
785
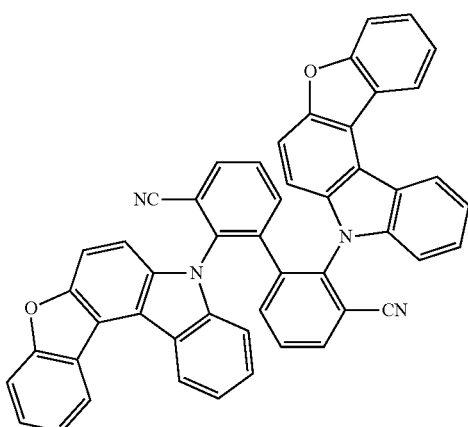
786
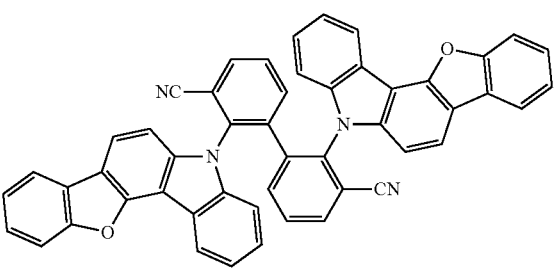
787
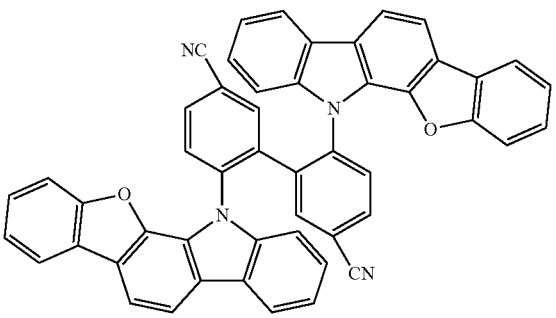

788
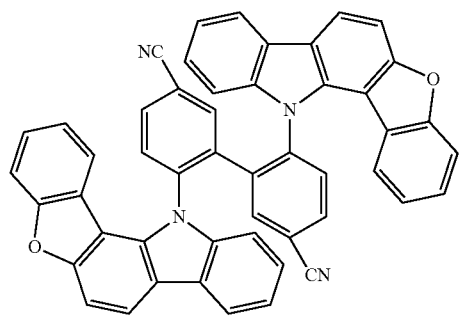
792
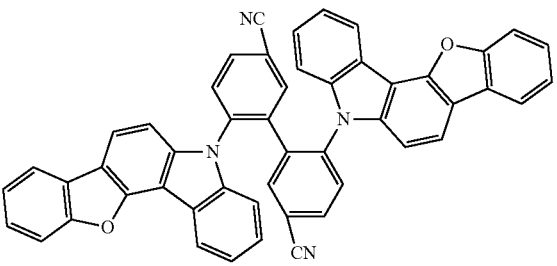
789
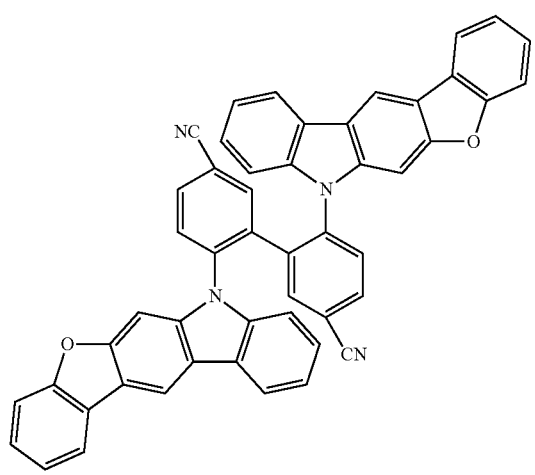
793
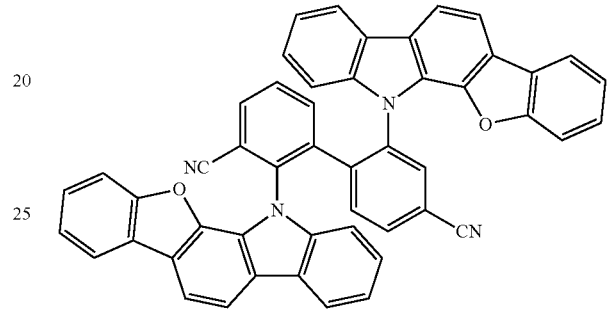
790
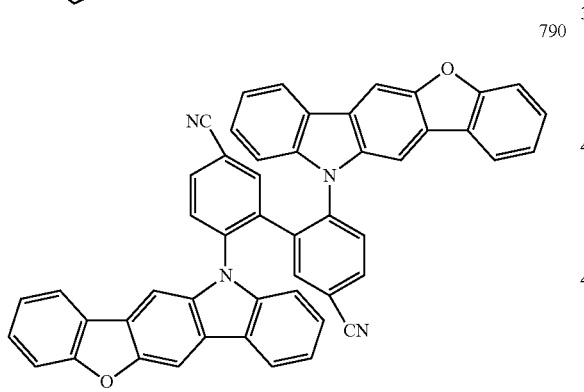
794
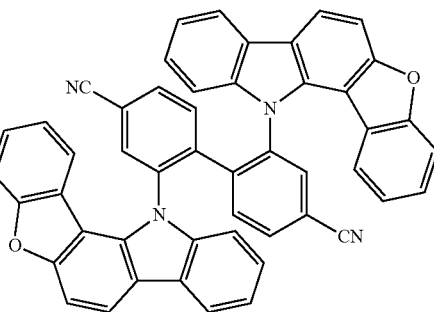
791
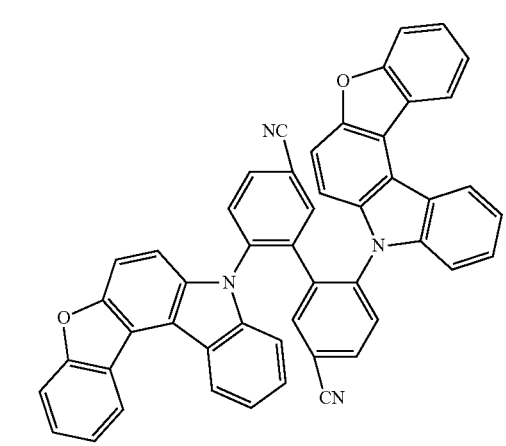
795
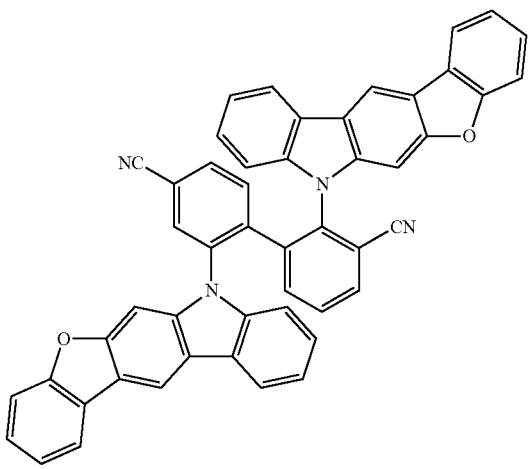

507
-continued
796
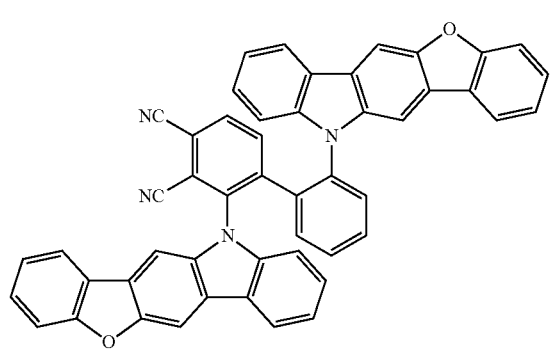
797
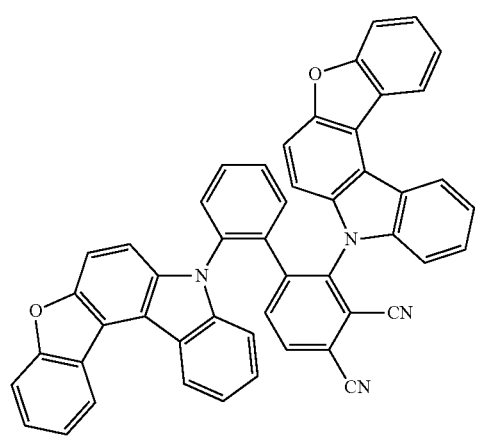
798
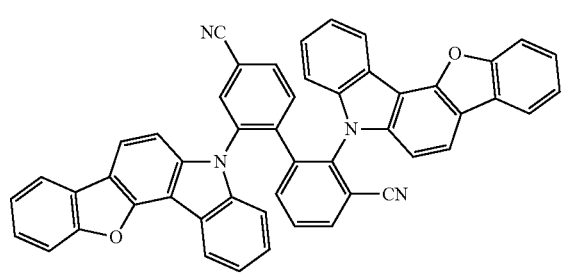
799
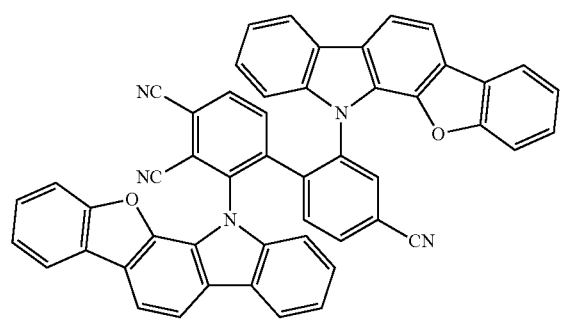
508
-continued
800
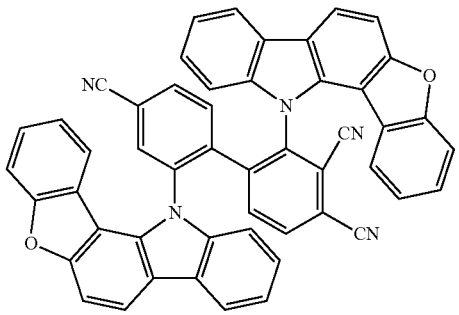
801
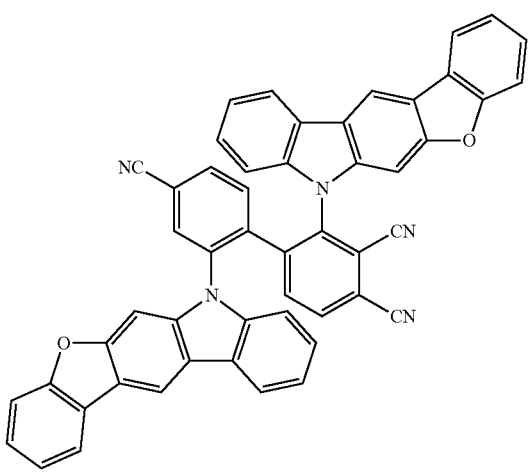
802
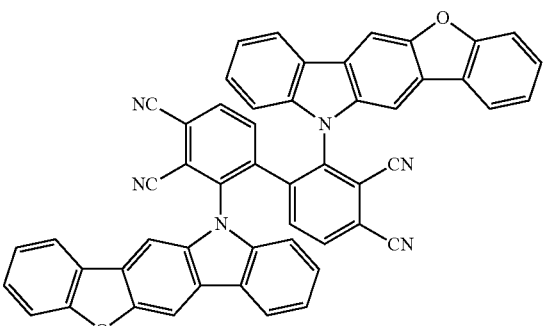
803
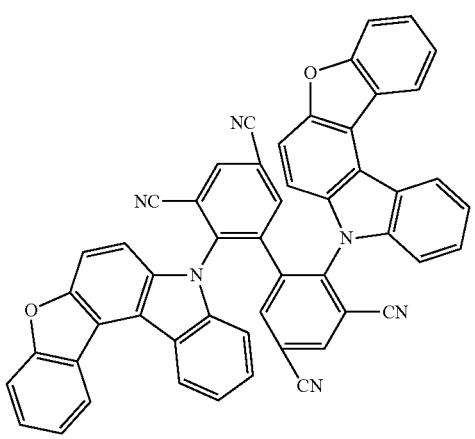

509
-continued
804
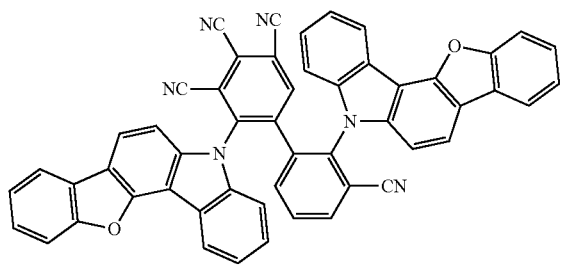
805
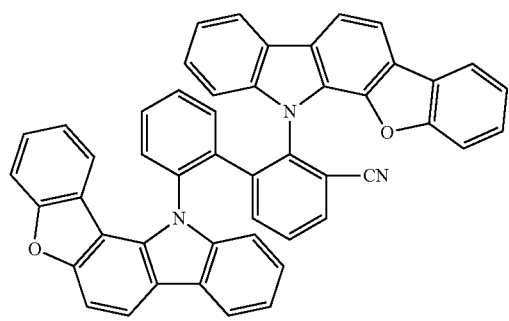
806
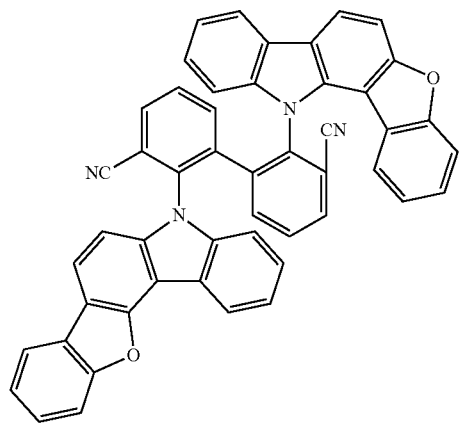
807
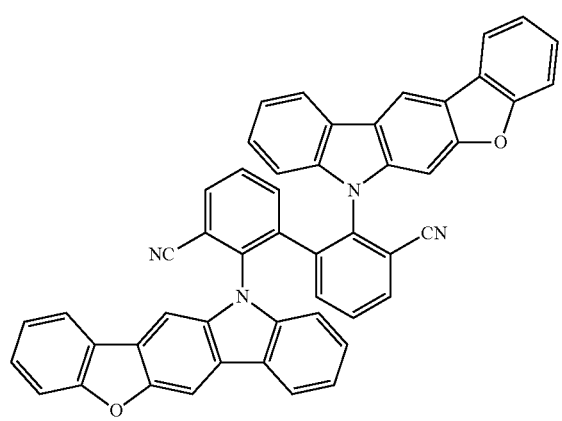
510
-continued
808
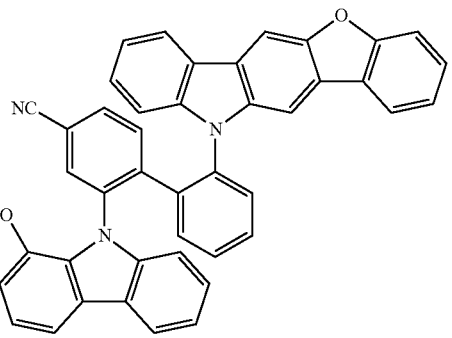
809
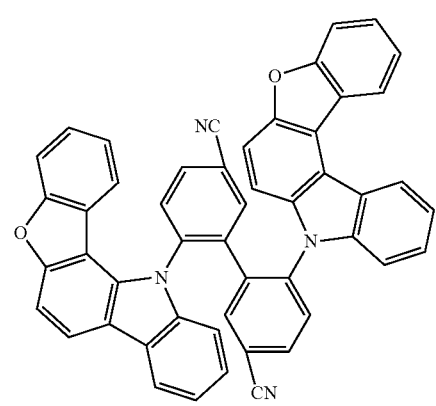
810
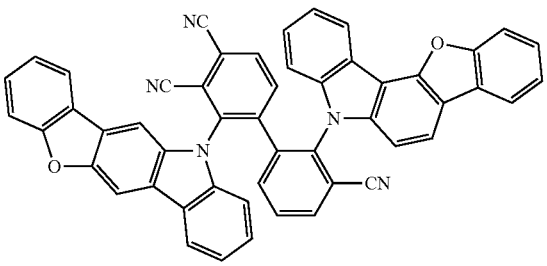
811
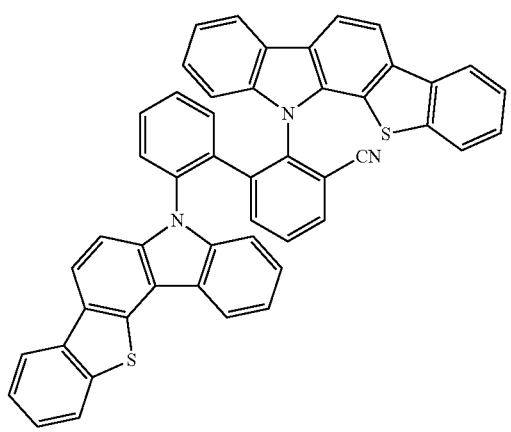

511
-continued
812
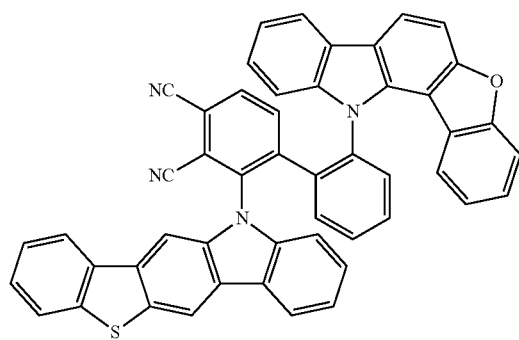
813
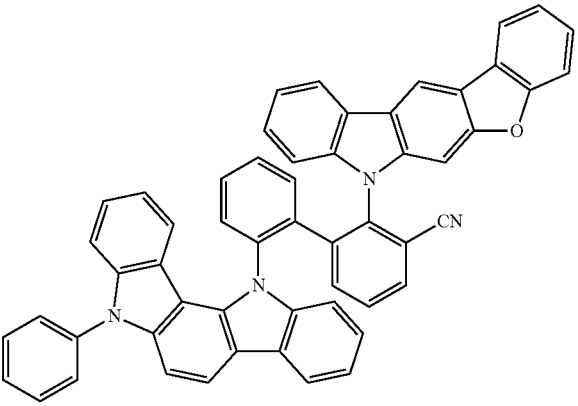
814
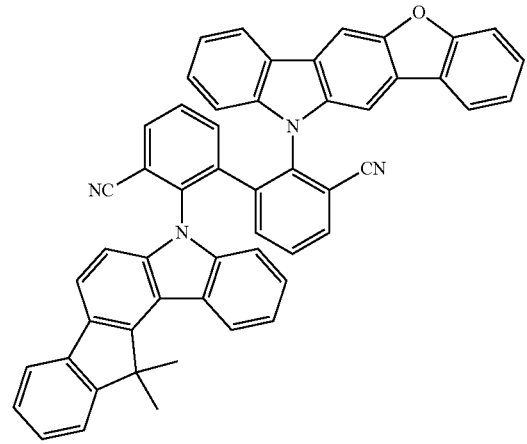
512
-continued
815
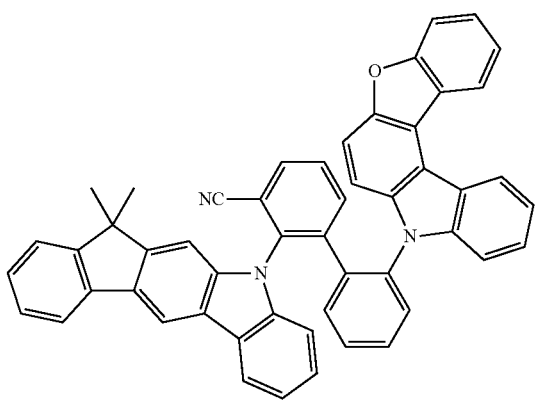
816
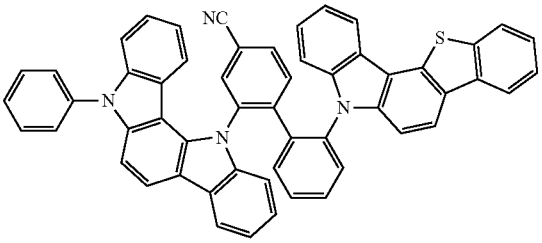
817
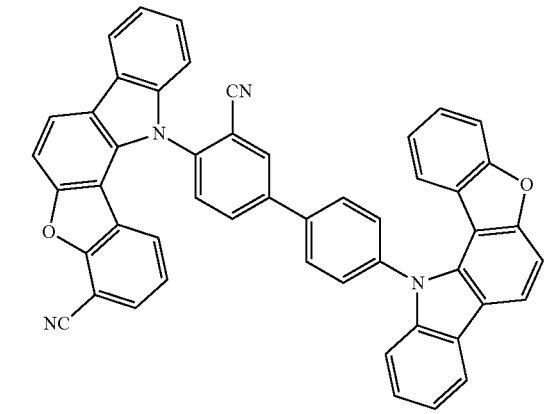
818
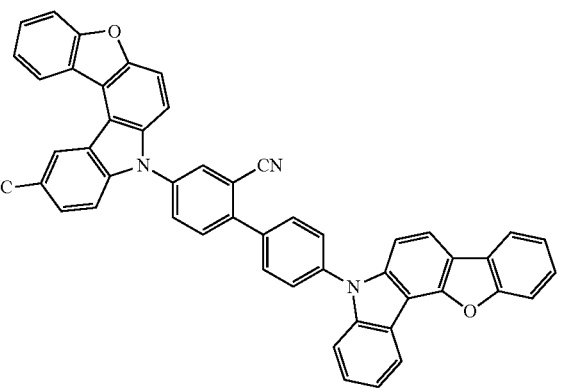

513
-continued
819
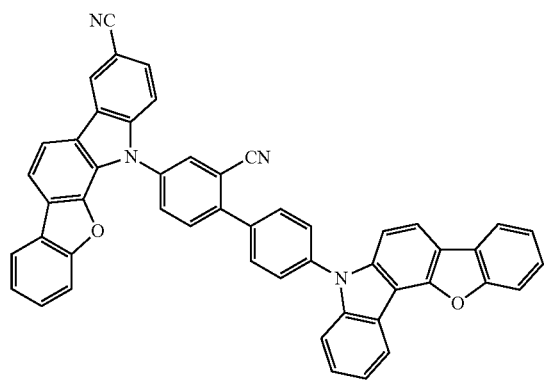
820
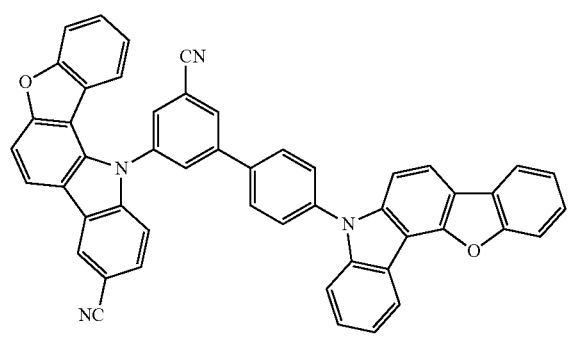
821
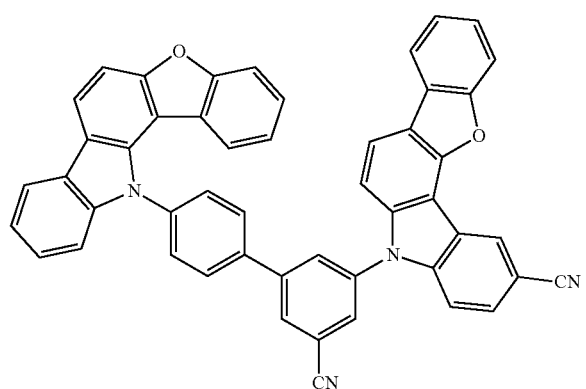
822
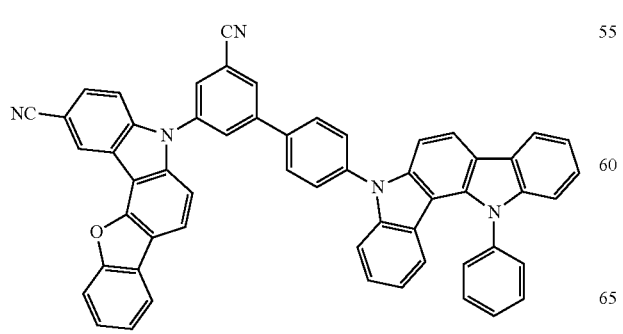
514
-continued
823
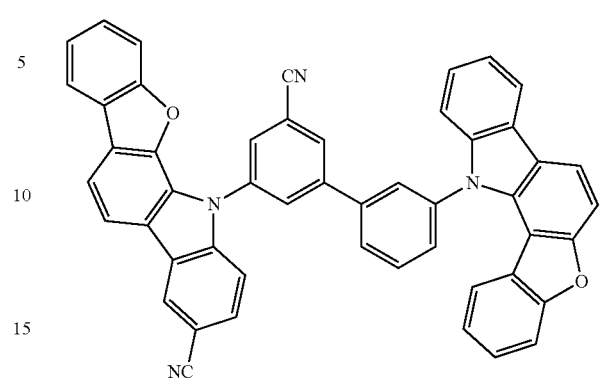
824
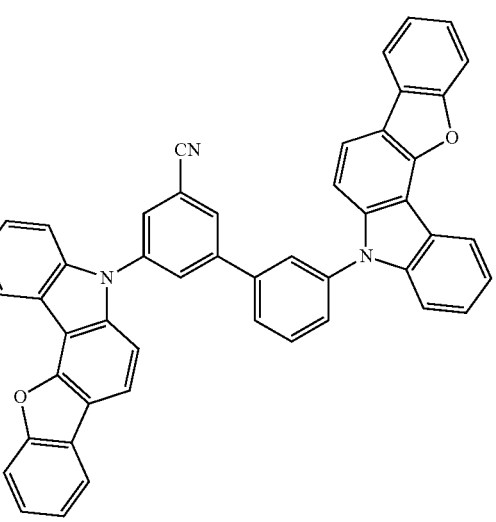
825
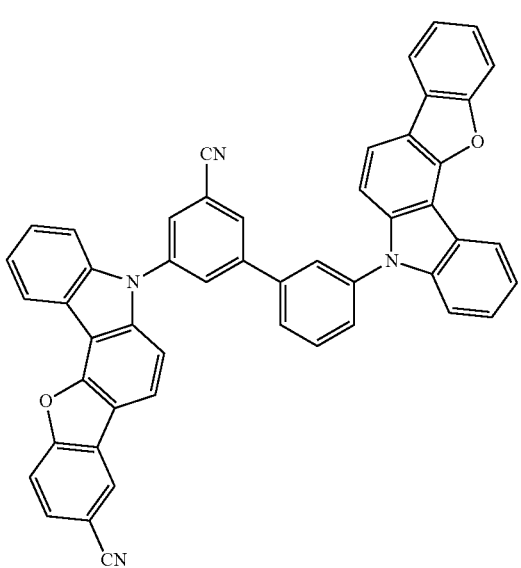

515
-continued
516
-continued
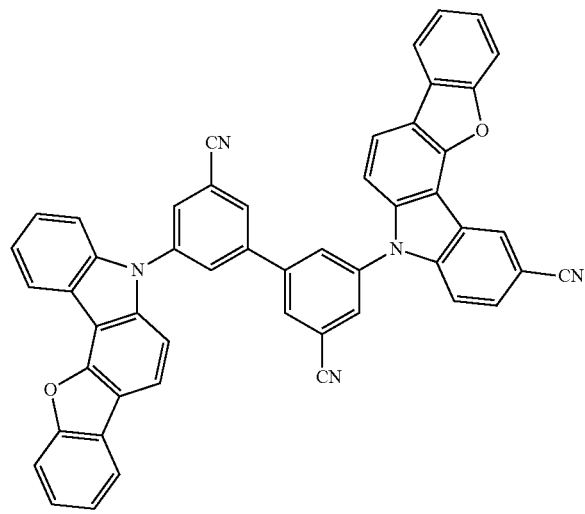
826
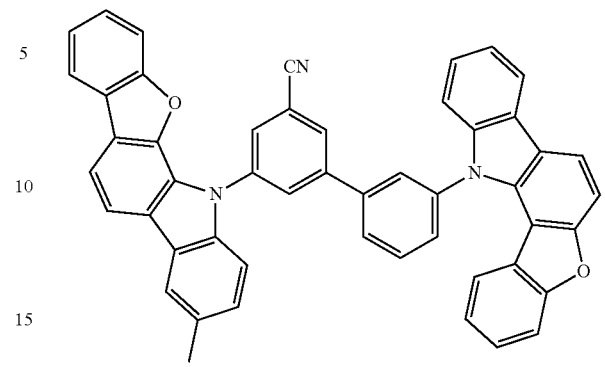
829
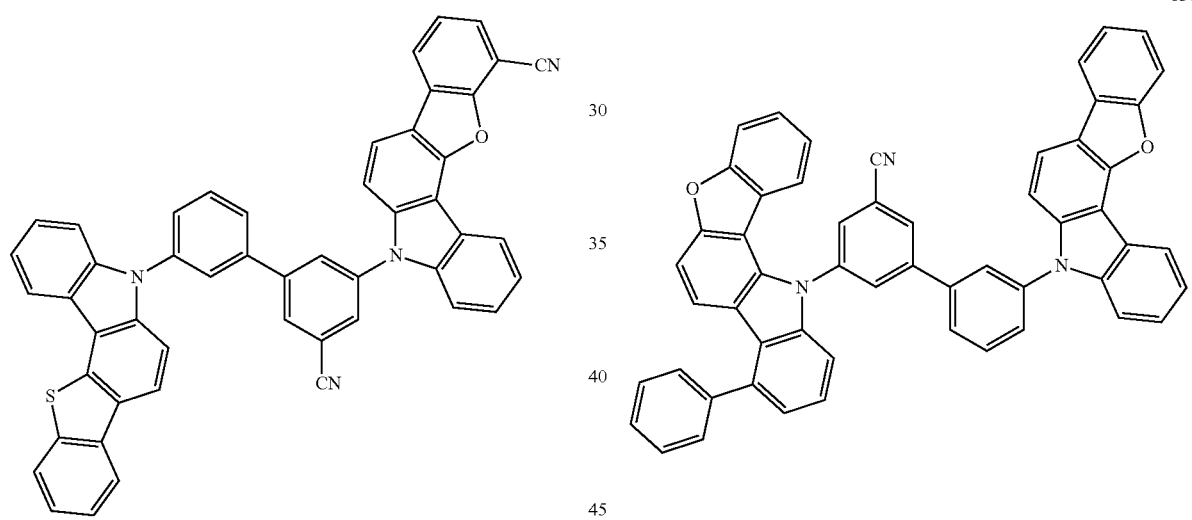
827
828
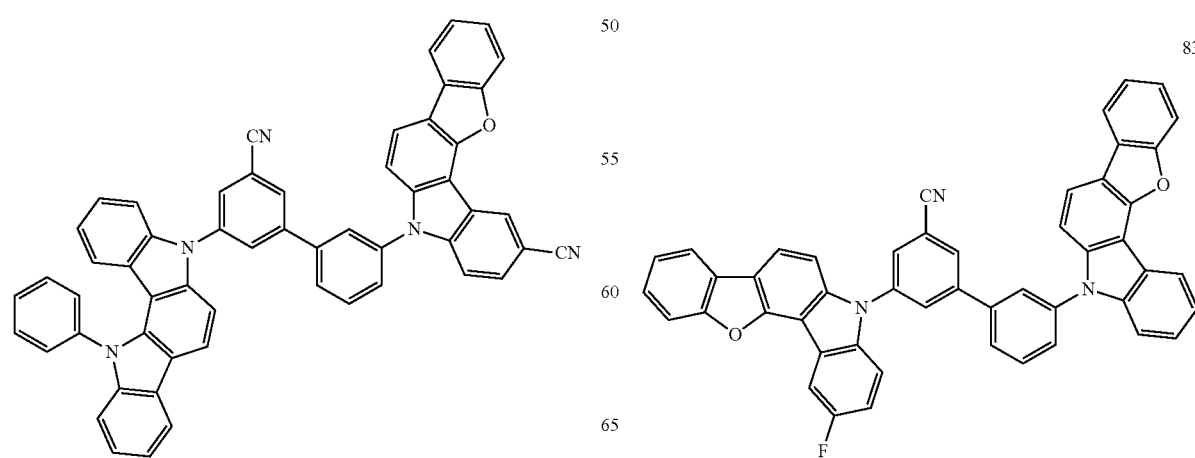
830
831

517
-continued
832
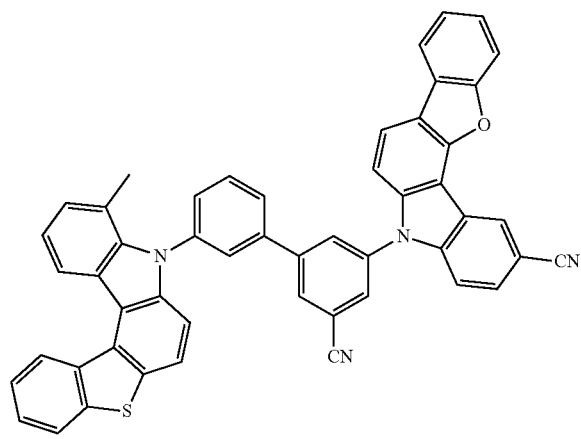
833
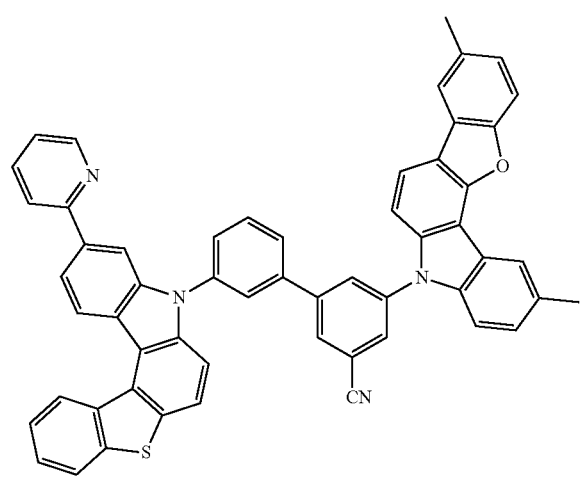
834
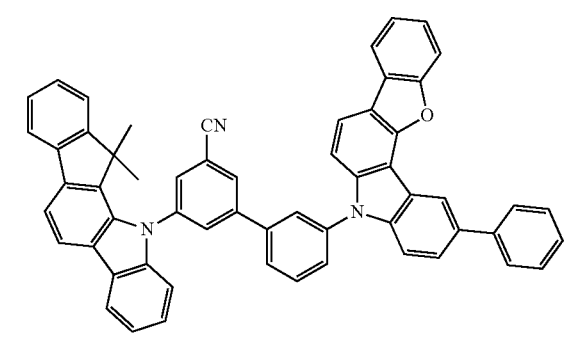
835
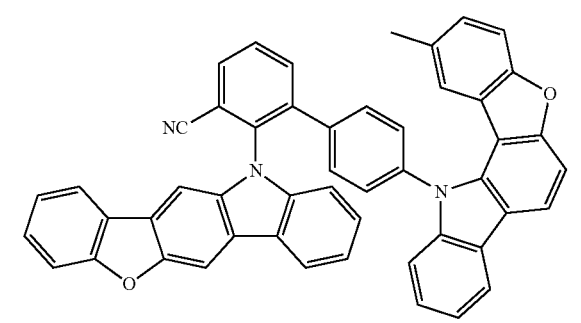
518
-continued
836
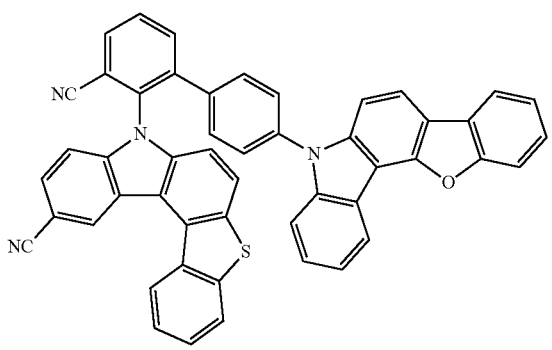
837
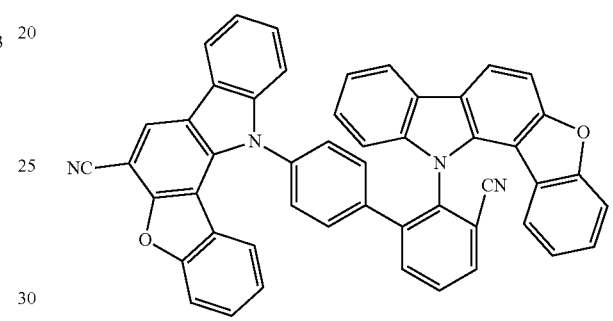
838
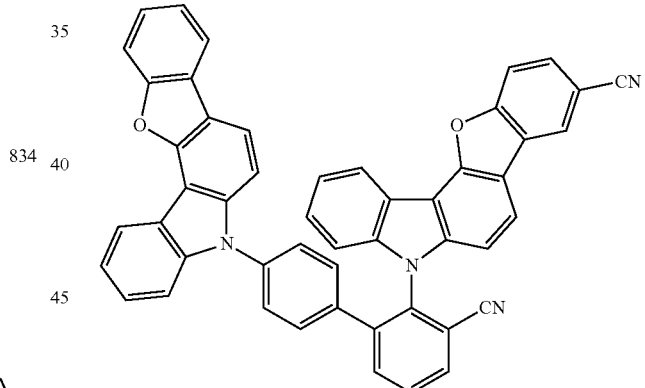
839
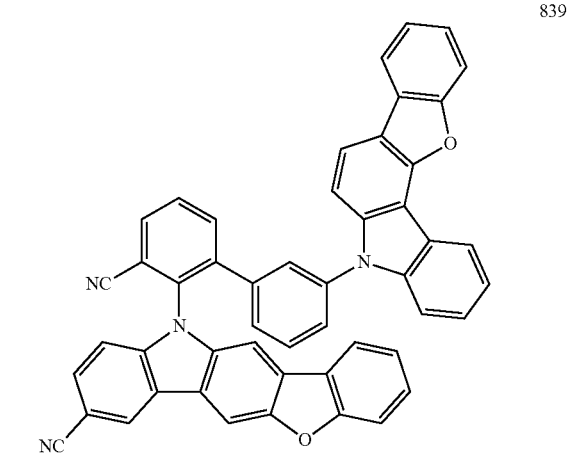

| 519 -continued | 520 -continued |
|---|---|
| 840 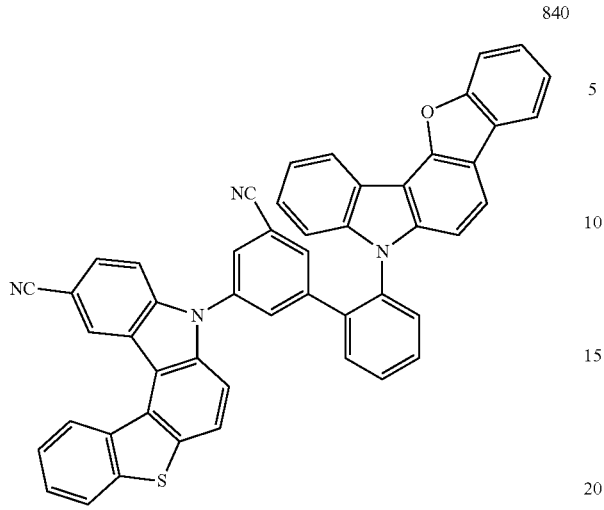 | 843 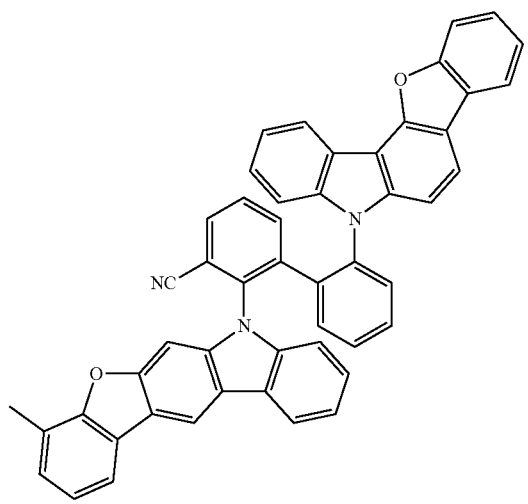 |
| 841 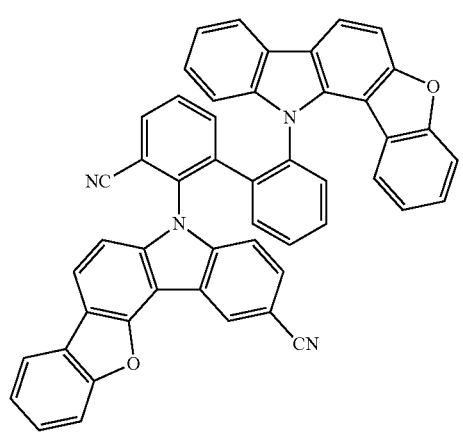 | 844 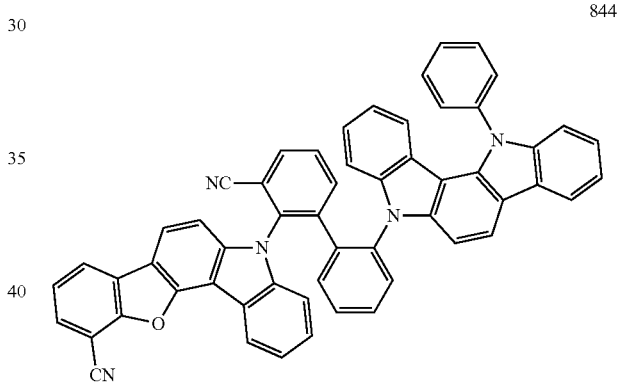 |
| 842 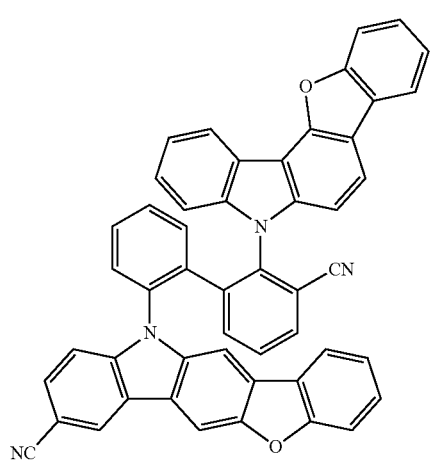 | 845 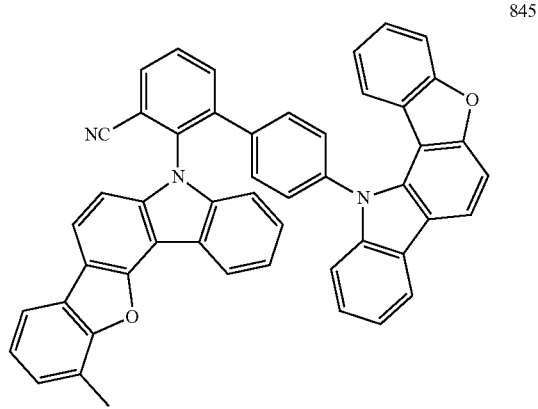 |

521
-continued
846
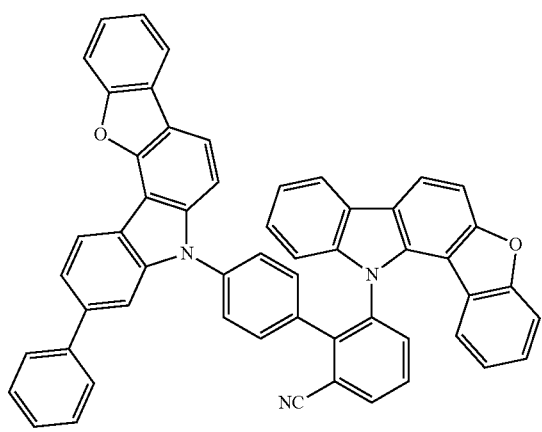
847
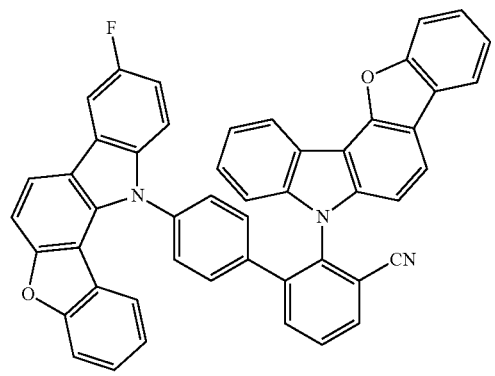
848
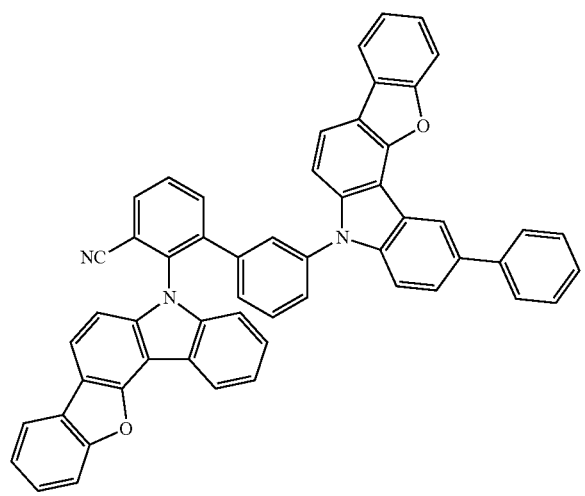
522
-continued
849
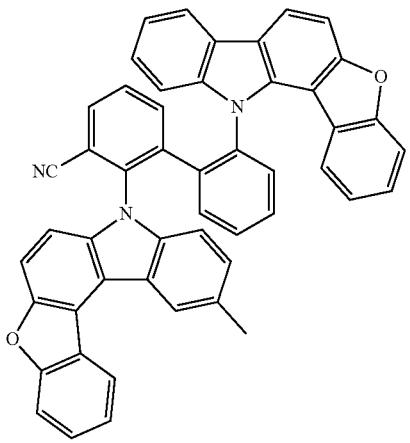
850
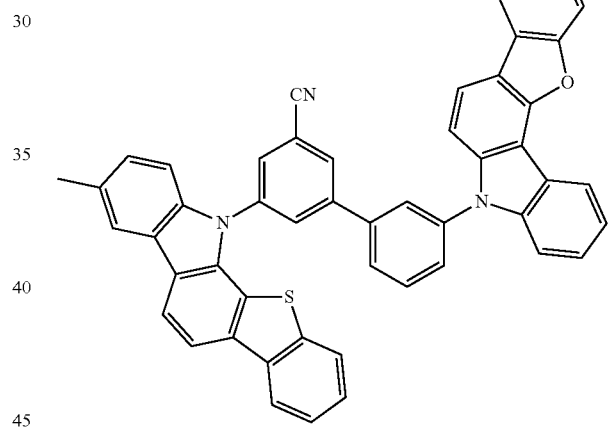
851
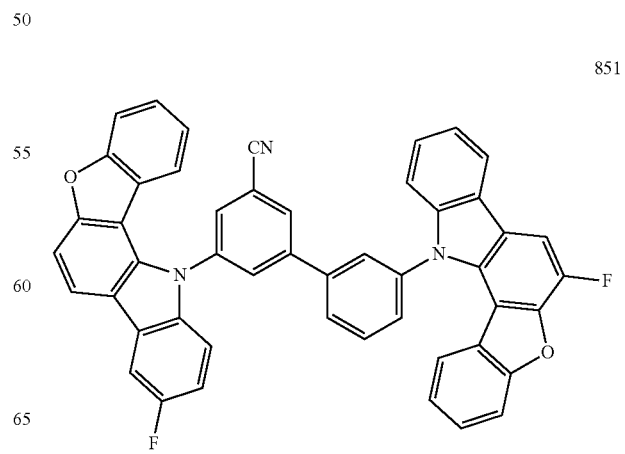

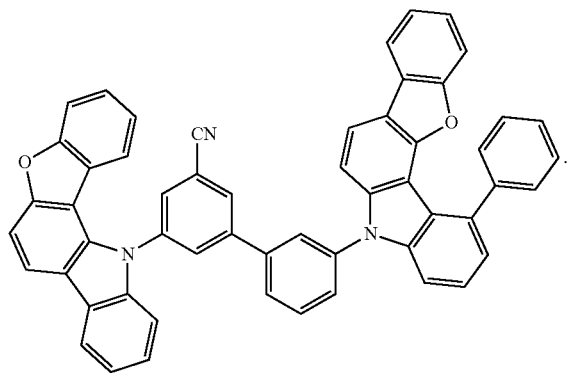

852

15. An organic light-emitting device comprising:
a first electrode;
a second electrode; and
an organic layer disposed between the first electrode and the second electrode,
wherein the organic layer comprises an emission layer, and
wherein the organic layer comprises at least one condensed cyclic compound represented by Formula 1 according to claim 1.

16. The organic light-emitting device of claim 15, wherein the first electrode is an anode,
the second electrode is a cathode, and
the organic layer comprises a hole transport region disposed between the first electrode and the emission layer and an electron transport region disposed between the emission layer and the second electrode,
wherein the hole transport region comprises a hole injection layer, a hole transport layer, an electron blocking layer, or any combination thereof, and
wherein the electron transport region comprises a hole blocking layer, an electron transport layer, an electron injection layer, or any combination thereof.

17. The organic light-emitting device of claim 15, wherein the emission layer comprises the at least one condensed cyclic compound represented by Formula 1.

18. The organic light-emitting device of claim 15,
wherein the emission layer comprises a host and a dopant,
wherein the host comprises the at least one condensed cyclic compound represented by Formula 1, and
wherein an amount of the host is greater than an amount of the dopant.

19. The organic light-emitting device of claim 18, wherein the emission layer emits blue light.

20. The organic light-emitting device of claim 16, wherein the electron transport region comprises a hole blocking layer, the hole blocking layer comprising the condensed cyclic compound represented by Formula 1.

* * * * *